United States Patent
Maruyama et al.

(10) Patent No.: US 8,207,223 B2
(45) Date of Patent: Jun. 26, 2012

(54) PHARMACEUTICAL COMPOSITION FOR TREATMENT OF DISEASES ASSOCIATED WITH DECREASE IN BONE MASS COMPRISING EP4 AGONIST AS ACTIVE INGREDIENT

(75) Inventors: Toru Maruyama, Osaka (JP); Kaoru Kobayashi, Osaka (JP); Tohru Kambe, Osaka (JP); Takayuki Maruyama, Osaka (JP); Hideyuki Yoshida, Osaka (JP); Akio Nishiura, Osaka (JP); Nobutaka Abe, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/549,136

(22) Filed: Aug. 27, 2009

(65) Prior Publication Data

US 2010/0010222 A1    Jan. 14, 2010

Related U.S. Application Data

(63) Continuation of application No. 10/484,500, filed as application No. PCT/JP02/07385 on Jul. 22, 2002, now Pat. No. 7,608,637.

(30) Foreign Application Priority Data

Jul. 23, 2001  (JP) ................................. 2001-222148
Aug. 7, 2001   (JP) ................................. 2001-239895
Mar. 1, 2002   (JP) ................................. 2002-56449

(51) Int. Cl.
*A01N 37/08*   (2006.01)
*A01N 53/00*   (2006.01)
*A61K 31/215*  (2006.01)
*A61K 31/19*   (2006.01)
*A61K 31/557*  (2006.01)

(52) U.S. Cl. ........................................ 514/530; 514/573
(58) Field of Classification Search ........................ None
See application file for complete search history.

(56) References Cited

U.S. PATENT DOCUMENTS

| | | | |
|---|---|---|---|
| 3,975,399 A | 8/1976 | DeFranco et al. | |
| 4,054,736 A | 10/1977 | Hayashi et al. | |
| 4,113,873 A | 9/1978 | Himizu et al. | |
| 4,115,401 A | 9/1978 | Nanthavong et al. | |
| 4,177,346 A | 12/1979 | Nelson | |
| 4,320,136 A | 3/1982 | Scribner | |
| 6,156,799 A | 12/2000 | Hartke et al. | |
| 6,211,226 B1 | 4/2001 | Hellberg et al. | |
| 6,414,006 B1 | 7/2002 | Harada et al. | |
| 6,462,081 B1 | 10/2002 | Maruyama et al. | |
| 6,476,074 B1 | 11/2002 | Stjernschantz et al. | |
| 6,552,067 B2 | 4/2003 | Cameron et al. | |
| 6,586,457 B2 | 7/2003 | Harada et al. | |
| 6,747,054 B2 | 6/2004 | Cameron et al. | |
| 6,849,657 B2 | 2/2005 | Elworthy et al. | |
| 7,192,979 B2 | 3/2007 | Cameron et al. | |

FOREIGN PATENT DOCUMENTS

| | | |
|---|---|---|
| BE | 841165 | 10/1976 |
| EP | 1097922 A1 | 5/2001 |
| EP | 1 121 939 A2 | 8/2001 |
| EP | 1 132 086 A2 | 9/2001 |
| EP | 1 232 757 A1 | 8/2002 |
| EP | 1 110 949 B1 | 9/2003 |
| GB | 1 553 595 | 10/1979 |
| GB | 1 569 982 | 6/1980 |
| GB | 1 583 163 | 1/1981 |
| GB | 2 330 307 A | 4/1999 |
| WO | 99/02164 A1 | 2/1999 |
| WO | 99/12551 A1 | 3/1999 |
| WO | 00/03980 A1 | 1/2000 |
| WO | 00/21532 A1 | 4/2000 |
| WO | 00/21542 A1 | 4/2000 |
| WO | 01/46140 A1 | 7/2001 |
| WO | 01/62724 | 8/2001 |
| WO | 02/24647 A1 | 3/2002 |
| WO | 02/42268 A2 | 5/2002 |

OTHER PUBLICATIONS

Hunt et al. "Cellular Mechanisms of Bone Resorption in Breast Carcinoma". British Journal of Cancer. 2001; 85(1):78-84.*
Zoretic, P.A. et al., Synthesis of (E)-7-[[2-[4-(m-trifluoromethylphenoxy)-3α and 3β3-Hydroxy-1-butenyl]-oxo-1-pyrrolidinyl]]heptanoic Acids, J. Heterocyclic Chem., Mar.-Apr. 1983, vol. 20, pp. 465-466.
Soda et al., "Prostaglandin E Receptor Subtypes in Mouse Osteoblastic Cell Line," Endocrinology, 1996, vol. 137, No. 5, pp. 1698-1705.
Suzawa et al., "The Role of Prostaglandin E Receptor Subtypes (EP1, EP2, EP3, and EP4) in Bone Resorption: An Analysis Using Specific Agonists for the Respective EPs," Endocrinology, 2000, vol. 141, No. 4, pp. 1554-1559.
Ono et al., Important role of $EP_4$, a subtype of prostaglandin (PG) E receptor, in osteoclast-like cell formation from mouse bone marrow cells induced by $PGE_2$, Journal of Endocrinology, 1998, vol. 158, pp. R1-R5.
Hazato et al., "Synthesis of Thiaprostaglandin $E_1$ Derivatives," Chem. Pharm, Bull., 1985, vol. 33(5), pp. 1815-1825.
Saijo et al., "Heterocyclic Prostaglandins. IV[1)] Synthesis of 8-Aza-1 $E_1$, and Its Related Compounds," Yakugaku Zasshi, 1980, vol. 100, No. 4, pp. 389-395.

(Continued)

*Primary Examiner* — Leslie A. Royds Draper
(74) *Attorney, Agent, or Firm* — Sughrue Mion, PLLC

(57) ABSTRACT

A pharmaceutical composition for topical administration for prevention and/or treatment of diseases associated with decrease in bone mass comprising an $EP_4$ agonist as an active ingredient. An $EP_4$ agonist, in which includes a compound possessing prostaglandin skeleton as a representative, possesses promoting action on bone formation, so it is useful for prevention and/or treatment of diseases associated with decrease in bone mass (bone diseases such as primary osteoporosis, secondary osteoporosis, bone metastasis of cancer, hypercalcemia, Paget's disease, bone loss and bone necrosis, postoperative osteogenesis, alternative therapy for bone grafting).

8 Claims, No Drawings

OTHER PUBLICATIONS

International Search Report, completed Oct. 10, 2002, issued in corresponding International Application No. PCT/JP02/07385, 2 pages.
Norwegian Office Action issued on Dec. 22, 2010 in the corresponding Norwegian Patent Application No. 20040331.
Decision of Rejection issued Jul. 28, 2003 in a counterpart Taiwanese Application.
Office Action issued Feb. 14, 2005 in counterpart Taiwanese Application No. 091116219.
Office Action issued Oct. 9, 2007 in counterpart Taiwanese Application No. 091116219.

* cited by examiner

PHARMACEUTICAL COMPOSITION FOR TREATMENT OF DISEASES ASSOCIATED WITH DECREASE IN BONE MASS COMPRISING EP4 AGONIST AS ACTIVE INGREDIENT

This application is a continuation of U.S. Ser. No. 10/484,500, filed Jan. 22, 2004, which is a 371 of PCT/JP02/07385, filed Jul. 22, 2002, which claims priority to JP 2001-222148, filed Jul. 23, 2001; JP 2001-239895, filed Aug. 7, 2001; and JP 2002-56449, filed Mar. 1, 2002, all of which are incorporated herein by reference in their entirety.

TECHNICAL FIELD

The present invention relates to
(1) a pharmaceutical composition for topical administration for prevention and/or treatment of diseases associated with decrease in bone mass comprising an $EP_4$ agonist as an active ingredient,
(2) a sustained release formulation comprising the agonist as an active ingredient,
(3) a prostaglandin derivative of formula (I-2)

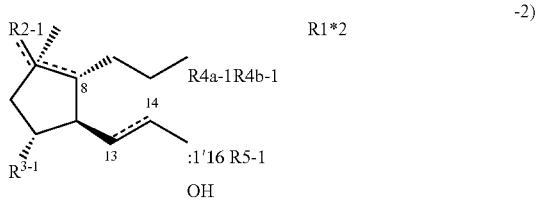

(wherein all symbols have the same meaning as defined hereinafter),
or a non-toxic salt thereof, or a cyclodextrin clathrate thereof, and a process for the preparation thereof and a pharmaceutical composition comprising thereof as an active ingredient,
(4) an 8-azaprostaglandin derivative of formula (I-3)

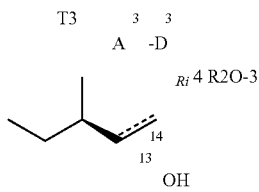

(wherein all symbols have the same meaning as defined hereinafter),
or a non-toxic salt thereof, or a cyclodextrin clathrate thereof, and a process for the preparation thereof and a pharmaceutical composition comprising thereof as an active ingredient, and
(5) a compound selected from the group consisting of
(1) (15a,13E)-9-Oxo-15-hydroxy-16-(3-chlorophenyl)-17,18,19,20-tetranor-8-azaprost-13-enoic acid,
(2) (15α,13E)-9-Oxo-15-hydroxy-16-(3-phenylphenyl)-17,18,19,20-tetranor-8-azaprost-13-enoic acid,
(3) (15α,13E)-9-Oxo-15-hydroxy-16-(3-methylphenyl)-17,18,19,20-tetranor-8-azaprost-13-enoic acid,
(4) (15α,13E)-9-Oxo-15-hydroxy-16-(3-fluorophenyl)-17,18,19,20-tetranor-8-azaprost-13-enoic acid,
(5) (15α,13E)-9-Oxo-15-hydroxy-16-(4-fluorophenyl)-17,18,19,20-tetranor-8-azaprost-13-enoic acid,
(6) (15α,13E)-9-Oxo-15-hydroxy-16-(4-methylphenyl)-17,18,19,20-tetranor-8-azaprost-13-enoic acid,
(7) (15α,13E)-9-Oxo-15-hydroxy-16-(2-methylphenyl)-17,18,19,20-tetranor-8-azaprost-13-enoic acid,
(8) (15α,13E)-9-Oxo-15-hydroxy-16-(2-fluorophenyl)-17,18,19,20-tetranor-8-azaprost-13-enoic acid,
(9) (15α,13E)-9-Oxo-15-hydroxy-16-(3-trifluoromethylphenyl)-17,18,19,20-tetranor-8-azaprost-13-enoic acid,
(10) (15α,13E)-9-Oxo-15-hydroxy-16-(3-methoxyphenyl)-17,18,19,20-tetranor-8-azaprost-13-enoic acid,
(11) (15α,13E)-9-Oxo-15-hydroxy-16-(3-ethylphenyl)-17,18,19,20-tetranor-8-azaprost-13-enoic acid,
(12) (15α,13E)-9-Oxo-15-hydroxy-16-(3,4-difluorophenyl)-17,18,19,20-tetranor-8-azaprost-13-enoic acid,
(13) (15α,13E)-9-Oxo-15-hydroxy-16-(3,5-difluorophenyl)-17,18,19,20-tetranor-8-azaprost-13-enoic acid,
(14) (15α,13E)-9-Oxo-15-hydroxy-16-(3-propylphenyl)-17,18,19,20-tetranor-8-azaprost-13-enoic acid,
(15) (15α,13E)-9-Oxo-15-hydroxy-16-(3-ethoxyphenyl)-17,18,19,20-tetranor-8-azaprost-13-enoic acid,
(16) (15α,13E)-9-Oxo-15-hydroxy-16-(3-isopropyloxyphenyl)-17,18,19,20-tetranor-8-azaprost-13-enoic acid,
(17) (15α,5Z,13E)-9-Oxo-15-hydroxy-16-(3-trifluoromethylphenyl)-17,18,19,20-tetranor-8-azaprost-5,13-dienoic acid,
(18) (15α,5Z,13E)-9-Oxo-15-hydroxy-16-(3-methylphenyl)-17,18,19,20-tetranor-8-azaprost-5,13-dienoic acid,
(19) (15α,13E)-9-Oxo-15-hydroxy-16-(3,5-dimethylphenyl)-17,18,19,20-tetranor-8-azaprost-13-enoic acid,
(20) (15α,5Z,13E)-9-Oxo-15-hydroxy-16-(3-chlorophenyl)-17,18,19,20-tetranor-8-azaprost-5,13-dienoic acid,
(21) (15α,13E)-9-Oxo-15-hydroxy-16-(3,4-difluorophenyl)-17,18,19,20-tetranor-8-azaprost-5,13-dienoic acid,
(22) (15α,5Z,13E)-9-Oxo-15-hydroxy-16-(3-fluorophenyl)-17,18,19,20-tetranor-8-azaprost-5,13-dienoic acid,
(23) (15α,5Z,13E)-9-Oxo-15-hydroxy-16-(4-fluorophenyl)-17,18,19,20-tetranor-8-azaprost-5,13-dienoic acid,
(24) (15α)-9-Oxo-15-hydroxy-16-(3-methylphenyl)-17,18,19,20-tetranor-8-azaprostanoic acid and
(25) (15α,13E)-9-Oxo-15-hydroxy-16-phenyl-17,18,19,20-tetranor-8-azaprost-13-enoic acid 3-phenylphenyl ester,
or a non-toxic salt thereof, or a cyclodextrin clathrate thereof, and a process for the preparation thereof and a pharmaceutical composition comprising thereof as an active ingredient.

BACKGROUND ART

Prostaglandin $E_2$ (abbreviated as $PGE_2$) has been known as a metabolite in the arachidonate cascade. It has been known that $PGE_2$ possesses cyto-protective activity, uterine contractive activity, a pain-inducing effect, a promoting effect on digestive peristalsis, an awakening effect, a suppressive effect on gastric acid secretion, hypotensive activity and diuretic activity and so on.

A recent study has proved existence of various PGE subtype receptors possessing a different physical role from each other. At present, four receptor subtypes are known and they are called $EP_1$, $EP_2$, $EP_3$, and $EP_4$ (Negishi M., et al., *J. Lipid Mediators Cell Signaling*, 12, 379-391 (1995)).

It is thought that $EP_4$ subtype receptor relates to inhibition of producing TNF-α and acceleration of producing IL-10. Therefore, the compounds which can bind on $EP_4$ subtype receptor are expected to be useful for the prevention and/or treatment of immunological diseases (autoimmune diseases such as amyotrophic lateral sclerosis (ALS), multiple sclerosis, Sjogren's syndrome, chronic rheumarthrosis and systemic lupus erythematosus etc., and rejection after organ transplantation etc.), asthma, neuronal cell death, arthritis, lung failure, pulmonary fibrosis, pulmonary emphysema, bronchitis, chronic obstructive pulmonary disease, liver damage, acute hepatitis, nephritis (acute nephritis, chronic nephritis), renal insufficiency, hypertension, myocardiac ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc.

It is also thought that $EP_4$ subtype receptor relates to protecting of mucosa. Therefore, the compounds which can bind on $EP_4$ subtype receptor are expected to be useful for the prevention and/or treatment of ulcer of gastrointestinal tract such as gastric ulcer and duodenal ulcer etc. and stomatitis. It is also thought that $EP_4$ subtype receptor relates to hair growth function. Therefore, the compounds which can bind on $EP_4$ subtype receptor are expected to be useful for the prevention and/or treatment of hair-disadvantaged and alopecia. Furthermore, it is also thought that $EP_4$ subtype receptor relates to maturation of cervix. Therefore, the compounds which can bind on $EP_4$ subtype receptor are expected to be useful for the promoter of maturation of cervix.

Furthermore, the compounds which can bind on $EP_4$ subtype receptor also have an action of accelerating bone formation, so it is expected to be useful for the prevention and/or treatment of diseases associated with decrease in bone mass, for example,
1) primary osteoporosis (e.g., primary osteoporosis followed by aging, postmenopausal primary osteoporosis, primary osteoporosis followed by ovariectomy etc.),
2) secondary osteoporosis (e.g., glucocorticoid-induced osteoporosis, hyperthyroidism-induced osteoporosis, immobilization-induced osteoporosis, heparin-induced osteoporosis, immunosuppressive-induced osteoporosis, osteoporosis due to renal failure, inflammatory osteoporosis, osteoporosis followed by Cushing's syndrome, rheumatoid osteoporosis etc.),
3) bone diseases such as bone metastasis of cancer, hypercalcemia, Paget's disease, bone loss (alveolar bone loss, mandibular bone loss, childhood idiopathic bone loss etc.), osteonecrosis etc.

Besides treatment of the above diseases, the present invention also includes a pharmaceutical composition for accelerating bone formation after bone operation (e.g., bone formation after fractures, bone formation after bone grafting, bone formation after operation of artificial joint, bone formation after spinal fusion and bone formation after the other operation for bone regeneration etc.), or promoting treatment thereof, or alternative treatment for bone grafting.

It is also thought that $EP_4$ subtype receptor relates to induction of physiological sleeping and suppression of blood platelet aggregation, so such compounds are expected to be useful for the prevention and/or treatment of sleep disorder and thrombosis The compound which can bind an $EP_4$ receptor selectively do not have inducing pain which may be caused by EPI, uterine relaxation which may be caused by $EP_2$ and uterine contraction which may be caused by $EP_3$, so they are thought to be agents having no effect on the above actions.

In the specification of U.S. Pat. No. 4,177,346, it is disclosed that the compound of formula (A)

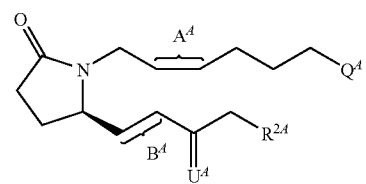

(A)

(wherein $Q^A$ is selected from the group consisting of —$COOR^{3A}$, tetrazol-5-yl and —$CONHR^{4A}$.
$A^A$ is single bond or cis-double bond;
$B^A$ is single bond or trans-double bond;
$U^A$ is

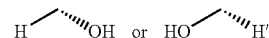

$R^{2A}$ is selected from the group consisting of α-thienyl, phenyl, phenoxy, mono-substituted phenyl and mono-substituted phenoxy, and the substituent is selected from the group consisting of chloro, fluoro, phenyl, methoxy, trifluoromethyl and C1-3 alkyl;
$R^{3A}$ is selected from the group consisting of hydrogen, C1-5 alkyl, phenyl and p-biphenyl;
$R^{4A}$ is selected from the group consisting of —$COR^{5A}$ and —$SO_2R^{5A}$;
$R^{5A}$ is selected from the group consisting of phenyl and C1-5 alkyl),
and a C5 epimer thereof, the salt of alkali metal and alkaline earth metals and ammonium salt of the compound which have carboxylate or tetrazol-5-yl.

And in the specification of JP-A-2001-181210, it is disclosed that the selective $EP_4$ receptor agonist of formula (A) is useful for the treatment of osteoporosis.

And in the specification of United Kingdom Patent No. 1,553,595, the pyrrolidone derivatives of formula (B)

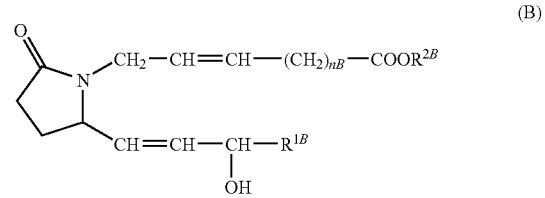

(B)

(wherein $R^{1B}$ is a straight- or branched-chain, saturated or unsaturated, aliphatic hydrocarbon radical having up to 10 carbon atoms, or a cycloaliphatic hydrocarbon radical having 3 to 7 carbon atoms, which radicals may be unsubstituted or substituted by one or more of the following:
e) a cycloalkyl group of 3 to 7 carbon atoms,
f) a phenyl, thienyl or furyl group which may carry one or two substituents selected from optionally halogenated alkyl group of 1 to 3 carbon atoms, halogen atoms and alkoxy group of 1 to 4 carbon atoms,
$R^{2B}$ is a straight- or branched-chain, saturated or unsaturated, aliphatic or cycloaliphatic hydrocarbon radical having up to 6 carbon atoms, or an araliphatic hydrocarbon radical having 7 or 8 carbon atoms, and
nB is the integer 2, 3 or 4, the definitions of the symbols are excerpt), and a corresponding acid, a salt, especially the physiologically acceptable e.g. metal or amine, a salt thereof is disclosed.

In the specifications of United Kingdom Patent No. 1,569, 982, and United Kingdom Patent No. 1,583,163, the compound close to the compound of formula (B) is disclosed.

In the specification of U.S. Pat. No. 4,320,136, the compound of formula (C)

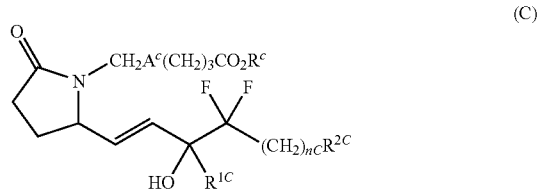

(C)

(wherein $A^C$ is CH=CH (cis or trans), C≡C or $CH_2CH_2$; $R^C$ is H, C1-C12 n-alkyl, branched alkyl or cycloalkyl etc.; $R^{1C}$ is H, $CH_3$ or $C_2H_5$;
$R^{2C}$ is phenyl or mono- or di-substituted phenyl, the substituent is selected from is selected from the group consisting of, F, Cl, $CH_3$, $OCH_3$, $NO_2$ or $CF_3$;
when $R^{2C}$ is phenyl or substituted phenyl, nC is 0-2, the definitions of the symbols are excerpt) is disclosed.

In the specification of WO00/03980, it is disclosed that the compound of formula (I-1) is useful as $EP_4$ receptor binding agent.

In the specification of WO01/37877, it is disclosed that the $EP_4$ receptor agonist of formula (I-1) is useful for treatment of diseases associated with decrease in bone mass.

It is disclosed that the $EP_4$ receptor agonist of formulae (A) and (I-1) is useful for treatment of diseases associated with bone, there is a general description about topical administration. Therefore it is unproved that topical administration of the $EP_4$ receptor agonist is useful for treatment of diseases associated with bone experimentally.

Four $PGE_2$ subtype receptors possessing a different physical role from each other exist, and each subtype is called $EP_1$, $EP_2$, $EP_3$, and $EP_4$ and has a different pharmacological action. So the compounds which can bind on $EP_4$ subtype receptor selectively and binds on the other subtype receptors weakly may be the drug with less side effect, because they show no any other activities. Therefore it is in need of finding the drug like this.

On the other hand, a lot of compounds which have the $EP_4$ agonistic activity are found until now. However, all of them have a prostanoid skeleton, so it is thought that they influence circulatory system (e.g. blood pressure lowered or increasing of the heart rate), or cause side-effect such as diarrhea when they are administered by systemic administration such as oral administration or intravenous infusion. Therefore, they have significant problem that there is a limitation of the dose that can be administered safely.

As a disease associated with $EP_4$ agonist, a lot of studies of diseases associated with decrease in bone mass have been done. It is also thought that systemic administration causes side-effects, so development of the drug with less side effects is expected. Finding a long-acting pharmaceutical which can be administrated topically is also expected.

DISCLOSURE OF THE INVENTION

The present inventors have studied to find out the compounds which can bind on $EP_4$ subtype receptor specifically, and which have strong agonistic activity. Finally, the compounds of formulae (I-2) and (I-3) were found out to meet this purpose, and this invention was accomplished.

The present inventors found out the compound which binds on both $EP_4$ and $EP_2$ subtype receptor. The compound which binds on both $EP_4$ and $EP_2$ subtype receptor is expected additive or multiplier effect when treatment of the disease associated with both subtype receptor.

The present inventors also thought that we can create the therapeutic agent (treatment of diseases associated with decrease in bone mass, particularly) with no side-effect in systemic administration if $EP_4$ agonist can be administered topically. We also conceived that we can create the therapeutic agent (treatment of diseases associated with decrease in bone mass, particularly) with no side-effect in systemic administration and with less frequency of administration if we can find the $EP_4$ agonist which can be a sustained release formulation and which can be administered topically.

Therefore the present inventors made further investigation to solve the former purpose to find that the purpose of the present invention can be accomplished by using a sustained release formulation of the compound of formulae (I-1), (I-2) and (I-3), and completed the present invention.

The compounds of formulae (I-2) and (I-3) is completely novel.

The present invention relates to
i) a pharmaceutical composition for topical administration for prevention and/or treatment of diseases associated with decrease in bone mass comprising an $EP_4$ agonist as an active ingredient,
ii) a sustained release formulation comprising an $EP_4$ agonist as an active ingredient,
iii) a pharmaceutical composition for topical administration for prevention and/or treatment of diseases associated with decrease in bone mass comprising a sustained release formulation comprising an $EP_4$ agonist as an active ingredient,
iv) a pharmaceutical composition for prevention and/or treatment of diseases associated with decrease in bone mass, characterized by topical administration of the formulation comprising a compound selected from the group of formula (I-1)

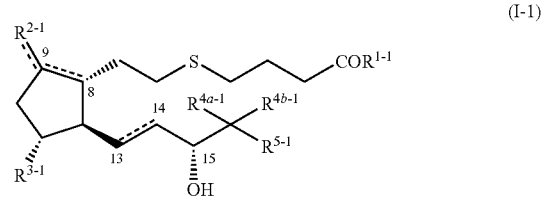

(I-1)

wherein $R^{1-1}$ is hydroxy, C1-6 alkyloxy, or $NR^{6-1}R^{7-1}$, wherein $R^{6-1}$ and $R^{7-1}$ are each independently, hydrogen atom or C1-4 alkyl,
$R^{2-1}$ is oxo, halogen, or O—$COR^{8-1}$, wherein $R^{8-1}$ is C1-4 alkyl, phenyl or phenyl(C1-4 alkyl),
$R^{3-1}$ is hydrogen atom or hydroxy,
$R^{4a-1}$ and $R^{4b-1}$ are each independently, hydrogen atom or C1-4 alkyl,
$R^{5-1}$ is phenyl substituted by the group listed below:
(i) 1 to 3 of
C1-4 alkyloxy-C1-4 alkyl,
C2-4 alkenyloxy-C1-4 alkyl,
C2-4 alkynyloxy-C1-4 alkyl,
C3-7 cycloalkyloxy-C1-4 alkyl,
C3-7 cycloalkyl(C1-4 alkyloxy)-C1-4 alkyl,
phenyloxy-C1-4 alkyl,
phenyl-C14 alkyloxy-C1-4 alkyl, C1-4 alkylthio-C1-4 alkyl,
C2-4 alkenylthio-C1-4 alkyl,
C2-4 alkynylthio-C1-4 alkyl,
C3-7 cycloalkylthio-C1-4 alkyl,
C3-7 cycloalkyl(C1-4 alkylthio)-C1-4 alkyl or
phenylthio-C1-4 alkyl or phenyl-C1-4 alkylthio-C1-4 alkyl,
(ii) C1-4 alkyloxy-C1-4 alkyl and C1-4 alkyl,
C1-4 alkyloxy-C1-4 alkyl and C1-4 alkyloxy,
C1-4 alkyloxy-C1-4 alkyl and hydroxy,
C1-4 alkyloxy-C1-4 alkyl and halogen,
C1-4 alkylthio-C1-4 alkyl and C1-4 alkyl,
C1-4 alkylthio-C1-4 alkyl and C1-4 alkyloxy,
C1-4 alkylthio-C1-4 alkyl and hydroxy or
C1-4 alkylthio-C1-4 alkyl and halogen,
(iii) haloalkyl or hydroxy-C1-4 alkyl, or
(iv) C1-4 alkyl and hydroxy;
⎓ is single bond or double bond,
wherein when $R^{2-1}$ is O—$COR^{8-1}$, C8-9 position is double bond,
or a non-toxic salt thereof, or a cyclodextrin clathrate thereof as an active ingredient,
v) the sustained release formulation comprising a compound selected from the group of formula (I-1), or a non-toxic salt thereof, or a cyclodextrin clathrate thereof as an active ingredient,
vi) a pharmaceutical composition for prevention and/or treatment of diseases associated with decrease in bone mass, characterized by topical administration of the formulation comprising a compound selected from the group of formula (I-2)

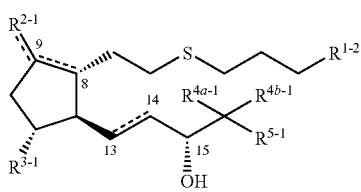

(I-2)

wherein $R^{1-2}$ is
(1) —CO—(NH-amino acid residue-CO)$_{m-2}$—OH,
(2) —COO—$Y^2$—$R^{9-2}$,
(3) —COO—$Z^{1-2}$—$Z^{2-2}$—$Z^{3-2}$,
wherein $Y^2$ is bond or C1-10 alkylene,
$R^{9-2}$ is (1) phenyl or (2) biphenyl optionally substituted by 1-3 C1-10 alkyl, C1-10 alkoxy or halogen atom,
$Z^{1-2}$ is
(1) C1-15 alkylene,
(2) C2-15 alkenylene or
(3) C2-15 alkynylene,
$Z^{2-2}$ is
(1) —CO—,
(2) —OCO—,
(3) —COO—,
(4) —$CONR^{11-2}$—,
(5) —$NR^{12-2}CO$—,
(6) —O—,
(7) —S—,
(8) —SO—,
(9) —$SO_2$—,
(10) —$NR^{13-2}$—,
(11) —$NR^{14-2}CONR^{15-2}$,
(12) —$NR^{16-2}COO$—,
(13) —$OCONR^{17-2}$— or
(14) —OCOO—,
$Z^{3-2}$ is
(1) hydrogen atom,
(2) C1-15 alkyl,
(3) C2-15 alkenyl,
(4) C2-15 alkynyl,
(5) ring1$^2$ or
(6) C1-10 alkyl substituted by C1-10 alkoxy, C1-10 alkylthio, C1-10 alkyl-$NR^{18-2}$— or ring1$^2$,
ring1$^2$ is
(1) C3-15 mono-, bi- or tri-carbocyclic aryl which may be partially or fully saturated or
(2) 3 to 15 membered mono-, bi- or tri-heterocyclic aryl containing 1 to 4 hetero atom selected from oxygen, nitrogen and sulfur atom(s) which may be partially or fully saturated,
$R^{11-2}$, $R^{12-2}$, $R^{13-2}$, $R^{14-2}$, $R^{15-2}$, $R^{16-2}$, $R^{17-2}$ and $R^{18-2}$ are each independently, hydrogen atom or C1-15 alkyl,
$R^{11-2}$ and $Z^{3-2}$ may be taken together with the nitrogen atom to which they are attached to form 5 to 7 membered saturated monoheterocyclic ring, and the heterocyclic ring may contain another one hetero atom selected from oxygen, nitrogen and sulfur atom,
ring1$^2$ and saturated monoheterocyclic ring formed by $R^{11-2}$, $Z^{3-2}$ and the nitrogen atom to which $Z^{3-2}$ is attached may be substituted by 1-3 group(s) selected from
(1) C1-15 alkyl,
(2) C2-15 alkenyl,
(3) C2-15 alkynyl and
(4) C1-10 alkyl substituted with C1-10 alkoxy, C1-10 alkylthio or C1-10 alkyl-$NR^{19-2}$,
$R^{19-2}$ is hydrogen atom or C1-10 alkyl,
m-2 is 1 or 2,
other symbols are same meaning as defined hereinbefore,
or a non-toxic salt thereof, or a cyclodextrin clathrate thereof as an active ingredient,
vii) the sustained release formulation comprising a compound selected from the group of formula (I-2), or a non-toxic salt thereof, or a cyclodextrin clathrate thereof as an active ingredient,
viii) a pharmaceutical composition for prevention and/or treatment of diseases associated with decrease in bone mass, characterized by topical administration of the formulation comprising a compound selected from the group of formula (I-3)

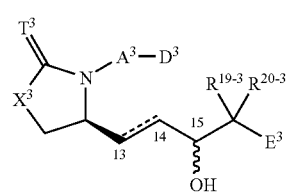

(I-3)

wherein ⁓ is (1) single bond or (2) double bond,
$R^{19-3}$ and $R^{20-3}$ are each independently, (1) hydrogen atom, (2) C1-10 alkyl or (3) halogen atom,
$T^3$ is (1) oxygen atom or (2) sulfur atom,
$X^3$ is (1) —$CH_2$—, (2) —O— or (3) —S—,
$A^3$ is $A^{1-3}$ or $A^{2-3}$,
$A^{1-3}$ is
(1) C2-8 straight-chain alkylene optionally substituted by 1-2 C1-4 alkyl,
(2) C2-8 straight-chain alkenylene optionally substituted by 1-2 C1-4 alkyl or (3) C2-8 straight-chain alkynylene optionally substituted by 1-2 C1-4 alkyl, $A^{2-3}$ is -$G^{1-3}$-$G^{2-3}$-$G^{3-3}$-, $G^{1-3}$ is
(1) C1-4 straight-chain alkylene optionally substituted by 1-2 C1-4 alkyl,
(2) C2-4 straight-chain alkenylene optionally substituted by 1-2 C1-4 alkyl or
(3) C2-4 straight-chain alkynylene optionally substituted by 1-2 C1-4 alkyl, $G^{2-3}$ is
(1) —$Y^3$—,
(2) -(ring$1^3$)-,
(3) —$Y^3$-(ring$1^3$)-,
(4) -(ring$1^3$)—$Y^3$— or
(5) —$Y^3$—(C1-4 alkylene)-(ring$1^3$)-, $Y^3$ is (1) —S—, (2) —SO—, (3) —SO$_2$—, (4) —O— or (5) —NR$^{1-3}$—, $R^{1-3}$ is (1) hydrogen atom, (2) C1-10 alkyl or (3) C2-10 acyl, $G^{3-3}$ is
(1) bond,
(2) C1-4 straight-chain alkylene optionally substituted by 1-2 C1-4 alkyl,
(3) C2-4 straight-chain alkenylene optionally substituted by 1-2 C1-4 alkyl or
(4) C2-4 straight-chain alkynylene optionally substituted by 1-2 C1-4 alkyl, $D^3$ is $D^{1-3}$ or $D^{2-3}$, $D^{1-3}$ is
(1) —COOH,
(2) —COOR$^{2-3}$,
(3) tetrazol-5-yl or
(4) CONR$^{3-3}$SO$_2$R$^{4-3}$, $R^{2-3}$ is (1) C1-10 alkyl, (2) phenyl, (3) C1-10 alkyl substituted by phenyl or (4) biphenyl, $R^{3-3}$ is (1) hydrogen atom or (2) C1-10 alkyl, $R^{4-3}$ is (1) C1-10 alkyl or (2) phenyl, $D^{2-3}$ is
(1) —CH$_2$OH,
(2) —CH$_2$OR$^{5-3}$,
(3) hydroxy,
(4) —OR$^{5-3}$,
(5) formyl,
(6) —CONR$^{6-3}$R$^{7-3}$,
(7) —CONR$^{6-3}$SO$_2$R$^{8-3}$,
(8) —CO—(NH-amino acid residue-CO)$_{m-3}$—OH,
(9) —O—(CO-amino acid residue —NH)$_{m-3}$—H,
(10) —COOR$^{9-3}$,
(11) —OCO—R$^{10-3}$,
(12) COO—Z$^{1-3}$—Z$^{2-3}$—Z$^{3-3}$,
(13)

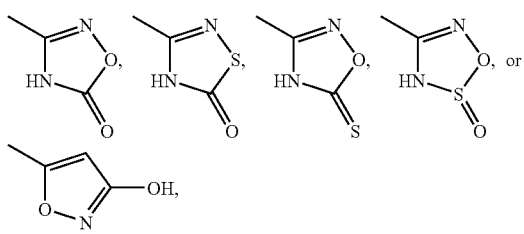

$R^{5-3}$ is C1-10 alkyl,
$R^{6-3}$ and $R^{7-3}$ are each independently, (1) hydrogen atom or (2) C1-10 alkyl, $R^{8-3}$ is C1-10 alkyl substituted by phenyl, $R^{9-3}$ is (1) C1-10 alkyl substituted by biphenyl optionally substituted by 1-3 C1-10 alkyl, C1-10 alkoxy or halogen atom or (2) biphenyl substituted by 1-3 C1-10 alkyl, C1-10 alkoxy or halogen atom, $R^{10-3}$ is (1) phenyl or (2) C1-10 alkyl, m-3 is 1 or 2, $Z^{1-3}$ is (1) C1-15 alkylene, (2) C2-15 alkenylene or (3) C2-15 alkynylene, $Z^{2-3}$ is (1) —CO—, (2) —OCO—, (3) —COO—, (4) —CONR$^{11-3}$—, (5) —NR$^{12-3}$CO—, (6) —O—, (7) —S—, (8) —SO—, (9) —SO$_2$—, (10) —NR$^{13-3}$—, (11) —NR$^{14-3}$CONR$^{15-3}$—, (12) —NR$^{16-3}$COO—, (13) —OCONR$^{17-3}$— or (14) —OCOO—, $Z^{3-3}$ is (1) hydrogen atom, (2) C1-15 alkyl, (3) C2-15 alkenyl, (4) C2-15 alkynyl, (5) ring$2^3$ or (6) C1-10 alkyl substituted by C1-10 alkoxy, C1-10 alkylthio, C1-10 alkyl-NR$^{18-3}$- or ring$2^3$, $R^{11-3}$, $R^{12-3}$, $R^{13-3}$, $R^{14-3}$, $R^{15-3}$, $R^{16-3}$, $R^{17-3}$ and $R^{18-3}$ are each independently, (1) hydrogen atom or (2) C1-15 alkyl, $R^{11-3}$ and $Z^{3-3}$ may be taken together with the nitrogen atom to which they are attached to form 5 to 7 membered saturated monoheterocyclic ring, and the heterocyclic ring may contain other one hetero atom selected from oxygen, nitrogen and sulfur atom, $E^3$ is $E^{1-3}$ or $E^{2-3}$, $E^{1-3}$ is
(1) C3-7 cycloalkyl or
(2) ring$3^3$, $E^{2-3}$ is
(1) C3-7 cycloalkyl,
(2) ring$4^3$ or
(3) ring$5^3$, ring$1^3$ and ring$5^3$ are optionally substituted by 1-3 R$^{21-3}$ and/or R$^{22-3}$, ring$3^3$ is optionally substituted by 1-2 R$^{21-3}$, C3-7 cycloalkyl represented by $E^{2-3}$ is substituted by one of R$^{21-3}$ or R$^{22-3}$, and optionally substituted by another 1-2 R$^{21-3}$ and/or R$^{22-3}$, ring$4^3$ is substituted by one of R$^{22-3}$, optionally substituted by another 1-2 R$^{21-3}$ and/or R$^{22-3}$, and optionally substituted by heterocyclic ring formed by R$^{11-3}$, Z$^{3-3}$ and the nitrogen to which Z$^{3-3}$ is attached or ring$2^3$ may be substituted by R$^{23-3}$, $R^{21-3}$ is (1) C1-10 alkyl, (2) C1-10 alkoxy, (3) halogen atom, (4) nitro, (5) C1-10 alkyl substituted by 1-3 halogen atom(s) or (6) phenyl, $R^{22-3}$ is (1) C2-10 alkenyl, (2) C2-10 alkynyl, (3) C1-10 alkylthio, (4) hydroxy, (5) —NR$^{24-3}$R$^{25-3}$, (6) C1-10 alkyl substituted by C1-10 alkoxy, (7) C1-10 alkyl substituted by C1-10 alkoxy substituted by 1-3 halogen atom(s), (8) C1-10 alkyl substituted by —NR$^{24-3}$R$^{25-3}$, (9) ring$6^3$, (10) —O-ring$7^3$, (11) C1-10 alkyl substituted by ring$7^3$, (12) C2-10 alkenyl substituted by ring$7^3$, (13) C2-10 alkynyl substituted by ring$7^3$, (14) C1-10 alkoxy substituted by ring$7^3$, (15) C1-10 alkyl substituted by —O-ring$7^3$, (16)-COOR$^{26-3}$ or (17) C1-10 alkoxy substituted by 1-3 halogen atom(s)(s), $R^{24-3}$, $R^{25-3}$ and $R^{26-3}$ are each independently, (1) hydrogen atom or (2) C1-10 alkyl, $R^{23-3}$ is (1) C1-15 alkyl, (2) C2-15 alkenyl, (3) C2-15 alkynyl or (4) C1-10 alkyl substituted by C1-10 alkoxy, C1-10 alkylthio or C1-10 alkyl-NR$^{27-3}$—, $R^{27-3}$ is (1) hydrogen atom or (2) C1-10 alkyl, ring$1^3$, ring$2^3$, ring$5^3$, ring$6^3$ and ring$7^3$ are
(1) C3-15 mono-, bi- or tri-carbocyclic aryl which may be partially or fully saturated or (2) 3 to 15 membered mono-, bi- or tri-heterocyclic aryl containing 1 to 4 hetero atom selected from oxygen, nitrogen and sulfur atom(s) which may be partially or fully saturated, ring3$^3$ and ring4$^3$ are (1) thienyl, (2) phenyl or (3) furyl,
ring6$^3$ and ring7$^3$ may be substituted by 1-3 R$^{28-3}$,
R$^{28-3}$ is (l) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1-3 halogen atom(s) or (9) C1-10 alkyl substituted by C1-10 alkoxy substituted by 1-3 halogen atom(s), and wherein (1) when T$^3$ is oxygen atom, X$^3$ is CH$_2$—, A$^3$ is A$^{1-3}$, and D$^3$ is D$^{1-3}$, E$^3$ is E$^{2-3}$,
(2) ring5$^3$ is not C3-7 cycloalkyl, phenyl, thienyl nor furyl,
(3) ring6$^3$ is phenyl, then phenyl have at least one R$^{28-3}$, or a non-toxic salt thereof, or a cyclodextrin clathrate thereof as an active ingredient, ix) the sustained release formulation comprising a compound selected from the group of formula (I-3), or a non-toxic salt thereof, or a cyclodextrin clathrate thereof as an active ingredient, x) a prostaglandin derivative of formula (I-2)

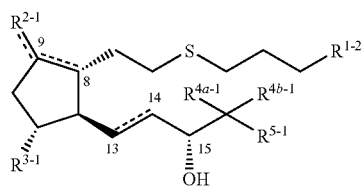

(I-2)

wherein all symbols have the same meaning as defined in yl), or a non-toxic salt thereof, or a cyclodextrin clathrate thereof, xi) a process for the preparation of a prostaglandin derivative of formula (I-2), or a non-toxic salt thereof, or a cyclodextrin clathrate thereof, xii) a pharmaceutical composition comprising of a prostaglandin derivative of formula (I-2), or a non-toxic salt thereof, or a cyclodextrin clathrate thereof as an active ingredient, xiii) a compound selected from the group of formula (I-3)

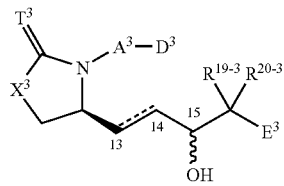

(I-3)

wherein all symbols have the same meaning as defined in viii), or a non-toxic salt thereof, or a cyclodextrin clathrate thereof xiv) a process for the preparation of an 8-azaprostaglandin derivative of formula (I-3), or a non-toxic salt thereof, or a cyclodextrin clathrate thereof, xv) a pharmaceutical composition comprising of an 8-azaprostaglandin derivative of formula (I-3), or a non-toxic salt thereof, or a cyclodextrin clathrate thereof as an active ingredient, xvi) a pharmaceutical composition for prevention and/or treatment of diseases associated with decrease in bone mass, characterized by topical administration of the formulation comprising a compound selected from the group consisting of (1) (15α,13E)-9-oxo-15-hydroxy-16-(3-chlorophenyl)-17,18,19,20-tetranor-8-azaprost-13-enoic acid,
(2) (15α,13E)-9-oxo-15-hydroxy-16-(3-phenylphenyl)-17,18,19,20-tetranor-8-azaprost-13-enoic acid,
(3) (15α,13E)-9-oxo-15-hydroxy-16-(3-methylphenyl)-17,18,19,20-tetranor-8-azaprost-13-enoic acid,
(4) (15α,13E)-9-oxo-15-hydroxy-16-(3-fluorophenyl)-17,18,19,20-tetranor-8-azaprost-13-enoic acid,
(5) (15α,13E)-9-oxo-15-hydroxy-16-(4-fluorophenyl)-17,18,19,20-tetranor-8-azaprost-13-enoic acid,
(6) (15α,13E)-9-oxo-15-hydroxy-16-(4-methylphenyl)-17,18,19,20-tetranor-8-azaprost-13-enoic acid,
(7) (15α,13E)-9-oxo-15-hydroxy-16-(2-methylphenyl)-17,18,19,20-tetranor-8-azaprost-13-enoic acid,
(8) (15α,13E)-9-oxo-15-hydroxy-16-(2-fluorophenyl)-17,18,19,20-tetranor-8-azaprost-13-enoic acid,
(9) (15α,13E)-9-oxo-15-hydroxy-16-(3-trifluoromethylphenyl)-17,18,19,20-tetranor-8-azaprost-13-enoic acid,
(10) (15α,13E)-9-oxo-15-hydroxy-16-(3-methoxyphenyl)-17,18,19,20-tetranor-8-azaprost-13-enoic acid,
(11) (15α,13E)-9-oxo-15-hydroxy-16-(3-ethylphenyl)-17,18,19,20-tetranor-8-azaprost-13-enoic acid,
(12) (15α,13E)-9-oxo-15-hydroxy-16-(3,4-difluorophenyl)-17,18,19,20-tetranor-8-azaprost-13-enoic acid,
(13) (15α,13E)-9-oxo-15-hydroxy-16-(3,5-difluorophenyl)-17,18,19,20-tetranor-8-azaprost-13-enoic acid,
(14) (15α,13E)-9-oxo-15-hydroxy-16-(3-propylphenyl)-17,18,19,20-tetranor-8-azaprost-13-enoic acid,
(15) (15α,13E)-9-oxo-15-hydroxy-16-(3-ethoxyphenyl)-17,18,19,20-tetranor-8-azaprost-13-enoic acid,
(16) (15α,13E)-9-oxo-15-hydroxy-16-(3-isopropyloxyphenyl)-17,18,19,20-tetranor-8-azaprost-13-enoic acid,
(17) (15α,5Z,13E)-9-oxo-15-hydroxy-16-(3-trifluoromethylphenyl)-17,18,19,20-tetranor-8-azaprost-5,13-dienoic acid,
(18) (15α,5Z,13E)-9-oxo-15-hydroxy-16-(3-methylphenyl)-17,18,19,20-tetranor-8-azaprost-5,13-dienoic acid,
(19) (15α,13E)-9-oxo-15-hydroxy-16-(3,5-dimethylphenyl)-17,18,19,20-tetranor-8-azaprost-13-enoic acid,
(20) (15α,5Z,13E)-9-oxo-15-hydroxy-16-(3-chlorophenyl)-17,18,19,20-tetranor-8-azaprost-5,13-dienoic acid,
(21) (15α,13E)-9-oxo-15-hydroxy-16-(3,4-difluorophenyl)-17,18,19,20-tetranor-8-azaprost-5,13-dienoic acid,
(22) (15α,5Z,13E)-9-oxo-15-hydroxy-16-(3-fluorophenyl)-17,18,19,20-tetranor-8-azaprost-5,13-dienoic acid,
(23) (15α,5Z,13E)-9-oxo-15-hydroxy-16-(4-fluorophenyl)-17,18,19,20-tetranor-8-azaprost-5,13-dienoic acid,
(24) (15α)-9-oxo-15-hydroxy-16-(3-methylphenyl)-17,18,19,20-tetranor-8-azaprostanoic acid, and
(25) (15α,13E)-9-oxo-15-hydroxy-16-phenyl-17,18,19,20-tetranor-8-azaprost-13-enoic acid 3-phenylphenyl ester, or a non-toxic salt thereof, or a cyclodextrin clathrate thereof as an active ingredient, or the sustained release formulation comprising a compound selected from the former group, or a non-toxic salt thereof, or a cyclodextrin clathrate thereof as an active ingredient, or a compound selected from the former group, or a non-toxic salt thereof, or a cyclodextrin clathrate thereof, and a process for the preparation thereof and a pharmaceutical composition comprising thereof as an active ingredient.

In the present invention, C1-4 alkyl means methyl, ethyl, propyl, butyl and the isomers thereof.

In the present invention, C1-10 alkyl means methyl, ethyl, propyl, butyl, pentyl, hexyl, heptyl, octyl, nonyl, decyl and the isomers thereof.

In the present invention, C1-15 alkyl means methyl, ethyl, propyl, butyl, pentyl, hexyl, heptyl, octyl, nonyl, decyl, undecyl, dodecyl, tridecyl, tetradecyl, pentadecyl and the isomers thereof.

In the present invention, C2-10 alkenyl means ethenyl, propenyl, butenyl, pentenyl, hexenyl, heptenyl, octenyl, nonenyl, decenyl and the isomers thereof.

In the present invention, C2-15 alkenyl means ethenyl, propenyl, butenyl, pentenyl, hexenyl, heptenyl, octenyl, nonenyl, decenyl, undecenyl, dodecenyl, tetradecenyl, pentadecenyl and the isomers thereof.

In the present invention, C2-10 alkynyl means ethynyl, propynyl, butynyl, pentynyl, hexynyl, heptynyl, octynyl, nonynyl, decynyl and the isomers thereof.

In the present invention, C2-15 alkynyl means ethynyl, propynyl, butynyl, pentynyl, hexynyl, heptynyl, octynyl, nonynyl, decynyl, undecynyl, dodecynyl, tridecynyl, tetradecynyl, pentadecynyl and the isomers thereof.

In the present invention, straight-chain C1-4 alkylene means methylene, ethylene, trimethylene and tetramethylene.

In the present invention, straight-chain C2-8 alkylene means methylene, ethylene, trimethylene, tetramethylene, pentamethylene, hexamethylene, heptamethylene and octamethylene.

In the present invention, C1-4 alkylene means methylene, ethylene, trimethylene, tetramethylene and the isomers thereof.

In the present invention, C1-10 alkylene means methylene, ethylene, trimethylene, tetramethylene, pentamethylene, hexamethylene, heptamethylene, octamethylene, nonamethylene, decamethylene and the isomers thereof.

In the present invention, C1-15 alkylene means methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene and the isomers thereof.

In the present invention, straight-chain C2-4 alkenylene means ethenylene, propenylene, butenylene and the isomers thereof.

In the present invention, straight-chain C2-8 alkenylene means C2-8 alkenylene which has 1 to 2 double bond(s). It means ethenylene, propenylene, butenylene, pentenylene, hexenylene, heptenylene, octenylene, pentadienylene, hexadienylene, heptadienylene and octadienylene.

In the present invention, C2-15 alkenylene means ethenylene, propenylene, butenylene, pentenylene, hexenylene, heptenylene, octenylene, nonenylene, decenylene, undecenylene, dodecenylene, tridecenylene, tetradecenylene, pentadecenylene and the isomers thereof.

In the present invention, straight-chain C2-4 alkynylene means ethynylene, propynylene, butynylene.

In the present invention, straight-chain C2-8 alkynylene means C2-8 alkynylene which has 1 to 2 triple bond(s). It means ethynylene, propynylene, butynylene, butadiynylene, pentynylene, pentadiynylene, hexynylene, hexadiynylene, heptynylene, heptadiynylene, octynylene, octadiynylene.

In the present invention, C2-15 alkynylene means ethynylene, propynylene, butynylene, pentynylene, hexynylene, heptynylene, octynylene, nonynylene, decynylene, undecynylene, dodecynylene, tridecynylene, tetradecynylene, pentadecynylene and the isomers thereof.

In the present invention, C1-10 alkoxy means methoxy, ethoxy, propoxy, butoxy, pentyloxy, hexyloxy, heptyloxy, octyloxy, nonyloxy, decyloxy and the isomers thereof.

In the present invention, C1-10 alkylthio means methylthio, ethylthio, propylthio, butylthio, pentylthio, hexylthio, heptylthio, octylthio, nonylthio, decylthio and the isomers thereof.

In the present invention, halogen atom means chloride, bromide, fluoride and iodide atom.

In the present invention, biphenyl means 2-phenylphenyl, 3-phenylphenyl or 4-phenylphenyl.

In the present invention, C2-10 acyl means ethanoyl, propanoyl, butanoyl, pentanoyl, hexanoyl, heptanoyl, octanoyl, nonanoyl, decanoyl and the isomers thereof.

In the present invention, phenylene means benzene ring which has two connectable bonds, i.e.,

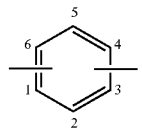

Any position can be substituted, and 1,4- or 1,3-disubstituted one is preferable.

In the present invention, thienylene means thiophene ring which has two connectable bonds, i.e.,

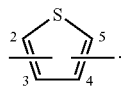

Any position can be substituted, and 2,5-disubstituted one is preferable.

In the present invention, furylene means furan ring which has two connectable bonds, i.e.,

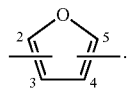

Any position can be substituted, and 2,5-disubstituted one is preferable.

In the present invention, thiazolylene means thiazole ring which has two connectable bonds, i.e.,

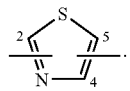

Any position can be substituted, and 2,5-disubstituted one is preferable.

In the present invention, oxazolylene means oxazole ring which has two connectable bonds, i.e.,

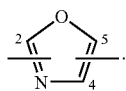

Any position can be substituted, and 2,5-disubstituted one is preferable.

In the present invention, C3-5cycloalkylene means cyclopropyl, cyclobutyl or cyclopenthyl which have two connectable bonds, i.e.,

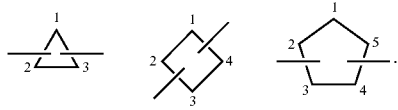

Any position can be substituted, and 1,1-disubstituted one is preferable.

In the present invention, amino acid residue means the amino acid residue of natural amino acid or abnormal amino acid. Natural amino acids or abnormal amino acid include, for example, glycine, alanine, valine, leucine, isoleucine, serine, threonine, cystein, methionine, proline, asparagine, glutamine, phenylalanine, tyrosine, tryptophan, aspartic acid, glutamic acid, lysine, arginine, histidine, β-alanine, cystathionine, cystine, homoserine, isoleucine, lanthionine, norleucine, norvaline, ornithine, sarcosine, thyronine.

When the amino acid residue has other amino groups, the amino acid with protecting group is included the former amino acid residue.

A protecting group of amino group includes, for example, benzyloxycarbonyl, t-butoxycarbonyl, trifluoroacetyl, 9-fluorenylmethoxycarbonyl.

In the present invention, 5 to 7 membered saturated monoheterocyclic ring means 5 to 7 membered saturated monoheterocyclic ring which may contains another one hetero atom selected from oxygen, nitrogen and sulfur atom. It includes, for example, pyrrolidine, imidazolidine, pyrazolidine, piperidine, piperazine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrooxazine, perhydrooxazepine, tetrahydrothiazine, perhydrothiazepine, morpholine, thiomorpholine ring.

In the present invention, C3-15 mono-, bi- or tri-carbocyclic ring which may be partially or fully saturated also includes spirocarbocyclic ring and bridged carbocyclic ring. It includes, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopropene, cyclobutene, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, 9,10-dihydroanthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[3.3.1]-2-heptene, bicyclo[2.2.2]octane, bicyclo[2.2.2]oct-2-ene, adamantane, noradamantane etc.

In the present invention, among the 3 to 15 membered mono-, bi- or tri-heterocyclic aryl which may be partially or fully saturated containing 1 to 4 hetero atom(s) selected from oxygen, nitrogen and sulfur atom(s), 3 to 15 membered mono-, bi- or tri-heterocyclic aryl containing 1 to 4 hetero atom(s) selected from oxygen, nitrogen and sulfur atom(s) includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine ring etc.

The 3 to 15 membered mono-, bi- or tri-heterocyclic aryl which may be partially or fully saturated containing 1 to 4 hetero atom(s) selected from oxygen, nitrogen and sulfur atom(s) includes aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, 8-aza-1,4-jioxaspiro[4.5]decane, 3-azaspiro[5.5]undecane, 1,3,8-triazaspiro[4.5]decane ring In the present invention, C1-6 alkyloxy means methoxy, ethoxy, propoxy, butoxy, pentyloxy, hexyloxy and the isomers thereof.

In the present invention, C1-4 alkyloxy means methoxy, ethoxy, propoxy, butoxy and the isomers thereof.

In the present invention, C1-4 alkylthio means methylthio, ethylthio, propylthio, butylthio and the isomers thereof.

In the present invention, C2-4 alkenyloxy means ethenyloxy, propenyloxy, butenyloxy and the isomers thereof.

In the present invention, C2-4 alkenylthio means ethenylthio, propenylthio, butenylthio and the isomers thereof.

In the present invention, C2-4 alkynyloxy means ethynyloxy, propynyloxy, butynyloxy and the isomers thereof.

In the present invention, C2-4 alkynylthio means ethynylthio, propynylthio, butynylthio and the isomers thereof.

In the present invention, C3-7 cycloalkyl means cyclopropyl, cyclobutyl, cyclopentyl, cyclohexyl, cycloheptyl and the isomers thereof.

In the present invention, C3-7 cycloalkyloxy means cyclopropyloxy, cyclobutyloxy, cyclopentyloxy, cyclohexyloxy, cycloheptyloxy and the isomers thereof.

In the present invention, C3-7 cycloalkylthio means cyclopropylthio, cyclobutylthio, cyclopentylthio, cyclohexylthio, cycloheptylthio and the isomers thereof.

Unless otherwise specified, all isomers are included in the present invention. For example, alkyl, alkenyl, alkynyl, alkoxy, alkylthio, alkylene alkenylene and alkynylene group means straight-chain or branched-chain ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the present invention, unless otherwise specified, the symbol  means that the substituent attached thereto is behind the sheet (i.e., α-configuration), the symbol  means that the substituent attached thereto is in front of the sheet (i.e., β-configuration), the symbol  means α-configuration, β-configuration or a mixture of α-configuration and β-configuration, and the symbol  means that there is a mixture of α-configuration and β-configuration as would be clear to the person skilled in the art.

The compound of the present invention may be converted into the corresponding non-toxic salt by conventional methods.

Non-toxic salts of the compounds of the present invention include all pharmaceutically acceptable salts, and water-soluble salts are preferred.

Non-toxic salts of the compounds of the present invention, for example, include: salts of alkali metals (e.g. potassium, sodium, lithium, etc.), salts of alkaline earth metals (e.g. calcium, magnesium, etc.), ammonium salts (e.g. tetramethylammonium salt, tetrabutylammonium salt, etc.), salts of organic amines (e.g. triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.) and acid addition salts (salts of inorganic acids (e.g. hydrochloride, hydrobromide, hydroiodide, sulfate, phosphate, nitrate, etc.), salts of organic acids (e.g. acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.), etc.).

Non-toxic salts of the compounds of the present invention include solvates thereof or solvates of the salts of alkali metals, salts of alkaline earth metals, ammonium salts, salts of organic amines and acid addition salts of the compounds of the present invention.

Non-toxic and water-soluble solvates are preferred. Solvates of the compounds of the present invention, for example, include: hydrates, solvates of the alcohols (ethanol etc.), etc.

The compounds of the present invention may be converted into the corresponding cyclodextrin clathrates by the method described in the specification of JP-B-50-3362, 52-31404 or 61-52146 using α-, β- or γ-cyclodextrin or a mixture thereof. Converting into the corresponding cyclodextrin clathrates serves to increase the stability and solubility in water of the compounds, and therefore it is useful in the use for pharmaceuticals.

It is enough to use the compound of the present invention as the $EP_4$ agonist if it has $EP_4$ agonistic activity. Both a selective $EP_4$ agonist and a non-selective $EP_4$ agonist can be used.

Furthermore, the $EP_4$ agonists of the present invention include the ones which will be found newly in future as well as known ones at present.

For example, the $EP_4$ agonists known at present are prostaglandin $E_1$ ($PGE_1$), prostaglandin $E_2$ ($PGE_2$), 13,14-dihydroprostaglandin $E_1$, the compound described in WO00/54808, the compound described in WO01/37877, the compound described in JP-A-2001-181210, the compounds of formulae (I-1), (I-2) and (I-3) described in WO00/03980. Prostaglandin $E_2$, the compounds of formulae (I-1), (I-2) and (I-3) is more preferable.

Among the compounds of formula (I-3) of the present invention, $A^3$ is preferably $A^{1-3}$ or $A^{2-3}$. More preferably, $A^3$ is $A^{2-3}$.

Among the compounds of formula (I-3) of the present invention, $G^{1-3}$ is preferably (1) C1-4 straight-chain alkylene optionally substituted by 1-2 C1-4 alkyl, or (2) C2-4 straight-chain alkenylene optionally substituted by 1-2 C1-4 alkyl. 1) C1-4 straight-chain alkylene optionally substituted by 1-2 C1-4 alkyl is more preferable.

Among the compounds of formula (I-3) of the present invention, $G^{2-3}$ is preferably (1)-$Y^3$—, (2)-(ring1$^3$)-, or (3) —$Y^3$-(ring1$^3$)-. 1) —$Y^3$— is more preferable.

Among the compounds of formula (I-3) of the present invention, $Y^3$ is preferably —S— or —O—. —S— is more preferable.

Among the compounds of formula (I-3) of the present invention, $G^{3-3}$ is preferably (1) bond, (2) C1-4 straight-chain alkylene optionally substituted by 1-2 C1-4 alkyl, or (3) C2-4 straight-chain alkenylene optionally substituted by 1-2 C1-4 alkyl. (2) C1-4 straight-chain alkylene optionally substituted by 1-2 C1-4 alkyl is more preferable.

Among the compounds of formula (I-3), $T^3$ is preferably oxygen atom or sulfur atom. Oxygen atom is more preferable.

Among the compounds of formula (I-3), $X^3$ is preferably —CH$_2$—, —O— or —S—. —CH$_2$— is more preferable.

Among the compounds of formula (I-3), $D^3$ is preferably —COOH, —COOR$^{2-3}$, —COOR$^{9-3}$—, COO—Z$^{1-3}$—Z$^{2-3}$—Z$^{3-3}$, tetrazol-5-yl,

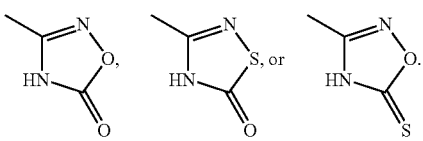

—COOH, —COOR$^{2-3}$, —COOR$^{9-3}$ or COO—Z$^{1-3}$—Z$^{2-3}$—Z$^{3-3}$ is more preferable. —COOH or COO—Z$^{1-3}$—Z$^{2-3}$—Z$^{3-3}$ is most preferable.

Among the compounds of formula (I-3), $R^{19-3}$ and $R^{20-3}$ are preferably hydrogen atom.

Among the compounds of formula (I-3), $E^3$ is preferably ring3$^3$, ring4$^3$ or ring5$^3$.

Among the compounds of formula (I-3), ring3$^3$ is preferably phenyl.

Among the compounds of formula (I-3), ring4$^3$ is preferably phenyl.

Among the compounds of formula (I-3), ring5$^3$ is preferably C5-10 mono- or bi-carbocyclic aryl which may be partially or fully saturated, or 5 to 10 membered mono- or bi-heterocyclic aryl containing 1 to 2 hetero atom selected from oxygen, nitrogen and sulfur atom(s) which may be partially or fully saturated. The 5 to 10 membered mono- or bi-heterocyclic aryl containing 1 to 2 hetero atom selected from oxygen, nitrogen and sulfur atom(s) which may be partially or fully saturated is preferably furan, thiophene, oxazole, thiazole, imidazole, pyridine, pyrimidine, benzofuran, indole, benzothiazole.

Among the compounds of formula (I-3), the hydroxy of 15-position is preferably α-configuration.

Among the compounds of formula (I-3), C13-14 is preferably double bond.

Among the compounds of formula (I-3), $Z^{1-3}$ is preferably C1-15 alkylene. C1-8 alkylene is more preferable. C1-4 alkylene is most preferable.

Among the compounds of formula (I-3), $Z^{2-3}$ is preferably —CO—, —OCO—, —COO—, —CONR$^{11-3}$—, —OCONR$^{17-3}$— or —OCOO—. —OCO—, —OCO NR$^{17-3}$—, —OCOO— is more preferable.

Among the compounds of formula (I-3), $Z^{3-3}$ is preferably C1-15 alkyl or C1-10 alkyl substituted by C1-10 alkoxy, C1-10 alkylthio, C1-10 alkyl-NR$^{18-3}$— or ring2$^3$. C4-12 alkyl is more preferable.

Among the compounds of formula (I-2), $R^{1-2}$ is preferably —COO—Y$^2$—R$^{9-2}$ or —COO—Z$^{1-2}$—Z$^{2-2}$—Z$^{3-2}$. COO—Z$^{1-2}$—Z$^{2-2}$—Z$^{3-2}$ is more preferable.

Among the compounds of formula (I-2), $Z^{1-2}$ is preferably C1-15 alkylene. C1-8 alkylene is more preferable. C1-4 alkylene is most preferable.

Among the compounds of formula (I-2), $Z^{2-2}$ is preferably —CO—, —OCO—, —COO—, —CONR$^{11-2}$—, —OCONR$^{17-2}$— or —OCOO—. —OCO—, —CO NR$^{17-2}$— or —OCOO— is more preferable.

Among the compounds of formula (I-2), $Z^{3-2}$ is preferably C1-15 alkyl, C1-10 alkyl substituted by C1-10 alkoxy, C1-10 alkylthio, C1-10 alkyl-NR$^{18-2}$— or ring1$^2$. C4-12 alkyl is more preferable.

Among the compounds of formula (I-3), preferable compounds are the compound of formula (I-3-A-1)

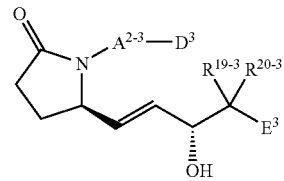

(wherein all symbols are the same meanings as defined hereinbefore), the compound of formula (I-3-A-2)

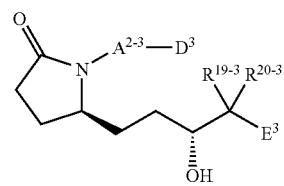

(wherein all symbols are the same meanings as defined hereinbefore), the compound of formula (I-3-A-3)

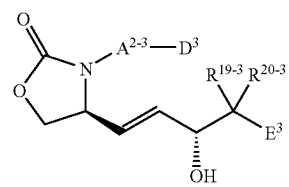

(wherein all symbols are the same meanings as defined hereinbefore), the compound of formula (I-3-A-4)

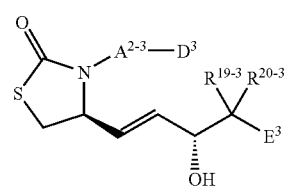

(wherein all symbols are the same meanings as defined hereinbefore), and the compound of formula (I-3-A-5)

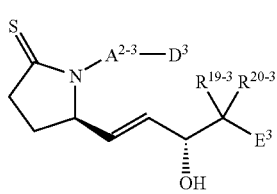
(I-3-A-5)

(wherein all symbols are the same meanings as defined hereinbefore).

Among the compounds of formula (I-2), preferable compounds are the compound of formula (I-2-A-1)

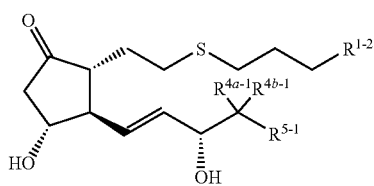
(I-2-A-1)

(wherein all symbols are the same meanings as defined hereinbefore), the compound of formula (I-2-A-2)

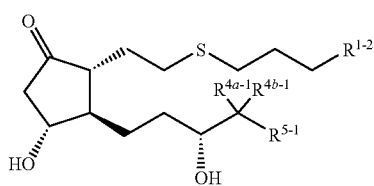
(I-2-A-2)

(wherein all symbols are the same meanings as defined hereinbefore), the compound of formula (I-2-A-3)

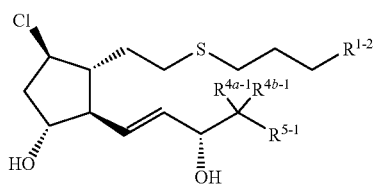
(I-2-A-3)

(wherein all symbols are the same meanings as defined hereinbefore), the compound of formula (I-2-A-4)

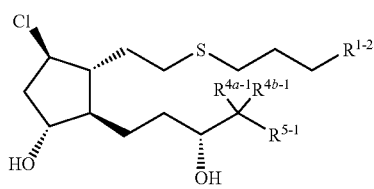
(I-2-A-4)

(wherein all symbols are the same meanings as defined hereinbefore), the compound of formula (I-2-A-5)

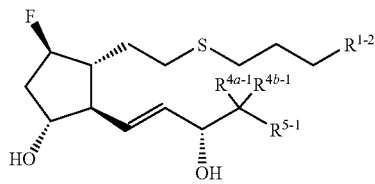
(I-2-A-5)

(wherein all symbols are the same meanings as defined hereinbefore), and the compound of formula (I-2-A-6)

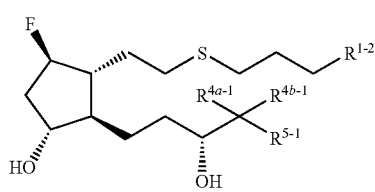
(I-2-A-6)

(wherein all symbols are the same meanings as defined hereinbefore).

Among the compounds of formula (I-1), preferable compounds are the compound of formula (I-1-A-1)

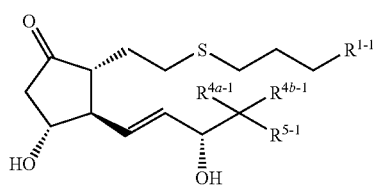
(I-1-A-1)

(wherein all symbols are the same meanings as defined hereinbefore), the compound of formula (I-1-A-2)

(I-1-A-2)

(wherein all symbols are the same meanings as defined hereinbefore), the compound of formula (I-1-A-3)

(I-1-A-3)

(wherein all symbols are the same meanings as defined hereinbefore), the compound of formula (I-1-A-4)

(I-1-A-4)

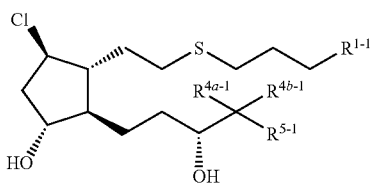

(wherein all symbols are the same meanings as defined hereinbefore), the compound of formula (I-1-A-5)

(I-1-A-5)

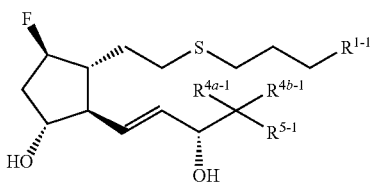

(wherein all symbols are the same meanings as defined hereinbefore), and the compound of formula (I-1-A-6)

(I-1-A-6)

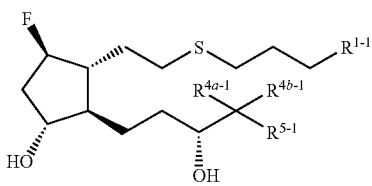

(wherein all symbols are the same meanings as defined hereinbefore).

Specifically, the compounds of the present invention are the compounds shown in the following tables 1 to 120, the compounds described in the Examples and non-toxic salts thereof.

TABLE 1

(I-3-A-1-1)

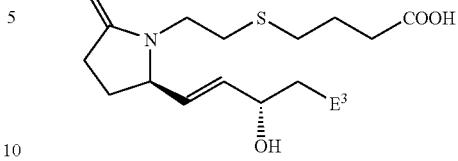

| No. | $E^3$ |
|---|---|
| 1 | 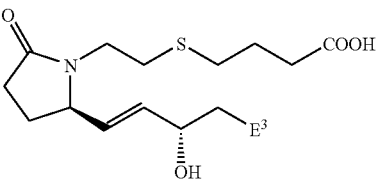 |
| 2 | 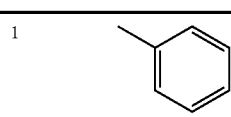 |

TABLE 1-continued (I-3-A-1-1)

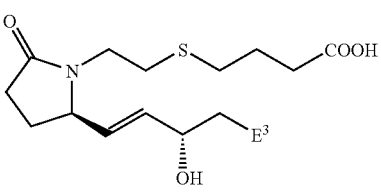

| No. | $E^3$ |
|---|---|
| 3 | 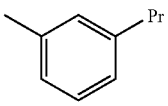 |
| 4 | 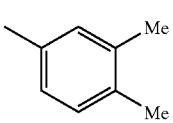 |
| 5 | 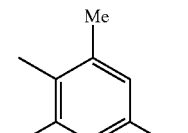 |
| 6 | 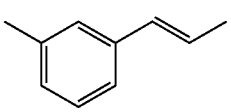 |
| 7 | 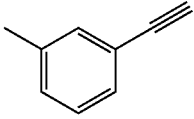 |
| 8 | 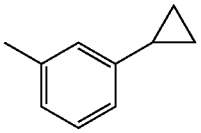 |
| 9 | 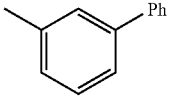 |
| 10 | 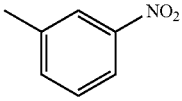 |
| 11 | 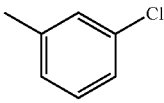 |
| 12 | 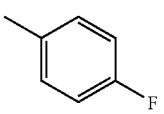 |

TABLE 1-continued (I-3-A-1-1)

[Structure: pyrrolidinone-N-CH2CH2-S-CH2CH2CH2-COOH with CH=CH-CH(OH)-CH2-E³ substituent]

| No. | E³ |
|-----|-----|
| 13 | 3,5-difluorophenyl |
| 14 | 3,4-difluorophenyl |
| 15 | 3-(trifluoromethyl)phenyl |
| 16 | 4-fluoro-3-(trifluoromethyl)phenyl |
| 17 | 3-chloro-4-fluorophenyl |
| 18 | 3-chloro-4-hydroxyphenyl |
| 19 | 3-methoxyphenyl |
| 20 | 4-methoxyphenyl |
| 21 | 3-(benzyloxy)phenyl |
| 22 | 3-phenoxyphenyl |
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethyl-4-methylpyridinyl |
| 27 | 2,5-dimethylfuranyl |
| 28 | 2,5-dimethyloxazolyl |
| 29 | 2,4-dimethylthiazolyl |
| 30 | 1-methylimidazolyl |
| 31 | 2-methylpyrimidinyl |
| 32 | naphthalenyl |
| 33 | benzofuranyl |
| 34 | 2-methyl-1H-indolyl |
| 35 | 2-methylbenzothiazolyl |

TABLE 2
(I-3-A-1-2)
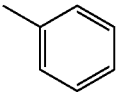
| No. | E³ |
|---|---|
| 1 | 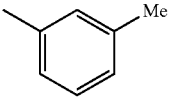 |
| 2 | 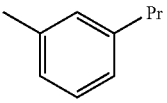 |
| 3 | 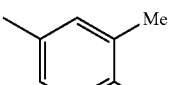 |
| 4 | 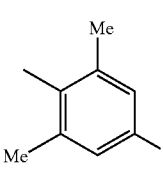 |
| 5 | 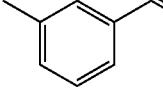 |
| 6 | 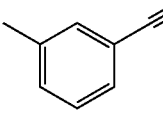 |
| 7 | 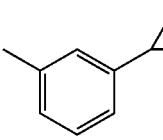 |
| 8 | 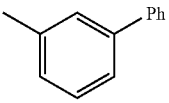 |
| 9 | 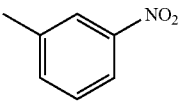 |
| 10 | 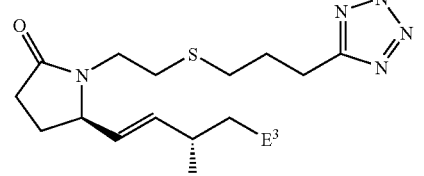 |
TABLE 2-continued
(I-3-A-1-2)
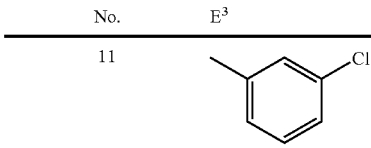
| No. | E³ |
|---|---|
| 11 | 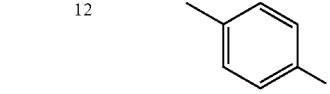 |
| 12 |  |
| 13 | 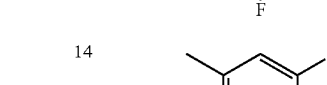 |
| 14 | 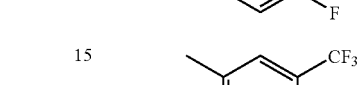 |
| 15 | 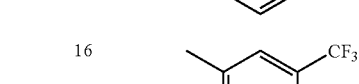 |
| 16 | 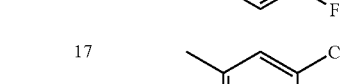 |
| 17 |  |
| 18 | 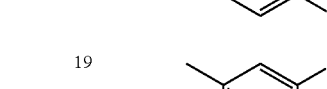 |
| 19 | 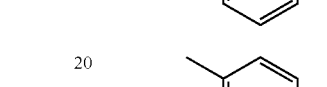 |
| 20 | 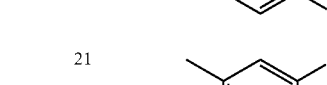 |
| 21 |  |

TABLE 2-continued (I-3-A-1-2)

| No. | E³ |
|---|---|
| 22 | 3-(phenoxy)phenyl (OPh) |
| 23 | 3,4-dimethoxyphenyl (OMe, OMe) |
| 24 | 3-(methoxymethyl)phenyl (CH₂OMe) |
| 25 | 3-((2,2,2-trifluoroethoxy)methyl)phenyl (CH₂OCH₂CF₃) |
| 26 | 2-ethyl-4-pyridyl (Et, N) |
| 27 | 5-methyl-2-furyl |
| 28 | 2-methyl-5-oxazolyl |
| 29 | 2-methyl-4-thiazolyl |
| 30 | 1-methylimidazol-?-yl |
| 31 | 2-pyrimidinyl |
| 32 | 6-methyl-2-naphthyl |
| 33 | 5-methylbenzofuran-?-yl |

TABLE 2-continued (I-3-A-1-2)

| No. | E³ |
|---|---|
| 34 | 2-methyl-1H-indol-?-yl |
| 35 | 2-methylbenzothiazol-?-yl |

TABLE 3

(I-3-A-1-3)

| No. | E³ |
|---|---|
| 1 | phenyl |
| 2 | 3-methylphenyl (Me) |
| 3 | 3-propylphenyl (Pr) |
| 4 | 2,5-dimethylphenyl (Me, Me) |
| 5 | 2,4,6-trimethylphenyl (mesityl) |
| 6 | 3-(1-propenyl)phenyl |

TABLE 3-continued (I-3-A-1-3)

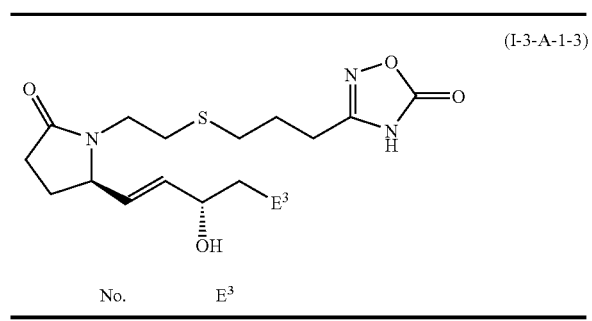

| No. | E³ |
|---|---|
| 7 | 3-ethynylphenyl |
| 8 | 3-cyclopropylphenyl |
| 9 | 3-phenylphenyl |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-trifluoromethylphenyl |
| 16 | 2-trifluoromethyl-4-fluorophenyl |

TABLE 3-continued (I-3-A-1-3)

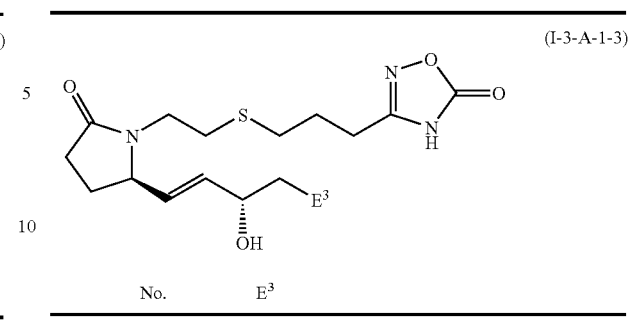

| No. | E³ |
|---|---|
| 17 | 3-chloro-4-fluorophenyl |
| 18 | 3-chloro-4-hydroxyphenyl |
| 19 | 3-methoxyphenyl |
| 20 | 4-methoxyphenyl |
| 21 | 3-benzyloxyphenyl |
| 22 | 3-phenoxyphenyl |
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethyl-4-methylpyridyl |
| 27 | 2,5-dimethylfuryl |

TABLE 3-continued
(I-3-A-1-3)
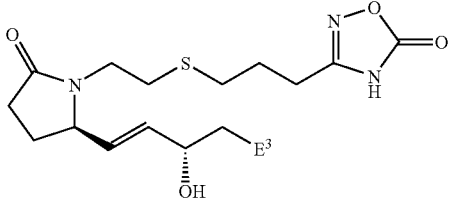
| No. | E³ |
|---|---|
| 28 | 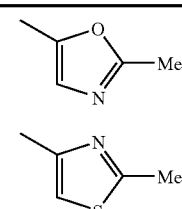 |
| 29 | 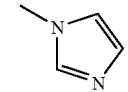 |
| 30 | 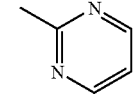 |
| 31 | 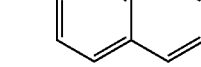 |
| 32 | 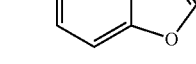 |
| 33 | 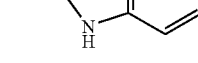 |
| 34 | 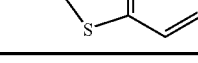 |
| 35 | 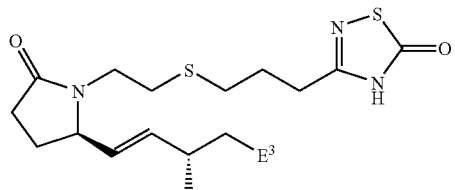 |
TABLE 4
(I-3-A-1-4)
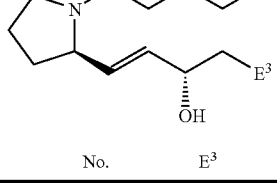
| No. | E³ |
|---|---|
| 1 | 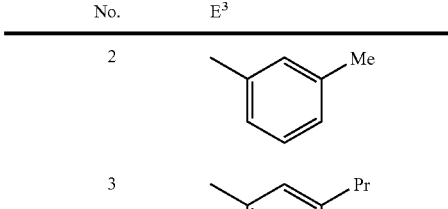 |
TABLE 4-continued
(I-3-A-1-4)
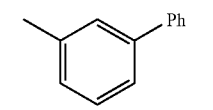
| No. | E³ |
|---|---|
| 2 | 3-Me-C₆H₄ |
| 3 | 3-Pr-C₆H₄ |
| 4 | 3,4-diMe-C₆H₃ |
| 5 | 2,4,6-triMe-C₆H₂ |
| 6 | 3-(1-propenyl)-C₆H₄ |
| 7 | 3-ethynyl-C₆H₄ |
| 8 | 3-cyclopropyl-C₆H₄ |
| 9 | 3-Ph-C₆H₄ |
| 10 | 3-NO₂-C₆H₄ |
| 11 | 3-Cl-C₆H₄ |
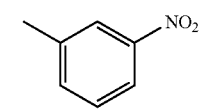
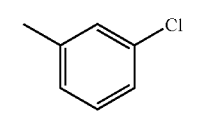

TABLE 4-continued (I-3-A-1-4)

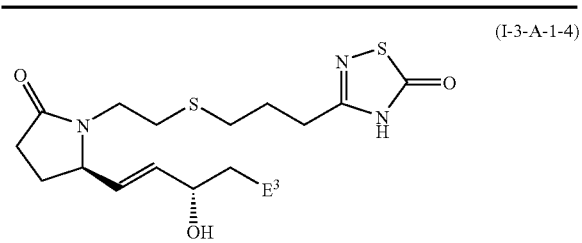

| No. | E³ |
|---|---|
| 12 | 4-fluorophenyl |
| 13 | 3,5-difluorophenyl |
| 14 | 3,4-difluorophenyl |
| 15 | 3-(trifluoromethyl)phenyl |
| 16 | 4-fluoro-3-(trifluoromethyl)phenyl |
| 17 | 3-chloro-4-fluorophenyl |
| 18 | 3-chloro-4-hydroxyphenyl |
| 19 | 3-methoxyphenyl |
| 20 | 4-methoxyphenyl |
| 21 | 3-(benzyloxy)phenyl |
| 22 | 3-phenoxyphenyl |

TABLE 4-continued (I-3-A-1-4)

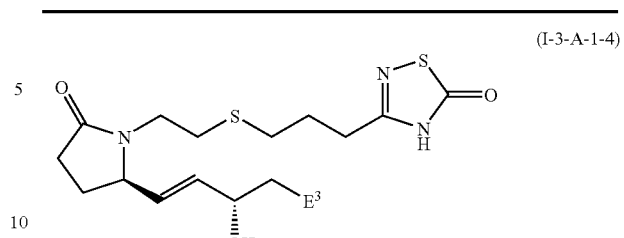

| No. | E³ |
|---|---|
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethyl-4-pyridyl |
| 27 | 2,5-dimethylfuran-3-yl |
| 28 | 2,5-dimethyloxazol-4-yl |
| 29 | 2-methylthiazol-4-yl |
| 30 | 1-methylimidazol-5-yl |
| 31 | 2-methylpyrimidin-4-yl |
| 32 | naphthalen-2-yl |
| 33 | benzofuran-5-yl |

TABLE 4-continued
(I-3-A-1-4)
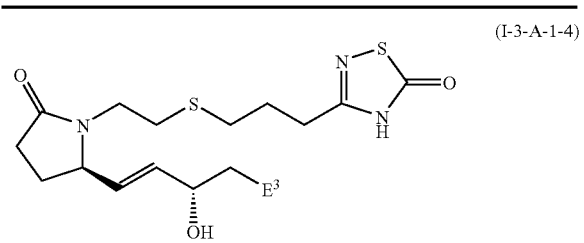
| No. | E³ |
|---|---|
| 34 | 2-indolyl (1H-indol-2-yl) |
| 35 | 2-benzothiazolyl |
TABLE 5
(I-3-A-1-5)
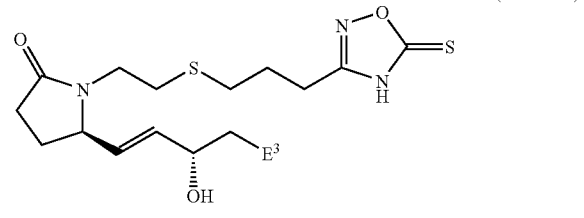
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,4,6-triMe-phenyl |
| 6 | 3-(1-propenyl)-phenyl |
TABLE 5-continued
(I-3-A-1-5)
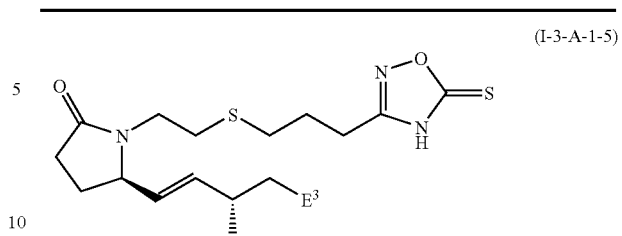
| No. | E³ |
|---|---|
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |

TABLE 5-continued
(I-3-A-1-5)
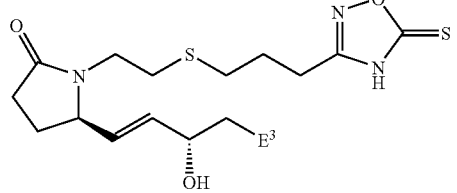
| No. | E³ |
|-----|-----|
| 17 | 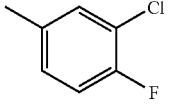 |
| 18 | 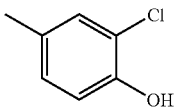 |
| 19 | 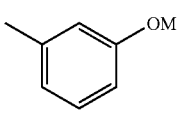 |
| 20 | 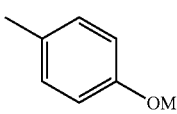 |
| 21 | 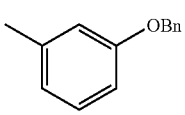 |
| 22 | 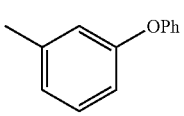 |
| 23 | 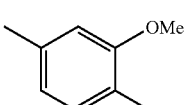 |
| 24 | 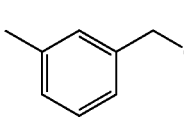 |
| 25 | 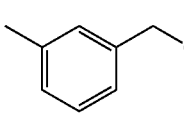 |
| 26 | 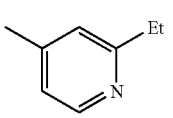 |
| 27 | 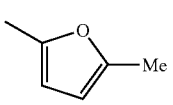 |
TABLE 5-continued
(I-3-A-1-5)
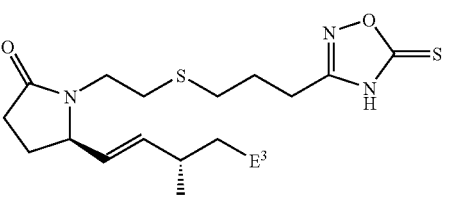
| No. | E³ |
|-----|-----|
| 28 | 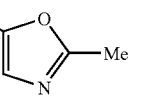 |
| 29 | 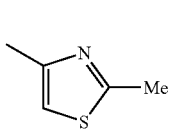 |
| 30 |  |
| 31 | 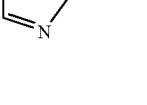 |
| 32 |  |
| 33 |  |
| 34 | 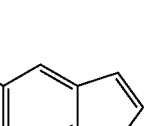 |
| 35 | 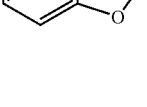 |

TABLE 6
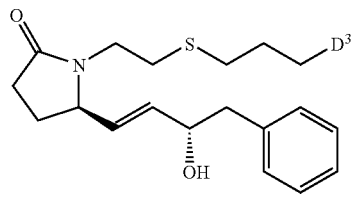
(I-3-A-1-6)
| No. | D³ |
|---|---|
| 1 | 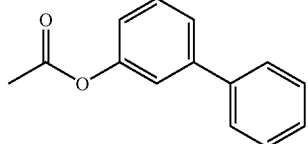 |
| 2 | 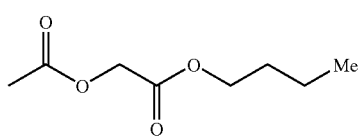 |
| 3 | 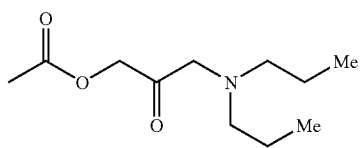 |
| 4 | 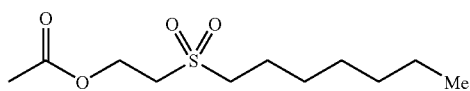 |
| 5 | 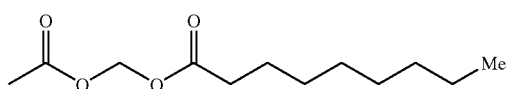 |
| 6 | 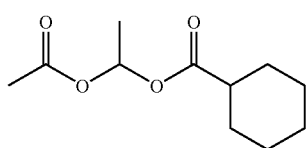 |
| 7 | 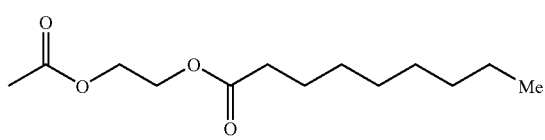 |
| 8 | 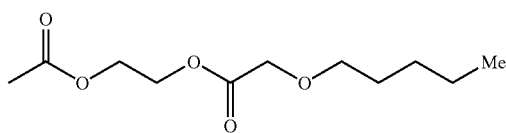 |
| 9 | 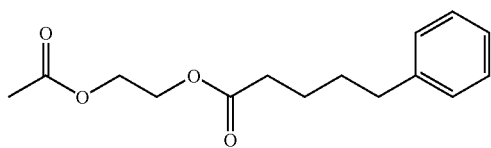 |

TABLE 6-continued
(I-3-A-1-6)
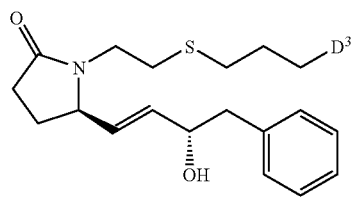
| No. | D³ |
|---|---|
| 10 | 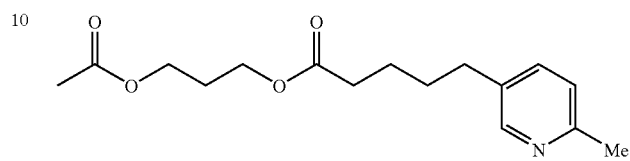 |
| 11 | 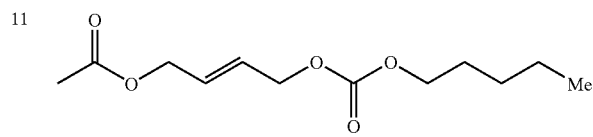 |
| 12 | 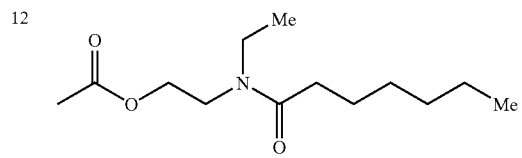 |
| 13 | 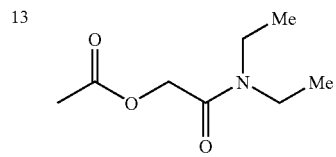 |
| 14 | 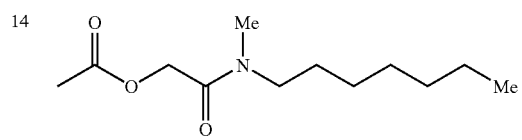 |
| 15 | 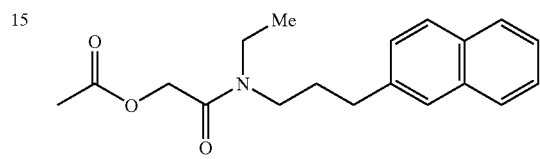 |

TABLE 7
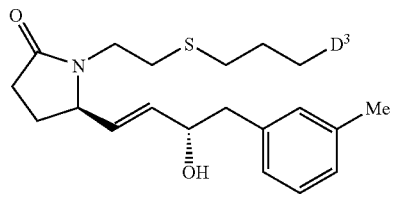
(I-3-A-1-7)
| No. | D³ |
|---|---|
| 1 | 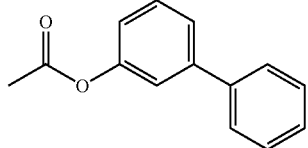 |
| 2 | 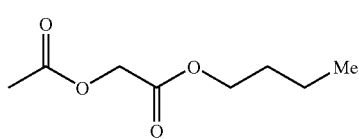 |
| 3 | 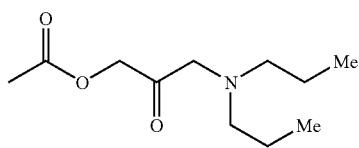 |
| 4 | 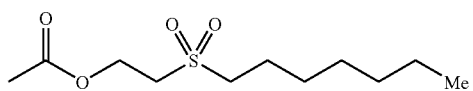 |
| 5 | 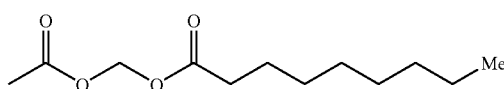 |
| 6 | 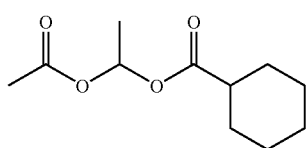 |
| 7 | 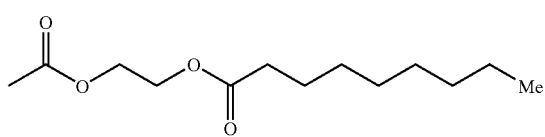 |
| 8 | 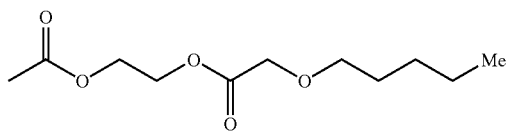 |
| 9 | 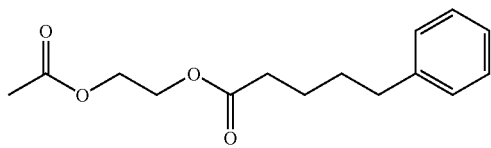 |

TABLE 7-continued
(I-3-A-1-7)
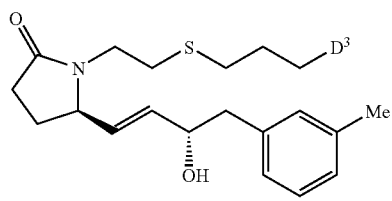
| No. | D³ |
|---|---|
| 10 | 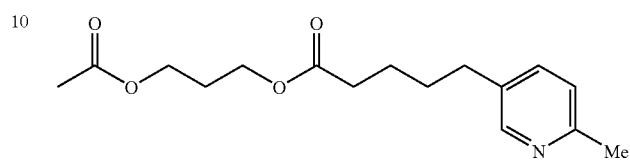 |
| 11 | 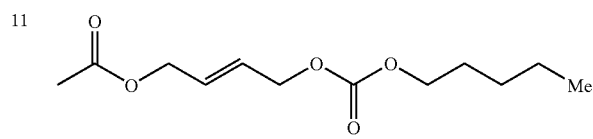 |
| 12 | 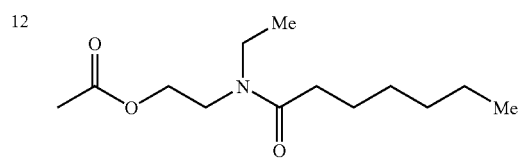 |
| 13 | 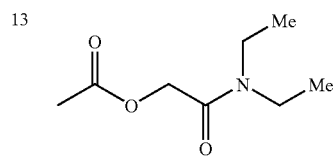 |
| 14 | 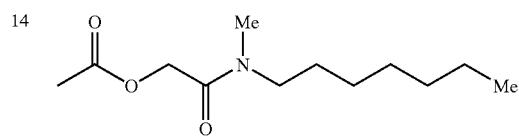 |
| 15 | 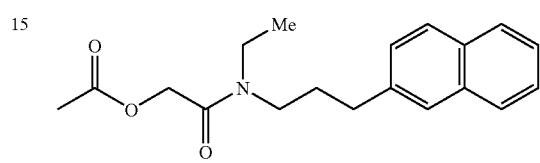 |

TABLE 8
(I-3-A-1-8)
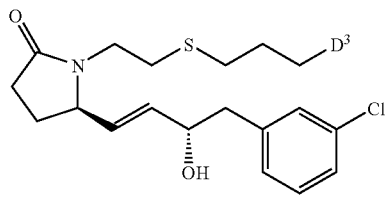
| No. | D³ |
|---|---|
| 1 | 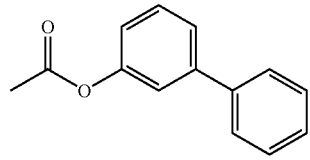 |
| 2 | 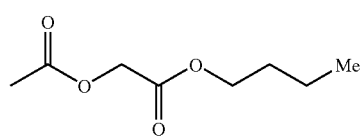 |
| 3 | 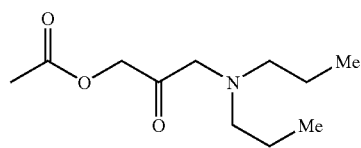 |
| 4 | 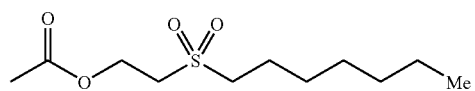 |
| 5 | 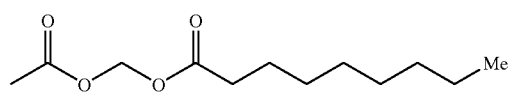 |
| 6 | 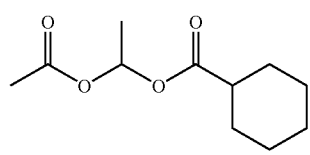 |
| 7 | 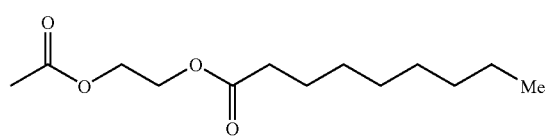 |
| 8 | 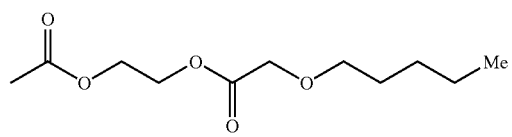 |
| 9 | 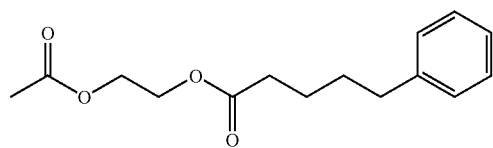 |

TABLE 8-continued
(I-3-A-1-8)
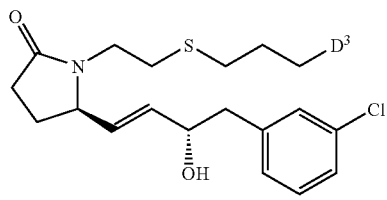
| No. | D³ |
|---|---|
| 10 | 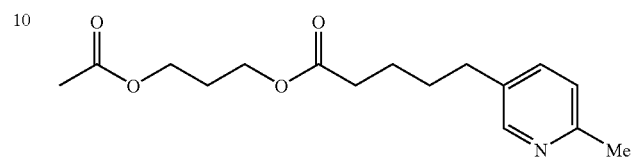 |
| 11 | 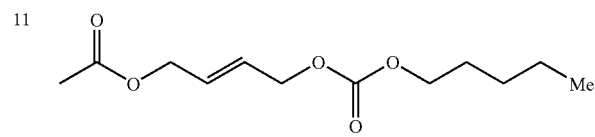 |
| 12 | 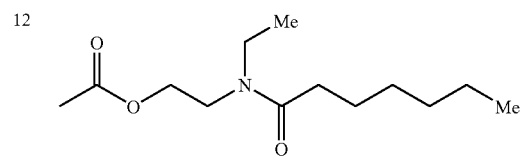 |
| 13 | 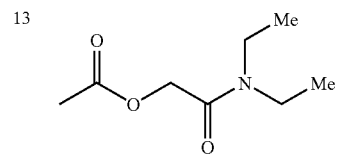 |
| 14 | 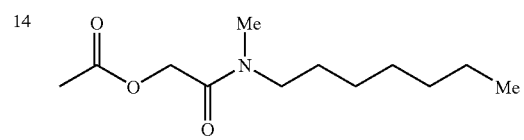 |
| 15 | 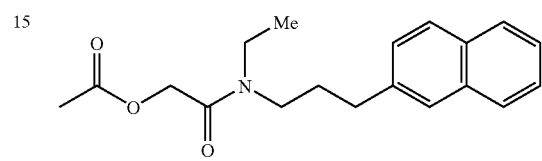 |

TABLE 9
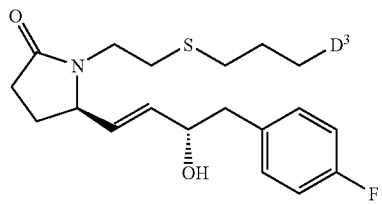
(I-3-A-1-9)
| No. | D³ |
|---|---|
| 1 | 3-phenylphenyl acetate |
| 2 | butyl 2-(acetyloxy)acetate |
| 3 | 3-(dipropylamino)-2-oxopropyl acetate |
| 4 | 2-(heptylsulfonyl)ethyl acetate |
| 5 | (nonanoyloxy)methyl acetate |
| 6 | 1-(cyclohexanecarbonyloxy)ethyl acetate |
| 7 | 2-(nonanoyloxy)ethyl acetate |
| 8 | 2-((pentyloxyacetyl)oxy)ethyl acetate |
| 9 | 2-((5-phenylpentanoyl)oxy)ethyl acetate |

TABLE 9-continued
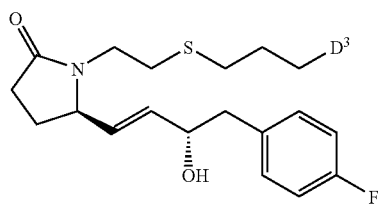
(I-3-A-1-9)
| No. | D³ |
|---|---|
| 10 | 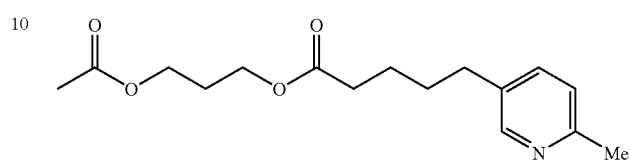 |
| 11 | 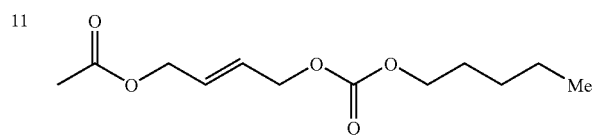 |
| 12 | 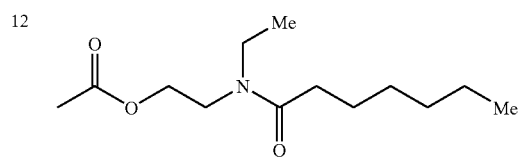 |
| 13 | 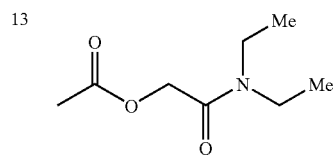 |
| 14 | 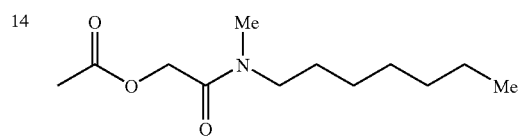 |
| 15 | 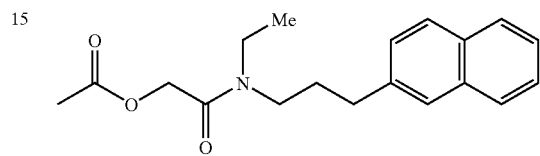 |

TABLE 10
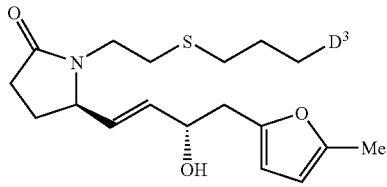
(I-3-A-1-10)
| No. | D³ |
|---|---|
| 1 | 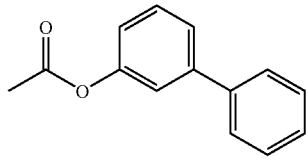 |
| 2 | 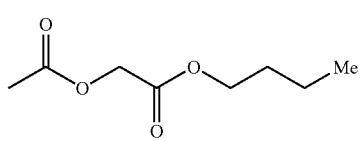 |
| 3 | 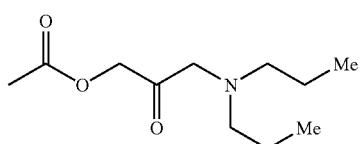 |
| 4 | 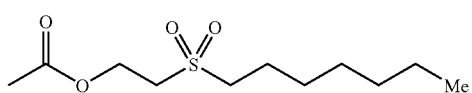 |
| 5 | 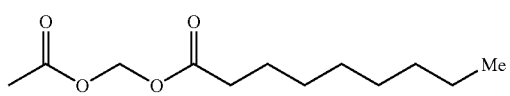 |
| 6 | 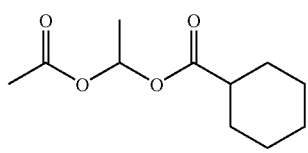 |
| 7 | 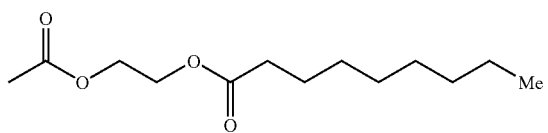 |
| 8 | 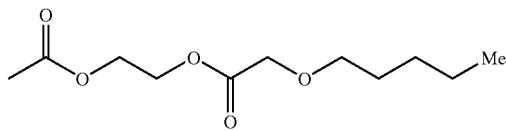 |
| 9 | 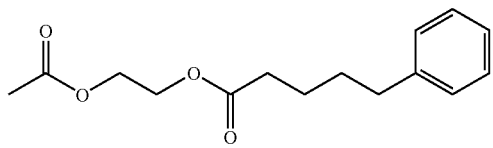 |

TABLE 10-continued
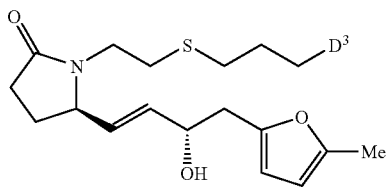
(I-3-A-1-10)
| No. | D³ |
|---|---|
| 10 | 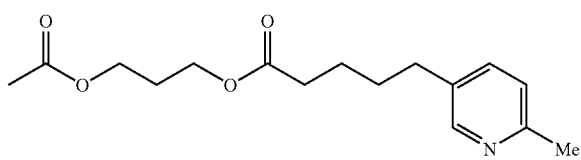 |
| 11 | 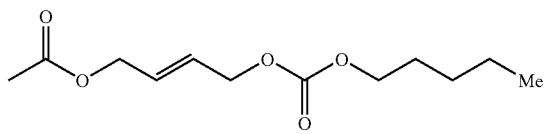 |
| 12 | 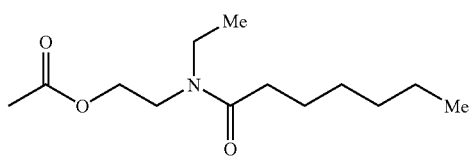 |
| 13 | 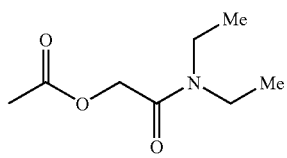 |
| 14 | 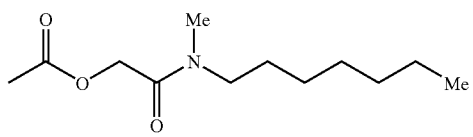 |
| 15 | 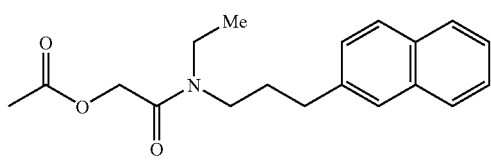 |

TABLE 11
(I-3-A-2-1)
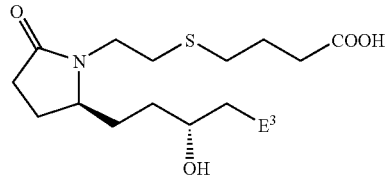
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,3,5-triMe-phenyl |
| 6 | 3-(1-propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
TABLE 11-continued
(I-3-A-2-1)
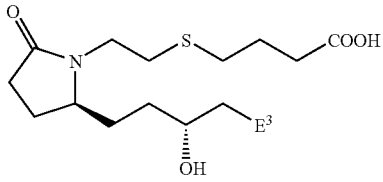
| No. | E³ |
|---|---|
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |
| 22 | 3-OPh-phenyl |

TABLE 11-continued (I-3-A-2-1)

Structure: pyrrolidinone-N-CH2CH2-S-CH2CH2CH2-COOH with 5-substituent CH2CH2-CH(OH)-CH2-E³

| No. | E³ |
|-----|-----|
| 23 | 3,4-dimethoxyphenyl (OMe, OMe) |
| 24 | 3-(methoxymethyl)phenyl (CH2OMe) |
| 25 | 3-((2,2,2-trifluoroethoxy)methyl)phenyl (CH2OCH2CF3) |
| 26 | 2-ethyl-4-pyridyl (Et, N) |
| 27 | 5-methyl-2-furyl (Me, O) |
| 28 | 2-methyl-5-oxazolyl (Me, O, N) |
| 29 | 2-methyl-4-thiazolyl (Me, N, S) |
| 30 | 1-methylimidazol-?-yl |
| 31 | 2-pyrimidinyl |
| 32 | 2-naphthyl |
| 33 | 5-benzofuranyl |
| 34 | 2-methyl-1H-indol-?-yl |
| 35 | 2-benzothiazolyl |

TABLE 12

(I-3-A-2-2)

Structure: pyrrolidinone-N-CH2CH2-S-CH2CH2CH2-tetrazole with 5-substituent CH2CH2-CH(OH)-CH2-E³

| No. | E³ |
|-----|-----|
| 1 | phenyl |
| 2 | 3-methylphenyl (Me) |
| 3 | 3-propylphenyl (Pr) |
| 4 | 3,4-dimethylphenyl (Me, Me) |
| 5 | 2,4,6-trimethylphenyl (Me, Me, Me) |
| 6 | 3-(1-propenyl)phenyl |
| 7 | 3-ethynylphenyl |

TABLE 12-continued
(I-3-A-2-2)
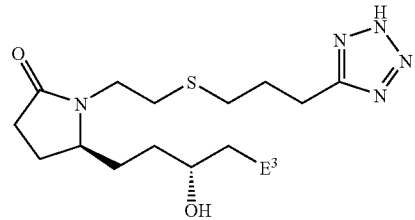
| No. | E³ |
|---|---|
| 8 | 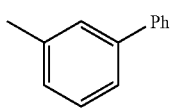 |
| 9 | 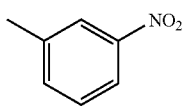 |
| 10 | 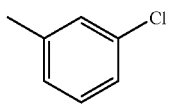 |
| 11 | 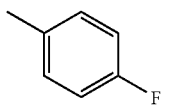 |
| 12 | 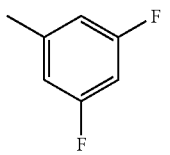 |
| 13 | 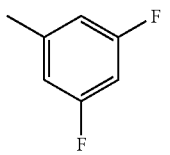 |
| 14 | 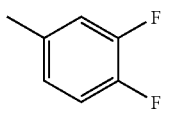 |
| 15 | 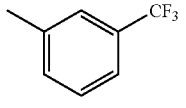 |
| 16 | 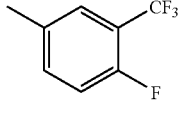 |
| 17 | 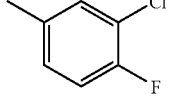 |
TABLE 12-continued
(I-3-A-2-2)
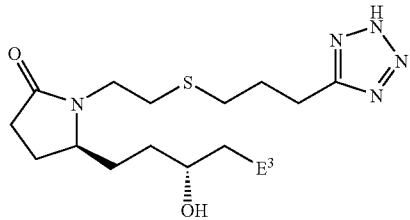
| No. | E³ |
|---|---|
| 18 | 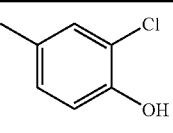 |
| 19 | 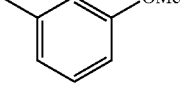 |
| 20 | 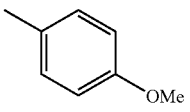 |
| 21 | 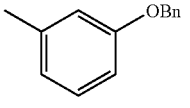 |
| 22 | 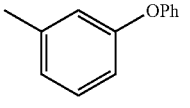 |
| 23 | 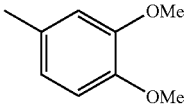 |
| 24 | 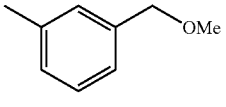 |
| 25 | 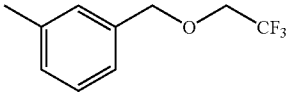 |
| 26 | 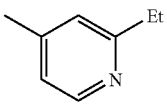 |
| 27 | 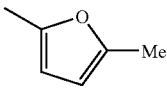 |
| 28 | 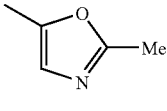 |

TABLE 12-continued
(I-3-A-2-2)
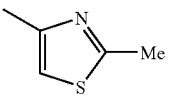
| No. | E³ |
|---|---|
| 29 |  |
| 30 |  |
| 31 | 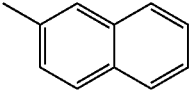 |
| 32 | 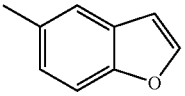 |
| 33 | 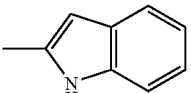 |
| 34 | 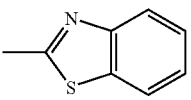 |
| 35 |  |
TABLE 13
(I-3-A-2-3)
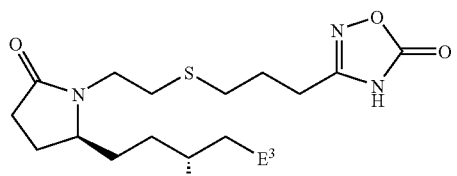
| No. | E³ |
|---|---|
| 1 | 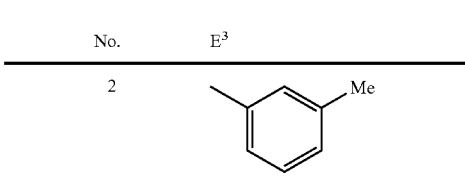 |
TABLE 13-continued
(I-3-A-2-3)
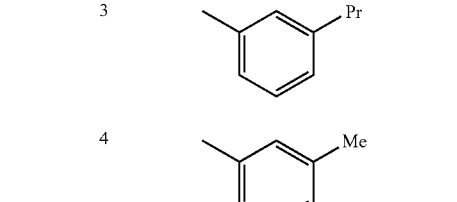
| No. | E³ |
|---|---|
| 2 | 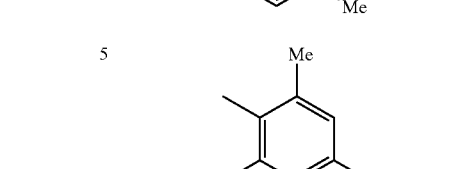 |
| 3 | 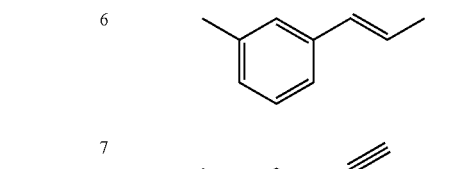 |
| 4 | 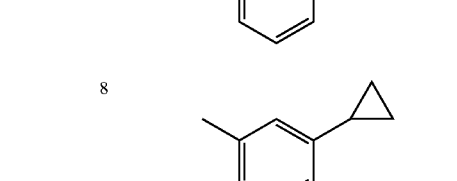 |
| 5 | 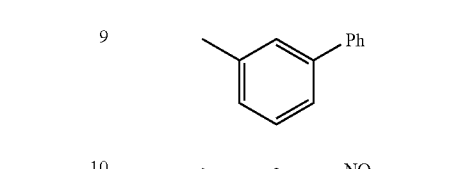 |
| 6 | 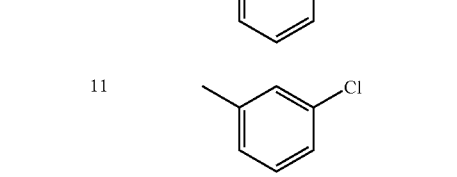 |
| 7 |  |
| 8 | |
| 9 | |
| 10 | |
| 11 | |

TABLE 13-continued
(I-3-A-2-3)
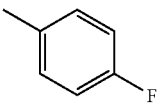
| No. | E³ |
|---|---|
| 12 | 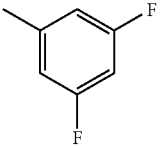 |
| 13 | 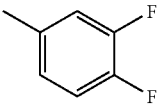 |
| 14 | 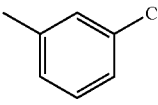 |
| 15 | 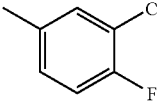 |
| 16 | 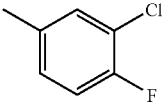 |
| 17 | 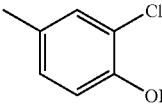 |
| 18 | 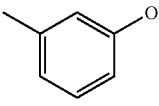 |
| 19 | 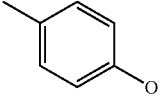 |
| 20 | 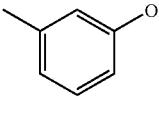 |
| 21 | 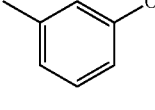 |
| 22 | 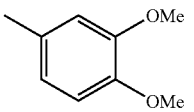 |
TABLE 13-continued
(I-3-A-2-3)
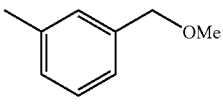
| No. | E³ |
|---|---|
| 23 | 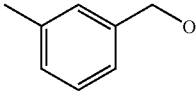 |
| 24 | 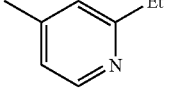 |
| 25 | 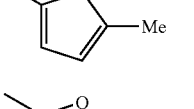 |
| 26 | 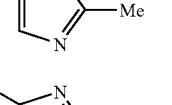 |
| 27 | 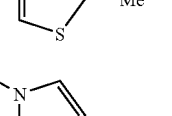 |
| 28 | 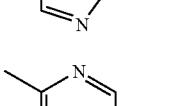 |
| 29 | 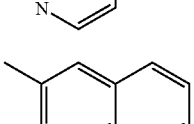 |
| 30 | 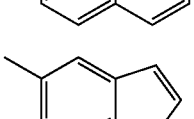 |
| 31 | 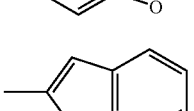 |
| 32 | 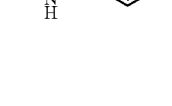 |
| 33 | |
| 34 | |

TABLE 13-continued
(I-3-A-2-3)
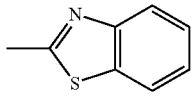
| No. | E³ |
|---|---|
| 35 | 2-benzothiazolyl |
TABLE 14
(I-3-A-2-4)
| No. | E³ |
|---|---|
| 1 | phenyl |
| 2 | 3,5-dimethylphenyl |
| 3 | 3-propylphenyl |
| 4 | 2,4-dimethylphenyl |
| 5 | 2,4,6-trimethylphenyl |
| 6 | 3-(prop-1-enyl)phenyl |
TABLE 14-continued
(I-3-A-2-4)
| No. | E³ |
|---|---|
| 7 | 3-ethynylphenyl |
| 8 | 3-cyclopropylphenyl |
| 9 | 3-phenylphenyl |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-trifluoromethylphenyl |
| 16 | 3-trifluoromethyl-4-fluorophenyl |

TABLE 14-continued
(I-3-A-2-4)
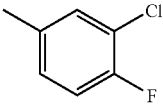
| No. | E³ |
|---|---|
| 17 | 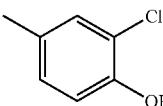 |
| 18 | 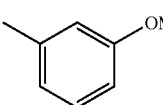 |
| 19 | 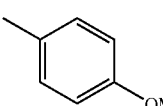 |
| 20 | 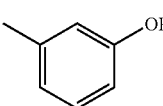 |
| 21 | 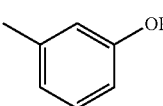 |
| 22 | 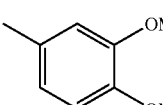 |
| 23 | 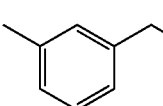 |
| 24 | 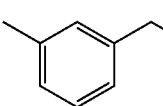 |
| 25 | 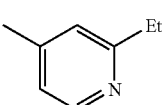 |
| 26 | 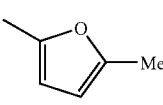 |
| 27 | 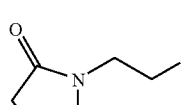 |
TABLE 14-continued
(I-3-A-2-4)
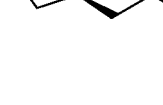
| No. | E³ |
|---|---|
| 28 | 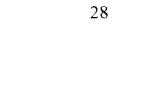 |
| 29 | 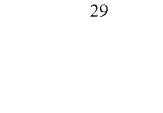 |
| 30 |  |
| 31 |  |
| 32 |  |
| 33 |  |
| 34 | 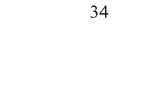 |
| 35 |  |

TABLE 15
(I-3-A-2-5)
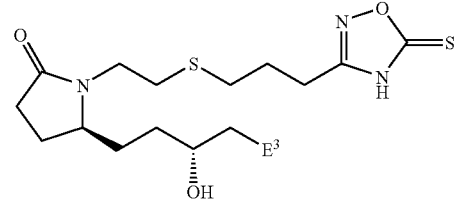
| No. | E³ |
|-----|-----|
| 1 | 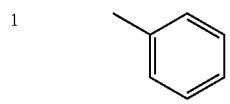 |
| 2 | 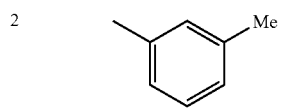 |
| 3 | 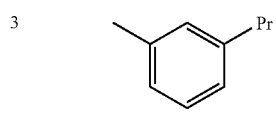 |
| 4 | 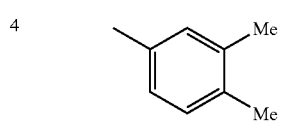 |
| 5 | 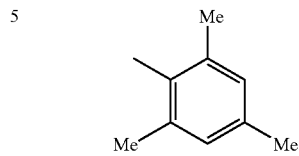 |
| 6 | 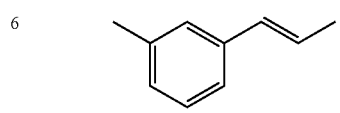 |
| 7 | 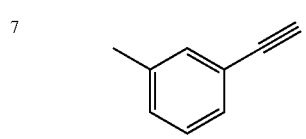 |
| 8 | 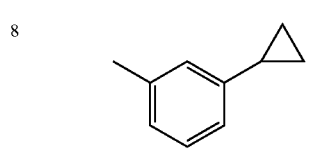 |
| 9 | 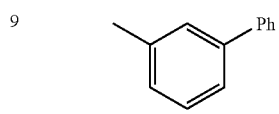 |
| 10 | 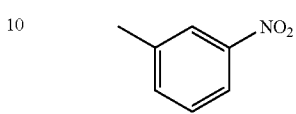 |
TABLE 15-continued
(I-3-A-2-5)
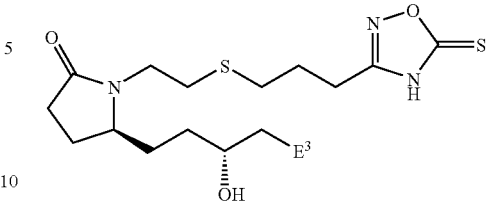
| No. | E³ |
|-----|-----|
| 11 |  |
| 12 |  |
| 13 |  |
| 14 | 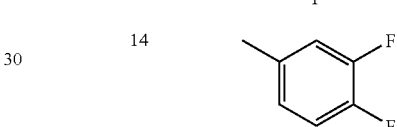 |
| 15 | 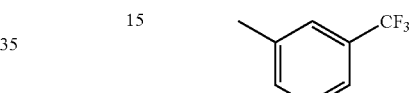 |
| 16 | 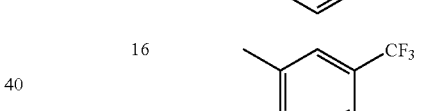 |
| 17 |  |
| 18 |  |
| 19 | 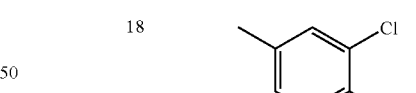 |
| 20 |  |
| 21 |  |

TABLE 15-continued
(I-3-A-2-5)
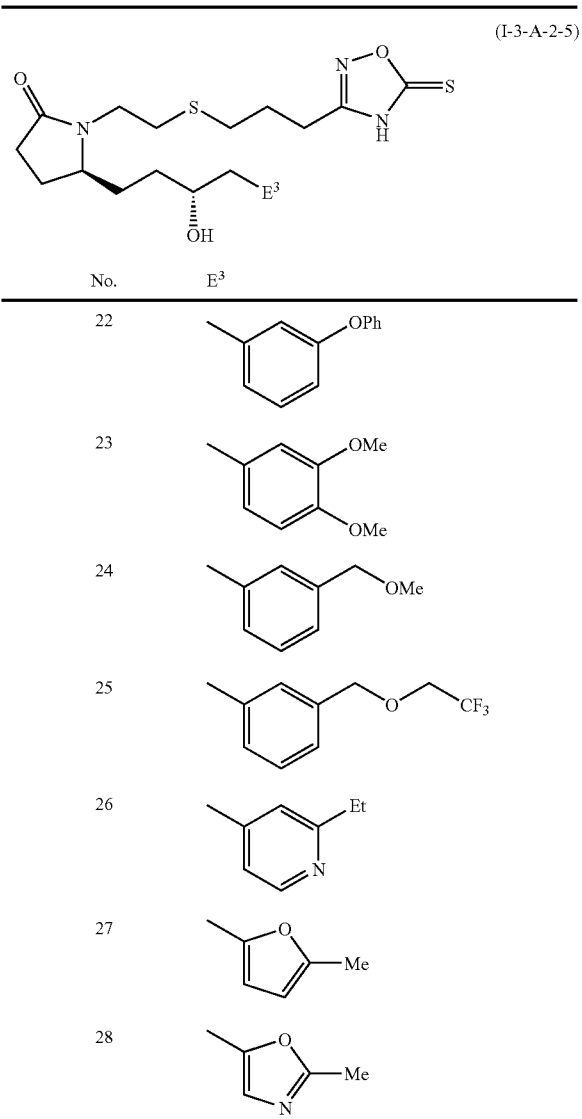
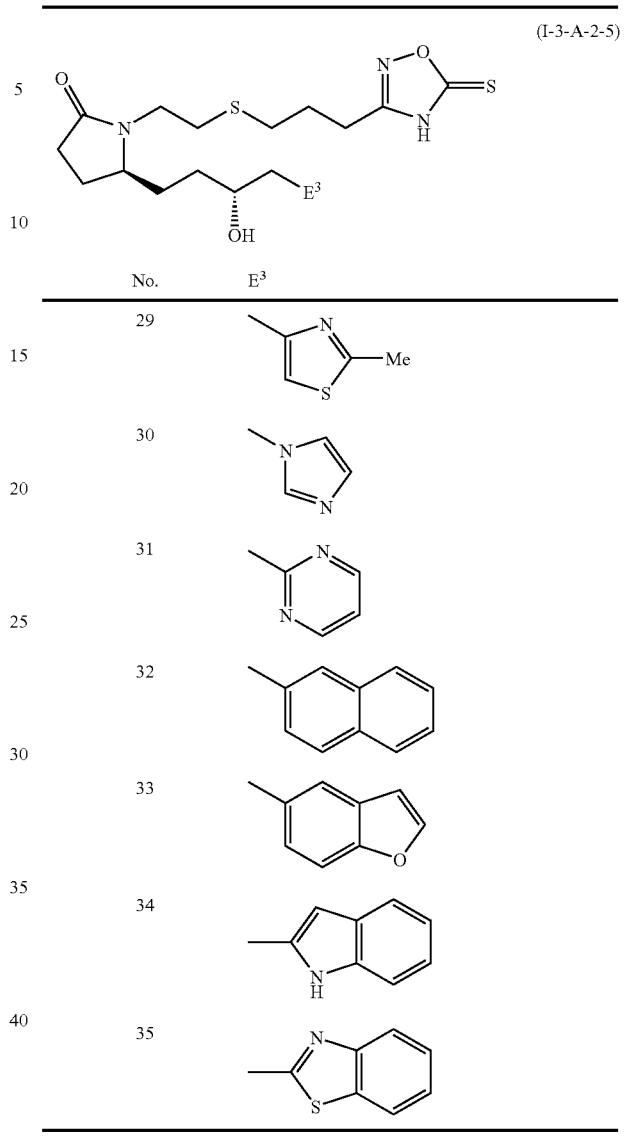
TABLE 16
(I-3-A-2-6)
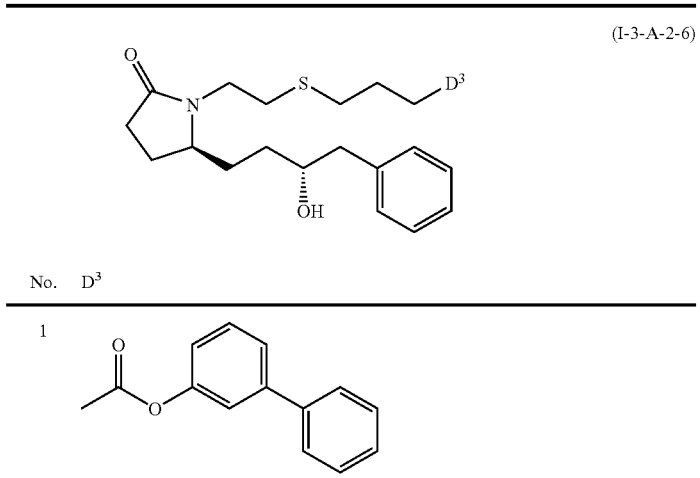

TABLE 16-continued
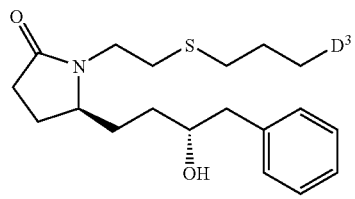
(I-3-A-2-6)
| No. | D³ |
|---|---|
| 2 | 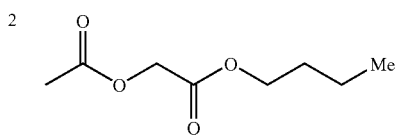 |
| 3 | 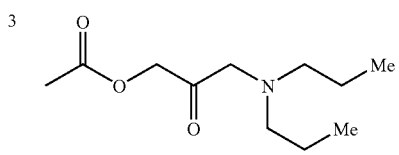 |
| 4 | 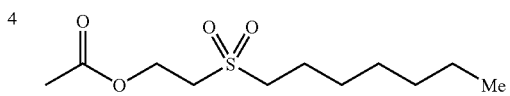 |
| 5 | 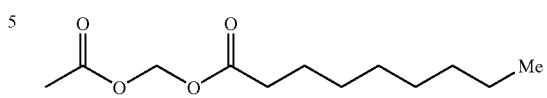 |
| 6 | 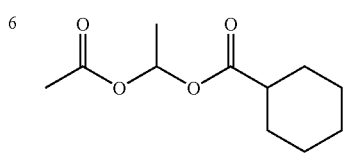 |
| 7 | 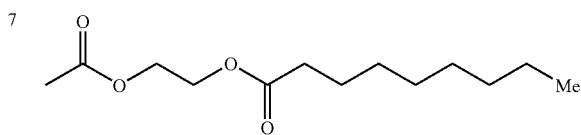 |
| 8 | 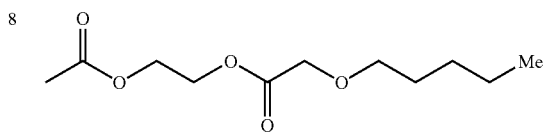 |
| 9 | 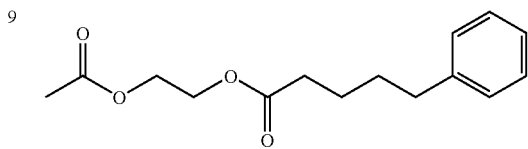 |
| 10 | 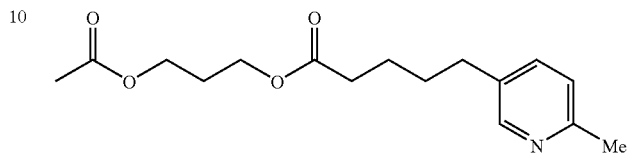 |

TABLE 16-continued
(I-3-A-2-6)
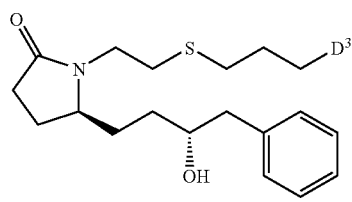
| No. | D³ |
|---|---|
| 11 | 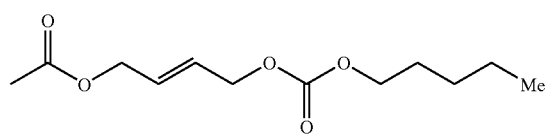 |
| 12 | 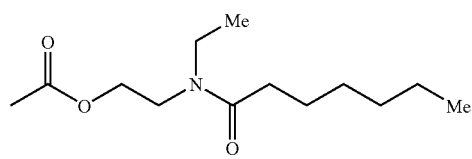 |
| 13 | 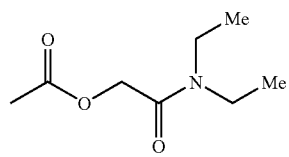 |
| 14 | 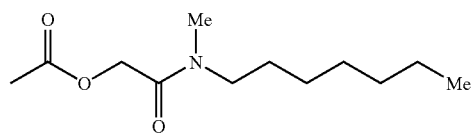 |
| 15 | 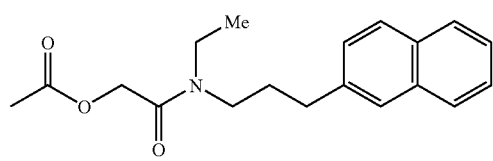 |

TABLE 17
(I-3-A-2-7)
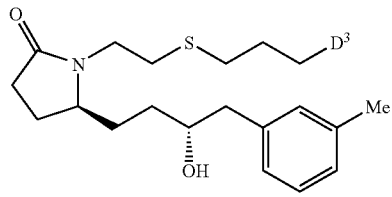
| No. | D³ |
|---|---|
| 1 |  |
| 2 |  |
| 3 | 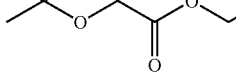 |
| 4 |  |
| 5 | 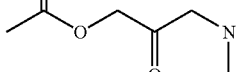 |
| 6 | 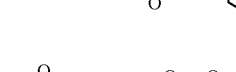 |
| 7 | 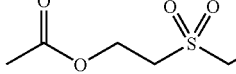 |
| 8 |  |
| 9 | 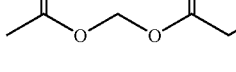 |

TABLE 17-continued
(I-3-A-2-7)
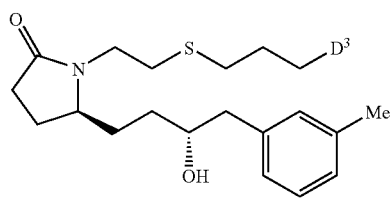
| No. | D³ |
|---|---|
| 10 | 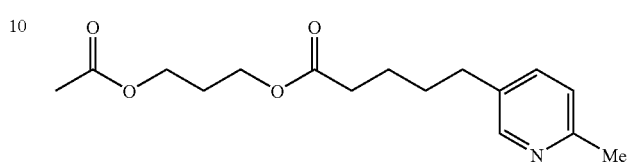 |
| 11 | 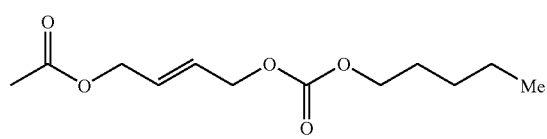 |
| 12 | 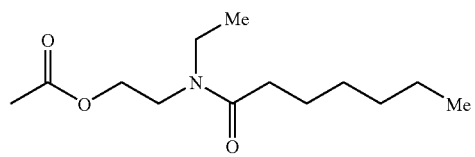 |
| 13 | 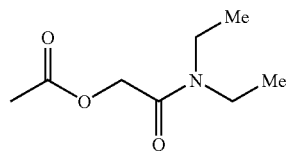 |
| 14 | 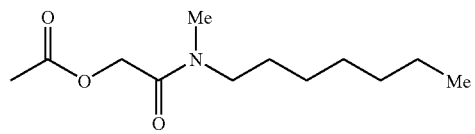 |
| 15 | 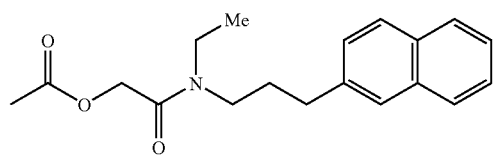 |

TABLE 18
(I-3-A-2-8)
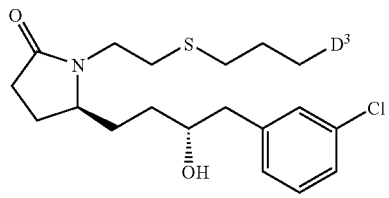
| No. | D³ |
|---|---|
| 1 | 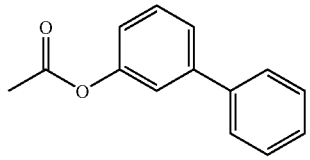 |
| 2 | 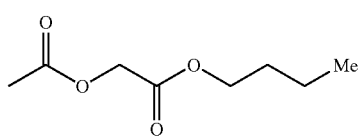 |
| 3 | 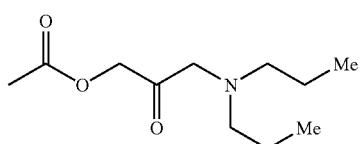 |
| 4 | 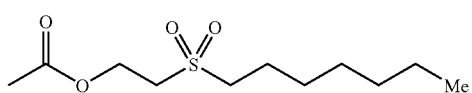 |
| 5 | 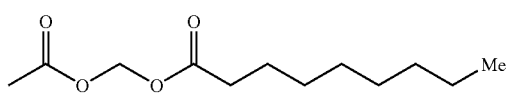 |
| 6 | 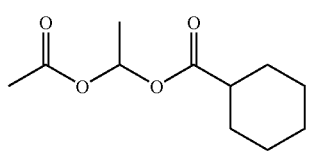 |
| 7 | 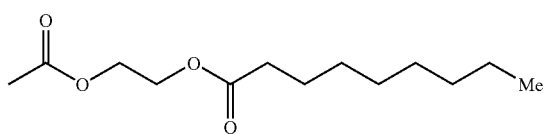 |
| 8 | 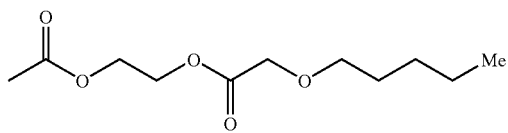 |
| 9 | 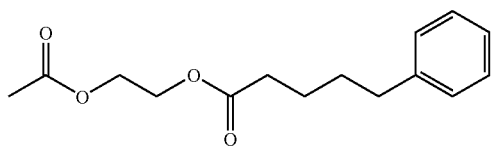 |

TABLE 18-continued
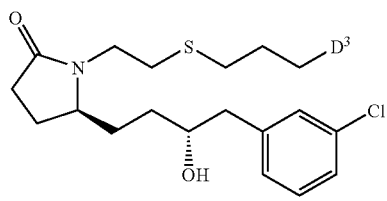
(I-3-A-2-8)
| No. | D³ |
|---|---|
| 10 | 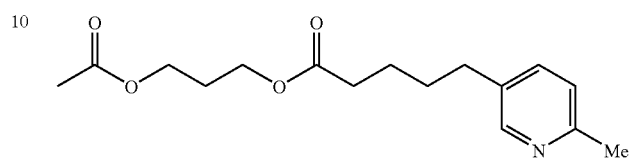 |
| 11 | 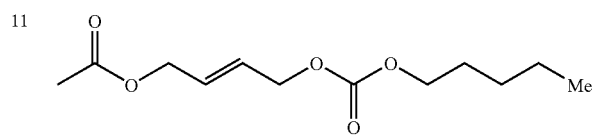 |
| 12 | 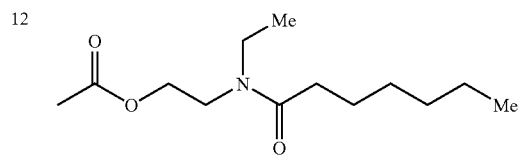 |
| 13 | 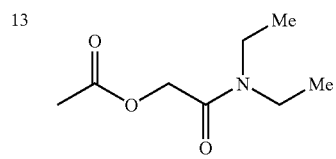 |
| 14 | 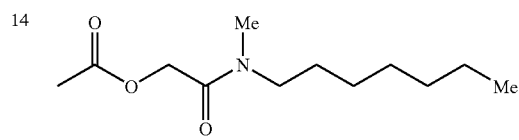 |
| 15 | 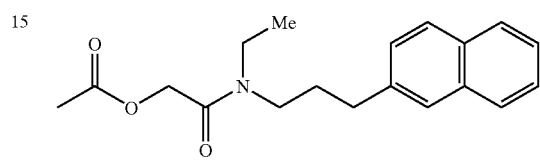 |

TABLE 19
(I-3-A-2-9)
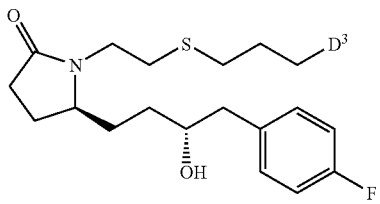
| No. | D³ |
|---|---|
| 1 | 3-phenylphenyl acetate group |
| 2 | butyl (acetoxy)acetate group |
| 3 | [(dipropylamino)methyl]-2-oxoethyl acetate group |
| 4 | 2-(heptylsulfonyl)ethyl acetate group |
| 5 | (acetoxy)methyl nonanoate group |
| 6 | 1-(cyclohexanecarbonyloxy)ethyl acetate group |
| 7 | 2-(nonanoyloxy)ethyl acetate group |
| 8 | 2-[(pentyloxyacetyl)oxy]ethyl acetate group |
| 9 | 2-(5-phenylpentanoyloxy)ethyl acetate group |

TABLE 19-continued
(I-3-A-2-9)
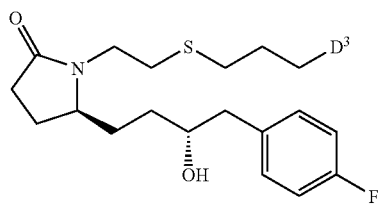
| No. | D³ |
|---|---|
| 10 | 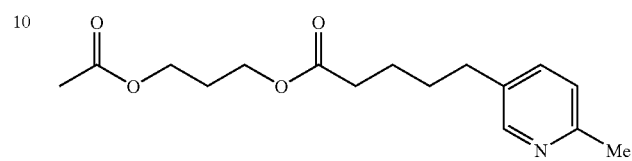 |
| 11 | 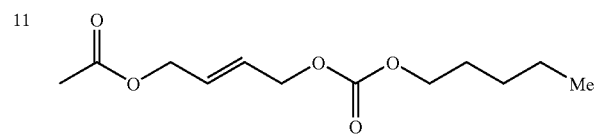 |
| 12 | 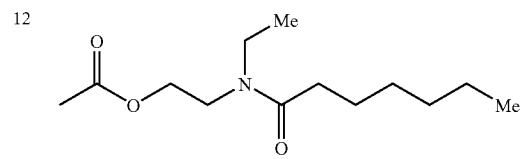 |
| 13 | 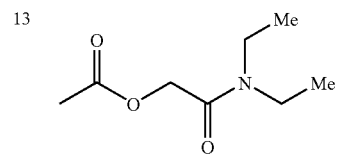 |
| 14 | 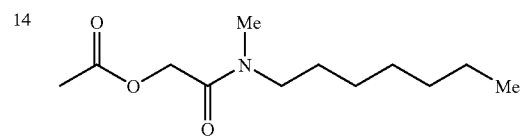 |
| 15 | 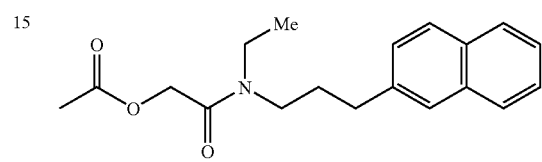 |

TABLE 20
(I-3-A-2-10)
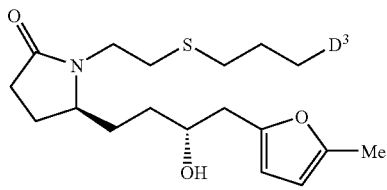
| No. | D³ |
|---|---|
| 1 |  |
| 2 | 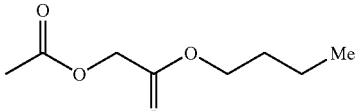 |
| 3 | 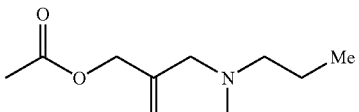 |
| 4 | 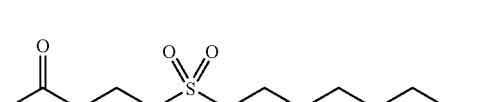 |
| 5 | 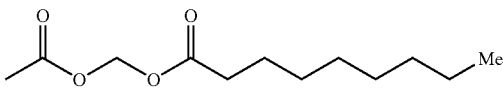 |
| 6 | 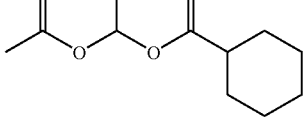 |
| 7 | 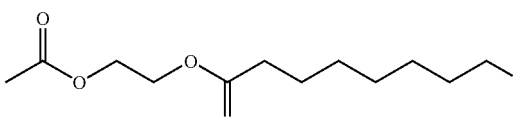 |
| 8 | 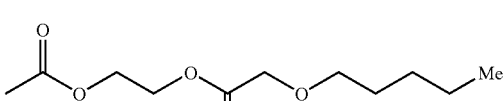 |
| 9 |  |

TABLE 20-continued
(I-3-A-2-10)
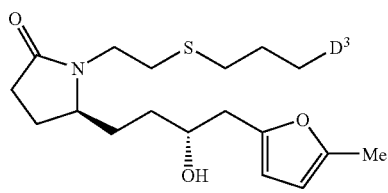
| No. | D³ |
|---|---|
| 10 | 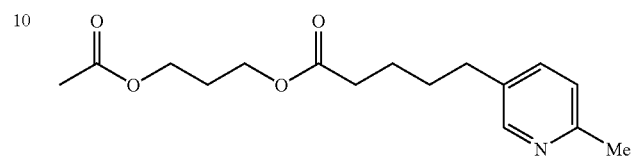 |
| 11 | 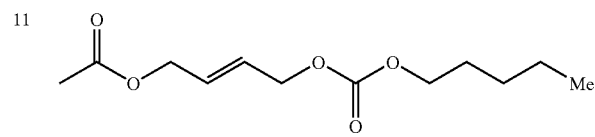 |
| 12 | 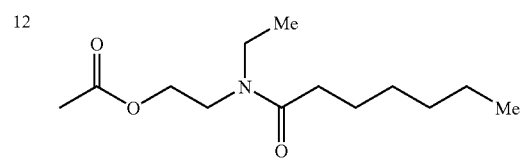 |
| 13 | 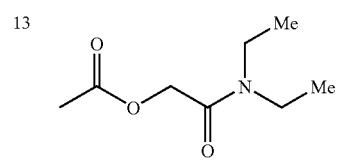 |
| 14 | 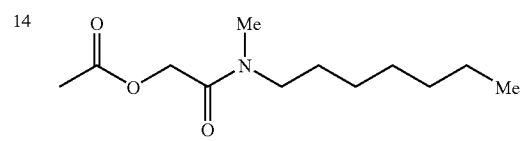 |
| 15 | 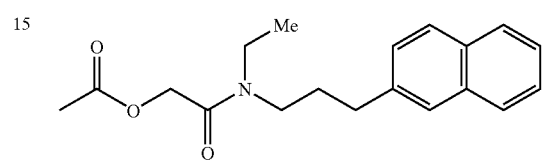 |

TABLE 21
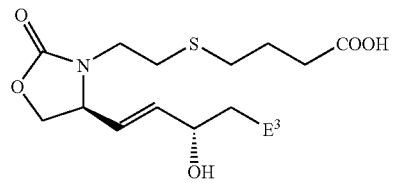
(I-3-A-3-1)
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,4,6-triMe-phenyl |
| 6 | 3-(1-propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
TABLE 21-continued
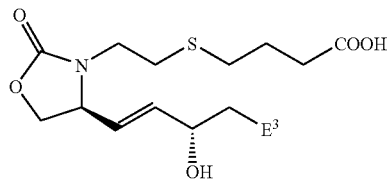
(I-3-A-3-1)
| No. | E³ |
|---|---|
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |
| 22 | 3-OPh-phenyl |

TABLE 21-continued (I-3-A-3-1)

| No. | E³ |
|---|---|
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethylpyridin-4-yl |
| 27 | 5-methylfuran-2-yl |
| 28 | 2-methyloxazol-5-yl |
| 29 | 2-methylthiazol-4-yl |
| 30 | 1-methyl-1H-imidazol-2-yl |
| 31 | 2-methylpyrimidin-5-yl |
| 32 | naphthalen-2-yl |
| 33 | benzofuran-5-yl |
| 34 | 2-methyl-1H-indol-5-yl |

TABLE 21-continued (I-3-A-3-1)

| No. | E³ |
|---|---|
| 35 | 2-methylbenzo[d]thiazol-5-yl |

TABLE 22

(I-3-A-3-2)

| No. | E³ |
|---|---|
| 1 | phenyl |
| 2 | 3-methylphenyl |
| 3 | 3-propylphenyl |
| 4 | 2,4-dimethylphenyl |
| 5 | 2,4,6-trimethylphenyl |
| 6 | 3-(prop-1-en-1-yl)phenyl |
| 7 | 3-ethynylphenyl |

TABLE 22-continued
(I-3-A-3-2)
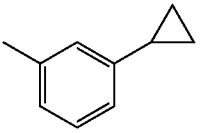
| No. | E³ |
|---|---|
| 8 | 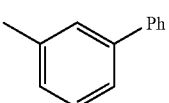 |
| 9 | 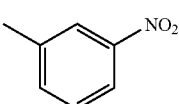 |
| 10 | 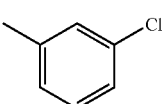 |
| 11 |  |
| 12 |  |
| 13 | 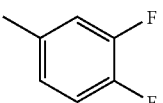 |
| 14 | 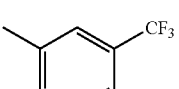 |
| 15 | 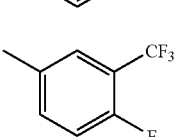 |
| 16 | 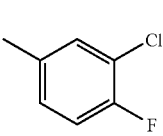 |
| 17 | 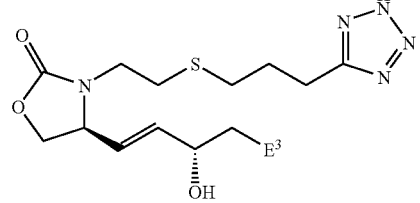 |
TABLE 22-continued
(I-3-A-3-2)
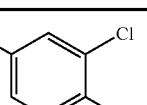
| No. | E³ |
|---|---|
| 18 | 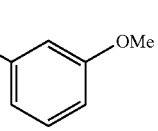 |
| 19 | 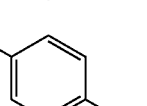 |
| 20 | 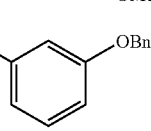 |
| 21 | 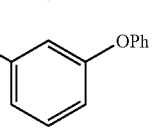 |
| 22 | 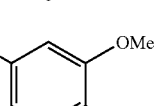 |
| 23 | 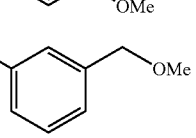 |
| 24 | 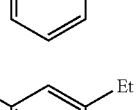 |
| 25 | 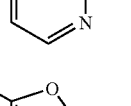 |
| 26 | 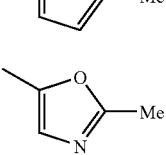 |
| 27 |  |
| 28 |  |

TABLE 22-continued
(I-3-A-3-2)
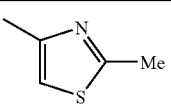
| No. | E³ |
|---|---|
| 29 | 4-methyl-2-methylthiazole |
| 30 | 1-methylimidazole |
| 31 | 2-pyrimidinyl |
| 32 | 2-naphthyl |
| 33 | 5-benzofuranyl |
| 34 | 2-methylindole |
| 35 | 2-methylbenzothiazole |
TABLE 23
(I-3-A-3-3)
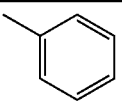
| No. | E³ |
|---|---|
| 1 | Ph |
TABLE 23-continued
(I-3-A-3-3)
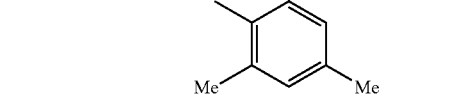
| No. | E³ |
|---|---|
| 2 | 3-Me-C₆H₄ |
| 3 | 3-Pr-C₆H₄ |
| 4 | 3,4-diMe-C₆H₃ |
| 5 | 2,3,5-triMe-C₆H₂ |
| 6 | 3-(propenyl)-C₆H₄ |
| 7 | 3-ethynyl-C₆H₄ |
| 8 | 3-cyclopropyl-C₆H₄ |
| 9 | 3-Ph-C₆H₄ |
| 10 | 3-NO₂-C₆H₄ |
| 11 | 3-Cl-C₆H₄ |

TABLE 23-continued
(I-3-A-3-3)
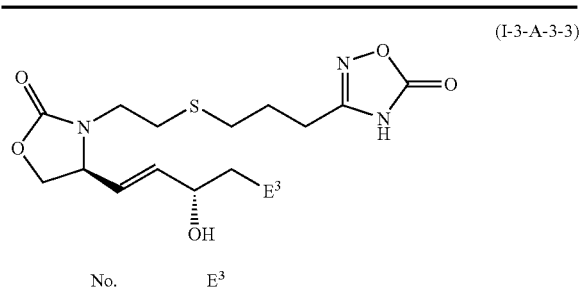
| No. | E³ |
|---|---|
| 12 | 4-F-C₆H₄ |
| 13 | 3,5-diF-C₆H₃ |
| 14 | 3,4-diF-C₆H₃ |
| 15 | 3-CF₃-C₆H₄ |
| 16 | 2-CF₃-4-F-C₆H₃ |
| 17 | 2-Cl-4-F-C₆H₃ |
| 18 | 2-Cl-4-OH-C₆H₃ |
| 19 | 3-OMe-C₆H₄ |
| 20 | 4-OMe-C₆H₄ |
| 21 | 3-OBn-C₆H₄ |
| 22 | 3-OPh-C₆H₄ |
TABLE 23-continued
(I-3-A-3-3)
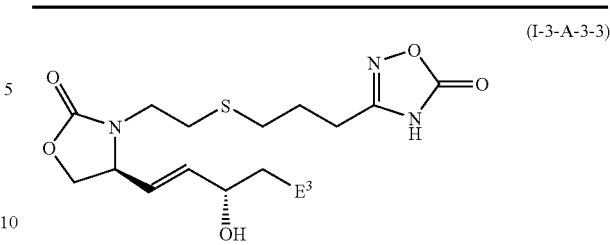
| No. | E³ |
|---|---|
| 23 | 3,4-diOMe-C₆H₃ |
| 24 | 3-(CH₂OMe)-C₆H₄ |
| 25 | 3-(CH₂OCH₂CF₃)-C₆H₄ |
| 26 | 2-Et-4-pyridyl |
| 27 | 5-Me-2-furyl |
| 28 | 2-Me-5-oxazolyl |
| 29 | 2-Me-4-thiazolyl |
| 30 | 1-Me-imidazol-4-yl |
| 31 | 2-pyrimidinyl |
| 32 | 2-naphthyl |
| 33 | 5-benzofuranyl |
| 34 | 2-indolyl |

TABLE 23-continued (I-3-A-3-3)

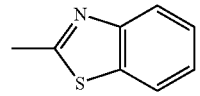

| No. | E³ |
|---|---|
| 35 | 2-benzothiazolyl |

TABLE 24

(I-3-A-3-4)

| No. | E³ |
|---|---|
| 1 | phenyl |
| 2 | 3-methylphenyl (with Me) |
| 3 | 3-propylphenyl (Pr) |
| 4 | 2,4-dimethylphenyl |
| 5 | 2,4,6-trimethylphenyl (mesityl) |
| 6 | 3-(1-propenyl)phenyl |

TABLE 24-continued (I-3-A-3-4)

| No. | E³ |
|---|---|
| 7 | 3-ethynylphenyl |
| 8 | 3-cyclopropylphenyl |
| 9 | 3-phenylphenyl (Ph) |
| 10 | 3-nitrophenyl (NO₂) |
| 11 | 3-chlorophenyl (Cl) |
| 12 | 4-fluorophenyl (F) |
| 13 | 3,5-difluorophenyl |
| 14 | 3,4-difluorophenyl |
| 15 | 3-trifluoromethylphenyl (CF₃) |
| 16 | 3-trifluoromethyl-4-fluorophenyl |

TABLE 24-continued
(I-3-A-3-4)
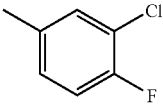
| No. | E³ |
|---|---|
| 17 | 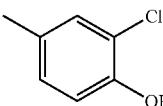 |
| 18 | 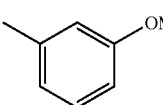 |
| 19 | 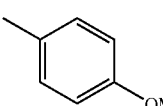 |
| 20 | 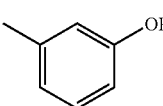 |
| 21 | 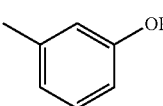 |
| 22 | 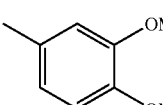 |
| 23 | 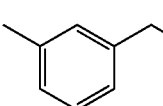 |
| 24 | 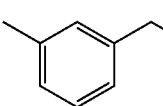 |
| 25 | 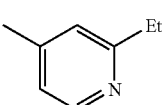 |
| 26 | 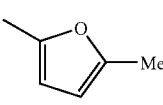 |
| 27 | 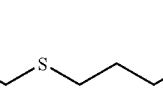 |
TABLE 24-continued
(I-3-A-3-4)
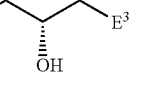
| No. | E³ |
|---|---|
| 28 | 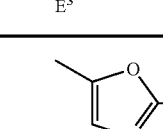 |
| 29 | 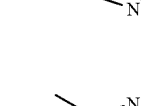 |
| 30 | 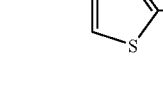 |
| 31 | 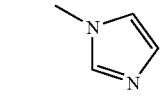 |
| 32 | 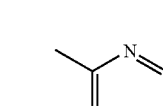 |
| 33 | 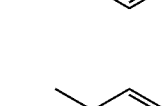 |
| 34 | 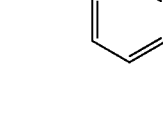 |
| 35 | 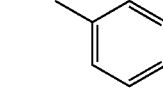 |

TABLE 25
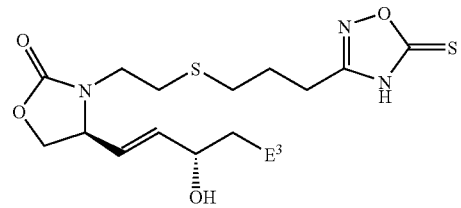
(I-3-A-3-5)
| No. | E³ |
|---|---|
| 1 | 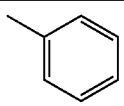 |
| 2 | 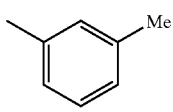 |
| 3 | 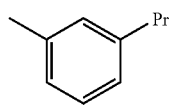 |
| 4 | 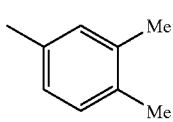 |
| 5 | 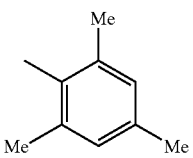 |
| 6 | 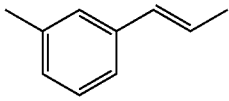 |
| 7 | 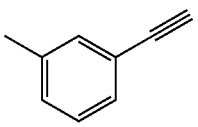 |
| 8 | 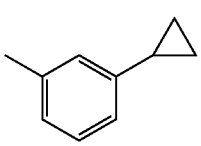 |
| 9 | 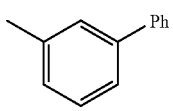 |
| 10 | 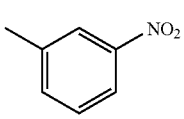 |
TABLE 25-continued
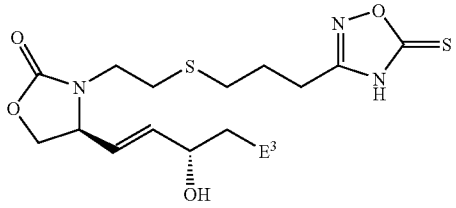
(I-3-A-3-5)
| No. | E³ |
|---|---|
| 11 | 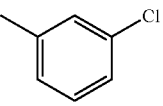 |
| 12 | 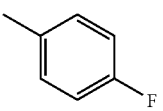 |
| 13 |  |
| 14 | 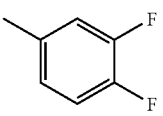 |
| 15 | 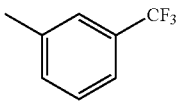 |
| 16 | 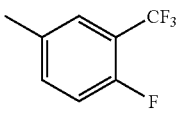 |
| 17 | 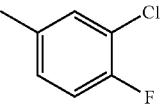 |
| 18 | 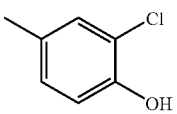 |
| 19 | 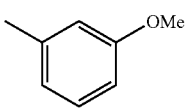 |
| 20 | 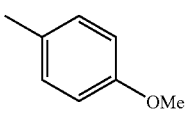 |
| 21 | 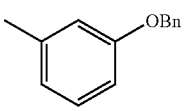 |

TABLE 25-continued
(I-3-A-3-5)
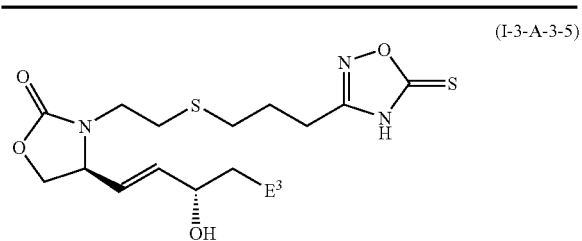
| No. | E³ |
|---|---|
| 22 | 3-PhO-phenyl |
| 23 | 3,4-(OMe)₂-phenyl |
| 24 | 3-(CH₂OMe)-phenyl |
| 25 | 3-(CH₂OCH₂CF₃)-phenyl |
| 26 | 2-Et-4-pyridyl |
| 27 | 5-Me-furan-2-yl |
| 28 | 5-Me-oxazol-2-yl |
| 29 | 2,4-dimethylthiazol-5-yl |
| 30 | 1-methylimidazol-2-yl |
| 31 | 2-methylpyrimidin-4-yl |
| 32 | 6-methylnaphthalen-2-yl |
| 33 | 5-methylbenzofuran-2-yl |
| 34 | 2-methyl-1H-indol-5-yl |
| 35 | 2-methylbenzothiazol-5-yl |
TABLE 26
(I-3-A-3-6)
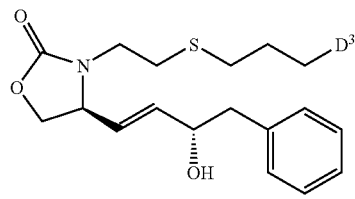
| No. | D³ |
|---|---|
| 1 | 3-acetoxy-biphenyl-3-yl |

TABLE 26-continued
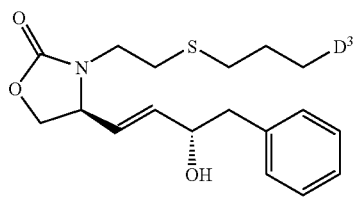
(I-3-A-3-6)
| No. | D³ |
|---|---|
| 2 | 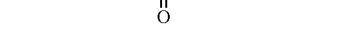 |
| 3 | 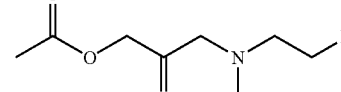 |
| 4 |  |
| 5 | 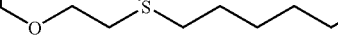 |
| 6 | 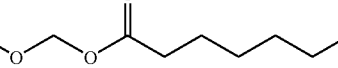 |
| 7 | 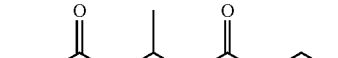 |
| 8 |  |
| 9 | 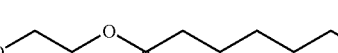 |
| 10 | 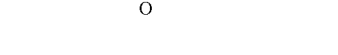 |

TABLE 26-continued
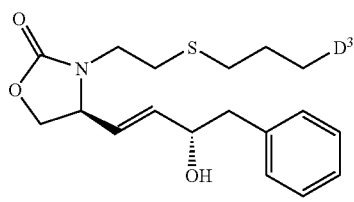
(I-3-A-3-6)
| No. | D³ |
|---|---|
| 11 | 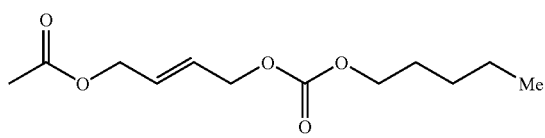 |
| 12 | 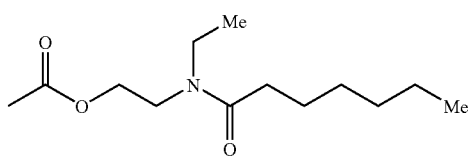 |
| 13 | 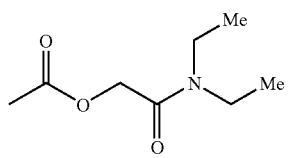 |
| 14 | 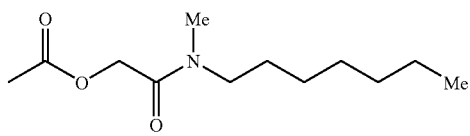 |
| 15 | 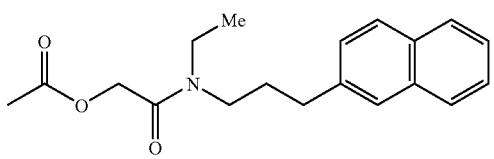 |

TABLE 27
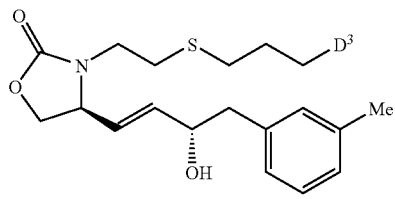
(I-3-A-3-7)
| No. | D³ |
|---|---|
| 1 | 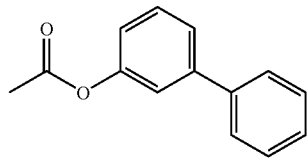 |
| 2 | 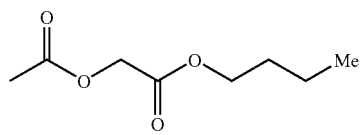 |
| 3 | 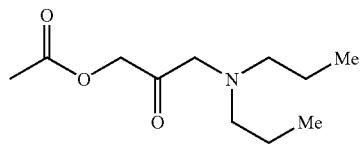 |
| 4 | 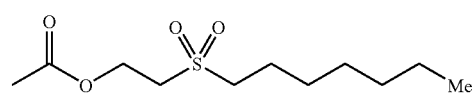 |
| 5 | 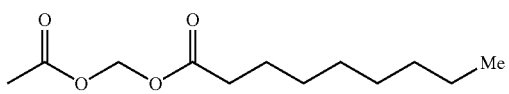 |
| 6 | 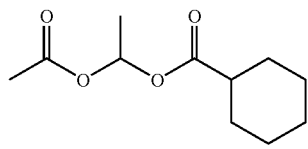 |
| 7 | 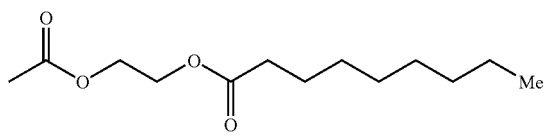 |
| 8 | 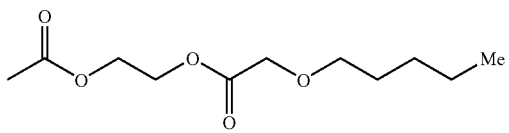 |
| 9 | 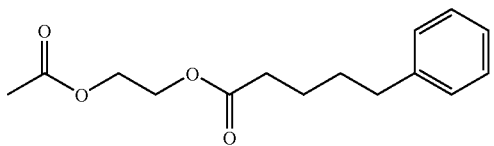 |

TABLE 27-continued
(I-3-A-3-7)
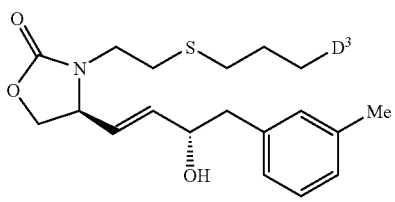
| No. | D³ |
|---|---|
| 10 | 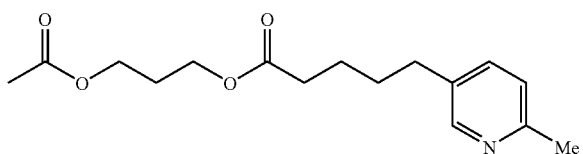 |
| 11 | 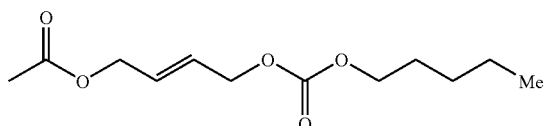 |
| 12 | 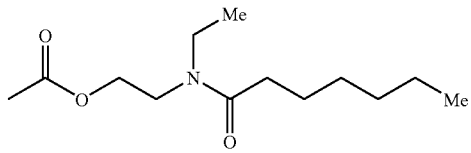 |
| 13 | 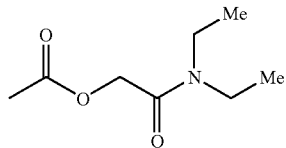 |
| 14 | 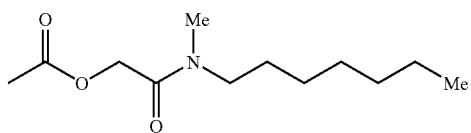 |
| 15 | 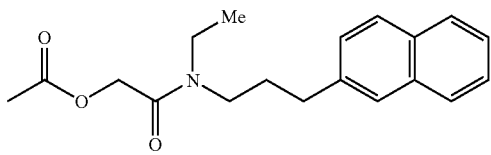 |

TABLE 28
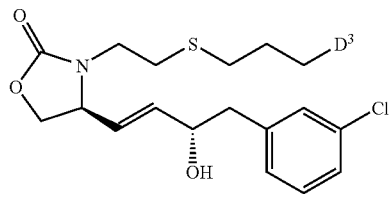
(I-3-A-3-8)
| No. | D³ |
|-----|-----|
| 1 | 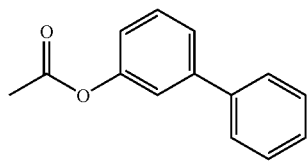 |
| 2 | 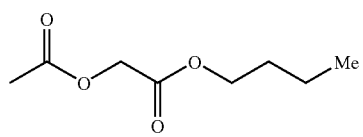 |
| 3 | 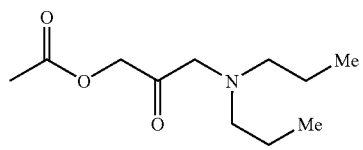 |
| 4 | 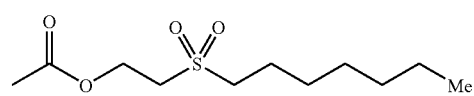 |
| 5 | 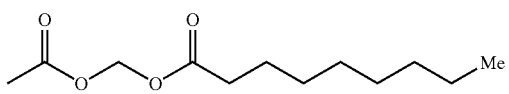 |
| 6 | 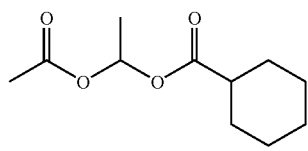 |
| 7 | 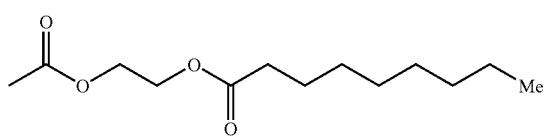 |
| 8 | 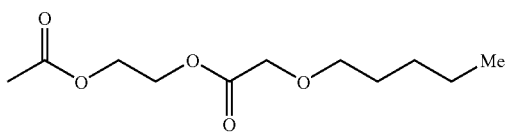 |
| 9 | 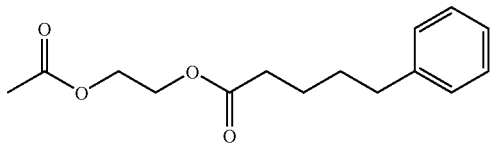 |

TABLE 28-continued
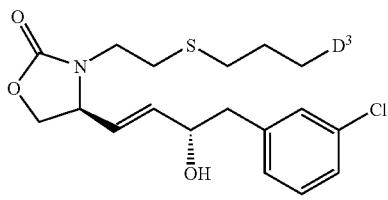
(I-3-A-3-8)
| No. | D³ |
|---|---|
| 10 | 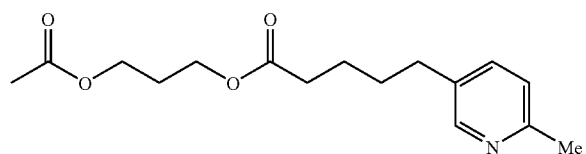 |
| 11 | 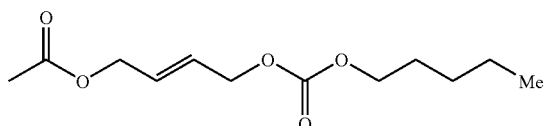 |
| 12 | 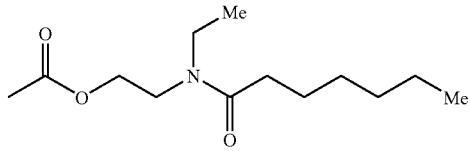 |
| 13 | 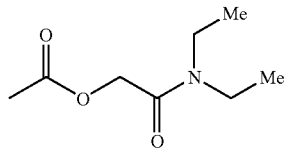 |
| 14 | 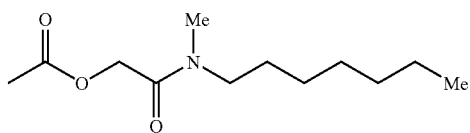 |
| 15 | 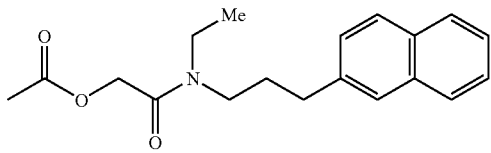 |

TABLE 29
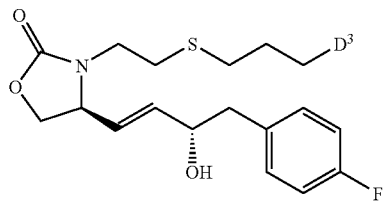
(I-3-A-3-9)
| No. | D³ |
|---|---|
| 1 | 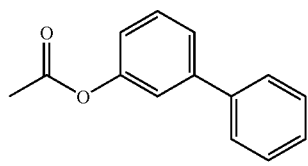 |
| 2 | 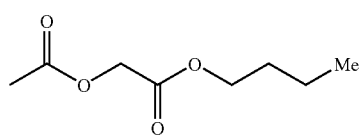 |
| 3 | 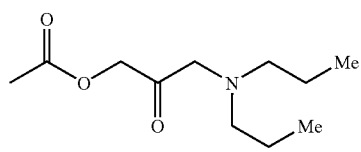 |
| 4 | 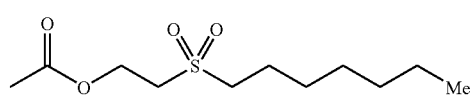 |
| 5 | 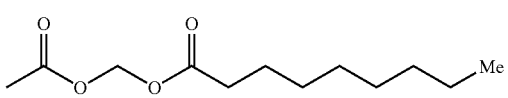 |
| 6 | 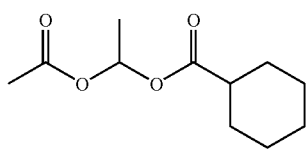 |
| 7 | 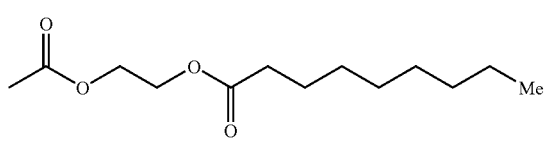 |
| 8 | 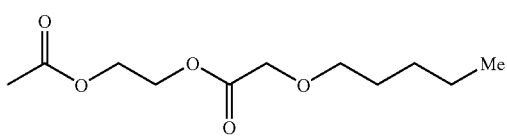 |
| 9 | 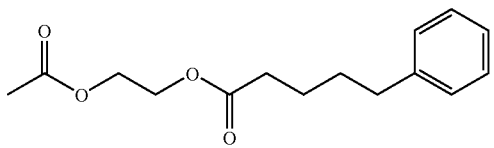 |

TABLE 29-continued
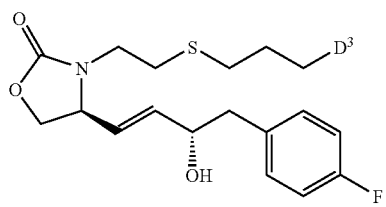
(I-3-A-3-9)
| No. | D³ |
|---|---|
| 10 | 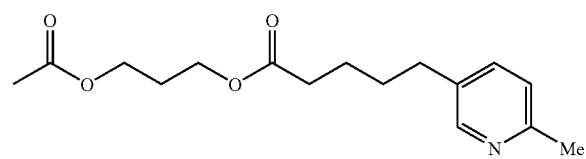 |
| 11 | 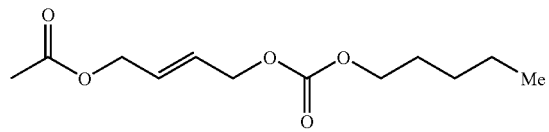 |
| 12 | 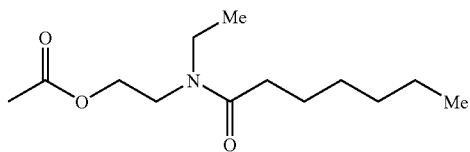 |
| 13 | 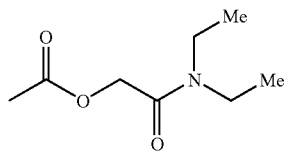 |
| 14 | 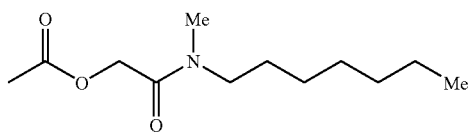 |
| 15 | 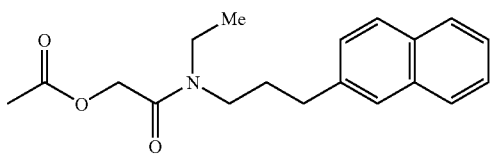 |

TABLE 30
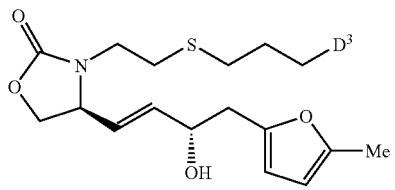
(I-3-A-3-10)
| No. | D³ |
|---|---|
| 1 | 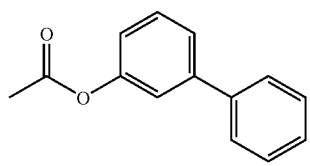 |
| 2 | 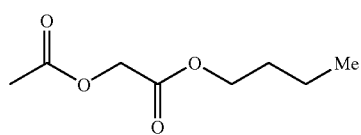 |
| 3 | 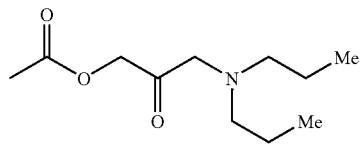 |
| 4 | 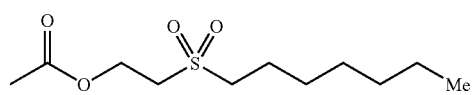 |
| 5 | 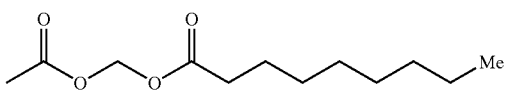 |
| 6 | 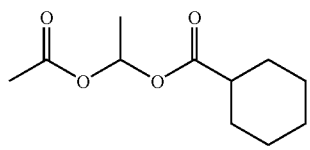 |
| 7 | 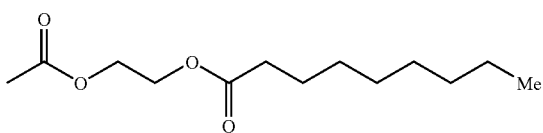 |
| 8 | 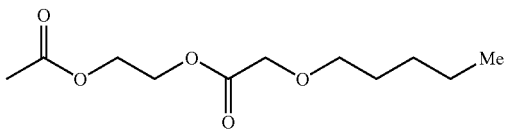 |
| 9 | 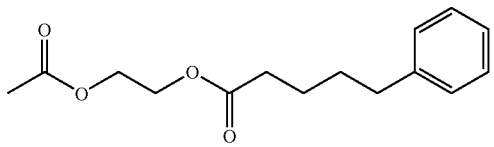 |

TABLE 30-continued
(I-3-A-3-10)
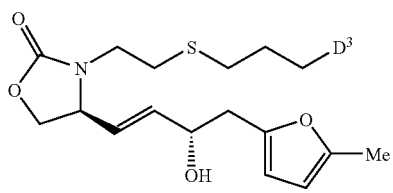
| No. | D³ |
|---|---|
| 10 | 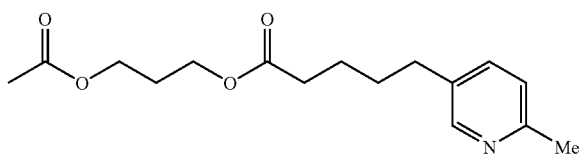 |
| 11 | 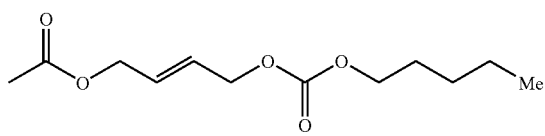 |
| 12 | 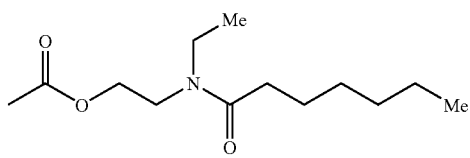 |
| 13 | 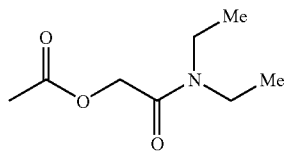 |
| 14 | 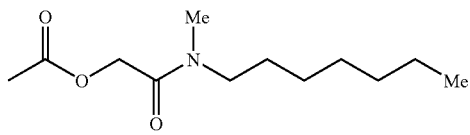 |
| 15 | 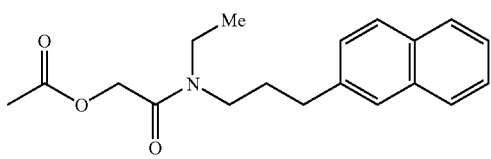 |

TABLE 31
(I-3-A-4-1)
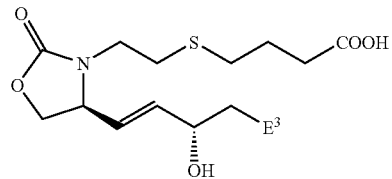
| No. | E³ |
|---|---|
| 1 | phenyl |
| 2 | 3-Me-phenyl |
| 3 | 3-Pr-phenyl |
| 4 | 2,4-diMe-phenyl |
| 5 | 2,3,5-triMe-phenyl |
| 6 | 3-(1-propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
TABLE 31-continued
(I-3-A-4-1)
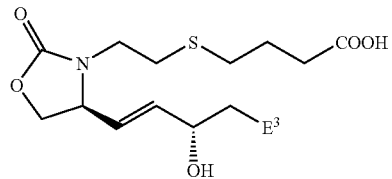
| No. | E³ |
|---|---|
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |
| 22 | 3-OPh-phenyl |

TABLE 31-continued (I-3-A-4-1)

| No. | E³ |
|---|---|
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethylpyridin-4-yl |
| 27 | 5-methylfuran-2-yl |
| 28 | 2-methyloxazol-5-yl |
| 29 | 2-methylthiazol-4-yl |
| 30 | 1-methyl-1H-imidazol-5-yl |
| 31 | 2-methylpyrimidin-5-yl |
| 32 | naphthalen-2-yl |
| 33 | benzofuran-5-yl |
| 34 | 2-methyl-1H-indol-5-yl |

TABLE 31-continued (I-3-A-4-1)

| No. | E³ |
|---|---|
| 35 | 2-methylbenzothiazol-5-yl |

TABLE 32

(I-3-A-4-2)

| No. | E³ |
|---|---|
| 1 | phenyl |
| 2 | 3-methylphenyl |
| 3 | 3-propylphenyl |
| 4 | 2,5-dimethylphenyl |
| 5 | 2,4,6-trimethylphenyl |
| 6 | 3-(prop-1-enyl)phenyl |
| 7 | 3-ethynylphenyl |

TABLE 32-continued
(I-3-A-4-2)

| No. | E³ |
|---|---|
| 8 |  |
| 9 |  |
| 10 |  |
| 11 |  |
| 12 |  |
| 13 |  |
| 14 |  |
| 15 |  |
| 16 |  |
| 17 |  |
TABLE 32-continued
(I-3-A-4-2)

| No. | E³ |
|---|---|
| 18 |  |
| 19 |  |
| 20 |  |
| 21 |  |
| 22 |  |
| 23 |  |
| 24 |  |
| 25 |  |
| 26 | |
| 27 | |
| 28 |  |

TABLE 32-continued
(I-3-A-4-2)

| No. | E³ |
|---|---|
| 29 |  |
| 30 |  |
| 31 |  |
| 32 |  |
| 33 |  |
| 34 |  |
| 35 | 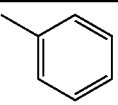 |
TABLE 33
(I-3-A-4-3)
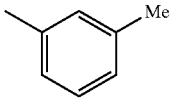
| No. | E³ |
|---|---|
| 1 | 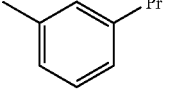 |
TABLE 33-continued
(I-3-A-4-3)
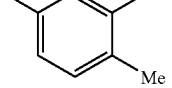
| No. | E³ |
|---|---|
| 2 | 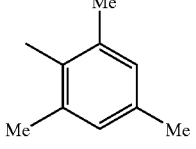 |
| 3 | 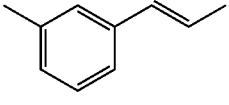 |
| 4 | 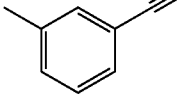 |
| 5 | 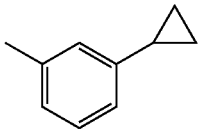 |
| 6 | 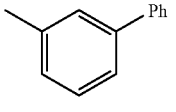 |
| 7 | 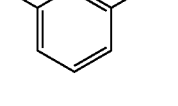 |
| 8 | 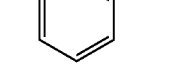 |
| 9 | Ph |
| 10 | NO₂ |
| 11 | Cl |

TABLE 33-continued
(I-3-A-4-3)
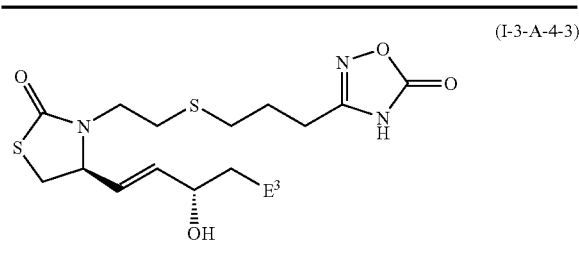
| No. | E³ |
|---|---|
| 12 | 4-F-C6H4 |
| 13 | 3,5-di-F-C6H3 |
| 14 | 3,4-di-F-C6H3 |
| 15 | 3-CF3-C6H4 |
| 16 | 3-CF3-4-F-C6H3 |
| 17 | 3-Cl-4-F-C6H3 |
| 18 | 3-Cl-4-OH-C6H3 |
| 19 | 3-OMe-C6H4 |
| 20 | 4-OMe-C6H4 |
| 21 | 3-OBn-C6H4 |
| 22 | 3-OPh-C6H4 |
TABLE 33-continued
(I-3-A-4-3)
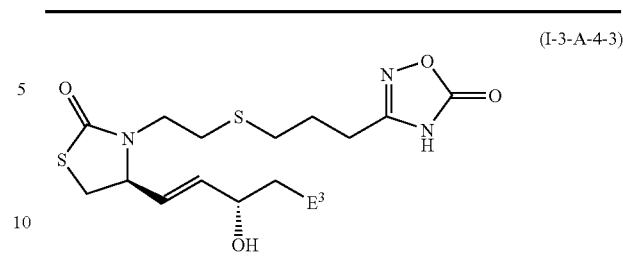
| No. | E³ |
|---|---|
| 23 | 3,4-di-OMe-C6H3 |
| 24 | 3-(CH2OMe)-C6H4 |
| 25 | 3-(CH2OCH2CF3)-C6H4 |
| 26 | 2-Et-4-pyridyl |
| 27 | 5-Me-2-furyl |
| 28 | 2-Me-5-oxazolyl |
| 29 | 2-Me-4-thiazolyl |
| 30 | 1-Me-imidazol-4-yl |
| 31 | 2-pyrimidinyl |
| 32 | 6-naphthyl |
| 33 | 5-benzofuranyl |

TABLE 33-continued
(I-3-A-4-3)
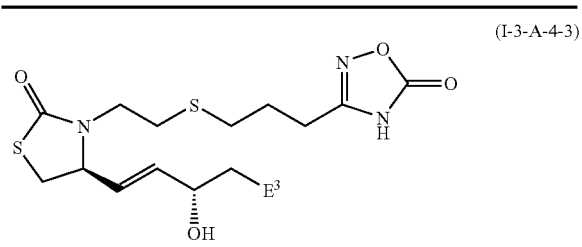
| No. | E³ |
|---|---|
| 34 | 2-indolyl (NH) |
| 35 | 2-benzothiazolyl |
TABLE 34
(I-3-A-4-4)
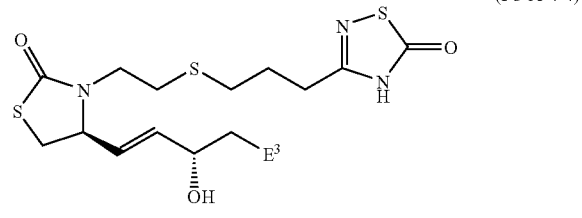
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,3,5-triMe-phenyl |
| 6 | 3-(propenyl)phenyl |
TABLE 34-continued
(I-3-A-4-4)
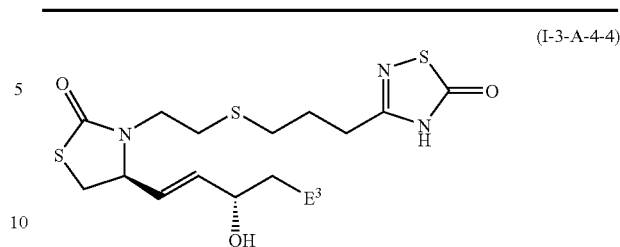
| No. | E³ |
|---|---|
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |

TABLE 34-continued
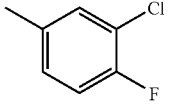
(I-3-A-4-4)
| No. | E³ |
|---|---|
| 17 | 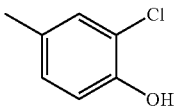 |
| 18 | 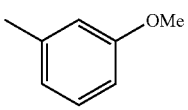 |
| 19 | 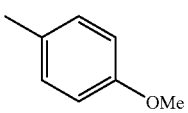 |
| 20 | 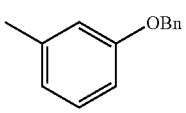 |
| 21 | 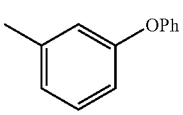 |
| 22 | 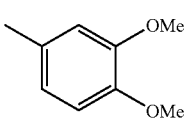 |
| 23 | 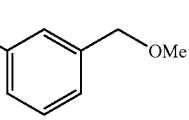 |
| 24 | 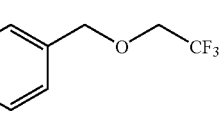 |
| 25 | 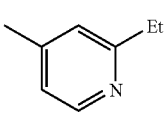 |
| 26 | 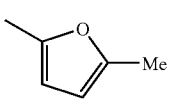 |
| 27 | 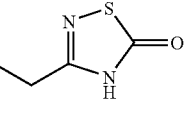 |
TABLE 34-continued
(I-3-A-4-4)
| No. | E³ |
|---|---|
| 28 | 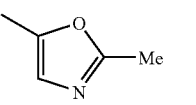 |
| 29 | 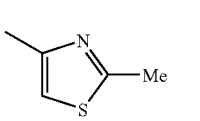 |
| 30 | 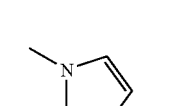 |
| 31 | 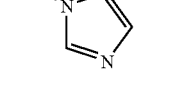 |
| 32 | 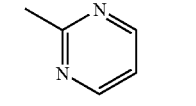 |
| 33 | 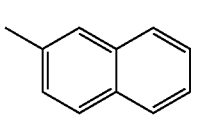 |
| 34 | 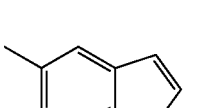 |
| 35 | 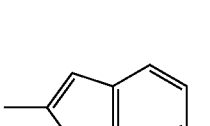 |

TABLE 35
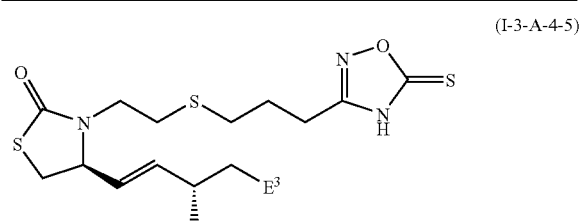
(I-3-A-4-5)
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,4,6-triMe-phenyl (mesityl) |
| 6 | 3-(1-propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
TABLE 35-continued
(I-3-A-4-5)
| No. | E³ |
|---|---|
| 11 | 3-Cl-phenyl |
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |

TABLE 35-continued
(I-3-A-4-5)
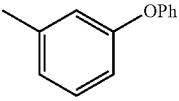
| No. | E³ |
|---|---|
| 22 | 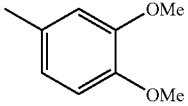 |
| 23 | 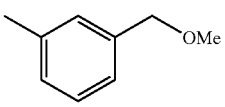 |
| 24 | 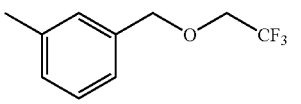 |
| 25 | 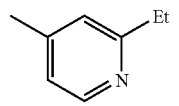 |
| 26 | 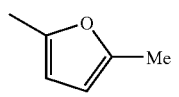 |
| 27 | 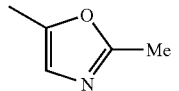 |
| 28 | 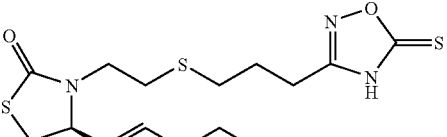 |
TABLE 35-continued
(I-3-A-4-5)
| No. | E³ |
|---|---|
| 29 | 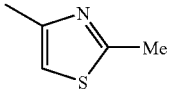 |
| 30 | 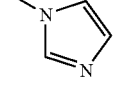 |
| 31 |  |
| 32 | 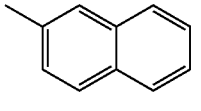 |
| 33 | 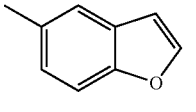 |
| 34 | 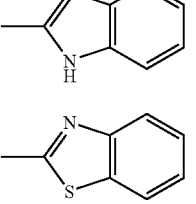 |
| 35 | 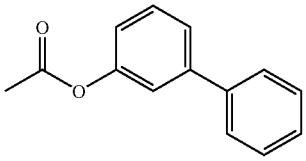 |
TABLE 36
(I-3-A-4-6)
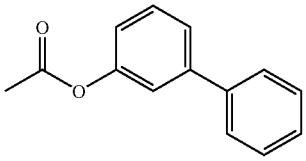
| No. | D³ |
|---|---|
| 1 | 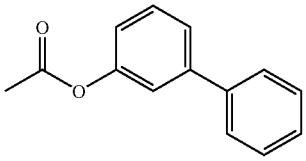 |

TABLE 36-continued
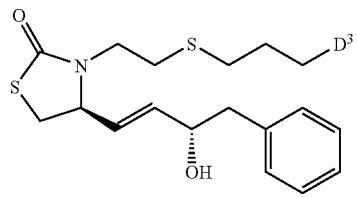
(I-3-A-4-6)
| No. | D³ |
|---|---|
| 2 | 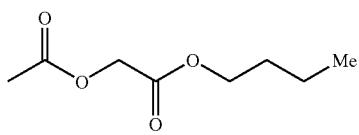 |
| 3 | 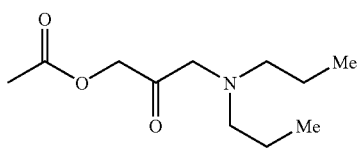 |
| 4 | 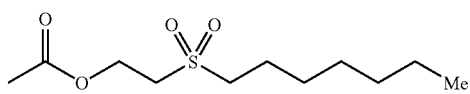 |
| 5 | 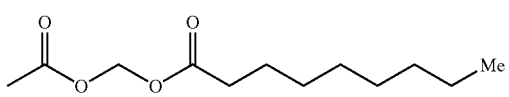 |
| 6 | 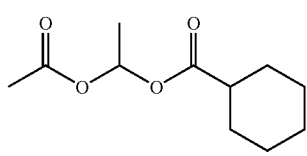 |
| 7 | 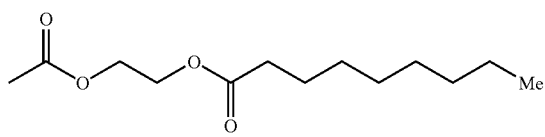 |
| 8 | 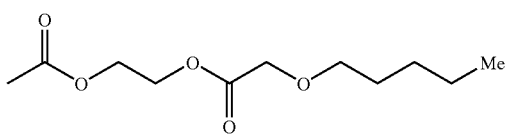 |
| 9 | 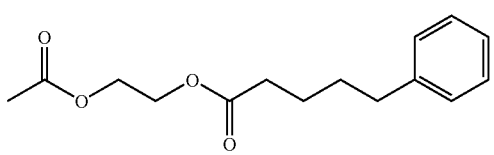 |
| 10 | 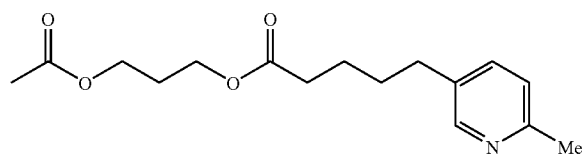 |

TABLE 36-continued
(I-3-A-4-6)
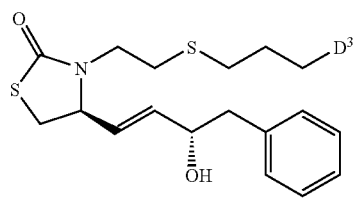
| No. | D³ |
|---|---|
| 11 | 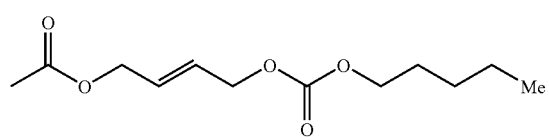 |
| 12 | 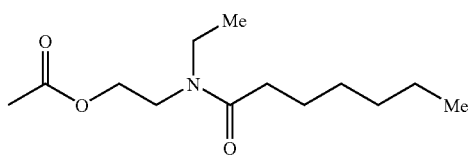 |
| 13 | 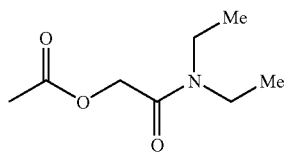 |
| 14 | 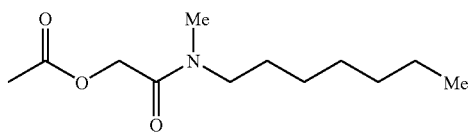 |
| 15 | 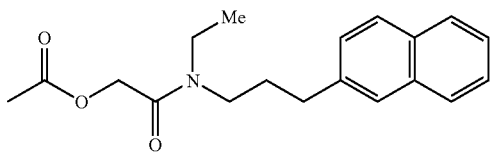 |

TABLE 37
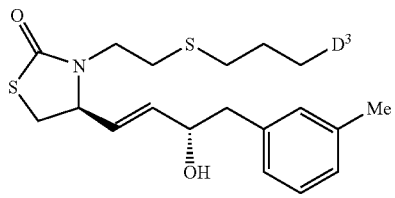
(I-3-A-4-7)
| No. | D³ |
|---|---|
| 1 | 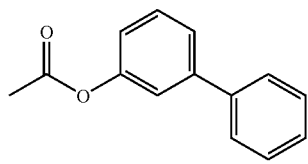 |
| 2 | 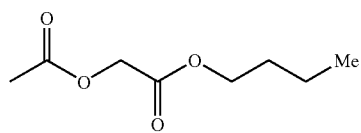 |
| 3 | 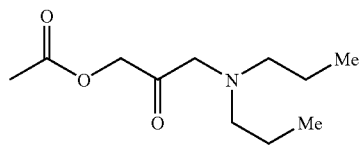 |
| 4 | 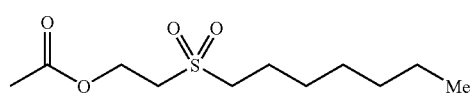 |
| 5 | 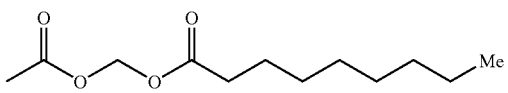 |
| 6 | 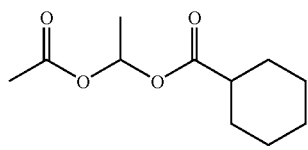 |
| 7 | 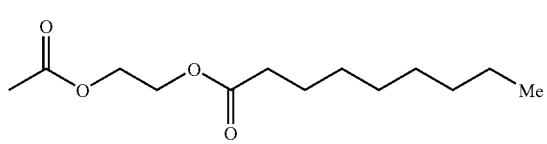 |
| 8 | 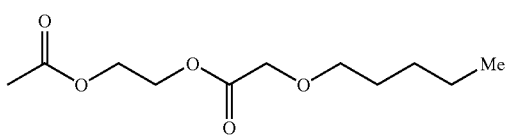 |
| 9 | 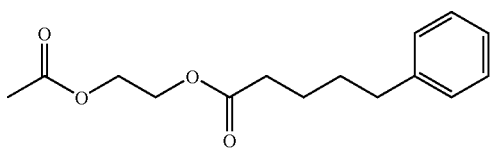 |

TABLE 37-continued
(I-3-A-4-7)
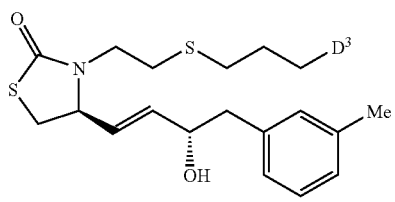
| No. | D³ |
|---|---|
| 10 | 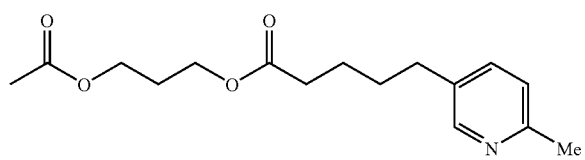 |
| 11 | 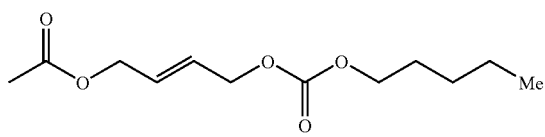 |
| 12 | 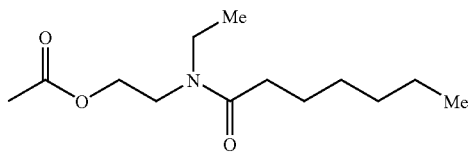 |
| 13 | 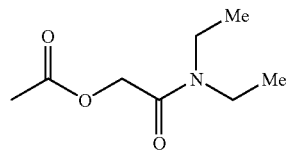 |
| 14 | 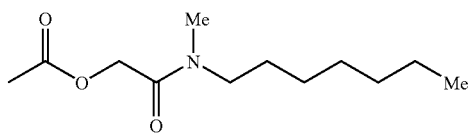 |
| 15 | 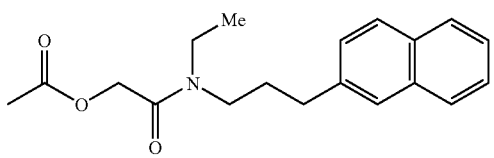 |

TABLE 38
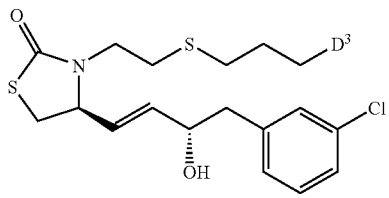
(I-3-A-4-8)
| No. | D³ |
|---|---|
| 1 | 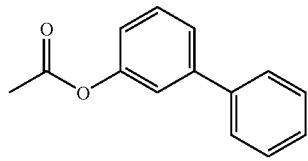 |
| 2 | 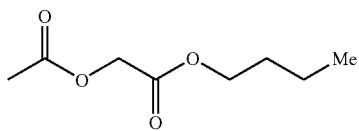 |
| 3 | 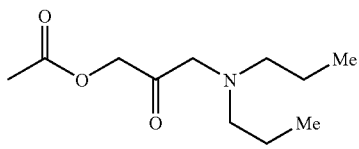 |
| 4 | 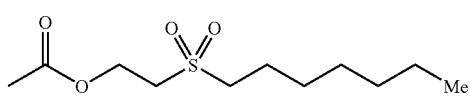 |
| 5 | 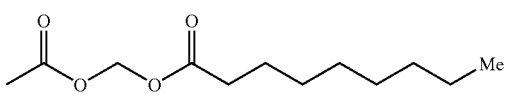 |
| 6 | 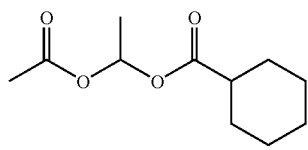 |
| 7 | 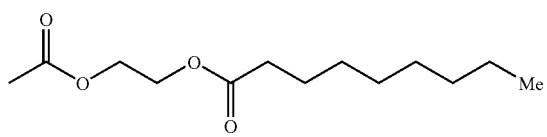 |
| 8 | 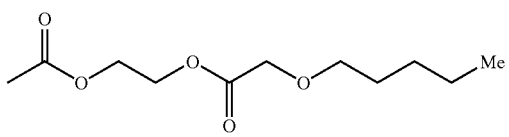 |
| 9 | 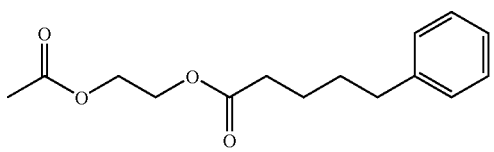 |

TABLE 38-continued
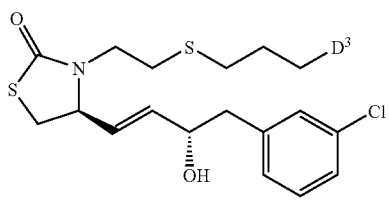
(I-3-A-4-8)
| No. | D³ |
|---|---|
| 10 | 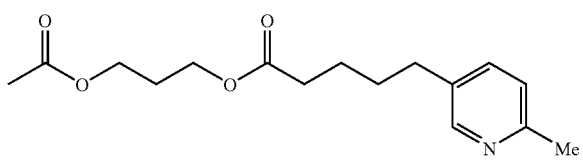 |
| 11 | 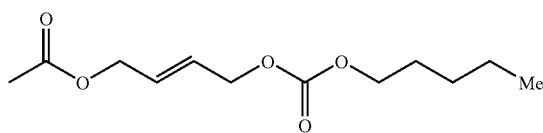 |
| 12 | 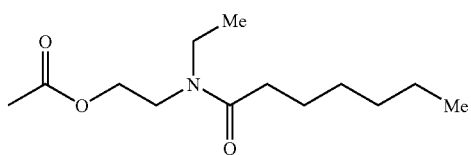 |
| 13 | 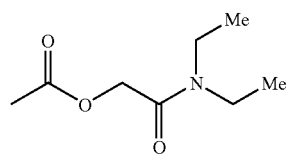 |
| 14 | 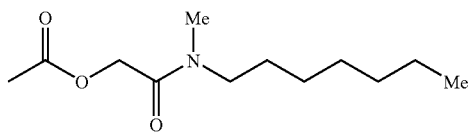 |
| 15 | 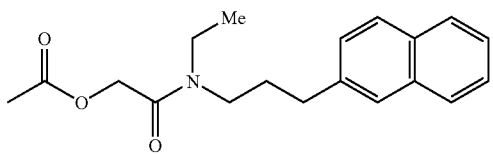 |

TABLE 39
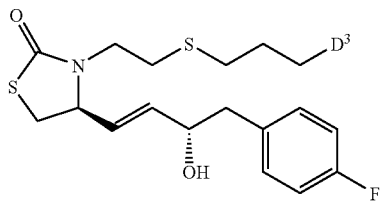
(I-3-A-4-9)
| No. | D³ |
|---|---|
| 1 | 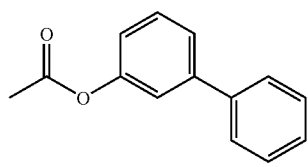 |
| 2 | 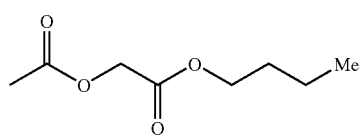 |
| 3 | 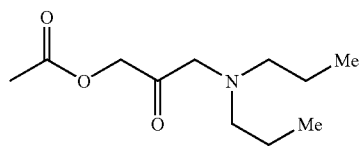 |
| 4 | 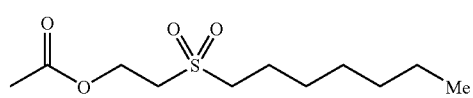 |
| 5 | 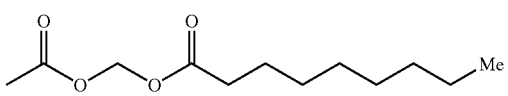 |
| 6 | 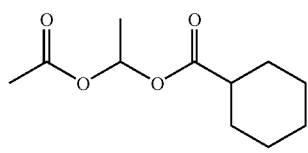 |
| 7 | 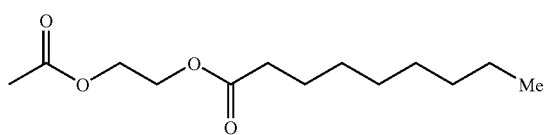 |
| 8 | 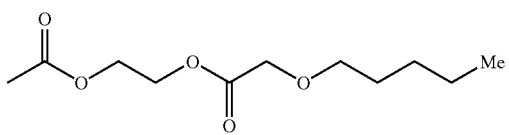 |
| 9 | 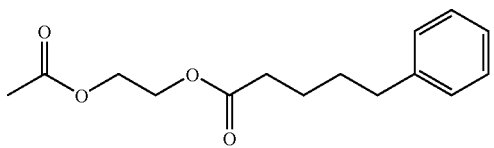 |

(I-3-A-4-9)
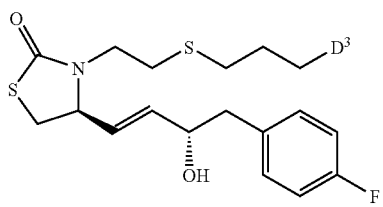
| No. | D³ |
|---|---|
| 10 | 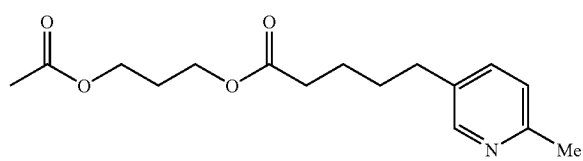 |
| 11 | 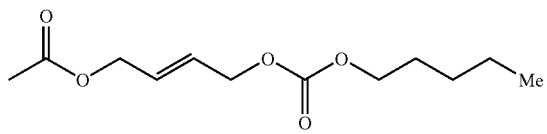 |
| 12 | 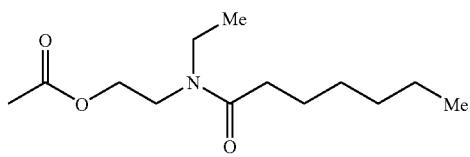 |
| 13 | 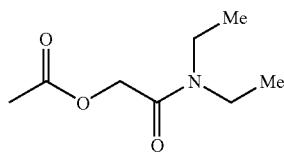 |
| 14 | 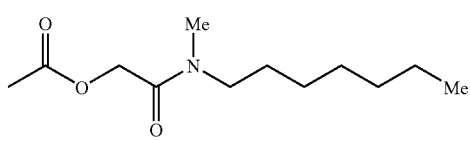 |
| 15 | 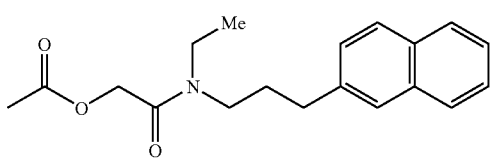 |

TABLE 40
(I-3-A-4-10)
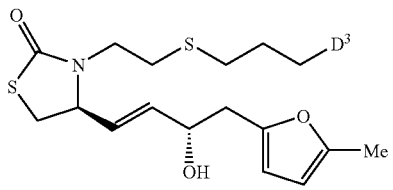
| No. | D³ |
|---|---|
| 1 | 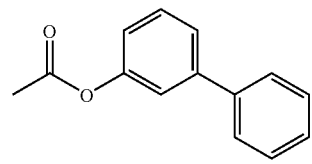 |
| 2 | 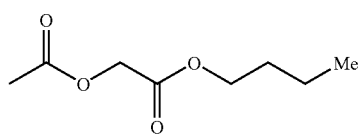 |
| 3 | 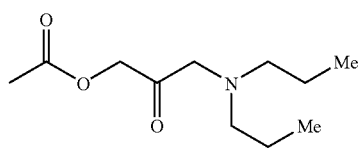 |
| 4 | 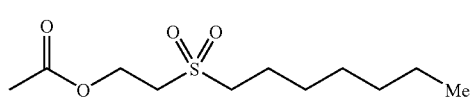 |
| 5 | 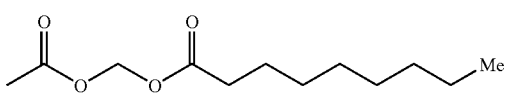 |
| 6 | 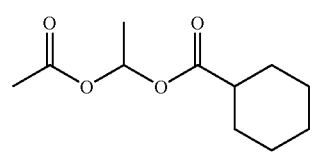 |
| 7 | 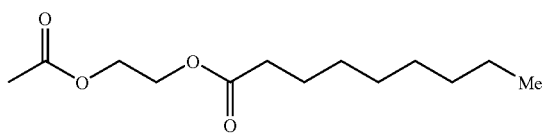 |
| 8 | 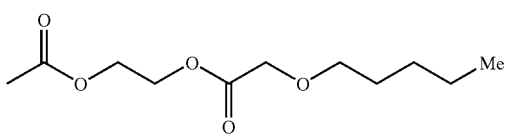 |
| 9 | 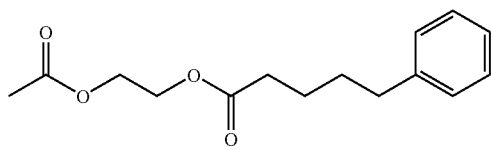 |

TABLE 40-continued
(I-3-A-4-10)
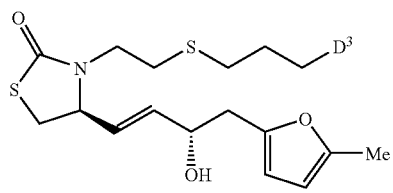
| No. | D³ |
|---|---|
| 10 | 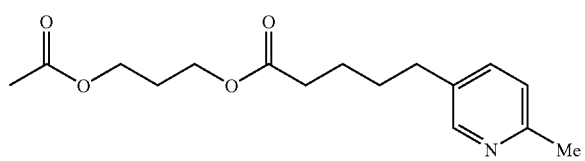 |
| 11 | 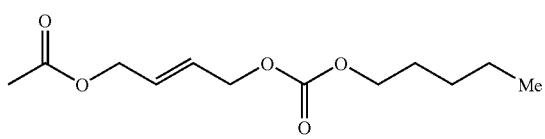 |
| 12 | 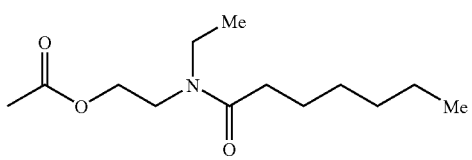 |
| 13 | 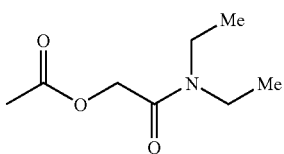 |
| 14 | 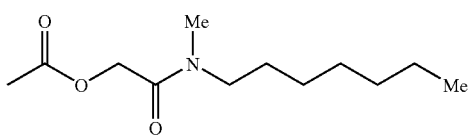 |
| 15 | 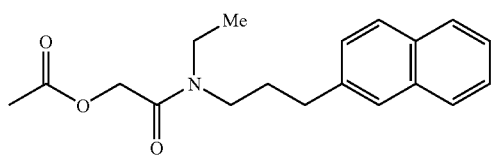 |

TABLE 41
(I-3-A-5-1)
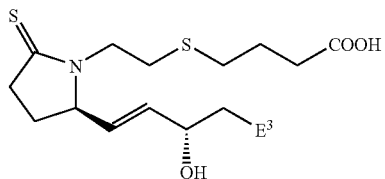
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,3,5-triMe-phenyl |
| 6 | 3-(1-propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
TABLE 41-continued
(I-3-A-5-1)
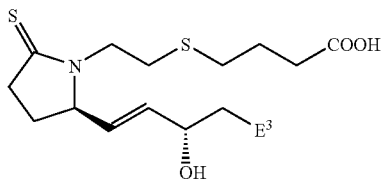
| No. | E³ |
|---|---|
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |
| 22 | 3-OPh-phenyl |

TABLE 41-continued (I-3-A-5-1)

| No. | E³ |
|---|---|
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethyl-4-pyridyl |
| 27 | 5-methyl-2-furyl |
| 28 | 2-methyl-5-oxazolyl |
| 29 | 2-methyl-4-thiazolyl |
| 30 | 1-methyl-1H-imidazol-? |
| 31 | 2-pyrimidinyl |
| 32 | 2-naphthyl |
| 33 | 5-benzofuranyl |
| 34 | 2-methyl-1H-indol-5-yl |
| 35 | 2-methylbenzothiazol-? |

TABLE 42

(I-3-A-5-2)

| No. | E³ |
|---|---|
| 1 | phenyl |
| 2 | 3-methylphenyl |
| 3 | 3-propylphenyl |
| 4 | 3,4-dimethylphenyl |
| 5 | 2,4,6-trimethylphenyl |
| 6 | 3-(1-propenyl)phenyl |
| 7 | 3-ethynylphenyl |

TABLE 42-continued
(I-3-A-5-2)
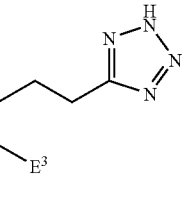
| No. | E³ |
|---|---|
| 8 | 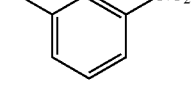 |
| 9 | 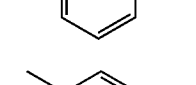 |
| 10 | 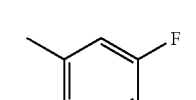 |
| 11 | 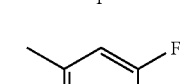 |
| 12 | 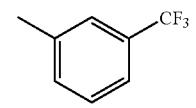 |
| 13 | 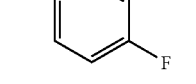 |
| 14 | 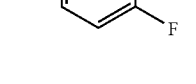 |
| 15 |  |
| 16 | 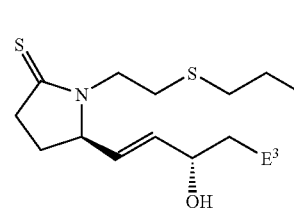 |
| 17 | 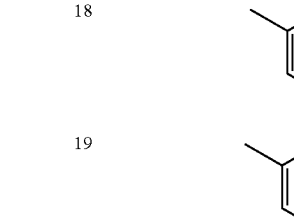 |
TABLE 42-continued
(I-3-A-5-2)
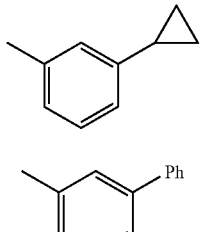
| No. | E³ |
|---|---|
| 18 |  |
| 19 | 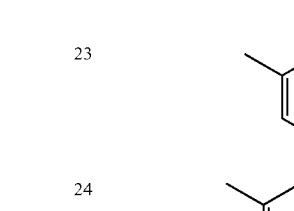 |
| 20 | 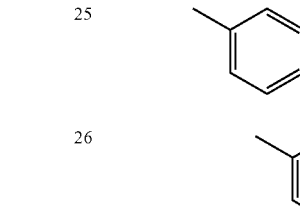 |
| 21 | 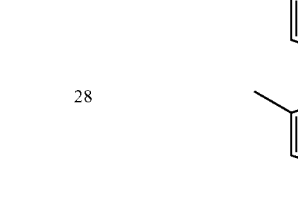 |
| 22 |  |
| 23 | 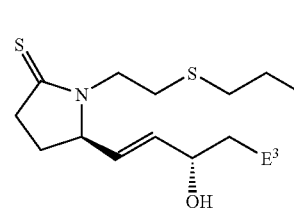 |
| 24 | 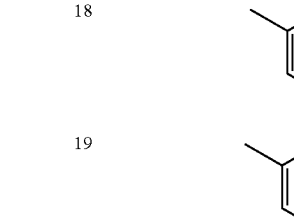 |
| 25 |  |
| 26 | 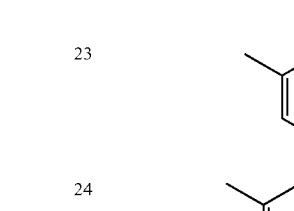 |
| 27 | 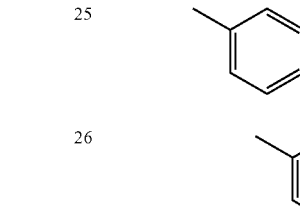 |
| 28 | 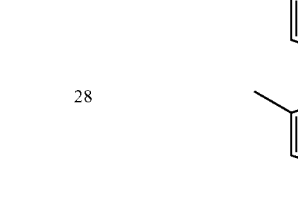 |

TABLE 42-continued
(I-3-A-5-2)
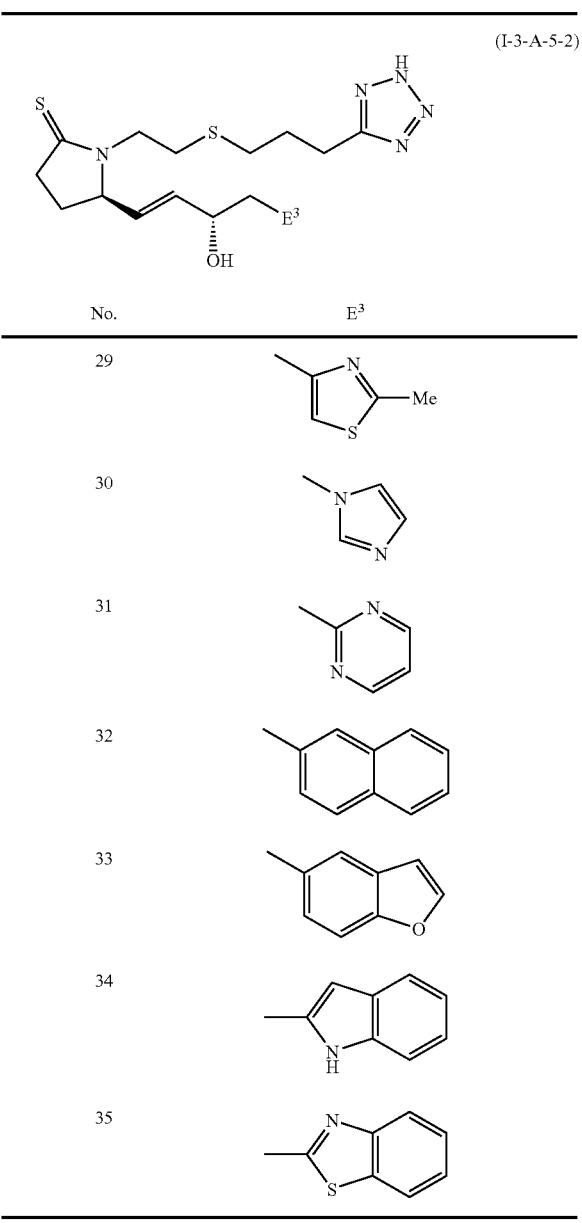
TABLE 43
(I-3-A-5-3)
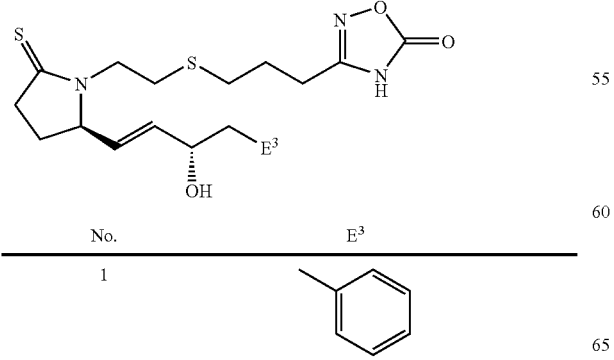
TABLE 43-continued
(I-3-A-5-3)
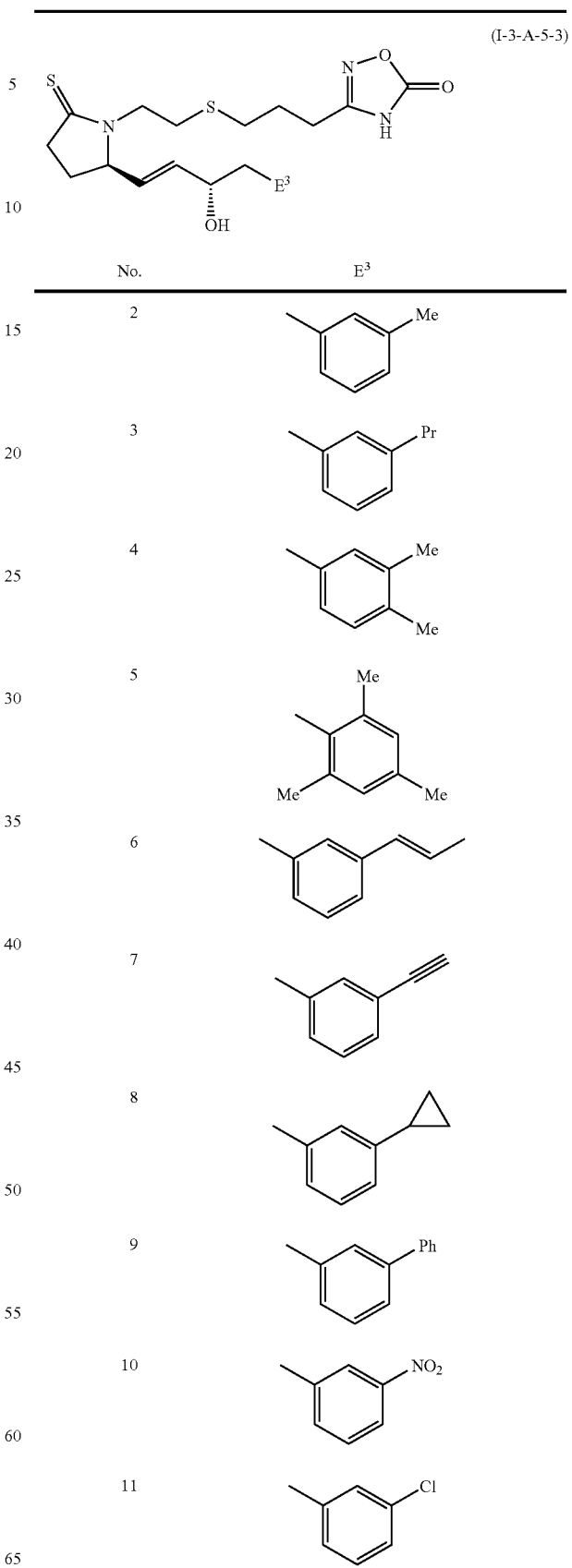

TABLE 43-continued
(I-3-A-5-3)
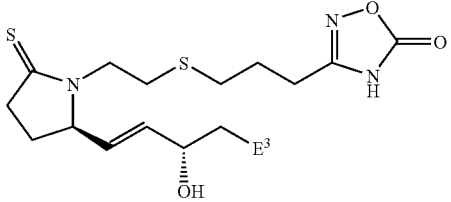
| No. | E³ |
|---|---|
| 12 | 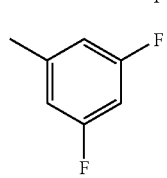 |
| 13 | 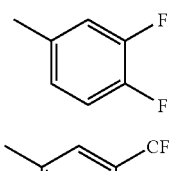 |
| 14 | 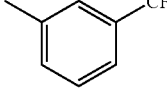 |
| 15 | 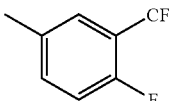 |
| 16 | 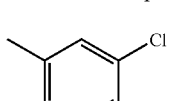 |
| 17 | 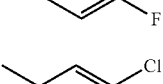 |
| 18 | 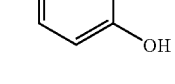 |
| 19 | 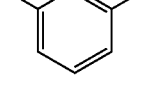 |
| 20 | 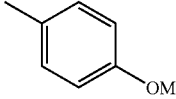 |
| 21 | 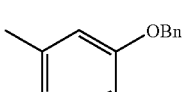 |
| 22 | 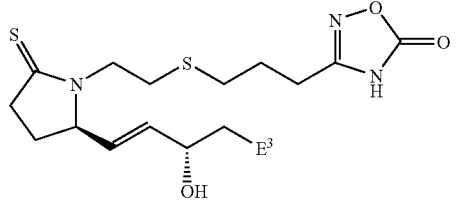 |
TABLE 43-continued
(I-3-A-5-3)
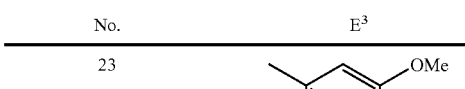
| No. | E³ |
|---|---|
| 23 | 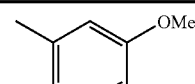 |
| 24 | 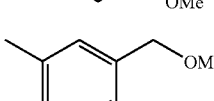 |
| 25 | 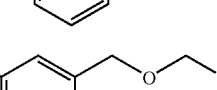 |
| 26 | 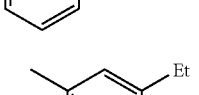 |
| 27 | 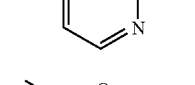 |
| 28 | 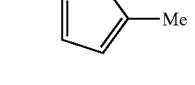 |
| 29 | 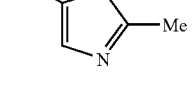 |
| 30 | 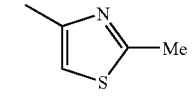 |
| 31 | 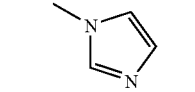 |
| 32 | 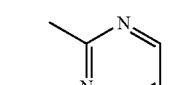 |
| 33 | 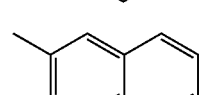 |
| 34 |  |

TABLE 43-continued
(I-3-A-5-3)
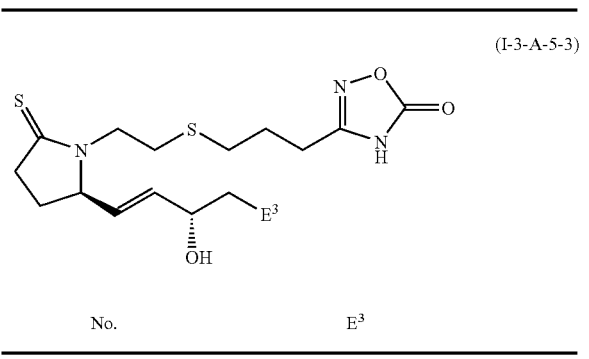
| No. | E³ |
|---|---|
| 35 | 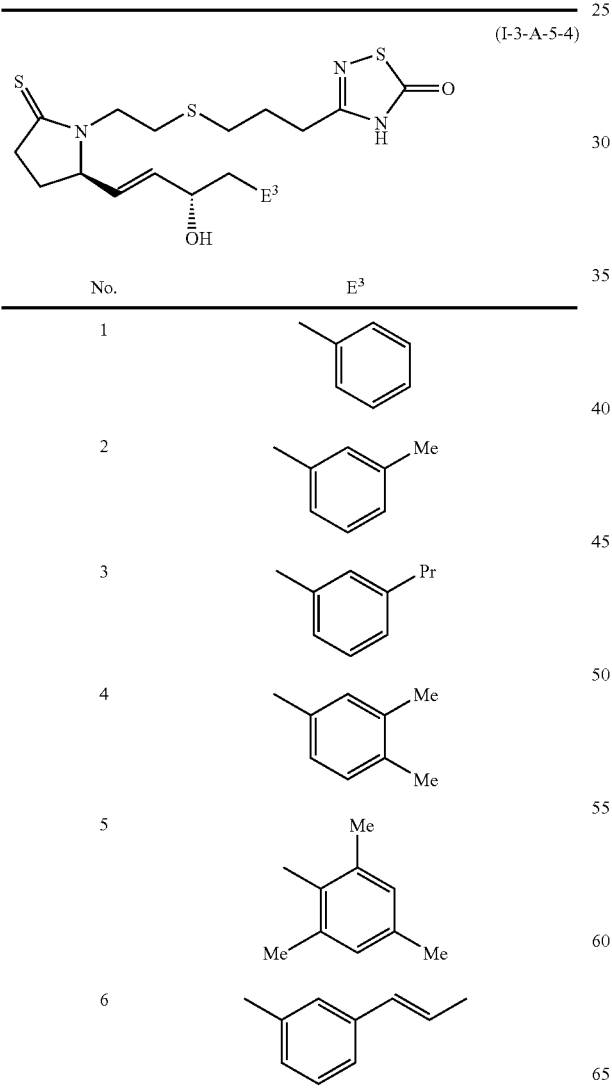 |
TABLE 44
(I-3-A-5-4)
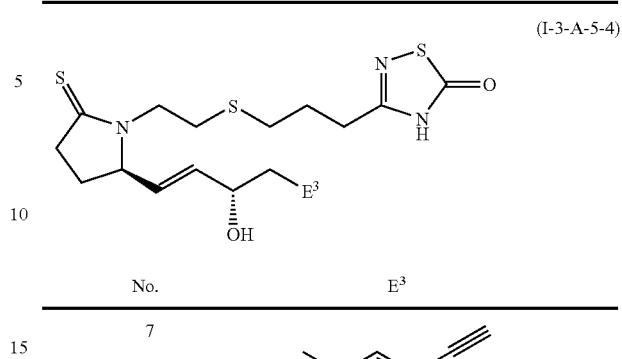
| No. | E³ |
|---|---|
| 1 | |
| 2 | Me |
| 3 | Pr |
| 4 | Me, Me |
| 5 | Me, Me, Me |
| 6 | |
| 7 | |
| 8 | cyclopropyl |
| 9 | Ph |
| 10 | NO₂ |
| 11 | Cl |
| 12 | F |
| 13 | F, F |
| 14 | F, F |
| 15 | CF₃ |
| 16 | CF₃, F |
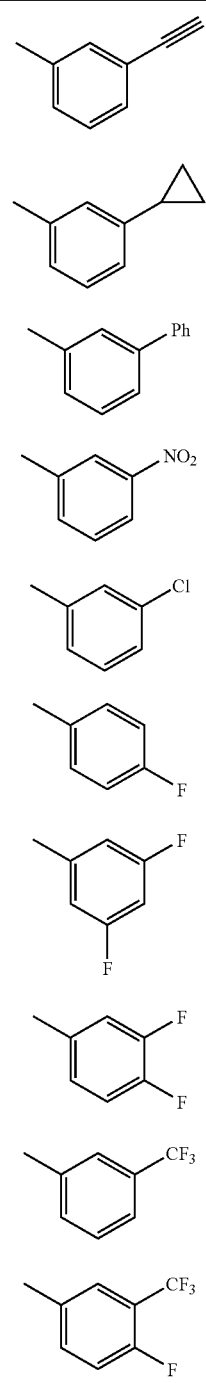

TABLE 44-continued
(I-3-A-5-4)

| No. | E³ |
|-----|-----|
| 17 |  |
| 18 |  |
| 19 |  |
| 20 | 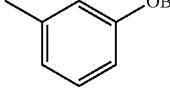 |
| 21 |  |
| 22 |  |
| 23 |  |
| 24 | 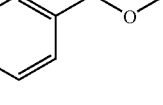 |
| 25 |  |
| 26 |  |
| 27 |  |
| 28 |  |
| 29 |  |
| 30 | 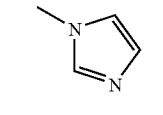 |
| 31 | 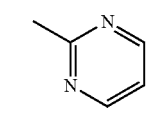 |
| 32 | 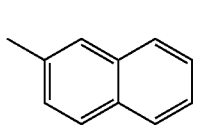 |
| 33 |  |
| 34 |  |
| 35 | 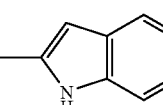 |

TABLE 45
(I-3-A-5-5)
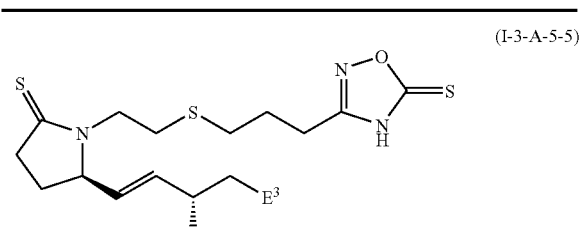
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,3,5-triMe-phenyl |
| 6 | 3-(1-propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
TABLE 45-continued
(I-3-A-5-5)
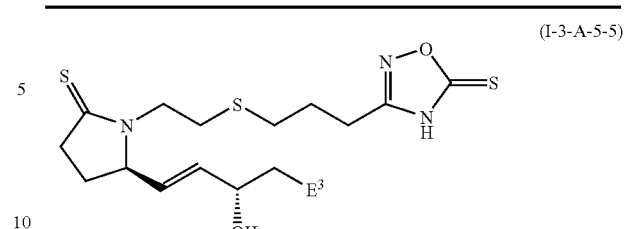
| No. | E³ |
|---|---|
| 11 | 3-Cl-phenyl |
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |

TABLE 45-continued
(I-3-A-5-5)
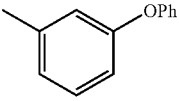
| No. | E³ |
|---|---|
| 22 |  |
| 23 |  |
| 24 | 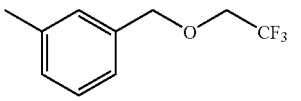 |
| 25 | 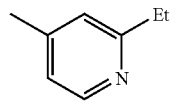 |
| 26 |  |
| 27 |  |
| 28 | 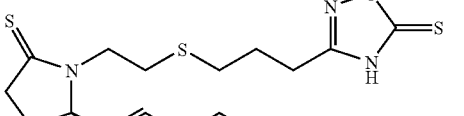 |
TABLE 45-continued
(I-3-A-5-5)
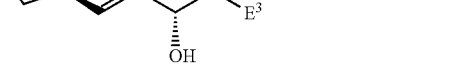
| No. | E³ |
|---|---|
| 29 | 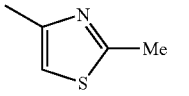 |
| 30 | 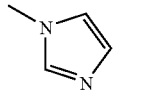 |
| 31 | 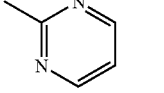 |
| 32 | 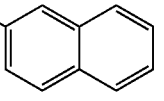 |
| 33 | 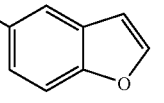 |
| 34 | 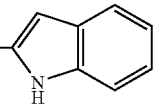 |
| 35 | 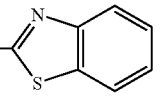 |
TABLE 46
(I-3-A-5-6)
| No. | D³ |
|---|---|
| 1 | 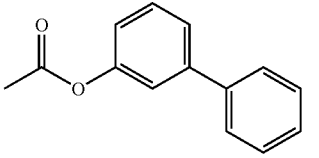 |

TABLE 46-continued
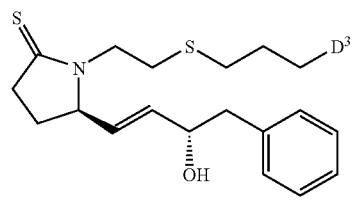
(I-3-A-5-6)
| No. | D³ |
|-----|-----|
| 2 | 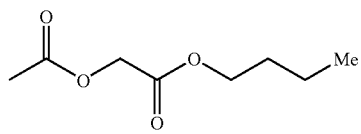 |
| 3 | 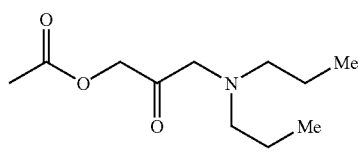 |
| 4 | 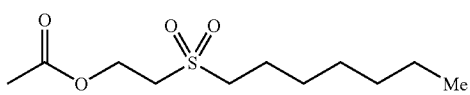 |
| 5 | 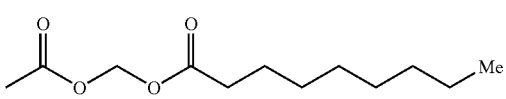 |
| 6 | 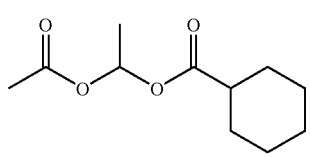 |
| 7 | 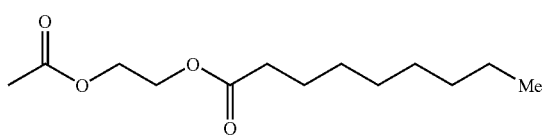 |
| 8 | 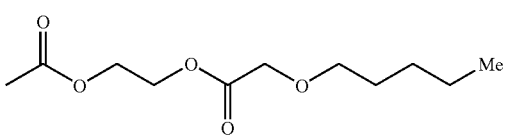 |
| 9 | 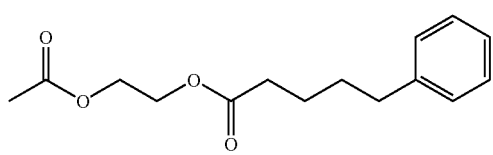 |
| 10 | 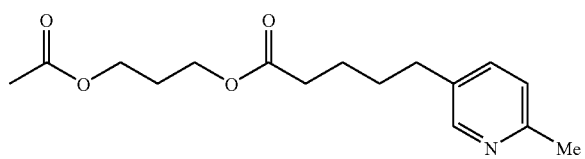 |

TABLE 46-continued
(I-3-A-5-6)
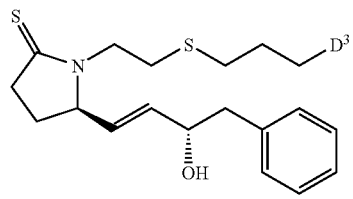
| No. | D³ |
|---|---|
| 11 | 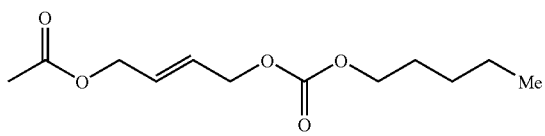 |
| 12 | 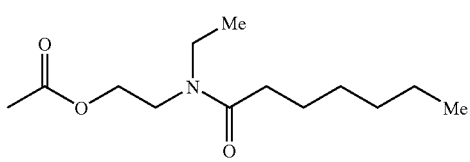 |
| 13 | 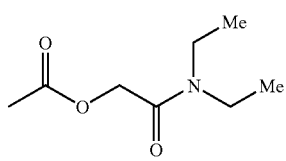 |
| 14 | 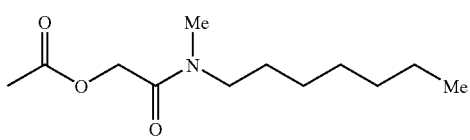 |
| 15 | 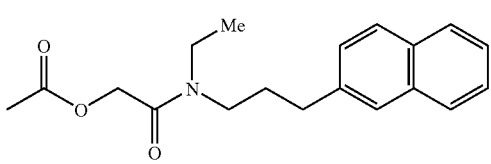 |
TABLE 47
(I-3-A-5-7)
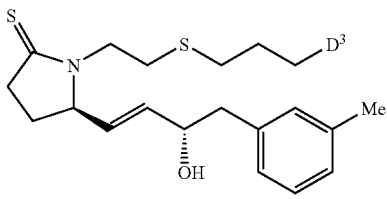
| No. | D³ |
|---|---|
| 1 | 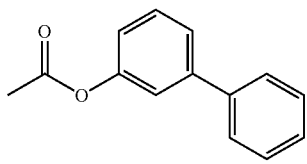 |

TABLE 47-continued
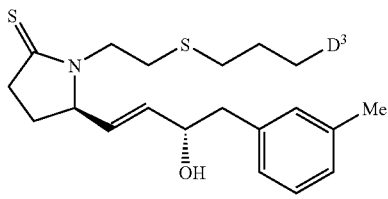
(I-3-A-5-7)
| No. | D³ |
|---|---|
| 2 | -O-butyl) |
| 3 | -CH2-N(propyl)(propyl)) |
| 4 | 2-heptyl) |
| 5 | -heptyl) |
| 6 | -O-C(=O)-cyclohexyl) |
| 7 | -heptyl) |
| 8 | -CH2-O-butyl) |
| 9 | -(CH2)3-phenyl) |
| 10 | 3-O-C(=O)-(CH2)3-(6-methylpyridin-3-yl)) |

TABLE 47-continued
(I-3-A-5-7)
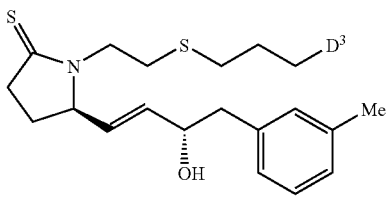
| No. | D³ |
|---|---|
| 11 | 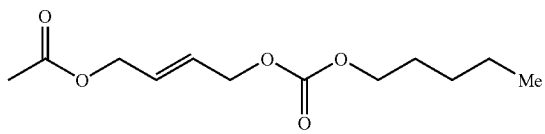 |
| 12 | 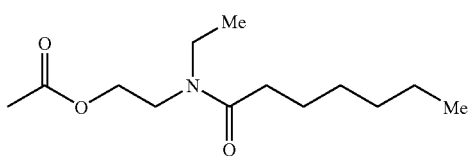 |
| 13 | 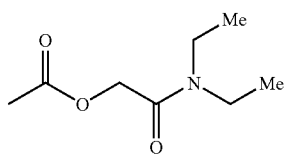 |
| 14 | 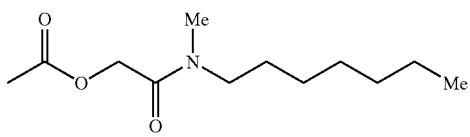 |
| 15 | 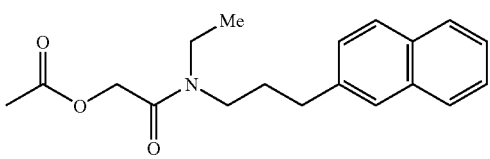 |
TABLE 48
(I-3-A-5-8)
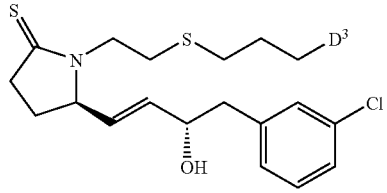
| No. | D³ |
|---|---|
| 1 | 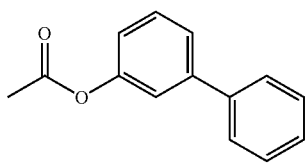 |

TABLE 48-continued
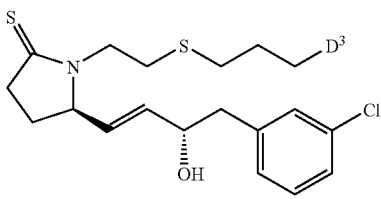
(I-3-A-5-8)
| No. | D³ |
|---|---|
| 2 | |
| 3 | |
| 4 | |
| 5 | |
| 6 | |
| 7 | |
| 8 | |
| 9 | |
| 10 | |

TABLE 48-continued
(I-3-A-5-8)
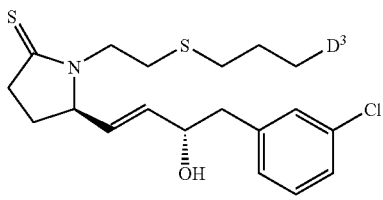
| No. | D³ |
|---|---|
| 11 | 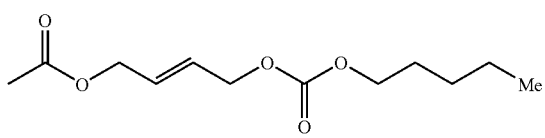 |
| 12 | 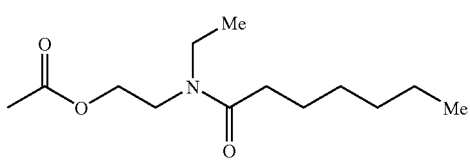 |
| 13 | 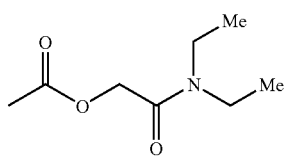 |
| 14 | 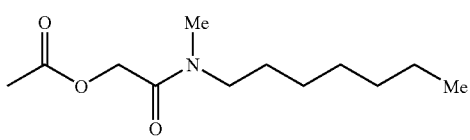 |
| 15 | 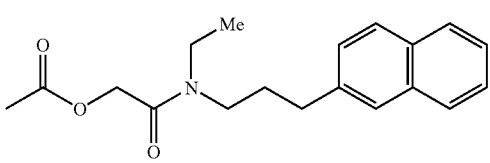 |
TABLE 49
(I-3-A-5-9)
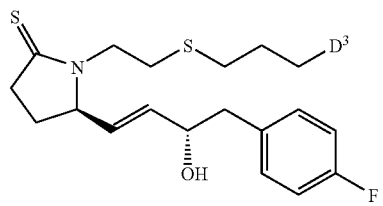
| No. | D³ |
|---|---|
| 1 | 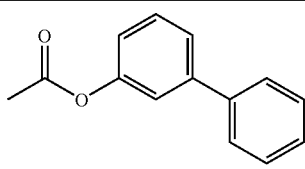 |

TABLE 49-continued
(I-3-A-5-9)
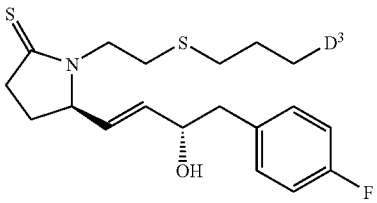
| No. | D³ |
|---|---|
| 2 | ![structure] |
| 3 | ![structure] |
| 4 | ![structure] |
| 5 | ![structure] |
| 6 | ![structure] |
| 7 | ![structure] |
| 8 | ![structure] |
| 9 | ![structure] |
| 10 | ![structure] |

TABLE 49-continued
(I-3-A-5-9)
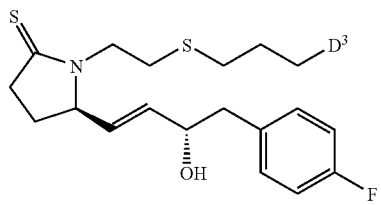
| No. | D³ |
|---|---|
| 11 | 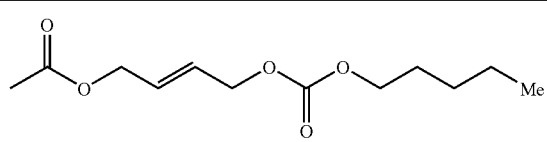 |
| 12 | 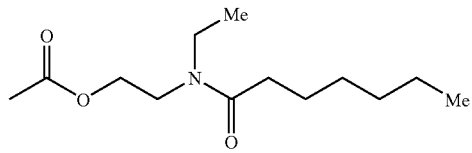 |
| 13 | 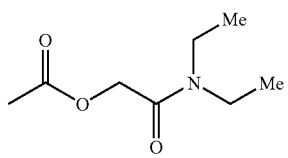 |
| 14 | 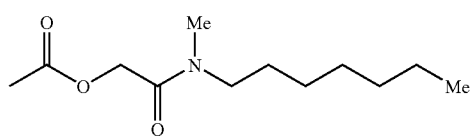 |
| 15 | 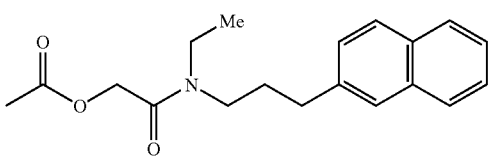 |
TABLE 50
(I-3-A-5-10)
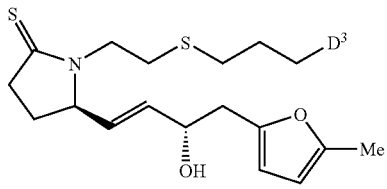
| No. | D³ |
|---|---|
| 1 | 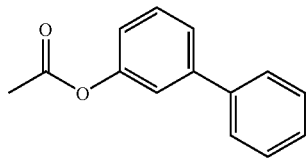 |

TABLE 50-continued
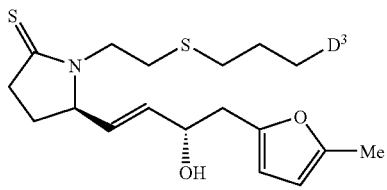
(I-3-A-5-10)
| No. | D³ |
|---|---|
| 2 | |
| 3 | |
| 4 | |
| 5 | |
| 6 | |
| 7 | |
| 8 | |
| 9 | |
| 10 | |

TABLE 50-continued
(I-3-A-5-10)
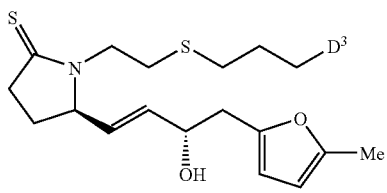
| No. | D³ |
|---|---|
| 11 | 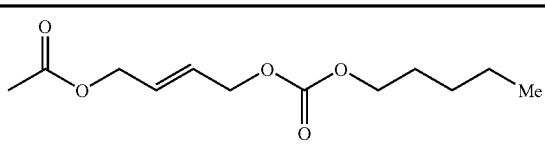 |
| 12 | 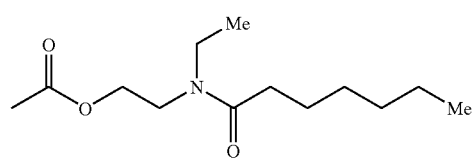 |
| 13 | 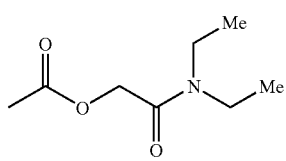 |
| 14 | 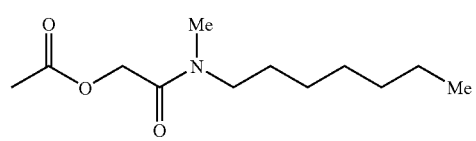 |
| 15 | 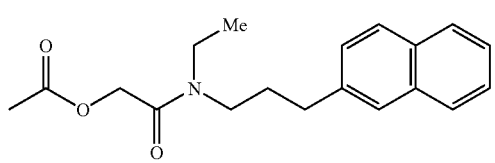 |
TABLE 51
(I-3-A-1-11)
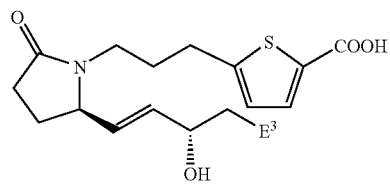
| No. | E³ |
|---|---|
| 1 | 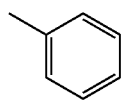 |
| 2 | 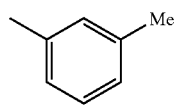 |
TABLE 51-continued
(I-3-A-1-11)
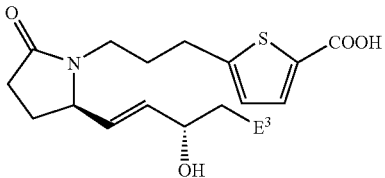
| No. | E³ |
|---|---|
| 3 | 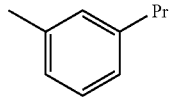 |
| 4 | 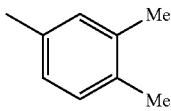 |

TABLE 51-continued (I-3-A-1-11)

| No. | E³ |
|---|---|
| 5 | 2,3,4-trimethylphenyl |
| 6 | 3-(1-propenyl)phenyl |
| 7 | 3-ethynylphenyl |
| 8 | 3-cyclopropylphenyl |
| 9 | 3-phenylphenyl |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |
| 22 | 3-OPh-phenyl |
| 23 | 3,4-di-OMe-phenyl |
| 24 | 3-(CH₂OMe)-phenyl |
| 25 | 3-(CH₂OCH₂CF₃)-phenyl |

TABLE 51-continued
(I-3-A-1-11)
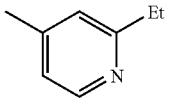
| No. | E³ |
|---|---|
| 26 | 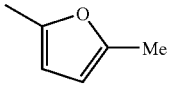 |
| 27 | 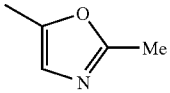 |
| 28 | 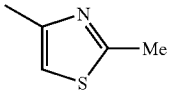 |
| 29 |  |
| 30 |  |
| 31 | 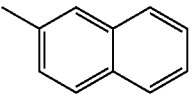 |
| 32 | 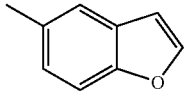 |
| 33 | 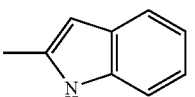 |
| 34 | 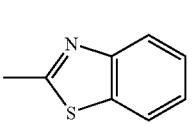 |
| 35 | 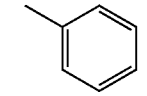 |
TABLE 52
(I-3-A-2-11)
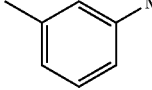
| No. | E³ |
|---|---|
| 1 | 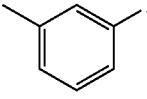 |
| 2 | 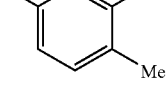 |
| 3 | 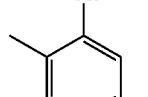 |
| 4 | 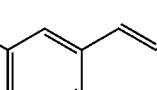 |
| 5 | 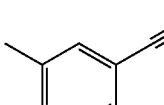 |
| 6 | 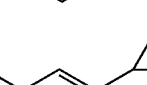 |
| 7 | 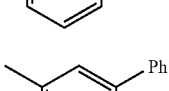 |
| 8 | 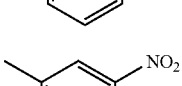 |
| 9 | 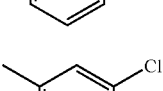 |
| 10 | |
| 11 | |

TABLE 52-continued
(I-3-A-2-11)
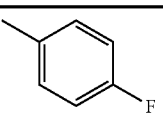
| No. | E³ |
|---|---|
| 12 | 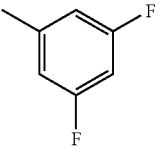 |
| 13 | 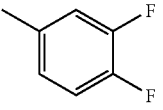 |
| 14 |  |
| 15 |  |
| 16 |  |
| 17 | 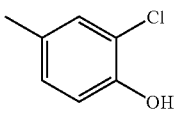 |
| 18 |  |
| 19 |  |
| 20 |  |
| 21 |  |
| 22 | 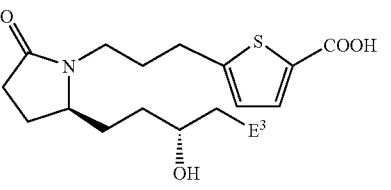 |
TABLE 52-continued
(I-3-A-2-11)
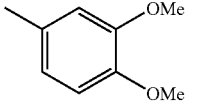
| No. | E³ |
|---|---|
| 23 | 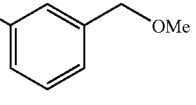 |
| 24 | 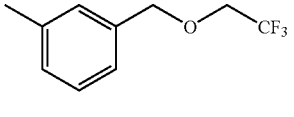 |
| 25 |  |
| 26 |  |
| 27 | 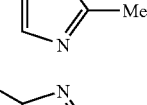 |
| 28 | 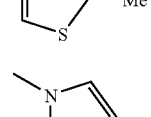 |
| 29 | 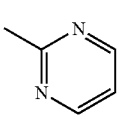 |
| 30 | 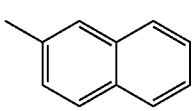 |
| 31 |  |
| 32 | 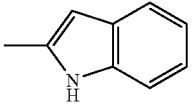 |
| 33 | |
| 34 | |

TABLE 52-continued (I-3-A-2-11)

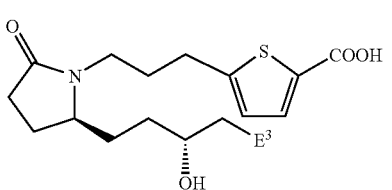

| No. | E³ |
|---|---|
| 35 | (2-benzothiazolyl) |

TABLE 53

(I-3-A-3-11)

| No. | E³ |
|---|---|
| 1 | phenyl |
| 2 | 3-methylphenyl |
| 3 | 3-propylphenyl |
| 4 | 3,4-dimethylphenyl |
| 5 | 2,3,5-trimethylphenyl |
| 6 | 3-(prop-1-enyl)phenyl |
| 7 | 3-ethynylphenyl |
| 8 | 3-cyclopropylphenyl |
| 9 | 3-phenylphenyl |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-(trifluoromethyl)phenyl |
| 16 | 3-(trifluoromethyl)-4-fluorophenyl |
| 17 | 3-chloro-4-fluorophenyl |
| 18 | 3-chloro-4-hydroxyphenyl |

TABLE 53-continued (I-3-A-3-11)

| No. | E³ |
|---|---|
| 19 | 3-OMe-phenyl |
| 20 | 4-OMe-phenyl |
| 21 | 3-OBn-phenyl |
| 22 | 3-OPh-phenyl |
| 23 | 3,4-diOMe-phenyl |
| 24 | 3-(CH₂OMe)-phenyl |
| 25 | 3-(CH₂OCH₂CF₃)-phenyl |
| 26 | 2-Et-4-methylpyridinyl |
| 27 | 5-Me-furan-2-yl |
| 28 | 2-Me-oxazol-5-yl |
| 29 | 2-Me-thiazol-4-yl |
| 30 | 1-methylimidazol-? |
| 31 | pyrimidin-2-yl |
| 32 | naphthalen-2-yl |
| 33 | benzofuran-5-yl |
| 34 | 2-Me-indol-? |
| 35 | benzothiazol-2-yl |

TABLE 54

(I-3-A-4-11)

| No. | E³ |
|---|---|
| 1 | phenyl |
| 2 | 3-Me-phenyl |
| 3 | 3-Pr-phenyl |
| 4 | 2,5-diMe-phenyl |

TABLE 54-continued (I-3-A-4-11)

| No. | E³ |
|---|---|
| 5 | 2,3,5-trimethylphenyl |
| 6 | 3-(1-propenyl)phenyl |
| 7 | 3-ethynylphenyl |
| 8 | 3-cyclopropylphenyl |
| 9 | 3-phenylphenyl |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-(trifluoromethyl)phenyl |
| 16 | 4-fluoro-3-(trifluoromethyl)phenyl |
| 17 | 3-chloro-4-fluorophenyl |
| 18 | 3-chloro-4-hydroxyphenyl |
| 19 | 3-methoxyphenyl |
| 20 | 4-methoxyphenyl |
| 21 | 3-benzyloxyphenyl |
| 22 | 3-phenoxyphenyl |
| 23 | 3,4-dimethoxyphenyl |
| 24 | 3-(methoxymethyl)phenyl |
| 25 | 3-(2,2,2-trifluoroethoxymethyl)phenyl |

TABLE 54-continued
(I-3-A-4-11)
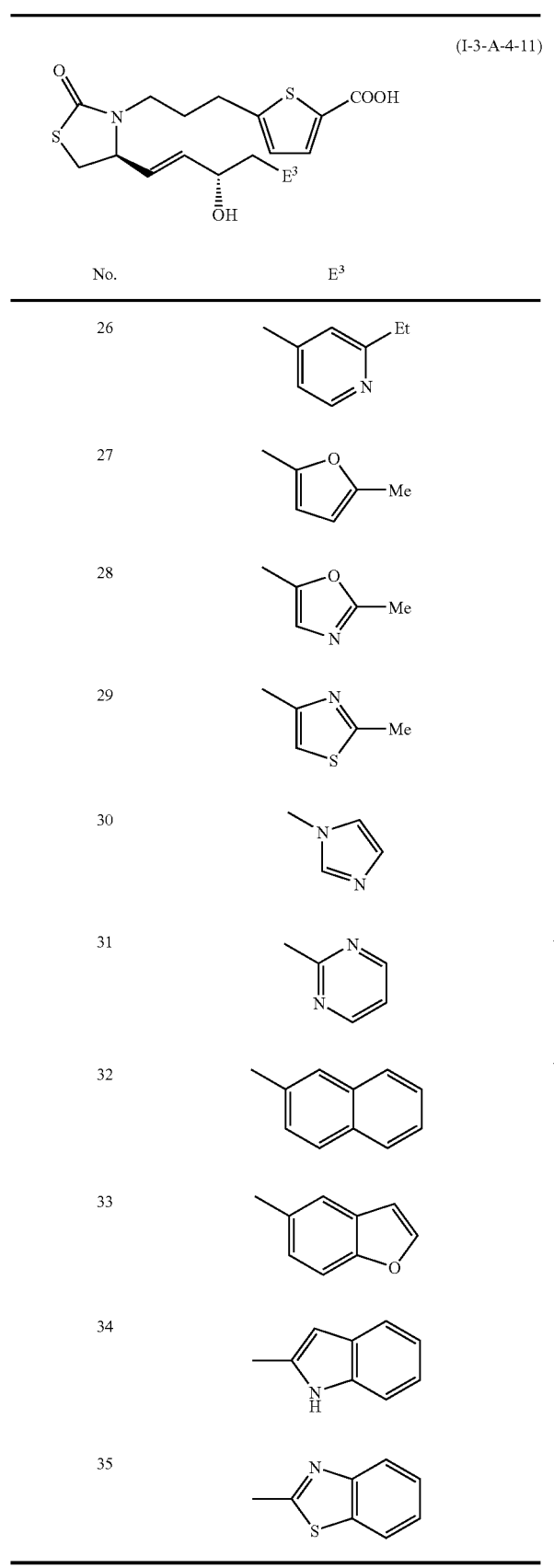
TABLE 55
(I-3-A-1-12)
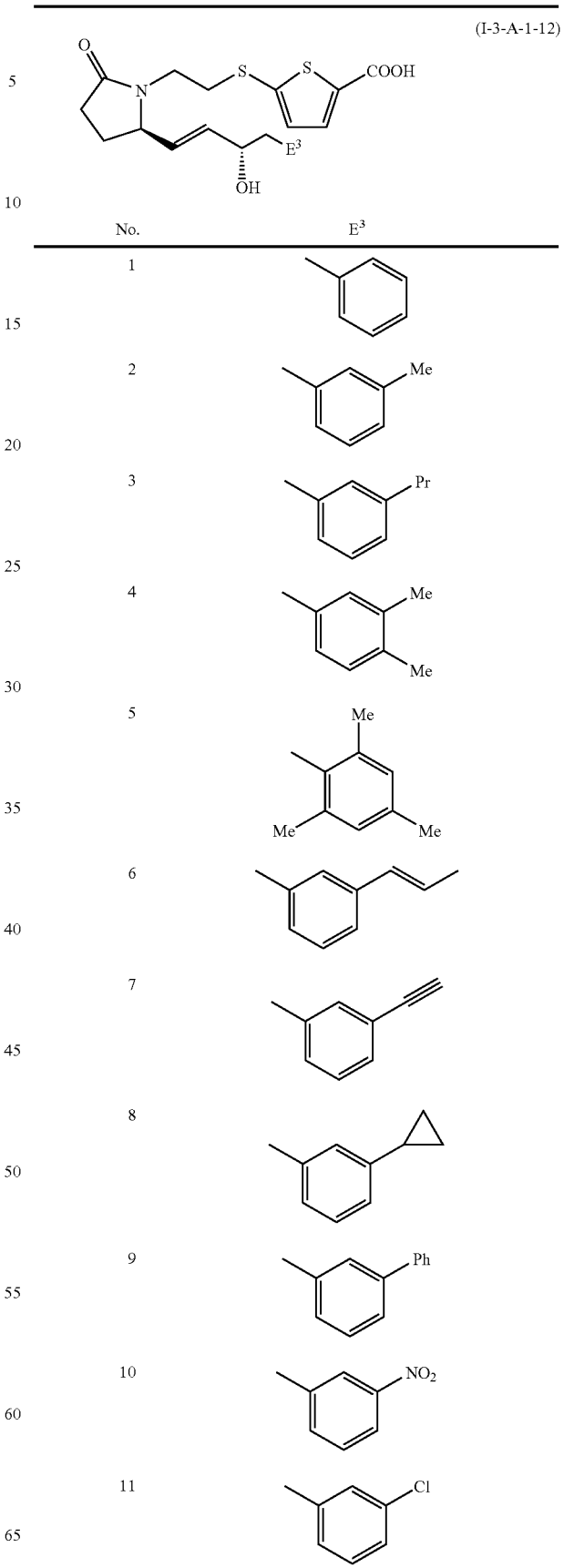

TABLE 55-continued
(I-3-A-1-12)
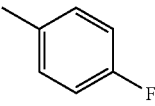
| No. | E³ |
|---|---|
| 12 | 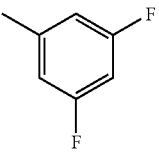 |
| 13 | 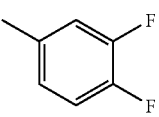 |
| 14 | 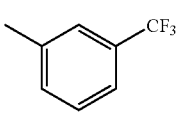 |
| 15 | 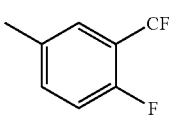 |
| 16 | 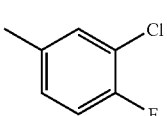 |
| 17 | 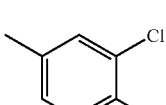 |
| 18 | 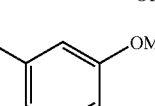 |
| 19 | 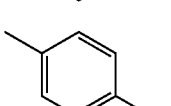 |
| 20 | 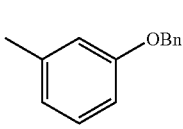 |
| 21 | 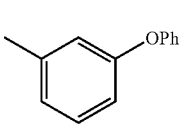 |
| 22 | 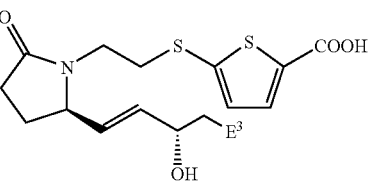 |
| 23 | 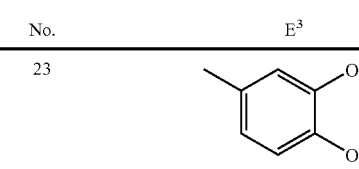 |
| 24 | 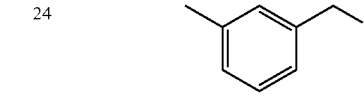 |
| 25 | 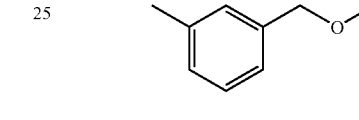 |
| 26 |  |
| 27 | 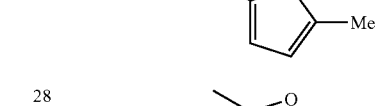 |
| 28 | 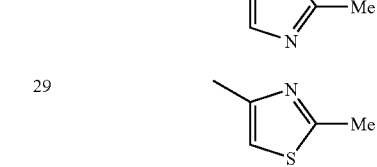 |
| 29 |  |
| 30 |  |
| 31 | 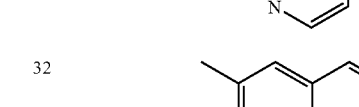 |
| 32 | 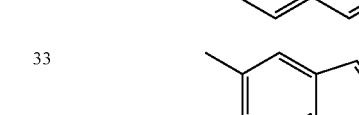 |
| 33 |  |
| 34 |  |

TABLE 55-continued
(I-3-A-1-12)
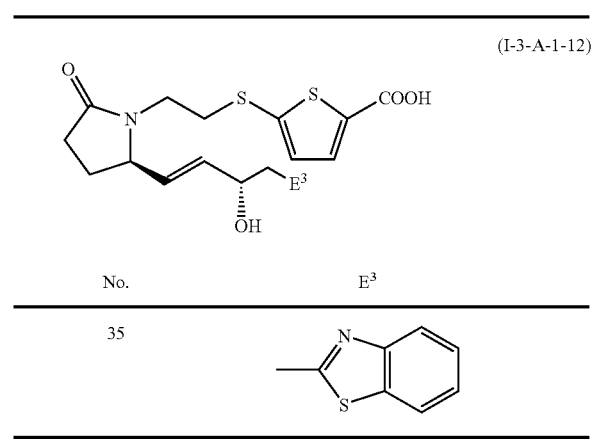
| No. | E³ |
|---|---|
| 35 | 2-benzothiazolyl |
TABLE 56
(I-3-A-2-12)
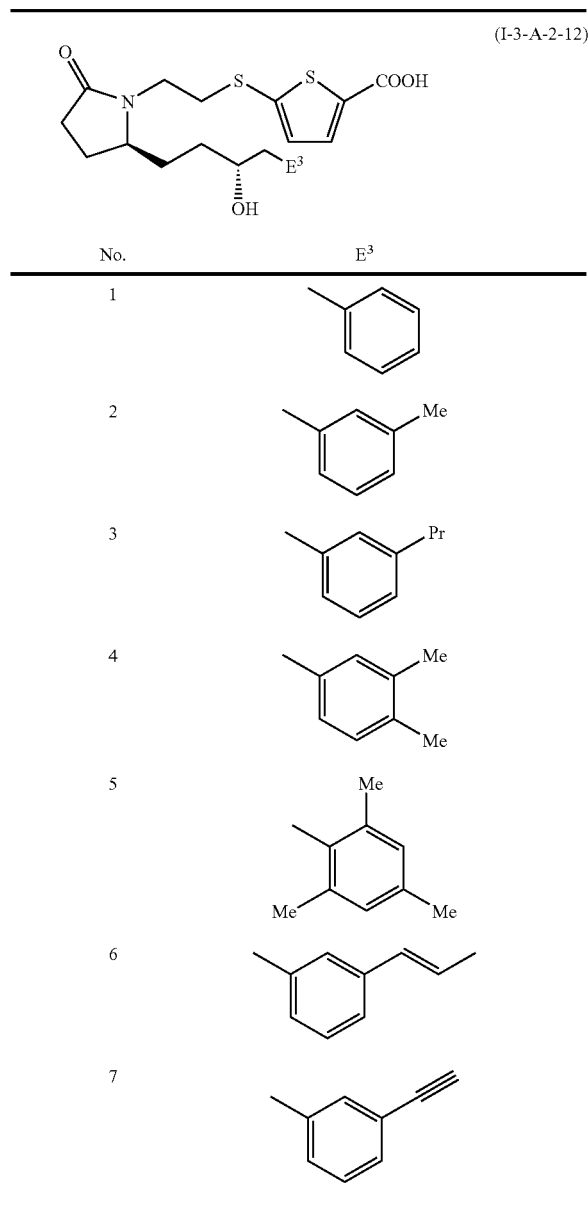
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,3,5-triMe-phenyl |
| 6 | 3-(propenyl)phenyl |
| 7 | 3-ethynyl-phenyl |
TABLE 56-continued
(I-3-A-2-12)
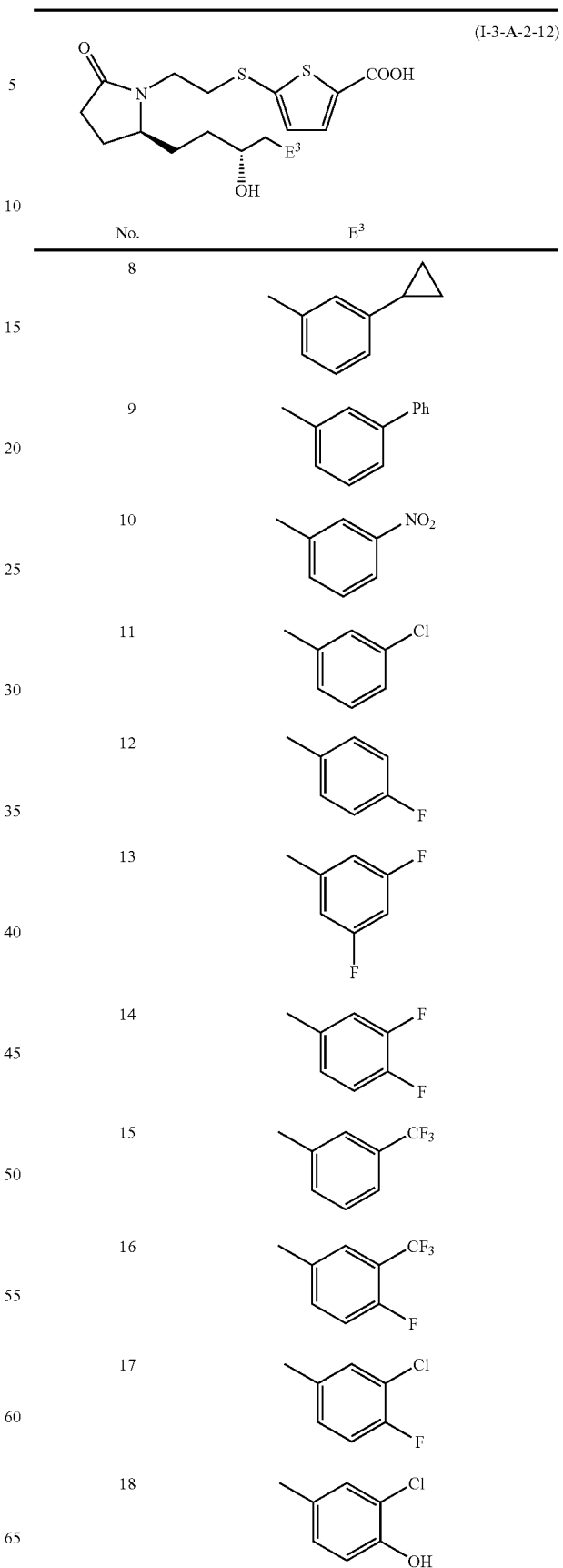
| No. | E³ |
|---|---|
| 8 | 3-cyclopropyl-phenyl |
| 9 | 3-Ph-phenyl |
| 10 | 3-NO₂-phenyl |
| 11 | 3-Cl-phenyl |
| 12 | 4-F-phenyl |
| 13 | 3,5-diF-phenyl |
| 14 | 3,4-diF-phenyl |
| 15 | 3-CF₃-phenyl |
| 16 | 2-CF₃-4-F-phenyl |
| 17 | 3-Cl-4-F-phenyl |
| 18 | 3-Cl-4-OH-phenyl |

TABLE 56-continued (I-3-A-2-12)

[Structure: pyrrolidinone with N-CH2CH2-S-thiophene-COOH, and side chain with OH and E³]

| No. | E³ |
|---|---|
| 19 | 3-methoxyphenyl |
| 20 | 4-methoxyphenyl |
| 21 | 3-OBn-phenyl |
| 22 | 3-OPh-phenyl |
| 23 | 3,4-dimethoxyphenyl |
| 24 | 3-(CH2OMe)phenyl |
| 25 | 3-(CH2OCH2CF3)phenyl |
| 26 | 2-ethyl-4-pyridyl |
| 27 | 5-methyl-2-furyl |
| 28 | 2-methyl-5-oxazolyl |
| 29 | 2-methyl-4-thiazolyl |
| 30 | 1-imidazolyl (N-methyl imidazole) |

TABLE 56-continued (I-3-A-2-12)

| No. | E³ |
|---|---|
| 31 | 2-pyrimidinyl |
| 32 | 6-naphthyl |
| 33 | 5-benzofuranyl |
| 34 | 2-indolyl |
| 35 | 2-benzothiazolyl |

TABLE 57

(I-3-A-3-12)

[Structure: oxazolidinone with N-CH2CH2-S-thiophene-COOH, and side chain with CH=CH, OH, and E³]

| No. | E³ |
|---|---|
| 1 | phenyl |
| 2 | 3,5-dimethylphenyl |
| 3 | 3-propylphenyl |

TABLE 57-continued (I-3-A-3-12)

[Structure: oxazolidinone-N-CH2CH2-S-thiophene-COOH with vinyl-CH(OH)-CH2-E³ substituent]

| No. | E³ |
|---|---|
| 4 | 2,4-dimethylphenyl |
| 5 | 2,3,5-trimethylphenyl |
| 6 | 3-(1-propenyl)phenyl |
| 7 | 3-ethynylphenyl |
| 8 | 3-cyclopropylphenyl |
| 9 | 3-phenylphenyl (Ph) |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-(trifluoromethyl)phenyl |
| 16 | 3-CF3-4-F-phenyl |
| 17 | 3-Cl-4-F-phenyl |
| 18 | 3-Cl-4-OH-phenyl |
| 19 | 3-methoxyphenyl |
| 20 | 4-methoxyphenyl |
| 21 | 3-(benzyloxy)phenyl (OBn) |
| 22 | 3-phenoxyphenyl (OPh) |
| 23 | 3,4-dimethoxyphenyl |
| 24 | 3-(methoxymethyl)phenyl |

TABLE 57-continued (I-3-A-3-12)

| No. | E³ |
|---|---|
| 25 | 3-(2,2,2-trifluoroethoxymethyl)phenyl |
| 26 | 4-methyl-6-ethylpyridin-3-yl |
| 27 | 5-methylfuran-2-yl |
| 28 | 2-methyl-5-oxazolyl |
| 29 | 2-methyl-4-thiazolyl |
| 30 | 1-methyl-1H-imidazol-2-yl |
| 31 | 2-pyrimidinyl |
| 32 | naphthalen-2-yl |
| 33 | benzofuran-5-yl |
| 34 | 2-indolyl |
| 35 | 2-benzothiazolyl |

TABLE 58

(I-3-A-4-12)

| No. | E³ |
|---|---|
| 1 | phenyl |
| 2 | 3-methylphenyl |
| 3 | 3-propylphenyl |
| 4 | 3,4-dimethylphenyl |
| 5 | 2,3,5-trimethylphenyl |
| 6 | 3-(1-propenyl)phenyl |
| 7 | 3-ethynylphenyl |
| 8 | 3-cyclopropylphenyl |
| 9 | 3-phenylphenyl |
| 10 | 3-nitrophenyl |
| 11 | 3-chlorophenyl |

TABLE 58-continued (I-3-A-4-12)

| No. | E³ |
|---|---|
| 12 | 4-F-C₆H₄ |
| 13 | 3,5-diF-C₆H₃ |
| 14 | 3,4-diF-C₆H₃ |
| 15 | 3-CF₃-C₆H₄ |
| 16 | 3-CF₃-4-F-C₆H₃ |
| 17 | 3-Cl-4-F-C₆H₃ |
| 18 | 3-Cl-4-OH-C₆H₃ |
| 19 | 3-OMe-C₆H₄ |
| 20 | 4-OMe-C₆H₄ |
| 21 | 3-OBn-C₆H₄ |
| 22 | 3-OPh-C₆H₄ |
| 23 | 3,4-diOMe-C₆H₃ |
| 24 | 3-(CH₂OMe)-C₆H₄ |
| 25 | 3-(CH₂OCH₂CF₃)-C₆H₄ |
| 26 | 2-Et-4-pyridyl |
| 27 | 5-Me-2-furyl |
| 28 | 2-Me-5-oxazolyl |
| 29 | 2-Me-4-thiazolyl |
| 30 | 1-methylimidazol-2-yl |
| 31 | 2-pyrimidinyl |
| 32 | 2-naphthyl |
| 33 | 5-benzofuranyl |
| 34 | 2-indolyl |

TABLE 58-continued
(I-3-A-4-12)
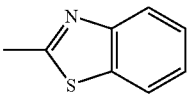
| No. | E³ |
|---|---|
| 35 | 2-benzothiazolyl |
TABLE 59
(I-3-A-1-13)
| No. | E³ |
|---|---|
| 1 | phenyl |
| 2 | 3-Me-phenyl |
| 3 | 3-Pr-phenyl |
| 4 | 3,4-diMe-phenyl |
| 5 | 2,3,5-triMe-phenyl |
| 6 | 3-(propenyl)-phenyl |
| 7 | 3-ethynyl-phenyl |
| 8 | 3-cyclopropyl-phenyl |
| 9 | 3-Ph-phenyl |
| 10 | 3-NO₂-phenyl |
| 11 | 3-Cl-phenyl |
| 12 | 4-F-phenyl |
| 13 | 3,5-diF-phenyl |
| 14 | 3,4-diF-phenyl |
| 15 | 3-CF₃-phenyl |
| 16 | 2-CF₃-4-F-phenyl |
| 17 | 3-Cl-4-F-phenyl |
| 18 | 3-Cl-4-OH-phenyl |

TABLE 59-continued (I-3-A-1-13)

| No. | E³ |
|---|---|
| 19 | 3-methoxyphenyl |
| 20 | 4-methoxyphenyl |
| 21 | 3-OBn-phenyl |
| 22 | 3-OPh-phenyl |
| 23 | 3,4-dimethoxyphenyl |
| 24 | 3-(CH₂OMe)phenyl |
| 25 | 3-(CH₂OCH₂CF₃)phenyl |
| 26 | 4-methyl-2-ethylpyridinyl |
| 27 | 5-methylfuran-2-yl |
| 28 | 2-methyloxazol-5-yl |
| 29 | 2-methylthiazol-4-yl |
| 30 | 1-methylimidazol-? |
| 31 | 2-methylpyrimidin-? |
| 32 | 6-methylnaphthalen-2-yl |
| 33 | 5-methylbenzofuran-? |
| 34 | 2-methyl-1H-indol-? |
| 35 | 2-methylbenzothiazol-? |

TABLE 60

(I-3-A-2-13)

| No. | E³ |
|---|---|
| 1 | phenyl |
| 2 | 3-methylphenyl |
| 3 | 3-propylphenyl |
| 4 | 2,5-dimethylphenyl |

TABLE 60-continued
(I-3-A-2-13)
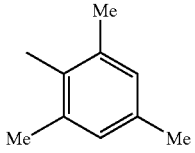
| No. | E³ |
|---|---|
| 5 | 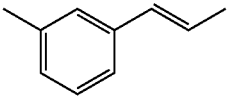 |
| 6 | 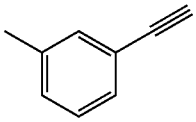 |
| 7 | 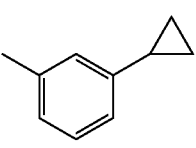 |
| 8 | 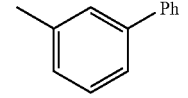 |
| 9 | 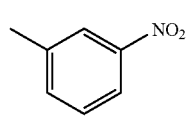 |
| 10 | 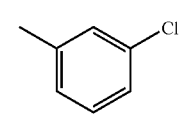 |
| 11 | 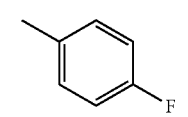 |
| 12 | 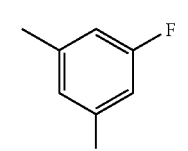 |
| 13 | 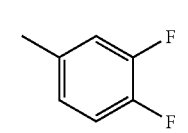 |
| 14 | 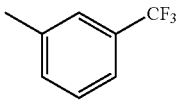 |
TABLE 60-continued
(I-3-A-2-13)
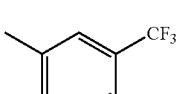
| No. | E³ |
|---|---|
| 15 | 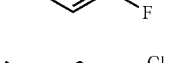 |
| 16 | 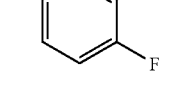 |
| 17 | 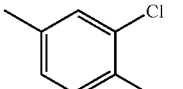 |
| 18 | 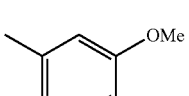 |
| 19 | 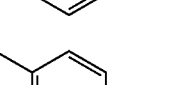 |
| 20 | 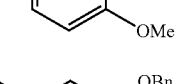 |
| 21 | 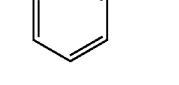 |
| 22 | 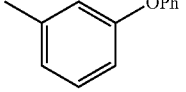 |
| 23 | 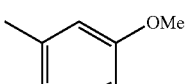 |
| 24 | 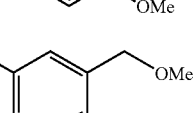 |
| 25 |  |

TABLE 60-continued
(I-3-A-2-13)
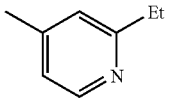
| No. | E³ |
|---|---|
| 26 | 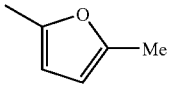 |
| 27 | 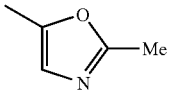 |
| 28 | 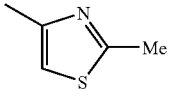 |
| 29 | 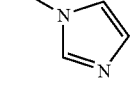 |
| 30 | 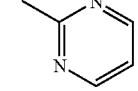 |
| 31 | 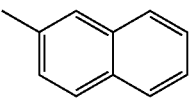 |
| 32 | 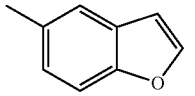 |
| 33 | 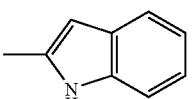 |
| 34 | 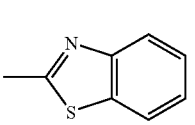 |
| 35 | 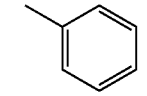 |
TABLE 61
(I-3-A-3-13)
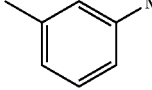
| No. | E³ |
|---|---|
| 1 | 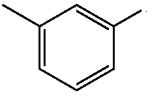 |
| 2 | 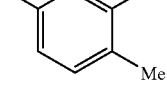 |
| 3 | 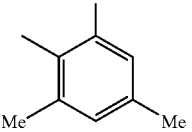 |
| 4 | 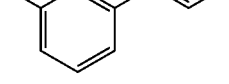 |
| 5 | 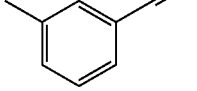 |
| 6 | 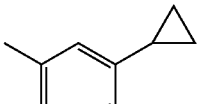 |
| 7 | 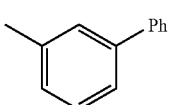 |
| 8 | 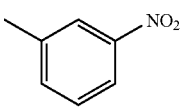 |
| 9 | 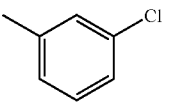 |
| 10 | |
| 11 | |

TABLE 61-continued (I-3-A-3-13)

| No. | E³ |
|---|---|
| 12 | 4-F-phenyl |
| 13 | 3,5-diF-phenyl |
| 14 | 3,4-diF-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |
| 19 | 3-OMe-phenyl |
| 20 | 4-OMe-phenyl |
| 21 | 3-OBn-phenyl |
| 22 | 3-OPh-phenyl |
| 23 | 3,4-diOMe-phenyl |
| 24 | 3-(CH₂OMe)-phenyl |
| 25 | 3-(CH₂OCH₂CF₃)-phenyl |
| 26 | 2-Et-4-pyridyl |
| 27 | 5-Me-2-furyl |
| 28 | 2-Me-5-oxazolyl |
| 29 | 2-Me-4-thiazolyl |
| 30 | 1-imidazolyl |
| 31 | 2-pyrimidyl |
| 32 | 2-naphthyl |
| 33 | 5-benzofuryl |
| 34 | 2-indolyl |

TABLE 61-continued
(I-3-A-3-13)
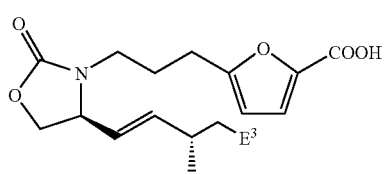
| No. | E³ |
|---|---|
| 35 | 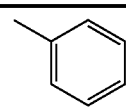 |
TABLE 62
(I-3-A-4-13)
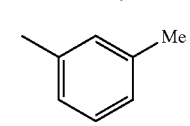
| No. | E³ |
|---|---|
| 1 | 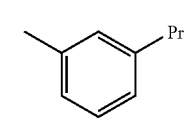 |
| 2 | 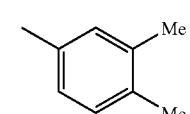 |
| 3 | 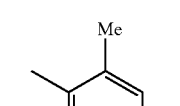 |
| 4 | 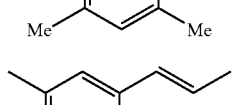 |
| 5 | 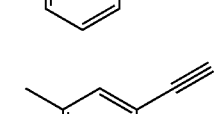 |
| 6 | 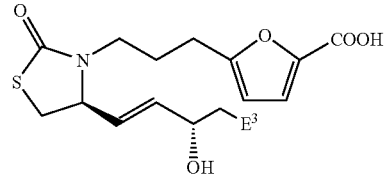 |
| 7 | 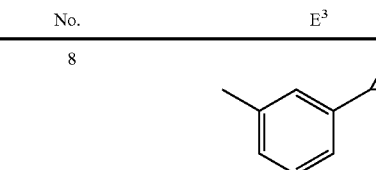 |
TABLE 62-continued
(I-3-A-4-13)
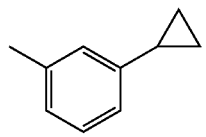
| No. | E³ |
|---|---|
| 8 | 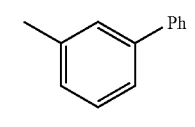 |
| 9 | 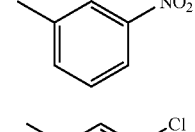 |
| 10 | 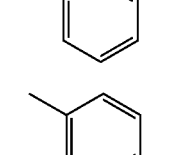 |
| 11 | 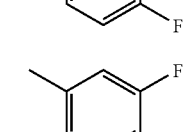 |
| 12 | 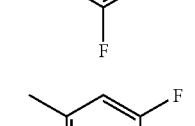 |
| 13 | 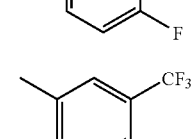 |
| 14 | 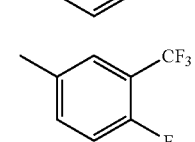 |
| 15 | 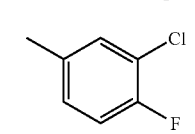 |
| 16 | 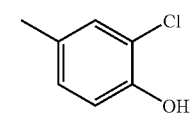 |
| 17 |  |
| 18 | 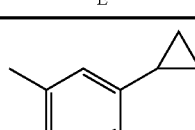 |

TABLE 62-continued (I-3-A-4-13)

Structure: thiazolidinone-N-propyl-furan-COOH with CH=CH-CH(OH)-CH2-E³ substituent

| No. | E³ |
|---|---|
| 19 | 3-methoxyphenyl |
| 20 | 4-methoxyphenyl |
| 21 | 3-(benzyloxy)phenyl |
| 22 | 3-phenoxyphenyl |
| 23 | 3,4-dimethoxyphenyl |
| 24 | 3-(methoxymethyl)phenyl |
| 25 | 3-((2,2,2-trifluoroethoxy)methyl)phenyl |
| 26 | 2-ethyl-4-pyridyl |
| 27 | 5-methylfuran-2-yl |
| 28 | 2-methyloxazol-5-yl |
| 29 | 2-methylthiazol-4-yl |
| 30 | 1-methylimidazol-?-yl |
| 31 | 2-pyrimidinyl |
| 32 | 2-naphthyl |
| 33 | benzofuran-5-yl |
| 34 | 1H-indol-2-yl |
| 35 | benzothiazol-2-yl |

TABLE 63

(I-3-A-1-14)

Structure: pyrrolidinone-N-ethyl-S-thiazole-COOH with CH=CH-CH(OH)-CH2-E³ substituent

| No. | E³ |
|---|---|
| 1 | phenyl |
| 2 | 3-methylphenyl |
| 3 | 3-propylphenyl |
| 4 | 2,4-dimethylphenyl |

TABLE 63-continued (I-3-A-1-14)

[Structure: pyrrolidinone-N-CH2CH2-S-thiazole-COOH with side chain containing CH=CH-CH(OH)-CH2-N(E³)]

| No. | E³ |
|---|---|
| 5 | 2,3,5-trimethylphenyl |
| 6 | 3-(1-propenyl)phenyl |
| 7 | 3-ethynylphenyl |
| 8 | 3-cyclopropylphenyl |
| 9 | 3-phenylphenyl (biphenyl) |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-(trifluoromethyl)phenyl |
| 16 | 3-CF3-4-F-phenyl |
| 17 | 3-Cl-4-F-phenyl |
| 18 | 3-Cl-4-OH-phenyl |
| 19 | 3-methoxyphenyl |
| 20 | 4-methoxyphenyl |
| 21 | 3-OBn-phenyl |
| 22 | 3-OPh-phenyl |
| 23 | 3,4-dimethoxyphenyl |
| 24 | 3-(methoxymethyl)phenyl |
| 25 | 3-(2,2,2-trifluoroethoxymethyl)phenyl |

TABLE 63-continued
(I-3-A-1-14)
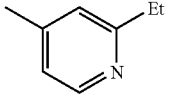
| No. | E³ |
|---|---|
| 26 | 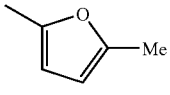 |
| 27 | 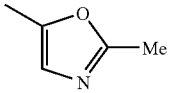 |
| 28 | 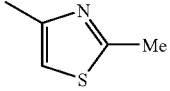 |
| 29 |  |
| 30 |  |
| 31 | 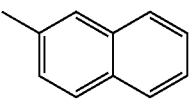 |
| 32 | 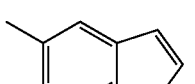 |
| 33 | 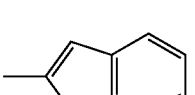 |
| 34 | 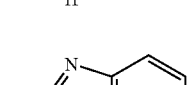 |
| 35 |  |
TABLE 64
(I-3-A-2-14)
| No. | E³ |
|---|---|
| 1 |  |
| 2 |  |
| 3 | 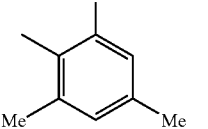 |
| 4 | 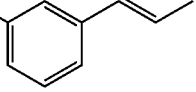 |
| 5 | 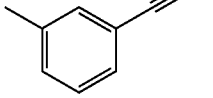 |
| 6 | 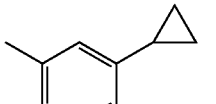 |
| 7 | 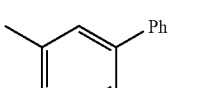 |
| 8 | 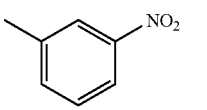 |
| 9 | 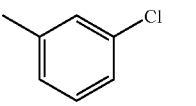 |
| 10 | |
| 11 | |

TABLE 64-continued
(I-3-A-2-14)
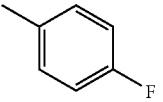
| No. | E³ |
|---|---|
| 12 | 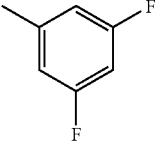 |
| 13 | 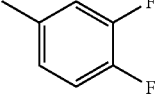 |
| 14 | 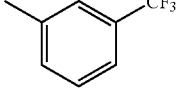 |
| 15 | 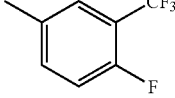 |
| 16 | 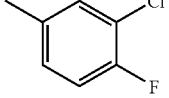 |
| 17 | 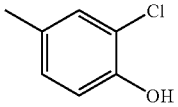 |
| 18 | 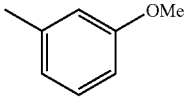 |
| 19 | 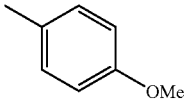 |
| 20 | 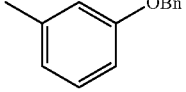 |
| 21 | 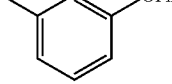 |
| 22 | 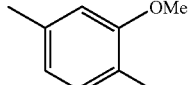 |
TABLE 64-continued
(I-3-A-2-14)
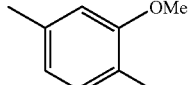
| No. | E³ |
|---|---|
| 23 | 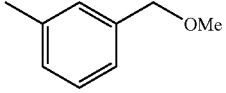 |
| 24 | 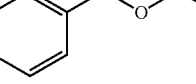 |
| 25 | 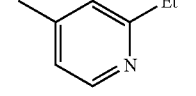 |
| 26 | 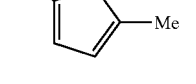 |
| 27 | 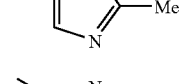 |
| 28 | 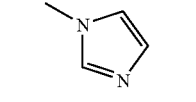 |
| 29 | 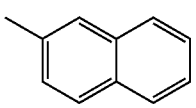 |
| 30 | 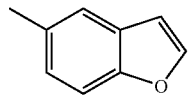 |
| 31 | 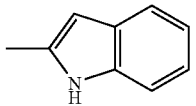 |
| 32 | |
| 33 | |
| 34 | |

TABLE 64-continued
(I-3-A-2-14)
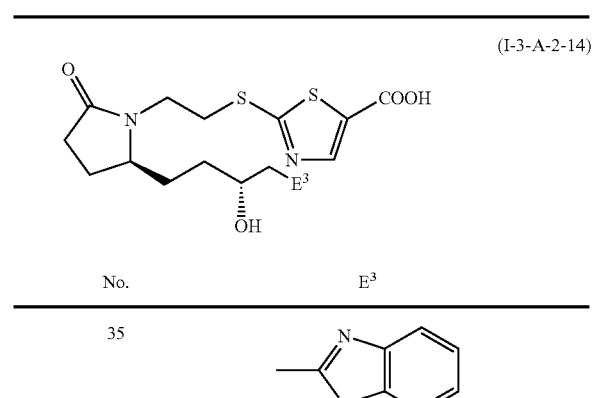
| No. | E³ |
|---|---|
| 35 | 2-benzothiazolyl |
TABLE 65
(I-3-A-3-14)
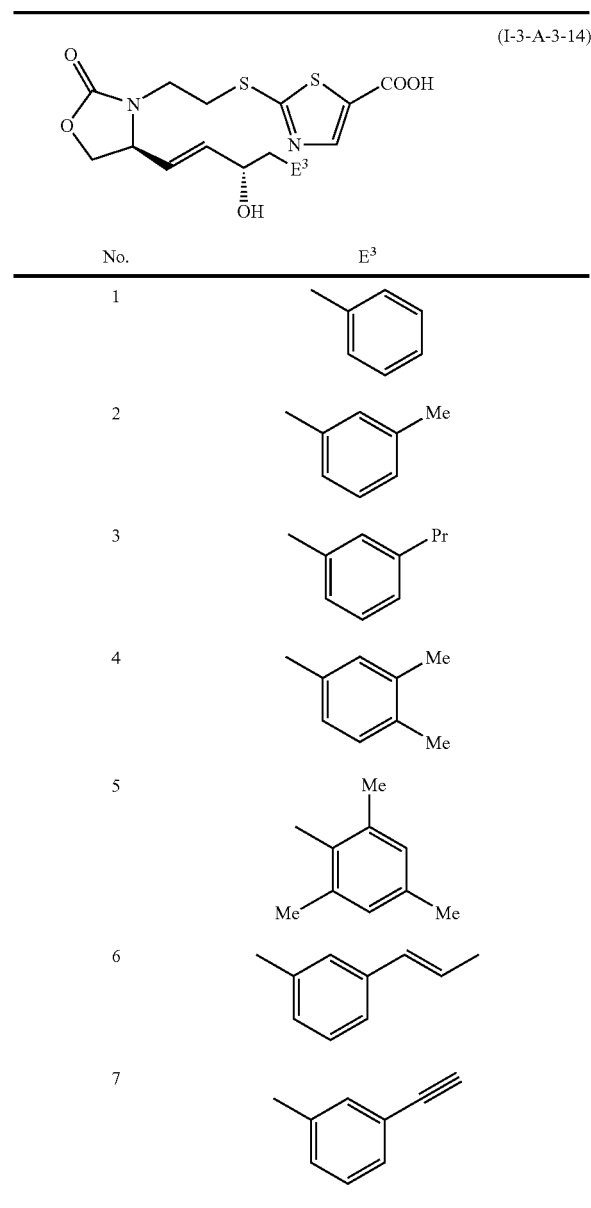
| No. | E³ |
|---|---|
| 1 | phenyl |
| 2 | 3-Me-phenyl |
| 3 | 3-Pr-phenyl |
| 4 | 2,4-Me₂-phenyl |
| 5 | 2,3,5-Me₃-phenyl |
| 6 | 3-(1-propenyl)-phenyl |
| 7 | 3-ethynyl-phenyl |
TABLE 65-continued
(I-3-A-3-14)
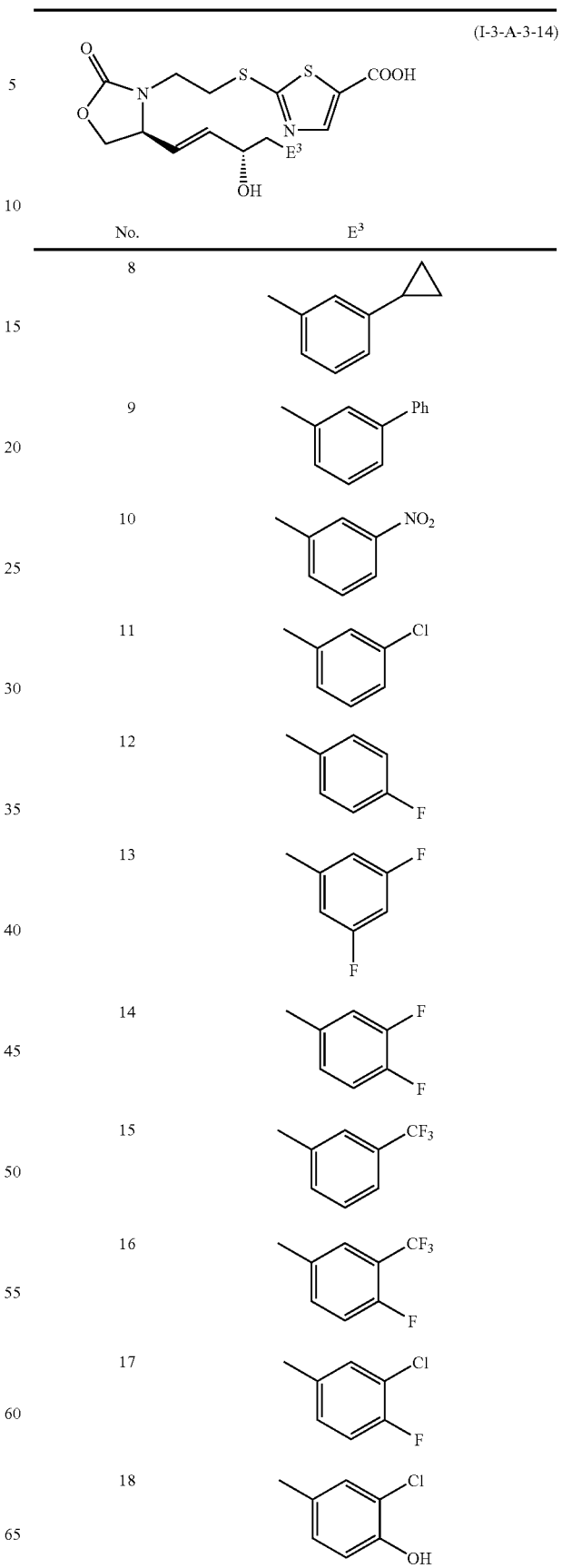
| No. | E³ |
|---|---|
| 8 | 3-cyclopropyl-phenyl |
| 9 | 3-Ph-phenyl |
| 10 | 3-NO₂-phenyl |
| 11 | 3-Cl-phenyl |
| 12 | 4-F-phenyl |
| 13 | 3,5-F₂-phenyl |
| 14 | 3,4-F₂-phenyl |
| 15 | 3-CF₃-phenyl |
| 16 | 3-CF₃-4-F-phenyl |
| 17 | 3-Cl-4-F-phenyl |
| 18 | 3-Cl-4-OH-phenyl |

TABLE 65-continued (I-3-A-3-14)

Structure: oxazolidinone-CH2CH2-S-thiazole-COOH with CH=CH-CH(OH)-CH2-E3 substituent

| No. | E3 |
|---|---|
| 19 | 3-methoxyphenyl |
| 20 | 4-methoxyphenyl |
| 21 | 3-benzyloxyphenyl (OBn) |
| 22 | 3-phenoxyphenyl (OPh) |
| 23 | 3,4-dimethoxyphenyl |
| 24 | 3-(methoxymethyl)phenyl |
| 25 | 3-(2,2,2-trifluoroethoxymethyl)phenyl |
| 26 | 2-ethyl-4-pyridyl |
| 27 | 2,5-dimethylfuran-yl |
| 28 | 2,5-dimethyloxazol-yl |
| 29 | 2,4-dimethylthiazol-yl |
| 30 | 1-methylimidazol-yl |

TABLE 65-continued (I-3-A-3-14)

| No. | E3 |
|---|---|
| 31 | 2-methylpyrimidinyl |
| 32 | 2-naphthyl |
| 33 | 5-benzofuranyl |
| 34 | 2-indolyl (NH) |
| 35 | 2-benzothiazolyl |

TABLE 66

(I-3-A-4-14)

Structure: thiazolidinone-CH2CH2-S-thiazole-COOH with CH=CH-CH(OH)-CH2-E3 substituent

| No. | E3 |
|---|---|
| 1 | phenyl |
| 2 | 3-methylphenyl (Me) |
| 3 | 3-propylphenyl (Pr) |
| 4 | 2,5-dimethylphenyl |

TABLE 66-continued (I-3-A-4-14)

| No. | E³ |
|---|---|
| 5 | 2,3,5-trimethylphenyl |
| 6 | 3-(1-propenyl)phenyl |
| 7 | 3-ethynylphenyl |
| 8 | 3-cyclopropylphenyl |
| 9 | 3-phenylphenyl |
| 10 | 3-nitrophenyl |
| 11 | 3-chlorophenyl |
| 12 | 4-fluorophenyl |
| 13 | 3,5-difluorophenyl |
| 14 | 3,4-difluorophenyl |
| 15 | 3-(trifluoromethyl)phenyl |
| 16 | 4-fluoro-3-(trifluoromethyl)phenyl |
| 17 | 3-chloro-4-fluorophenyl |
| 18 | 3-chloro-4-hydroxyphenyl |
| 19 | 3-methoxyphenyl |
| 20 | 4-methoxyphenyl |
| 21 | 3-benzyloxyphenyl |
| 22 | 3-phenoxyphenyl |
| 23 | 3,4-dimethoxyphenyl |
| 24 | 3-(methoxymethyl)phenyl |
| 25 | 3-((2,2,2-trifluoroethoxy)methyl)phenyl |

TABLE 66-continued (I-3-A-4-14)

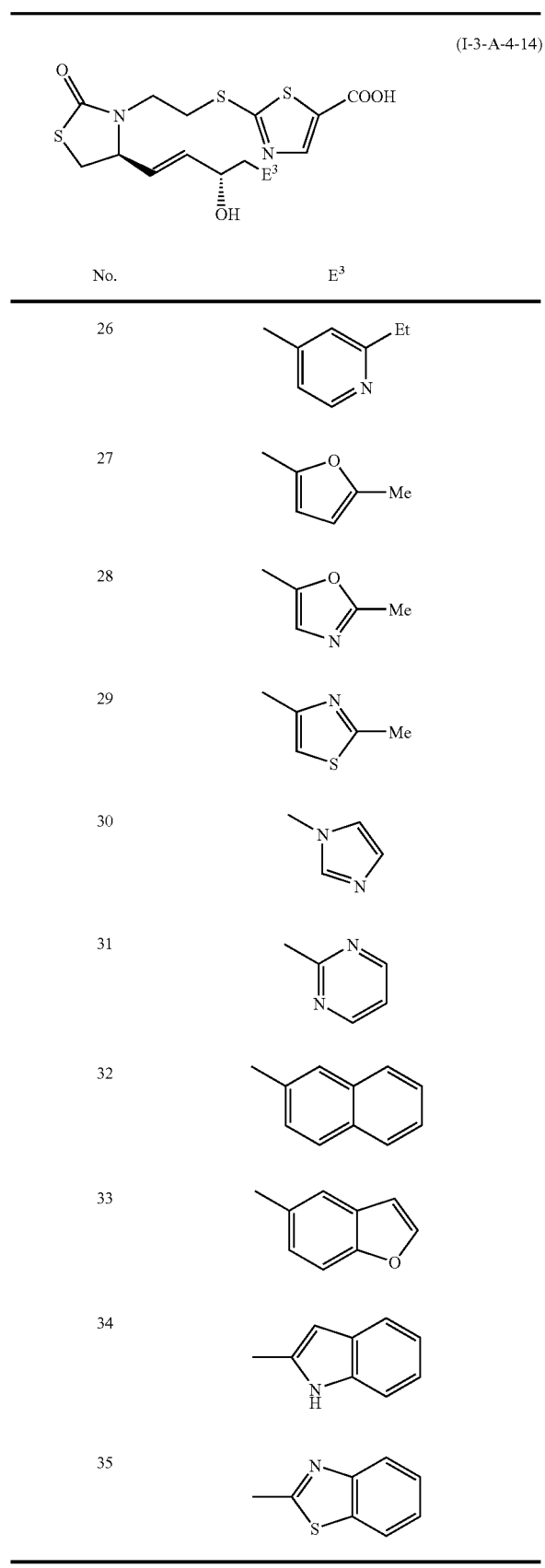

| No. | E³ |
|---|---|
| 26 | 4-methyl-2-ethyl-pyridine |
| 27 | 2,5-dimethyl-furan |
| 28 | 2,5-dimethyl-oxazole |
| 29 | 2,4-dimethyl-thiazole |
| 30 | 1-methyl-imidazole |
| 31 | 2-methyl-pyrimidine |
| 32 | methyl-naphthalene |
| 33 | 5-methyl-benzofuran |
| 34 | 2-methyl-indole |
| 35 | 2-methyl-benzothiazole |

TABLE 67

(I-2-A-1-1)

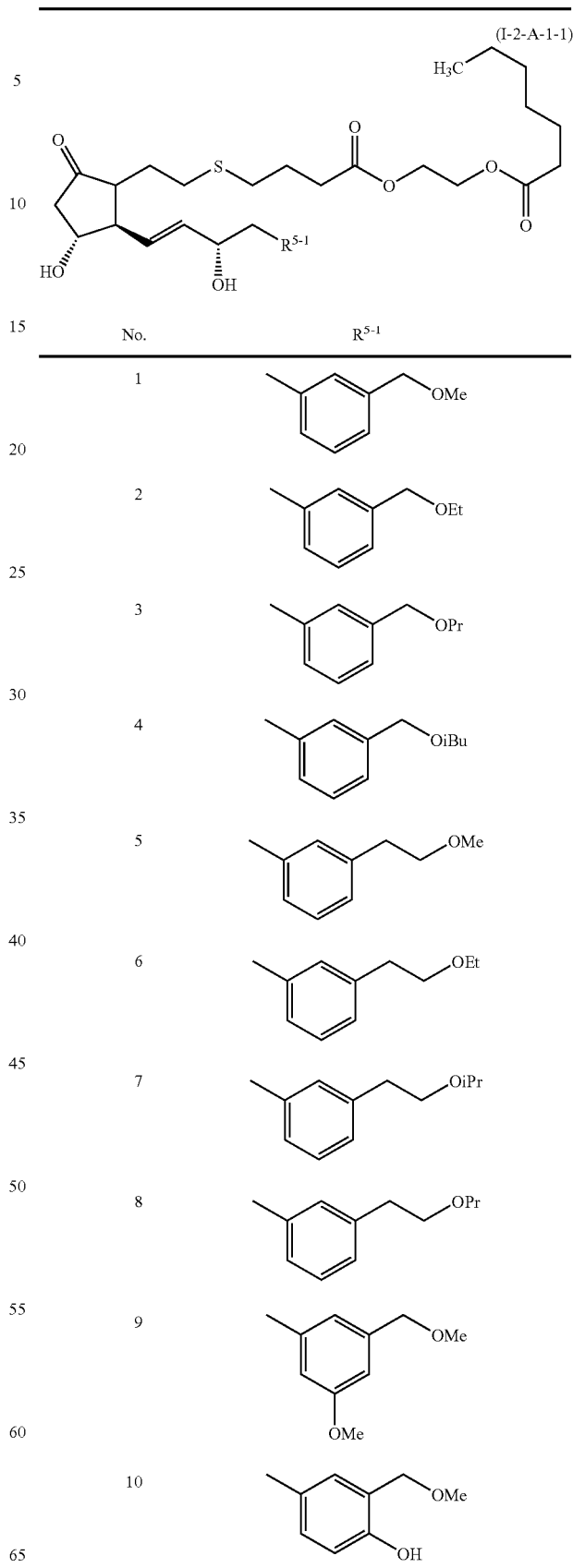

| No. | R⁵⁻¹ |
|---|---|
| 1 | 3-methylbenzyl-OMe |
| 2 | 3-methylbenzyl-OEt |
| 3 | 3-methylbenzyl-OPr |
| 4 | 3-methylbenzyl-OiBu |
| 5 | 3-methylphenethyl-OMe |
| 6 | 3-methylphenethyl-OEt |
| 7 | 3-methylphenethyl-OiPr |
| 8 | 3-methylphenethyl-OPr |
| 9 | 3,5-dimethoxy-methylbenzyl-OMe |
| 10 | 4-methyl-2-hydroxy-benzyl-OMe |

TABLE 67-continued

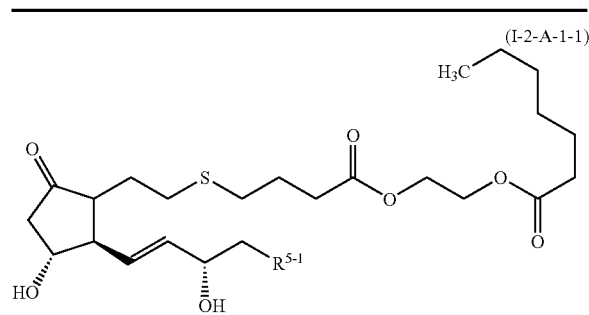

(I-2-A-1-1)

| No. | R^{5-1} |
|---|---|
| 11 | 4-methyl-2-(2-methoxyethyl)phenol |
| 12 | 4-methyl-2-(2-ethoxyethyl)phenol |
| 13 | 4-methyl-2-methylphenol |
| 14 | 4-methyl-2-ethylphenol |
| 15 | 4-methyl-2-propylphenol |
| 16 | 3-methylbenzyl alcohol |
| 17 | 4-methyl-2-(2-fluoroethyl)phenol |
| 18 | 3-methylbenzyl allyl ether |
| 19 | 3-methylbenzyl phenyl ether |
| 20 | 3-methylbenzyl cyclopentyl ether |

TABLE 67-continued

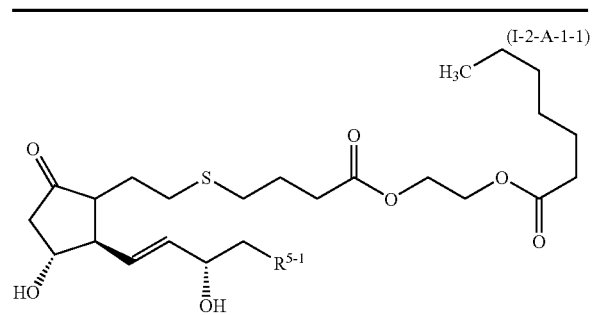

(I-2-A-1-1)

| No. | R^{5-1} |
|---|---|
| 21 | 3-methylbenzyl methyl sulfide |
| 22 | 3-methylbenzyl ethyl sulfide |
| 23 | 3-methylbenzyl propyl sulfide |
| 24 | 4-methyl-2-(methylthiomethyl)phenol |
| 25 | 3-methyl-(2-methylthioethyl)benzene |
| 26 | 3-methoxy-5-methyl-benzyl methyl sulfide |
| 27 | 2-fluoro-5-methyl-benzyl methyl ether |
| 28 | 2-chloro-5-methyl-benzyl methyl ether |
| 29 | 2-fluoro-5-methyl-benzyl methyl sulfide |
| 30 | 2-chloro-5-methyl-benzyl methyl sulfide |

TABLE 68

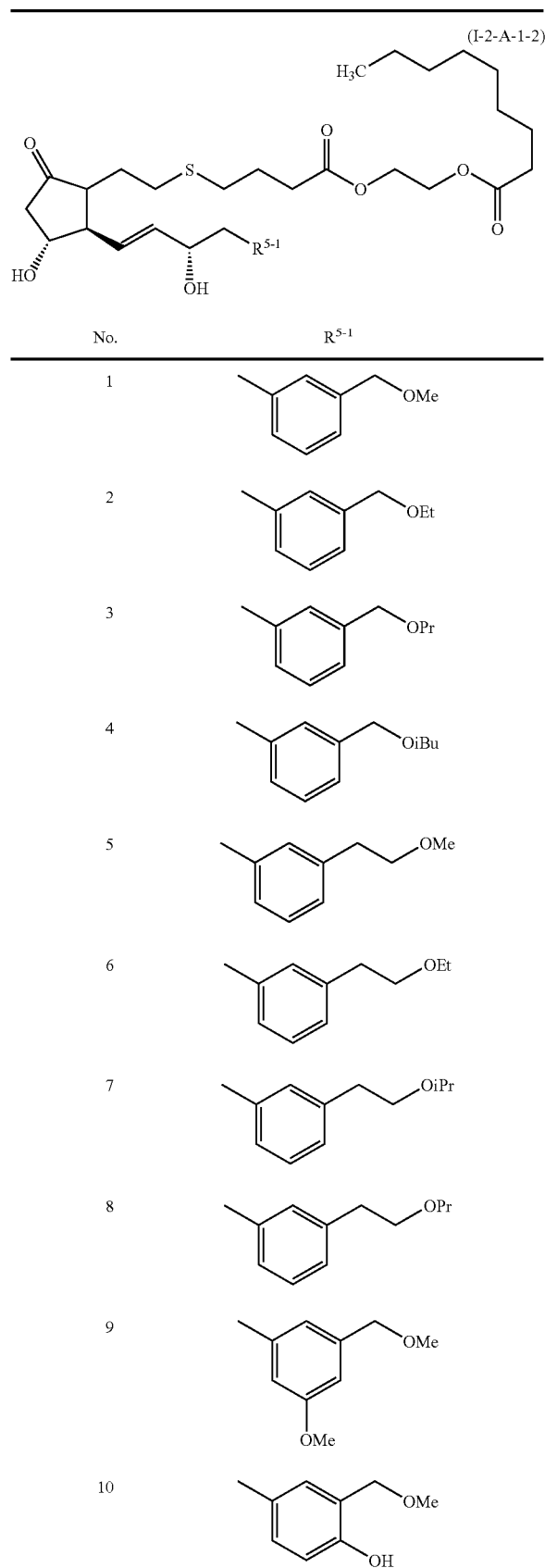

| No. | R<sup>5-1</sup> |
|---|---|
| 1 | 3-(MeOCH₂)-phenyl (OMe) |
| 2 | 3-(EtOCH₂)-phenyl (OEt) |
| 3 | 3-(PrOCH₂)-phenyl (OPr) |
| 4 | 3-(iBuOCH₂)-phenyl (OiBu) |
| 5 | 3-(MeOCH₂CH₂)-phenyl (OMe) |
| 6 | 3-(EtOCH₂CH₂)-phenyl (OEt) |
| 7 | 3-(iPrOCH₂CH₂)-phenyl (OiPr) |
| 8 | 3-(PrOCH₂CH₂)-phenyl (OPr) |
| 9 | 3,5-(MeO)₂-benzyl ether type |
| 10 | 2-(MeOCH₂)-4-... phenol (OH) |

TABLE 68-continued

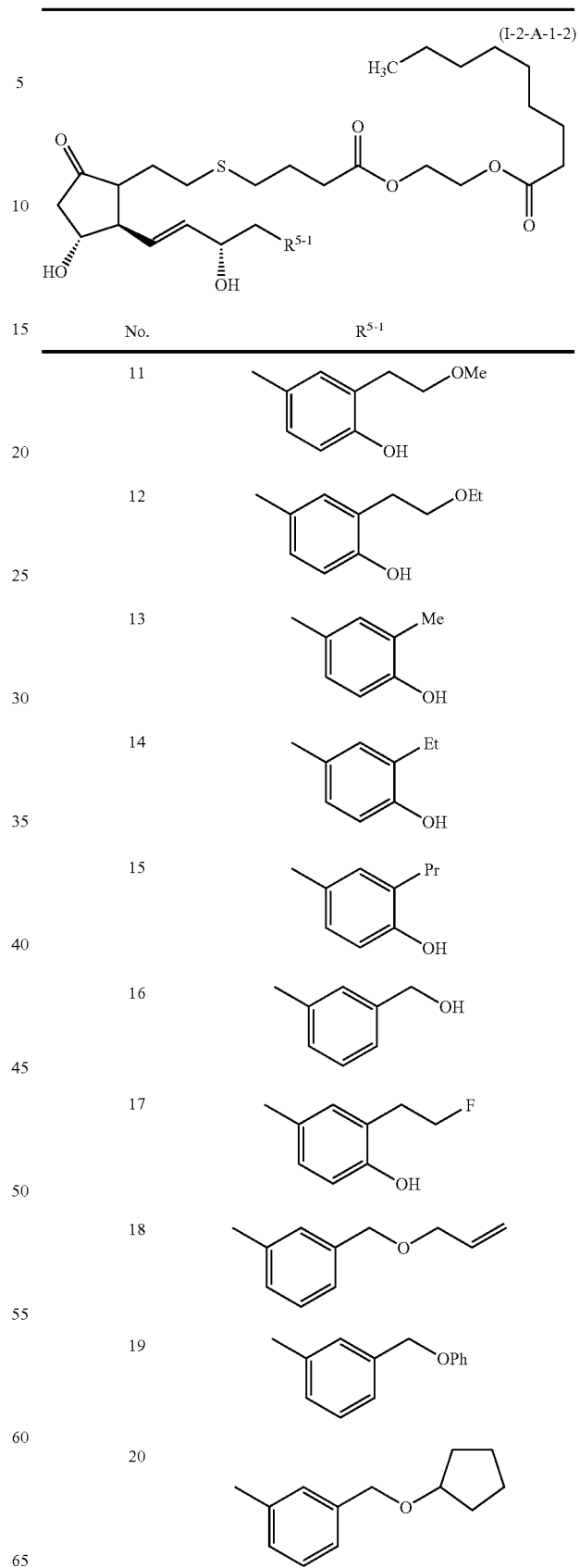

| No. | R<sup>5-1</sup> |
|---|---|
| 11 | 2-(MeOCH₂CH₂)-4-methyl-phenol |
| 12 | 2-(EtOCH₂CH₂)-4-methyl-phenol |
| 13 | 2-Me-4-methyl-phenol |
| 14 | 2-Et-4-methyl-phenol |
| 15 | 2-Pr-4-methyl-phenol |
| 16 | 3-(HOCH₂)-phenyl |
| 17 | 2-(FCH₂CH₂)-4-methyl-phenol |
| 18 | 3-(allyl-O-CH₂)-phenyl |
| 19 | 3-(PhO-CH₂)-phenyl |
| 20 | 3-(cyclopentyl-O-CH₂)-phenyl |

TABLE 68-continued (I-2-A-1-2)

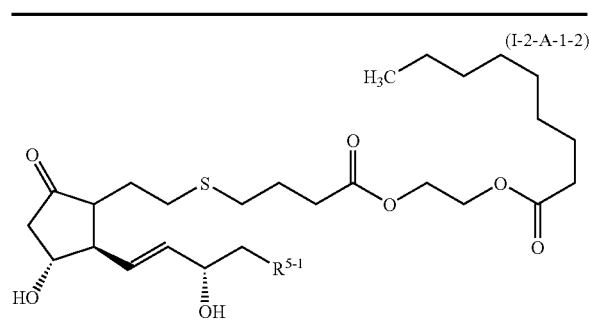

| No. | R⁵⁻¹ |
|---|---|
| 21 | 3-(SMe-CH2)-phenyl |
| 22 | 3-(SEt-CH2)-phenyl |
| 23 | 3-(SPr-CH2)-phenyl |
| 24 | 4-Me, 2-(SMe-CH2), 1-OH phenyl |
| 25 | 3-(CH2CH2SMe)-phenyl |
| 26 | 3-OMe, 5-(CH2SMe)-phenyl |
| 27 | 5-Me, 2-(CH2OMe), 1-F phenyl |
| 28 | 5-Me, 2-(CH2OMe), 1-Cl phenyl |
| 29 | 5-Me, 2-(CH2SMe), 1-F phenyl |
| 30 | 5-Me, 2-(CH2SMe), 1-Cl phenyl |

TABLE 69

(I-2-A-1-3)

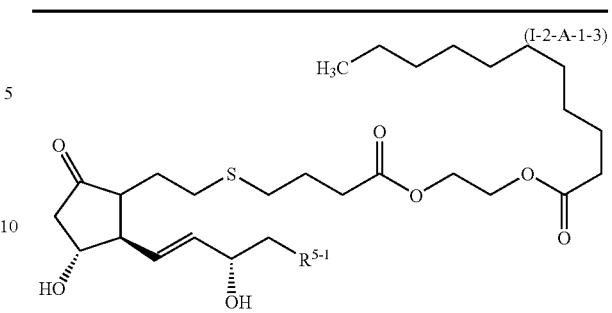

| No. | R⁵⁻¹ |
|---|---|
| 1 | 3-(CH2OMe)-phenyl |
| 2 | 3-(CH2OEt)-phenyl |
| 3 | 3-(CH2OPr)-phenyl |
| 4 | 3-(CH2OiBu)-phenyl |
| 5 | 3-(CH2CH2OMe)-phenyl |
| 6 | 3-(CH2CH2OEt)-phenyl |
| 7 | 3-(CH2CH2OiPr)-phenyl |
| 8 | 3-(CH2CH2OPr)-phenyl |
| 9 | 3,5-di-OMe, (CH2OMe)-phenyl |
| 10 | 4-Me, 2-(CH2OMe), 1-OH phenyl |
| 11 | 4-Me, 2-(CH2CH2OMe), 1-OH phenyl |

TABLE 69-continued

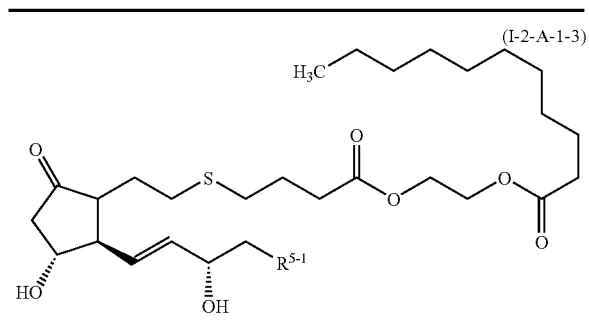

(I-2-A-1-3)

| No. | R^{5-1} |
|---|---|
| 12 | 4-methyl-2-(2-ethoxyethyl)phenol |
| 13 | 2,4-dimethylphenol (Me, OH) |
| 14 | 4-methyl-2-ethylphenol (Et, OH) |
| 15 | 4-methyl-2-propylphenol (Pr, OH) |
| 16 | 3-methylbenzyl alcohol (OH) |
| 17 | 4-methyl-2-(2-fluoroethyl)phenol (F, OH) |
| 18 | 3-methylbenzyl allyl ether |
| 19 | 3-methylbenzyl phenyl ether (OPh) |
| 20 | 3-methylbenzyl cyclopentyl ether |
| 21 | 3-methylbenzyl methyl sulfide (SMe) |

TABLE 69-continued

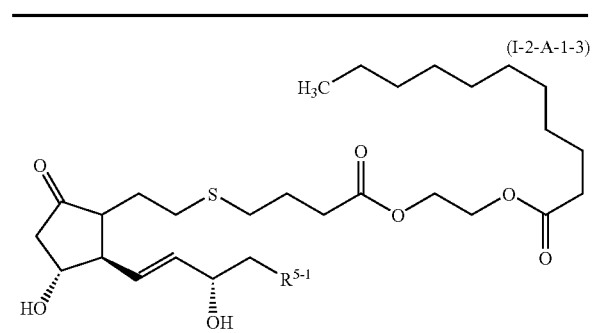

(I-2-A-1-3)

| No. | R^{5-1} |
|---|---|
| 22 | 3-methylbenzyl ethyl sulfide (SEt) |
| 23 | 3-methylbenzyl propyl sulfide (SPr) |
| 24 | 4-methyl-2-(methylthiomethyl)phenol (SMe, OH) |
| 25 | 3-methylphenethyl methyl sulfide (SMe) |
| 26 | 3-methyl-5-methoxybenzyl methyl sulfide (SMe, OMe) |
| 27 | 5-methyl-2-fluorobenzyl methyl ether (OMe, F) |
| 28 | 5-methyl-2-chlorobenzyl methyl ether (OMe, Cl) |
| 29 | 5-methyl-2-fluorobenzyl methyl sulfide (SMe, F) |
| 30 | 5-methyl-2-chlorobenzyl methyl sulfide (SMe, Cl) |

TABLE 70

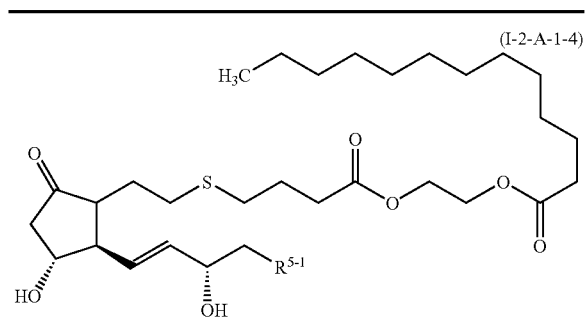
(I-2-A-1-4)

| No. | R^{5-1} |
|---|---|
| 1 | 3-methylbenzyl-OMe |
| 2 | 3-methylbenzyl-OEt |
| 3 | 3-methylbenzyl-OPr |
| 4 | 3-methylbenzyl-OiBu |
| 5 | 3-methylphenethyl-OMe |
| 6 | 3-methylphenethyl-OEt |
| 7 | 3-methylphenethyl-OiPr |
| 8 | 3-methylphenethyl-OPr |
| 9 | 3,5-dimethoxybenzyl (3-Me, 5-OMe, CH2OMe) |
| 10 | 4-methyl-2-(methoxymethyl)phenol |

TABLE 70-continued

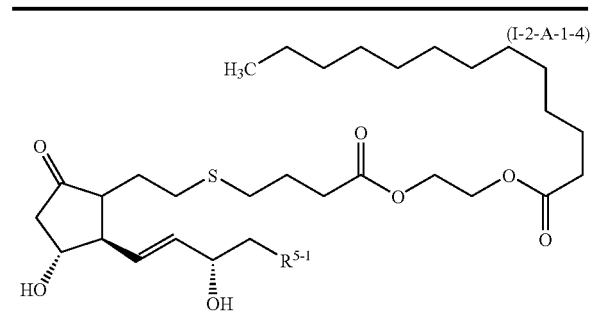
(I-2-A-1-4)

| No. | R^{5-1} |
|---|---|
| 11 | 4-methyl-2-(2-methoxyethyl)phenol |
| 12 | 4-methyl-2-(2-ethoxyethyl)phenol |
| 13 | 4-methyl-2-methylphenol |
| 14 | 4-methyl-2-ethylphenol |
| 15 | 4-methyl-2-propylphenol |
| 16 | 3-methylbenzyl alcohol |
| 17 | 4-methyl-2-(2-fluoroethyl)phenol |
| 18 | 3-methylbenzyl allyl ether |
| 19 | 3-methylbenzyl phenyl ether |
| 20 | 3-methylbenzyl cyclopentyl ether |

TABLE 70-continued (I-2-A-1-4)

No. | R^{5-1}
--- | ---
21 | 3-(SMe-methyl)phenyl
22 | 3-(SEt-methyl)phenyl
23 | 3-(SPr-methyl)phenyl
24 | 2-(SMe-methyl)-4-methylphenyl with OH
25 | 3-(2-SMe-ethyl)phenyl
26 | 3-(SMe-methyl)-5-OMe-phenyl
27 | 2-(OMe-methyl)-5-methyl-phenyl with F
28 | 2-(OMe-methyl)-5-methyl-phenyl with Cl
29 | 2-(SMe-methyl)-5-methyl-phenyl with F
30 | 2-(SMe-methyl)-5-methyl-phenyl with Cl

TABLE 71

(I-2-A-1-5)

No. | R^{1-2}
--- | ---
1 | 3-phenylphenyl acetate
2 | butyl (acetyloxy)acetate
3 | [2-oxo-3-(dipropylamino)propyl] acetate
4 | 2-(heptylsulfonyl)ethyl acetate
5 | (acetyloxy)methyl nonanoate
6 | 1-(cyclohexanecarbonyloxy)ethyl acetate
7 | 2-(nonanoyloxy)ethyl acetate
8 | 2-[(pentyloxyacetyl)oxy]ethyl acetate
9 | 2-(5-phenylpentanoyloxy)ethyl acetate TABLE 71-continued
(I-2-A-1-5)
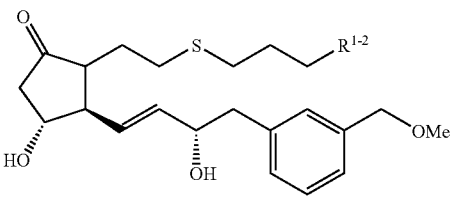
| No. | R[1-2] |
|---|---|
| 10 | 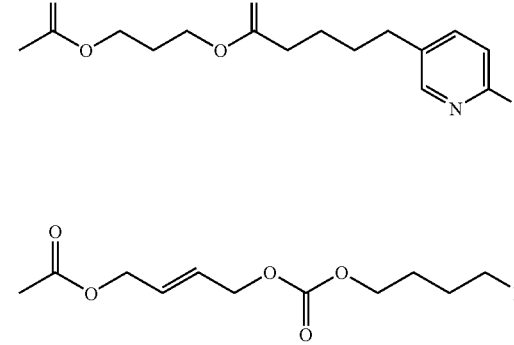 |
| 11 | 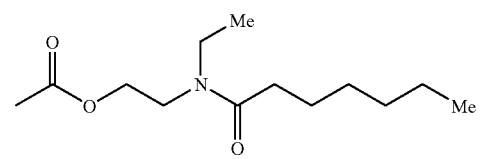 |
| 12 | 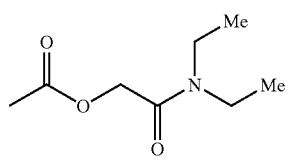 |
| 13 | 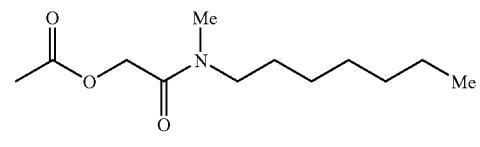 |
| 14 | 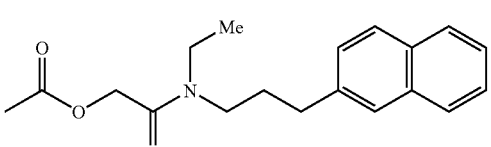 |
| 15 | 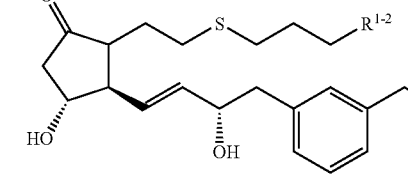 |
TABLE 72
(I-2-A-1-6)
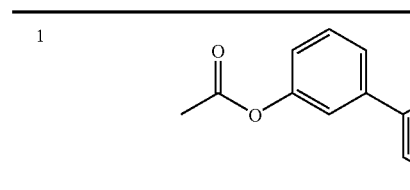
| No. | R[1-2] |
|---|---|
| 1 | 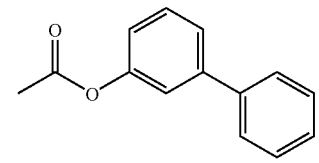 |
| 2 | 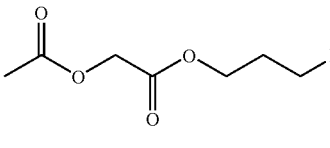 |
| 3 | 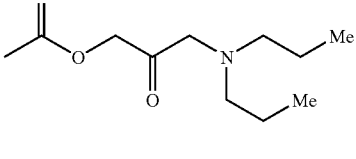 |
| 4 | 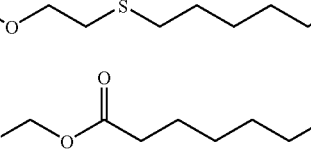 |
| 5 | 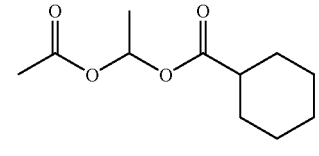 |
| 6 | 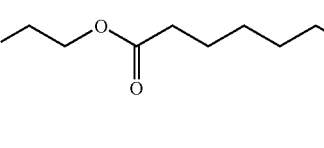 |
| 7 | 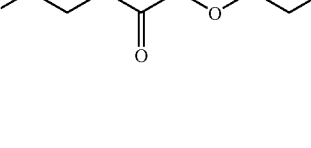 |
| 8 | 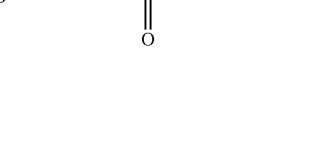 |
| 9 |  |

TABLE 72-continued
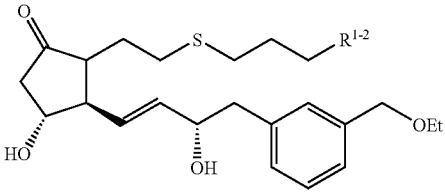
(I-2-A-1-6)
| No. | R[1-2] |
|---|---|
| 10 | 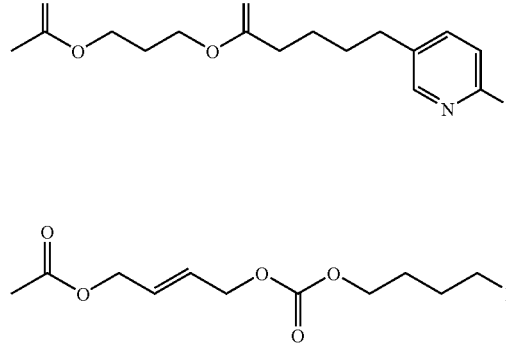 |
| 11 | 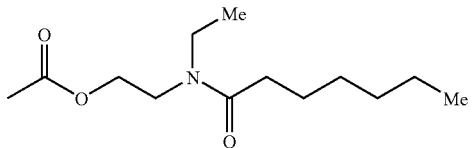 |
| 12 | 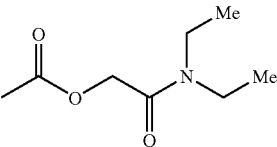 |
| 13 | 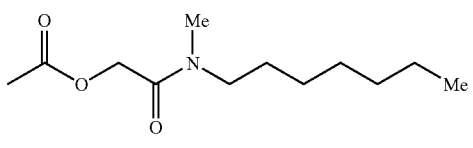 |
| 14 | 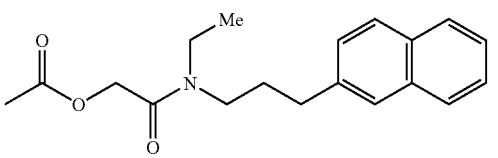 |
| 15 | 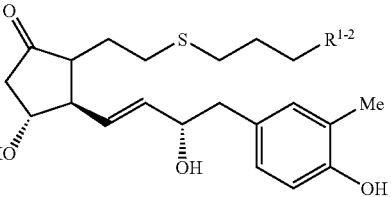 |
TABLE 73
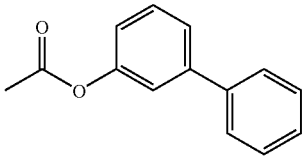
(I-2-A-1-7)
| No. | R[1-2] |
|---|---|
| 1 | 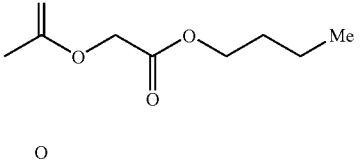 |
| 2 | 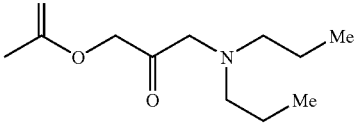 |
| 3 | 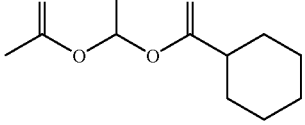 |
| 4 | 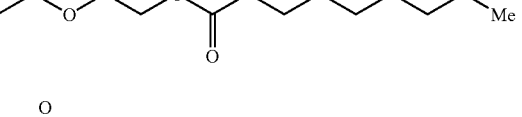 |
| 5 | 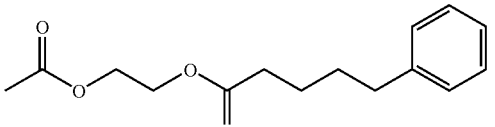 |
| 6 | |
| 7 | |
| 8 | |
| 9 | |

TABLE 73-continued (I-2-A-1-7)

| No. | R<sup>1-2</sup> |
|---|---|
| 10 | acetoxy-propyl ester of 5-(6-methylpyridin-3-yl)pentanoic acid |
| 11 | (E)-4-acetoxybut-2-enyl pentyl carbonate |
| 12 | 2-(N-ethyl-heptanamido)ethyl acetate |
| 13 | 2-(diethylamino)-2-oxoethyl acetate |
| 14 | 2-(N-methyl-heptylamino)-2-oxoethyl acetate |
| 15 | 2-(N-ethyl-3-(naphthalen-2-yl)propylamino)-2-oxoethyl acetate |

TABLE 74

(I-2-A-2-1)

| No. | R<sup>5-1</sup> |
|---|---|
| 1 | 3-methyl-(methoxymethyl)benzene |
| 2 | 3-methyl-(ethoxymethyl)benzene |
| 3 | 3-methyl-(propoxymethyl)benzene |
| 4 | 3-methyl-(isobutoxymethyl)benzene |
| 5 | 3-methyl-(2-methoxyethyl)benzene |
| 6 | 3-methyl-(2-ethoxyethyl)benzene |
| 7 | 3-methyl-(2-isopropoxyethyl)benzene |
| 8 | 3-methyl-(2-propoxyethyl)benzene |
| 9 | 3,5-dimethoxy-(methoxymethyl) benzene analog |
| 10 | 2-hydroxy-4-methyl-(methoxymethyl)benzene |
| 11 | 2-hydroxy-4-methyl-(2-methoxyethyl)benzene |

TABLE 74-continued
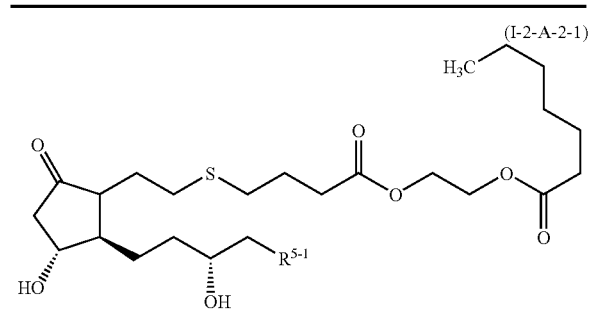
(I-2-A-2-1)
| No. | R^{5-1} |
|---|---|
| 12 | 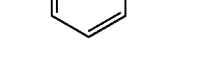 (4-Me, 2-CH2CH2OEt, phenol-OH) |
| 13 | 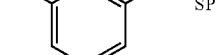 (4-Me, 2-Me, phenol-OH) |
| 14 | 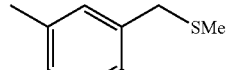 (4-Me, 2-Et, phenol-OH) |
| 15 | 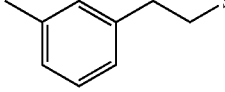 (4-Me, 2-Pr, phenol-OH) |
| 16 | 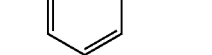 (3-Me, CH2OH) |
| 17 | 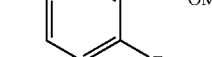 (4-Me, 2-CH2CH2F, phenol-OH) |
| 18 | 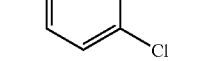 (3-Me, CH2-O-allyl) |
| 19 | 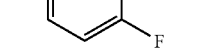 (3-Me, CH2-OPh) |
| 20 | 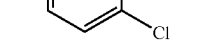 (3-Me, CH2-O-cyclopentyl) |
| 21 | 3-Me-C6H4-CH2-SMe |
TABLE 74-continued
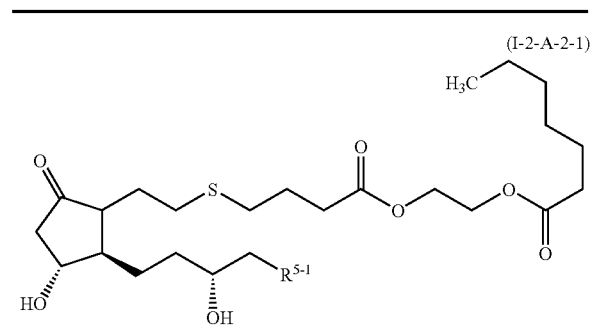
(I-2-A-2-1)
| No. | R^{5-1} |
|---|---|
| 22 | 3-Me-C6H4-CH2-SEt |
| 23 | 3-Me-C6H4-CH2-SPr |
| 24 | 4-Me, 2-CH2SMe, phenol-OH |
| 25 | 3-Me-C6H4-CH2CH2-SMe |
| 26 | 3-Me, 5-OMe, CH2-SMe |
| 27 | 5-Me, 2-F, CH2-OMe |
| 28 | 5-Me, 2-Cl, CH2-OMe |
| 29 | 5-Me, 2-F, CH2-SMe |
| 30 | 5-Me, 2-Cl, CH2-SMe |

TABLE 75

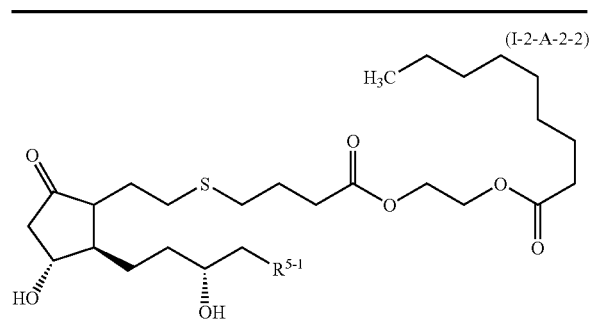

(I-2-A-2-2)

TABLE 75-continued

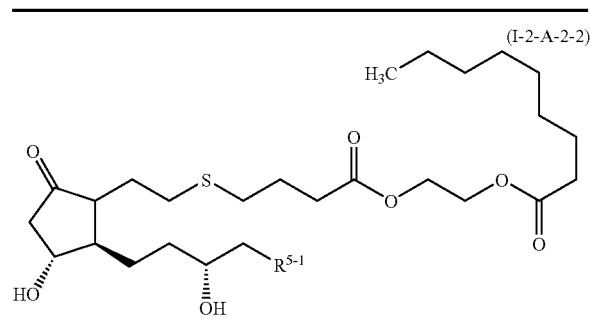

(I-2-A-2-2)

| No. | R$^{5-1}$ |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3,5-bis(OMe)benzyl OMe |
| 10 | 2-(OMe-methyl)-4-methylphenol |

| No. | R$^{5-1}$ |
|---|---|
| 11 | 2-(2-OMe-ethyl)-4-methylphenol |
| 12 | 2-(2-OEt-ethyl)-4-methylphenol |
| 13 | 2,4-dimethylphenol |
| 14 | 2-Et-4-methylphenol |
| 15 | 2-Pr-4-methylphenol |
| 16 | 3-methylbenzyl alcohol |
| 17 | 2-(2-fluoroethyl)-4-methylphenol |
| 18 | 3-methylbenzyl allyl ether |
| 19 | 3-methylbenzyl phenyl ether |
| 20 | 3-methylbenzyl cyclopentyl ether |

TABLE 75-continued
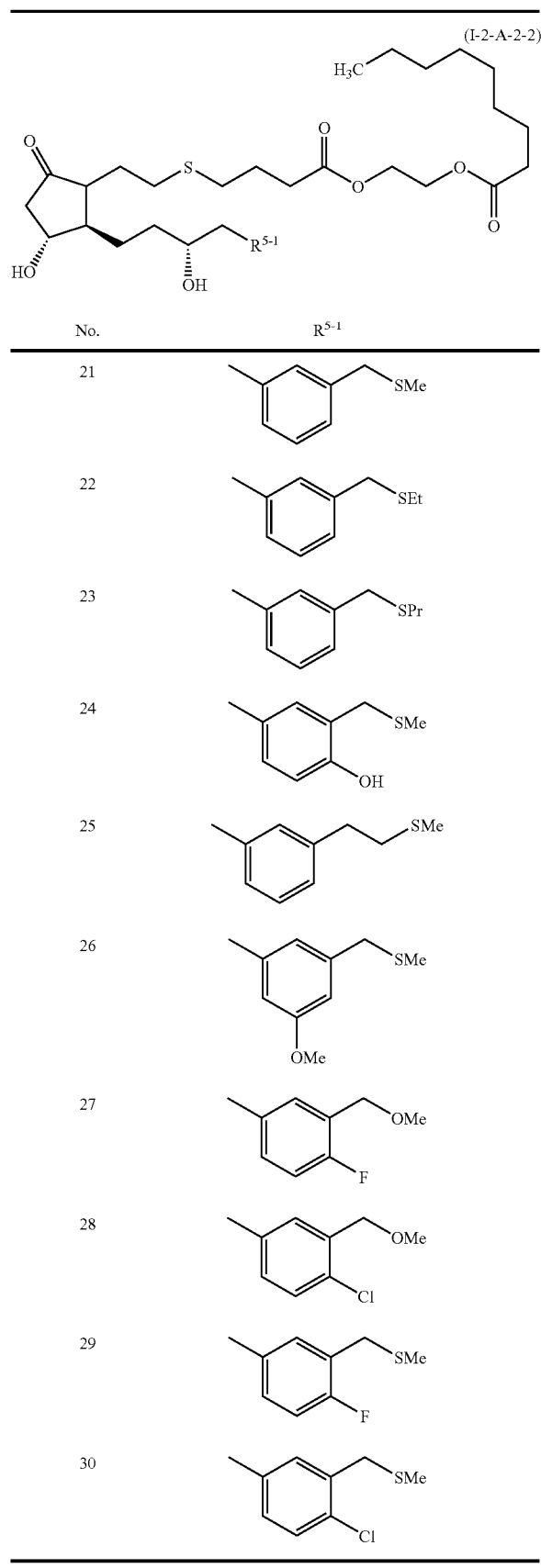
TABLE 76
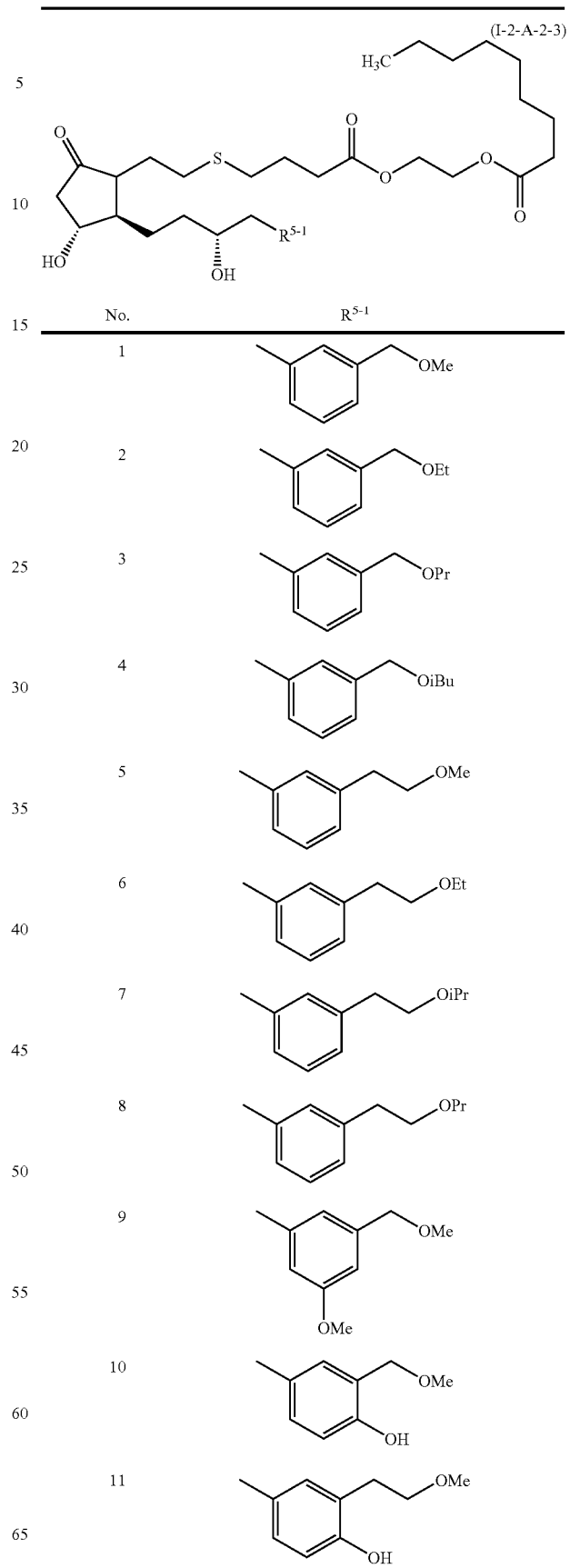

TABLE 76-continued
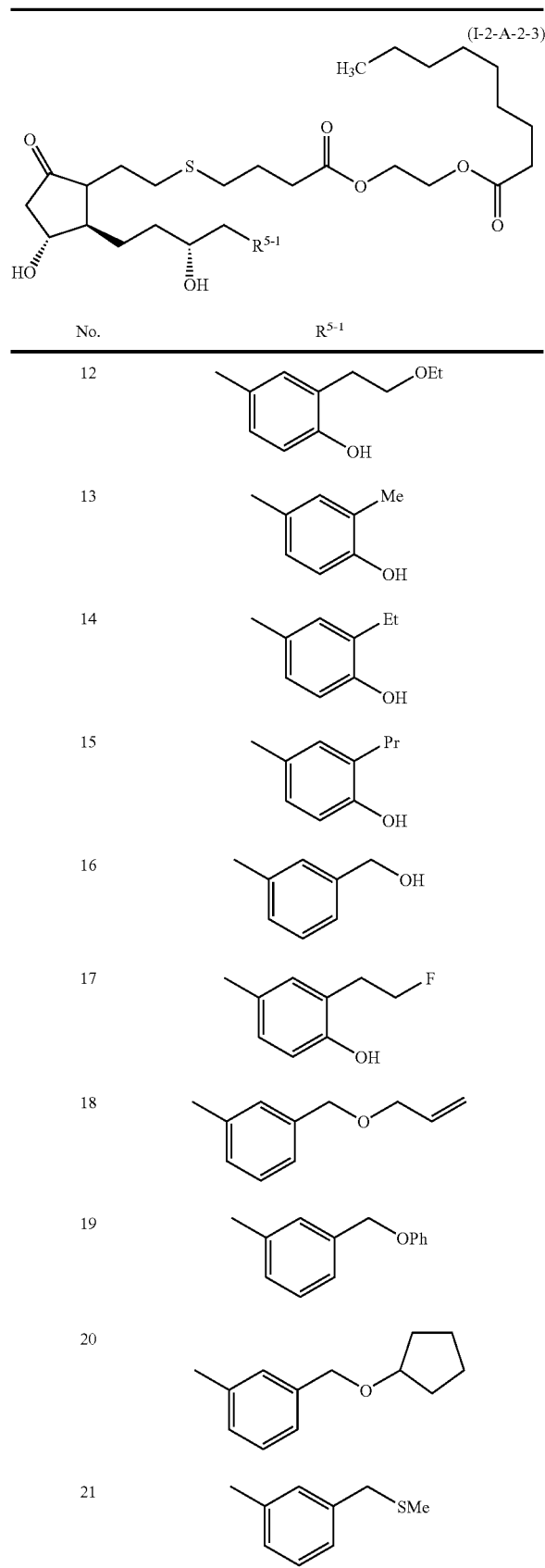
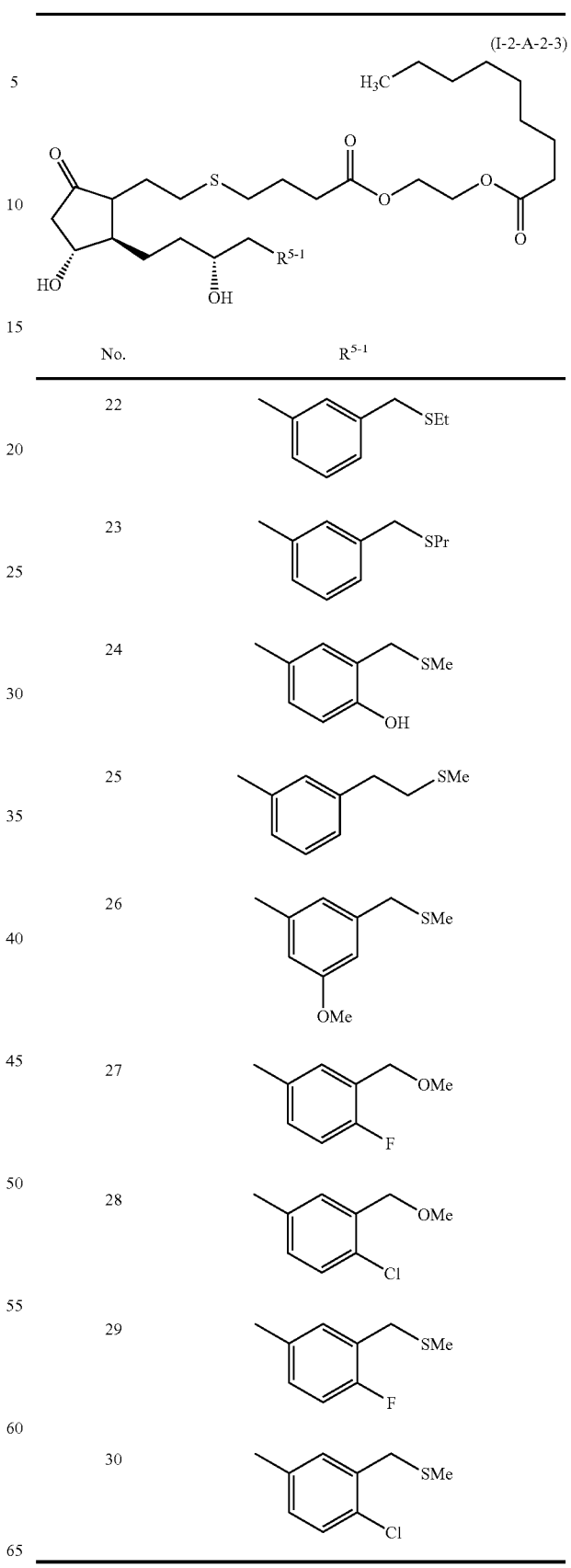

TABLE 77

(I-2-A-2-4)

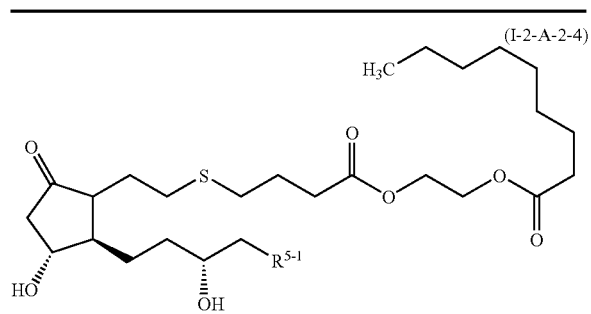

| No. | R^{5-1} |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3,5-dimethoxybenzyl (OMe, OMe) |
| 10 | 4-methyl-2-(methoxymethyl)phenol |
| 11 | 4-methyl-2-(2-methoxyethyl)phenol |

TABLE 77-continued (I-2-A-2-4)

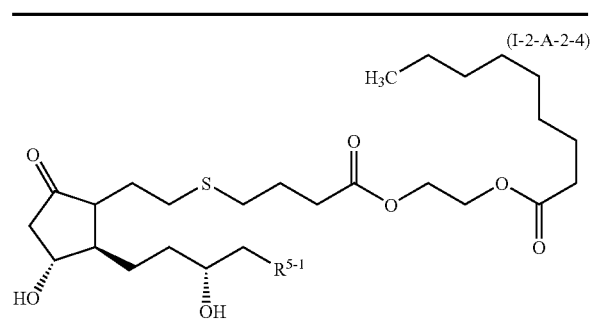

| No. | R^{5-1} |
|---|---|
| 12 | 4-methyl-2-(2-ethoxyethyl)phenol |
| 13 | 2,4-dimethylphenol (Me, OH) |
| 14 | 2-ethyl-4-methylphenol |
| 15 | 4-methyl-2-propylphenol |
| 16 | 3-methylbenzyl OH |
| 17 | 2-(2-fluoroethyl)-4-methylphenol |
| 18 | 3-methylbenzyl O-allyl |
| 19 | 3-methylbenzyl OPh |
| 20 | 3-methylbenzyl O-cyclopentyl |
| 21 | 3-methylbenzyl SMe |

TABLE 77-continued (I-2-A-2-4)

| No. | R^{5-1} |
|---|---|
| 22 | 3-methylbenzyl-SEt |
| 23 | 3-methylbenzyl-SPr |
| 24 | 2-(SMe)-4-methylphenol |
| 25 | 3-methylphenethyl-SMe |
| 26 | 3-OMe-5-methylbenzyl-SMe |
| 27 | 2-F-4-methylbenzyl-OMe |
| 28 | 2-Cl-4-methylbenzyl-OMe |
| 29 | 2-F-5-methylbenzyl-SMe |
| 30 | 2-Cl-5-methylbenzyl-SMe |

TABLE 78

(I-2-A-2-5)

| No. | R^{1-2} |
|---|---|
| 1 | 3-phenylphenyl acetate |
| 2 | butyl 2-(acetyloxy)acetate |
| 3 | [3-(dipropylamino)-2-oxopropyl] acetate |
| 4 | 2-(heptylsulfonyl)ethyl acetate |
| 5 | (acetyloxy)methyl nonanoate |
| 6 | 1-(acetyloxy)ethyl cyclohexanecarboxylate |
| 7 | 2-(acetyloxy)ethyl nonanoate |
| 8 | 2-(acetyloxy)ethyl (pentyloxy)acetate |
| 9 | 2-(acetyloxy)ethyl 5-phenylpentanoate |

TABLE 78-continued (I-2-A-2-5)

| No. | R^{1-2} |
|---|---|
| 10 | (acetyloxy-propyl ester of 5-(6-methylpyridin-3-yl)pentanoic acid) |
| 11 | (acetyloxy-but-2-enyl pentyl carbonate) |
| 12 | (2-(acetyloxy)ethyl-N-ethyl-heptanamide) |
| 13 | (acetyloxy-N,N-diethyl acetamide) |
| 14 | (acetyloxy-N-methyl-N-heptyl acetamide) |
| 15 | (acetyloxy-N-ethyl-N-(3-(naphthalen-2-yl)propyl) acetamide) |

TABLE 79

(I-2-A-2-6)

| No. | R^{1-2} |
|---|---|
| 1 | (biphenyl-3-yl acetate) |
| 2 | (butyl 2-(acetyloxy)acetate) |
| 3 | (acetyloxy-N,N-dipropyl-aminoacetone) |
| 4 | (2-(acetyloxy)ethylsulfonyl heptane) |
| 5 | (acetyloxymethyl nonanoate) |
| 6 | (1-(acetyloxy)ethyl cyclohexanecarboxylate) |
| 7 | (2-(acetyloxy)ethyl octanoate) |
| 8 | (2-(acetyloxy)ethyl 2-(pentyloxy)acetate) |
| 9 | (2-(acetyloxy)ethyl 4-phenylbutanoate) |

TABLE 79-continued
(I-2-A-2-6)
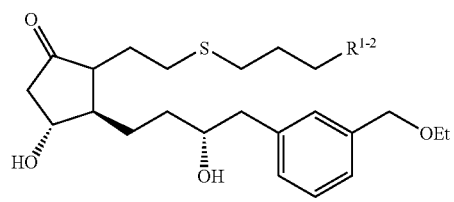
| No. | $R^{1-2}$ |
|---|---|
| 10 | 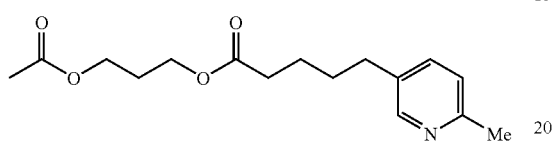 |
| 11 | 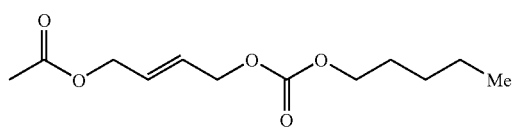 |
| 12 | 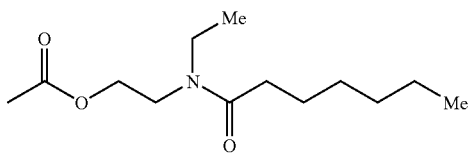 |
| 13 | 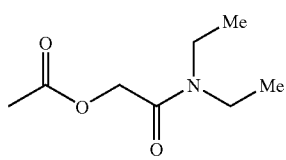 |
| 14 | 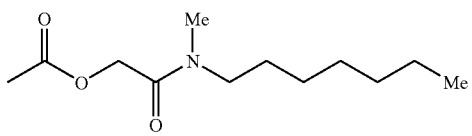 |
| 15 | 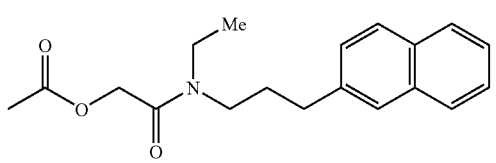 |
TABLE 80
(I-2-A-2-7)
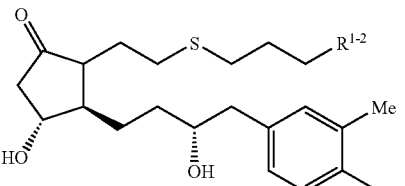
| No. | $R^{1-2}$ |
|---|---|
| 1 | 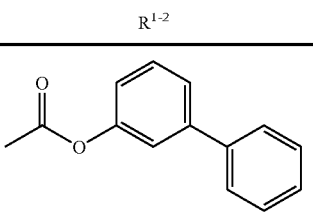 |
| 2 | 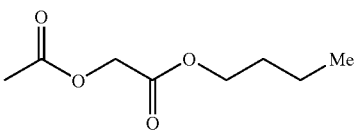 |
| 3 | 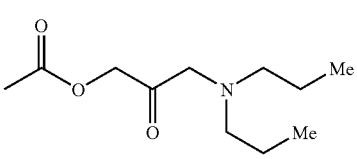 |
| 4 | 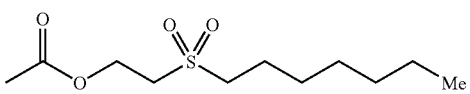 |
| 5 | 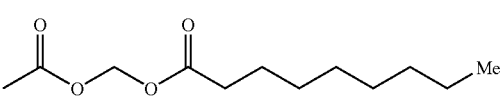 |
| 6 | 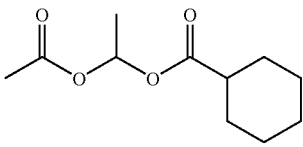 |
| 7 | 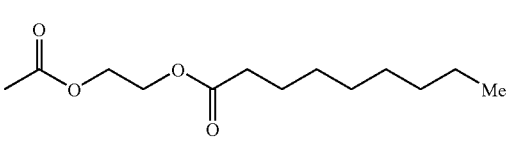 |
| 8 | 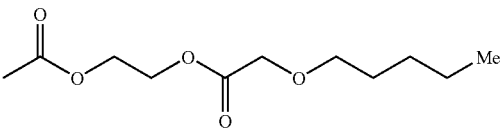 |
| 9 | 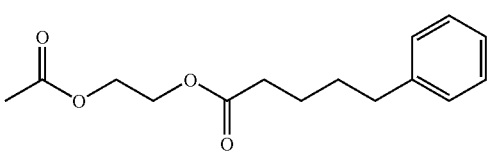 |

TABLE 80-continued
(I-2-A-2-7)
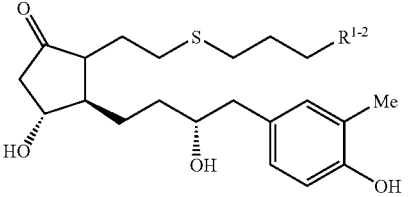
| No. | R[1-2] |
|---|---|
| 10 | 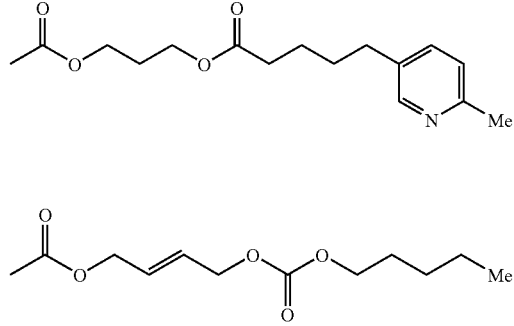 |
| 11 | 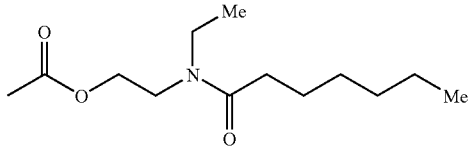 |
| 12 | 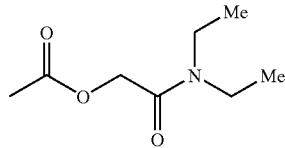 |
| 13 | 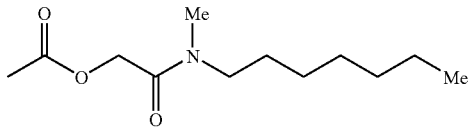 |
| 14 | 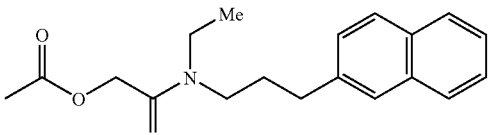 |
| 15 | 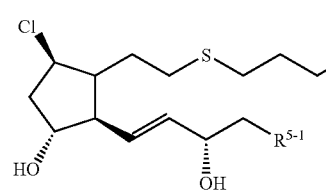 |
TABLE 81
(I-2-A-3-1)
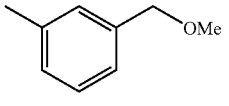
| No. | R[5-1] |
|---|---|
| 1 | 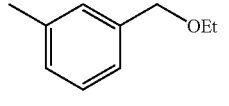 |
| 2 | 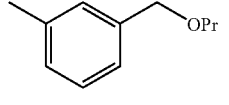 |
| 3 | 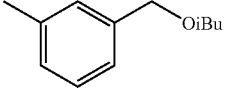 |
| 4 | 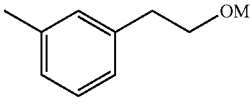 |
| 5 | 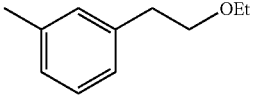 |
| 6 | 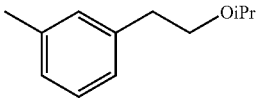 |
| 7 | 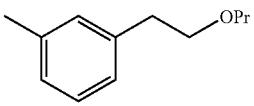 |
| 8 | 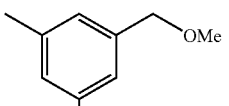 |
| 9 | 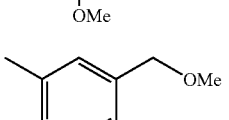 |
| 10 | |

TABLE 81-continued

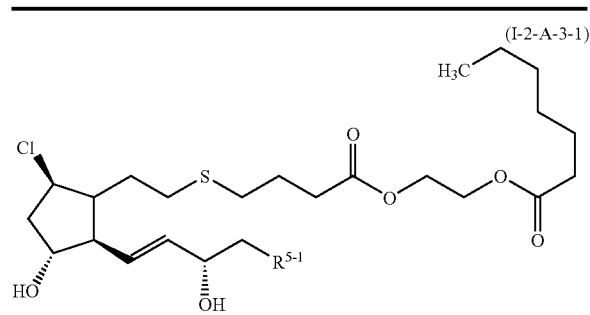

| No. | R<sup>5-1</sup> |
|---|---|
| 11 | 4-methyl-2-(2-methoxyethyl)phenol |
| 12 | 4-methyl-2-(2-ethoxyethyl)phenol |
| 13 | 4-methyl-2-methylphenol |
| 14 | 4-methyl-2-ethylphenol |
| 15 | 4-methyl-2-propylphenol |
| 16 | 3-(hydroxymethyl)methylbenzene |
| 17 | 4-methyl-2-(2-fluoroethyl)phenol |
| 18 | 3-methyl-(allyloxymethyl)benzene |
| 19 | 3-methyl-(phenoxymethyl)benzene |
| 20 | 3-methyl-(cyclopentyloxymethyl)benzene |

TABLE 81-continued

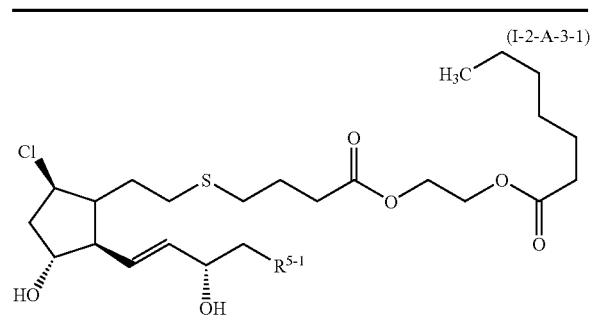

| No. | R<sup>5-1</sup> |
|---|---|
| 21 | 3-methyl-(methylthiomethyl)benzene |
| 22 | 3-methyl-(ethylthiomethyl)benzene |
| 23 | 3-methyl-(propylthiomethyl)benzene |
| 24 | 4-methyl-2-(methylthiomethyl)phenol |
| 25 | 3-methyl-(2-methylthioethyl)benzene |
| 26 | 3-methyl-5-(methylthiomethyl)-methoxybenzene |
| 27 | 5-methyl-2-fluoro-(methoxymethyl)benzene |
| 28 | 5-methyl-2-chloro-(methoxymethyl)benzene |
| 29 | 5-methyl-2-fluoro-(methylthiomethyl)benzene |
| 30 | 5-methyl-2-chloro-(methylthiomethyl)benzene |

TABLE 82

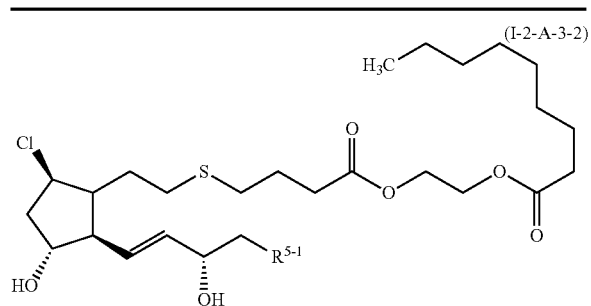

| No. | R<sup>5-1</sup> |
|---|---|
| 1 | 3-(methoxymethyl)phenyl (OMe) |
| 2 | 3-(ethoxymethyl)phenyl (OEt) |
| 3 | 3-(propoxymethyl)phenyl (OPr) |
| 4 | 3-(isobutoxymethyl)phenyl (OiBu) |
| 5 | 3-(2-methoxyethyl)phenyl (OMe) |
| 6 | 3-(2-ethoxyethyl)phenyl (OEt) |
| 7 | 3-(2-isopropoxyethyl)phenyl (OiPr) |
| 8 | 3-(2-propoxyethyl)phenyl (OPr) |
| 9 | 3,5-bis(methoxymethyl)phenyl |
| 10 | 2-(methoxymethyl)-4-methyl-phenol |
| 11 | 2-(2-methoxyethyl)-4-methylphenol |

TABLE 82-continued

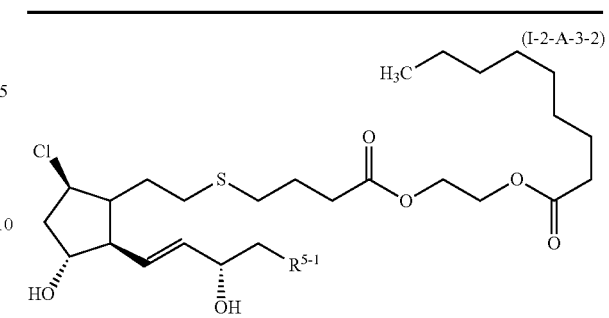

| No. | R<sup>5-1</sup> |
|---|---|
| 12 | 2-(2-ethoxyethyl)-4-methylphenol |
| 13 | 2,4-dimethylphenol |
| 14 | 2-ethyl-4-methylphenol |
| 15 | 2-propyl-4-methylphenol |
| 16 | (3-methylphenyl)methanol |
| 17 | 2-(2-fluoroethyl)-4-methylphenol |
| 18 | 1-(allyloxymethyl)-3-methylbenzene |
| 19 | 1-(phenoxymethyl)-3-methylbenzene |
| 20 | 1-(cyclopentyloxymethyl)-3-methylbenzene |
| 21 | 3-methylbenzyl methyl sulfide (SMe) |

TABLE 82-continued (I-2-A-3-2)

| No. | R⁵⁻¹ |
|---|---|
| 22 | 3-(SEt-CH₂)-phenyl |
| 23 | 3-(SPr-CH₂)-phenyl |
| 24 | 4-methyl-2-(SMe-CH₂)-phenol |
| 25 | 3-(CH₂CH₂SMe)-phenyl |
| 26 | 3-OMe-5-(SMe-CH₂)-phenyl |
| 27 | 5-methyl-2-F-(OMe-CH₂)-phenyl |
| 28 | 5-methyl-2-Cl-(OMe-CH₂)-phenyl |
| 29 | 5-methyl-2-F-(SMe-CH₂)-phenyl |
| 30 | 5-methyl-2-Cl-(SMe-CH₂)-phenyl |

TABLE 83

(I-2-A-3-3)

| No. | R⁵⁻¹ |
|---|---|
| 1 | 3-(OMe-CH₂)-phenyl |
| 2 | 3-(OEt-CH₂)-phenyl |
| 3 | 3-(OPr-CH₂)-phenyl |
| 4 | 3-(OiBu-CH₂)-phenyl |
| 5 | 3-(CH₂CH₂OMe)-phenyl |
| 6 | 3-(CH₂CH₂OEt)-phenyl |
| 7 | 3-(CH₂CH₂OiPr)-phenyl |
| 8 | 3-(CH₂CH₂OPr)-phenyl |
| 9 | 3-OMe-5-(OMe-CH₂)-phenyl |
| 10 | 4-methyl-2-(OMe-CH₂)-phenol |
| 11 | 4-methyl-2-(CH₂CH₂OMe)-phenol |

TABLE 83-continued

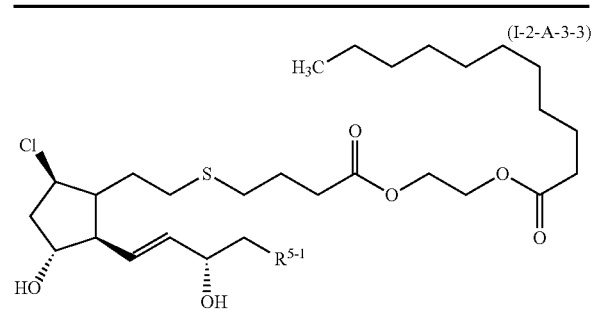
(I-2-A-3-3)

| No. | R<sup>5-1</sup> |
|---|---|
| 12 | 4-methyl-2-(2-ethoxyethyl)phenol |
| 13 | 4-methyl-2-methylphenol |
| 14 | 4-methyl-2-ethylphenol |
| 15 | 4-methyl-2-propylphenol |
| 16 | 3-methylbenzyl alcohol |
| 17 | 4-methyl-2-(2-fluoroethyl)phenol |
| 18 | 3-methylbenzyl allyl ether |
| 19 | 3-methylbenzyl phenyl ether |
| 20 | 3-methylbenzyl cyclopentyl ether |
| 21 | 3-methylbenzyl methyl sulfide (SMe) |

TABLE 83-continued

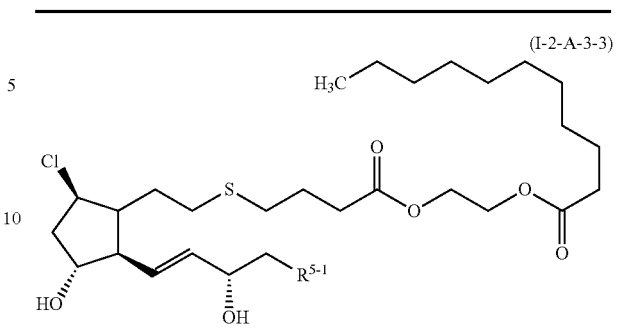
(I-2-A-3-3)

| No. | R<sup>5-1</sup> |
|---|---|
| 22 | 3-methylbenzyl ethyl sulfide (SEt) |
| 23 | 3-methylbenzyl propyl sulfide (SPr) |
| 24 | 4-methyl-2-(methylthiomethyl)phenol |
| 25 | 3-methyl-(2-methylthioethyl)benzene |
| 26 | 3-methyl-5-methoxybenzyl methyl sulfide |
| 27 | 5-methyl-2-fluorobenzyl methyl ether |
| 28 | 5-methyl-2-chlorobenzyl methyl ether |
| 29 | 5-methyl-2-fluorobenzyl methyl sulfide |
| 30 | 5-methyl-2-chlorobenzyl methyl sulfide |

TABLE 84

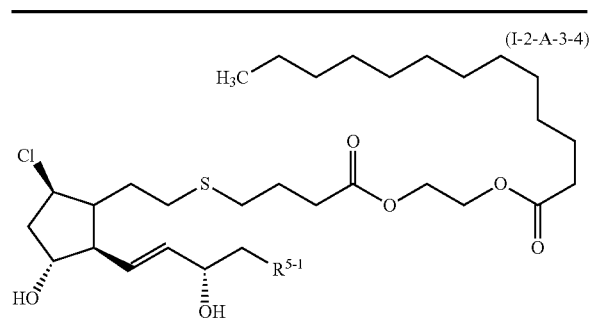

(I-2-A-3-4)

| No. | R<sup>5-1</sup> |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3,5-dimethoxybenzyl OMe |
| 10 | 2-hydroxy-4-methylbenzyl OMe |

TABLE 84-continued

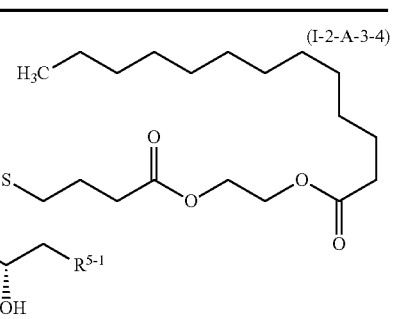

(I-2-A-3-4)

| No. | R<sup>5-1</sup> |
|---|---|
| 11 | 2-(2-methoxyethyl)-4-methylphenol |
| 12 | 2-(2-ethoxyethyl)-4-methylphenol |
| 13 | 2,4-dimethylphenol |
| 14 | 2-ethyl-4-methylphenol |
| 15 | 2-propyl-4-methylphenol |
| 16 | 3-methylbenzyl OH |
| 17 | 2-(2-fluoroethyl)-4-methylphenol |
| 18 | 3-methylbenzyl O-allyl |
| 19 | 3-methylbenzyl OPh |
| 20 | 3-methylbenzyl O-cyclopentyl |

TABLE 84-continued
(I-2-A-3-4)
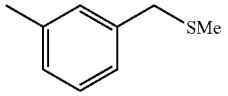
| No. | R^{5-1} |
|---|---|
| 21 | 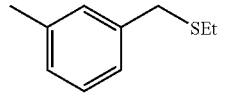 |
| 22 | 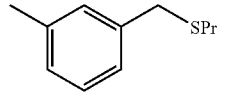 |
| 23 | 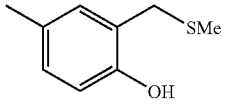 |
| 24 | 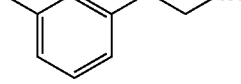 |
| 25 | 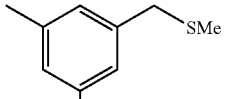 |
| 26 | 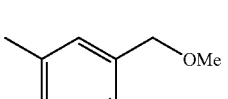 |
| 27 | 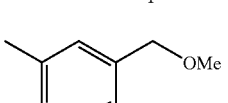 |
| 28 | 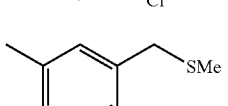 |
| 29 | 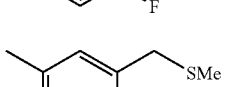 |
| 30 | 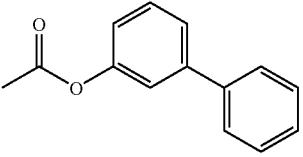 |
TABLE 85
(I-2-A-3-5)
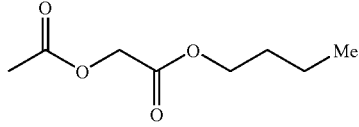
| No. | R^{1-2} |
|---|---|
| 1 | 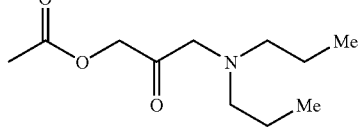 |
| 2 | 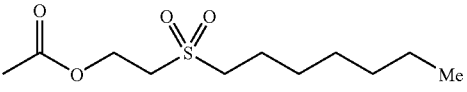 |
| 3 | 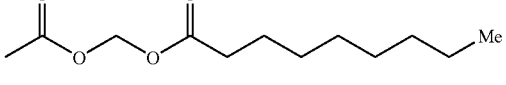 |
| 4 | 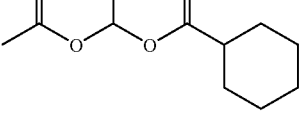 |
| 5 | 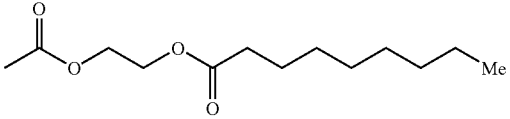 |
| 6 | 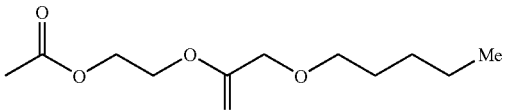 |
| 7 | 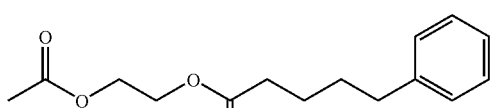 |
| 8 | |
| 9 | |

TABLE 85-continued (I-2-A-3-5)

| No. | R^{1-2} |
|---|---|
| 10 | |
| 11 | |
| 12 | |
| 13 | |
| 14 | |
| 15 | |

TABLE 86

(I-2-A-3-6)

| No. | R^{1-2} |
|---|---|
| 1 | |
| 2 | |
| 3 | |
| 4 | |
| 5 | |
| 6 | |
| 7 | |
| 8 | |
| 9 | |

TABLE 86-continued
(I-2-A-3-6)
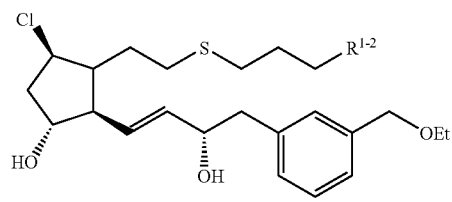
| No. | R$^{1-2}$ |
|---|---|
| 10 | 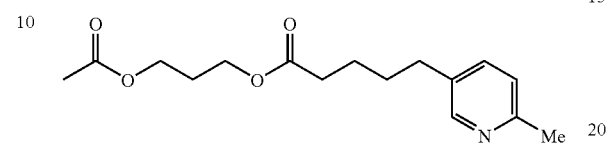 |
| 11 | 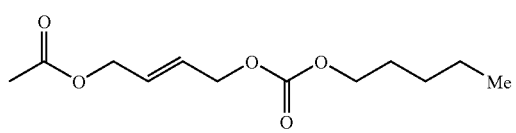 |
| 12 | 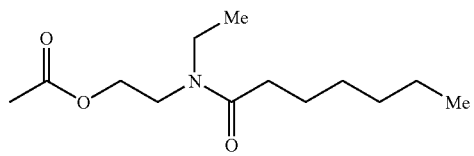 |
| 13 | 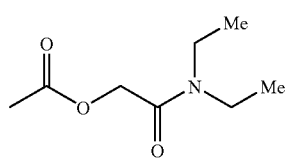 |
| 14 | 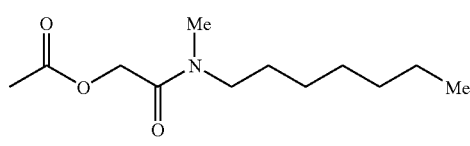 |
| 15 | 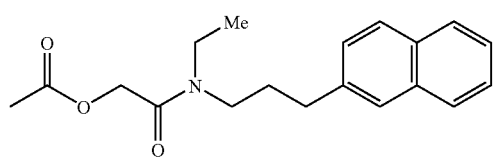 |
TABLE 87
(I-2-A-3-7)
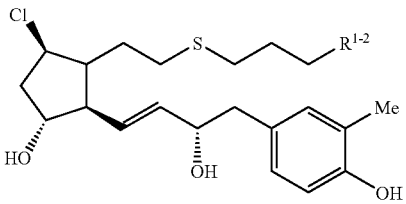
| No. | R$^{1-2}$ |
|---|---|
| 1 | 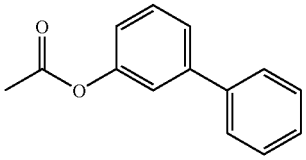 |
| 2 | 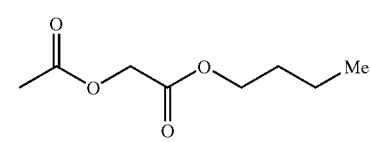 |
| 3 | 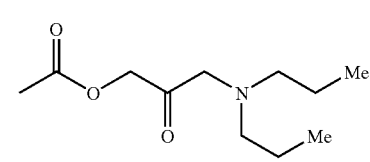 |
| 4 | 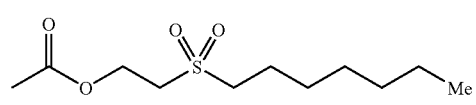 |
| 5 | 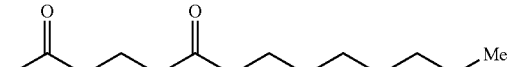 |
| 6 | 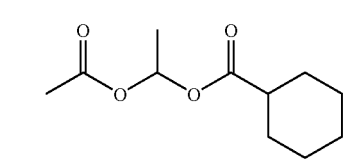 |
| 7 | 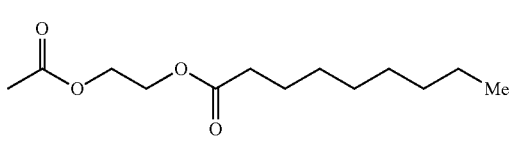 |
| 8 | 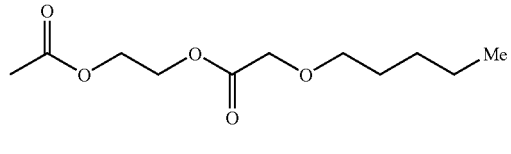 |
| 9 | 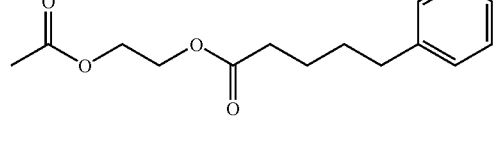 |

TABLE 87-continued
(I-2-A-3-7)
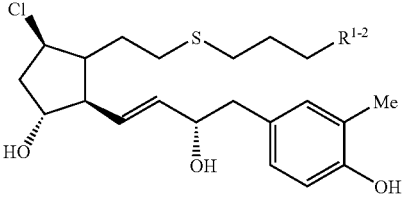
| No. | R$^{1-2}$ |
|---|---|
| 10 | 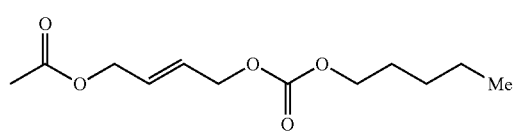 |
| 11 | 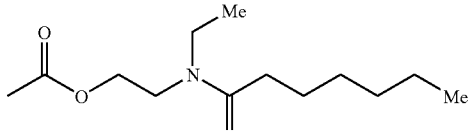 |
| 12 | 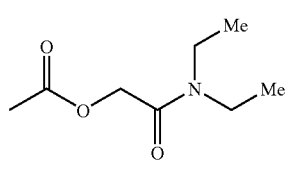 |
| 13 | 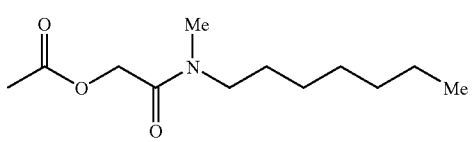 |
| 14 | 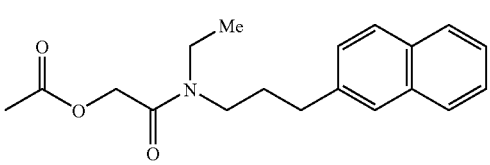 |
| 15 | 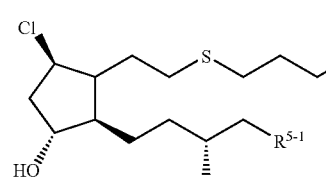 |
TABLE 88
(I-2-A-4-1)
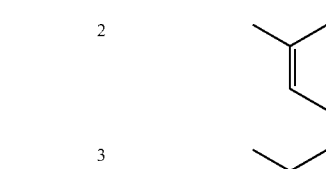
| No. | R$^{5-1}$ |
|---|---|
| 1 | 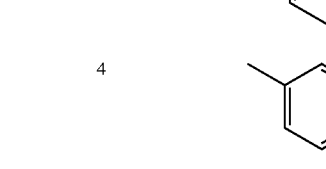 |
| 2 | 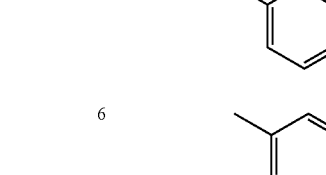 |
| 3 | 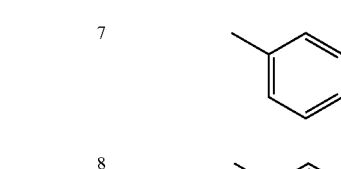 |
| 4 | 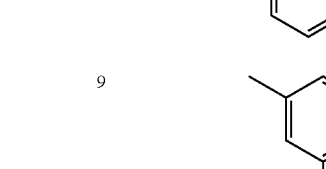 |
| 5 | 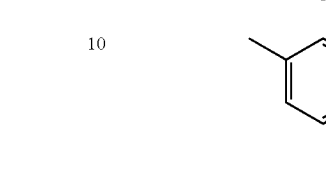 |
| 6 |  |
| 7 |  |
| 8 |  |
| 9 |  |
| 10 |  |

TABLE 88-continued
(I-2-A-4-1)
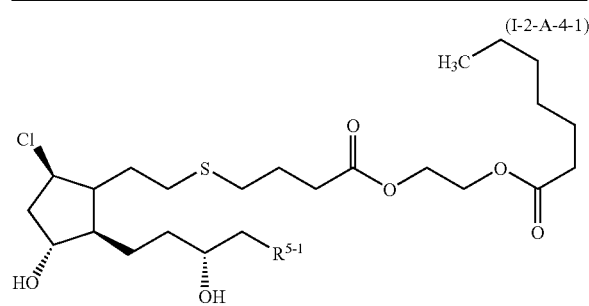
| No. | R^{5-1} |
|---|---|
| 11 |  |
| 12 |  |
| 13 |  |
| 14 |  |
| 15 |  |
| 16 |  |
| 17 |  |
| 18 |  |
| 19 |  |
| 20 |  |
TABLE 88-continued
(I-2-A-4-1)
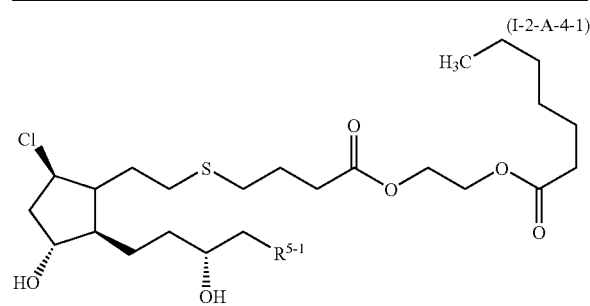
| No. | R^{5-1} |
|---|---|
| 21 |  |
| 22 |  |
| 23 |  |
| 24 |  |
| 25 |  |
| 26 |  |
| 27 |  |
| 28 |  |
| 29 |  |
| 30 |  |

TABLE 89

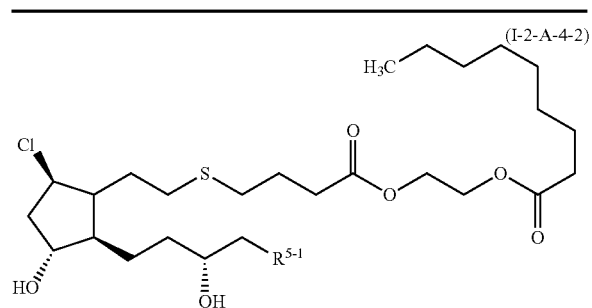

(I-2-A-4-2)

| No. | R<sup>5-1</sup> |
|---|---|
| 1 | 3-(MeOCH₂)-phenyl |
| 2 | 3-(EtOCH₂)-phenyl |
| 3 | 3-(PrOCH₂)-phenyl |
| 4 | 3-(iBuOCH₂)-phenyl |
| 5 | 3-(MeOCH₂CH₂)-phenyl |
| 6 | 3-(EtOCH₂CH₂)-phenyl |
| 7 | 3-(iPrOCH₂CH₂)-phenyl |
| 8 | 3-(PrOCH₂CH₂)-phenyl |
| 9 | 3,5-di(MeO)-phenyl (with CH₂OMe) |
| 10 | 4-Me-2-(MeOCH₂)-3-OH-phenyl |
| 11 | 4-Me-2-(MeOCH₂CH₂)-3-OH-phenyl |

TABLE 89-continued

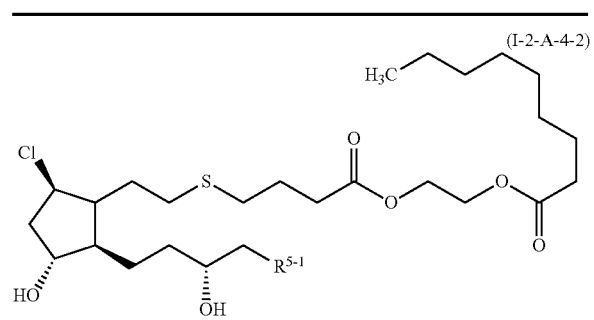

(I-2-A-4-2)

| No. | R<sup>5-1</sup> |
|---|---|
| 12 | 4-Me-2-(EtOCH₂CH₂)-phenol |
| 13 | 4-Me-2-Me-phenol |
| 14 | 4-Me-2-Et-phenol |
| 15 | 4-Me-2-Pr-phenol |
| 16 | 3-(HOCH₂)-phenyl |
| 17 | 4-Me-2-(FCH₂CH₂)-phenol |
| 18 | 3-(allyl-O-CH₂)-phenyl |
| 19 | 3-(PhOCH₂)-phenyl |
| 20 | 3-(cyclopentyl-O-CH₂)-phenyl |
| 21 | 3-(MeSCH₂)-phenyl |

TABLE 89-continued (I-2-A-4-2)

Structure with R⁵⁻¹ substituent on chlorinated cyclopentane with thioether-ester chain.

| No. | R⁵⁻¹ |
|---|---|
| 22 | 3-(SEt)benzyl |
| 23 | 3-(SPr)benzyl |
| 24 | 2-(SMe)-4-methyl-phenol |
| 25 | 3-(CH₂CH₂SMe)benzyl |
| 26 | 3-(SMe)-5-(OMe)benzyl |
| 27 | 2-(OMe-methyl)-4-methyl-1-F-phenyl |
| 28 | 2-(OMe-methyl)-4-methyl-1-Cl-phenyl |
| 29 | 2-(SMe-methyl)-4-methyl-1-F-phenyl |
| 30 | 2-(SMe-methyl)-4-methyl-1-Cl-phenyl |

TABLE 90

(I-2-A-4-3)

| No. | R⁵⁻¹ |
|---|---|
| 1 | 3-(CH₂OMe)benzyl |
| 2 | 3-(CH₂OEt)benzyl |
| 3 | 3-(CH₂OPr)benzyl |
| 4 | 3-(CH₂OiBu)benzyl |
| 5 | 3-(CH₂CH₂OMe)benzyl |
| 6 | 3-(CH₂CH₂OEt)benzyl |
| 7 | 3-(CH₂CH₂OiPr)benzyl |
| 8 | 3-(CH₂CH₂OPr)benzyl |
| 9 | 3-(OMe)-5-(CH₂OMe)benzyl |
| 10 | 2-(CH₂OMe)-4-methyl-phenol |
| 11 | 2-(CH₂CH₂OMe)-4-methyl-phenol |

TABLE 90-continued
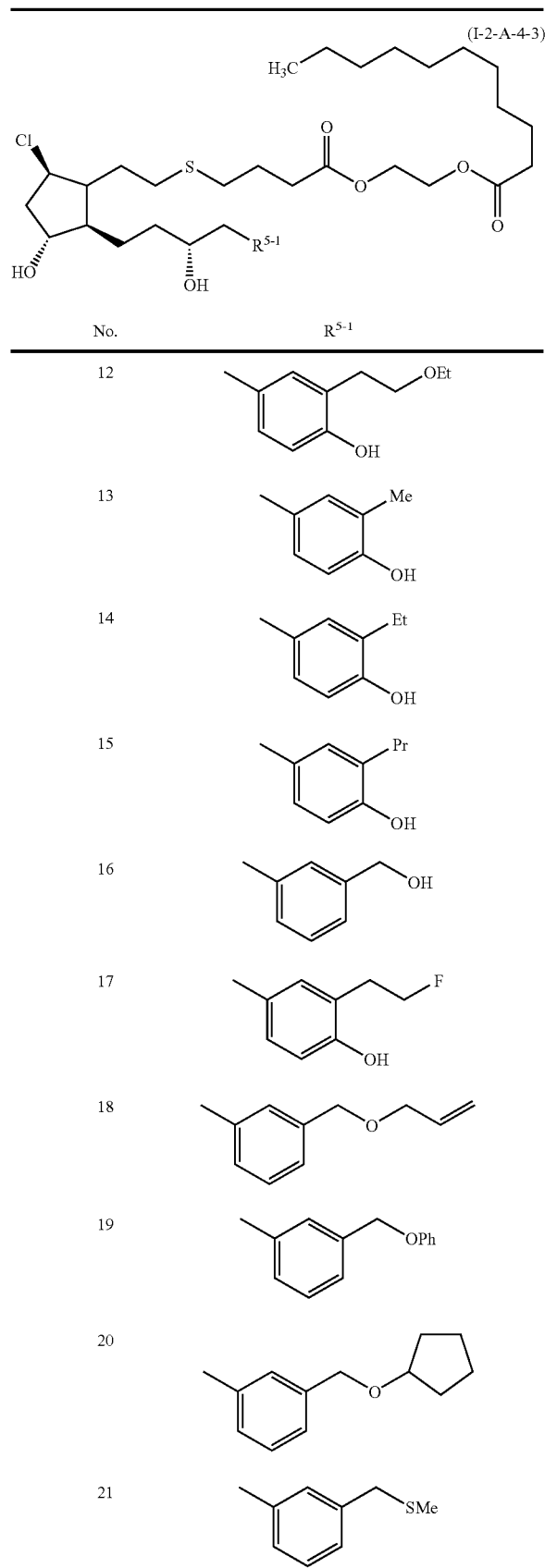
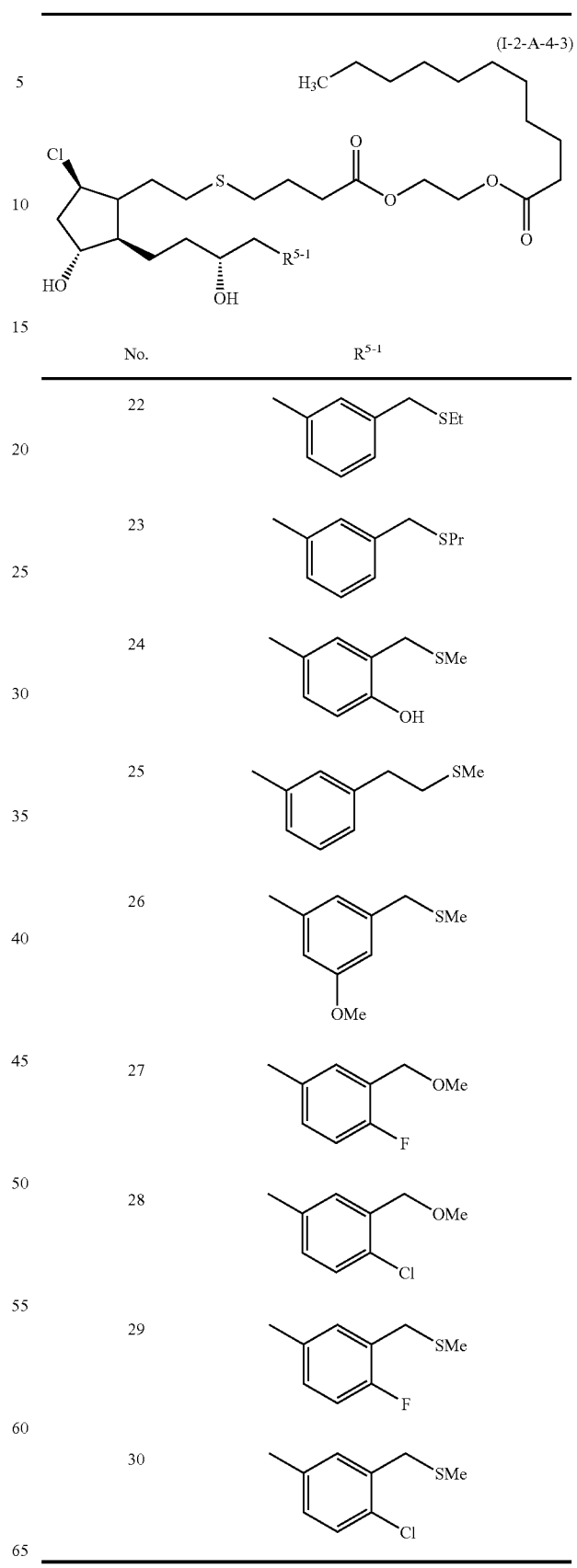

TABLE 91

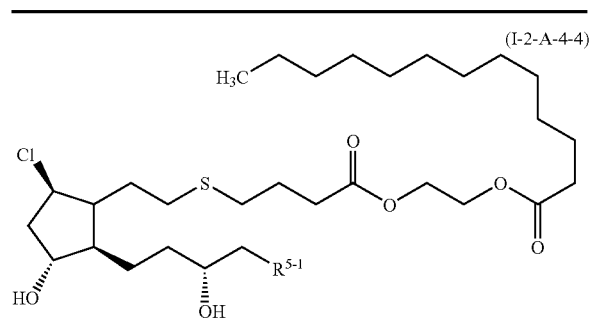
(I-2-A-4-4)

| No. | R⁵⁻¹ |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3,5-dimethoxybenzyl OMe |
| 10 | 4-methyl-2-(methoxymethyl)phenol |

TABLE 91-continued

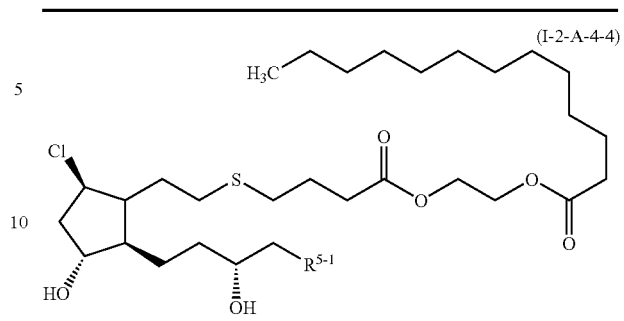
(I-2-A-4-4)

| No. | R⁵⁻¹ |
|---|---|
| 11 | 4-methyl-2-(2-methoxyethyl)phenol |
| 12 | 4-methyl-2-(2-ethoxyethyl)phenol |
| 13 | 2,4-dimethylphenol |
| 14 | 2-ethyl-4-methylphenol |
| 15 | 4-methyl-2-propylphenol |
| 16 | 3-methylbenzyl alcohol |
| 17 | 2-(2-fluoroethyl)-4-methylphenol |
| 18 | 3-methylbenzyl allyl ether |
| 19 | 3-methylbenzyl phenyl ether |
| 20 | 3-methylbenzyl cyclopentyl ether |

TABLE 91-continued (I-2-A-4-4)

| No. | R^{5-1} |
|---|---|
| 21 | 3-(methylthiomethyl)phenyl (m-CH2SMe-C6H4) |
| 22 | 3-(ethylthiomethyl)phenyl (m-CH2SEt-C6H4) |
| 23 | 3-(propylthiomethyl)phenyl (m-CH2SPr-C6H4) |
| 24 | 4-hydroxy-2-(methylthiomethyl)-5-methylphenyl |
| 25 | 3-(2-(methylthio)ethyl)phenyl |
| 26 | 3-methoxy-5-(methylthiomethyl)phenyl |
| 27 | 2-fluoro-6-(methoxymethyl)-4-methylphenyl |
| 28 | 2-chloro-6-(methoxymethyl)-4-methylphenyl |
| 29 | 2-fluoro-6-(methylthiomethyl)-4-methylphenyl |
| 30 | 2-chloro-6-(methylthiomethyl)-4-methylphenyl |

TABLE 92

(I-2-A-4-5)

| No. | R^{1-2} |
|---|---|
| 1 | biphenyl-3-yl acetate |
| 2 | butyl 2-(acetoxy)acetate |
| 3 | 3-(dipropylamino)-2-oxopropyl acetate |
| 4 | 2-(octylsulfonyl)ethyl acetate |
| 5 | (acetoxy)methyl nonanoate |
| 6 | 1-(acetoxy)ethyl cyclohexanecarboxylate |
| 7 | 2-(acetoxy)ethyl octanoate |
| 8 | 2-(acetoxy)ethyl 2-(pentyloxy)acetate |
| 9 | 2-(acetoxy)ethyl 4-phenylbutanoate |

TABLE 92-continued
(I-2-A-4-5)
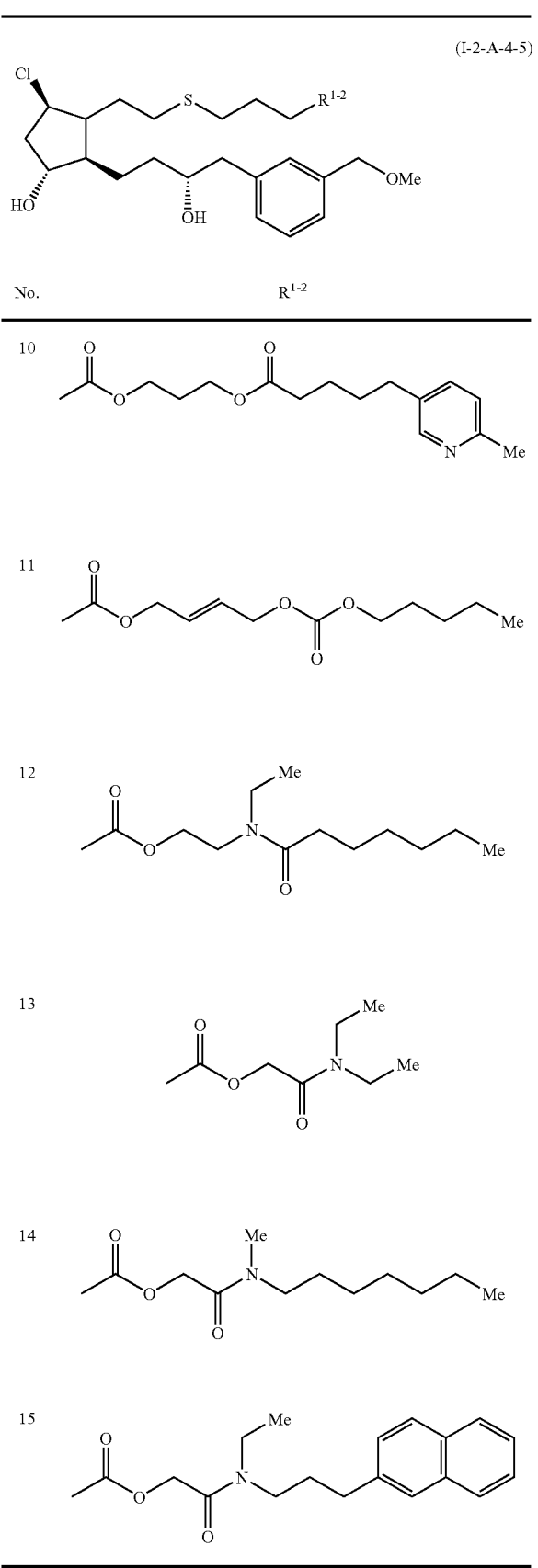
TABLE 93
(I-2-A-4-6)
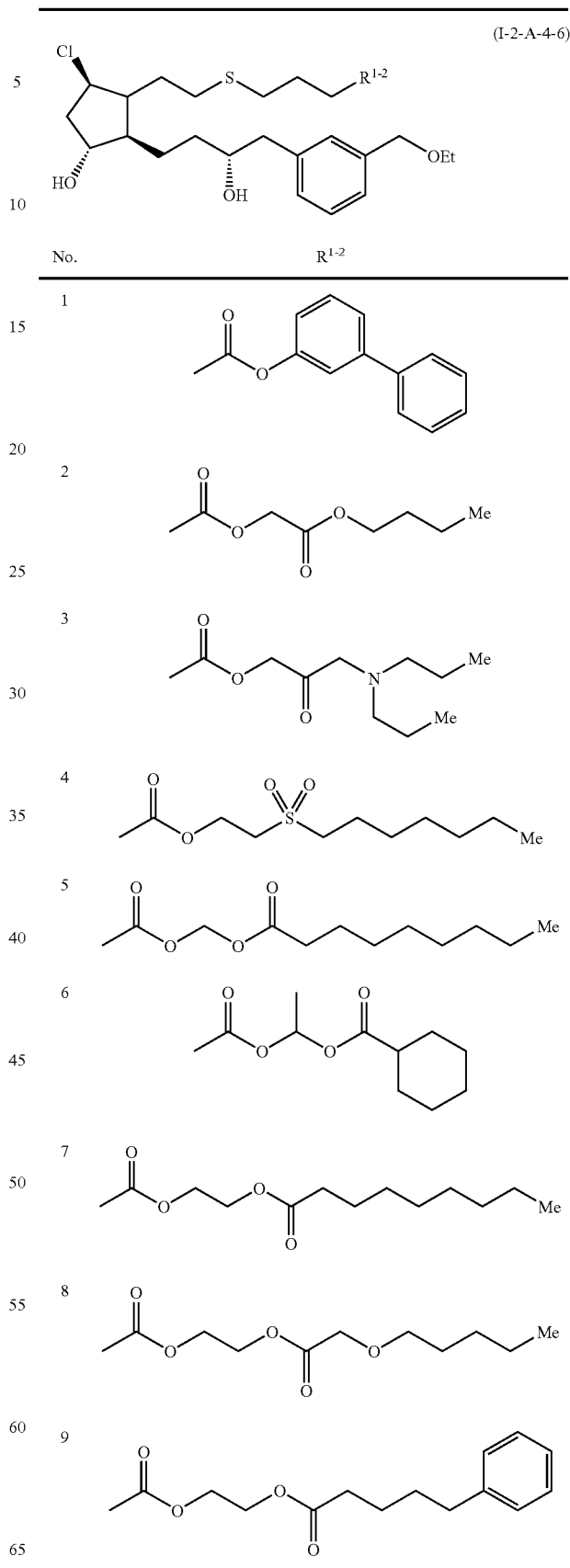

TABLE 93-continued
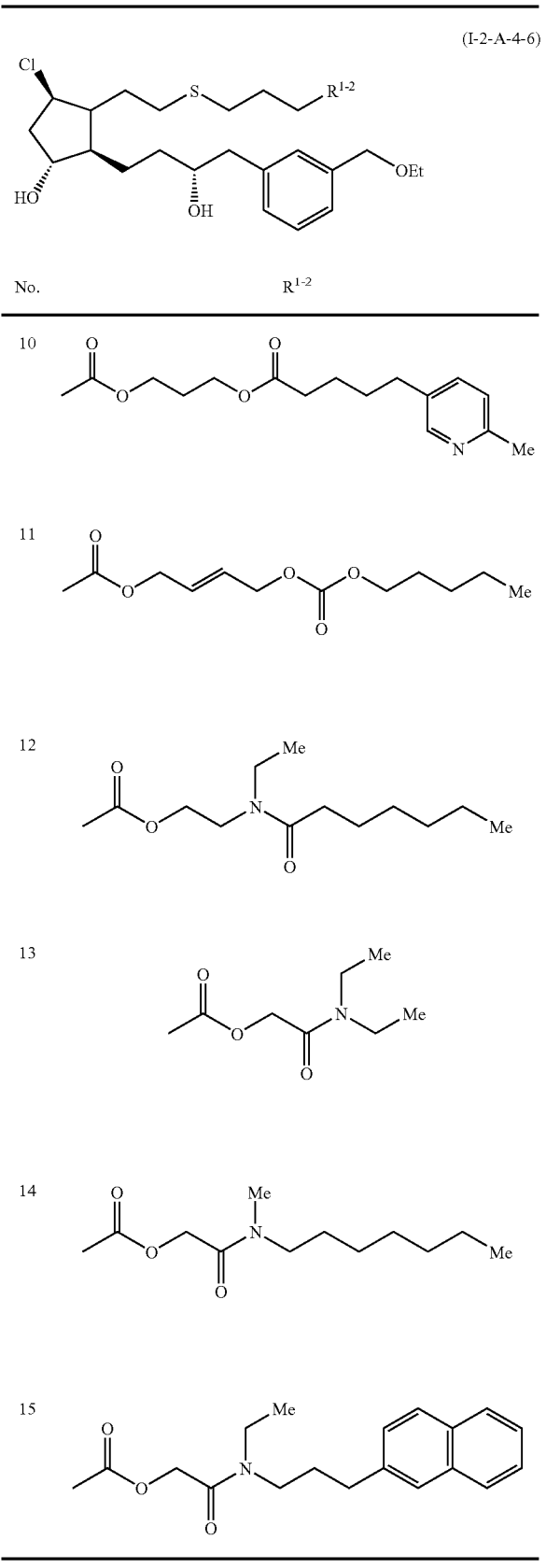
TABLE 94
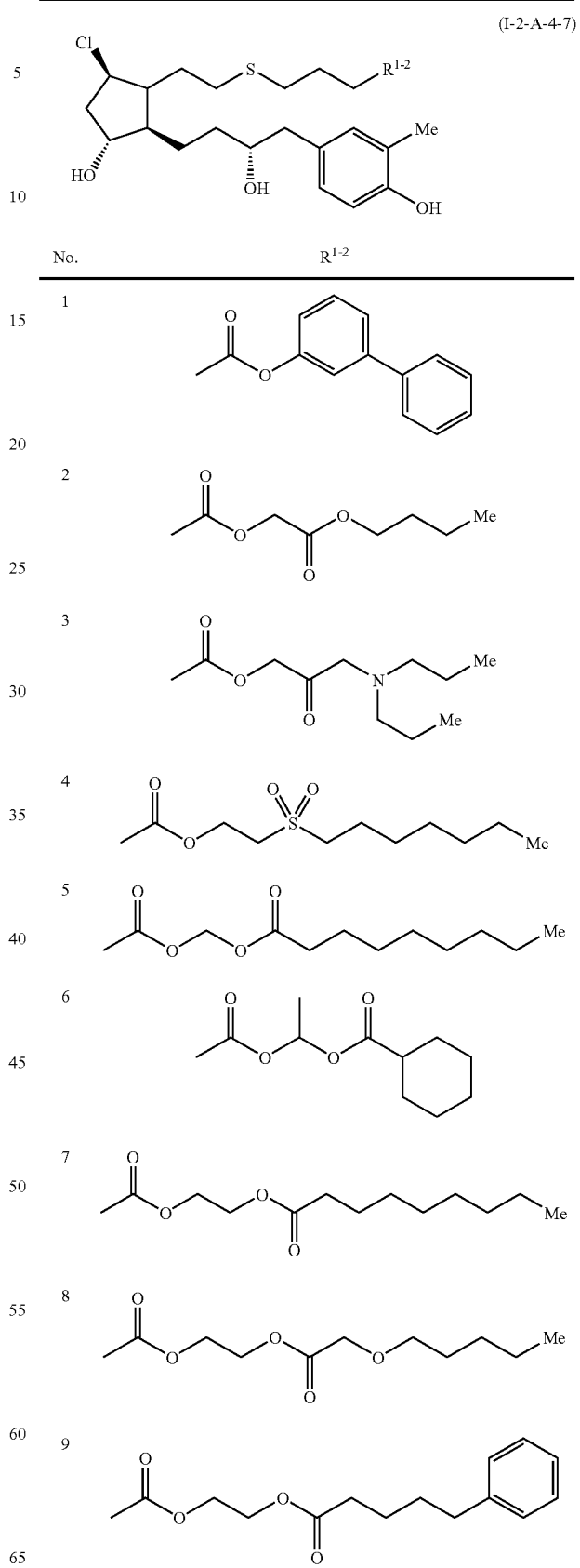

TABLE 94-continued (I-2-A-4-7)

[Structure: cyclopentane with Cl, HO, and side chains bearing S-CH2CH2CH2-R^{1-2} and CH2CH2-CH(OH)-CH2-(3-methyl-4-hydroxyphenyl)]

| No. | R^{1-2} |
|---|---|
| 10 | AcO-CH2CH2CH2-O-C(=O)-(CH2)3-(5-(6-methylpyridyl)) |
| 11 | AcO-CH2-CH=CH-CH2-O-C(=O)-O-(CH2)4-Me |
| 12 | AcO-CH2CH2-N(Et)-C(=O)-(CH2)5-Me |
| 13 | AcO-CH2-C(=O)-N(Et)2 |
| 14 | AcO-CH2-C(=O)-N(Me)-(CH2)6-Me |
| 15 | AcO-CH2-C(=O)-N(Et)-(CH2)3-(2-naphthyl) |

TABLE 95

(I-2-A-5-1)

[Structure: cyclopentane with F, HO, and side chains bearing S-CH2CH2CH2-C(=O)-O-CH2CH2-O-C(=O)-(CH2)5-CH3 and CH=CH-CH(OH)-CH2-R^{5-1}]

| No. | R^{5-1} |
|---|---|
| 1 | 3-methylbenzyl-OMe |
| 2 | 3-methylbenzyl-OEt |
| 3 | 3-methylbenzyl-OPr |
| 4 | 3-methylbenzyl-OiBu |
| 5 | 3-methylphenethyl-OMe |
| 6 | 3-methylphenethyl-OEt |
| 7 | 3-methylphenethyl-OiPr |
| 8 | 3-methylphenethyl-OPr |
| 9 | 3,5-disubstituted (Me, OMe) benzyl-OMe |
| 10 | 2-(methoxymethyl)-4-methylphenol |

TABLE 95-continued

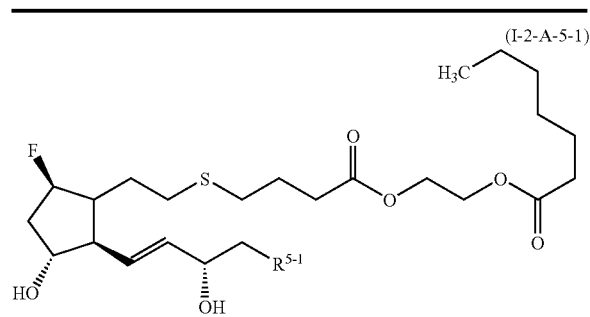

(I-2-A-5-1)

| No. | R$^{5-1}$ |
|---|---|
| 11 | 4-methyl-2-(2-methoxyethyl)phenol, OH |
| 12 | 4-methyl-2-(2-ethoxyethyl)phenol, OH |
| 13 | 4-methyl-2-methylphenol (Me, OH) |
| 14 | 4-methyl-2-ethylphenol (Et, OH) |
| 15 | 4-methyl-2-propylphenol (Pr, OH) |
| 16 | 3-(hydroxymethyl)phenyl (CH2OH) |
| 17 | 4-methyl-2-(2-fluoroethyl)phenol |
| 18 | 3-((allyloxy)methyl)phenyl |
| 19 | 3-((phenoxy)methyl)phenyl (OPh) |
| 20 | 3-((cyclopentyloxy)methyl)phenyl |

TABLE 95-continued

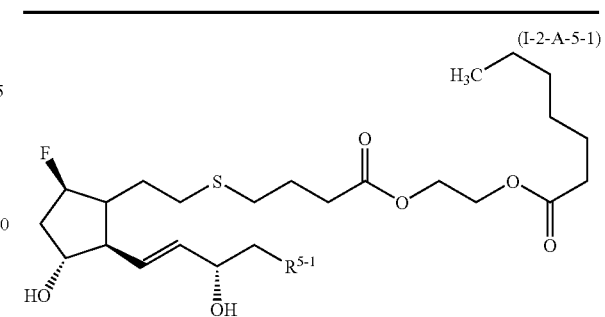

(I-2-A-5-1)

| No. | R$^{5-1}$ |
|---|---|
| 21 | 3-((methylthio)methyl)phenyl (SMe) |
| 22 | 3-((ethylthio)methyl)phenyl (SEt) |
| 23 | 3-((propylthio)methyl)phenyl (SPr) |
| 24 | 4-methyl-2-((methylthio)methyl)phenol |
| 25 | 3-(2-(methylthio)ethyl)phenyl |
| 26 | 3-methoxy-5-((methylthio)methyl)phenyl |
| 27 | 5-methyl-2-fluoro-(methoxymethyl)phenyl |
| 28 | 5-methyl-2-chloro-(methoxymethyl)phenyl |
| 29 | 5-methyl-2-fluoro-((methylthio)methyl)phenyl |
| 30 | 5-methyl-2-chloro-((methylthio)methyl)phenyl |

TABLE 96
(I-2-A-5-2)
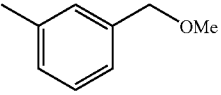
| No. | R<sup>5-1</sup> |
|---|---|
| 1 | 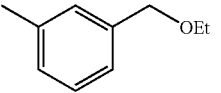 |
| 2 | 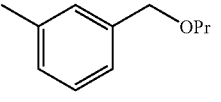 |
| 3 | 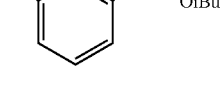 |
| 4 | 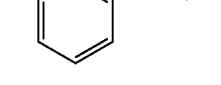 |
| 5 | 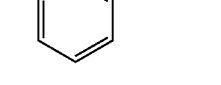 |
| 6 | 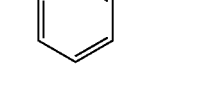 |
| 7 | 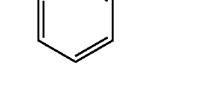 |
| 8 | 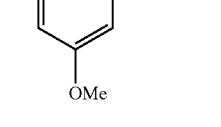 |
| 9 | 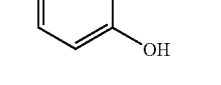 |
| 10 | 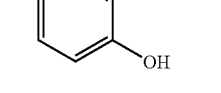 |
| 11 | 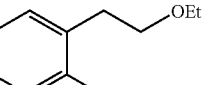 |
| 12 | 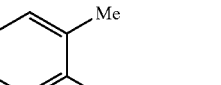 |
| 13 | 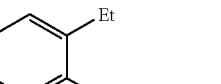 |
| 14 | 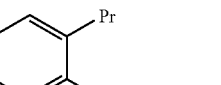 |
| 15 | 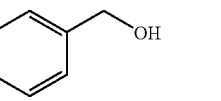 |
| 16 | 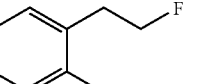 |
| 17 | 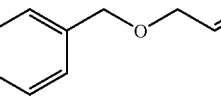 |
| 18 | 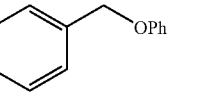 |
| 19 | 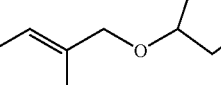 |
| 20 | 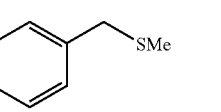 |
| 21 | 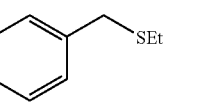 |
| 22 |  |

TABLE 96-continued
(I-2-A-5-2)
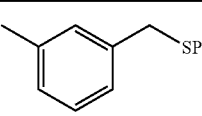
| No. | R<sup>5-1</sup> |
|---|---|
| 23 | 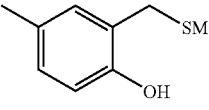 |
| 24 | 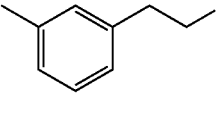 |
| 25 | 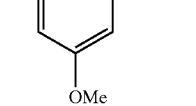 |
| 26 | 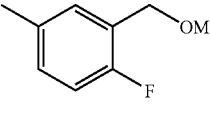 |
| 27 | 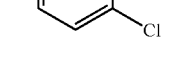 |
| 28 | 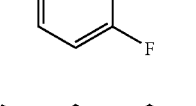 |
| 29 | 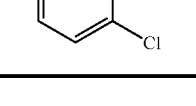 |
| 30 | 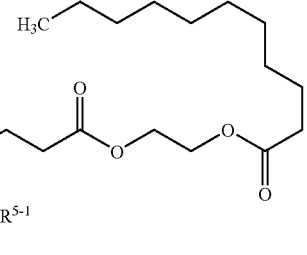 |
TABLE 97
(I-2-A-5-3)
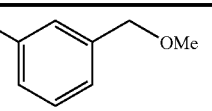
| No. | R$^{5-1}$ |
|---|---|
| 1 | 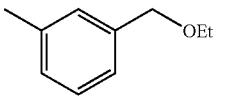 |
| 2 | 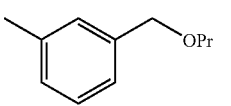 |
| 3 | 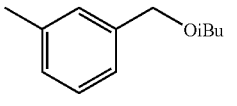 |
| 4 | 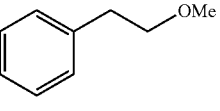 |
| 5 | 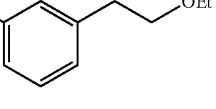 |
| 6 | 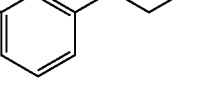 |
| 7 | 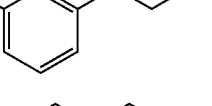 |
| 8 | 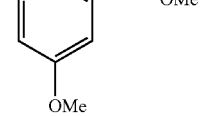 |
| 9 | 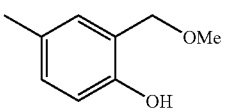 |
| 10 | 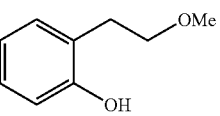 |
| 11 | |

TABLE 97-continued (I-2-A-5-3)

| No. | R⁵⁻¹ |
|---|---|
| 12 | 4-methyl-2-(2-ethoxyethyl)phenol |
| 13 | 4-methyl-2-methylphenol (Me, OH) |
| 14 | 4-methyl-2-ethylphenol (Et, OH) |
| 15 | 4-methyl-2-propylphenol (Pr, OH) |
| 16 | 3-methylbenzyl alcohol (OH) |
| 17 | 4-methyl-2-(2-fluoroethyl)phenol |
| 18 | 3-methylbenzyl allyl ether |
| 19 | 3-methylbenzyl phenyl ether (OPh) |
| 20 | 3-methylbenzyl cyclopentyl ether |
| 21 | 3-methylbenzyl methyl sulfide (SMe) |
| 22 | 3-methylbenzyl ethyl sulfide (SEt) |
| 23 | 3-methylbenzyl propyl sulfide (SPr) |
| 24 | 4-methyl-2-(methylthiomethyl)phenol (SMe, OH) |
| 25 | 3-methyl-(2-methylthioethyl)benzene (SMe) |
| 26 | 3-methyl-5-methoxybenzyl methyl sulfide (SMe, OMe) |
| 27 | 5-methyl-2-fluorobenzyl methyl ether (OMe, F) |
| 28 | 5-methyl-2-chlorobenzyl methyl ether (OMe, Cl) |
| 29 | 5-methyl-2-fluorobenzyl methyl sulfide (SMe, F) |
| 30 | 5-methyl-2-chlorobenzyl methyl sulfide (SMe, Cl) |

TABLE 98

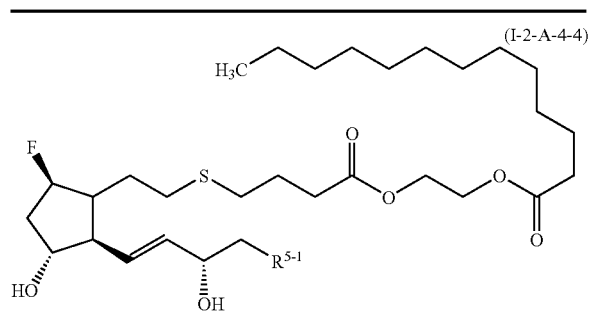
(I-2-A-4-4)

| No. | R^{5-1} |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3,5-dimethyl(OMe)(OMe) benzyl |
| 10 | 4-methyl-2-(OMe)-phenol |
| 11 | 4-methyl-2-(CH2CH2OMe)-phenol |

TABLE 98-continued

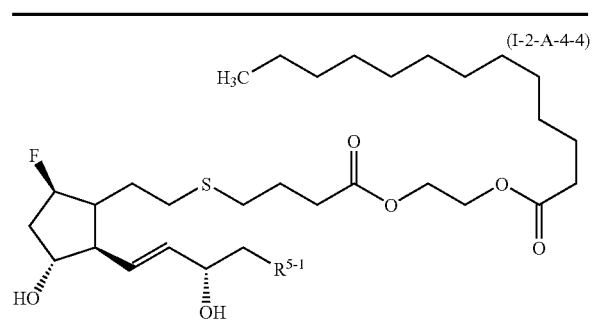
(I-2-A-4-4)

| No. | R^{5-1} |
|---|---|
| 12 | 4-methyl-2-(CH2CH2OEt)-phenol |
| 13 | 4-methyl-2-Me-phenol |
| 14 | 4-methyl-2-Et-phenol |
| 15 | 4-methyl-2-Pr-phenol |
| 16 | 3-methylbenzyl OH |
| 17 | 4-methyl-2-(CH2CH2F)-phenol |
| 18 | 3-methylbenzyl O-allyl |
| 19 | 3-methylbenzyl OPh |
| 20 | 3-methylbenzyl O-cyclopentyl |
| 21 | 3-methylbenzyl SMe |

TABLE 98-continued
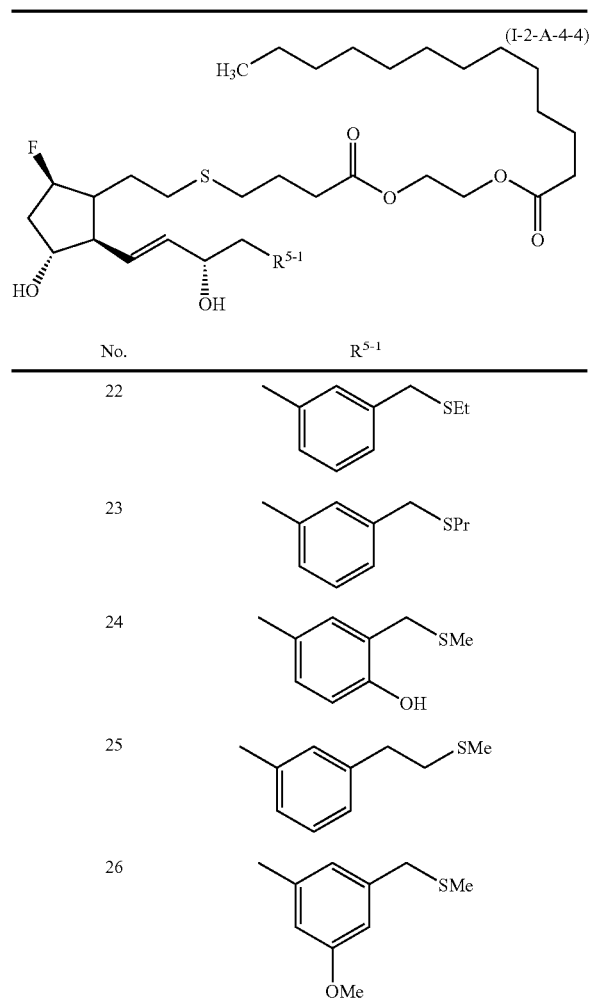
TABLE 98-continued
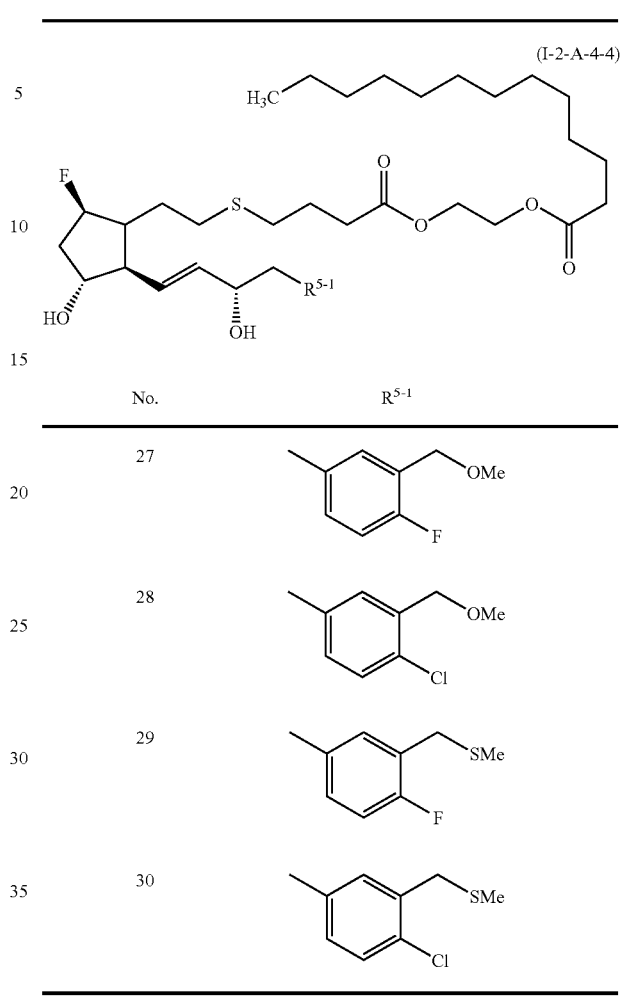
TABLE 99
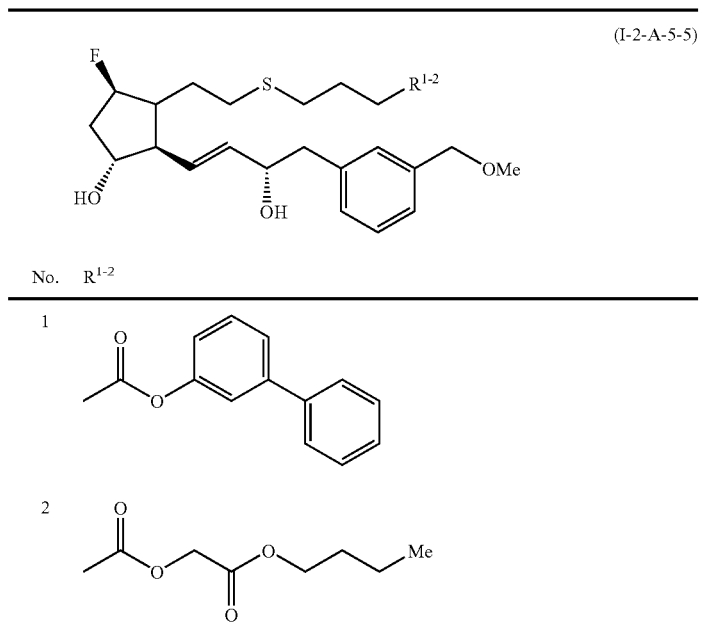

TABLE 99-continued

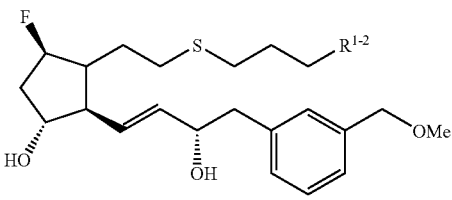

(I-2-A-5-5)

| No. | $R^{1-2}$ |
|---|---|
| 3 | (structure: acetate-CH2-C(=O)-CH2-N(CH2CH2Me)2) |
| 4 | (structure: acetate-CH2CH2-S(=O)2-hexyl-Me) |
| 5 | (structure: acetate-CH2-O-C(=O)-heptyl-Me) |
| 6 | (structure: acetate-CH(Me)-O-C(=O)-cyclohexyl) |
| 7 | (structure: acetate-CH2CH2-O-C(=O)-heptyl-Me) |
| 8 | (structure: acetate-CH2CH2-O-C(=O)-CH2-O-butyl-Me) |
| 9 | (structure: acetate-CH2CH2-O-C(=O)-(CH2)3-phenyl) |
| 10 | (structure: acetate-(CH2)3-O-C(=O)-(CH2)3-(6-methylpyridin-3-yl)) |
| 11 | (structure: acetate-CH2-CH=CH-CH2-O-C(=O)-O-butyl-Me) |

TABLE 99-continued
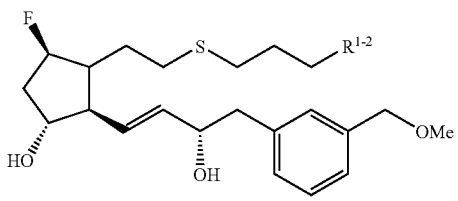
(I-2-A-5-5)
| No. | R^{1-2} |
|---|---|
| 12 | 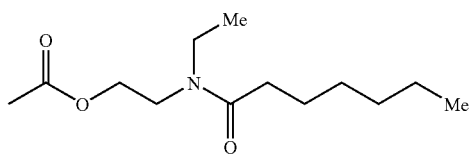 |
| 13 | 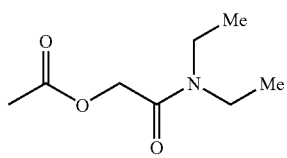 |
| 14 | 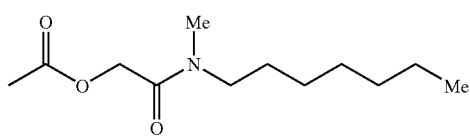 |
| 15 | 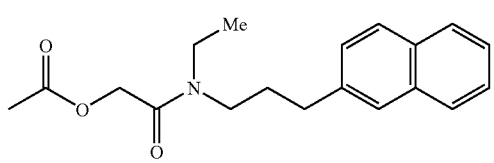 |
TABLE 100
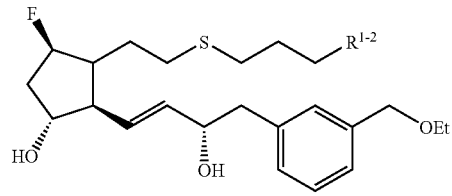
(I-2-A-5-6)
| No. | R^{1-2} |
|---|---|
| 1 | 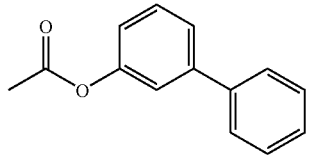 |
| 2 | 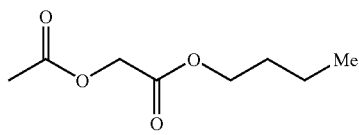 |

TABLE 100-continued
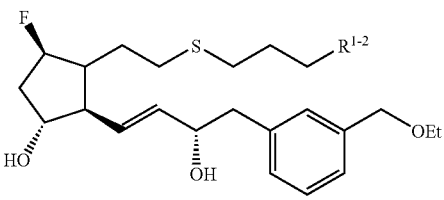
(I-2-A-5-6)
| No. | $R^{1-2}$ |
|---|---|
| 3 | ![structure] acetate-CH2-C(=O)-CH2-N(CH2CH2Me)2 |
| 4 | acetate-CH2CH2-S(=O)2-(CH2)6-Me |
| 5 | acetate-O-CH2-O-C(=O)-(CH2)6-Me |
| 6 | acetate-O-CH(Me)-O-C(=O)-cyclohexyl |
| 7 | acetate-O-CH2CH2-O-C(=O)-(CH2)7-Me |
| 8 | acetate-O-CH2CH2-O-C(=O)-CH2-O-(CH2)4-Me |
| 9 | acetate-O-CH2CH2-O-C(=O)-(CH2)3-Ph |
| 10 | acetate-O-(CH2)3-O-C(=O)-(CH2)3-(6-Me-pyridin-3-yl) |
| 11 | acetate-O-CH2-CH=CH-CH2-O-C(=O)-O-(CH2)4-Me |

TABLE 100-continued
(I-2-A-5-6)
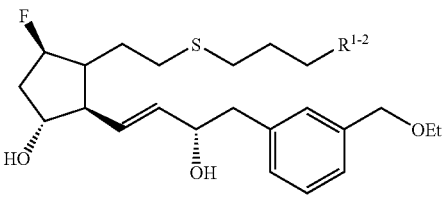
| No. | R[1-2] |
|---|---|
| 12 | 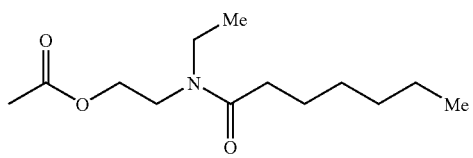 |
| 13 | 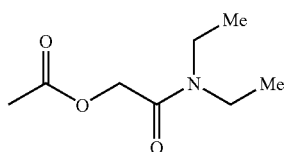 |
| 14 | 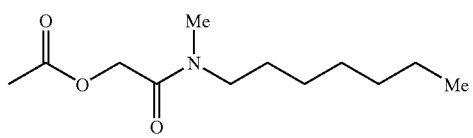 |
| 15 | 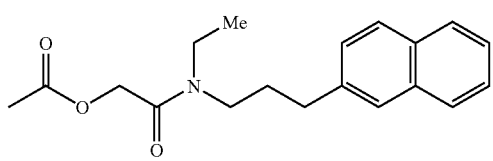 |
TABLE 101
(I-2-A-5-7)
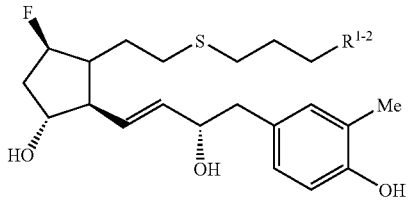
| No. | R[1-2] |
|---|---|
| 1 | 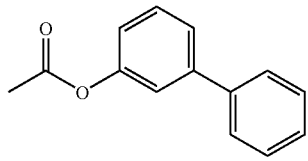 |
| 2 | 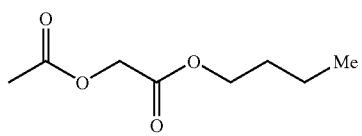 |

TABLE 101-continued
(I-2-A-5-7)
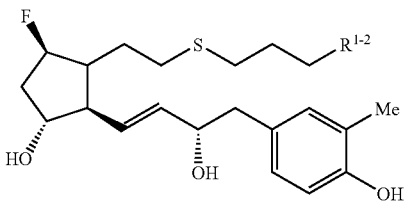
| No. | R$^{1-2}$ |
|---|---|
| 3 | -CH2-N(CH2CH2Me)2) |
| 4 | 2-hexyl-Me) |
| 5 | -heptyl-Me) |
| 6 | -O-C(=O)-cyclohexyl) |
| 7 | -heptyl-Me) |
| 8 | -CH2-O-butyl-Me) |
| 9 | -(CH2)3-Ph) |
| 10 | 3-O-C(=O)-(CH2)3-pyridyl-Me) |
| 11 | -O-butyl-Me) |

TABLE 101-continued
(I-2-A-5-7)
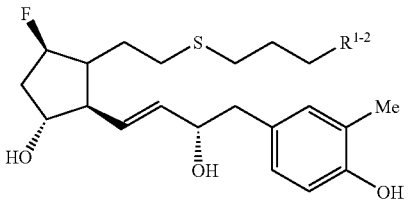
| No. | R^{1-2} |
|---|---|
| 12 | 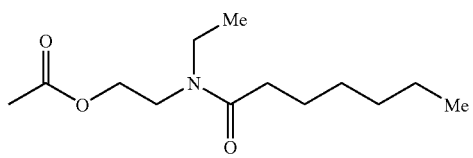 |
| 13 | 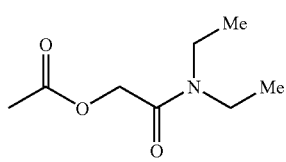 |
| 14 | 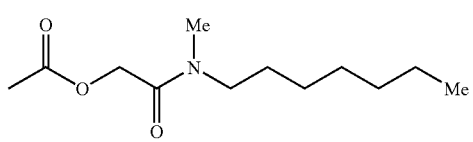 |
| 15 | 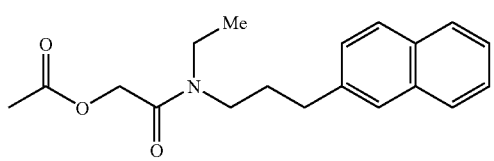 |
TABLE 102
(I-2-A-6-1)
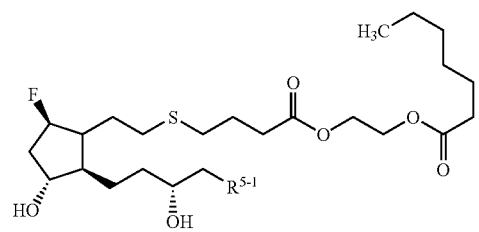
| No. | R^{5-1} |
|---|---|
| 1 | 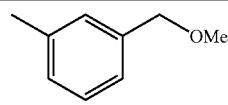 |
| 2 | 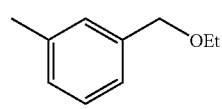 |
| 3 | 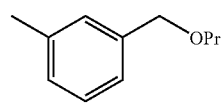 |
TABLE 102-continued
(I-2-A-6-1)
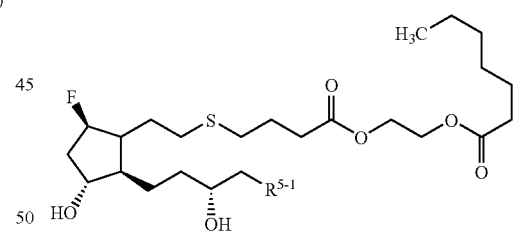
| No. | R^{5-1} |
|---|---|
| 4 | 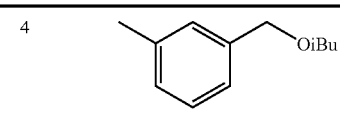 |
| 5 | 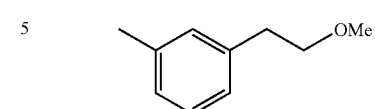 |
| 6 | 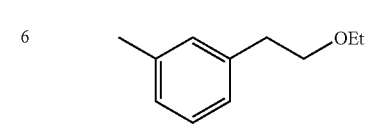 |

TABLE 102-continued (I-2-A-6-1)

| No. | R⁵⁻¹ |
|---|---|
| 7 | 3-(2-OiPr-ethyl)phenyl |
| 8 | 3-(2-OPr-ethyl)phenyl |
| 9 | 3,5-dimethoxymethyl... (3-CH₂OMe, 5-OMe phenyl) |
| 10 | 4-methyl-2-CH₂OMe, phenol (2-OMe-CH₂, OH) |
| 11 | 2-(2-OMe-ethyl)-phenol |
| 12 | 2-(2-OEt-ethyl)-phenol |
| 13 | 2-Me-phenol |
| 14 | 2-Et-phenol |
| 15 | 2-Pr-phenol |
| 16 | 3-(CH₂OH)phenyl |

TABLE 102-continued (I-2-A-6-1)

| No. | R⁵⁻¹ |
|---|---|
| 17 | 2-(2-F-ethyl)-phenol |
| 18 | 3-(CH₂OCH₂CH=CH₂)phenyl |
| 19 | 3-(CH₂OPh)phenyl |
| 20 | 3-(CH₂O-cyclopentyl)phenyl |
| 21 | 3-(CH₂SMe)phenyl |
| 22 | 3-(CH₂SEt)phenyl |
| 23 | 3-(CH₂SPr)phenyl |
| 24 | 2-CH₂SMe-phenol |
| 25 | 3-(2-SMe-ethyl)phenyl |
| 26 | 3-CH₂SMe-5-OMe-phenyl |
| 27 | 2-F-5-methyl, CH₂OMe phenyl |

TABLE 102-continued
(I-2-A-6-1)
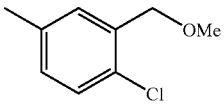
| No. | R⁵⁻¹ |
|---|---|
| 28 |  |
| 29 | 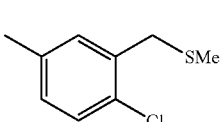 |
| 30 | 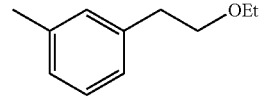 |
TABLE 103
(I-2-A-6-2)
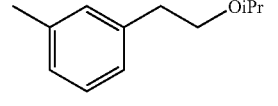
| No. | R⁵⁻¹ |
|---|---|
| 1 | 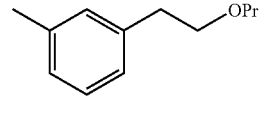 |
| 2 | 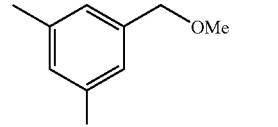 |
| 3 | 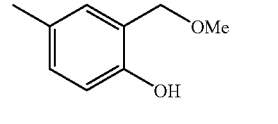 |
| 4 | 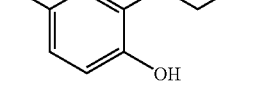 |
| 5 | 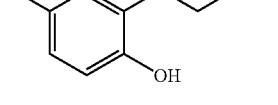 |
TABLE 103-continued
(I-2-A-6-2)
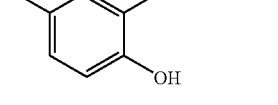
| No. | R⁵⁻¹ |
|---|---|
| 6 | 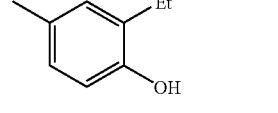 |
| 7 | 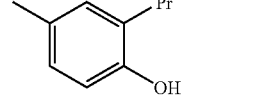 |
| 8 | 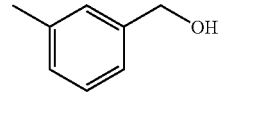 |
| 9 | 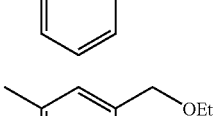 |
| 10 | 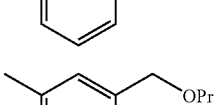 |
| 11 | 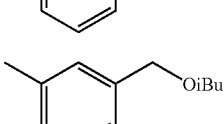 |
| 12 | 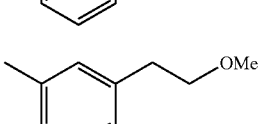 |
| 13 | |
| 14 | |
| 15 | |
| 16 | 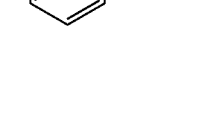 |

TABLE 103-continued (I-2-A-6-2)

| No. | R⁵⁻¹ |
|---|---|
| 17 | 2-(2-fluoroethyl)-4-methylphenol, 4-OH |
| 18 | 3-methylbenzyl allyl ether |
| 19 | 3-methylbenzyl phenyl ether (OPh) |
| 20 | 3-methylbenzyl cyclopentyl ether |
| 21 | 3-methylbenzyl SMe |
| 22 | 3-methylbenzyl SEt |
| 23 | 3-methylbenzyl SPr |
| 24 | 2-(SMe)methyl-4-methylphenol, OH |
| 25 | 3-methylphenethyl SMe |
| 26 | 3-methyl-5-OMe-benzyl SMe |

TABLE 103-continued (I-2-A-6-2)

| No. | R⁵⁻¹ |
|---|---|
| 27 | 2-(OMe)methyl-4-methyl-1-F-phenyl |
| 28 | 2-(OMe)methyl-4-methyl-1-Cl-phenyl |
| 29 | 2-(SMe)methyl-4-methyl-1-F-phenyl |
| 30 | 2-(SMe)methyl-4-methyl-1-Cl-phenyl |

TABLE 104

(I-2-A-6-3)

| No. | R⁵⁻¹ |
|---|---|
| 1 | 3-methylbenzyl OMe |
| 2 | 3-methylbenzyl OEt |
| 3 | 3-methylbenzyl OPr |
| 4 | 3-methylbenzyl OiBu |

TABLE 104-continued
(I-2-A-6-3)
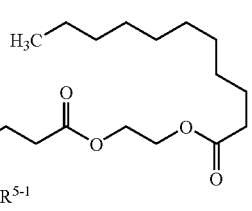
| No. | R<sup>5-1</sup> |
|---|---|
| 5 | 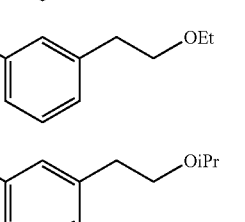 |
| 6 | 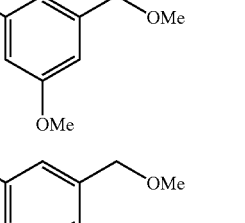 |
| 7 | 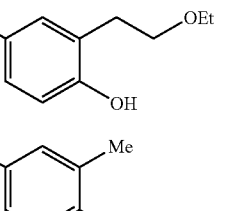 |
| 8 | 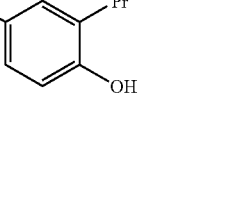 |
| 9 | 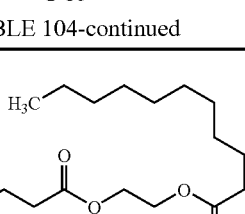 |
| 10 | 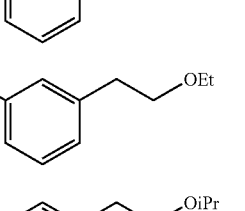 |
| 11 | 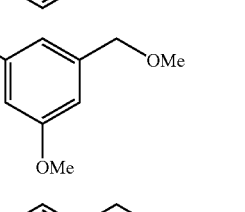 |
| 12 | 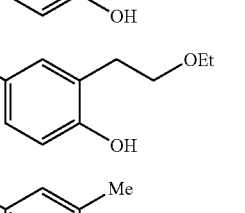 |
| 13 | 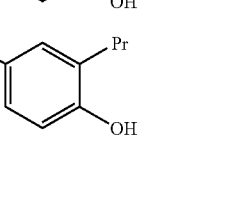 |
| 14 |  |
| 15 | 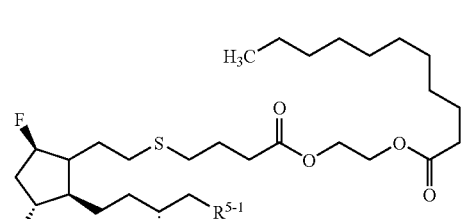 |
TABLE 104-continued
(I-2-A-6-3)
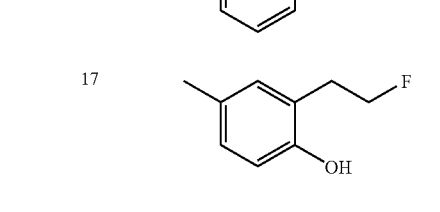
| No. | R$^{5-1}$ |
|---|---|
| 16 | 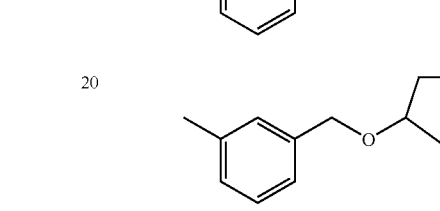 |
| 17 | 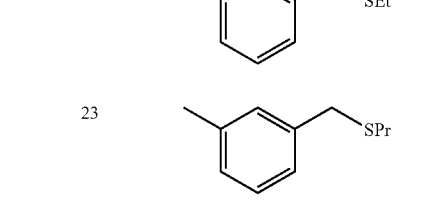 |
| 18 | 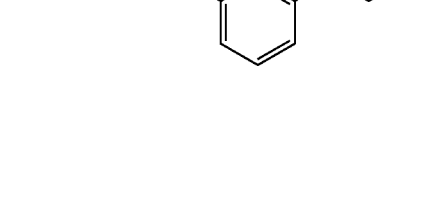 |
| 19 | 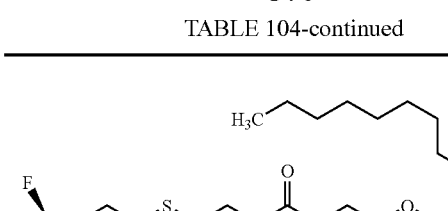 |
| 20 | 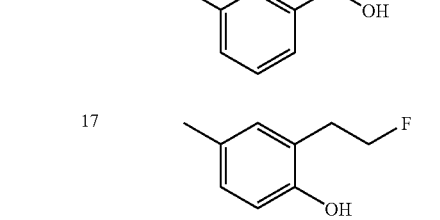 |
| 21 | 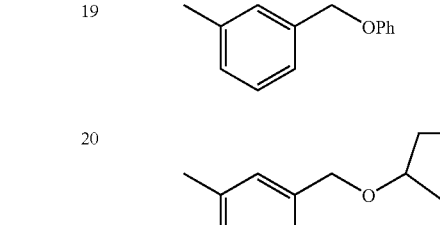 |
| 22 | 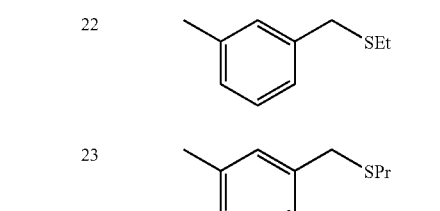 |
| 23 | 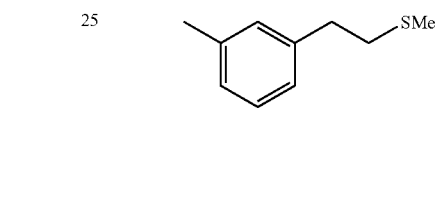 |
| 24 |  |
| 25 | 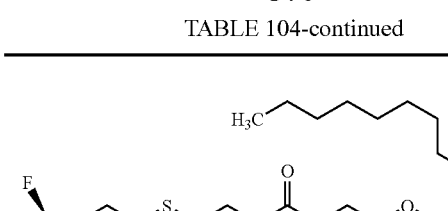 |

TABLE 104-continued
(I-2-A-6-3)
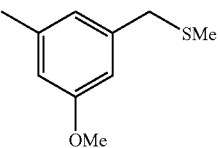
| No. | R^{5-1} |
|---|---|
| 26 | 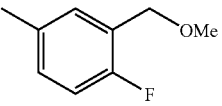 |
| 27 | 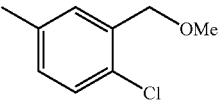 |
| 28 | 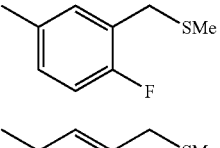 |
| 29 | 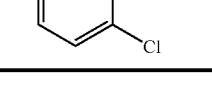 |
| 30 | 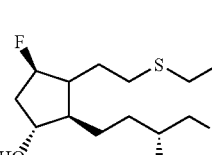 |
TABLE 105
(I-2-A-6-4)
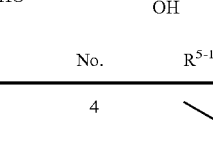
| No. | R^{5-1} |
|---|---|
| 1 | 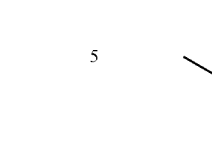 |
| 2 | 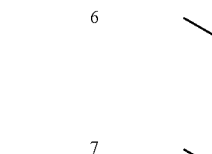 |
| 3 |  |
TABLE 105-continued
(I-2-A-6-4)
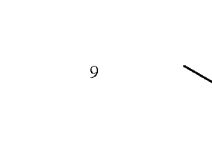
| No. | R^{5-1} |
|---|---|
| 4 | 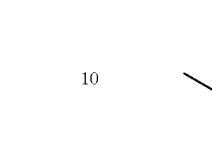 |
| 5 | 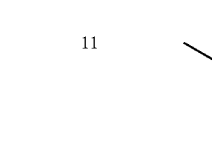 |
| 6 | 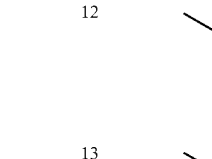 |
| 7 |  |
| 8 |  |
| 9 | 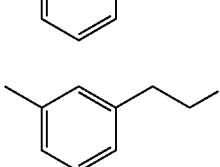 |
| 10 | 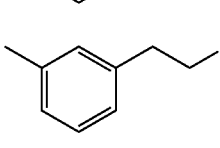 |
| 11 | 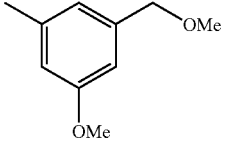 |
| 12 | 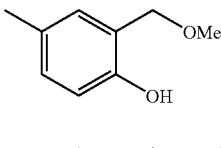 |
| 13 | 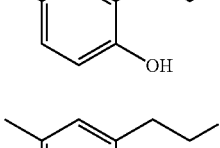 |

TABLE 105-continued
(I-2-A-6-4)
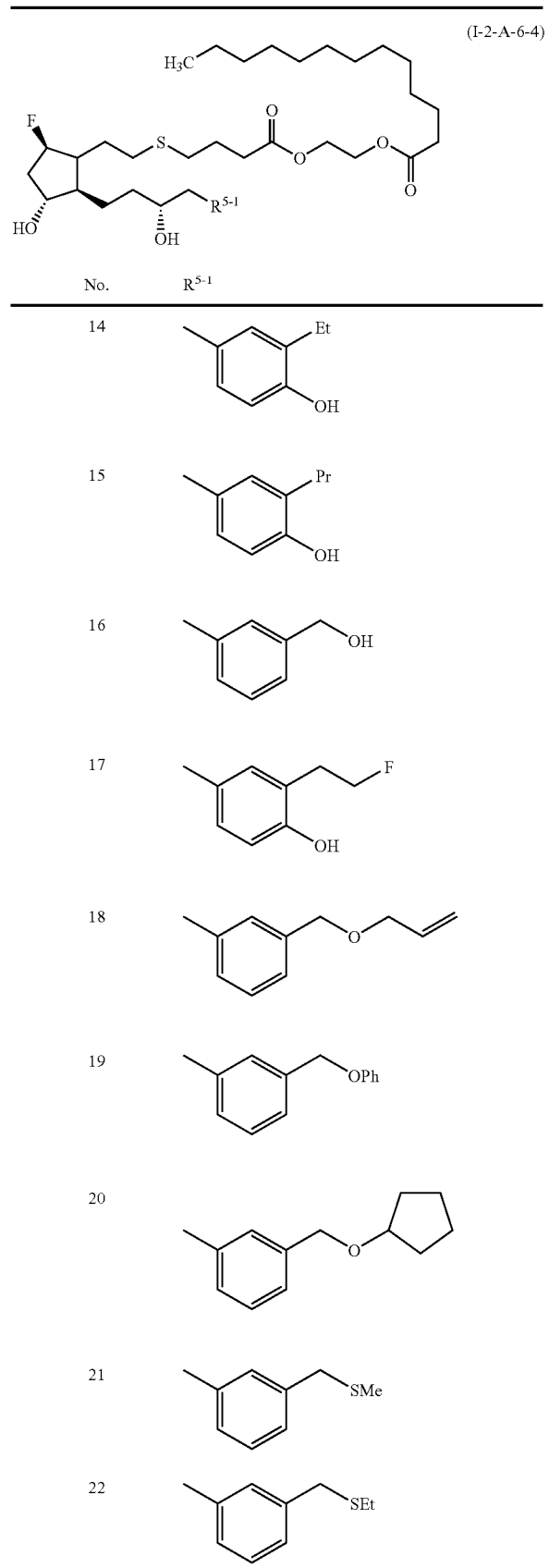
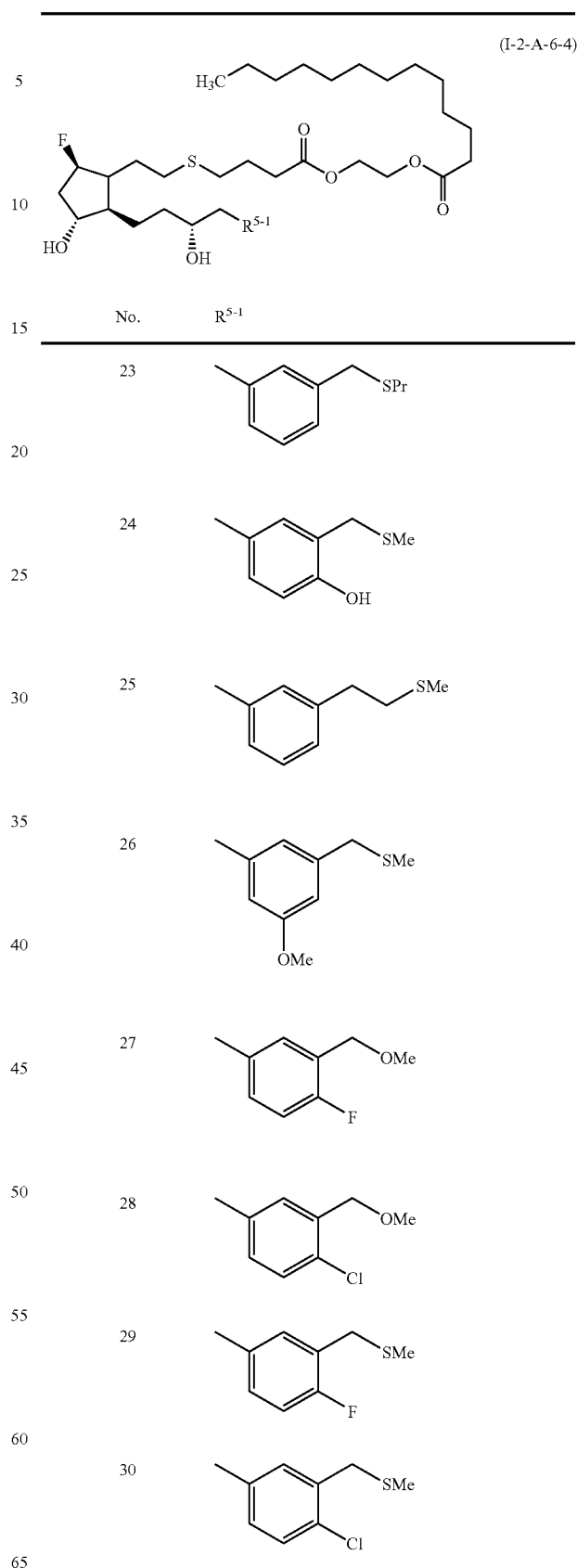

TABLE 106
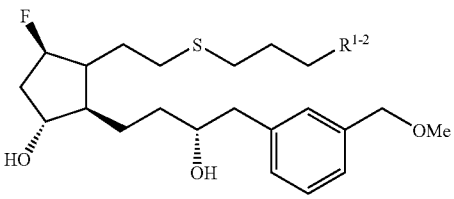
(I-2-A-6-5)
| No. | R$^{1-2}$ |
|---|---|
| 1 | 3-phenylphenyl acetate group |
| 2 | butyl (acetyloxy)acetate group |
| 3 | [3-(dipropylamino)-2-oxopropyl] acetate group |
| 4 | 2-(heptylsulfonyl)ethyl acetate group |
| 5 | (acetyloxy)methyl nonanoate group |
| 6 | 1-(acetyloxy)ethyl cyclohexanecarboxylate group |
| 7 | 2-(acetyloxy)ethyl nonanoate group |
| 8 | 2-(acetyloxy)ethyl (pentyloxy)acetate group |
| 9 | 2-(acetyloxy)ethyl 5-phenylpentanoate group |

TABLE 106-continued
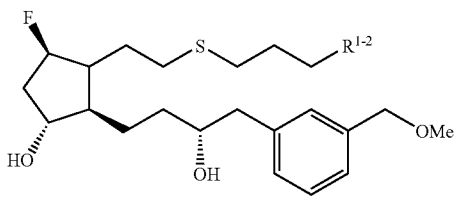
(I-2-A-6-5)
| No. | R$^{1-2}$ |
|---|---|
| 10 | 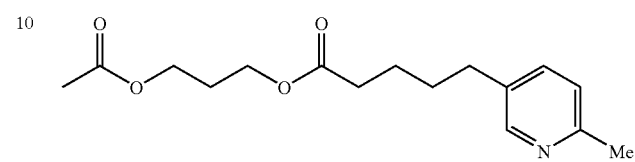 |
| 11 | 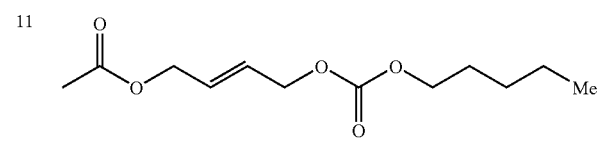 |
| 12 | 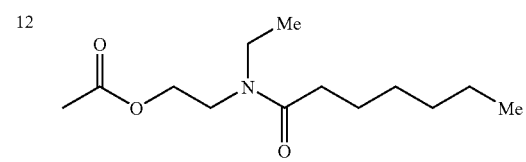 |
| 13 | 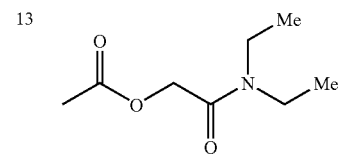 |
| 14 | 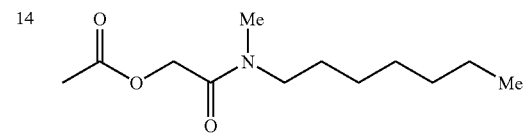 |
| 15 | 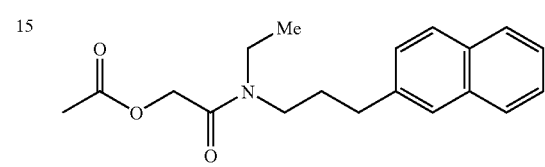 |

TABLE 107
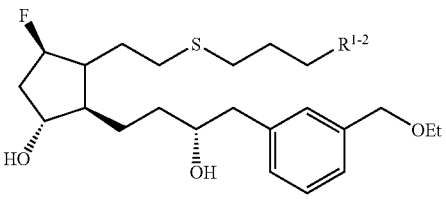
(I-2-A-6-6)
| No. | R^{1-2} |
|---|---|
| 1 | |
| 2 | |
| 3 | |
| 4 | |
| 5 | |
| 6 | |
| 7 | |
| 8 | |
| 9 | |

TABLE 107-continued
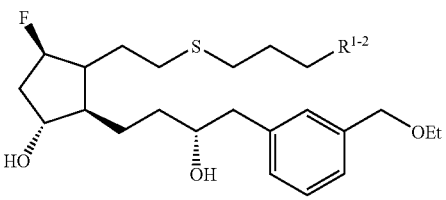
(I-2-A-6-6)
| No. | R$^{1-2}$ |
|---|---|
| 10 | 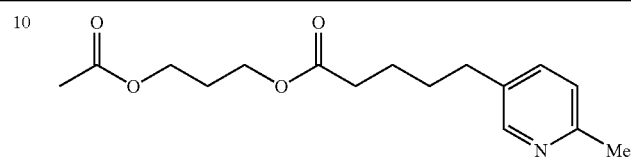 |
| 11 | 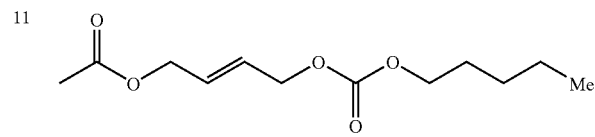 |
| 12 | 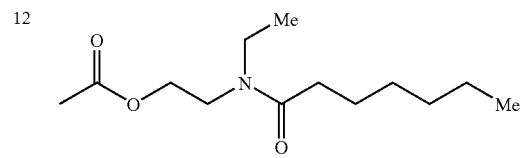 |
| 13 | 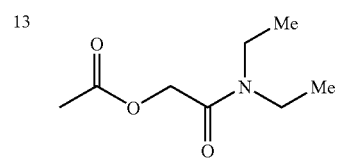 |
| 14 | 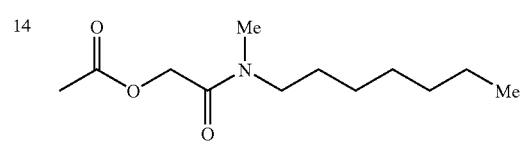 |
| 15 | 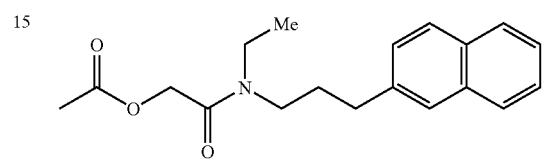 |

TABLE 108
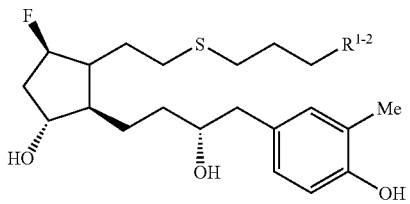
(I-2-A-6-7)
| No. | R^{1-2} |
|---|---|
| 1 | 3-phenylphenyl acetate |
| 2 | butyl (acetyloxy)acetate |
| 3 | [3-(dipropylamino)-2-oxopropyl] acetate |
| 4 | 2-(heptylsulfonyl)ethyl acetate |
| 5 | (acetyloxy)methyl nonanoate |
| 6 | 1-(acetyloxy)ethyl cyclohexanecarboxylate |
| 7 | 2-(acetyloxy)ethyl nonanoate |
| 8 | 2-(acetyloxy)ethyl (pentyloxy)acetate |
| 9 | 2-(acetyloxy)ethyl 5-phenylpentanoate |

TABLE 108-continued
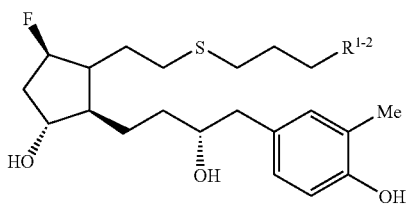
(I-2-A-6-7)
| No. | $R^{1-2}$ |
|---|---|
| 10 | 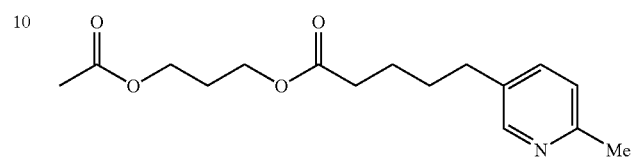 |
| 11 | 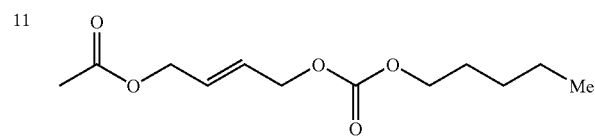 |
| 12 | 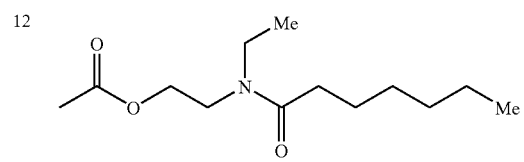 |
| 13 | 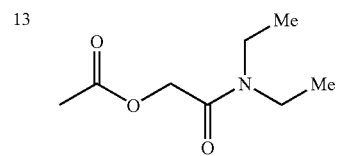 |
| 14 | 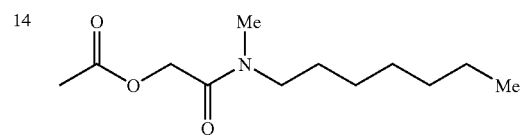 |
| 15 | 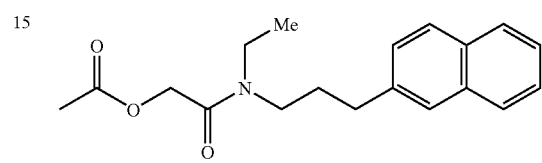 |

TABLE 109
(I-1-A-1-1)
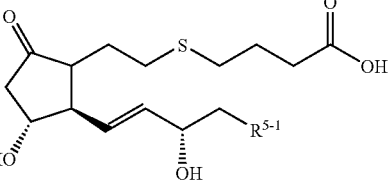
| No. | R⁵⁻¹ |
|---|---|
| 1 |  |
| 2 | 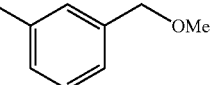 |
| 3 | 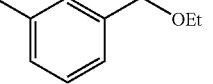 |
| 4 | 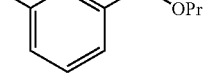 |
| 5 | 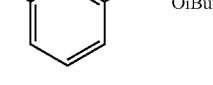 |
| 6 | 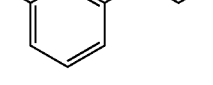 |
| 7 | 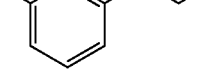 |
| 8 | 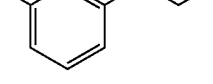 |
| 9 | 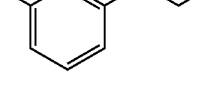 |
| 10 | 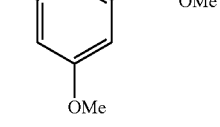 |
| 11 | 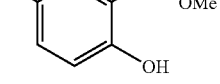 |
TABLE 109-continued
(I-1-A-1-1)
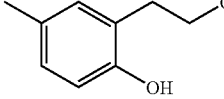
| No. | R⁵⁻¹ |
|---|---|
| 12 | 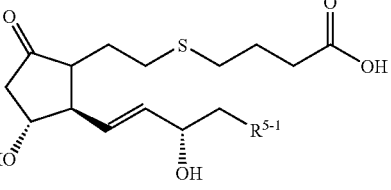 |
| 13 |  |
| 14 | 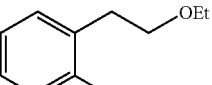 |
| 15 | 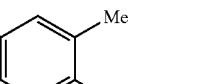 |
| 16 | 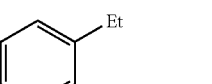 |
| 17 | 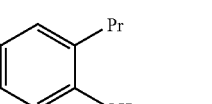 |
| 18 | 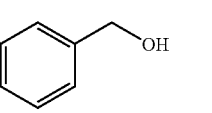 |
| 19 | 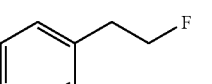 |
| 20 | 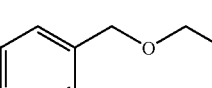 |
| 21 | 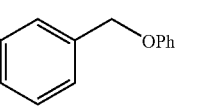 |
| 22 | 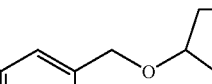 |

TABLE 109-continued (I-1-A-1-1)

| No. | R⁵⁻¹ |
|---|---|
| 23 | 3-(SPr-CH2)-phenyl |
| 24 | 2-(SMe-CH2)-4-methyl-phenol |
| 25 | 3-(CH2CH2SMe)-phenyl |
| 26 | 3-(SMe-CH2)-5-OMe-phenyl |
| 27 | 2-(OMe-CH2)-4-F-phenyl (F at position shown) |
| 28 | 2-(OMe-CH2)-4-Cl-phenyl |
| 29 | 2-(SMe-CH2)-4-F-phenyl |
| 30 | 2-(SMe-CH2)-4-Cl-phenyl |

TABLE 110

(I-1-A-1-2)

| No. | R⁵⁻¹ |
|---|---|
| 1 | 3-(CH2OMe)-phenyl |
| 2 | 3-(CH2OEt)-phenyl |
| 3 | 3-(CH2OPr)-phenyl |
| 4 | 3-(CH2OiBu)-phenyl |
| 5 | 3-(CH2CH2OMe)-phenyl |
| 6 | 3-(CH2CH2OEt)-phenyl |
| 7 | 3-(CH2CH2OiPr)-phenyl |
| 8 | 3-(CH2CH2OPr)-phenyl |
| 9 | 3-(CH2OMe)-5-OMe-phenyl |
| 10 | 2-(CH2OMe)-4-methyl-phenol |
| 11 | 2-(CH2CH2OMe)-4-methyl-phenol |

TABLE 110-continued
(I-1-A-1-2)
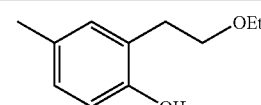
| No. | R[5-1] |
|---|---|
| 12 | 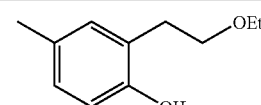 |
| 13 | 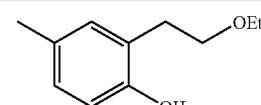 |
| 14 | 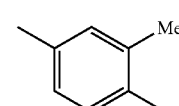 |
| 15 | 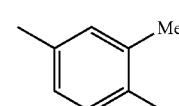 |
| 16 | 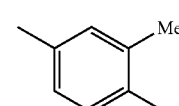 |
| 17 | 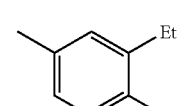 |
| 18 | 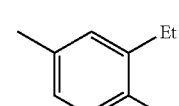 |
| 19 | 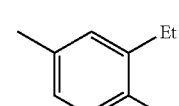 |
| 20 | 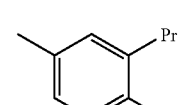 |
| 21 | 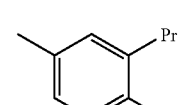 |
| 22 | 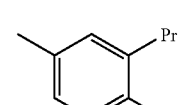 |
TABLE 110-continued
(I-1-A-1-2)
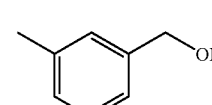
| No. | R[5-1] |
|---|---|
| 23 | 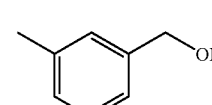 |
| 24 | 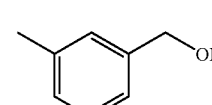 |
| 25 | 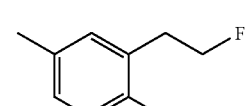 |
| 26 | 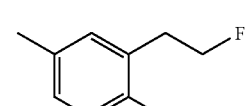 |
| 27 | 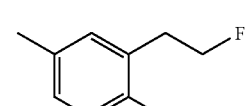 |
| 28 | 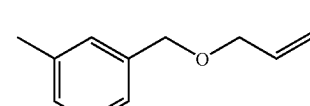 |
| 29 | 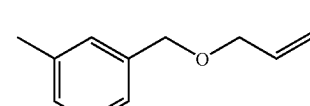 |
| 30 | 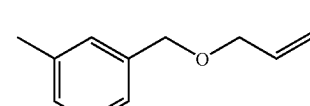 |

TABLE 111
(I-1-A-2-1)
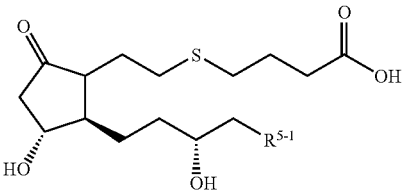
| No. | R<sup>5-1</sup> |
|---|---|
| 1 | 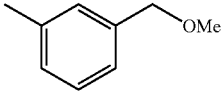 |
| 2 | 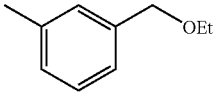 |
| 3 | 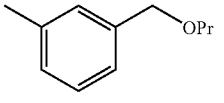 |
| 4 | 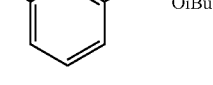 |
| 5 | 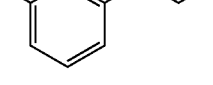 |
| 6 | 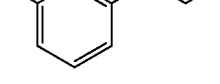 |
| 7 | 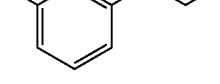 |
| 8 | 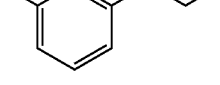 |
| 9 | 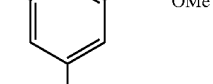 |
| 10 | 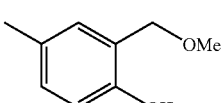 |
| 11 | 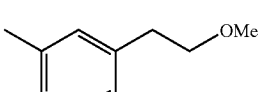 |
TABLE 111-continued
(I-1-A-2-1)
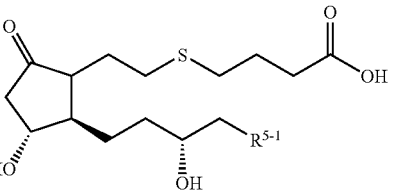
| No. | $R^{5-1}$ |
|---|---|
| 12 | 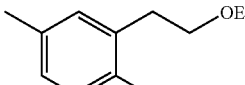 |
| 13 | 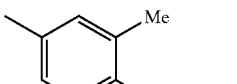 |
| 14 | 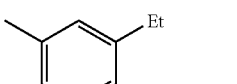 |
| 15 | 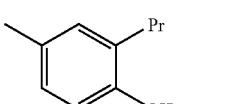 |
| 16 | 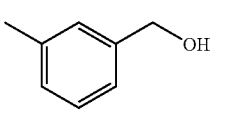 |
| 17 | 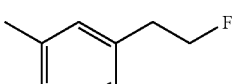 |
| 18 | 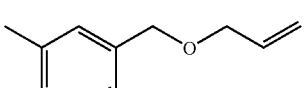 |
| 19 | 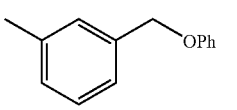 |
| 20 | 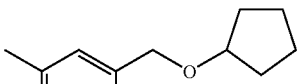 |
| 21 | 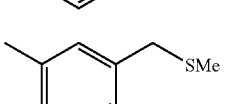 |
| 22 | 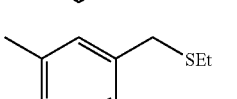 |

TABLE 111-continued (I-1-A-2-1)

| No. | R⁵⁻¹ |
|---|---|
| 23 | 3-(SPr-CH2)-phenyl |
| 24 | 2-(SMe-CH2)-4-methyl-phenol (2-SMe-CH2, 4-Me, OH) |
| 25 | 3-(CH2CH2SMe)-phenyl |
| 26 | 3-SMe-CH2, 5-OMe-phenyl |
| 27 | 2-(OMe-CH2)-4-Me, F-phenyl (with F) |
| 28 | 2-(OMe-CH2)-Cl-phenyl |
| 29 | 2-(SMe-CH2)-F-phenyl |
| 30 | 2-(SMe-CH2)-Cl-phenyl |

TABLE 112

(I-1-A-2-2)

| No. | R⁵⁻¹ |
|---|---|
| 1 | 3-(CH2OMe)-phenyl |
| 2 | 3-(CH2OEt)-phenyl |
| 3 | 3-(CH2OPr)-phenyl |
| 4 | 3-(CH2OiBu)-phenyl |
| 5 | 3-(CH2CH2OMe)-phenyl |
| 6 | 3-(CH2CH2OEt)-phenyl |
| 7 | 3-(CH2CH2OiPr)-phenyl |
| 8 | 3-(CH2CH2OPr)-phenyl |
| 9 | 3-(CH2OMe), 5-OMe-phenyl |
| 10 | 2-(CH2OMe)-4-Me-phenol |
| 11 | 2-(CH2CH2OMe)-4-Me-phenol |

TABLE 112-continued
(I-1-A-2-2)
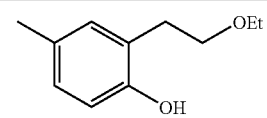
| No. | R<sup>5-1</sup> |
|---|---|
| 12 | 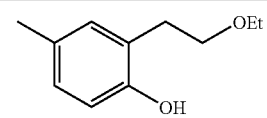 |
| 13 | 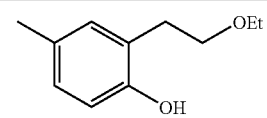 |
| 14 | 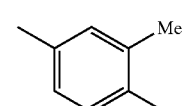 |
| 15 | 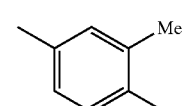 |
| 16 | 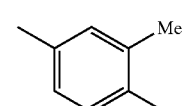 |
| 17 | 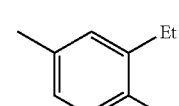 |
| 18 | 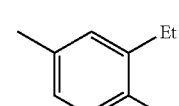 |
| 19 | 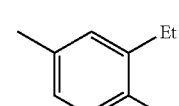 |
| 20 | 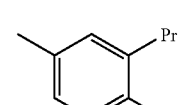 |
| 21 | 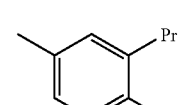 |
| 22 | 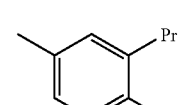 |
TABLE 112-continued
(I-1-A-2-2)
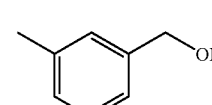
| No. | R<sup>5-1</sup> |
|---|---|
| 23 | 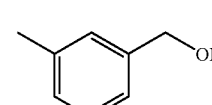 |
| 24 | 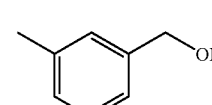 |
| 25 | 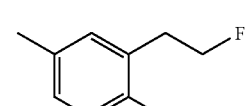 |
| 26 | 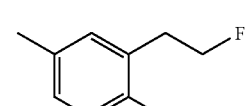 |
| 27 | 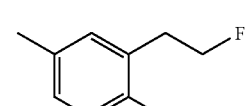 |
| 28 | 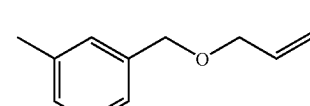 |
| 29 | 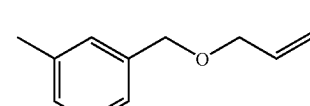 |
| 30 | 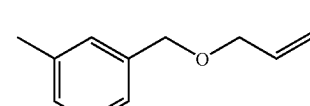 |

TABLE 113
(I-1-A-3-1)
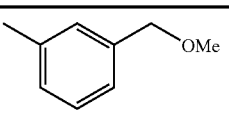
| No. | R$^{5-1}$ |
|---|---|
| 1 | 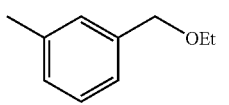 |
| 2 | 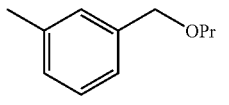 |
| 3 | 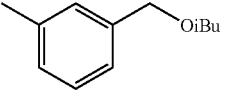 |
| 4 | 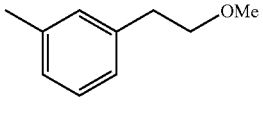 |
| 5 | 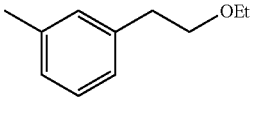 |
| 6 | 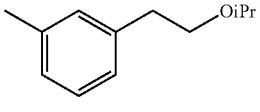 |
| 7 | 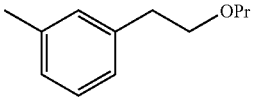 |
| 8 | 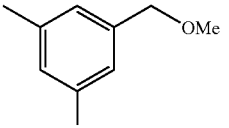 |
| 9 | 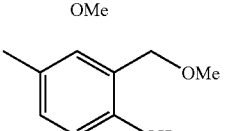 |
| 10 | 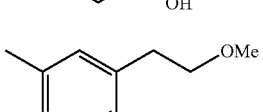 |
| 11 | 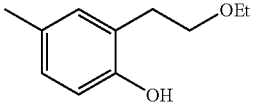 |
TABLE 113-continued
(I-1-A-3-1)
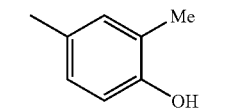
| No. | R$^{5-1}$ |
|---|---|
| 12 | 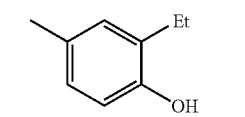 |
| 13 | 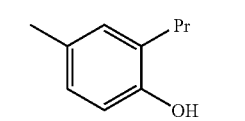 |
| 14 | 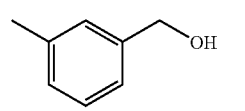 |
| 15 | 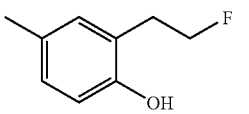 |
| 16 | 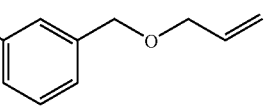 |
| 17 | 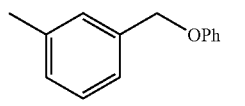 |
| 18 | 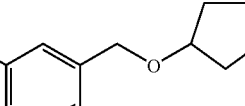 |
| 19 | 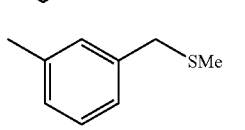 |
| 20 | 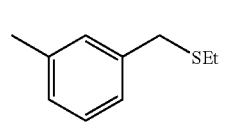 |
| 21 |  |
| 22 |  |

TABLE 113-continued (I-1-A-3-1)

| No. | R⁵⁻¹ |
|---|---|
| 23 | 3-methylbenzyl-SPr |
| 24 | 4-methyl-2-(SMe-methyl)phenol |
| 25 | 3-methylphenethyl-SMe |
| 26 | 3-methyl-5-(SMe-methyl)-anisole |
| 27 | 4-methyl-2-(OMe-methyl)-fluorobenzene |
| 28 | 4-methyl-2-(OMe-methyl)-chlorobenzene |
| 29 | 4-methyl-2-(SMe-methyl)-fluorobenzene |
| 30 | 4-methyl-2-(SMe-methyl)-chlorobenzene |

TABLE 114

(I-1-A-3-2)

| No. | R⁵⁻¹ |
|---|---|
| 1 | 3-methylbenzyl-OMe |
| 2 | 3-methylbenzyl-OEt |
| 3 | 3-methylbenzyl-OPr |
| 4 | 3-methylbenzyl-OiBu |
| 5 | 3-methylphenethyl-OMe |
| 6 | 3-methylphenethyl-OEt |
| 7 | 3-methylphenethyl-OiPr |
| 8 | 3-methylphenethyl-OPr |
| 9 | 3-methyl-5-(OMe-methyl)-anisole |
| 10 | 4-methyl-2-(OMe-methyl)phenol |
| 11 | 4-methyl-2-(OMe-ethyl)phenol |

TABLE 114-continued
(I-1-A-3-2)
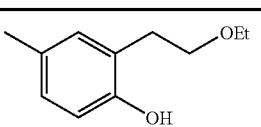
| No. | R⁵⁻¹ |
|---|---|
| 12 | 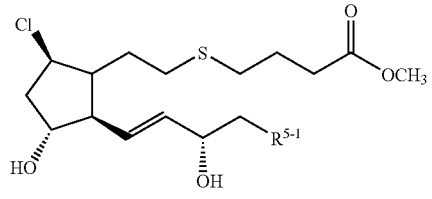 |
| 13 | 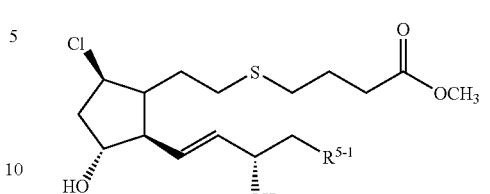 |
| 14 | 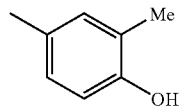 |
| 15 | 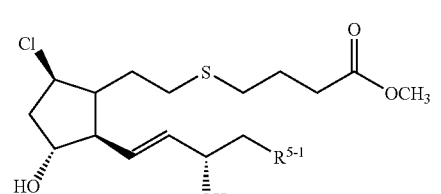 |
| 16 | 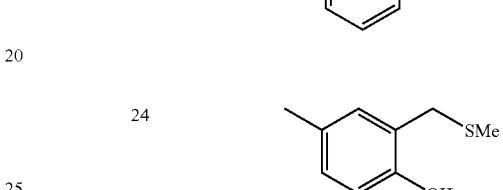 |
| 17 | 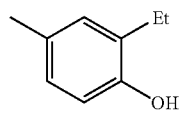 |
| 18 | 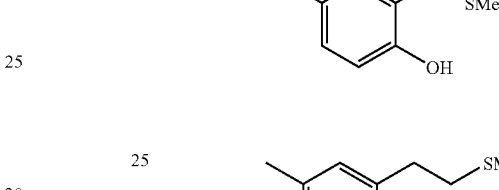 |
| 19 | 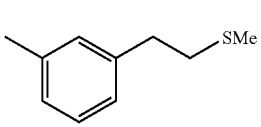 |
| 20 | 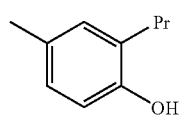 |
| 21 | 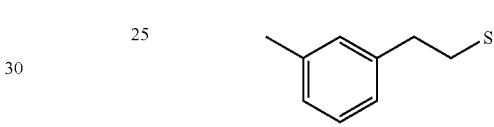 |
| 22 | 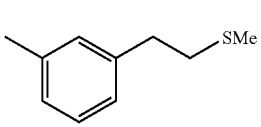 |
TABLE 114-continued
(I-1-A-3-2)
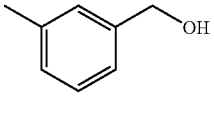
| No. | R⁵⁻¹ |
|---|---|
| 23 |  |
| 24 | 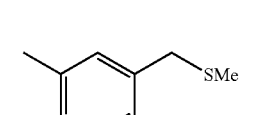 |
| 25 | 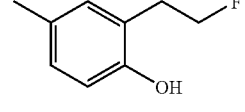 |
| 26 |  |
| 27 | 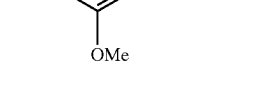 |
| 28 | 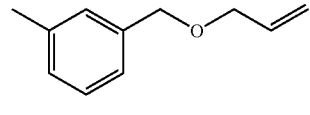 |
| 29 |  |
| 30 | 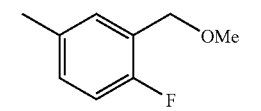 |

TABLE 115

(I-1-A-4-1)

| No. | R^{5-1} |
|---|---|
| 1 | 3-(MeOCH₂)-phenyl |
| 2 | 3-(EtOCH₂)-phenyl |
| 3 | 3-(PrOCH₂)-phenyl |
| 4 | 3-(iBuOCH₂)-phenyl |
| 5 | 3-(MeOCH₂CH₂)-phenyl |
| 6 | 3-(EtOCH₂CH₂)-phenyl |
| 7 | 3-(iPrOCH₂CH₂)-phenyl |
| 8 | 3-(PrOCH₂CH₂)-phenyl |
| 9 | 3,5-(MeO)₂-phenyl-CH₂- (structure: 3,5-dimethoxy with OMe linker) |
| 10 | 2-(MeOCH₂)-4-methyl-phenol (2-OH, with CH₂OMe) |
| 11 | 2-(MeOCH₂CH₂)-4-methyl-phenol |

TABLE 115-continued (I-1-A-4-1)

| No. | R^{5-1} |
|---|---|
| 12 | 2-(EtOCH₂CH₂)-4-methyl-phenol |
| 13 | 2-Me-4-methyl-phenol |
| 14 | 2-Et-4-methyl-phenol |
| 15 | 2-Pr-4-methyl-phenol |
| 16 | 3-(HOCH₂)-phenyl |
| 17 | 2-(FCH₂CH₂)-4-methyl-phenol |
| 18 | 3-(CH₂=CHCH₂OCH₂)-phenyl |
| 19 | 3-(PhOCH₂)-phenyl |
| 20 | 3-(cyclopentyl-O-CH₂)-phenyl |
| 21 | 3-(MeSCH₂)-phenyl |
| 22 | 3-(EtSCH₂)-phenyl |

TABLE 115-continued (I-1-A-4-1)

| No. | R^{5-1} |
|---|---|
| 23 | 3-methylbenzyl SPr |
| 24 | 4-methyl-2-(SMe)methyl-phenol |
| 25 | 3-methylphenethyl SMe |
| 26 | 3-methoxy-5-methylbenzyl SMe |
| 27 | 2-fluoro-5-methylbenzyl OMe |
| 28 | 2-chloro-5-methylbenzyl OMe |
| 29 | 2-fluoro-5-methylbenzyl SMe |
| 30 | 2-chloro-5-methylbenzyl SMe |

TABLE 116

(I-1-A-4-2)

| No. | R^{5-1} |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3,5-dimethoxybenzyl-methyl OMe |
| 10 | 4-methyl-2-(OMe)methyl-phenol |
| 11 | 4-methyl-2-(2-methoxyethyl)-phenol |

TABLE 116-continued
(I-1-A-4-2)
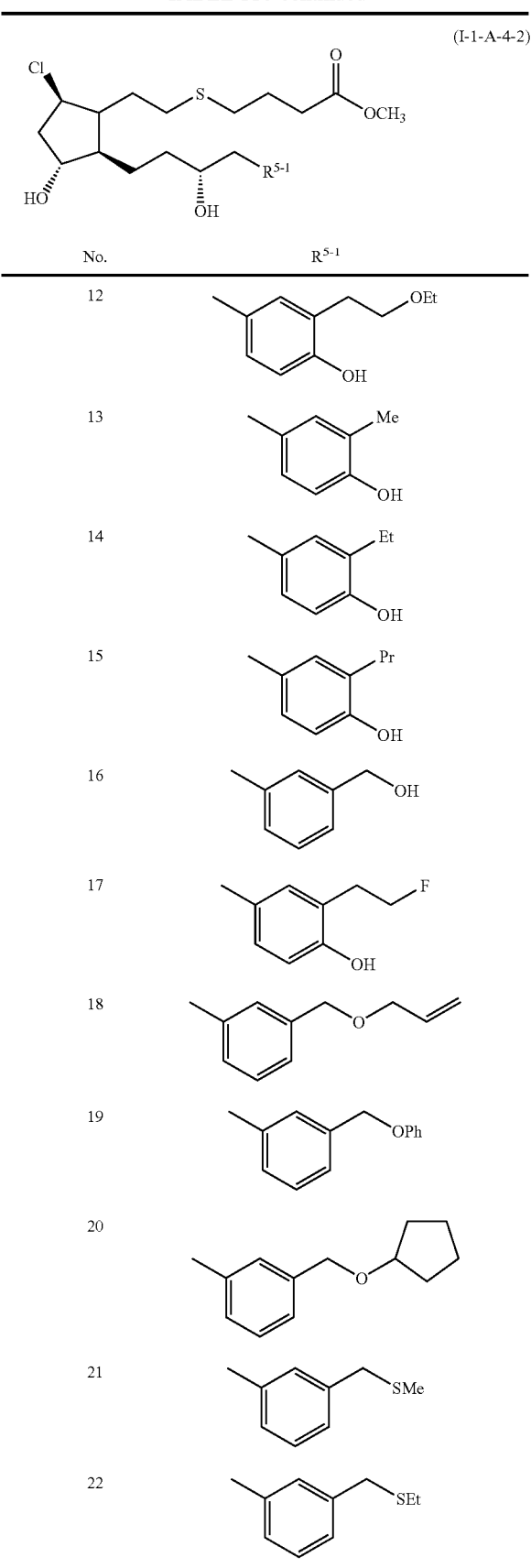
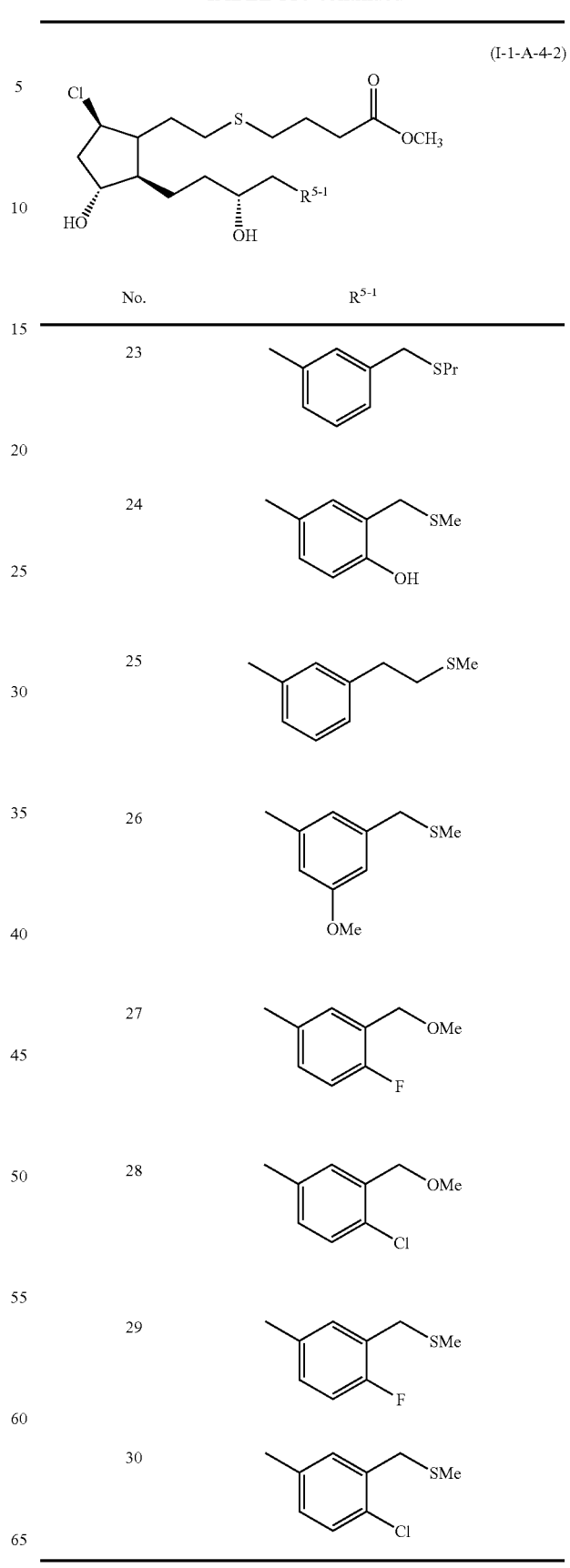

TABLE 117
(I-1-A-5-1)
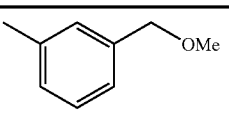
| No. | R<sup>5-1</sup> |
|---|---|
| 1 | 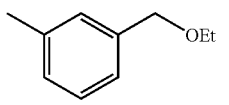 |
| 2 | 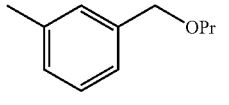 |
| 3 | 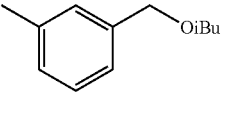 |
| 4 | 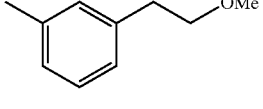 |
| 5 | 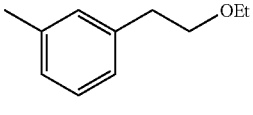 |
| 6 | 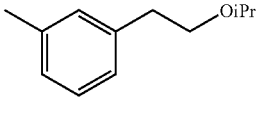 |
| 7 | 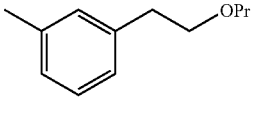 |
| 8 | 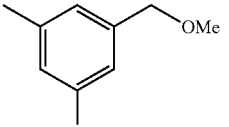 |
| 9 | 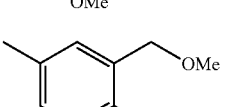 |
| 10 | 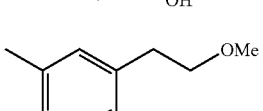 |
| 11 | 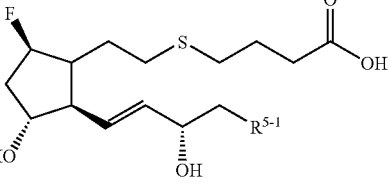 |
TABLE 117-continued
(I-1-A-5-1)
| No. | R<sup>5-1</sup> |
|---|---|
| 12 | 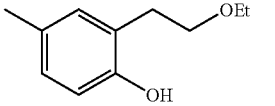 |
| 13 | 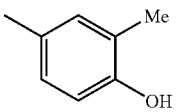 |
| 14 | 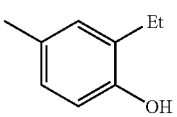 |
| 15 | 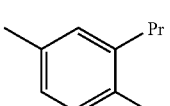 |
| 16 | 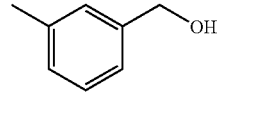 |
| 17 | 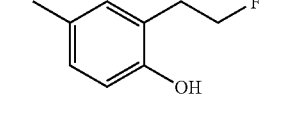 |
| 18 | 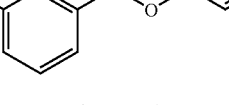 |
| 19 | 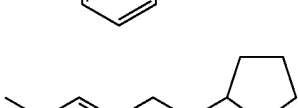 |
| 20 | 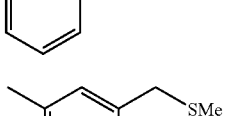 |
| 21 | 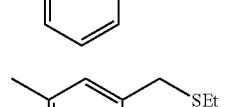 |
| 22 | 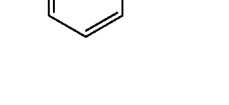 |

TABLE 117-continued (I-1-A-5-1)

| No. | R^{5-1} |
|---|---|
| 23 | 3-methylbenzyl SPr |
| 24 | 4-methyl-2-(SMe)phenol |
| 25 | 3-methylphenethyl SMe |
| 26 | 3-methyl-5-OMe-benzyl SMe |
| 27 | 5-methyl-2-F-benzyl OMe |
| 28 | 5-methyl-2-Cl-benzyl OMe |
| 29 | 5-methyl-2-F-benzyl SMe |
| 30 | 5-methyl-2-Cl-benzyl SMe |

TABLE 118

(I-1-A-5-2)

| No. | R^{5-1} |
|---|---|
| 1 | 3-methylbenzyl OMe |
| 2 | 3-methylbenzyl OEt |
| 3 | 3-methylbenzyl OPr |
| 4 | 3-methylbenzyl OiBu |
| 5 | 3-methylphenethyl OMe |
| 6 | 3-methylphenethyl OEt |
| 7 | 3-methylphenethyl OiPr |
| 8 | 3-methylphenethyl OPr |
| 9 | 3-methyl-5-OMe-benzyl OMe |
| 10 | 4-methyl-2-(OMe)phenol |
| 11 | 4-methyl-2-(OMe-ethyl)phenol |

TABLE 118-continued (I-1-A-5-2)

[Structure of compound with cyclopentane ring bearing F, OH, OH, and side chain with S, ester group OCH₃, and R⁵⁻¹ substituent]

| No. | R⁵⁻¹ |
|---|---|
| 12 | 4-methyl-2-(2-ethoxyethyl)phenol |
| 13 | 2,4-dimethylphenol |
| 14 | 2-ethyl-4-methylphenol |
| 15 | 2-propyl-4-methylphenol |
| 16 | 3-methylbenzyl alcohol |
| 17 | 2-(2-fluoroethyl)-4-methylphenol |
| 18 | 3-methylbenzyl allyl ether |
| 19 | 3-methylbenzyl phenyl ether |
| 20 | 3-methylbenzyl cyclopentyl ether |
| 21 | 3-methylbenzyl methyl sulfide (SMe) |
| 22 | 3-methylbenzyl ethyl sulfide (SEt) |
| 23 | 3-methylbenzyl propyl sulfide (SPr) |
| 24 | 2-(methylthiomethyl)-4-methylphenol |
| 25 | 3-methylphenethyl methyl sulfide |
| 26 | 3-methoxy-5-(methylthiomethyl)toluene |
| 27 | 2-fluoro-5-methylbenzyl methyl ether |
| 28 | 2-chloro-5-methylbenzyl methyl ether |
| 29 | 2-fluoro-5-methylbenzyl methyl sulfide |
| 30 | 2-chloro-5-methylbenzyl methyl sulfide |

TABLE 119
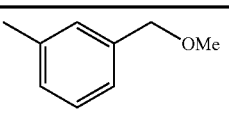
(I-1-A-6-1)
| No. | R⁵⁻¹ |
|---|---|
| 1 | 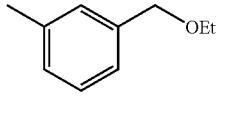 |
| 2 | 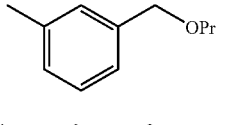 |
| 3 | 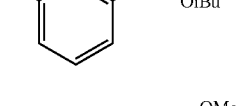 |
| 4 | 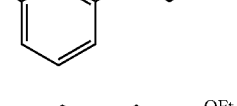 |
| 5 | 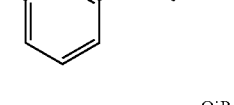 |
| 6 | 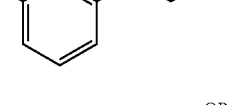 |
| 7 | 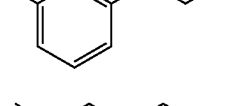 |
| 8 | 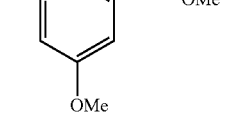 |
| 9 | 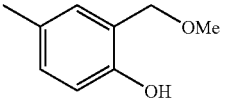 |
| 10 | 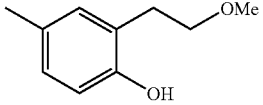 |
| 11 | 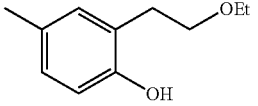 |
TABLE 119-continued
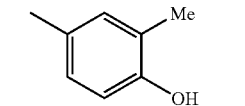
(I-1-A-6-1)
| No. | R⁵⁻¹ |
|---|---|
| 12 | 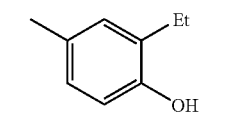 |
| 13 | 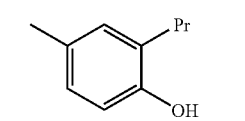 |
| 14 | 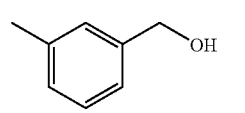 |
| 15 | 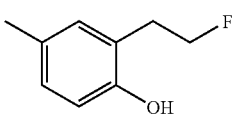 |
| 16 | 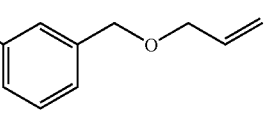 |
| 17 | 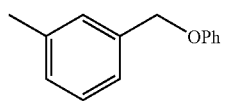 |
| 18 | 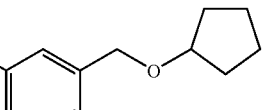 |
| 19 | 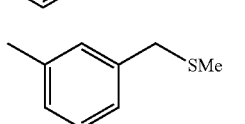 |
| 20 | 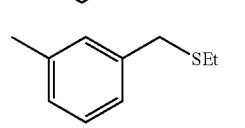 |
| 21 |  |
| 22 |  |

TABLE 119-continued
(I-1-A-6-1)
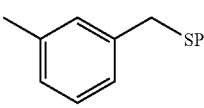
| No. | R^5-1 |
|---|---|
| 23 | 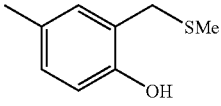 |
| 24 | 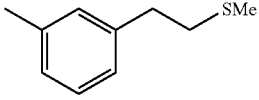 |
| 25 | 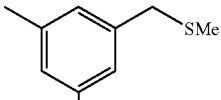 |
| 26 | 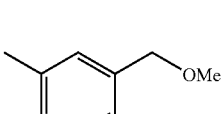 |
| 27 | 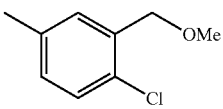 |
| 28 | 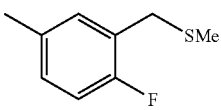 |
| 29 | 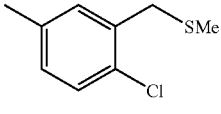 |
| 30 | 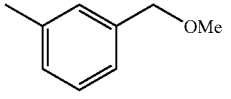 |
TABLE 120
(I-1-A-6-2)
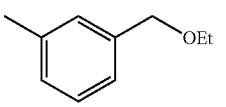
| No. | R^5-1 |
|---|---|
| 1 | 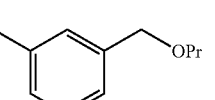 |
| 2 | 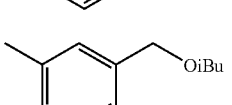 |
| 3 | 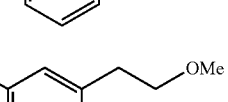 |
| 4 | 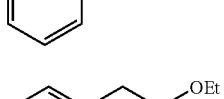 |
| 5 | 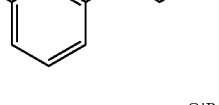 |
| 6 | 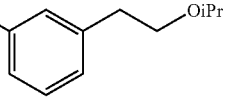 |
| 7 | 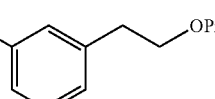 |
| 8 | 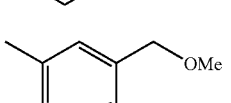 |
| 9 | 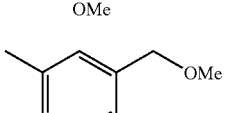 |
| 10 | |
| 11 | |

TABLE 120-continued (I-1-A-6-2)

[Structure: cyclopentane with F, OH substituents, thioether linker to -CH2CH2CH2C(=O)OCH3, and side chain -CH2CH2CH(OH)CH2-R^{5-1}]

| No. | R^{5-1} |
|---|---|
| 12 | 4-methyl-2-(2-ethoxyethyl)phenol (with OEt) |
| 13 | 4-methyl-2-methylphenol (Me, OH) |
| 14 | 4-methyl-2-ethylphenol (Et, OH) |
| 15 | 4-methyl-2-propylphenol (Pr, OH) |
| 16 | 3-methylbenzyl alcohol (CH2OH) |
| 17 | 4-methyl-2-(2-fluoroethyl)phenol (F, OH) |
| 18 | 3-methylbenzyl allyl ether (CH2-O-CH2CH=CH2) |
| 19 | 3-methylbenzyl phenyl ether (CH2-OPh) |
| 20 | 3-methylbenzyl cyclopentyl ether |
| 21 | 3-methylbenzyl methyl sulfide (CH2-SMe) |
| 22 | 3-methylbenzyl ethyl sulfide (CH2-SEt) |
| 23 | 3-methylbenzyl propyl sulfide (CH2-SPr) |
| 24 | 4-methyl-2-(methylthiomethyl)phenol (CH2-SMe, OH) |
| 25 | 3-methylphenethyl methyl sulfide (CH2CH2-SMe) |
| 26 | 3-methyl-5-methoxybenzyl methyl sulfide (CH2-SMe, OMe) |
| 27 | 4-methyl-2-(methoxymethyl)fluorobenzene (CH2-OMe, F) |
| 28 | 4-methyl-2-(methoxymethyl)chlorobenzene (CH2-OMe, Cl) |
| 29 | 4-methyl-2-(methylthiomethyl)fluorobenzene (CH2-SMe, F) |
| 30 | 4-methyl-2-(methylthiomethyl)chlorobenzene (CH2-SMe, Cl) |

Among the compounds of formula (I-1), preferable compounds are the compound described in the Example of WO00/03980. More preferable compounds are the Compound (1) to (8) listed below.

Compound (1)

(11α,15α,13E)-9-Oxo-11,15-dihydroxy-16-(3-methoxymethylphenyl)-17,18,19,20-tetranor-5-thiaprost-13-enoic acid methyl ester

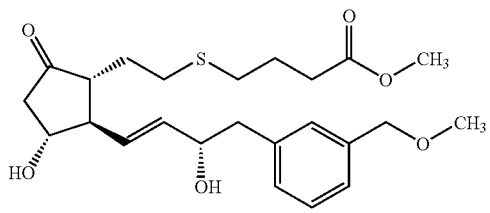

Compound (2)

(11α,15α,13E)-9-Oxo-11,15-dihydroxy-16-(3-methyl-4-hydroxyphenyl)-17,18,19,20-tetranor-5-thiaprost-13-enoic acid methyl ester

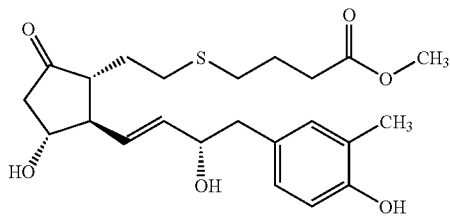

Compound (3)

(11α,15α,13E)-9-Oxo-11,15-dihydroxy-16-(3-ethoxymethylphenyl)-17,18,19,20-tetranor-5-thiaprost-13-enoic acid methyl ester

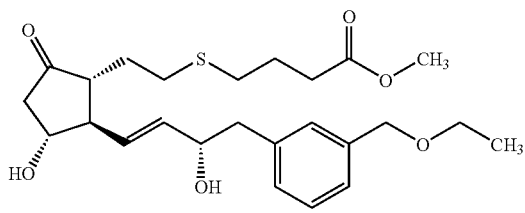

Compound (4)

(9β,11α,15α,13E)-9-Fluoro-11,15-dihydroxy-16-(3-methoxymethylphenyl)-17,18,19,20-tetranor-5-thiaprost-13-enoic acid methyl ester

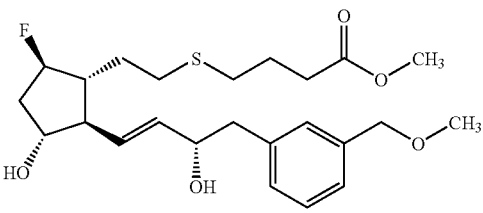

Compound (5)

(11α,15α,13E)-9-Oxo-11,15-dihydroxy-16-(3-methoxymethylphenyl)-17,18,19,20-tetranor-5-thiaprost-13-enoic acid

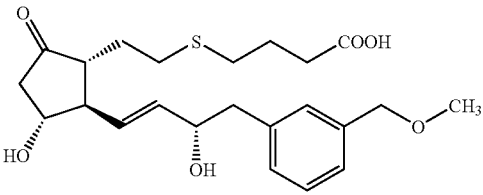

Compound (6)

(11α,15α,13E)-9-Oxo-11,15-dihydroxy-16-(3-methyl-4-hydroxyphenyl)-17,18,19,20-tetranor-5-thiaprost-13-enoic acid

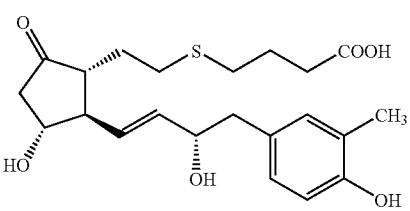

Compound (7)

(11α,15α,13E)-9-Oxo-11,15-dihydroxy-16-(3-ethoxymethylphenyl)-17,18,19,20-tetranor-5-thiaprost-13-enoic acid

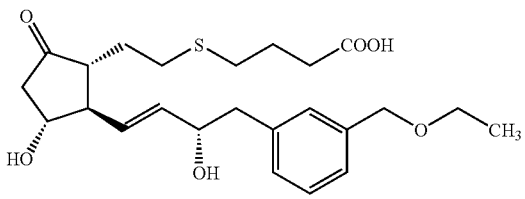

Compound (8)

(9β,11α,15α,13E)-9-Fluoro-11,15-dihydroxy-16-(3-methoxymethylphenyl)-17,18,19,20-tetranor-5-thiaprost-13-enoic acid

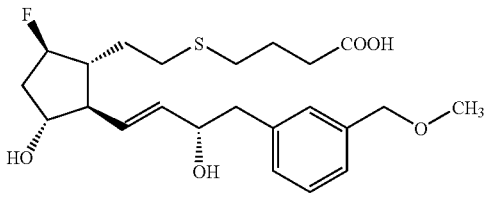

Process for Producing Compounds of the Invention:

Among the compounds of the invention, those of formula (I-1) can be produced according to the methods described in WO00/03980.

Among the compounds of the invention, those of formula (I-3) can be produced according to the methods mentioned below or according to the methods described in the Examples mentioned below.

1) Among the compounds of formula (I-3), those in which $T^3$ is oxygen and the 13-14 position is a double bond, or that is, those of formula (IA):

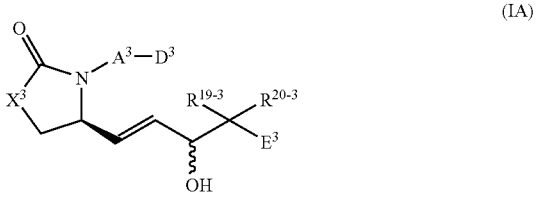

(IA)

wherein all symbols have the same meanings as defined above, can be produced according to the methods mentioned below.

The compounds of formula (IA) can be produced by reducing a compound of formula (II):

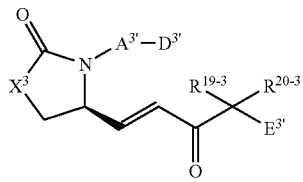

(II)

wherein $A^{3'}$, $D^{3'}$ and $E^{3'}$ have the same meanings as $A^3$, $D^3$ and $E^3$, respectively, but the hydroxyl, the amino, the carboxyl or the formyl in the group represented by $A^{3'}$, $D^{3'}$ and $E^{3'}$ may be protected, if necessary; and the other symbols have the same meanings as defined above, and then optionally removing the protective group from the resulting product.

The reaction for reduction is known, and it may be effected, for example, by processing the compound in an organic solvent (e.g., tetrahydrofuran, dimethoxyethane, toluene, methylene chloride, diethyl ether, dioxane) in the presence of a reducing agent (e.g., borohydride-tetrahydrofuran complex, borohydride-dimethyl sulfide complex, diborane) and an asymmetric inducer (e.g., (R)-2-methyl-CBS-oxazaborolysine, (S)-2-methyl-CBS-oxazaborolysine) at −20 to 50° C.

The removal of the protective group may be effected according to the methods mentioned below.

The reaction for removing the protective group for carboxyl, hydroxyl, amino or formyl is well known, including, for example, the following:

(1) alkali hydrolysis,
(2) deprotection under acidic condition,
(3) deprotection through hydrogenolysis,
(4) silyl deprotection,
(5) deprotection with metal,
(6) deprotection with organic metal.

These methods are described concretely.

(1) The deprotection through alkali hydrolysis may be effected, for example, in an organic solvent (e.g., methanol, tetrahydrofuran, dioxane) by the use of an alkali metal hydroxide (e.g., sodium hydroxide, potassium hydroxide, lithium hydroxide), an alkaline earth metal hydroxide (e.g., barium hydroxide, calcium hydroxide) or a carbonate (e.g., sodium carbonate, potassium carbonate), or an aqueous solution thereof or their mixture, at 0 to 40° C.

(2) The deprotection under acidic condition may be effected, for example, in an organic solvent (e.g., dichloromethane, chloroform, dioxane, ethyl acetate, anisole) with an organic solvent (e.g., acetic acid, trifluoroacetic acid, methanesulfonic acid, p-toluenesulfonic acid) or an inorganic acid (e.g., hydrochloric acid, sulfuric acid) or their mixture (hydrogen bromide/acetic acid), at 0 to 100° C.

(3) The deprotection through hydrogenolysis may be effected, for example, in a solvent (e.g., ether-type (e.g., tetrahydrofuran, dioxane, dimethoxyethane, diethyl ether), alcohol-type (e.g., methanol, ethanol), benzene-type (e.g., benzene, toluene), ketone-type (e.g., acetone, methyl ethyl ketone), nitrile-type (e.g., acetonitrile), amide-type (e.g., dimethylformamide), water, ethyl acetate, acetic acid, or mixed solvent of two or more of these), in the presence of a catalyst (e.g., palladium-carbon, palladium-black, palladium hydroxide, platinum oxide, Raney nickel), in a normal-pressure or increased-pressure hydrogen atmosphere or in the presence of ammonium formate, at 0 to 200° C.

(4) The silyl deprotection may be effected, for example, in a water-miscible organic solvent (e.g., tetrahydrofuran, acetonitrile) by the use of tetrabutylammonium fluoride, at 0 to 40° C.

(5) The deprotection with metal may be effected, for example, in an acidic solvent (acetic acid, buffer having pH of from 4.2 to 7.2, or mixture of their solution with organic solvent such as tetrahydrofuran) in the presence of zinc powder with or without ultrasonic waves applied thereto, at 0 to 40° C.

(6) The deprotection with metal complex may be effected, for example, in an organic solvent (e.g., dichloromethane, dimethylformamide, tetrahydrofuran, ethyl acetate, acetonitrile, dioxane, ethanol), water or their mixed solvent, in the presence of a trapping reagent (e.g., tributyltin hydride, triethylsilane, dimedone, morpholine, diethylamine, pyrrolidine), an organic acid (e.g., acetic acid, formic acid, 2-ethylhexanoic acid) and/or an organic acid salt (e.g., sodium 2-ethylhexanoate, potassium 2-ethylhexanoate), in the presence or absence of a phosphine-type reagent (e.g., triphenyl phosphine), by the use of a metal complex (tetrakistriphenylphosphine palladium(0), dichlorobis(triphenylphosphine) palladium(II), palladium(II) acetate, chlorotris(triphenylphosphine) rhodium(I)), at 0 to 40° C.

Apart from the above, the deprotection may also be effected, for example, according to the methods described in T. W. Greene, *Protective Groups in Organic Synthesis*, Wiley, New York, 1999.

The carboxyl-protective group includes, for example, methyl, ethyl, allyl, t-butyl, trichloroethyl, benzyl (Bn), and phenacyl.

The hydroxyl-protective group includes, for example, methyl, trityl, methoxymethyl (MOM), 1-ethoxyethyl (EE), methoxyethoxyethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc).

The amino-protective group includes, for example, benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), and 2-(trimethylsilyl) ethoxymethyl (SEM).

The formyl-protective group is, for example, acetal (e.g., dimethylacetal).

The carboxyl, hydroxyl, amino or formyl-protective may be any others than those mentioned above, capable of being readily and selectively removed, and are not specifically defined. For example, those described in T. W. Greene, *Protective Groups in Organic Synthesis*, 3rd Ed., Wiley, New York, 1999 may be used.

The intended compounds of the invention may be readily produced through selective use of the deprotecting reaction, which could be readily understood by anyone skilled in the art.

2) Among the compounds of formula (I-3), those in which $T^3$ is oxygen and the 13-14 position is a single bond, or that is, those of formula (IB):

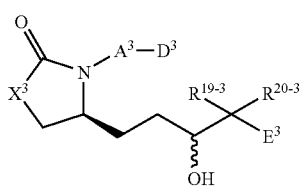

wherein all symbols have the same meanings as defined above, can be produced according to the methods mentioned below.

The compounds of formula (IB) can be produced by hydrogenating a compound of formula (III):

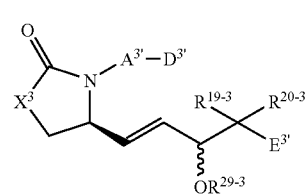

wherein $R^{29-3}$ represents hydrogen, or a hydroxyl-protective group, and the other symbols have the same meanings as defined above, and then optionally removing the protective group from the resulting product.

The reaction for hydrogenation is known, and it may be effected, for example, by processing the compound in an organic solvent (e.g., ether-type (e.g., tetrahydrofuran, dioxane, dimethoxyethane, diethyl ether), alcohol-type (e.g., methanol, ethanol), benzene-type (e.g., benzene, toluene), ketone-type (e.g., acetone, methyl ethyl ketone), nitrile-type (e.g., acetonitrile), amide-type (e.g., dimethylformamide), water, ethyl acetate, acetic acid, or mixed solvent of two or more of these), in the presence of a catalyst (e.g., palladium-carbon, palladium-black, palladium hydroxide, platinum oxide, Raney nickel), in a normal-pressure or increased-pressure hydrogen atmosphere or in the presence of ammonium formate, at 0 to 200° C.

The removal of the protective group may be effected in the same manner as herein.

3) Among the compounds of formula (I-3), those in which $T^3$ is sulfur, or that is, those of formula (IC):

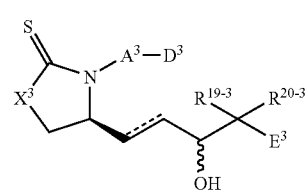

wherein all symbols have the same meanings as defined above, can be produced according to the methods mentioned below.

The compounds of formula (IC) can be produced by thioamidating a compound of formula (IV):

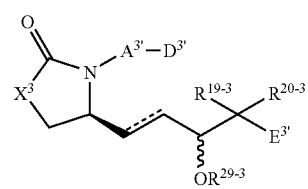

wherein all symbols have the same meanings as defined above, and then optionally removing the protective group from the resulting product.

The reaction for thioamidation is known, and it may be effected, for example, by processing the compound in an organic solvent (e.g., toluene, diethyl ether, methylene chloride, chloroform, dioxane, tetrahydrofuran) in the presence of a thionating agent (e.g., Rawson reagent (2,4-bis(4-methoxyphenyl)-1,3-dithia-2,4-diphosphetan-2,4-disulfide), diphosphorus pentoxide) at 0 to 150° C.

The removal of the protective group may be effected in the same manner as herein.

4) Among the compounds of formula (I-3), those in which $D^3$ is —$CH_2OH$, or that is, those of formula (ID):

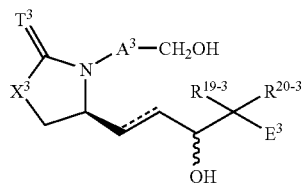
(ID)

wherein all symbols have the same meanings as defined above, can be produced according to the methods mentioned below.

The compounds of formula (ID) can be produced by reducing a compound of formula (V):

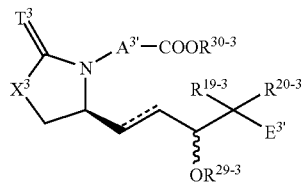
(V)

wherein $R^{30-3}$ represents C1-10 alkyl, and the other symbols have the same meanings as defined above, and then optionally removing the protective group from the resulting product.

The reaction for reduction is known, and it may be effected, for example, by processing the compound in an organic solvent (e.g., tetrahydrofuran, dimethoxyethane, diethyl ether, dimethylformamide, dioxane, methanol, ethanol, isopropanol) or in its aqueous solution, in the presence of a reducing agent (e.g., sodium borohydride, lithium borohydride), at 0 to 70° C.

The removal of the protective group may be effected in the same manner as herein.

5) Among the compounds of formula (I-3), those in which $D^3$ is —$CONR^{3-3}SO_2R^{4-3}$, —$CONR^{6-3}R^{7-3}$, —$CONR^{6-3}SO_2R^{8-3}$, or —CO—(NH-amino acid residue-CO)$_{m-3}$—OH, or that is, those of formula (IE):

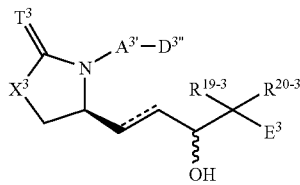
(IE)

wherein $D^{3''}$ represents —$CONR^{3-3}SO_2R^{4-3}$, —$CONR^{6-3}R^{7-3}$, —$CONR^{6-3}SO_2R^{8-3}$, or —CO—(NH-amino acid residue-CO)$_{m-3}$—OH, and the other symbols have the same meanings as defined above, can be produced according to the methods mentioned below.

The compounds of formula (IE) can be produced by amidating a compound of formula (VI):

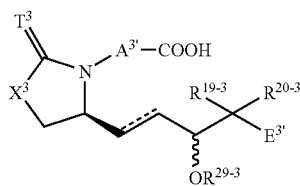
(VI)

wherein all symbols have the same meanings as defined above, with a compound of formula (VII-1):

H—$NR^{3-3}SO_2R^{4-3}$ (VII-1)

wherein all symbols have the same meanings as defined above, or a compound of formula (VII-2):

H—$NR^{6-3}R^{7-3}$ (VII-2)

wherein all symbols have the same meanings as defined above, or a compound of formula (VII-3):

H—$NR^{6-3}SO_2R^{8-3}$ (VII-3)

wherein all symbols have the same meanings as defined above, or a compound of formula (VII-4):

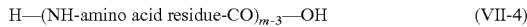
H—(NH-amino acid residue-CO)$_{m-3}$—OH (VII-4)

wherein all symbols have the same meanings as defined above, but the amino, the hydroxyl or the carboxyl in the compound of formula (VII-4) may be protected, if necessary, and then optionally removing the protective group from the resulting product.

The reaction for amidation is known, for example, including the following:

(1) with acid halide,
(2) with mixed acid halide,
(3) with condensing agent.

These methods are described concretely.

(1) The method with an acid halide comprises, for example, reacting the carboxylic acid with an acid-halogenating agent (e.g., oxalyl chloride, thionyl chloride) in an organic solvent (e.g., chloroform, dichloromethane, diethyl ether, tetrahydrofuran) or in the absence of a solvent, at −20° C. to a reflux temperature, followed by reacting the resulting acid halide with the amine in an inert organic solvent (e.g., chloroform, dichloromethane, diethyl ether, tetrahydrofuran) in the presence of a base (pyridine, triethylamine, dimethylaniline, dimethylaminopyridine, diisopropylethylamine), at 0 to 40° C. If necessary, the acid halide may be reacted in an organic solvent (e.g., dioxane, tetrahydrofuran) by the use of an aqueous alkali solution (e.g., aqueous sodium bicarbonate, sodium hydroxide solution) at 0 to 40° C.

(2) The method with a mixed acid anhydride comprises, for example, reacting the carboxylic acid with an acid halide (e.g., pivaloyl chloride, tosyl chloride, mesyl chloride) or an acid derivative (e.g., ethyl chloroformate, isobutyl chloroformate) in an organic solvent (e.g., chloroform, dichloromethane, diethyl ether, tetrahydrofuran) or in no solvent, in the presence of a base (e.g., pyridine, triethylamine, dimethylaniline, dimethylaminopyridine, diisopropylethylamine), at 0 to 40° C., followed by reacting the resulting mixed acid anhydride with the amine in an organic solvent (e.g., chloroform, dichloromethane, diethyl ether, tetrahydrofuran) at 0 to 40° C.

(3) The method with a condensing agent comprises, for example, reacting the carboxylic acid with the amine in an organic solvent (e.g., chloroform, dichloromethane, dimethylformamide, diethyl ether, tetrahydrofuran) or in no solvent, in the presence or absence of a base (e.g., pyridine, triethylamine, dimethylaniline, dimethylaminopyridine) by the use of a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propanephosphonic acid cyclic anhydride (PPA)), and by the use of or with no use of 1-hydroxybenzotriazole (HOBt) or 1-methanesulfonyloxybenzotriazole, at 0 to 40° C.

Preferably, the reactions (1), (2) and (3) are all effected in an inert gas (e.g., argon, nitrogen) atmosphere with no water.

The removal of the protective group may be effected in the same manner as herein.

6) Among the compounds of formula (I-3), those in which $D^3$ is —O—(CO-amino acid residue-NH)$_{m-3}$—H or —OCO—$R^{10-3}$, or that is, those of formula (IF):

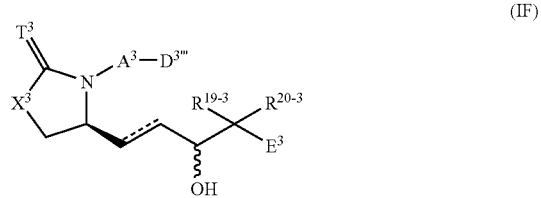

(IF)

wherein $D^{3''}$ represents —O—(CO-amino acid residue-NH)$_{m-3}$—H or —OCO—$R^{10-3}$, and the other symbols have the same meanings as defined above,
can be produced according to the methods mentioned below.

The compounds of formula (IF) can be produced by esterifying a compound of formula (VIII):

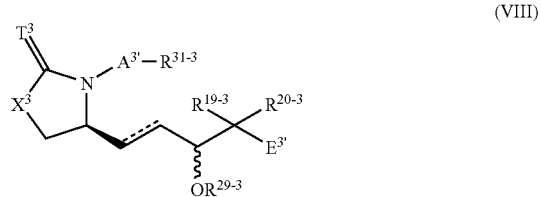

(VIII)

wherein $R^{31-3}$ represents —OH or —CH$_2$OH, and the other symbols have the same meanings as defined above,
with a compound of formula (IX-1):

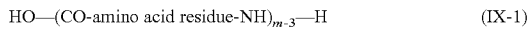

HO—(CO-amino acid residue-NH)$_{m-3}$—H    (IX-1)

wherein all symbols have the same meanings as defined above, but the amino, the hydroxyl or the carboxyl in the compound of formula (IX-1) may be protected, if necessary, or a compound of formula (IX-2):

HOOC—$R^{10-3}$    (IX-2)

wherein $R^{10-3}$ has the same meaning as above,
and then optionally removing the protective group from the resulting product.

The reaction for esterification is known, for example, including the following:
(1) with acid halide,
(2) with mixed acid halide,
(3) with condensing agent.

These methods are described concretely.

(1) The method with an acid halide comprises, for example, reacting the carboxylic acid with an acid-halogenating agent (e.g., oxalyl chloride, thionyl chloride) in an organic solvent (e.g., chloroform, dichloromethane, diethyl ether, tetrahydrofuran) or in the absence of a solvent, at −20° C. to a reflux temperature, followed by reacting the resulting acid halide with the alcohol in the presence of a base (pyridine, triethylamine, dimethylaniline, dimethylaminopyridine, diisopropylethylamine), in an inert organic solvent (e.g., chloroform, dichloromethane, diethyl ether, tetrahydrofuran) at 0 to 40° C. If necessary, the acid halide may be reacted in an organic solvent (e.g., dioxane, tetrahydrofuran) by the use of an aqueous alkali solution (e.g., aqueous sodium bicarbonate, sodium hydroxide solution) at 0 to 40° C.

(2) The method with a mixed acid anhydride comprises, for example, reacting the carboxylic acid with an acid halide (e.g., pivaloyl chloride, tosyl chloride, mesyl chloride) or an acid derivative (e.g., ethyl chloroformate, isobutyl chloroformate) in an organic solvent (e.g., chloroform, dichloromethane, diethyl ether, tetrahydrofuran) or in no solvent, in the presence of a base (e.g., pyridine, triethylamine, dimethylaniline, dimethylaminopyridine, diisopropylethylamine), at 0 to 40° C., followed by reacting the resulting mixed acid anhydride with the alcohol in an organic solvent (e.g., chloroform, dichloromethane, diethyl ether, tetrahydrofuran) at 0 to 40° C.

(3) The method with a condensing agent comprises, for example, reacting the carboxylic acid with the amine in an organic solvent (e.g., chloroform, dichloromethane, dimethylformamide, diethyl ether, tetrahydrofuran) or in no solvent, in the presence or absence of a base (e.g., pyridine, triethylamine, dimethylaniline, dimethylaminopyridine) by the use of a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propanephosphonic acid cyclic anhydride (PPA)), and by the use of or with no use of 1-hydroxybenzotriazole (HOBt), at 0 to 40° C.

Preferably, the reactions (1), (2) and (3) are all effected in an inert gas (e.g., argon, nitrogen) atmosphere with no water.

The removal of the protective group may be effected in the same manner as herein.

7) Among the compounds of formula (I-3), those in which $D^3$ is formyl, or that is, those of formula (IG):

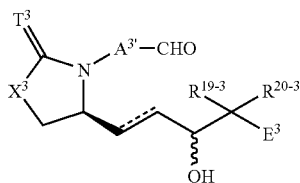

(IG)

wherein all symbols have the same meanings as defined above,
can be produced according to the methods mentioned below.

The compounds of formula (IG) can be produced by oxidizing a compound of formula (X):

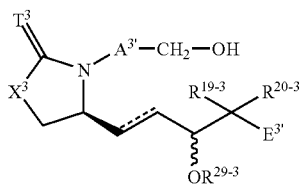

(X)

wherein all symbols have the same meanings as defined above,
and then optionally removing the protective group from the resulting product.

The reaction for oxidation is known, for example, including the following:
(1) Swern oxidation,
(2) oxidation with Dess-Martin reagent,
(3) oxidation with TEMPO reagent.

These methods are described concretely.
(1) The method of Swern oxidation comprises, for example, reacting oxalyl chloride with dimethyl sulfoxide in an organic solvent (e.g., chloroform, dichloromethane) at −78° C., and then reacting the resulting solution with the alcohol compound, and further with a tertiary amine (e.g., triethylamine, N,N-diisopropylethylamine, N-methylmorpholine, N-ethylpiperidine, diazabicyclo[5.4.0]undec-7-ene) at −78 to 20° C.
(2) The method with a Dess-Martin reagent comprises, for example, processing the compound in an organic solvent (e.g., chloroform, dichloromethane, 1,2-dichloroethane, tetrahydrofuran, acetonitrile, t-butyl alcohol) in the presence of a Dess-Martin reagent (1,1,1-triacetoxy-1,1-dihydro-1,2-benzoiodoxol-3-(1H)-one), in the presence or absence of a base (e.g., pyridine) at 0 to 40° C.
(3) The method with a TEMPO reagent comprises, for example, processing the compound in an organic solvent (e.g., chloroform, dichloromethane, tetrahydrofuran, toluene, acetonitrile, ethyl acetate, water) or in a mixed solvent thereof, in the presence of a TEMPO reagent (2,2,6,6-tetramethyl-1-piperidinyloxy, free radical) and a re-oxidizing agent (aqueous hydrogen peroxide, sodium hypochlorite, 3-chloroperbenzoic acid, iodobenzene diacetate, potassium peroxymonosulfate (Oxon, trade name)), in the presence or absence of a quaternary ammonium salt (e.g., tetrabutylammonium chloride, tetrabutylammonium bromide), in the presence or absence of an inorganic salt (e.g., sodium bromide, potassium bromide), in the presence or absence of an inorganic base (e.g., sodium hydrogencarbonate, sodium acetate), at 20 to 60° C.

The oxidation is not limited to the above, and may be any other oxidation capable of readily and selectively oxidizing the alcohol into a ketone. For example, herein employable is any of Johns oxidation, oxidation with PCC (pyridinium chlorochromate), oxidation with sulfur trioxide-pyridine complex, or those described in *Comprehensive Organic Transformations* (Richard C. Larock, VCH Publishers, Inc., (1989), pp. 604-614).

The removal of the protective group may be effected in the same manner as herein.

8) Among the compounds of formula (I-3), those in which $D^3$ is —$COOR^{2-3}$, —$COOR^{9-3}$, or —$COO$—$Z^{1-3}$—$Z^{2-3}$—$Z^{3-3}$, or that is, those of formula (IH):

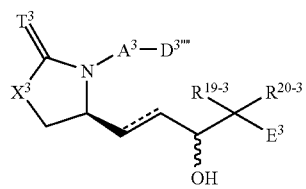

(IH)

wherein $D^{3''''}$ represents —$COOR^{2-3}$, —$COOR^{9-3}$, or —$COO$—$Z^{1-3}$—$Z^{2-3}$—$Z^{3-3}$, and the other symbols have the same meanings as defined above,
can be produced according to the methods mentioned below.

The compounds of formula (IH) can be produced by esterifying a compound of formula (VI):

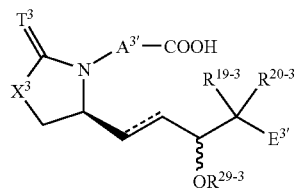

(VI)

wherein all symbols have the same meanings as defined above,
with a compound of formula (XI-1):

(XI-1)

wherein $R^{31-3}$ represents hydroxyl or halogen, and the other symbols have the same meanings as defined above,
or a compound of formula (XI-2):

(XI-2)

wherein all symbols have the same meanings as defined above,
or a compound of formula (XI-3):

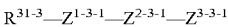

(XI-3)

wherein $Z^{1-3-1}$, $Z^{2-3-1}$ and $Z^{3-3-1}$ have the same meanings as $Z^{1-3}$, $Z^{2-3}$ and $Z^{3-3}$, respectively, but the hydroxyl, the amino, the carboxyl or the formyl in the group of $Z^{1-3-1}$-$Z^{2-3-1}$-$Z^{3-3-1}$ may be optionally protected, if necessary,
and then optionally removing the protective group from the resulting product.

The esterification with the compound of formulae (XI-1), (XI-2) and (XI-3) in which $R^{31-3}$ is hydroxyl may be effected in the same manner as above.

The esterification with the compound of formulae (XI-1), (XI-2) and (XI-3) in which $R^{31-3}$ is halogen may be effected, for example, in an organic solvent (e.g., dimethylformamide, tetrahydrofuran, dioxane, diethyl ether, dimethylacetamide), in the presence of a base (e.g., potassium carbonate, cesium carbonate, sodium carbonate, potassium hydrogencarbonate, sodium hydrogencarbonate, potassium hydroxide, sodium hydroxide) at 0 to 150° C.

The removal of the protective group may be effected in the same manner as herein.

9) Among the compounds of formula (I-3), those in which the substituent of $E^3$ is amino can be produced through reduction of nitro.

The reaction for nitro reduction is known, and it may be effected, for example through hydrogenolysis and reduction with organic metal.

The reaction for hydrogenolysis is known, and the deprotection through hydrogenolysis may be effected, for example, in an inert solvent (e.g., ether-type (e.g., tetrahydrofuran, dioxane, dimethoxyethane, diethyl ether), alcohol-type (e.g., methanol, ethanol), benzene-type (e.g., benzene, toluene), ketone-type (e.g., acetone, methyl ethyl ketone), nitrile-type (e.g., acetonitrile), amide-type (e.g., dimethylformamide), water, ethyl acetate, acetic acid, or mixed solvent of two or more of these), in the presence of a hydrogenation catalyst (e.g., palladium-carbon, palladium-black, palladium, palladium hydroxide, platinum dioxide, nickel, Raney nickel, ruthenium chloride), in the presence or absence of an inorganic acid (e.g., hydrochloric acid, sulfuric acid, hypochlorous acid, boric acid, tetrafluoroboric acid) or an organic acid (e.g., acetic acid, p-toluenesulfonic acid, oxalic acid, trifluoroacetic acid, formic acid), in a normal-pressure or increased-pressure hydrogen atmosphere or in the presence of ammonium formate at 0 to 200° C. In place of the acid, if used, its salt may also be used.

The reaction for reduction with organic metal is known, and it may be effected, for example, in a water-miscible solvent (e.g., ethanol, methanol) in the presence or absence of aqueous hydrochloric acid solution by the use of an organic metal (e.g., zinc, iron, tin, tin chloride, iron chloride) at 50 to 150° C.

10) Among the compounds of formula (I-3), those in which $T^3$ is oxygen ad $X^3$ is —CH$_2$—, or that is, those of formula (IJ):

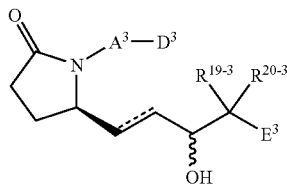

wherein all symbols have the same meanings as defined above, can be produced according to the methods mentioned below.

The compounds of formula (IJ) can be produced through reductive amination of a compound of formula (XII):

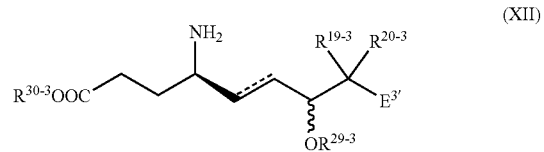

wherein all symbols have the same meanings as defined above, with a compound of formula (XIII):

$$\text{OHC-A}^{3''}\text{-D}^{3'} \quad (XIII)$$

wherein $A^{3'''}$ represents $A^{1'-3}$ or $A^{2'-3}$, $A^{1'-3}$ represents 1) linear C1-7 alkylene optionally substituted by one or two C1-4 alkyl(s),
2) linear C2-7 alkenylene optionally substituted by one or two C1-4 alkyl(s), or
3) linear C2-7 alkynylene optionally substituted by one or two C1-4 alkyl(s), $A^{2'-3}$ represents -$G^{1'-3}$-$G^{2'-3}$-$G^{3'-3}$-, $G^{1'-3}$ represents 1) a single bond,
2) linear C1-3 alkylene optionally substituted by one or two C1-4 alkyl(s),
3) linear C2-3 alkenylene optionally substituted by one or two C1-4 alkyl(s), or
4) linear C2-3 alkynylene optionally substituted by one or two C1-4 alkyl(s), and the other symbols have the same meanings as defined above, and then optionally removing the protective group from the resulting product.

The reaction for reductive amination is known, and it may be effected, for example, in an organic solvent (e.g., ethyl acetate, dichloroethane, dichloromethane, dimethylformamide, tetrahydrofuran, acetic acid, or their mixture) in the presence of a reducing agent (e.g., sodium triacetoxyborohydride, sodium borocyanohydride, sodium borohydride, zinc borohydride, diisobutylaluminium hydride) at −15 to 100° C., or in an organic solvent (e.g., ethyl acetate, dichloroethane, dichloromethane, methanol, ethanol, acetic acid, or their mixture) in the presence of a catalyst (e.g., palladium-carbon, palladium-black, palladium hydroxide, platinum oxide, Raney nickel) in a normal-pressure or increased-pressure hydrogen atmosphere at 0 to 200° C.

The removal of the protective group may be effected in the same manner as herein.

Among the compounds of the invention, those of formula (I-2) can be produced according to the methods mentioned below or according to the methods described in the Examples mentioned below.

1) Among the compounds of formula (I-2), those in which $R^{1-2}$ is —CO—(NH-amino acid residue-CO)$_{m-2}$—OH, or that is, those of formula (IK):

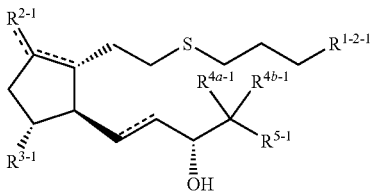

(IK)

wherein $R^{1-2-1}$ represents —CO—(NH-amino acid residue-CO)$_{m-2}$—OH, and the other symbols have the same meanings as defined above, can be produced according to the methods mentioned below.

The compounds of formula (IK) can be produced through amidation of a compound of formula (I-1) in which $R^{1-1}$ is hydroxy, or that is, a compound of formula (I-1-1):

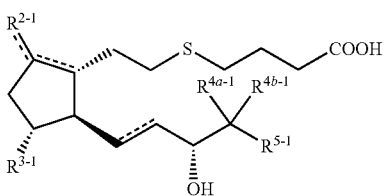

(I-1-1)

wherein all symbols have the same meanings as defined above, with a compound of formula (XIV):

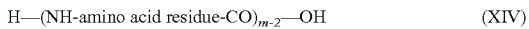

H—(NH-amino acid residue-CO)$_{m-2}$—OH   (XIV)

wherein all symbols have the same meanings as defined above, but the amino, the hydroxyl or the carboxyl in the compound of formula (XIV) may be optionally protected, if necessary, and then optionally removing the protective group from the resulting product.

The amidation and the deprotection may be effected in the same manner as above.

2) Among the compounds of formula (I-2), those in which $R^{1-2}$ is —COO—Y$^2$—R$^{9-2}$, or —COO—Z$^{1-2}$—Z$^{2-2}$—Z$^{2-3}$, or that is, those of formula (IL):

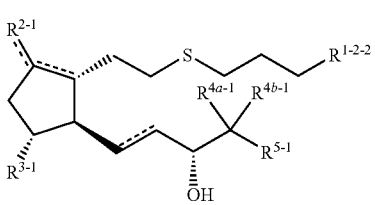

(IL)

wherein $R^{1-3-2}$ represents —COO—Y$^2$—R$^{9-2}$, or —COO—Z$^{1-2}$—Z$^{2-2}$—Z$^{2-3}$, and the other symbols have the same meanings as defined above, can be produced according to the methods mentioned below.

The compounds of formula (IL) can be produced through esterification of a compound of formula (I-1-1):

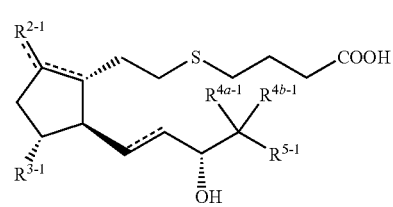

(I-1-1)

wherein all symbols have the same meanings as defined above, with a compound of formula (XV-1):

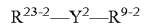

$R^{23-2}$—Y$^2$—R$^{9-2}$   (XV-1)

wherein $R^{23-2}$ represents hydroxyl or halogen, and the other symbols have the same meanings as defined above, or a compound of formula (XV-2):

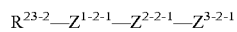

$R^{23-2}$—Z$^{1-2-1}$—Z$^{2-2-1}$—Z$^{3-2-1}$   (XV-2)

wherein $Z^{1-2-1}$, $Z^{2-2-1}$ and $Z^{3-2-1}$ have the same meanings as $Z^{1-2}$, $Z^{2-2}$ and $Z^{3-2}$, respectively, but the hydroxyl, the amino, the carboxyl or the formyl in the group of $Z^{1-2-1}$-$Z^{2-2-1}$-$Z^{3-2-1}$ may be optionally protected, if necessary, and then optionally removing the protective group from the resulting product.

The esterification with the compound of formulae (XV-1) and (XV-2) in which $R^{23-2}$ is hydroxyl may be effected in the same manner as above.

The esterification with the compound of formulae (XV-1) and (XV-2) in which $R^{23-2}$ is halogen may be effected also in the same manner as above.

The deprotection may be effected also in the same manner as above.

The compounds of formulae (II), (VII-1), (VII-2), (VII-3), (IX-1), (IX-2), (XI-1), (XI-2), (XII), (XIII), (XIV), (XV-1) and (XV-2) are per se known, or are readily produced in known methods.

For example, the compounds of formulae (II) and (XII) can be produced according to the following reaction processes 1, 2 and 3.

In these reaction processes, Boc represents t-butoxycarbonyl, $R^{32-3}$ represents hydroxyl-protective, Ac represents an acetyl group, $R^{33-3}$ represents halogen, $R^{34-3}$ represents C1-3 alkylene, $R^{35-3}$ represents C1-4 alkylene, $R^{36-3}$ represents an amino-protective group, and the other symbols have the same meanings as defined above.

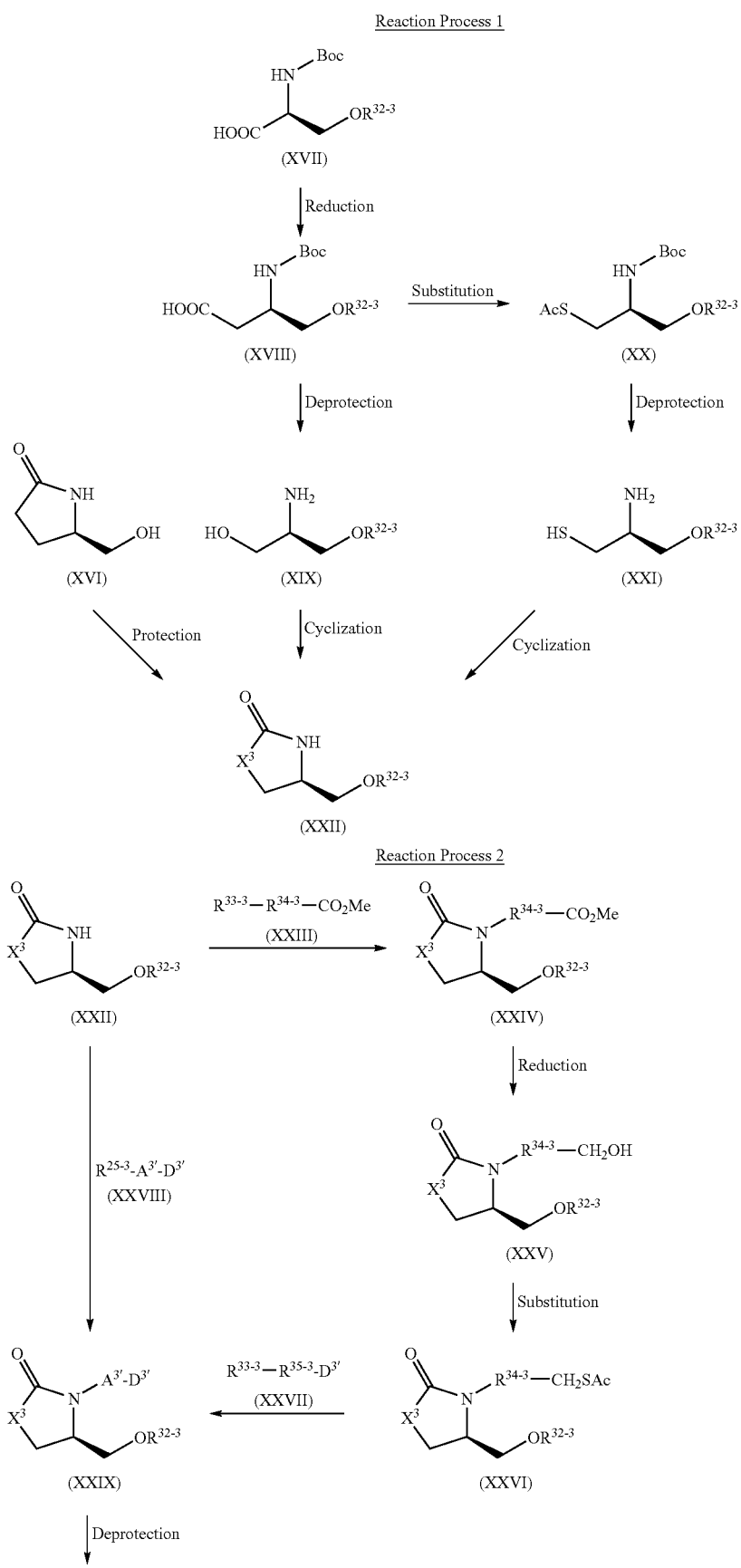

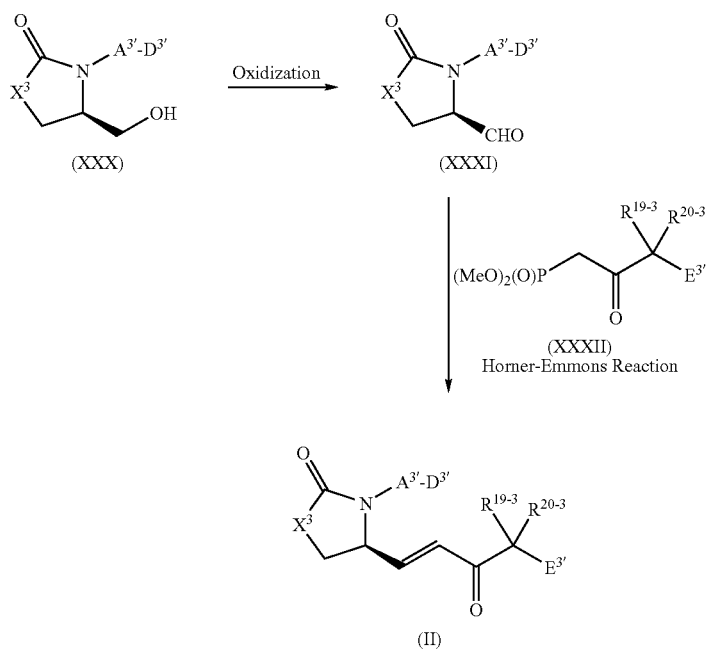
Reaction Process 3
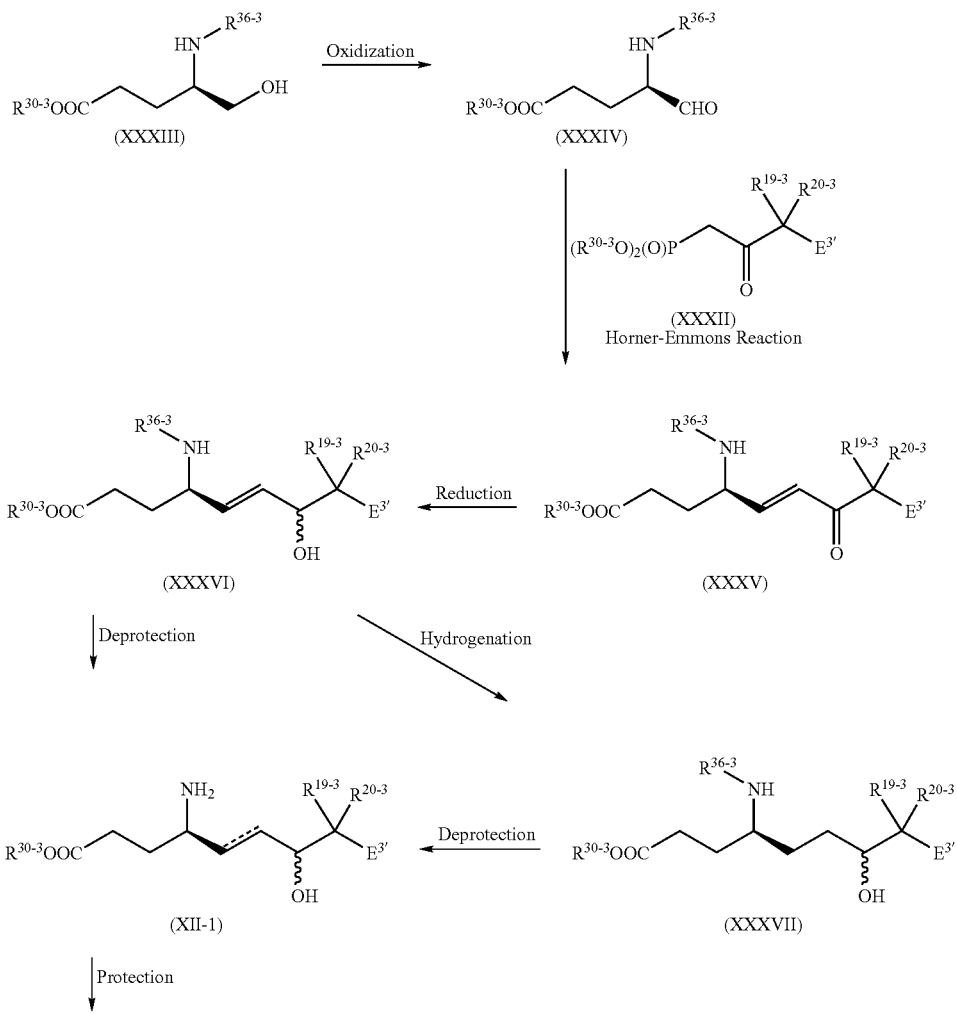

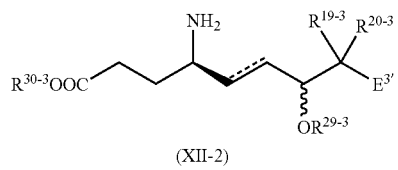

(XII-2)

In the reaction processes 1, 2 and 3, the starting compounds of formulae (XVI), (XVII), (XXIII), (XXVII), (XXVIII), (XXXII) and (XXXIII) are known, or are readily produced in known methods.

The reaction product in each reaction stage in this description may be purified in an ordinary manner, for example, through normal-pressure or reduced-pressure distillation, or through high-performance liquid chromatography, thin-layer chromatography or column chromatography with silica gel or magnesium silicate, or through washing or recrystallization. The purification may be effected in every reaction stage or after some reaction stages.

Industrial Applicability

Application to Pharmaceutical Preparations:

The compounds of the invention represented by formulae (I-2) and (I-3) act on PGE receptor $EP_4$ subtype specifically and strongly and thus are considered useful for prevention and/or treatment of immunodiseases (e.g., autoimmune diseases such as amyotrophic lateral sclerosis (ALS), multiple sclerosis, Sjogren's syndrome, chronic rheumatism and systemic lupus erythematosus, rejection after organ implantation) and diseases such as asthma, death of neurocyte, arthritis, lung disorder, fibroid lung, pulmonary emphysema, bronchitis, chronic obstructive respiratory disease, hepatopathy, acute hepatitis, nephritis (acute nephritis, chronic nephritis), renal insufficiency, hypertension, myocardial ischemia, systemic inflammatory response syndrome, septicemia, hemophagocytosis syndrome, macrophage activation syndrome, still disease, Kawasaki Disease, thermal burn, systemic granuloma, ulcerative colitis, Crohn disease, hypercytokinemia during dialysis, multiple organ dysfunction syndrome and shock. $EP_4$ receptor also takes part in mucous membrane protective action and thus is considered useful for prevention and/or treatment of digestive tract ulcer such as gastric ulcer and duodenal ulcer and stomatitis. $EP_4$ receptor further takes part in trichogenous action and hair growing action and is considered useful for prevention and/or treatment of alopecia. Moreover, $EP_4$ receptor takes part in maturation of cervical canal and thus is considered useful as a cervical canal maturing agent.

Furthermore, the compound bound to $EP_4$ receptor has an osteogenesis accelerating action and thus is considered not only useful for prevention and/or treatment of bone diseases in which the amount of bone is decreased, e.g., 1) primary osteoporosis due to, e.g., aging, menopause, overietomy, 2) secondary osteoporosis (e.g., glucocorticoid-induced osteoporosis, hyperhyroidismic osteoporosis, fixed induced osteoporosis, haparin-induced osteoporosis, immunosuppression-induced osteoporosis, osteoporosis due to renal insufficiency, inflammatory osteoporosis, osteoporosis due to Cushing's syndrome, rheumatic osteoporosis), 3) bone diseases such as transfer of cancer to bone, hypercalcemia, Behcet's disease, bone deficiency (e.g., alveolar bone deficiency, mandible deficiency, infantile idiopathic bone deficiency) and osteonecrosis but also useful as a agent for accelerating the osteogenesis/treatment after bone surgery (e.g., fracture, bone graft, artificial arthrogenesis, spinal fusion, other bone repair) or substitute for bone transfer.

Moreover, $EP_4$ acts to induce physiologic sleep and inhibit platelet aggregation and the compound bound to $EP_4$ receptor is considered useful for prevention of somnipathy and thrombosis.

The compound selectively bound to $EP_4$ has neither pain-giving effect presumably attributed to $EP_1$ nor uterine contracting effect presumably attributed to $EP_3$ and thus is considered to be a pharmaceutical preparation having no such effects.

Among the compounds represented by formula (I-3) are those which are connected to $EP_4$ receptor as well as $EP_2$ receptor. The compound connected to EP2 receptor is considered useful for prevention and/or treatment of immunodiseases (e.g., autoimmune diseases such as amyotrophic lateral sclerosis (ALS), multiple sclerosis, Sjogren's syndrome, chronic rheumatism and systemic lupus erythematosus, rejection after organ implantation) and diseases such as asthma, death of neurocyte, premature birth, miscarriage, pars nervosa retinae trouble such a glaucoma, erectile insufficiency, arthritis, lung disorder, fibroid lung, pulmonary emphysema, bronchitis, chronic obstructive respiratory disease, hepatopathy, acute hepatitis, shock, nephritis, renal insufficiency, circulatory system disorder (e.g., hypertension, myocardial ischemia, chronic arterial obstruction, vibration disease), systemic inflammatory response syndrome, septicemia, hemophagocytosis syndrome, macrophage activation syndrome, still disease, Kawasaki Disease, thermal burn, systemic granuloma, ulcerative colitis, Crohn disease, hypercytokinemia during dialysis, multiple organ dysfunction syndrome and bone disease (e.g., fracture, refracture, bone union insufficiency, pseudarthrosis, osteomalacia, bone Behcet's disease, spondylism, transfer of cancer to bone, osteroarthritis, destruction of bone/cartilage due to these analogous diseases). The compound connected to EP2 receptor is also considered useful as an agent for accelerating the osteogenesis/treatment after bone surgery (e.g., fracture, bone graft, artificial arthrogenesis, spinal fusion, surgery for multiple myeloma, lung cancer, breast cancer, etc., other bone repair) or substitute for bone transfer. This compound is further considered useful as an agent for accelerating the regeneration of peridontium in peridontium disease.

The compound connected both to $EP_4$ receptor and $EP_2$ receptor can be expected to exert an additive or synergistic effect on diseases related to both the receptors.

The compound represented by formula (I-1), (I-2) or (I-3) or nontoxic salt thereof may be administered in combination with other pharmaceutical preparations to accomplish the following purposes:

1) To compensate for and/or enhance the preventive and/or treatment effect of the compound to be combined;
2) To improve the kinetics/absorption of the compound to be combined and reduce the dose of the compound; and/or
3) To eliminate the side effect of the compound to be combined The compound represented by formula (I-1), (I-2) or (I-3) and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compound represented by formula (I-1), (I-2) or (I-3) may be administered before the other pharmaceutical preparations. Alternatively, the other pharmaceutical preparations may be administered before the compound represented by formula (I-1), (I-2) or (I-3). The method for the administration of these pharmaceutical preparations may be the same or different.

The diseases on which the preventive and/or treatment effect of the aforementioned combined preparations works are not specifically limited but may be those for which the preventive and/or treatment effect of the compound represented by formula (I-1), (I-2) or (I-3) is compensated for and/or enhanced.

Examples of the other pharmaceutical preparations for compensating for and/or enhancing the preventive and/or treatment effect of the compound represented by formula (I-1), (I-2) or (I-3) on bone diseases include phosphodiesterases-4 inhibitor, bisphosphonate preparation, vitamin D preparation, calcium adjuvant, estrogen preparation, calcitonin preparation, isoflavone-based preparation, anabolic steroid preparation, vitamin K preparation, cathepsin K inhibitor, prostaglandins, statin, parathyroid hormone, and growth factors.

Examples of the other pharmaceutical preparations for compensating for and/or enhancing the preventive and/or treatment effect of the compound represented by formula (I-1), (I-2) or (I-3) on chronic obstructive lung diseases and/or asthma include phosphodiesterases-4 inhibitor, steroid preparation, $\beta_2$ adrenoreceptor stimulant, leukotriene receptor antagonist, thromboxane synthesis enzyme inhibitor, thromboxane $A_2$ receptor antagonist, mediator liberation inhibitor, antihistamines, xanthine derivatives, anticholinergic preparation, cytokine inhibitor, prostaglandins, metaprotease inhibitor, expectorant, and antibiotic.

Examples of the other pharmaceutical preparations for compensating for and/or enhancing the preventive and/or treatment effect of the compound represented by formula (I-1), (I-2) or (I-3) on arthritis or chronic articular rheumatism include metaprotease inhibitor, immunosuppressant, nonsteroid-based antiphlogistic (NSAID), steroid preparation, and phosphodiesterases-4 inhibitor.

Examples of the other pharmaceutical preparations for compensating for and/or enhancing the preventive and/or treatment effect of the compound represented by formula (I-1), (I-2) or (I-3) on erectile insufficiency include phosphodiesterases-5 inhibitor.

Examples of the other pharmaceutical preparations for compensating for and/or enhancing the preventive and/or treatment effect of the compound represented by formula (I-1), (I-2) or (I-3) on shock include elastase inhibitor.

Examples of the other pharmaceutical preparations for compensating for and/or enhancing the preventive and/or treatment effect of the compound represented by formula (I-1), (I-2) or (I-3) on colitis include steroid preparation, phosphodiesterases-4 inhibitor, nonsteroid-based antiphlogistic, thromboxane $A_2$ receptor antagonist, leukotriene receptor antagonist, angiotensin II antagonist, angiotensin converting enzyme inhibitor, and diuretic.

Examples of the other pharmaceutical preparations for compensating for and/or enhancing the preventive and/or treatment effect of the compound represented by formula (I-1), (I-2) or (I-3) on hypertension include calcium antagonist, angiotensin II antagonist, angiotensin converting enzyme inhibitor, phosphodiesterases-4 inhibitor, and diuretic.

Examples of the phosphodiesterases-4 inhibitor include rolipram, cilomilast (trade name: Ariflo), Bay 19-8004, NIK-616, cilomilast (BY-217), cipamfylline (BGL-61063), atizolam (CP-80633), SCH-351591, YM-976, V-11294A, PD-168787, D-4386, and IC-485.

Examples of the phosphodiesterases-5 inhibitor include sildenafil.

Examples of the bisphonate preparation include sodium alendronate, disodium chlodronate, disodium pamidronate, disodium ethydronate, ivandronate, disodium incadronate, minodronate, olpadronate, sodium risedronate, tildronate, and zoledronate.

Examples of the calcitonin preparation include calcitonin, and elcatonin.

Examples of the prostaglandins (hereinafter abbreviated as "PG") include PG receptor agonist, and PG receptor antagonist.

Examples of PG receptor include PGE receptors ($EP_1$, $EP_2$, $EP_3$, $EP_4$), PGD receptors (DP), PGF receptors (FP), and PGI receptors (IP).

Examples of the steroid preparation for external application include clobetasol propionate, diflorasone acetate, fluocinonide, monometasone furancarboxylate, betamesone dipropionate, betamesone butyropropionate, betamesone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone acetopropionate, deprodone propionate, prednisolone valeroacetate, fluocinolone acetonide, beclometasone dipropionate, triamcinonide acetonide, flumethasone pivalate, prednisolone, beclometasone propionate, and fludroxycortide.

Examples of the steroid preparation for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredon acetate, methyl prednisolone, methyl prednisolone acetate, methyl prednisolone sodium succinate, triamicinolon, triamicinolon acetate, triamicinonolon acetonide, dexamethasone, dexamethasone acetate, dexamethasone sodium phosphate, dexamethasone palmitate, paramethasone acetate, and betamethasone.

Examples of the steroid preparation as an inhalant include beclomethasone propionate, fluticasone propionate, budesonide, flunisolide, triamicinolon, ST-126P, ciclesonide, dexamethasone palomitionate, monometasone furancarboxylate, prasterone sulfonate, deflazacort, methyl prednisolone sreptanate, and methyl prednisolone sodium succinate.

Examples of the $\beta_2$ adrenoreceptor stimulant include fenoterol hydrobromide, salbutamol sulfate, terbutaline sulfate, formoterol fumarate, salmeterol xinafoate, isoprotenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamin hydrochloride, meradrin tartrate, AR-C68397, levosalbutamol, R,R-formoterol, KUR-1246, KUL-7211, AR-C89855, and S-1319.

Examples of the leukotriene receptor antagonist include pranlukast hydrate, montelukast, zafirlukast, seratrodast, MCC-847, KCA-757, CD-615, YM-158, L-740515, CP-195494, LM-1484, RS-635, A-93178, S-36496, BIIL-284, and ONO-4057.

Examples of the thromboxane synthesis enzyme inhibitor include ozagrel hydrochloride, and imitrodast sodium.

Examples of the thromboxane $A_2$ receptor antagonist include seratrodast, ramatroban, domitroban calcium dihydrate, and KT-2-962.

Examples of the mediator liberation inhibitor include tranilast, sodium cromoglicate, anlexanox, repirinast, ibudilast, tazanolast, and pemilolast sodium.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acribastin.

Examples of the xanthine derivatives include aminophylline, thoeophyline, doxophylline, cipamphilline, and diprophilline.

Examples of the anticholinergic preparation include ipratropium bromide, oxitropium bromide, flutropium bromide, temiverine, tiotropium bromide, and revatropate (UK-112166).

Examples of the cytokine inhibitor include suplatast tosilate (trade name: IPD).

Examples of the expectorant include foeniculated ammonia spirit, sodium hydrogencarbonate, bromhexine hydrochloride, carbocisteine, ambroxol hydrochloride, extended-release ambroxol hydrochloride, methylcysteine hydrochloride, acetyl cysteine, L-ethylcysteine hydrochloride, and tyloxapol.

Examples of the growth factors include fibroblast growth factor (FGF), vascular endothelium growth factor (VEGF), hepatocyte growth factor (HGF), and insulin-like growth factor.

Examples of the nonsteroid-based antiphlogistic include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, and antipyrine system antipyretics.

Examples of the diuretic include mannitol, furosemide, acetazolamide, diclofenamide, matazolamide, trichlormethiazide, mefruside, spinolactone, and aminophylline.

The weight proportion of the compound represented by formula (I-1), (I-2) or (I-3) and the other pharmaceutical preparations is not specifically limited.

Arbitrary two or more of the other pharmaceutical preparations may be administered in combination.

Examples of the other pharmaceutical preparations for compensating for and/or enhancing the preventive and/or treatment effect of the compound represented by formula (I-1), (I-2) or (I-3) include not only those which have so far been found but also those which will be found on the basis of the aforementioned mechanism.

In order to use the compound of the invention represented by formulae (I-2) and (I-3) or the compound represented by formula (I-1), (I-2) or (I-3) in combination with the other pharmaceutical preparations, these compounds are normally administered to the entire or local part of human body orally or parenterally.

The dose of these compounds depends on the age, weight and symptom of the patient, the remedial value, the administration method, the treatment time, etc. In practice, however, these compounds are administered orally once or several times per day each in an amount of from 1 ng to 100 mg per adult, parenterally once or several times per day each in an amount of from 0.1 ng to 00 mg per adult or continuously administered into vein for 1 hour to 24 hours per day.

It goes without saying that the dose of these compounds may be less than the aforementioned value or may need to exceed the aforementioned range because the dose varies under various conditions as mentioned above.

When the compounds of the invention represented by formulae (I-2) and (I-3) or the compound represented by formula (I-1), (I-2) or (I-3) is administered in combination with the other pharmaceutical preparations, they are used in the form of solid or liquid agent for oral administration, injection, agent for external application, suppository, dye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch), binder (e.g., hydroxypropyl cellulose, polyvinyl pyrrolidone, magnesium metasilicoaluminate), disintegrant (e.g., calcium fibrinoglycolate), glidant (e.g., magnesium stearate), stabilizer, dissolution aid (e.g., glutamic acid, aspartic acid) or the like. The solid agent may be coated with a coating agent (e.g., white sugar, gelatin, hydroxypropyl cellulose, hydroxypropyl methyl cellulose phthalate) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof). Furthermore, such a liquid agent may comprise a wetting agent, a suspending agent, an emulsifier, a sweetening agent, a flavor, a preservative, a buffer, etc.

The agent for parenteral administration may be in the form of, e.g., ointment, gel, cream, wet compress, paste, liniment, nebula, inhalant, spray, eye drops, collunarium or the like. These agents each contain one or more active materials and are prepared by any known method or commonly used formulation.

The ointment is prepared by any known or commonly used formulation. For example, one or more active materials are titurated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester), wax (e.g., beeswax, whale wax, ceresin), surface active agent (e.g., polyoxyethylenealkyletherphosphoric acid ester), higher alcohol (e.g., cetanol, stearyl alcohol, setostearyl alcohol), silicon oil (e.g., dimethyl polysiloxane), hydrocarbon (e.g., hydrophilic petrolatum, white petrolatum, purified lanolin, liquid paraffin), glycol (e.g., ethylene glycol, diethylene glycol, propylene glycol, polyethylene glycol, macrogol), vegetable oil (e.g., castor oil, olive oil, sesame oil, turpentine oil), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol), gelling agent (e.g., carboxymethyl cellulose, hydroxyethyl cellulose, hydroxypropyl cellulose, ethyl cellulose), neutralizing agent (e.g., triethanolamine, diisopropanolamine), surface active agent (e.g., polyethylene glycol monostearate), gum, water, absorption accelerator, and rash preventive are used singly or in admixture of two or more thereof. The gel base may further comprise a humectant, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol), higher alcohol (e.g., 2-hexyl decanol, cetanol), emulsifier (e.g., polyoxyethylene alkyl ether, aliphatic acid ester), water, absorption accelerator, and rash preventive are used singly or in admixture of two or more thereof. The cream base may further comprise a humectant, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose), wetting agent (e.g., urea, glycerin, propylene glycol), filler (e.g., kaolin, zinc oxide, talc, calcium, magnesium), water, dissolution aid, tackifier, and rash preventive may be used singly or in admixture of two or more thereof. The wet compress base may further comprise a humectant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a humectant, an antioxidant, a perfume, etc.

The liniment is prepared by any known or commonly used formulation. For example, one or more active materials are dissolved, suspended or emulsified in water, alcohol (e.g., ethanol, polyethylene glycol), higher aliphatic acid, glycerin, soap, emulsifier, suspending agent, etc., singly or in combination of two or more thereof, to prepare such a liniment. The liniment may further comprise a humectant, an antioxidant, a perfume, etc.

The nebula, inhalant and spray each may comprise a stabilizer such as sodium hydrogensulfite and a buffer capable of providing isotonicity such as isotonic agent (e.g., sodium chloride, sodium citrate, citric acid). For the process for the preparation of spray, reference can be made to U.S. Pat. Nos. 2,868,691 and 3,095,355. These agents may be in the form of aerosol.

The injection for parenteral administration may be in the form of solution, suspension, emulsion or solid injection to be dissolved or suspended in a solvent in use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination. The injection may further comprise a stabilizer, a dissolution aid (e.g., glutamic acid, aspartic acid, Polysolvate 80 (trade name)), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvent before use.

The eye drops for parenteral administration may be in the form of liquid, suspension, emulsion or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic process. Alternatively, an aseptic solid agent such as freeze-dried product which has previously been prepared may be rendered aseptic or dissolved in an aseptic distilled water for injection or other solvent before use.

The inhalant for parenteral administration may be in the form of aerosol, powder for inhalation or liquid for inhalation. The liquid for inhalation may be dissolved or suspended in water or other proper medium in use.

These inhalants are prepared by an known method.

For example, the liquid for inhalation is prepared from materials properly selected from preservatives (e.g., benzalconium chloride, Paraben), colorants, buffering agents (e.g., sodium phosphate, sodium acetate), isotonic agents (e.g., sodium chloride, concentrated glycerin), thickening agents (e.g., carboxyvinyl polymer), absorption accelerators, etc. as necessary.

The powder for inhalation is prepared from materials properly selected from glidants (e.g., stearic acid and salt thereof), binders (e.g., starch, dextrin), vehicles (e.g., lactose, cellulose), colorants, preservatives (e.g., benzalconium chloride, Paraben), absorption accelerators, etc., if necessary.

In order to administer the liquid for inhalation, a sprayer (e.g., atomizer, nebulizer) is normally used. In order to administer the powder for inhalation, a powder inhaler is normally used.

Other examples of the composition for oral administration include suppository for rectal administration and pessary for vaginal administration prepared by an ordinary formulation comprising one or more active materials.

Local Application:

Referring to the local administration of the invention, $EP_4$ agonist may be locally administered to site of disease (particularly bone diseases in which the amount of bone is decreased). The form of $EP_4$ agonist is not limited to its administration method. $EP_4$ agonist may be in the form of injection, solid agent such as embedding agent, pellet and powder ointment to be administered to intramuscular, subcutaneous or articular site.

The extended-release preparation is not limited to its form so far as $EP_4$ agonist can be continuously administered to site of disease (particularly bone diseases in which the amount of bone is decreased). The extended-release preparation may be in the form of, e.g., extended-release injection (e.g., microcapsuled preparation, microspheric preparation, nanospheric preparation), embedding preparation (e.g., film-like preparation) or the like.

The microcapsuled preparation, microspheric preparation and nanospheric preparation of the invention each are a finely divided pharmaceutical composition with an in vivo degradable polymer comprising as active components the compound represented by formula (I-1), (I-2) or (I-3) optionally in combination with other pharmaceutical preparations.

Examples of the in vivo degradable polymer of the invention include aliphatic acid ester polymers and copolymers thereof, polyacrylic acid esters, polyhydroxybutyric acids, polyalkylene oxalates, polyorthoesters, polycarbonates, and polyaminoacids. These compounds may be used singly or in admixture of two or more thereof. Examples of the aliphatic acid ester polymers and copolymers thereof include polylactic acid, polyglycolic acid, polycitric acid, polymalic acid, and lactic acid-glycolic acid copolymer. These compounds may be used singly or in admixture of two or more thereof. Besides these compounds, poly-α-cyanoacrylic acid esters, poly-β-hydroxybutyric acids, polytrimethyleneoxates, polyorthoesters, polyorthocarbonates, polyethylene carbonates, poly-γ-benzyl-L-glutamic acids and poly-L-alanines may be used singly or in admixture of two or more thereof. Preferred among these compounds are polylactic acids, polyglycolic acids and lactic acid-glycolic acid copolymers, more preferably lactic acid-glycolic acid copolymers.

The average molecular weight of these in vivo degradable polymers to be used in the invention is preferably from about 2,000 to 800,000, more preferably from about 5,000 to 200,000. For example, the polylactic acid preferably has a weight-average molecular weight of from about 5,000 to 100,000, more preferably from about 6,000 to 50,000. The polylactic acid can be synthesized according to any known preparation method per se. In the lactic acid-glycolic cid copolymer, the composition ratio of the lactic acid to the glycolic acid is preferably from about 100/0 to 50/50 (w/w), particularly from about 90/10 to 50/50. The weight-average molecular weight of the lactic acid-glycolic acid copolymer is preferably from about 5,000 to 100,000, more preferably from about 10,000 to 80,000. The lactic acid-glycolic acid copolymer can be synthesized according to any known preparation method per se.

The term "weight-average molecular weight" as used herein is meant to indicate molecular weight in polystyrene equivalence determined by gel permeation chromatography (GPC).

The aforementioned in vivo degradable polymer may be changed depending on the intensity of pharmacological activity of the compounds represented by formulae (I-1), (I-2) and (I-3) and the desired medicines to be released so far as the aforementioned aims of the invention are accomplished. For example, the in vivo degradable polymer may be used in an amount of from about 0.2 to 10,000 times, preferably from about 1 to 1,000 times, more preferably from about 1 to 100 times (by weight) that of the physiologically active material.

Examples of the process for the preparation of microspheric, microcapsuled and nanospheric preparations include submerged drying method (e.g., o/w method, w/o method, w/o/w method), phase separation method, spray drying method, granulation method by ulractritical fluid, and methods analogous thereto.

The submerged drying method (o/w method) and spray drying method will be further described hereinafter.

(1) In the submerged drying method (o/w method), a solution of an in vivo degradable polymer in an organic solvent is prepared at first. The organic solvent to be used in the preparation of the microspheric, microcapsuled and nanospheric preparations preferably has a boiling point of 120° C. or less. Examples of the organic solvent employable herein include halogenated hydrocarbons (e.g., dichloromethane, chloroform), aliphatic esters (e.g., ethyl acetate), ethers, aromatic hydrocarbons, and ketones (e.g., acetone). These compounds may be used in admixture of two or more at a proper ratio. Preferred among these organic solvents are dichloromethane and acetonitrile, particularly dichloromethane. The concentration of the in vivo degradable polymer in the organic solution depends on the molecular weight of the in vivo degradable polymer, the kind of the organic solvent, etc. but is normally predetermined to be from about 0.01 to 80% (v/w), preferably from about 0.1 to 70% (v/w), more preferably from about 1 to 60% (v/w).

The compound represented by formula (I-1), (I-2) or (I-3) is then added to and dissolved in the solution of the in vivo degradable polymer in an organic solvent thus obtained, optionally in combination with other pharmaceutical preparations. The amount of the compound represented by formula (I-1), (I-2) or (I-3) to be added optionally in combination with the other pharmaceutical preparations depends on the kind of the pharmaceutical preparations to be added, the action of the pharmaceutical preparations in osteogenesis, the duration of the action, etc. but is normally from about 0.001% to 90% (w/w), preferably from about 0.01% to 80% (w/w), more preferably from about 0.3 to 30% (w/w) as calculated in terms of concentration in the solution of in vivo degradable polymer in an organic solvent.

Subsequently, the organic solution thus prepared is added to an aqueous phase which is then processed by an agitator, emulsifier or the like to form an o/w emulsion. The volume of the aqueous phase during this procedure is predetermined to be from about 1 to 10,000 times, preferably from about 2 to 5,000 times, particularly from about 5 to 2,000 times that of the oil phase. An emulsifier may be added to the aqueous phase which is an external phase. As such an emulsifier there may be normally used any material capable of forming a stable o/w emulsion. Examples of the emulsifier employable herein include anionic surface active agents, nonionic surface active agents, polyoxyethylene castor oil derivatives, polyvinyl pyrrolidone, polyvinyl alcohol, carboxymethyl cellulose, lecitine, and gelatin. These compounds may be used in proper combination. The concentration of the emulsifier in the external aqueous phase is preferably from about 0.001% to 20% (w/w), more preferably from about 0.01% to 10% (w/w), particularly from about 0.05% to 5% (w/w).

The evaporation of the solvent which is an oil phase can be accomplished by any commonly used method. In some detail, the evaporation of the solvent may be effected at ordinary pressure or gradually falling pressure with stirring by an agitator, magnetic stirrer or the like or may be effected while the pressure is being adjusted using a rotary evaporator. The microspheric preparation thus obtained is then fractionated by centrifugal separation or filtration. The microspheric preparation is washed with a surface active agent solution, alcohol or the like several times to remove the free compound represented by formula (I-1), (I-2) or (I-3), optionally in combination with other pharmaceutical preparations, and the emulsifier from the surface thereof, again dispersed in distilled water or a dispersant containing a vehicle (e.g., mannitol, sorbitol, lactose), and then freeze-dried. In the aforementioned o/w method, the microspheric preparation may be prepared by a method involving the dispersion of the compound represented by formula (I-1), (I-2) or (I-3) in a solvent of an in vivo degradable polymer in an organic solvent, optionally in combination with other pharmaceutical preparations, i.e., s/o/w method.

(2) In order to prepare the microspheric preparation by the spray drying method, an organic solvent or emulsion having the in vivo degradable polymer and the compound represented by formula (I-1), (I-2) or (I-3), optionally in combination with other pharmaceutical preparations, dissolved therein is sprayed into the drying chamber of a spray dryer (spray dryer) through a nozzle so that the organic solvent or water in the atomized droplets is evaporated in an extremely short period of time to prepare a microspheric preparation. Examples of the nozzle employable herein include two liquid nozzle, pressure nozzle, and rotary disc. It is useful to spray an organic solvent or an aqueous solution of an aggregation inhibitor (e.g., mannitol, lactose, gelatin) at the same time with the spray of o/w emulsion as necessary for the purpose of inhibiting the aggregation of microspheres. The microspheric preparation thus obtained is then put under reduced pressure optionally under heating to remove water and solvent therefrom.

Examples of the film-like preparation include film-like material obtained by dissolving the aforementioned in vivo degradable polymer and compound represented by formula (I-1), (I-2) or (I-3), optionally in combination with other pharmaceutical preparations, in an organic solvent, and then subjecting the solution to evaporation to dryness and gelled material obtained by dissolving the aforementioned in vivo degradable polymer and compound represented by formula (I-1), (I-2) or (I-3), optionally in combination with other pharmaceutical preparations, in a proper solvent, and then adding a granulating agent (e.g., cellulose, polycarbonate) to the solution.

The microsphere, microcapsule and nanosphere of the invention may be used as they are. Alternatively, a spherical, rod-like, acicular, pelletized, film-like or cream-like pharmaceutical composition may be processed as a starting material to provide preparations in various forms.

Furthermore, this preparation may be used as a parenteral for local administration (e.g., injection, solid agent such as embedding agent, pellet and powder, liquid agent such as suspension, ointment, etc. to be administered to intramuscular, subcutaneous, organic or articular site). For example, in order to make an injection from the microspheric preparation, the microspheric preparation is suspended with a dispersant, a preservative, an isotonic agent, a buffer, a pH adjustor, etc. to make an aqueous suspension as a practical preparation for injection. Alternatively, the microspheric preparation may be dispersed with a vegetable oil optionally in admixture with a phospholipid such as lecitine or with a middle-chain aliphatic acid triglyceride (e.g., Mygliol-812) to make an oil suspension as an injection which can be practically used.

The particle diameter of the microspheric preparation may be arbitrary so far as it suffices the desired dispersibility and passage through syringe if the preparation is used as a suspension for injection. By way of example, the average particle diameter of the microspheric preparation is from about 0.1 to 300 µm, preferably from about 1 to 150 µm, more preferably from about 2 to 100 µm. The pharmaceutical composition of the invention is preferably in the form of suspension as mentioned above. The pharmaceutical composition of the invention is also preferably in particulate form. This is because the pharmaceutical composition gives less excessive pain to patients when administered through a syringe for use in ordinary hypodermic or intramuscular injection. It is particularly preferred that the pharmaceutical composition of the invention be in the form of injection. Examples of the method for rendering the microspheric preparation aseptic include method which is aseptic throughout the entire steps, method involving sterilization by gamma rays, and method involving the addition of preservative. However, the invention is not limited to these methods.

The pharmaceutical composition of the invention can be used for the treatment of bone diseases in which the amount of bone is decreased because the compound represented by formula (I-1), (I-2) or (I-3), optionally in combination with other pharmaceutical preparations, can be gradually released normally for 1 week to 3 months, though depending on the kind and added amount of the in vivo degradable polymer. Among these bone disease treatments, the treatment of fracture often requires that the affected part be fixed and covered with a plaster bandage and the administration of pharmaceutical preparations be conducted only once rather than frequently. Accordingly, the pharmaceutical preparations thus administered are required to accelerate treatment continuously. Thus, the pharmaceutical composition of the invention is useful particularly in this treatment.

The dose of the pharmaceutical composition of the invention depends on the kind, content and form of the compound represented by formula (I-1), (I-2) or (I-3), optionally in combination with other pharmaceutical preparations, the duration of release of pharmaceutical preparations, the animal to be administered, etc., but may be the effective amount of the compound represented by formula (I-1), (I-2) or (I-3), optionally in combination with other pharmaceutical preparations. When administered to fracture as a microspheric preparation, for example, one time dose for adult (weight: 50 kg) is from about 0.001 mg to 500 mg, preferably from about 0.01 mg to 50 mg as calculated in terms of effective component. The pharmaceutical composition of the invention may be administered once 1 week to 3 months in the aforementioned amount.

BEST MODE FOR CARRYING OUT THE INVENTION

The following Reference Examples and Examples are intend to illustrate, but not to limit the present invention.

The solvents in parentheses at chromatographic separations section show the developing or eluting solvents and the ratios of the solvents used are indicated by volume.

Without special explanation, NMR data was determined in CDCl$_3$ solution. And the solvents in parentheses at NMR data section show solvents used in determination.

TBS is t-butyldimethylsilyl, THP is tetrahydropyran-2-yl, Boc is t-butoxycarbonyl, Me is methyl, Et is ethyl, Ac is acetyl, Bu is butyl, Ms is mesyl and TMS is trimethylsilyl.

REFERENCE EXAMPLE 1

(5R)-5-t-Butyldimethylsilyloxymethylpyrrolidin-2-one

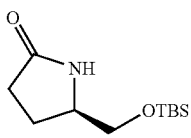

Under atmosphere of argon, a solution of (5R)-5-hydroxymethylpyrollidin-2-one (10 g) and imidazole (8.8 g) in dry dimethylformamide (50 mL) was added by a solution of t-butyldimethylsilyl chloride (15.6 g) in dry dimethylformamide (50 mL) at room temperature, and the mixture was stirred for 5 hours. To the mixture, a mixed solvent of ethyl acetate and hexane was added. The diluted solution was washed with water and brine successively, dried over an anhydrous sodium sulfate, concentrated under reduced pressure to give the title compound (21.41 g) having the following physical data.

TLC: Rf 0.52 (Ethyl Acetate).

REFERENCE EXAMPLE 2

9-Oxo-13-t-butyldimethylsilyloxy-14,15,16,17,18,19,20-heptanor-8-azaprostanoic acid ethyl ester

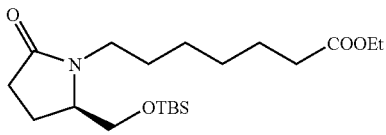

Under atmosphere of argon, a suspension of sodium hydride (3.42 g; 63.1% in oil) in dry tetrahydrofuran (90 mL) was added by a solution of the compound prepared in Reference Example 1 (20.8 g) in dry tetrahydrofuran (90 mL) at room temperature. Then dimethylformamide (180 mL) was added to the mixture, and the mixture was stirred for 45 minutes at 50° C. To the mixture, a solution of 7-bromoheptanoic acid ethyl ester (22.4 g) in dimethylformamide (20 mL) was added, and the mixture was stirred for 4 hours. After cooling, a mixed solvent of ethyl acetate and hexane was added. The organic layer was washed with 0.5N hydrochloric acid, water and brine successively, dried over an anhydrous sodium sulfate, concentrated under reduced pressure to give the title compound (34.9 g) having the following physical data.

TLC: Rf 0.51 (Ethyl Acetate:Hexane=2:1).

REFERENCE EXAMPLE 3

9-Oxo-13-hydroxy-14,15,16,17,18,19,20-heptanor-8-azaprostanoic acid ethyl ester

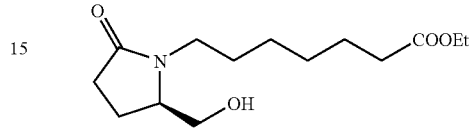

To a solution of the compound prepared in Reference Example 2 (34.9 g) in ethanol (43 mL), p-toluenesulfonic acid (2.96 g) was added, and the mixture was stirred overnight at 50° C. It was cooled to room temperature, the mixture was added by triethylamine (2.4 mL), concentrated under reduced pressure and was purified by column chromatography on silica gel (from ethyl acetate:hexane=1:1 to ethyl acetate only) to give the title compound (13.15 g) having the following physical data.

TLC: Rf 0.18 (Ethyl Acetate);

NMR: δ 4.12 (q, J=7 Hz, 2H), 3.85-3.6 (m, 4H), 3.05-2.9 (m, 1H), 2.55-2.4 (m, 1H), 2.4-2.25 (m, 3H), 2.2-2.05 (m, 1H), 2.0-1.9 (m, 1H), 1.85-1.7 (br, 1H), 1.7-1.2 (m, 8H), 1.27 (t, J=7 Hz, 3H).

REFERENCE EXAMPLE 4

9-Oxo-12-formyl-13,14,15,16,17,18,19,20-octanor-8-azaprostanoic acid ethyl ester

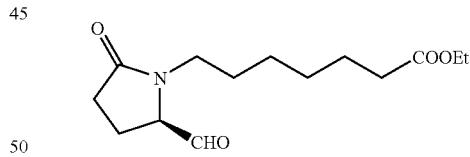

Under atmosphere of argon, a solution of the compound prepared in Reference Example 3 (1.25 g) in ethyl acetate (10 mL) and dry dimethylsulfoxide (7 mL) was added by diisopropylethylamine (5.1 mL). Then sulfur trioxide pyridine complex (2.32 g) was added to the mixture on ice bath, and the mixture was stirred for 1 hour at 0~15° C. Small amount of water was added to the reaction mixture, the reaction was terminated. Chloroform (10 mL) was added to the mixture. The organic layer was washed with 0.5N hydrochloric acid, dried over an anhydrous sodium sulfate, concentrated under reduced pressure to give the title compound (1.25 g) having the following physical data, which was used for the next reaction without purification.

TLC: Rf 0.45 (Chloroform:Methanol=9:1).

REFERENCE EXAMPLE 5

(13E)-9,15-Dioxo-16-(3-methoxymethylphenyl)-17,18,19,20-tetranor-8-azaprost-13-enoic acid ethyl ester

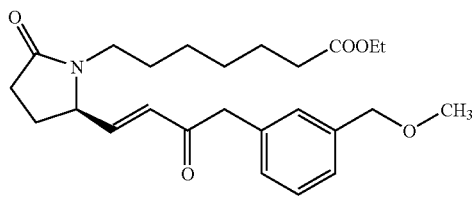

Under atmosphere of argon, a solution of 3-(3-methoxymethylphenyl)-2-oxopropylphosphonic acid dimethyl ester (1.81 g) in dry tetrahydrofuran (35 mL) was added by sodium hydride (222 mg; 63.1% in oil), and the mixture was stirred for 30 minutes at room temperature. To the suspension, a solution of the compound prepared in Reference Example 4 (1.25 g) in tetrahydrofuran (5 mL) was added, and the mixture was stirred for 3 hours. Then ethyl acetate was added to the mixture. The diluted solution was washed with water and brine successively, dried over an anhydrous sodium sulfate, concentrated under reduced pressure and was purified by column chromatography on silica gel (ethyl acetate:hexane=from 2:1 to 3:1, then ethyl acetate only) to give the title compound (1.23 g) having the following physical data.

TLC: Rf 0.72 (Chloroform:Methanol=9:1);
NMR: δ 7.35-7.10 (m, 4H), 6.65 (dd, J=16, 8 Hz, 1H), 6.23 (d, J=16 Hz, 1H), 4.42 (s, 2H), 4.2-4.1 (m, 3H), 3.85 (s, 2H), 3.6-3.5 (m, 1H), 3.38 (s, 3H), 2.8-2.65 (m, 1H), 2.5-2.2 (m, 5H), 1.85-1.7 (m, 1H), 1.7-1.5 (m, 2H), 1.5-1.2 (m, 9H).

EXAMPLE 1

(15α,13E)-9-Oxo-15-hydroxy-16-(3-methoxymethylphenyl)-17,18,19,20-tetranor-8-azaprost-13-enoic acid ethyl ester

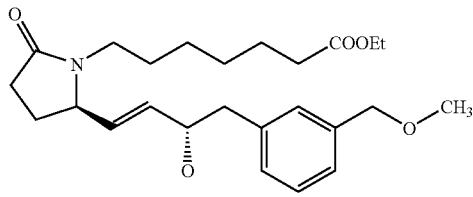

Under atmosphere of argon, a solution of the compound prepared in Reference Example 5 (1.23 g) in dry tetrahydrofuran (10 mL) was added by a 1.0M (R)-2-methyl-CBS-oxazaborolidine/toluene solution (0.57 mL) at room temperature. Then borane tetrahydrofuran complex (2.32 mL) was dropped to the mixture, and the mixture was stirred for 45 minutes. To the mixture, 1N hydrochloric acid and ethyl acetate was added. The organic layer was washed with water and brine successively, dried over an anhydrous sodium sulfate, concentrated under reduced pressure and was purified by column chromatography on silica gel (from ethyl acetate only to ethyl acetate:hexane 19:1) to give the title compound (1.05 g) having the following physical data.

TLC: Rf 0.60 (Chloroform:Methanol=9:1);
NMR: δ 7.38-7.10 (m, 4H), 5.73 (dd, J=15.3, 6.0 Hz, 1H), 5.50 (dd, J=15.3, 8.0 Hz, 1H), 4.48-4.35 (m, 3H), 4.17-3.98 (m, 3H), 3.53-3.36 (m, 4H), 2.92-2.68 (m, 3H), 2.44-2.05 (m, 6H), 1.81-1.20 (m, 12H).

EXAMPLE 2

(15α,13E)-9-Oxo-15-hydroxy-16-(3-methoxymethylphenyl)-17,18,19,20-tetranor-8-azaprost-13-enoic acid

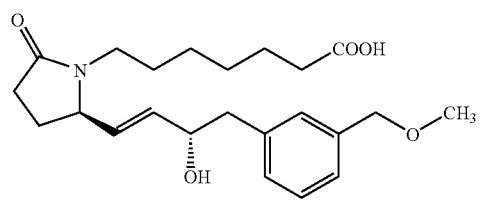

A solution of the compound prepared in Example 1 (1.05 g) in methanol (5 mL) was added by 2N aqueous sodium hydroxide (4 ml), and the mixture was stirred overnight. To the mixture, diethyl ether (10 mL) and water (20 mL) was added, and the mixture was stirred. 1N hydrochloric acid was added to the aqueous layer to acidify, then extracted by ethyl acetate. The organic layer was washed with water and brine successively, dried over an anhydrous sodium sulfate, concentrated under reduced pressure and was purified by column chromatography on silica gel (from chloroform only to chloroform:methanol=100:1, then 50:1, then 25:1) to give the title compound (837 mg) having the following physical data.

TLC: Rf 0.41 (Chloroform:Methanol=9:1);
NMR: δ 7.36-7.11 (m, 4H), 5.75 (dd, J=15.3, 6.0 Hz, 1H), 5.51 (dd, J=15.3, 8.0 Hz, 1H), 4.49-4.38 (m, 3H), 4.08-3.99 (m, 1H), 3.50-3.36 (m, 4H), 2.94-2.75 (m, 3H), 2.49-2.14 (m, 6H), 1.79-1.20 (m, 9H).

EXAMPLE 2(a) to EXAMPLE 2(bbb)

By the same procedure as describe in Reference Examples 1, 2, 3, 45, Examples 1 and 2 using 7-bromoheptanoic acid ethyl ester or corresponding halide derivatives, and 3-(3-methoxymethylphenyl)-3-oxopropylphosphonic acid dimethyl ester or corresponding phosphonic ester derivatives, the compound of the present invention having the following physical data were obtained.

Example 2(a)

(5S,15α,13E)-5-Methyl-9-oxo-15-hydroxy-16-(3-methoxymethylphenyl)-17,18,19,20-tetranor-8-aza-prost-13-enoic acid

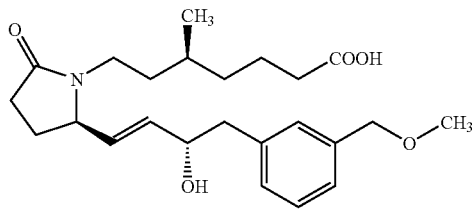

TLC: Rf 0.28 (Methanol:Chloroform=1:10);
NMR: δ 7.40-7.10 (m, 4H), 5.78 (dd, J=15.2, 5.2 Hz, 1H), 5.55 (dd, J=15.2, 8.4 Hz, 1H), 4.50-4.35 (m, 1H), 4.46 (s, 2H), 4.10-3.95 (m, 1H), 3.60-3.35 (m, 1H), 3.42 (s, 3H), 3.00-2.70 (m, 4H), 2.50-2.10 (m, 5H), 1.80-1.00 (m, 8H), 0.91 (d, J=5.8 Hz, 3H).

Example 2(b)

(15α,13E)-5,5-Dimethyl-9-oxo-15-hydroxy-16-(3-methoxymethylphenyl)-17,18,19,20-tetranor-8-aza-prost-13-enoic acid

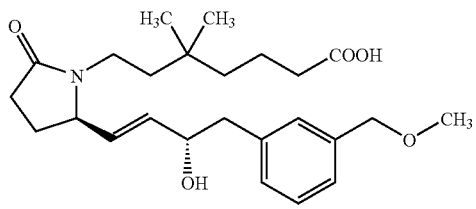

TLC: Rf 0.38 (Chloroform:Methanol=9:1);
NMR: δ 7.33-7.12 (m, 4H), 5.78 (dd, J=15, 5 Hz, 1H), 5.59 (dd, J=15, 8 Hz, 1H), 4.48 (s, 2H), 4.45-4.36 (m, 1H), 4.12-4.03 (m, 1H), 3.51 (dt, J=12, 5 Hz, 1H), 3.43 (s, 3H), 2.91-2.81 (m, 2H), 2.76 (dd, J=14, 8 Hz, 1H), 2.47-2.10 (m, 5H), 1.78-1.63 (m, 1H), 1.61-1.40 (m, 3H), 1.32-1.10 (m, 3H), 0.92 (s, 3H), 0.89 (s, 3H).

Example 2(c)

(15α,13E)-5,5-Ethano-9-oxo-15-hydroxy-16-(3-methoxymethylphenyl)-17,18,19,20-tetranor-8-aza-prost-13-enoic acid

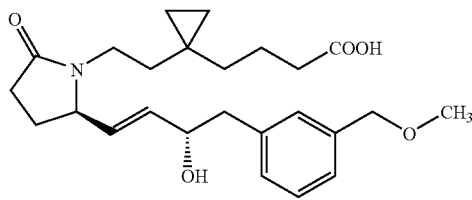

TLC: Rf 0.38 (Chloroform:Methanol=9:1);
NMR: δ 7.33-7.13 (m, 4H), 5.81 (dd, J=15, 5 Hz, 1H), 5.61 (dd, J=15, 8 Hz, 1H), 4.46 (s, 2H), 4.48-4.39 (m, 1H), 4.12-4.04 (m, 1H), 3.54 (ddd, J=14, 11, 5 Hz, 1H), 3.43 (s, 3H), 2.98 (ddd, J=14, 11, 5 Hz, 1H), 2.90 (dd, J=14, 9 Hz, 1H), 2.47-2.12 (m, 5H), 1.79-1.52 (m, 4H), 1.36-1.10 (m, 3H), 0.37-0.22 (m, 4H).

Example 2(d)

(5R,15α,13E)-5-Methyl-9-oxo-15-hydroxy-16-(3-methoxymethylphenyl)-17,18,19,20-tetranor-8-aza-prost-13-enoic acid

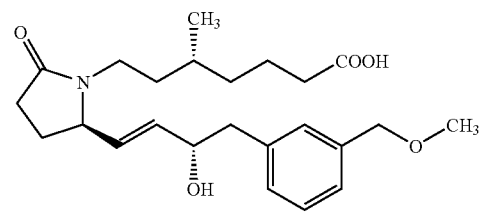

TLC: Rf 0.55 (Methanol:Chloroform=1:5);
NMR: δ 7.40-7.10 (m, 4H), 5.78 (dd, J=15.4, 5.6 Hz, 1H), 5.54 (dd, J=15.4, 8.4 Hz, 1H), 4.50-4.35 (m, 1H), 4.41 (s, 2H), 4.10-3.98 (m, 1H), 3.60-3.45 (m, 1H), 3.42 (s, 3H), 3.00-2.75 (m, 3H), 2.50-2.10 (m, 5H), 1.80-1.10 (m, 8H), 0.91 (d, J=5.8 Hz, 3H).

Example 2(e)

(15α,13E)-9-Oxo-15-hydroxy-16-(3-(2,2,2-trifluoro-ethoxymethyl)phenyl)-17,18,19,20-tetranor-8-aza-prost-13-enoic acid

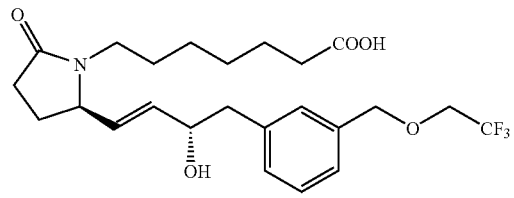

TLC: Rf 0.38 (Methanol:Ethyl Acetate=1:10);
NMR: δ 7.40-7.10 (m, 4H), 5.75 (dd, J=15.6, 5.6 Hz, 1H), 5.52 (dd, J=15.6, 8.4 Hz, 1H), 4.67 (s, 2H), 4.50-4.35 (m, 1H), 4.10-3.98 (m, 1H), 3.86 (q, J=8.8 Hz, 2H), 3.60-3.35 (m, 1H), 3.00-1.80 (m, 6H), 2.33 (t, J=7.0 Hz, 2H), 1.80-1.55 (m, 3H), 1.55-1.10 (m, 6H).

Example 2(f)

(15α,13E)-9-Oxo-15-hydroxy-16-(3-chlorophenyl)-17,18,19,20-tetranor-8-azaprost-13-enoic acid

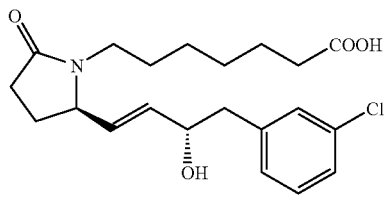

TLC: Rf 0.36 (Methanol:Ethyl Acetate=1:10);

NMR: δ 7.35-7.15 (m, 3H), 7.15-7.00 (m, 1H), 5.72 (dd, J=15.8, 5.8 Hz, 1H), 5.48 (dd, J=15.8, 8.2 Hz, 1H), 4.42 (q, J=6.6 Hz, 1H), 4.10-3.98 (m, 1H), 3.60-3.40 (m, 1H), 2.83 (d, J=6.6 Hz, 2H), 3.00-2.10 (m, 4H), 2.34 (t, J=7.2 Hz, 2H), 1.80-1.55 (m, 3H), 1.55-1.10 (m, 6H).

Example 2(g)

(15α,13E)-9-Oxo-15-hydroxy-16-(3-methoxymethylphenyl)-2,3,4,17,18,19,20-heptanor-1,5-(2,5-interthienylene)-8-azaprost-13-enoic acid

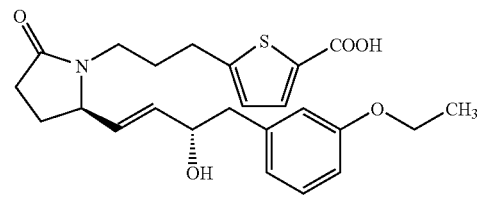

TLC: Rf 0.22 (Chloroform:Methanol=9:1);

NMR: δ 7.63 (d, J=3 Hz, 1H), 7.33-7.25 (m, 2H), 7.19 (d, J=8 Hz, 1H), 7.13 (d, J=8 Hz, 1H), 6.81 (d, J=3 Hz, 1H), 5.73 (dd, J=15, 5 Hz, 1H), 5.50 (dd, J=15, 9 Hz, 1H), 4.52 (d, J=11 Hz, 1H), 4.45 (d, J=11 Hz, 1H), 4.40-4.30 (m, 1H), 4.2-3.0 (br), 4.02 (q, J=9 Hz, 1H), 3.46 (s, 3H), 3.50-3.35 (m, 1H), 2.98-2.68 (m, 5H), 2.50-2.10 (m, 3H), 2.00-1.68 (m, 3H).

Example 2(h)

(15α,13E)-9-Oxo-15-hydroxy-16-(3-phenylphenyl)-17,18,19,20-tetranor-8-azaprost-13-enoic acid

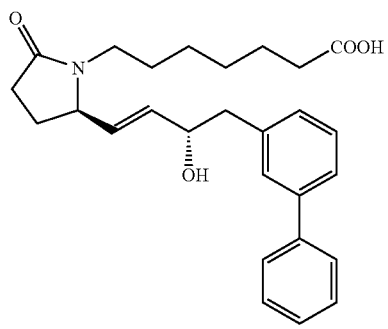

TLC: Rf 0.32 (Chloroform:Methanol=9:1);

NMR: δ 7.60-7.37 (m, 8H), 7.24-7.17 (d, J=8.2 Hz, 1H), 5.74 (dd, J=15.0, 6.0 Hz, 1H), 5.49 (ddd, J=15.0, 8.6, 1.2 Hz, 1H), 4.51-4.40 (m, 1H), 4.08-3.99 (m, 1H), 3.50-3.39 (m, 1H), 2.91 (d, J=6.6 Hz, 2H), 2.78-2.64 (m, 1H), 2.42-2.05 (m, 6H), 1.77-1.51 (m, 3H), 1.42-1.06 (m, 6H).

Example 2(i)

(15α,13E)-9-Oxo-15-hydroxy-16-(3-methylphenyl)-17,18,19,20-tetranor-8-azaprost-13-enoic acid

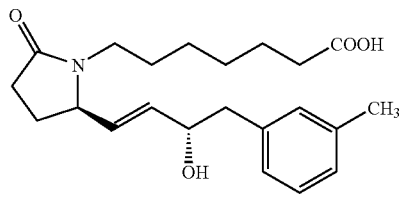

TLC: Rf 0.34 (Chloroform:Methanol=10:1);

NMR: δ 7.22-7.17 (m, 1H), 7.07-6.98 (m, 3H), 5.74 (dd, J=15.3, 5.7 Hz, 1H), 5.50 (ddd, J=15.3, 8.4, 1.2 Hz, 1H), 4.41 (m, 1H), 4.03 (m, 1H), 3.47 (m, 1H), 2.90-2.70 (m, 3H), 2.40-2.10 (m, 6H), 2.33 (s, 3H), 1.76-1.22 (m, 9H).

Example 2(j)

(15α,13E)-9-Oxo-15-hydroxy-16-(3-fluorophenyl)-17,18,19,20-tetranor-8-azaprost-13-enoic acid

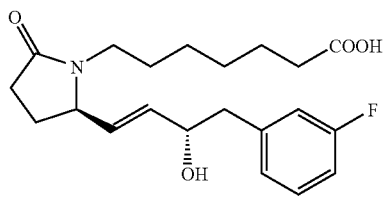

TLC: Rf 0.30 (Chloroform:Methanol=10:1);
NMR: δ 7.32-7.23 (m, 1H), 6.99-6.90 (m, 3H), 5.72 (dd, J=15.3, 6.0 Hz, 1H), 5.50 (ddd, J=15.3, 8.4, 1.2 Hz, 1H), 4.42 (m, 1H), 4.03 (m, 1H), 3.46 (m, 1H), 2.85 (d, J=6.0 Hz, 2H), 2.70 (m, 1H), 2.40-2.10 (m, 6H), 1.75-1.20 (m, 9H).

Example 2(k)

(15α,13E)-9-Oxo-15-hydroxy-16-(4-fluorophenyl)-17,18,19,20-tetranor-8-azaprost-13-enoic acid

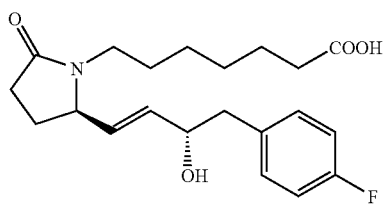

TLC: Rf 0.47 (Chloroform:Methanol:Water=9:1:0.1);
NMR: δ 7.16 (m, 2H), 7.00 (m, 2H), 5.72 (dd, J=15.4, 6.0 Hz, 1H), 5.49 (dd, J=15.4, 8.2 Hz, 1H), 4.38 (m, 1H), 4.03 (m, 1H), 3.47 (m, 1H), 2.82 (d, J=6.6 Hz, 2H), 2.72 (m, 1H), 2.41-2.31 (m, 2H), 2.34 (t, J=7.2 Hz, 2H), 2.21 (m, 1H), 1.67 (m, 1H), 1.66-1.58 (m, 2H), 1.50-1.20 (m, 6H).

Example 2(l)

(15α,13E)-9-Oxo-15-hydroxy-16-(4-methylphenyl)-17,18,19,20-tetranor-8-azaprost-13-enoic acid

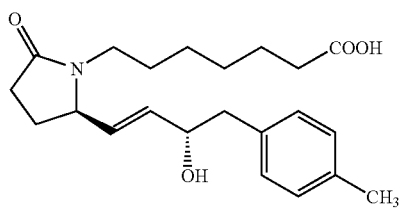

TLC: Rf 0.26 (Chloroform:Methanol:Water=9:1:0.1);
NMR: δ 7.12 (d, J=8.2 Hz, 2H), 7.07 (d, J=8.2 Hz, 2H), 5.73 (dd, J=15.4, 5.8 Hz, 1H), 5.47 (dd, J=15.4, 8.8 Hz, 1H), 4.38 (m, 1H), 4.03 (m, 1H), 3.46 (m, 10H), 2.81 (d, J=6.9 Hz, 2H), 2.72 (m, 1H), 2.40-2.27 (m, 4H), 2.34 (s, 3H), 2.21 (m, 1H), 1.72 (m, 10H), 1.67-1.58 (m, 2H), 1.50-1.18 (m, 6H).

Example 2(m)

(15α,13E)-9-Oxo-15-hydroxy-16-(2-methylphenyl)-17,18,19,20-tetranor-8-azaprost-13-enoic acid

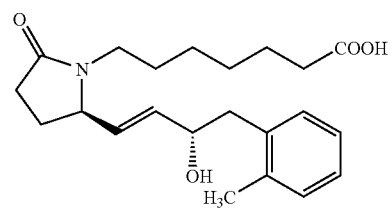

TLC: Rf 0.27 (Chloroform:Methanol=8:1);
NMR: δ 7.28-7.00 (m, 4H), 5.76 (dd, J=15.2, 6.0 Hz, 1H), 5.49 (ddd, J=15.2, 8.4, 0.6 Hz, 1H), 4.42 (m, 1H), 4.04 (m, 1H), 3.46 (m, 1H), 2.87 (d, J=7.0 Hz, 2H), 2.72 (m, 1H), 2.50-2.04 (m, 6H), 2.34 (s, 3H), 1.85-1.10 (m, 9H).

Example 2(n)

(15α,13E)-9-Oxo-15-hydroxy-16-(2-fluorophenyl)-17,18,19,20-tetranor-8-azaprost-13-enoic acid

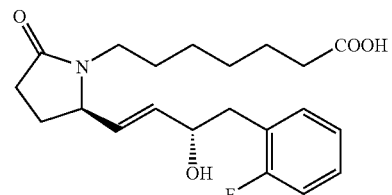

TLC: Rf 0.27 (Chloroform:Methanol=8:1);
NMR: δ 7.34-6.94 (m, 4H), 5.74 (dd, J=15.2, 6.0 Hz, 1H), 5.45 (ddd, J=15.2, 8.4, 0.8 Hz, 1H), 4.47 (m, 1H), 4.02 (m, 1H), 3.44 (m, 1H), 3.40-1.90 (m, 9H), 1.80-0.90 (m, 9H).

Example 2(o)

(15α,13E)-9-Oxo-15-hydroxy-16-(3-trifluoromethylphenyl)-17,18,19,20-tetranor-8-azaprost-13-enoic acid

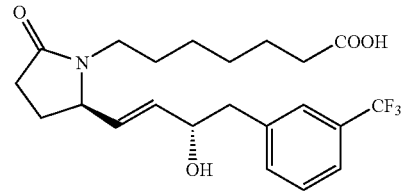

TLC: Rf 0.18 (Chloroform:Methanol=8:1);
NMR: δ 7.60-7.35 (m, 4H), 5.73 (dd, J=15.3, 5.9 Hz, 1H), 5.50 (ddd, J=15.3, 8.3, 0.9 Hz, 1H), 4.46 (m, 1H), 4.03 (m, 1H), 4.00-3.00 (br, 2H), 3.46 (m, 1H), 2.91 (d, J=6.3 Hz, 2H), 2.71 (m, 1H), 2.48-2.06 (m, 5H), 1.76-1.12 (m, 9H).

Example 2(p)

(15α,13E)-9-Oxo-15-hydroxy-16-(3-methoxyphenyl)-17,18,19,20-tetranor-8-azaprost-13-enoic acid

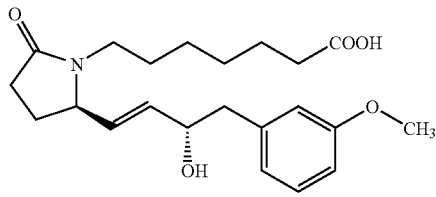

TLC: Rf 0.16 (Chloroform:Methanol=8:1);
NMR: δ 7.23 (dd, J=7.8, 7.8 Hz, 1H), 6.86-6.70 (m, 3H), 5.73 (dd, J=15.3, 6.0 Hz, 1H), 5.48 (dd, J=15.3, 8.4 Hz, 1H), 4.41 (m, 1H), 4.03 (m, 1H), 3.80 (s, 3H), 3.46 (m, 1H), 2.82 (d, J=6.6 Hz, 2H), 2.71 (m, 1H), 2.50-2.04 (m, 5H), 1.80-1.10 (m, 10H).

Example 2(q)

(15α,13E)-9-Oxo-15-hydroxy-16-(3-ethylphenyl)-17,18,19,20-tetranor-8-azaprost-13-enoic acid

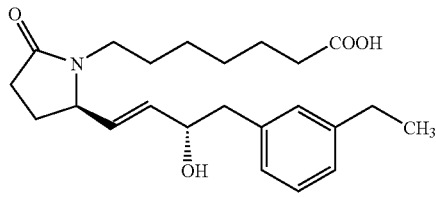

TLC: Rf 0.25 (Chloroform:Methanol:Water=9:1:0.1);
NMR: δ 7.24 (t, J=7.3 Hz, 1H), 7.11-6.97 (m, 3H), 5.74 (dd, J=15.1, 5.9 Hz, 1H), 5.50 (ddd, J=15.1, 8.3, 1.0 Hz, 1H), 4.42 (m, 1H), 4.04 (m, 1H), 3.45 (m, 1H), 2.84-2.80 (m, 2H), 2.75 (m, 1H), 2.63 (q, J=7.8 Hz, 2H), 2.43-2.32 (m, 2H), 2.35 (t, J=7.3 Hz, 2H), 2.21 (m, 1H), 1.71 (m, 1H), 1.68-1.57 (m, 2H), 1.54-1.20 (m, 6H), 1.24 (t, J=7.8 Hz, 3H).

Example 2(r)

(15α,13E)-9-Oxo-15-hydroxy-16-(3,4-difluorophenyl)-17,18,19,20-tetranor-8-azaprost-13-enoic acid

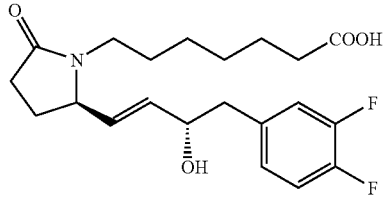

TLC: Rf 0.30 (Chloroform:Methanol:Water=9:1:0.1);
NMR: δ 7.14-7.00 (m, 3H), 6.92 (m, 1H), 5.71 (dd, J=15.4, 5.8 Hz, 1H), 5.50 (dd, J=15.4, 8.6 Hz, 1H), 4.38 (m, 1H), 4.04 (m, 1H), 3.44 (m, 1H), 2.82 (d, J=6.6 Hz, 2H), 2.73 (m, 1H), 2.43-2.32 (m, 2H), 2.34 (t, J=7.1 Hz, 2H), 2.22 (m, 1H), 1.69 (m, 1H), 1.65-1.55 (m, 2H), 1.51-1.20 (m, 6H).

Example 2(s)

(15α,13E)-9-Oxo-15-hydroxy-16-(3-chloro-4-hydroxyphenyl)-17,18,19,20-tetranor-8-azaprost-13-enoic acid

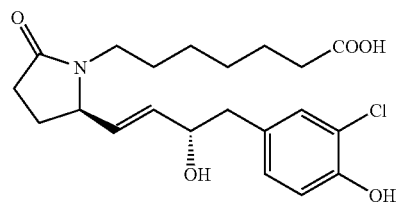

TLC: Rf 0.26 (Chloroform:Methanol=9:1);
NMR: δ 7.14 (d, J=2.1 Hz, 1H), 6.94 (dd, J=8.4, 2.1 Hz, 1H), 6.88 (d, J=8.4 Hz, 1H), 5.65 (dd, J=15, 6.3 Hz, 1H), 5.41 (ddd, J=15, 8.0, 1.2 Hz, 1H), 4.33 (m, 1H), 4.01 (m, 1H), 3.41 (m, 1H), 2.85-2.62 (m, 3H), 2.57-2.10 (m, 8H), 1.79-1.56 (m, 3H), 1.54-1.19 (m, 6H).

The hydroxyl group bound benzene ring was protected by THP group, and was removed protecting group by acid before hydrolysis of the ester (procedure of Example 2)

Example 2(t)

(15α,13E)-9-Oxo-15-hydroxy-16-(3,5-difluorophenyl)-17,18,19,20-tetranor-8-azaprost-13-enoic acid

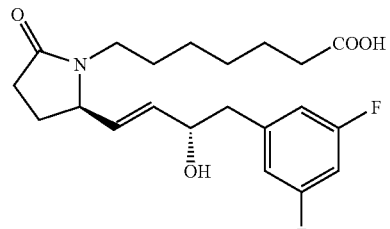

TLC: Rf 0.34 (Chloroform:Methanol=9:1);
NMR: δ 6.80-6.65 (m, 3H), 5.71 (dd, J=15, 5.7 Hz, 1H), 5.50 (dd, J=15, 8.7 Hz, 1H), 4.41 (m, 1H), 4.03 (m, 1H), 3.48 (m, 1H), 3.10-2.50 (m, 4H), 2.47-2.10 (m, 6H), 1.79-1.59 (m, 3H), 1.58-1.20 (m, 6H).

Example 2(u)

(15α,13E)-9-Oxo-15-hydroxy-16-(3-propylphenyl)-17,18,19,20-tetranor-8-azaprost-13-enoic acid

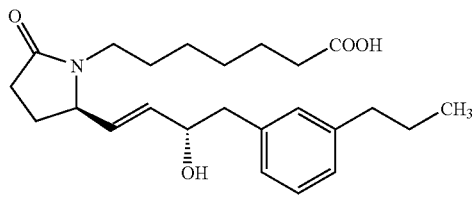

TLC: Rf 0.26 (Chloroform:Methanol=10:1);

NMR: δ 7.25-7.19 (m, 1H), 7.08-7.00 (m, 3H), 5.75 (dd, J=15.3, 5.7 Hz, 1H), 5.51 (ddd, J=15.3, 8.4, 0.9 Hz, 1H), 4.41 (m, 1H), 4.05 (m, 1H), 3.48 (m, 1H), 2.90-2.70 (m, 3H), 2.57 (t, J=7.2 Hz, 2H), 2.50-2.10 (m, 5H), 1.80-1.20 (m, 11H), 0.94 (t, J=7.2 Hz, 3H).

Example 2(v)

(15α,13E)-9-Oxo-15-hydroxy-16-((E)-1-propenylphenyl)-17,18,19,20-tetranor-8-azaprost-13-enoic acid

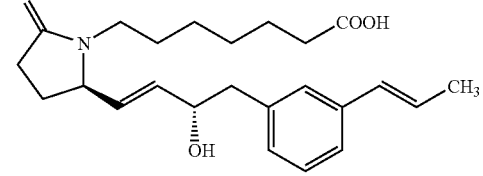

TLC: Rf 0.30 (Chloroform:Methanol=10:1);

NMR: δ 7.23-7.21 (m, 2H), 7.14 (s, 1H), 7.02 (m, 1H), 6.37 (dd, J=15.6, 1.5 Hz, 1H), 6.27 (dq, J=15.6, 6.3 Hz, 1H), 5.74 (dd, J=15.3, 6.0 Hz, 1H), 5.49 (ddd, J=15.3, 8.4, 1.2 Hz, 1H), 4.41 (m, 1H), 4.02 (m, 1H), 3.45 (m, 1H), 2.83 (d, J=6.9 Hz, 2H), 2.70 (m, 1H), 2.40-2.10 (m, 5H), 1.88 (dd, J=6.3, 1.5 Hz, 3H), 1.80-1.20 (m, 9H).

Example 2(w)

(15α,13E)-9-Oxo-15-hydroxy-16-(3-(2-fluorophenyl)phenyl)-17,18,19,20-tetranor-8-azaprost-13-enoic acid

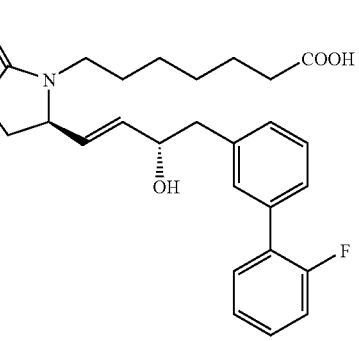

TLC: Rf 0.27 (Chloroform:Methanol=8:1);

NMR: δ 7.60-6.80 (m, 8H), 5.72 (m, 1H), 5.48 (m, 1H), 5.00-3.00 (br, 2H), 4.43 (m, 1H), 4.01 (m, 1H), 3.43 (m, 1H), 2.98-2.60 (m, 3H), 2.48-2.00 (m, 5H), 1.98-0.88 (m, 9H).

Example 2(x)

(15α,13E)-9-Oxo-15-hydroxy-16-(3-(4-fluorophenyl)phenyl)-17,18,19,20-tetranor-8-azaprost-13-enoic acid

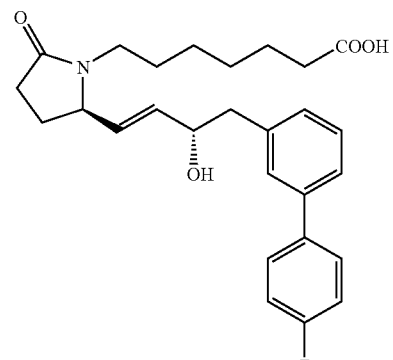

TLC: Rf 0.27 (Chloroform:Methanol 8:1);

NMR: δ 7.64-7.00 (m, 8H), 5.72 (m, 1H), 5.48 (m, 1H), 4.60-3.00 (br, 2H), 4.45 (m, 1H), 4.02 (m, 1H), 3.44 (m, 1H), 2.96-2.60 (m, 3H), 2.48-2.02 (m, 5H), 1.78-0.78 (m, 9H).

Example 2(y)

(15α,13E)-9-Oxo-15-hydroxy-16-(3-(5-methylfuran-2-yl)phenyl)-17,18,19,20-ttranor-8-azaprost-13-enoic acid

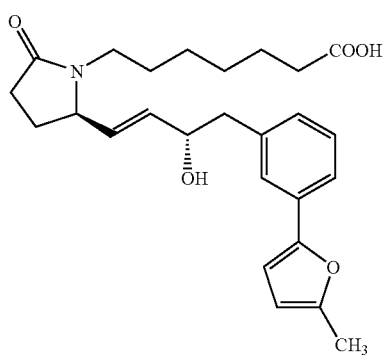

TLC: Rf 0.25 (Chloroform:Methanol 8:1);

NMR: δ 7.60-6.96 (m, 4H), 6.53 (d, J=3.0 Hz, 1H), 6.05 (m, 1H), 5.72 (m, 1H), 5.48 (m, 1H), 4.60-2.80 (br, 2H), 4.44 (m, 1H), 4.02 (m, 1H), 3.44 (m, 1H), 2.96-2.60 (m, 3H), 2.48-2.02 (m, 8H), 1.80-1.06 (m, 9H).

Example 2(z)

(15α,13E)-9-Oxo-15-hydroxy-16-(naphthalen-2-yl)-17,18,19,20-tetranor-8-azaprost-13-enoic acid

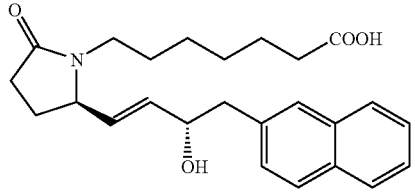

TLC: Rf 0.45 (Chloroform:Methanol:Water=9:1:0.1);

NMR: δ 7.83-7.76 (m, 3H), 7.65 (s, 1H), 7.51-7.41 (m, 2H), 7.33 (dd, J=8.5, 1.7 Hz, 1H), 5.77 (dd, J=15.4, 6.1 Hz, 1H), 5.44 (ddd, J=15.4, 8.5, 0.8 Hz, 1H), 4.54 (m, 1H), 4.01 (m, 1H), 3.38 (m, 1H), 3.02 (d, J=6.9 Hz, 2H), 2.63 (m, 1H), 2.37-2.32 (m, 2H), 2.34 (t, J=7.2 Hz, 2H), 2.19 (m, 1H), 1.64 (m, 1H), 1.63-1.55 (m, 2H), 1.40-1.12 (m, 6H).

Example 2(aa)

(15α,13E)-9-Oxo-15-hydroxy-16-(3-(2-methoxyphenyl)phenyl)-17,18,19,20-tetranor-8-azaprost-13-enoic acid

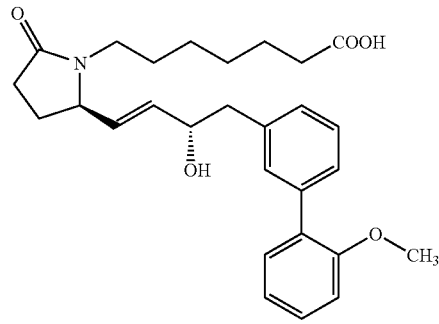

TLC: Rf 0.23 (Chloroform:Methanol=8:1);

NMR: δ 7.50-6.92 (m, 8H), 5.74 (m, 1H), 5.50 (m, 1H), 4.43 (m, 1H), 4.03 (m, 1H), 3.81 (s, 3H), 3.45 (m, 1H), 3.40-1.90 (br, 2H), 3.00-2.64 (m, 3H), 2.48-2.14 (m, 5H), 1.78-1.10 (m, 9H).

Example 2(bb)

(15α,13E)-9-Oxo-15-hydroxy-16-(3-(2-hydroxyphenyl)phenyl)-17,18,19,20-tetranor-8-azaprost-13-enoic acid

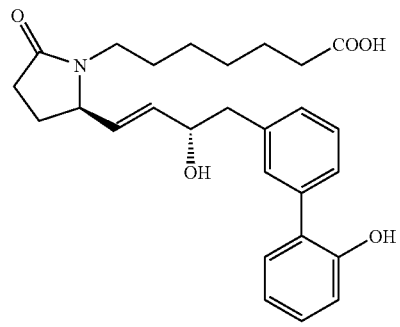

TLC: Rf 0.26 (Chloroform:Methanol=8:1);

NMR: δ 7.46-7.08 (m, 7H), 6.97 (m, 1H), 5.72 (m, 1H), 5.47 (m, 1H), 4.42 (m, 1H), 4.02 (m, 1H), 3.43 (m, 1H), 2.98-2.62 (m, 3H), 2.50-2.06 (m, 5H), 1.80-1.08 (m, 9H).

The hydroxyl group bound benzene ring was protected by THP group, and was removed protecting group by acid before hydrolysis of the ester (procedure of Example 2)

Example 2(cc)

(15α,13E)-9-Oxo-15-hydroxy-16-(3-(3-hydroxyphenyl)phenyl)-17,18,19,20-tetranor-8-azaprost-13-enoic acid

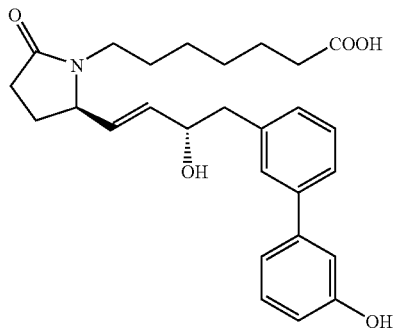

TLC: Rf 0.21 (Chloroform:Methanol=8:1);

NMR: δ 7.48-6.80 (m, 8H), 5.70 (dd, J=15.3, 6.3 Hz, 1H), 5.51 (m, 1H), 4.44 (m, 1H), 4.06 (m, 1H), 3.49 (m, 1H), 3.06-2.60 (m, 3H), 2.54-1.96 (m, 5H), 1.82-1.00 (m, 9H).

The hydroxyl group bound benzene ring was protected by THP group, and was removed protecting group at final step.

Example 2(dd)

(15α,13E)-1,5-(2,5-Interthienylene)-9-oxo-15-hydroxy-16-(3-chlorophenyl)-2,3,4,17,18,19,20-heptanor-8-azaprost-13-enoic acid

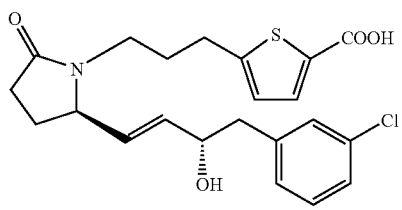

TLC: Rf 0.20 (Chloroform:Methanol=10:1);

NMR: δ 7.68 (d, J=3.6 Hz, 1H), 7.23-7.18 (m, 3H), 7.08 (m, 1H), 6.83 (d, J=3.6 Hz, 1H), 5.71 (dd, J=15.3, 6.0 Hz, 1H), 5.48 (ddd, J=15.3, 8.7, 0.9 Hz, 1H), 4.39 (m, 1H), 4.02 (m, 1H), 3.53 (m, 1H), 3.40 (br s, 1H), 2.90-2.70 (m, 5H), 2.50-2.10 (m, 3H), 1.90-1.60 (m, 3H).

Example 2(ee)

(15α,13E)-9-Oxo-15-hydroxy-16-(3-cyclopropylphenyl)-17,18,19,20-tetranor-8-azaprost-13-enoic acid

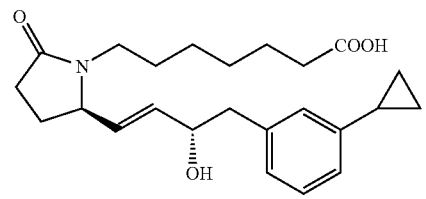

TLC: Rf 0.45 (Chloroform:Methanol:Water=9:1:0.1);

NMR: δ 7.19 (t, J=7.7 Hz, 1H), 7.02-6.89 (m, 3H), 5.73 (dd, J=15.4, 5.8 Hz, 1H), 5.48 (ddd, J=15.4, 8.5, 1.0 Hz, 1H), 4.42 (m, 1H), 4.04 (m, 1H), 3.45 (m, 1H), 2.81 (d, J=6.6 Hz, 2H), 2.75 (m, 10H), 2.43-2.30 (m, 2H), 2.32 (t, J=7.1 Hz, 2H), 2.21 (m, 1H), 1.86 (m, 1H), 1.71 (m, 1H), 1.67-1.56 (m, 2H), 1.52-1.19 (m, 6H), 1.00-0.90 (m, 2H), 0.74-0.63 (m, 2H).

Example 2(ff)

(13E)-9-Oxo-15-hydroxy-16,16-difluoro-16-(3-methoxymethylphenyl)-17,18,19,20-tetranor-8-azaprost-13-enoic acid

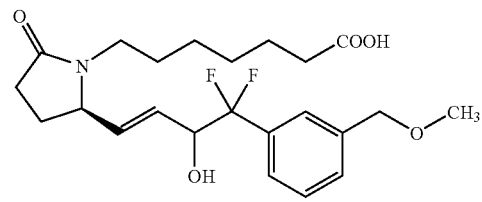

TLC: Rf 0.34 (Chloroform:Methanol=9:1);

NMR: δ 7.57-7.35 (m, 4H), 5.78-5.59 (m, 2H), 4.61-4.43 (m, 3H), 4.04 (m, 1H), 3.50-3.32 (m, 4H), 2.82 (m, 1H), 2.43-2.10 (m, 5H), 1.72-1.20 (m, 9H).

Example 2(gg)

(15α,13E)-9-Oxo-15-hydroxy-16-(3-ethoxyphenyl)-17,18,19,20-tetranor-8-azaprost-13-enoic acid

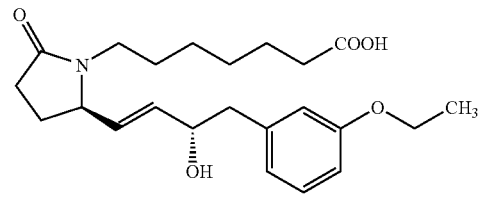

TLC: Rf 0.48 (Chloroform:Methanol:Water=9:1:0.1);

NMR: δ 7.22 (t, J=7.7 Hz, 1H), 6.81-6.73 (m, 3H), 5.73 (dd, J=15.4, 6.1 Hz, 1H), 5.48 (ddd, J=15.4, 8.5, 1.1 Hz, 1H), 4.41 (m, 1H), 4.03 (m, 1H), 4.02 (q, J=7.1 Hz, 2H), 3.45 (m, 1H), 2.81 (d, J=6.6 Hz, 2H), 2.72 (m, 1H), 2.42-2.32 (m, 4H), 2.21 (m, 1H), 1.76-1.58 (m, 3H), 1.48-1.20 (m, 6H), 1.42 (t, J=7.1 Hz, 3H).

Example 2(hh)

(15α,13E)-9-Oxo-15-hydroxy-16-(3-isopropyloxyphenyl)-17,18,19,20-tetranor-8-azaprost-13-enoic acid

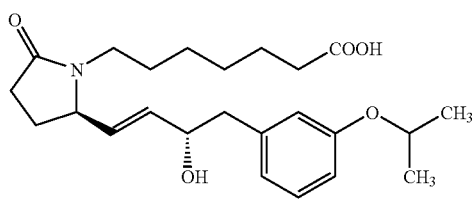

TLC: Rf 0.45 (Chloroform:Methanol Water=9:1:0.1);

NMR: δ 7.20 (t, J=7.7 Hz, 1H), 6.80-6.75 (m, 3H), 5.73 (dd, J=15.4, 6.0 Hz, 1H), 5.49 (ddd, J=15.4, 8.5, 1.1 Hz, 1H), 4.55 (m, 1H), 4.40 (m, 1H), 4.04 (m, 1H), 3.54 (m, 1H), 2.80 (d, J=6.6 Hz, 2H), 2.74 (m, 1H), 2.42-2.32 (m, 4H), 2.21 (m, 1H), 1.77-1.58 (m, 3H), 1.50-1.20 (m, 6H), 1.38 (d, J=6.0 Hz, 6H).

Example 2(ii)

(15α,13E)-9-Oxo-15-hydroxy-16-(3-benzyloxyphenyl)-17,18,19,20-tetranor-8-azaprost-13-enoic acid

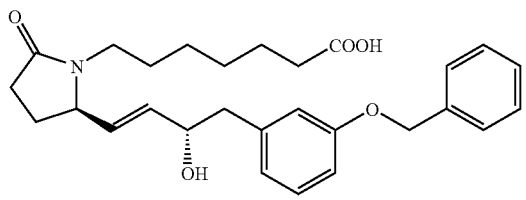

TLC: Rf 0.49 (Chloroform:Methanol:Water=9:1:0.1);

NMR: δ 7.45-7.28 (m, 5H), 7.23 (t, J=7.7 Hz, 1H), 6.89-6.76 (m, 3H), 5.71 (dd, J=15.4, 6.0 Hz, 1H), 5.45 (ddd, J=15.4, 8.5, 0.8 Hz, 1H), 5.03 (s, 2H), 4.39 (m, 1H), 4.01 (m, 1H), 3.45 (m, 1H), 2.81 (d, J=6.9 Hz, 2H), 2.71 (m, 10H), 2.41-2.27 (m, 4H), 2.20 (m, 1H), 1.75-1.54 (m, 3H), 1.48-1.20 (m, 6H).

Example 2(jj)

(15α,5Z,13E)-9-Oxo-15-hydroxy-16-(3-methoxymethylphenyl)-17,18,19,20-tetranor-8-azaprost-5,13-dienoic acid

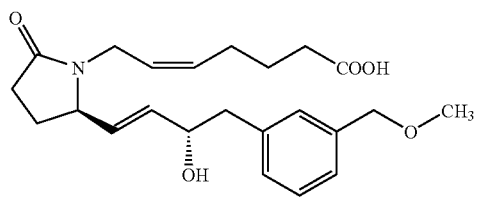

TLC: Rf 0.31 (Chloroform:Methanol=9:1);

NMR: δ 7.32-7.11 (m, 4H), 5.70 (dd, J=16, 5 Hz, 1H), 5.60-5.48 (m, 2H), 5.34-5.25 (m, 1H), 4.44 (s, 2H), 4.50-4.39 (m, 10H), 4.20 (dd, J=15, 5 Hz, 1H), 4.03 (dt, J=8, 5 Hz, 1H), 3.49 (dd, J=15, 8 Hz, 1H), 3.42 (s, 3H), 2.92-2.78 (m, 2H), 2.50-2.05 (m, 7H), 1.77-1.61 (m, 3H).

Example 2(kk)

(15α,5Z,13E)-9-Oxo-15-hydroxy-16-(3-trifluoromethylphenyl)-17,18,19,20-tetranor-8-azaprost-5,13-dienoic acid

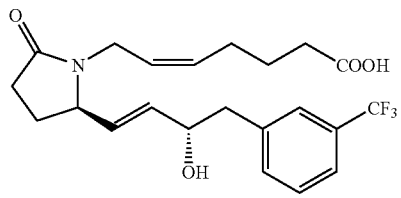

TLC: Rf 0.27 (Chloroform:Methanol=8:1);

NMR: δ 7.62-7.26 (m, 4H), 5.67 (dd, J=15.6, 5.7 Hz, 1H), 5.62-5.44 (m, 2H), 5.28 (m, 1H), 4.45 (m, 1H), 4.21 (dd, J=15.0, 6.6 Hz, 1H), 4.03 (m, 1H), 3.80-2.40 (br, 2H), 3.45 (m, 1H), 2.90 (d, J=6.6 Hz, 2H), 2.48-2.02 (m, 7H), 1.76-1.52 (m, 3H).

Example 2(ll)

(15α,5Z,13E)-9-Oxo-15-hydroxy-16-(3-methylphenyl)-17,18,19,20-tetranor-8-azaprost-5,13-dienoic acid

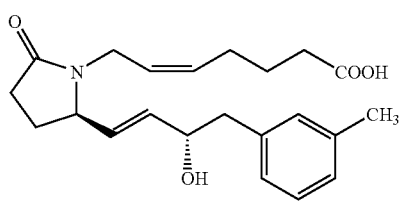

TLC: Rf 0.32 (Chloroform:Methanol=8:1);
NMR: δ 7.19 (dd, J=7.5, 7.5 Hz, 1H), 7.10-7.05 (m, 3H), 5.68 (dd, J=15.6, 5.7 Hz, 1H), 5.61-5.40 (m, 2H), 5.30 (m, 1H), 4.41 (m, 1H), 4.21 (m, 1H), 4.03 (m, 1H), 3.70-2.60 (br, 2H), 3.44 (m, 1H), 2.80 (d, J=6.6 Hz, 2H), 2.48-2.04 (m, 10H), 1.78-1.56 (m, 3H).

Example 2(mm)

(15α,13E)-9-Oxo-15-hydroxy-16-(3,5-dimethylphenyl)-17,18,19,20-tetranor-8-azaprost-13-enoic acid

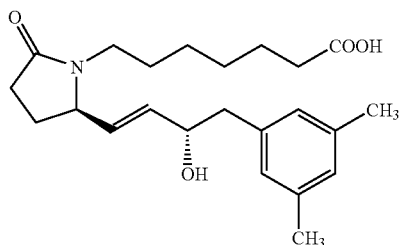

TLC: Rf 0.36 (Chloroform:Methanol=10:1);
NMR: δ 6.88 (s, 1H), 6.81 (s, 2H), 5.74 (dd, J=15.3, 5.7 Hz, 1H), 5.51 (dd, J=15.3, 8.4 Hz, 1H), 4.39 (m, 1H), 4.04 (m, 1H), 3.48 (m, 1H), 2.83-2.69 (m, 3H), 2.50-2.10 (m, 5H), 2.29 (s, 6H), 1.80-1.20 (m, 9H).

Example 2(nn)

(15α,13E)-9-Oxo-15-hydroxy-16-(3-(benzofuran-2-yl)phenyl)-17,18,19,20-tetranor-8-azaprost-13-enoic acid

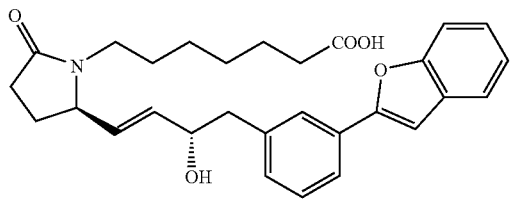

TLC: Rf 0.26 (Chloroform:Methanol=10:1);
NMR: δ 7.74-7.72 (m, 2H), 7.59-7.50 (m, 2H), 7.39 (m, 1H), 7.32-7.18 (m, 3H), 7.03 (d, J=1.2 Hz, 1H), 5.77 (dd, J=15.3, 6.3 Hz, 1H), 5.51 (ddd, J=15.3, 8.7, 0.9 Hz, 1H), 4.48 (m, 1H), 4.03 (m, 1H), 3.43 (m, 1H), 2.93 (d, J=6.6 Hz, 2H), 2.69 (m, 1H), 2.45-2.10 (m, 5H), 1.75-1.10 (m, 9H).

Example 2(oo)

(15α,13E)-2,7-(1,3-Interphenylene)-9-oxo-15-hydroxy-16-(3-methlphenyl)-3,4,5,6,17,18,19,20-octanor-8-azaprost-13-enoic acid

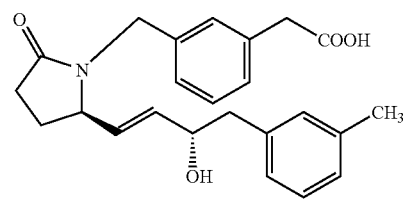

TLC: Rf 0.42 (Chloroform:Methanol:Water=9:1:0.1);
NMR: δ 7.27-6.97 (m, 8H), 5.62 (dd, J=15.4, 5.8 Hz, 1H), 5.41 (ddd, J=15.4, 8.8, 1.1 Hz, 1H), 4.74 (d, J=14.6 Hz, 1H), 4.36 (m, 1H), 3.87 (m, 1H), 3.81 (d, J=14.6 Hz, 1H), 3.60 (s, 2H), 2.78 (d, J=6.6 Hz, 2H), 2.55-2.35 (m, 2H), 2.32 (s, 3H), 2.15 (m, 1H), 1.69 (m, 1H).

Example 2(pp)

(15α,13E)-9-Oxo-15-hydroxy-16-(3-(2-phenylethynyl)phenyl)-17,18,19,20-tetranor-8-azaprost-13-enoic acid

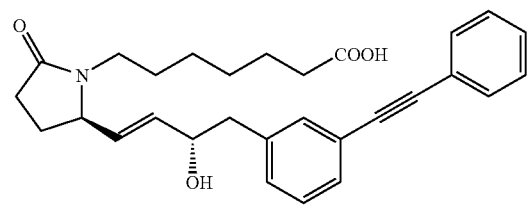

TLC: Rf 0.21 (Chloroform:Methanol=8:1);
NMR: δ 7.60-7.14 (m, 9H), 5.72 (dd, J=15.3, 6.0 Hz, 1H), 5.47 (dd, J=15.3, 8.4 Hz, 1H), 4.43 (m, 1H), 4.03 (m, 1H), 3.46 (m, 1H), 2.94-2.62 (m, 3H), 2.48-2.12 (m, 5H), 1.80-1.16 (m, 9H).

Example 2(qq)

(15α,5Z,13E)-9-Oxo-15-hydroxy-16-(3-chlorophenyl)-17,18,19,20-tetranor-8-azaprost-5,13-dienoic acid

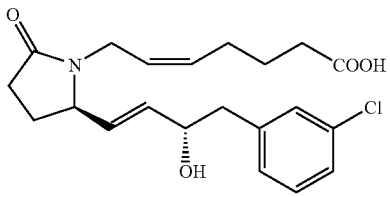

TLC: Rf 0.31 (Chloroform:Methanol=8:1);
NMR: δ 7.40-7.00 (m, 4H), 5.66 (dd, J=15.6, 5.7 Hz, 1H), 5.61-5.22 (m, 3H), 4.41 (m, 1H), 4.22 (m, 1H), 4.03 (m, 1H), 3.80-2.80 (br, 2H), 3.44 (m, 1H), 2.90-2.70 (m, 3H), 2.48-2.02 (m, 6H), 1.76-1.54 (m, 3H).

Example 2(rr)

(15α,13E)-9-Oxo-15-hydroxy-16-(3,4-difluorophenyl)-17,18,19,20-tetranor-8-azaprost-5,13-dienoic acid

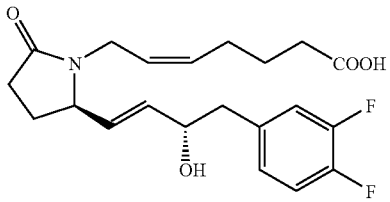

TLC: Rf 0.24 (Chloroform:Methanol=8:1);
NMR: δ 7.20-6.84 (m, 3H), 5.66 (dd, J=15.3, 5.7 Hz, 1H), 5.62-5.22 (m, 3H), 4.38 (m, 1H), 4.21 (m, 1H), 4.04 (m, 1H), 4.02-3.00 (br, 2H), 3.46 (m, 1H), 2.79 (d, J=6.6 Hz, 2H), 2.50-2.02 (m, 7H), 1.80-1.54 (m, 3H).

Example 2(ss)

(15α,13E)-2,7-(1,4-Interphenylene)-9-oxo-15-hydroxy-16-(3-methylphenyl)-3,4,5,6,17,18,19,20-octanor-8-azaprost-13-enoic acid

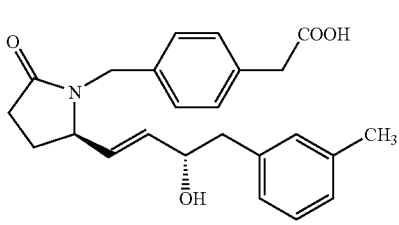

TLC: Rf 0.25 (Chloroform:Methanol:Water 9:1:0.1);
NMR: δ 7.24-6.96 (m, 8H), 5.62 (dd, J=15.4, 6.0 Hz, 1H), 5.43 (ddd, J=15.4, 8.2, 0.8 Hz, 1H), 4.78 (d, J=14.8 Hz, 1H), 4.37 (m, 1H), 3.89 (m, 1H), 3.77 (d, J=14.8 Hz, 1H), 3.62 (s, 2H), 2.80 (d, J=6.6 Hz, 2H), 2.55-2.37 (m, 2H), 2.36 (s, 3H), 2.15 (m, 1H), 1.74 (m, 1H).

Example 2(tt)

(15α,5Z,13E)-9-Oxo-15-hydroxy-16-(3-fluorophenyl)-17,18,19,20-tetranor-8-azaprost-5,13-dienoic acid

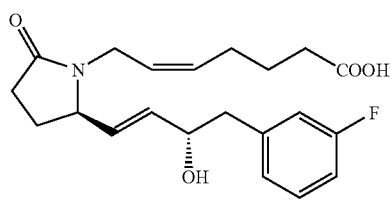

TLC: Rf 0.28 (Chloroform:Methanol=8:1);
NMR: δ 7.25 (m, 1H), 7.04-6.86 (m, 3H), 5.66 (dd, J=15.3, 5.7 Hz, 1H), 5.60-5.20 (m, 3H), 4.42 (m, 1H), 4.40-2.80 (br, 2H), 4.21 (m, 1H), 4.03 (m, 1H), 3.44 (m, 1H), 2.90-2.72 (m, 2H), 2.48-2.02 (m, 7H), 1.78-1.56 (m, 3H).

Example 2(uu)

(15α,5Z,13E)-9-Oxo-15-hydroxy-16-(4-fluorophenyl)-17,18,19,20-tetranor-8-azaprost-5,13-dienoic acid

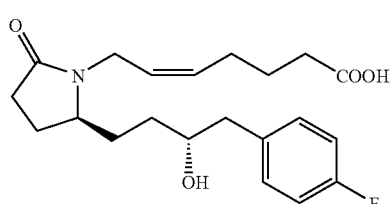

TLC: Rf 0.28 (Chloroform:Methanol=8:1);
NMR: δ 7.22-7.10 (m, 2H), 7.05-6.93 (m, 2H), 5.66 (dd, J=15.6, 5.7 Hz, 1H), 5.61-5.20 (m, 3H), 4.70-3.20 (br, 2H), 4.38 (m, 1H), 4.20 (m, 1H), 4.02 (m, 1H), 3.44 (m, 1H), 2.81 (d, J=6.6 Hz, 2H), 2.48-2.02 (m, 7H), 1.78-1.56 (m, 3H).

Example 2(vv)

(15α,5Z,13E)-9-Oxo-15-hydroxy-16-(3-chlorophenyl)-2,6-(1,3-interphenylene)-3,4,5,17,18,19,20-heptanor-8-azaprost-13-enoic acid

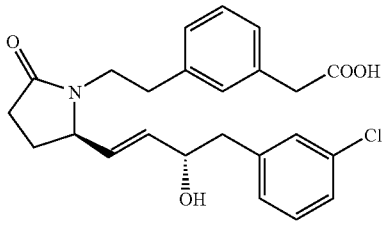

TLC: Rf 0.30 (Chloroform:Methanol 9:1);
NMR: δ 7.25-7.0 (m, 8H), 5.51 (dd, J=15, 6 Hz, 1H), 5.25 (dd, J=15, 8 Hz, 1H), 4.4-4.3 (m, 1H), 3.75-3.65 (m, 1H), 3.62 (s, 2H), 3.65-3.55 (m, 1H), 3.3-2.4 (br), 3.0-2.7 (m, 5H), 2.4-2.2 (m, 2H), 2.1-1.95 (m, 1H), 1.65-1.5 (m, 1H).

Example 2(ww)

(15α,13E)-9-Oxo-15-hydroxy-16-(3-methylphenyl)-1,5-(2,5-interthienylene)-2,3,4,17,18,19,20-heptanor-8-azaprost-13-enoic acid

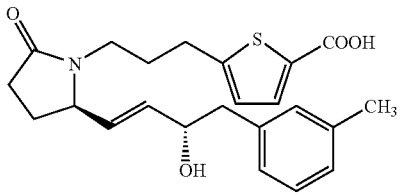

TLC: Rf 0.31 (Chloroform:Methanol:Water 9:1:0.1);
NMR: δ 7.68 (d, J=3.8 Hz, 1H), 7.19 (t, J=7.4 Hz, 1H), 7.07-6.96 (m, 3H), 6.83 (d, J=3.8 Hz, 1H), 5.75 (dd, J=15.4, 6.0 Hz, 1H), 5.47 (ddd, J=15.4, 8.8, 1.1 Hz, 1H), 4.38 (m, 1H), 4.02 (m, 1H), 3.53 (m, 1H), 2.90-2.76 (m, 5H), 2.46-2.37 (m, 2H), 2.33 (s, 3H), 2.21 (m, 1H), 1.90-1.65 (m, 3H).

Example 2(xx)

(15α,13E)-9-Oxo-15-hydroxy-16-(4-fluorophenyl)-5-(5-(5-oxo-1,2,4-oxadiazol-3-yl)thiophen-2-yl)-1,2,3,4,17,18,19,20-octanor-8-azaprost-13-ene

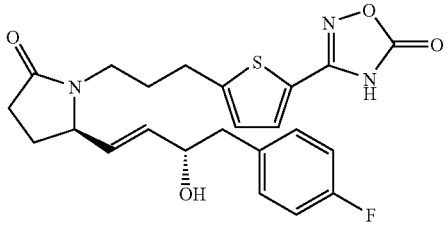

TLC: Rf 0.24 (Chloroform:Methanol=9:1);
NMR (DMSO-d$_6$): δ 12.98 (br. s, 1H), 7.52 (d, J=4.0 Hz, 1H), 7.22-7.14 (m, 2H), 7.08-6.99 (m, 3H), 5.62 (dd, J=15.0, 6.2 Hz, 1H), 5.30 (dd, J=15.0, 8.8 Hz, 1H), 4.97 (br. s, 1H), 4.16 (m, 1H), 4.00 (m, 1H), 3.28 (m, 2H), 2.81-2.58 (m, 4H), 2.22-2.03 (m, 3H), 1.77-1.50 (m, 3H).

Hydrolysis of the ester (procedure of Example 2) was not done. The NH group bound 1,2,4-oxadiazole ring was protected by Boc group, and was removed protecting group at final step.

Example 2(yy)

(15α,13E)-9-Oxo-15-hydroxy-16-(4-fluorophenyl)-1,5-(2,5-interfurylene)-2,3,4,17,18,19,20-heptanor-8-azaprost-13-enoic acid

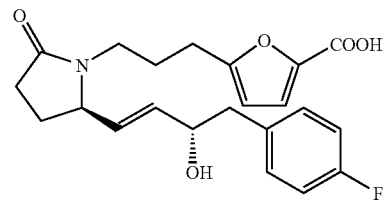

TLC: Rf 0.25 (Chloroform:Methanol=2:1);
NMR: δ 7.20-7.14 (m, 3H), 7.04-6.94 (m, 2H), 6.21 (d, J=3.6 Hz, 1H), 5.73 (dd, J=15.4, 5.8 Hz, 1H), 5.49 (dd, J=15.4, 8.8 Hz, 1H), 5.14 (brs, 2H), 4.38 (m, 1H), 4.06 (m, 1H), 3.51 (m, 1H), 2.86 (m, 1H), 2.81 (d, J=6.6 Hz, 2H), 2.66 (t, J=7.4 Hz, 2H), 2.48-2.29 (m, 2H), 2.18 (m, 1H), 1.93-1.80 (m, 2H), 1.72 (m, 1H).

Example 2(zz)

(15α,13E)-9-Oxo-15-hydroxy-16-(4-fluorophenyl)-3,7-(2,5-interthienylene)-4,5,6,17,18,19,20-heptanor-8-azaprost-13-enoic acid

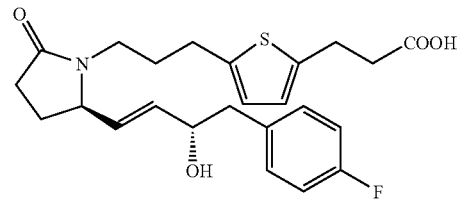

TLC: Rf 0.48 (Chloroform:Methanol=9:1);
NMR (CDCl$_3$+CD$_3$OD): δ 7.25-7.15 (m, 2H), 7.05-6.95 (m, 2H), 6.7-6.6 (m, 2H), 5.72 (dd, J=16, 6 Hz, 1H), 5.45 (dd, J=16, 8 Hz, 1H), 4.78 (d, J=15 Hz, 1H), 4.37 (q, J=6 Hz, 1H), 4.05-3.95 (m, 1H), 3.90 (d, J=15 Hz, 1H), 3.09 (t, J=7 Hz, 2H), 2.83 (d, J=6 Hz, 2H), 2.65 (t, J=7 Hz, 2H), 2.5-2.25 (m, 2H), 2.25-2.1 (m, 1H), 1.8-1.6 (m, 1H).

Example 2(aaa)

(15α,13E)-9-Oxo-15-hydroxy-16-(4-fluorophenyl)-5-(5-(tetrazol-5-yl)thiophen-2-yl)-1,2,3,4,17,18,19,20-octanor-8-azaprost-13-ene

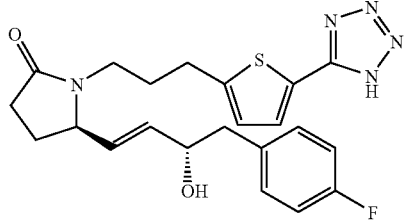

TLC: Rf 0.52 (Chloroform:Methanol=2:1);

NMR (DMSO-d$_6$): δ 7.59 (d, J=3.7 Hz, 1H), 7.21-7.13 (m, 2H), 7.08-6.99 (m, 3H), 5.62 (dd, J=15.4, 6.2 Hz, 1H), 5.31 (dd, J=15.4, 8.8 Hz, 1H), 4.97 (br, 1H), 4.17 (m, 1H), 4.02 (m, 1H), 3.33 (m, 1H), 2.82-2.58 (m, 5H), 2.27-2.03 (m, 3H), 1.80-1.49 (m, 3H).

Hydrolysis of the ester (procedure of Example 2) was not done. The NH group bound 1,2,4-oxadiazole ring was protected by Boc group, and was removed protecting group at final step.

Example 2(bbb)

(15α,13E)-9-Oxo-15-hydroxy-16-(naphthalen-1-yl)-17,18,19,20-tetranor-8-azaprost-13-enoic acid

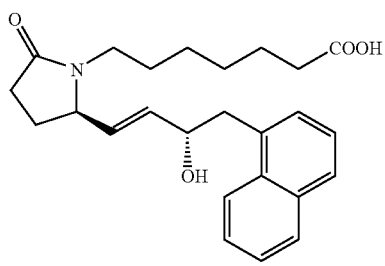

TLC: Rf 0.45 (Chloroform:Methanol:Water=9:1:0.1);

NMR: δ 8.04 (m, 1H), 7.87 (m, 1H), 7.76 (m, 1H), 7.57-7.46 (m, 2H), 7.44-7.32 (m, 2H), 5.78 (dd, J=15.4, 6.1 Hz, 1H), 5.45 (ddd, J=15.4, 8.5, 1.1 Hz, 1H), 4.57 (m, 1H), 3.97 (m, 1H), 3.35 (m, 1H), 3.32 (d, J=6.6 Hz, 2H), 2.64 (m, 1H), 2.37-2.32 (m, 2H), 2.34 (t, J=7.1 Hz, 2H), 2.15 (m, 1H), 1.64-1.55 (m, 3H), 1.43-1.15 (m, 6H).

REFERENCE EXAMPLE 6

2-((5R)-5-t-Butyldimethylsilyloxymethyl-2-oxopyrrolidin-1-yl)acetic aci methyl ester

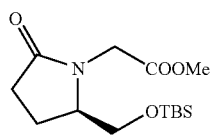

Under atmosphere of argon, a solution of potassium t-butoxide (11.58 g) in dry tetrahydrofuran (100 mL) was added to the solution of the compound prepared in Reference Example 1 (21.41 g) in tetrahydrofuran (200 mL) on water bath. After the mixture was stirred for 1 hour, a solution of bromoacetic acid methyl ester (9.75 mL) in tetrahydrofuran (50 mL) was added hereto. Then hexane was added to the mixture. The diluted solution was washed with water and brine successively, dried over an anhydrous sodium sulfate, concentrated under reduced pressure and was purified by column chromatography on silica gel (ethyl acetate:hexane=from 1:2 to 1:1, then 3:1) to give the title compound (22.13 g) having the following physical data.

TLC: Rf 0.48 (Ethyl Acetate:Hexane=1:1).

REFERENCE EXAMPLE 7

2-((5R)-5-t-Butyldimethylsilyloxymethyl-2-oxopyrrolidin-1-yl)ethanol

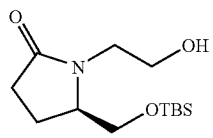

To a solution of the compound prepared in Reference Example 6 (22.0 g) in tetrahydrofuran (100 mL), sodium borohydride (8.28 g) was added, and the mixture was stirred for 5 minutes. Methanol (20 mL) was added hereto, and the mixture was stirred for 15 minutes. Methanol (30 mL) was added hereto again, and the mixture was stirred for 1 hour. After water was added to the mixture, ethyl acetate was added hereto. The organic layer was washed with water and brine successively, dried over an anhydrous sodium sulfate, concentrated under reduced pressure to give the title compound (19.75 g) having the following physical data.

TLC: Rf 0.43 (Ethyl Acetate).

REFERENCE EXAMPLE 8

(5R)-2-(5-t-Butyldimethylsilyloxymetoxopyrrolidinyl)ethyl thioacetate

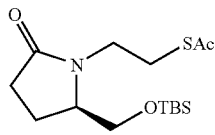

Under atmosphere of argon, a mixture of the compound prepared in Reference Example 7 (22.0 g), triethylamine (13.0 mL) and dry tetrahydrofuran (150 mL) was dropped by mesyl chloride (6.7 mL) at −5° C., and the mixture was stirred for 45 minutes. After reaction was terminated, methanol (0.81 mL) was added hereto, and the mixture was stirred for 15 minutes. To the mixture, a mixture of potassium carbonate (20.0 g), potassium thioacetate and dry dimethylformamide (150 mL) was added, and the mixture was stirred for 3 hours at 50° C., then for 2 days at room temperature. Then mixed solvent of ethyl acetate and hexane was added to the mixture. The diluted solution was washed with water and brine successively, dried over an anhydrous sodium sulfate, concentrated under reduced pressure to give the title compound (26.8 g) having the following physical data.

TLC: Rf 0.83 (Ethyl Acetate).

REFERENCE EXAMPLE 9

9-Oxo-13-(t-butyldimethylsilyloxy)-14,15,16,17,18,19,20-heptanor-5-thia-8-azaprostanoic acid methyl ester

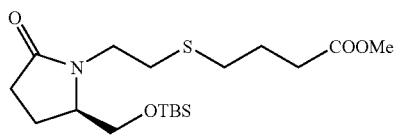

Under atmosphere of argon, a solution of the compound prepared in Reference Example 8 (26.8 g) and 4-iodobutanoic acid methyl ester (19.9 g) in dry methanol (150 mL) was added by potassium carbonate (14.0 g), and the mixture was stirred for 2 hours. Then mixed solvent of diethyl ether and ethyl acetate was added to the mixture. The diluted solution was washed with 0.5N hydrochloric acid, water and brine successively, dried over an anhydrous sodium sulfate, concentrated under reduced pressure to give the title compound (31.28 g) having the following physical data.

TLC: Rf 0.67 (Ethyl Acetate:Hexane=1:1).

REFERENCE EXAMPLE 10

9-Oxo-13-hydroxy-14,15,16,17,18,19,20-heptanor-5-thia-8-azaprostanoic acid methyl ester

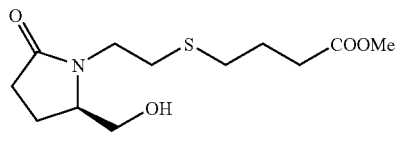

To a solution of the compound prepared in Reference Example 9 (31.28 g) in methanol (70 mL), p-toluenesulfonic acid monohydrate (2.41 g) was added, and the mixture was stirred for 4 hours at 50° C. It was cooled to room temperature, the mixture was added by triethylamine (1.95 mL), concentrated under reduced pressure and was purified by column chromatography on silica gel (from ethyl acetate:hexane=1:1 to ethyl acetate:methanol=100:1) to give the title compound (16.67 g) having the following physical data.

TLC: Rf 0.14 (Ethyl Acetate).

REFERENCE EXAMPLE 11

9-Oxo-12-formyl-13,14,15,16,17,18,19,20-octanor-5-thia-8-azaprostanoic acid methyl ester

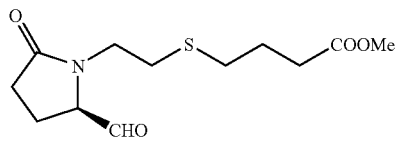

Under atmosphere of argon, a solution of the compound prepared in Reference Example 10 (1.04 g) and diisopropylethylamine (3.8 mL) in mixed solvent of ethyl acetate (6 mL) and dimethylsulfoxide (6 mL) was added by sulfur trioxide pyridine complex (1.72 g) on ice bath, and the mixture was stirred for 40 minutes. 0.5N hydrochloric acid was added to the reaction mixture, then the mixture was extracted by chloroform. The organic layer was dried over an anhydrous sodium sulfate, concentrated under reduced pressure to give the title compound (1.0 g) having the following physical data.

TLC: Rf 0.50 (Chloroform:Methanol=9:1).

EXAMPLE 3(a) TO EXAMPLE 3(rr)

By the same procedure as describe in Reference Example 5, Examples 1 and 2 using the compound prepared in Reference Example 11 or corresponding aldehyde derivatives instead of the compound prepared in Reference Example 4, the compound of the present invention having the following physical data were obtained.

Example 3(a)

(15α,13E)-9-Oxo-15-hydroxy-16-(3-methoxymethylphenyl)-17,18,19,20-tetranor-5-thia-8-azaprost-13-enoic acid

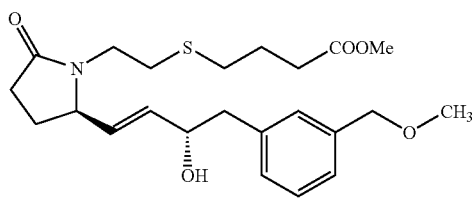

TLC: Rf 0.35 (Methanol:Chloroform=1:5);
NMR: δ 7.40-7.10 (m, 4H), 5.79 (dd, J=15.4, 5.2 Hz, 1H), 5.54 (dd, J=15.4, 8.4 Hz, 1H), 4.50-4.40 (m, 1H), 4.46 (s, 2H), 4.20-4.05 (m, 1H), 3.70-3.50 (m, 1H), 3.42 (s, 3H), 3.20-2.90 (m, 1H), 2.90-2.80 (m, 2H), 2.80-2.10 (m, 9H), 2.00-1.60 (m, 3H).

Example 3(b)

(15α,13E)-9-Oxo-15-hydroxy-16-(3-chlorophenyl)-17,18,19,20-tetranor-5-thia-8-azaprost-13-enoic acid

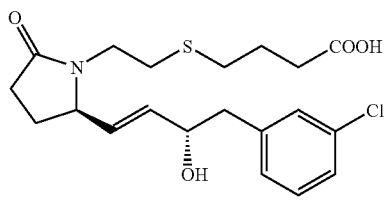

TLC: Rf 0.45 (Methanol:Chloroform=1:5);
NMR: δ 7.30-7.20 (m, 3H), 7.20-7.05 (m, 1H), 5.75 (dd, J=15.4, 5.4 Hz, 1H), 5.49 (dd, J=15.4, 8.6 Hz, 1H), 4.50-4.35 (m, 1H), 4.20-4.05 (m, 1H), 3.75-3.55 (m, 1H), 3.10-2.85 (m, 1H), 2.85 (d, J=6.6 Hz, 2H), 2.80-2.10 (m, 9H), 2.00-1.80 (m, 2H), 1.80-1.60 (m, 1H).

Example 3(c)

(15α,13E)-9-Oxo-15-hydroxy-16-(3-cyclopropyloxymethylphenyl)-17,18,19,20-tetranor-5-thia-8-azaprost-13-enoic acid

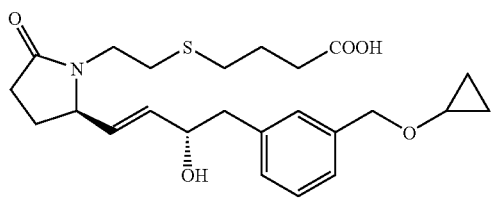

TLC: Rf 0.47 (Chloroform:Methanol=9:1);
NMR: δ 7.37-7.11 (m, 4H), 5.80 (dd, J=15, 5 Hz, 1H), 5.55 (dd, J=15, 8 Hz, 1H), 4.56 (s, 2H), 4.50-4.40 (m, 1H), 4.17-4.08 (m, 1H), 3.63-3.51 (m, 1H), 3.42-3.36 (m, 1H), 3.11-3.00 (m, 1H), 2.89 (dd, J=14, 6 Hz, 1H), 2.80 (dd, J=14, 8 Hz, 1H), 2.72-2.32 (m, 8H), 2.31-2.17 (m, 1H), 1.98-1.83 (m, 2H), 1.79-1.65 (m, 1H), 0.71-0.49 (m, 4H).

Example 3(d)

(15α,13E)-9-Oxo-15-hydroxy-16-(3-(2,2,2-trifluoroethoxymethyl)phenyl)-17,18,19,20-tetranor-5-thia-8-azaprost-13-enoic acid

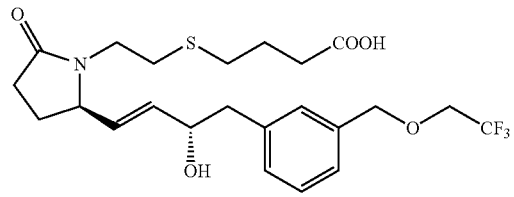

TLC: Rf 0.47 (Chloroform:Methanol=9:1);
NMR: δ 7.38-7.14 (m, 4H), 5.77 (dd, J=15, 6 Hz, 1H), 5.53 (dd, J=15, 8 Hz, 1H), 4.65 (s, 2H), 4.50-4.40 (m, 1H), 4.18-4.08 (m, 1H), 3.86 (q, J=9 Hz, 2H), 3.68-3.55 (m, 1H), 3.08-2.94 (m, 1H), 2.94-2.79 (m, 2H), 2.68-2.32 (m, 8H), 2.32-2.17 (m, 1H), 1.98-1.82 (m, 2H), 1.78-1.63 (m, 1H).

Example 3(e)

(15α,13E)-9-Oxo-15-hydroxy-16-(3-propylphenyl)-17,18,19,20-tetranor-5-thia-8-azaprost-13-enoic acid

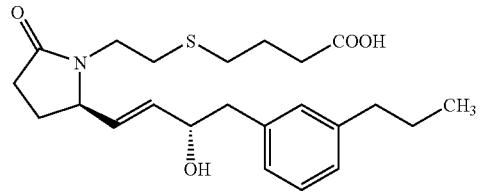

TLC: Rf 0.50 (Methanol:Ethyl Acetate=1:5);
NMR: δ 7.30-7.20 (m, 1H), 7.10-7.00 (m, 3H), 5.78 (dd, J=15.4, 5.4 Hz, 1H), 5.52 (dd, J=15.4, 8.4 Hz, 1H), 4.50-4.40 (m, 1H), 4.20-4.05 (m, 1H), 3.75-3.55 (m, 1H), 3.20-2.10 (m, 14H), 2.00-1.80 (m, 2H), 1.80-1.55 (m, 3H), 0.94 (t, J=7.2 Hz, 3H).

Example 3(f)

(15α,13E)-9-Oxo-15-hydroxy-16-cyclopentyl-17,18,19,20-tetranor-5-thia-8-azaprost-13-enoic acid

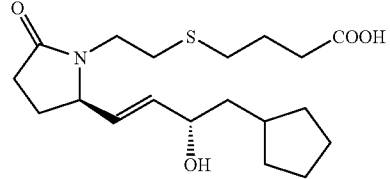

TLC: Rf 0.26 (Chloroform:Methanol=9:1);
NMR: δ 5.75 (dd, J=15.3, 6.0 Hz, 1H), 5.53 (ddd, J=15.3, 8.0, 1.0 Hz, 1H), 4.29-4.10 (m, 2H), 3.77-3.60 (m, 1H), 3.20-3.08 (m, 1H), 2.79-1.43 (m, 22H), 1.22-1.04 (m, 2H).

Example 3(g)

(15α,13E)-9-Oxo-15-hydroxy-16-(thiophen-2-yl)-17,18,19,20-tetranor-5-thia-8-azaprost-13-enoic acid

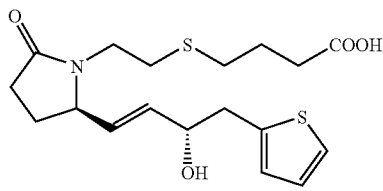

TLC: Rf 0.18 (Chloroform:Methanol=9:1);
NMR: δ 7.19 (d, J=5.1 Hz, 1H), 6.95 (dd, J=5.1, 3.3 Hz, 1H), 6.86 (d, J=3.3 Hz, 1H), 5.75 (dd, J=15.0, 5.4 Hz, 1H), 5.55 (dd, J=15.0, 8.6 Hz, 1H), 4.48-4.39 (m, 1H), 4.19-4.06 (m, 1H), 3.70-3.59 (m, 1H), 3.42-2.75 (m, 4H), 2.70-2.18 (m, 10H), 1.99-1.84 (m, 2H), 1.79-1.62 (m, 1H).

Example 3(h)

(15α,13E)-9-Oxo-15-hydroxy-16-(3-trifluoromethylphenyl)-17,18,19,20-tetranor-5-thia-8-azaprost-13-enoic acid

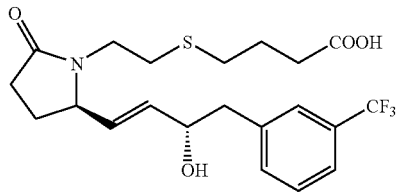

TLC: Rf 0.40 (Chloroform:Methanol=9:1);
NMR: δ 7.59-7.38 (m, 4H), 5.82-5.71 (m, 1H), 5.60-5.41 (m, 1H), 4.57-4.40 (m, 1H), 4.20-4.06 (m, 1H), 3.70-3.59 (m, 10H), 3.15-2.81 (m, 3H), 2.80-2.01 (m, 10H), 1.99-1.80 (m, 2H), 1.79-1.60 (m, 1H).

Example 3(i)

(15α,13E)-9-Oxo-15-hydroxy-16-phenyl-17,18,19,20-tetranor-5-thia-8-azaprost-13-enoic acid

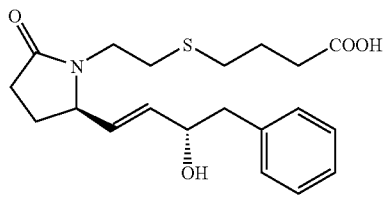

TLC: Rf 0.40 (Chloroform:Methanol=10:1);
NMR: δ 7.32-7.19 (m, 5H), 5.77 (dd, J=15.3, 5.4 Hz, 1H), 5.51 (ddd, J=15.3, 8.4, 1.2 Hz, 1H), 4.41 (m, 1H), 4.11 (m, 1H), 3.62 (m, 1H), 2.95 (m, 1H), 2.86 (d, J=6.6 Hz, 2H), 2.65-2.20 (m, 9H), 2.00-1.80 (m, 2H), 1.70 (m, 1H).

Example 3(j)

(15α,13E)-9-Oxo-15-hydroxy-16-(3-methylphenyl)-17,18,19,20-tetranor-5-thia-8-azaprost-13-enoic acid

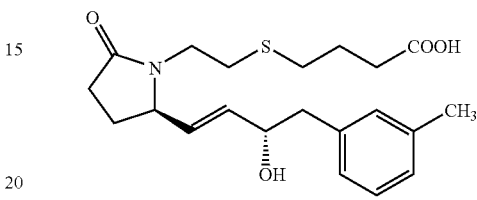

TLC: Rf 0.32 (Chloroform:Methanol=10:1);
NMR: δ 7.21 (m, 1H), 7.07-6.98 (m, 3H), 5.78 (dd, J=15.3, 5.4 Hz, 1H), 5.52 (ddd, J=15.3, 8.7, 1.2 Hz, 1H), 4.43 (m, 1H), 4.11 (m, 1H), 3.62 (m, 1H), 2.95 (m, 1H), 2.83-2.20 (m, 11H), 2.34 (S, 3H), 2.00-1.80 (m, 2H), 1.70 (m, 1H).

Example 3(k)

(15α,13E)-9-Oxo-15-hydroxy-16-(3-fluorophenyl)-17,18,19,20-tetranor-5-thia-8-azaprost-13-enoic acid

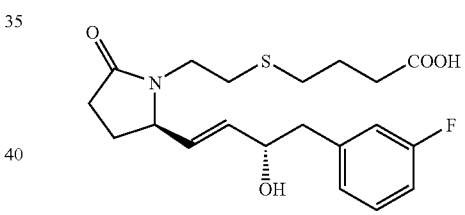

TLC: Rf 0.38 (Chloroform:Methanol:Water 9:1:0.1);
NMR: δ 7.27 (m, 1H), 7.00-6.89 (m, 3H), 5.75 (dd, J=15.4, 5.5 Hz, 1H), 5.50 (dd, J=15.4, 8.5 Hz, 1H), 4.42 (m, 1H), 4.11 (m, 1H), 3.62 (m, 1H), 2.92 (m, 1H), 2.84 (d, J=6.9 Hz, 2H), 2.67-2.51 (m, 4H), 2.50-2.41 (m, 2H), 2.38 (t, J=7.1 Hz, 2H), 2.22 (m, 1H), 1.94-1.83 (m, 2H), 1.66 (m, 1H).

Example 3(l)

(15α,13E)-9-Oxo-15-hydroxy-16-(4-fluorophenyl)-17,18,19,20-tetranor-5-thia-8-azaprost-13-enoic acid

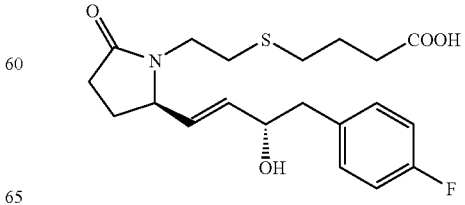

TLC: Rf 0.38 (Chloroform:Methanol:Water=9:1:0.1);

NMR: δ 7.20-7.16 (m, 2H), 7.04-6.96 (m, 2H), 5.75 (dd, J=15.4, 6.0 Hz, 1H), 5.50 (ddd, J=15.4, 8.5, 1.1 Hz, 1H), 4.39 (m, 1H), 4.11 (m, 1H), 3.62 (m, 1H), 2.95 (m, 1H), 2.82 (d, J=6.6 Hz, 2H), 2.67-2.53 (m, 4H), 2.52-2.43 (m, 2H), 2.39 (t, J=7.1 Hz, 2H), 2.22 (m, 1H), 1.94-1.83 (m, 2H), 1.68 (m, 1H).

Example 3(m)

(15α,13E)-9-Oxo-15-hydroxy-16-(3,4-difluorophenyl)-17,18,19,20-tetranor-5-thia-8-azaprost-13-enoic acid

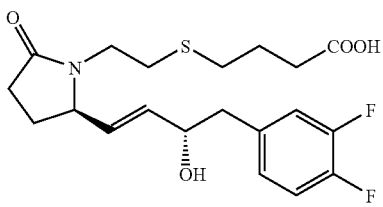

TLC: Rf 0.24 (Chloroform:Methanol=10:1);

NMR: δ 7.14-7.00 (m, 2H), 6.92 (m, 1H), 5.76 (dd, J=15.6, 5.4 Hz, 1H), 5.54 (ddd, J=15.6, 8.4, 1.2 Hz, 1H), 4.40 (m, 1H), 4.12 (m, 1H), 3.63 (m, 1H), 3.00 (m, 1H), 2.82-2.10 (m, 1H), 2.00-1.60 (m, 3H).

Example 3(n)

(15α,13E)-9-Oxo-15-hydroxy-16-(naphthalen-2-yl)-17,18,19,20-tetranor-5-thia-8-azaprost-13-enoic acid

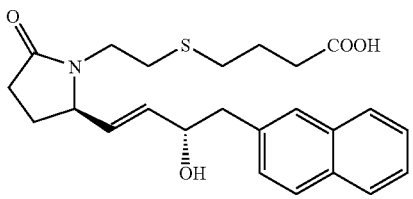

TLC: Rf 0.27 (Chloroform:Methanol=10:1);

NMR: δ 7.82-7.77 (m, 3H), 7.65 (s, 1H), 7.50-7.40 (m, 2H), 7.32 (dd, J=8.4, 1.5 Hz, 1H), 5.80 (dd, J=15.6, 5.1 Hz, 1H), 5.51 (ddd, J=15.6, 8.4, 1.2 Hz, 1H), 4.53 (m, 1H), 4.11 (m, 1H), 3.53 (m, 1H), 3.02 (d, J=6.6 Hz, 2H), 2.86 (m, 1H), 2.60-2.10 (m, 9H), 2.00-1.60 (m, 3H).

Example 3(o)

(15α,13E)-2,3-Methano-9-oxo-15-hydroxy-16-(3-chlorophenyl)-17,18,19,20-tetranor-5-thia-8-azaprost-13-enoic acid

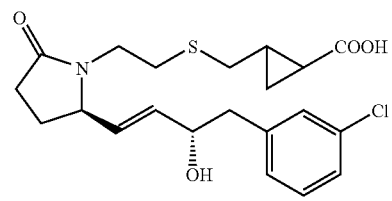

TLC: Rf 0.37 (Chloroform:Methanol=10:1);

NMR: δ 7.26-7.19 (m, 3H), 7.09 (m, 1H), 5.73 (dd, J=15.3, 5.7 Hz, 1H), 5.48 (m, 10H), 4.41 (m, 1H), 4.12 (m, 1H), 3.62 (m, 1H), 3.05-2.20 (m, 9H), 2.83 (d, J=6.3 Hz, 2H), 1.80-1.60 (m, 2H), 1.34 (m, 1H), 0.90 (m, 1H).

Example 3(p)

(15α,13E)-9-Oxo-15-hydroxy-16-(3-t-butylphenyl)-17,18,19,20-tetranor-5-thia-8-azaprost-13-enoic acid

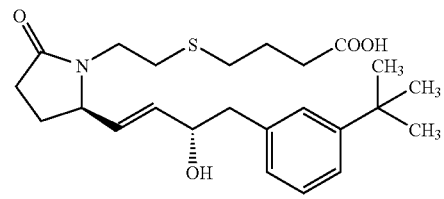

TLC: Rf 0.43 (Chloroform:Methanol=9:1);

NMR: δ 7.38-7.20 (m, 3H), 7.06-6.99 (m, 1H), 5.79 (dd, J=15.3, 5.4 Hz, 1H), 5.54 (dd, J=15.3, 8.4 Hz, 1H), 4.43 (m, 1H), 4.12 (m, 1H), 3.62 (m, 1H), 3.37-2.20 (m, 14H), 1.99-1.83 (m, 2H), 1.73 (m, 1H), 1.31 (s, 9H).

Example 3(q)

(13E)-9-Oxo-15-hydroxy-16α-methyl-16-phenyl-17,18,19,20-tetranor-5-thia-8-azaprost-13-enoic acid

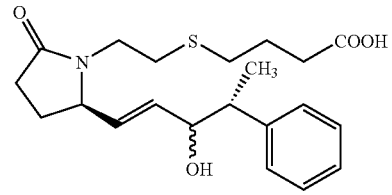

TLC: Rf 0.32 (Chloroform:Methanol=8:1);

NMR: δ 7.40-7.12 (m, 5H), 5.58 (dd, J=15.3, 6.3 Hz, 1H), 5.36 (ddd, J=15.3, 8.4, 0.9 Hz, 1H), 4.26 (m, 1H), 4.02 (m, 1H), 3.90-2.80 (br, 2H), 3.52 (m, 1H), 2.85 (m, 1H), 2.66 (m, 1H), 2.60-2.06 (m, 9H), 1.98-1.80 (m, 2H), 1.61 (m, 1H), 1.35 (d, J=7.2 Hz, 3H).

Stereochemistry at C15 position is not determined, but this compound is a single isomer.

Example 3(r)

(13E)-9-Oxo-15-hydroxy-16β-methyl-16-phenyl-17,18,19,20-tetranor-5-thia-8-azaprost-13-enoic acid

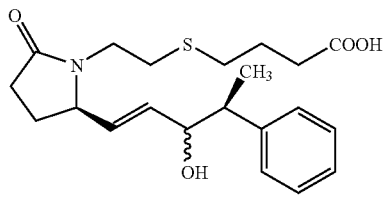

TLC: Rf 0.25 (Chloroform:Methanol=8:1);

NMR: δ 7.42-7.14 (m, 5H), 5.73 (dd, J=15.3, 6.3 Hz, 1H), 5.55 (dd, J=15.3, 8.1 Hz, 1H), 4.24 (dd, J=6.6, 6.3 Hz, 1H), 4.15 (m, 1H), 3.71 (m, 1H), 3.60-2.70 (br, 2H), 3.06 (m, 1H), 2.84 (m, 1H), 2.76-2.14 (m, 9H), 2.00-1.82 (m, 2H), 1.71 (m, 1H), 1.27 (d, J=7.2 Hz, 3H).

Stereochemistry at C15 position is not determined, but this compound is a single isomer.

Example 3(s)

(15α,13E)-9-Oxo-15-hydroxy-16-(3-ethylphenyl)-17,18,19,20-tetranor-5-thia-8-azaprost-13-enoic acid

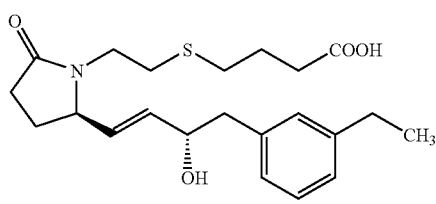

TLC: Rf 0.49 (Chloroform:Methanol=9:1);

NMR: δ 7.24 (m, 1H), 7.13-6.98 (m, 3H), 5.78 (dd, J=15.4, 5.5 Hz, 1H), 5.52 (ddd, J=15.4, 8.2, 1.1 Hz, 1H), 4.42 (m, 1H), 4.12 (m, 1H), 3.63 (m, 1H), 3.00 (m, 1H), 2.90-2.77 (m, 2H), 2.67-2.35 (m, 10H), 2.23 (m, 1H), 1.95-1.85 (m, 2H), 1.72 (m, 1H), 1.22 (t, J=7.4 Hz, 3H).

Example 3(t)

(15α,13E)-9-Oxo-15-hydroxy-16-(4-fluoro-3-trifluoromethylphenyl)-17,18,19,20-tetranor-5-thia-8-azaprost-13-enoic acid

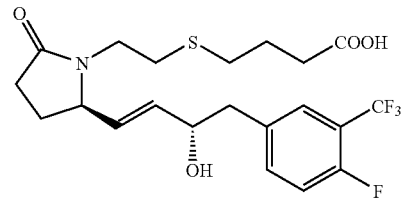

TLC: Rf 0.35 (Chloroform:Methanol=8:1);

NMR: δ 7.52-7.35 (m, 2H), 7.14 (dd, J=9.3, 9.3 Hz, 1H), 5.77 (dd, J=15.3, 5.4 Hz, 1H), 5.54 (ddd, J=15.3, 8.1, 0.9 Hz, 1H), 4.42 (m, 1H), 4.14 (m, 1H), 4.06-1.10 (m, 18H).

Example 3(u)

(15α,13E)-9-Oxo-15-hydroxy-16-(4-fluoro-3-methylphenyl)-17,18,19,20-tetranor-5-thia-8-azaprost-13-enoic acid

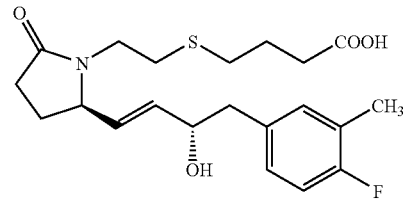

TLC: Rf 0.26 (Chloroform:Methanol=8:1);

NMR: δ 7.06-6.88 (m, 3H), 5.75 (dd, J=15.3, 5.4 Hz, 1H), 5.51 (dd, J=15.3, 8.4 Hz, 1H), 4.39 (m, 1H), 4.12 (m, 1H), 3.80-2.80 (br, 2H), 3.63 (m, 1H), 2.99 (m, 1H), 2.86-2.06 (m, 14H), 1.98-1.62 (m, 3H).

Example 3(v)

(15α,13E)-9-Oxo-15-hydroxy-16-(3-chloro-4-fluorophenyl)-17,18,19,20-tetranor-5-thia-8-azaprost-13-enoic acid

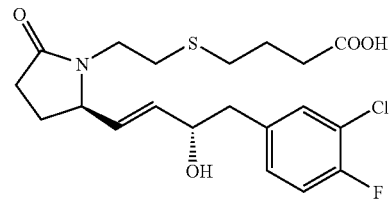

TLC: Rf 0.22 (Chloroform:Methanol=8:1);

NMR: δ 7.24 (m, 1H), 7.13-7.04 (m, 2H), 5.75 (dd, J=15.3, 5.7 Hz, 1H), 5.51 (ddd, J=15.3, 8.4, 0.9 Hz, 1H), 4.40 (m, 1H), 4.13 (m, 1H), 4.10-3.10 (br, 2H), 3.63 (m, 1H), 2.99 (m, 1H), 2.88-2.14 (m, 11H), 2.00-1.56 (m, 3H).

Example 3(w)

(15β,13E)-9-Oxo-15-hydroxy-16-(3-chlorophenyl)-17,18,19,20-tetranor-5-thia-8-azaprost-13-enoic acid

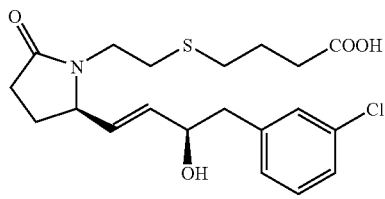

TLC: Rf 0.48 (Chloroform:Methanol=9:1);
NR: δ 7.32-7.18 (m, 3H), 7.10 (m, 1H), 5.75 (dd, J=15.0, 6.6 Hz, 1H), 5.41 (dd, J=15.0, 8.7 Hz, 1H), 4.39 (m, 1H), 4.11 (m, 1H), 3.62 (m, 1H), 3.18-2.12 (m, 13H), 1.98-1.82 (m, 2H), 1.60 (m, 1H).

Example 3(x)

(15α,13E)-9-Oxo-15-hydroxy-16-(3-methylphenyl)-5-(5-carboxythiazol-2-yl)-1,2,3,4,17,18,19,20-octanor-5-thia-8-azaprost-13-ene

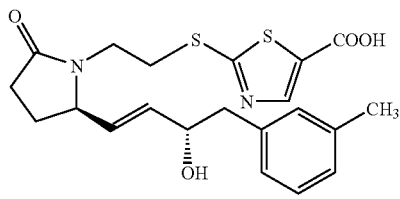

TLC: Rf 0.62 (Chloroform:Methanol:Acetic Acid=18:2:1);
NMR: δ 8.17 (s, 1H), 7.14 (t, J=8 Hz, 1H), 7.0-6.9 (m, 3H), 5.68 (dd, J=15, 7 Hz, 1H), 5.35 (dd, J=15, 9 Hz, 1H), 4.31 (q, J=7 Hz, 1H), 4.25-4.1 (m, 1H), 3.7-3.55 (m, 1H), 3.4-3.2 (m, 2H), 3.05-2.9 (m, 1H), 2.88 (dd, J=13, 6 Hz, 1H), 2.63 (dd, J=13, 7 Hz, 1H), 2.4-2.25 (m, 5H), 2.25-2.1 (m, 1H), 1.75-1.6 (m, 1H).

Example 3(y)

(15α,13E)-9-Oxo-15-hydroxy-16-(3-chlorophenyl)-4-(3-hydroxyisoxazol-5-yl)-1,2,3,17,18,19,20-heptanor-5-thia-8-azaprost-13-ene

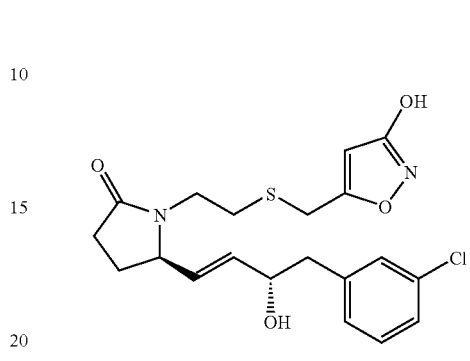

TLC: Rf 0.44 (Chloroform:Methanol=8:1);
NMR: δ 7.25-7.16 (m, 3H), 7.08 (m, 1H), 5.87 (s, 1H), 5.72 (dd, J=15.3, 5.7 Hz, 1H), 5.48 (ddd, J=15.3, 8.4, 1.2 Hz, 1H), 4.44 (m, 1H), 4.06 (m, 1H), 3.75-3.52 (m, 3H), 2.93 (m, 1H), 2.88-2.48 (m, 6H), 2.42-2.30 (m, 2H), 2.22 (m, 1H), 1.67 (m, 1H).

Hydrolysis of the ester (procedure of Example 2) was not done. The hydroxyl group bound isoxazole ring was protected by methoxymethyl group, and was removed protecting group at final step.

Example 3(z)

(15α,13E)-9-Oxo-15-hydroxy-16-(3-chlorophenyl)-2-(5-oxo-1,2,4-oxadiazol-3-yl)-1,17,18,19,20-pentanor-5-thia-8-azaprost-13-ene

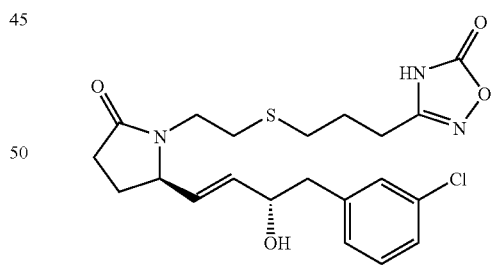

TLC: Rf 0.39 (Chloroform:Methanol=9:1);
NMR: δ 7.38-7.15 (m, 3H), 7.14-7.02 (m, 1H), 5.74 (dd, J=15.3, 6.0 Hz, 1H), 5.46 (ddd, J=15.3, 8.7, 1.0 Hz, 1H), 4.41 (m, 1H), 4.02 (m, 1H), 3.57 (m, 1H), 3.00-2.19 (m, 12H), 2.17-1.60 (m, 3H).

Hydrolysis of the ester (procedure of Example 2) was not done. The NH group bound 1,2,4-oxadiazole ring was protected by Boc group, and was removed protecting group at final step.

Example 3(aa)

(15α,13E)-9-Oxo-15-hydroxy-16-(3-chlorophenyl)-2-(5-oxo-1,2,4-thiadiazol-3-yl)-1,17,18,19,20-pentanor-5-thia-8-azarost-13-ene

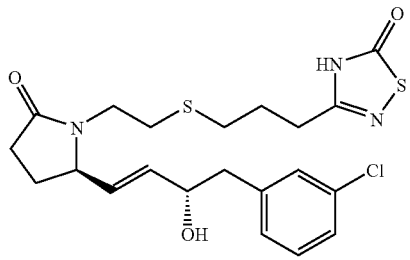

TLC: Rf 0.30 (Chloroform:Methanol=9:1);

NMR: δ 7.37-7.18 (m, 3H), 7.12-7.04 (m, 1H), 5.74 (dd, J=15.0, 6.0 Hz, 1H), 5.47 (ddd, J=15.0, 8.7, 1.2 Hz, 1H), 4.42 (m, 1H), 4.03 (m, 1H), 3.60 (m, 1H), 3.00-2.70 (m, 4H), 2.69-2.38 (m, 7H), 2.28 (m, 1H), 2.15-1.70 (m, 3H).

Hydrolysis of the ester (procedure of Example 2) was not done. The NH group bound 1,2,4-oxadiazole ring was protected by Boc group, and was removed protecting group at final step.

Example 3(bb)

(15α,13E)-1-Methoxy-9-oxo-15-hydroxy-16-(3-chlorophenyl)-17,18,19,20-tetranor-5-thia-8-aza-prost-13-ene

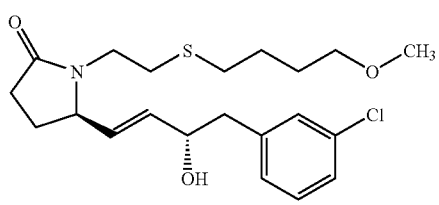

TLC: Rf 0.57 (Chloroform:Methanol=9:1);

NMR: δ 7.32-7.18 (m, 3H), 7.10 (m, 1H), 5.74 (dd, J=15.4, 5.8 Hz, 1H), 5.51 (ddd, J=15.4, 8.5, 0.8 Hz, 1H), 4.41 (m, 1H), 4.14 (m, 1H), 3.62 (m, 1H), 3.40 (m, 2H), 3.32 (s, 3H), 2.94 (m, 1H), 2.82 (d, J=6.6 Hz, 2H), 2.71-2.48 (m, 4H), 2.42-2.35 (m, 2H), 2.24 (m, 1H), 1.77-1.63 (m, 5H).

Hydrolysis of the ester (procedure of Example 2) was not done.

Example 3(cc)

(15α,13E)-9-Oxo-15-hydroxy-16-(4-fluorophenyl)-5-(4-carboxythiazol-2-yl)-1,2,3,4,17,18,19,20-octanor-5-thia-8-zaprost-13-ene

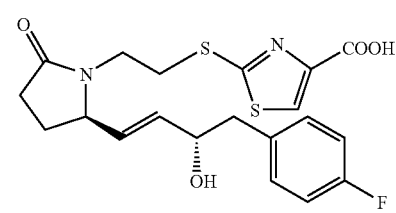

TLC: Rf 0.18 (Chloroform:Methanol:Acetic Acid=9:1:0.1);

NMR: δ 8.09 (s, 1H), 7.18-7.12 (m, 2H), 7.06-6.95 (m, 2H), 5.79 (dd, J=15.3, 5.7 Hz, 1H), 5.51 (dd, J=15.3, 9.0 Hz, 1H), 4.39 (m, 1H), 4.11 (m, 1H), 3.73 (m, 1H), 3.40-2.19 (m, 10H), 1.74 (m, 1H).

Example 3(dd)

(15α,13E)-1-Methoxy-9-oxo-15-hydroxy-16-(4-fluorophenyl)-17,18,19,20-tetranor-5-thia-8-aza-prost-13-ene

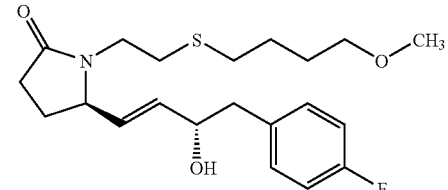

TLC: Rf 0.59 (Chloroform:Methanol=9:1);

NMR: δ 7.19-7.15 (m, 2H), 7.04-6.98 (m, 2H), 5.74 (dd, J=15.3, 5.7 Hz, 1H), 5.50 (ddd, J=15.3, 8.4, 1.2 Hz, 1H), 4.37 (m, 1H), 4.10 (m, 1H), 3.62 (m, 1H), 3.40-3.36 (m, 2H), 3.30 (s, 3H), 2.96 (m, 1H), 2.88-2.75 (m, 2H), 2.69-2.49 (m, 4H), 2.40-2.34 (m, 2H), 2.24 (m, 1H), 1.76-1.64 (m, 5H).

Hydrolysis of the ester (procedure of Example 2) was not done.

Example 3(ee)

(15α,13E)-9-Oxo-15-hydroxy-16-(4-fluorophenyl)-5-(5-(5-oxo-1,2,4-oxadiazol-3-yl)thiazol-2-yl)-1,2,3,4,17,18,19,20-octanor-5-thia-8-azaprost-13-ene

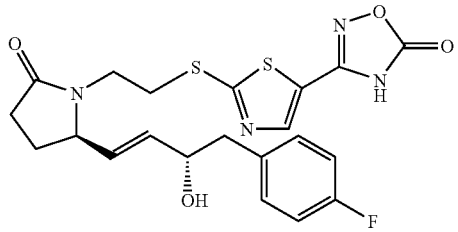

TLC: Rf 0.50 (Chloroform:Methanol:Acetic Acid=9:1:0.2);

NMR (CDCl$_3$+CD$_3$OD): δ 8.03 (s, 1H), 7.20-7.07 (m, 2H), 7.02-6.94 (m, 2H), 5.72 (dd, J=15.3, 5.7 Hz, 1H), 5.44 (dd, J=15.3, 8.7 Hz, 1H), 4.35 (m, 1H), 4.14 (m, 1H), 3.68 (m, 1H), 3.65-3.10 (m, 3H), 2.91-2.67 (m, 2H), 2.46-2.11 (m, 3H), 1.72 (m, 1H).

Hydrolysis of the ester (procedure of Example 2) was not done. The NH group bound 1,2,4-oxadiazole ring was protected by Boc group, and was removed protecting group at final step.

Example 3(ff)

(15α,13E)-9-Oxo-15-hydroxy-16-(3-chlorophenyl)-17,18,19,20-tetranor-5-thia-8-aza-10-oxaprost-13-enoic acid

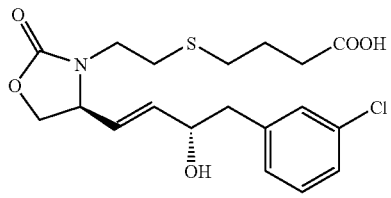

TLC: Rf 0.35 (Chloroform:Methanol=9:1);

NMR: δ 7.32-7.20 (m, 3H), 7.10 (m, 1H), 5.88 (dd, J=15.4, 5.2 Hz, 1H), 5.56 (ddd, J=15.4, 8.5, 1.4 Hz, 1H), 4.50-4.29 (m, 2H), 4.43 (dd, J=8.5, 8.2 Hz, 1H), 3.89 (dd, J=8.5, 8.2 Hz, 1H), 3.46 (m, 1H), 3.10 (m, 1H), 2.84-2.80 (m, 2H), 2.77-2.44 (m, 6H), 1.98-1.87 (m, 2H).

Example 3(g)

(15α,13E)-9-Oxo-15-hydroxy-16-(4-fluorophenyl)-17,18,19,20-tetranor-5-thia-8-aza-10-oxaprost-13-enoic acid

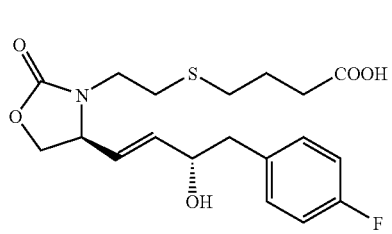

TLC: Rf 0.34 (Chloroform:Methanol=9:1);

NMR: δ 7.20-7.13 (m, 2H), 7.08-6.98 (m, 2H), 5.88 (dd, J=15.4, 5.2 Hz, 1H), 5.57 (ddd, J=15.4, 8.5, 1.4 Hz, 1H), 4.47-4.28 (m, 2H), 4.42 (dd, J=8.5, 8.2 Hz, 1H), 3.91 (dd, J=8.5, 8.2 Hz, 1H), 3.46 (m, 1H), 3.12 (m, 1H), 2.90-2.78 (m, 2H), 2.75-2.43 (m, 6H), 1.97-1.86 (m, 2H).

Example 3(hh)

(15α,13E)-9-Oxo-15-hydroxy-16-(3-methylphenyl)-17,18,19,20-tetranor-5-thia-8-aza-10-oxaprost-13-enoic acid

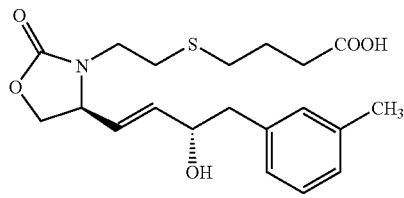

TLC: Rf 0.35 (Chloroform:Methanol=9:1);

NMR: δ 7.22 (t, J=7.4 Hz, 1H), 7.11-6.97 (m, 3H), 5.90 (dd, J=15.4, 5.2 Hz, 1H), 5.57 (ddd, J=15.4, 8.8, 1.4 Hz, 1H), 4.51-4.28 (m, 3H), 3.91 (dd, J=8.2, 8.0 Hz, 1H), 3.45 (m, 1H), 3.11 (m, 1H), 2.89-2.44 (m, 8H), 2.36 (s, 3H), 1.96-1.85 (m, 2H).

Example 3(ii)

(15α,13E)-9-Oxo-15-hydroxy-16-(3-methylaminomethylphenyl)-17,18,19,20-tetranor-5-thia-8-azaprost-13-enoic acid hydrochloride

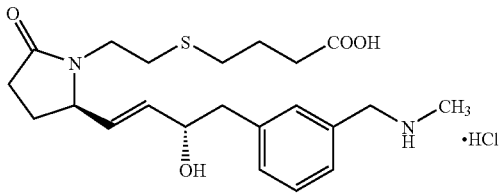

TLC: Rf 0.11 (Chloroform:Methanol:Acetic Acid=9:1:0.1);
NMR (CD$_3$OD): δ 7.50-7.30 (m, 4H), 5.76 (dd, J=15.0, 6.6 Hz, 1H), 5.45 (dd, J=15.0, 8.7 Hz, 1H), 4.40 (m, 1H), 4.24-4.11 (m, 3H), 3.50 (m, 1H), 2.96-2.80 (m, 3H), 2.71 (s, 3H), 2.63-2.43 (m, 3H), 2.42-2.20 (m, 4H), 1.93-1.62 (m, 3H).
The amino group bound benzene ring was protected by Boc group, and was removed protecting group at final step.

Example 3(jj)

(15α,13E)-9-Oxo-5-hydroxy-16-(3-ethyl-4-fluorophenyl)-17,18,19,20-tetranor-5-thia-8-azaprost-13-enoic acid

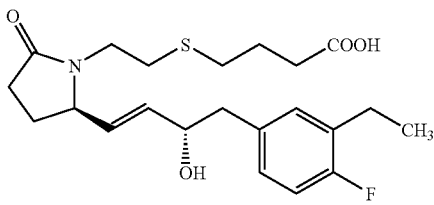

TLC: Rf 0.35 (Chloroform:Methanol=9:1);
NMR: δ 7.08-6.93 (m, 3H), 5.75 (dd, J=15.3, 5.4 Hz, 1H), 5.52 (ddd, J=15.3, 8.7, 1.2 Hz, 1H), 4.40 (m, 1H), 4.12 (m, 1H), 3.62 (m, 1H), 3.00 (m, 1H), 2.87-2.18 (m, 11H), 1.98-1.82 (m, 2H), 1.71 (m, 1H), 1.22 (t, J=7.5 Hz, 3H).

Example 3(kk)

(15α,13E)-9-Oxo-5-hydroxy-16-(5-methylfuran-2-yl)-17,18,19,20-tetranor-5-thia-8-azaprost-13-enoic acid

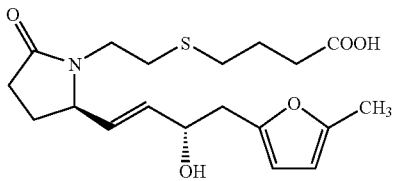

TLC: Rf 0.34 (Chloroform:Methanol=9:1);
NMR: δ 5.99 (d, J=2.7 Hz, 1H), 5.88 (m, 1H), 5.75 (dd, J=15.3, 5.4 Hz, 1H), 5.55 (ddd, J=15.3, 8.7, 1.0 Hz, 1H), 4.47 (m, 1H), 4.15 (m, 1H), 3.63 (m, 1H), 3.06 (m, 1H), 2.92-2.78 (m, 2H), 2.75-2.18 (m, 12H), 2.00-1.81 (m, 2H), 1.72 (m, 1H).

Example 3(ll)

(15α,13E)-9-Oxo-15-hydroxy-16-(2-methyloxazol-5-yl)-17,18,19,20-tetranor-5-thia-8-azaprost-13-enoic acid

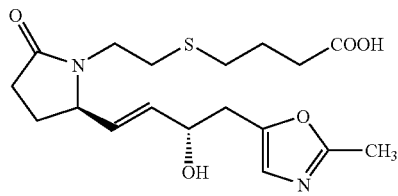

TLC: Rf 0.35 (Chloroform:Methanol:Acetic Acid=18:2:1);
NMR: δ 6.95 (s, 1H), 5.80 (dd, J=16, 5 Hz, 1H), 5.66 (dd, J=16, 8 Hz, 1H), 4.6-4.5 (m, 1H), 4.25-4.1 (m, 10H), 3.7-3.55 (m, 1H), 3.2-3.05 (m, 1H), 3.0-2.8 (m, 2H), 2.75-2.5 (m, 7H), 2.5-2.35 (m, 4H), 2.35-2.2 (m, 1H), 2.0-1.85 (m, 2H), 1.85-1.7 (m, 1H).

Example 3(mm)

(15α,13E)-9-Oxo-15-hydroxy-16-(benzofuran-2-yl)-17,18,19,20-tetranor-5-thia-8-azaprost-13-enoic acid

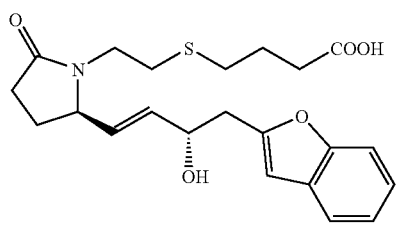

TLC: Rf 0.43 (Chloroform:Methanol=19:1);
NMR: δ 7.55-7.5 (m, 1H), 7.41 (d, J=7 Hz, 1H), 7.25-7.15 (m, 2H), 6.52 (s, 1H), 5.80 (dd, J=15, 6 Hz, 1H), 5.57 (dd, J=15, 8 Hz, 1H), 4.63 (q, J=6 Hz, 1H), 4.15-4.05 (m, 1H), 3.58 (pent, J=7 Hz, 1H), 3.04 (d, J=6 Hz, 2H), 3.0-2.9 (m, 1H), 2.65-2.3 (m, 8H), 2.3-2.1 (m, 1H), 1.95-1.8 (m, 2H), 1.75-1.6 (m, 1H).

Example 3(nn)

(15α,13E)-9-Oxo-15-hydroxy-16-(5-ethylfuran-2-yl)-17,18,19,20-tetranor-5-thia-8-azaprost-13-enoic acid

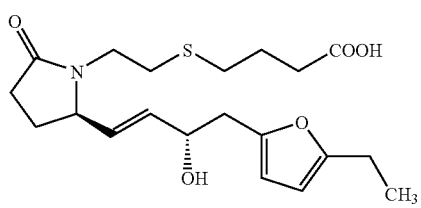

TLC: Rf 0.29 (Chloroform:Methanol=9:1);
NMR: δ 6.00 (d, J=3.0 Hz, 1H), 5.88 (d, J=3.0 Hz, 1H), 5.75 (dd, J=15.3, 5.4 Hz, 1H), 5.55 (ddd, J=15.3, 8.4, 1.0 Hz, 1H), 4.48 (m, 1H), 4.15 (m, 1H), 3.64 (m, 1H), 3.03 (m, 1H), 2.93-2.78 (m, 2H), 2.71-2.18 (m, 12H), 1.99-1.82 (m, 2H), 1.72 (m, 1H), 1.21 (t, J=7.2 Hz, 3H).

Example 3(oo)

(15α,13E)-9-Oxo-15-hydroxy-16-(4,5-dimethylfuran-2-yl)-17,18,19,20-tetranor-5-thia-8-azaprost-13-enoic acid

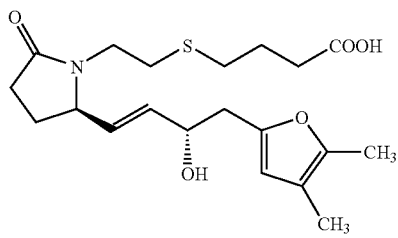

TLC: Rf 0.31 (Chloroform:Methanol=9:1);
NMR: δ 5.89 (s, 1H), 5.75 (dd, J=15.3, 5.1 Hz, 1H), 5.55 (dd, J=15.3, 8.7 Hz, 1H), 4.44 (m, 1H), 4.15 (m, 1H), 3.63 (m, 1H), 3.07 (m, 1H), 2.86-2.09 (m, 15H), 1.99-1.63 (m, 6H).

Example 3(pp)

(15α,13E)-9-Oxo-15-hydroxy-16-(3-methylfuran-2-yl)-17,18,19,20-tetranor-5-thia-8-azaprost-13-enoic acid

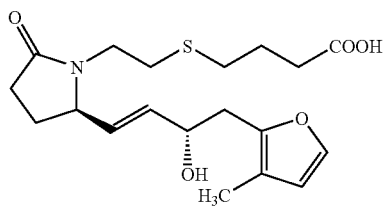

TLC: Rf 0.41 (Chloroform:Methanol=9:1);
NMR: δ 7.24 (d, J=1.8 Hz, 1H), 6.19 (d, J=1.8 Hz, 1H), 5.75 (dd, J=16, 6 Hz, 1H), 5.53 (dd, J=16, 9 Hz, 1H), 4.53- 4.44 (m, 1H), 4.18-4.08 (m, 1H), 3.70-3.59 (m, 1H), 3.10-2.97 (m, 1H), 2.83 (d, J=6 Hz, 2H), 2.72-2.32 (m, 8H), 2.30-2.18 (m, 1H), 2.0-1.8 (m, 5H), 1.81-1.64 (m, 1H).

Example 3(qq)

(15α,13E)-9-Oxo-15-hydroxy-16-(3-nitrophenyl)-17,18,19,20-tetranor-5-thia-8-azaprost-13-enoic acid

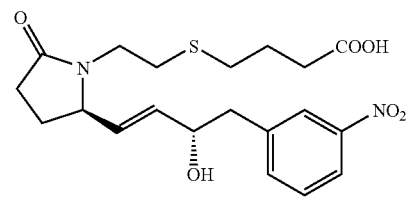

TLC: Rf 0.59 (Chloroform:Methanol=9:1);
NMR: δ 8.01 (m, 1H), 7.60-7.42 (m, 3H), 5.78 (dd, J=15.0, 5.4 Hz, 1H), 5.55 (dd, J=15.0, 8.4 Hz, 1H), 4.50 (m, 1H), 4.16 (m, 1H), 3.60 (m, 1H), 3.10-2.18 (m, 13H), 1.98-1.81 (m, 2H), 1.78-1.59 (m, 1H).

Example 3(rr)

(15α,13E)-9-Oxo-15-hydroxy-16-(3-methylisoxazol-5-yl)-17,18,19,20-tetranor-5-thia-8-azaprost-13-enoic acid

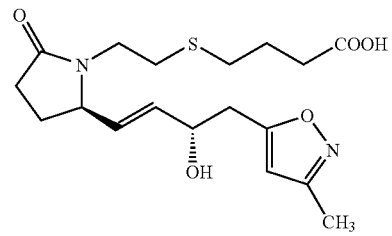

TLC: Rf 0.42 (Chloroform:Methanol=9:1);
NMR: δ 5.96 (s, 1H), 5.79 (dd, J=15.3, 5.1 Hz, 1H), 5.60 (dd, J=15.3, 8.1 Hz, 1H), 4.59 (m, 1H), 4.17 (m, 1H), 4.00-3.20 (m, 2H), 3.10-2.99 (m, 3H), 2.75-2.20 (m, 12H), 1.98-1.80 (m, 2H), 1.71 (m, 1H).

EXAMPLE 4

(15α,13E)-9-Oxo-15-hydroxy-16-(3-methoxymethylphenyl)-17,18,19,20-tetranor-8-azaprost-13-en-1-ol

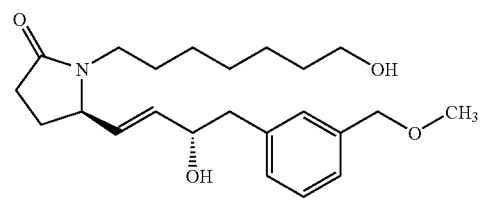

To a solution of the compound prepared in Example 1 (220 mg) in tetrahydrofuran (2 mL), lithium borohydride (23 mg) was added at room temperature, and the mixture was stirred for 2.5 hours at room temperature then 3 hours at 50° C. After cooling, the mixture was added by ethanol and water, and extracted by ethyl acetate. The organic layer was washed with brine, dried over an anhydrous sodium sulfate, concentrated under reduced pressure and was purified by column chromatography on silica gel (from ethyl acetate:hexane=from 50:1 to 10:1) to give the title compound (171 mg) having the following physical data.

TLC: Rf 0.16 (Ethyl Acetate:Methanol=85:15);
NMR: δ 7.38-7.11 (m, 4H), 5.73 (dd, J=15.3, 6.0 Hz, 1H), 5.50 (ddd, J=15.3, 8.0, 1.2 Hz, 1H), 4.50-4.37 (m, 3H), 4.08-3.99 (m, 1H), 3.62 (t, J=6.6 Hz, 2H), 3.53-3.37 (m, 4H), 2.92-2.70 (m, 3H), 2.46-2.12 (m, 3H), 1.94 (bs, 1H), 1.78-1.20 (m, 12H).

Example 4(a) to Example 4(w)

By the same procedure as describe in Example 4 using corresponding carboxylic acid ester derivatives instead of the compound prepared in Example 1, the compound of the present invention having the following physical data were obtained.

Example 4(a)

(15α,13E)-9-Oxo-15-hydroxy-16-(3-methoxymethylphenyl)-17,18,19,20-tetranor-5-thia-8-azaprost-13-en-1-ol

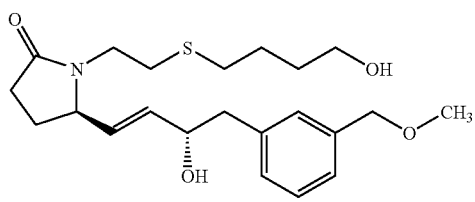

TLC: Rf 0.18 (Ethyl Acetate:Methanol=50:1);
NMR: δ 7.35-7.10 (m, 4H), 5.77 (dd, J=15, 6 Hz, 1H), 5.52 (dd, J=15, 9 Hz, 1H), 4.43 (s, 2H), 4.45-4.35 (m, 1H), 4.15-4.05 (m, 1H), 3.70-3.55 (m, 3H), 3.42 (s, 3H), 3.05-2.95 (m, 1H), 2.9-2.75 (m, 2H), 2.7-2.45 (m, 4H), 2.4-2.3 (m, 2H), 2.3-2.15 (m, 1H), 2.1-1.9 (br, 2H), 1.8-1.5 (m, 5H).

Example 4(b)

(15α,13E)-9-Oxo-15-hydroxy-16-(3,4-difluorophenyl)-17,18,19,20-tetranor-8-azaprost-13-en-1-ol

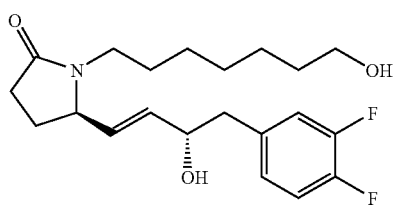

TLC: Rf 0.18 (Ethyl Acetate);
NMR: δ 7.15-7.00 (m, 2H), 6.93 (m, 1H), 5.72 (dd, J=15.4, 5.8 Hz, 1H), 5.50 (dd, J=15.4, 9.3 Hz, 1H), 4.38 (m, 1H), 4.03 (m, 1H), 3.62 (t, J=6.3 Hz, 2H), 3.48 (m,H), 2.80 (d, J=6.6 Hz, 2H), 2.74 (m, 1H), 2.46-2.26 (m, 2H), 2.22 (m, 1H), 1.76-1.20 (m, 11H).

Example 4(c)

(15α,13E)-9-Oxo-15-hydroxy-16-(3-chlorophenyl)-17,18,19,20-tetranor-8-azaprost-13-en-1-ol

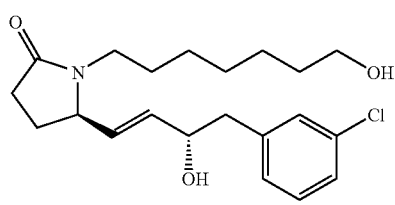

TLC: Rf 0.39 (Chloroform:Methanol=9:1);
NMR: δ 7.24-7.18 (m, 3H), 7.08 (m, 1H), 5.71 (dd, J=15.4, 6.0 Hz, 1H), 5.48 (ddd, J=15.4, 8.2, 0.8 Hz, 1H), 4.42 (m, 1H), 4.04 (m, 1H), 3.63 (t, J=6.6 Hz, 2H), 3.47 (m, 1H), 2.82 (d, J=6.6 Hz, 2H), 2.72 (m, 1H), 2.44-2.26 (m, 2H), 2.21 (m, 1H), 1.77-1.20 (m, 11H).

Example 4(d)

(15α,13E)-9-Oxo-15-hydroxy-16-(3-chlorophenyl)-17,18,19,20-tetranor-5-thia-8-azaprost-13-en-1-ol

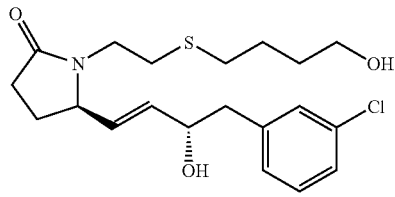

TLC: Rf 0.17 (Ethyl Acetate);
NMR: δ 7.29-7.19 (m, 3H), 7.08 (m, 1H), 5.74 (dd, J=15.4, 5.8 Hz, 1H), 5.49 (dd, J=15.4, 8.5 Hz, 1H), 4.40 (m, 1H), 4.10 (m, 1H), 3.70-3.67 (m, 2H), 3.65 (m, 1H), 2.95 (m, 1H), 2.84 (d, J=6.6 Hz, 2H), 2.68-2.47 (m, 4H), 2.40-2.34 (m, 2H), 2.23 (m, 1H), 2.09 (br. s, 1H), 1.75-1.58 (m, 5H).

Example 4(e)

(15α,13E)-9-Oxo-15-hydroxy-16-phenyl-17,18,19,20-tetranor-5-thia-8-azaprost-13-en-1-ol

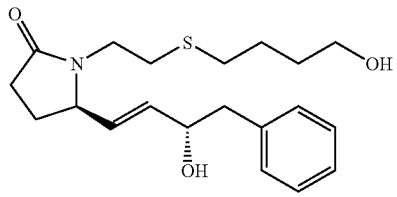

TLC: Rf 0.18 (Ethyl Acetate);
NMR: δ 7.37-7.16 (m, 5H), 5.76 (dd, J=15.4, 5.8 Hz, 1H), 5.49 (ddd, J=15.4, 8.5, 1.1 Hz, 1H), 4.42 (m, 1H), 4.09 (m, 1H), 3.71-3.56 (m, 3H), 2.96 (m, 1H), 2.84 (d, J=6.6 Hz, 2H), 2.67-2.43 (m, 4H), 2.41-2.35 (m, 2H), 2.23 (m, 1H), 1.79-1.60 (m, 5H).

Example 4(f)

(15α,13E)-9-Oxo-15-hydroxy-16-(3-methylphenyl)-17,18,19,20-tetranor-5-thia-8-azaprost-13-en-1-ol

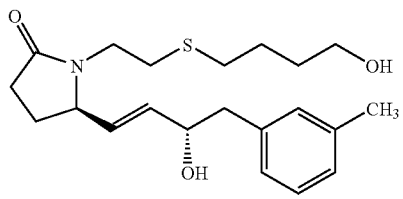

TLC: Rf 0.32 (Chloroform:Methanol:Water=9:1:0.1);
NMR: δ 7.21 (t, J=7.4 Hz, 1H), 7.19-6.97 (m, 3H), 5.76 (dd, J=15.4, 5.8 Hz, 1H), 5.50 (ddd, J=15.4, 8.5, 1.1 Hz, 1H), 4.40 (m, 1H), 4.10 (m, 1H), 3.68-3.58 (m, 3H), 2.95 (m, 1H), 2.84-2.78 (m, 2H), 2.67-2.48 (m, 4H), 2.41-2.35 (m, 2H), 2.36 (s, 3H), 2.26 (m, 1H), 1.78-1.62 (m, 5H).

Example 4(g)

(15α,13E)-9-Oxo-15-hydroxy-16-(3-fluorophenyl)-17,18,19,20-tetranor-5-thia-8-azaprost-13-en-1-ol

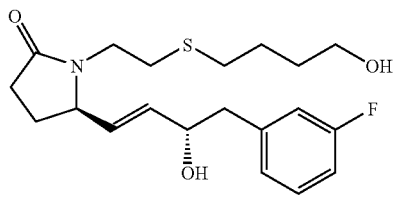

TLC: Rf 0.35 (Chloroform:Methanol:Water=9:1:0.1);
NMR: δ 7.29 (m, 1H), 7.01-6.89 (m, 3H), 5.75 (dd, J=15.4, 5.8 Hz, 1H), 5.50 (ddd, J=15.4, 8.5, 1.1 Hz, 1H), 4.41 (m, 1H), 4.12 (m, 1H), 3.70-3.57 (m, 3H), 2.94 (m, 1H), 2.84 (d, J=6.6 Hz, 2H), 2.66-2.54 (m, 4H), 2.41-2.35 (m, 2H), 2.24 (m, 1H), 1.78-1.60 (m, 5H).

Example 4(h)

(15α,13E)-9-Oxo-15-hydroxy-16-(4-fluorophenyl)-17,18,19,20-tetranor-5-thia-8-azaprost-13-en-1-ol

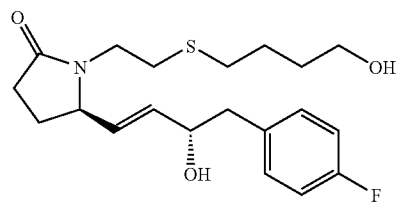

TLC: Rf 0.35 (Chloroform:Methanol:Water=9:1:0.1);
NMR: δ 7.20-7.13 (m, 2H), 7.05-6.96 (m, 2H), 5.74 (dd, J=15.4, 5.5 Hz, 1H), 5.50 (ddd, J=15.4, 8.5, 1.4 Hz, 1H), 4.38 (m, 1H), 4.10 (m, 1H), 3.71-3.57 (m, 3H), 2.95 (m, 1H), 2.82 (d, J=6.9 Hz, 2H), 2.66-2.48 (m, 4H), 2.40-2.33 (m, 2H), 2.24 (m, 1H), 1.78-1.60 (m, 5H).

Example 4(i)

(15α,13E)-9-Oxo-15-hydroxy-16-(3-propylphenyl)-17,18,19,20-tetranor-5-thia-8-azaprost-13-en-1-ol

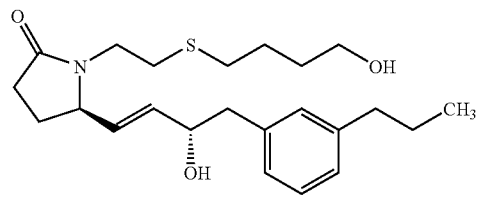

TLC: Rf 0.20 (Ethyl Acetate);
NMR: δ 7.21 (d, J=7.8 Hz, 1H), 7.06 (d, J=7.8 Hz, 1H), 7.04-7.00 (m, 2H), 5.76 (dd, J=15.0, 6.0 Hz, 1H), 5.51 (ddd, J=15.0, 8.0, 1.2 Hz, 1H), 4.40 (m, 1H), 4.10 (m, 1H), 3.72-3.59 (m, 3H), 2.98 (m, 1H), 2.90-2.78 (m, 2H), 2.73-2.43 (m, 8H), 2.41-2.10 (m, 3H), 1.90 (bs, 1H), 1.80-1.75 (m, 6H), 0.94 (t, J=7.5 Hz, 3H).

Example 4(j)

(1α,13E)-9-Oxo-15-hydroxy-16-(3-trifluoromethylphenyl)-17,18,19,20-tetranor-5-thia-8-azaprost-13-en-1-ol

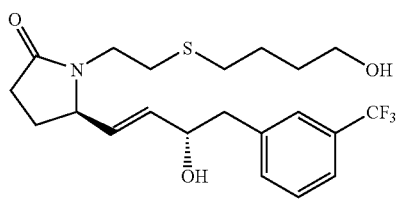

TLC: Rf 0.20 (Ethyl Acetate);
NMR: δ 7.60-7.30 (m, 4H), 5.76 (dd, J=15.0, 5.7 Hz, 1H), 5.52 (ddd, J=15.0, 8.0, 1.0 Hz, 1H), 4.43 (m, 1H), 4.11 (m, 1H), 3.73-3.69 (m, 3H), 3.06-2.83 (m, 3H), 2.72-2.50 (m, 4H), 2.42-2.00 (m, 5H), 1.80-1.53 (m, 5H).

Example 4(k)

(15α,13E)-9-Oxo-15-hydroxy-16-(3-ethylphenyl)-17,18,19,20-tetranor-5-thia-8-azaprost-13-en-1-ol

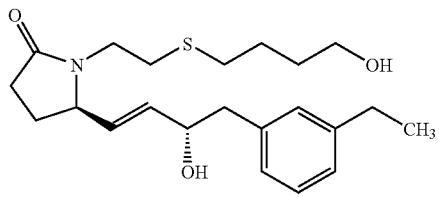

TLC: Rf 0.43 (Chloroform:Methanol=9:1);
NMR: δ 7.24 (m, 1H), 7.13-6.98 (m, 3H), 5.78 (dd, J=15.4, 6.0 Hz, 1H), 5.52 (ddd, J=15.4, 8.5, 1.1 Hz, 1H), 4.41 (m, 1H), 4.12 (m, 1H), 3.68-3.57 (m, 3H), 3.00 (m, 1H), 2.90-2.75 (m, 2H), 2.67-2.52 (m, 6H), 2.42-2.35 (m, 2H), 2.25 (m, 1H), 1.77-1.60 (m, 5H), 1.23 (t, J=7.7 Hz, 3H).

Example 4(l)

(15α,13E)-9-Oxo-15-hydroxy-16-(3,4-difluorophenyl)-17,18,19,20-tetranor-5-thia-8-azaprost-13-en-1-ol

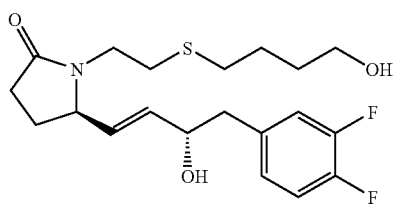

TLC: Rf 0.18 (Ethyl Acetate);
NMR: δ 7.15-7.00 (m, 2H), 6.93 (m, 1H), 5.74 (dd, J=15.4, 5.5 Hz, 1H), 5.52 (dd, J=15.4, 8.5 Hz, 1H), 4.38 (m, 1H), 4.12 (m, 1H), 3.71-3.57 (m, 3H), 2.98 (m, 1H), 2.80 (d, J=6.9 Hz, 2H), 2.68-2.48 (m, 4H), 2.42-2.36 (m, 2H), 2.25 (m, 1H), 1.77-1.60 (m, 5H).

Example 4(m)

(15α,13E)-9-Oxo-15-hydroxy-16-(4-fluoro-3-trifluoromethylphenyl)-17,18,19,20-tetranor-5-thia-8-azaprost-13-en-1-ol

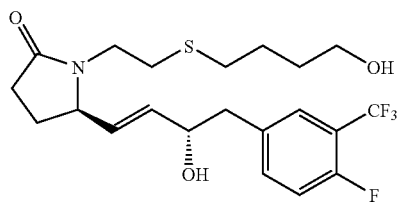

TLC: Rf 0.47 (Chloroform:Methanol=8:1);
NMR: δ 7.52-7.34 (m, 2H), 7.15 (dd, J=9.6, 9.6 Hz, 1H), 5.76 (dd, J=15.3, 5.4 Hz, 1H), 5.53 (ddd, J=15.3, 8.7, 0.9 Hz, 1H), 4.42 (m, 1H), 4.12 (m, 1H), 3.74-3.54 (m, 3H), 3.26-1.40 (m, 17H).

Example 4(n)

(15α,13E)-9-Oxo-15-hydroxy-16-(4-fluoro-3-methylphenyl)-17,18,19,20-tetranor-5-thia-8-azaprost-13-en-1-ol

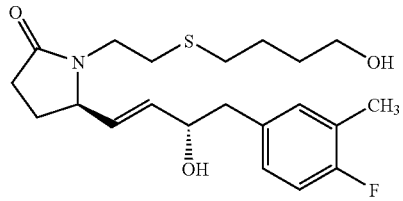

TLC: Rf 0.33 (Chloroform:Methanol=8:1);
NMR: δ 7.06-6.90 (m, 3H), 5.75 (dd, J=15.3, 5.4 Hz, 1H), 5.51 (ddd, J=15.3, 8.4, 0.9 Hz, 1H), 4.37 (m, 1H), 4.10 (m, 1H), 3.74-3.56 (m, 3H), 2.99 (m, 1H), 2.86-2.16 (m, 12H), 2.00-1.44 (m, 7H).

Example 4(o)

(15α,13E)-9-Oxo-15-hydroxy-16-(3-chloro-4-fluorophenyl)-17,18,19,20-tetranor-5-thia-8-azaprost-13-en-1-ol

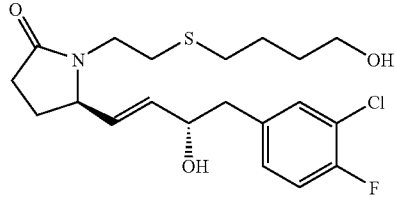

TLC: Rf 0.35 (Chloroform:Methanol=8:1);

NMR: δ 7.26 (m, 1H), 7.14-7.04 (m, 2H), 5.74 (dd, J=15.3, 5.4 Hz, 1H), 5.51 (ddd, J=15.3, 8.7, 0.9 Hz, 1H), 4.39 (m, 1H), 4.11 (m, 1H), 3.78-3.56 (m, 3H), 2.99 (m, 1H), 2.84-1.86 (m, 10H), 1.82-1.54 (m, 6H).

Example 4(p)

(15α,13E)-9-Oxo-15-hydroxy-16-(3-methylphenyl)-1,5-(2,5-interthienylene)-2,3,4,17,18,19,20-heptanor-8-azaprost-13-en-1-ol

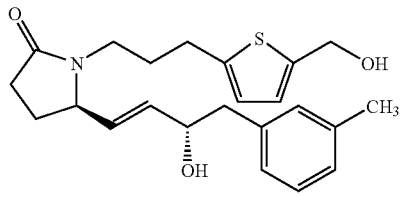

TLC: Rf 0.22 (Ethyl Acetate);

NMR: δ 7.19 (t, J=7.4 Hz, 1H), 7.08-6.94 (m, 3H), 6.79 (d, J=3.3 Hz, 1H), 6.64 (d, J=3.3 Hz, 1H), 5.69 (dd, J=15.4, 6.0 Hz, 1H), 5.43 (ddd, J=15.4, 8.5, 1.1 Hz, 1H), 4.72 (s, 2H), 4.37 (m, 1H), 4.02 (m, 1H), 3.53 (m, 1H), 2.85-2.74 (m, 5H), 2.44-2.33 (m, 2H), 2.36 (s, 3H), 2.20 (m, 1H), 1.87-1.64 (m, 3H).

Example 4(q)

(15α,13E)-9-Oxo-15-hydroxy-16-(3-methylphenyl)-5-(5-hydroxymethylthiazol-2-yl)-1,2,3,4,17,18,19,20-octanor-5-thia-8-azaprost-13-ene

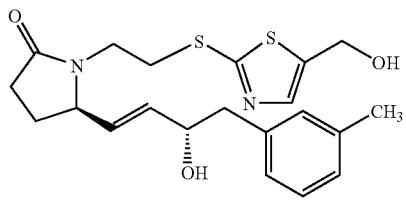

TLC: Rf 0.20 (Ethyl Acetate);

NMR: δ 7.48 (s, 1H), 7.20 (t, J=8 Hz, 1H), 7.1-6.95 (m, 3H), 5.68 (dd, J=15, 6 Hz, 1H), 5.47 (dd, J=15, 9 Hz, 1H), 4.78 (s, 2H), 4.34 (q, J=6 Hz, 1H), 4.13 (q, J=7 Hz, 1H), 3.7-3.6 (m, 1H), 3.4-3.15 (m, 3H), 2.77 (d, J=6 Hz, 2H), 2.4-2.1 (m, 6H), 1.8-1.6 (m, 1H).

Example 4(r)

(15α,13E)-9-Oxo-15-hydroxy-16-(3-chlorophenyl)-17,18,19,20-tetranor-5-thia-8-aza-10-oxaprost-13-en-1-ol

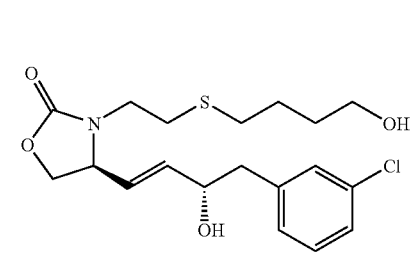

TLC: Rf 0.36 (Chloroform:Methanol=9:1);

NMR: δ 7.32-7.20 (m, 3H), 7.10 (m, 1H), 5.86 (dd, J=15.4, 5.5 Hz, 1H), 5.56 (ddd, J=15.4, 8.8, 1.4 Hz, 1H), 4.48-4.29 (m, 2H), 4.43 (dd, J=8.2, 8.2 Hz, 1H), 3.91 (dd, J=8.2, 8.2 Hz, 1H), 3.70-3.63 (m, 2H), 3.45 (m, 1H), 3.09 (m, 1H), 2.82 (d, J=6.0 Hz, 2H), 2.75-2.56 (m, 4H), 1.78-1.54 (m, 4H).

Example 4(s)

(15α,13E)-9-Oxo-15-hydroxy-16-(4-fluorophenyl)-17,18,19,20-tetranor-5-thia-8-aza-10-oxaprost-13-en-1-ol

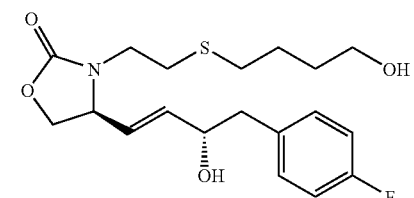

TLC: Rf 0.37 (Chloroform:Methanol=9:1);

NMR: δ 7.20-7.13 (m, 2H), 7.06-6.98 (m, 2H), 5.87 (dd, J=15.4, 5.5 Hz, 1H), 5.57 (ddd, J=15.4, 8.5, 1.4 Hz, 1H), 4.44-4.28 (m, 2H), 4.43 (dd, J=8.5, 8.2 Hz, 1H), 3.91 (dd, J=8.5, 8.2 Hz, 1H), 3.69-3.64 (m, 2H), 3.46 (m, 1H), 3.11 (m, 1H), 2.90-2.76 (m, 2H), 2.74-2.55 (m, 4H), 1.78-1.62 (m, 4H).

Example 4(t)

(15α,13E)-9-Oxo-15-hydroxy-16-(4-fluorophenyl)-3,7-(2,5-interthienylene)-4,5,6,17,18,19,20-heptanor-8-azaprost-13-en-1-ol

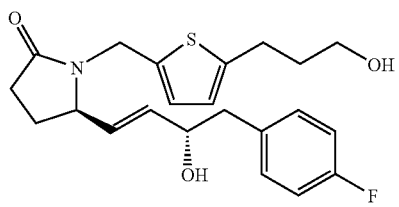

TLC: Rf 0.46 (Ethyl Acetate:Methanol=19:1);
NMR: δ 7.25-7.1 (m, 2H), 7.05-6.95 (m, 2H), 6.66 (d, J=3 Hz, 1H), 6.62 (d, J=3 Hz, 1H), 5.73 (dd, J=16, 6 Hz, 1H), 5.47 (dd, J=16, 9 Hz, 1H), 4.85 (d, J=15 Hz, 1H), 4.45-4.35 (m, 1H), 4.05-3.95 (m, 1H), 3.88 (d, J=15 Hz, 1H), 3.70 (t, J=6 Hz, 2H), 2.95-2.8 (m, 4H), 2.5-2.3 (m, 2H), 2.25-2.1 (m, 1H), 2.0-1.85 (m, 2H), 1.8-1.6 (m, 1H).

Example 4(u)

(15α,13E)-9-Oxo-15-hydroxy-16-(3-ethyl-4-fluorophenyl)-17,18,19,20-tetranor-5-thia-8-azaprost-13-en-1-ol

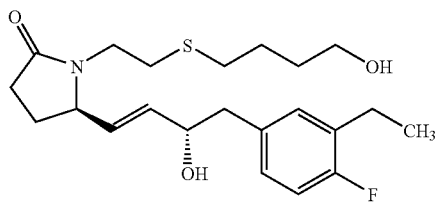

TLC: Rf 0.28 (Ethyl Acetate:Methanol=9:1);
NMR: δ 7.06-6.91 (m, 3H), 5.75 (dd, J=15.6, 5.7 Hz, 1H), 5.52 (ddd, J=15.6, 9.0, 1.5 Hz, 1H), 4.39 (m, 1H), 4.10 (m, 1H), 3.72-3.59 (m, 3H), 3.00 (m, 1H), 2.84-2.43 (m, 8H), 2.41-2.19 (m, 3H), 1.90 (bs, 2H), 1.80-1.60 (m, 5H), 1.22 (t, J=7.5 Hz, 3H).

Example 4(v)

(15α,13E)-9-Oxo-15-hydroxy-16-(5-methylfuran-2-yl)-17,18,19,20-tetranor-5-thia-8-azaprost-13-en-1-ol

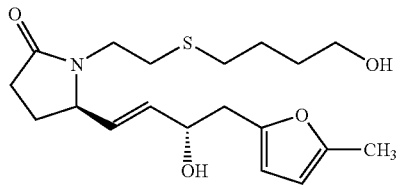

TLC: Rf 0.35 (Ethyl Acetate:Methanol=19:1);
NMR: δ 5.99 (d, J=3.0 Hz, 1H), 5.88 (m, 1H), 5.76 (dd, J=15.3, 5.7 Hz, 1H), 5.55 (ddd, J=15.3, 8.4, 1.0 Hz, 1H), 4.42 (m, 1H), 4.11 (m, 1H), 3.74-3.60 (m, 3H), 3.06 (m, 1H), 2.94-2.77 (m, 2H), 2.71-2.50 (m, 4H), 2.43-2.09 (m, 7H), 1.92-1.56 (m, 6H).

Example 4(w)

(15α,13E)-9-Oxo-15-hydroxy-16-(5-ethylfuran-2-yl)-17,18,19,20-tetranor-5-thia-8-azaprost-13-en-1-ol

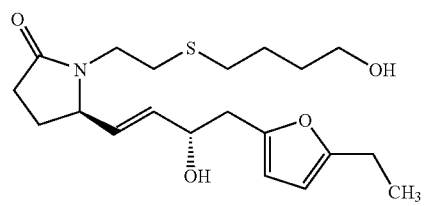

TLC: Rf 0.16 (Ethyl Acetate:Methanol=19:1);
NMR: δ 6.01 (d, J=3.0 Hz, 1H), 5.89 (d, J=3.0 Hz, 1H), 5.75 (dd, J=15.3, 5.4 Hz, 1H), 5.55 (dd, J=15.3, 8.7 Hz, 1H), 4.45 (m, 1H), 4.10 (m, 1H), 3.71-3.59 (m, 3H), 3.03 (m, 1H), 2.92-2.78 (m, 2H), 2.72-2.45 (m, 6H), 2.42-2.10 (m, 4H), 2.00-1.59 (m, 6H), 1.21 (t, J=7.8 Hz, 3H).

EXAMPLE 5

(15α)-9-Oxo-15-hydroxy-16-(3-methoxymethylphenyl)-17,18,19,20-tetranor-8-azaprostanoic acid ethyl ester

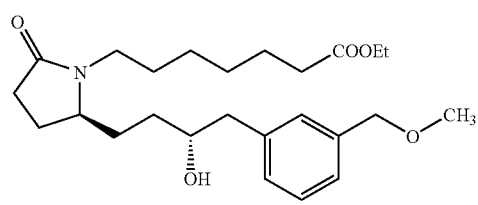

Under atmosphere of argon, Palladium on carbon (44 mg) was added to the solution of the compound prepared in Example 1 (440 mg) in ethanol (10 mL), and argon was displaced by hydrogen. After the mixture was stirred for 4 hours, the catalyst was removed by filtration. The filtrate was concentrated under reduced pressure and was purified by column chromatography on silica gel (ethyl acetate:methanol=from 50:1 to 20:1) to give the title compound (384 mg) having the following physical data.
TLC: Rf 0.16 (Ethyl Acetate:Methanol=85:15).

EXAMPLE 6

(15α)-9-Oxo-15-hydroxy-16-(3-methoxymethylphenyl)-17,18,19,20-tetranor-8-azaprostanoic acid

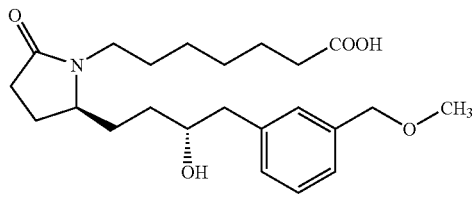

By the same procedure as describe in Example 2 using the compound prepared in Example 5 (227 mg) instead of the compound prepared in Example 1, the compound (173 mg) of the present invention having the following physical data was obtained.

TLC: Rf 0.45 (Chloroform:Methanol=9:1);

NMR: δ 7.38-7.11 (m, 4H), 4.45 (s, 2H), 3.91-3.80 (m, 1H), 3.67-3.53 (m, 2H), 3.42 (s, 3H), 3.00-2.64 (m, 3H), 2.50-2.03 (m, 5H), 1.94-1.89 (m, 1H), 1.86-1.20 (m, 13H).

EXAMPLE 6(a) TO EXAMPLE 6(c)

By the same procedure as describe in Examples 5 and 6 using corresponding carboxylic acid ester derivatives instead of the compound prepared in Example 1, the compound of the present invention having the following physical data were obtained.

Example 6(a)

(15α)-9-Oxo-15-hydroxy-16-(3-methylphenyl)-17,18,19,20-tetranor-8-azaprostanoic acid

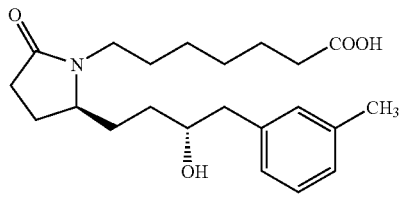

TLC: Rf 0.37 (Chloroform:Methanol=10:1);

NMR: δ 7.22 (t, J=6.9 Hz, 1H), 7.08-6.99 (m, 3H), 3.86 (m, 1H), 3.63-3.54 (m, 2H), 2.92 (m, 1H), 2.80 (dd, J=13.5, 4.8 Hz, 1H), 2.67 (dd, J=13.5, 8.4 Hz, 1H), 2.34 (s, 3H), 2.40-1.20 (m, 18H).

Example 6(b)

(15α)-9-Oxo-15-hydroxy-16-(3-methylphenyl)-17,18,19,20-tetranor-5-thia-8-azaprostanoic acid

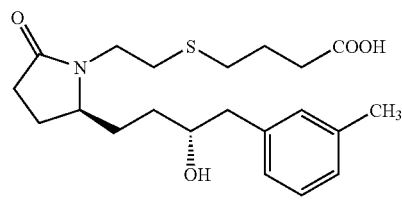

TLC: Rf 0.32 (Chloroform:Methanol=10:1);

NMR: δ 7.21 (t, J=7.8 Hz, 1H), 7.08-6.98 (m, 3H), 3.90 (m, 1H), 3.78-3.62 (m, 2H), 3.40 (br s, 1H), 3.17 (m, 1H), 2.80-2.30 (m, 10H), 2.34 (s, 3H), 2.14 (m, 1H), 2.00-1.40 (m, 7H).

Example 6(c)

(15α)-9-Oxo-15-hydroxy-16-(3-trifluoromethylphenyl)-17,18,19,20-tetranor-5-thia-8-azaprostanoic acid

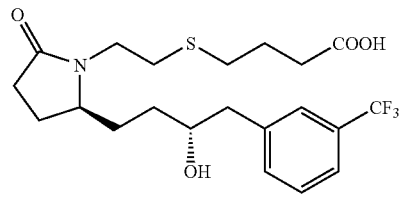

TLC: Rf 0.6 (Chloroform:Methanol:Water=9:1:0.1);

NMR: δ 7.57-7.39 (m, 4H), 3.95 (m, 1H), 3.78-3.63 (m, 2H), 3.19 (m, 1H), 2.92-2.67 (m, 4H), 2.65-2.34 (m, 6H), 2.16 (m, 1H), 2.00-1.47 (m, 7H).

REFERENCE EXAMPLE 12

(15α,13E)-9-Oxo-15-(t-butyldimethylsilyloxy)-16-(3-methoxymethylphenyl)-17,18,19,20-tetranor-8-azaprost-13-enoic acid ethyl ester

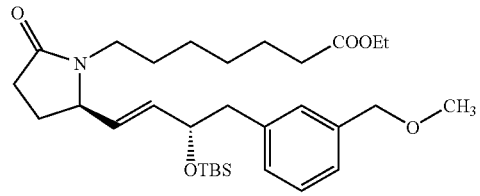

A solution of the compound prepared in Example 1 (1.26 g) in dimethylformamide (3 mL) was cooled, and was added by the solution of imidazole (275 mg) and t-butyldimethylsilyl chloride (446 mg) in dimethylformamide (2 mL). After the mixture was stirred for 1 hour at room temperature, water was added hereto, and was extracted by ethyl acetate. The extraction was washed with water and brine successively, dried over an anhydrous sodium sulfate, concentrated under reduced pressure to give the title compound (3.39 g) having the following physical data.

TLC: Rf 0.62 (Ethyl Acetate).

REFERENCE EXAMPLE 13

(15α,13E)-9-Oxo-15-(t-butyldimethylsilyloxy)-16-(3-methoxymethylphenyl)-17,18,19,20-tetranor-8-azaprost-13-enoic acid

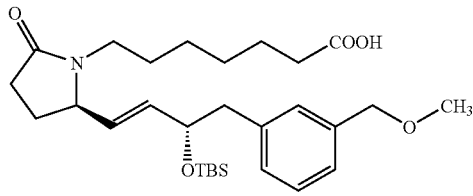

To a solution of the compound prepared in Reference Example 12 (420 mg) in mixed solvent of methanol (2 mL) and tetrahydrofuran (2 mL), 2N aqueous sodium hydroxide (1.2 mL) was added, and the mixture was stirred for 2 hours. Hydrochloric acid was added to the mixture to acidify, then was extracted by ethyl acetate. The extract was washed with brine, dried over an anhydrous sodium sulfate, concentrated under reduced pressure to give the title compound (398 mg) having the following physical data.

TLC: Rf 0.48 (Chloroform:Methanol=8:1).

REFERENCE EXAMPLE 14

(15α,13E)-9-Oxo-15-(t-butyldimethylsilyloxy)-16-(3-methoxymethylphenyl)-17,18,19,20-tetranor-8-azaprost-13-enoic acid N-mesylamide

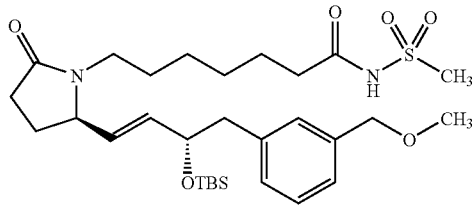

To a solution of the compound prepared in Reference Example 13 (90 mg) in methylene chloride (1 mL), methansulfonamide (41 mg), dimethylaminopyridine (32 mg) and 1-ethyl-3-(3-dimethylaminopropyl)carbodiimide monohydyochloride (67 mg) was added, and the mixture was stirred overnight at room temperature. Diluted hydrochloric acid was added to the mixture, then was extracted by ethyl acetate. The extract was washed with brine, dried over an anhydrous sodium sulfate, concentrated under reduced pressure to give the title compound (100 mg) having the following physical data.

TLC: Rf 0.23 (Hexane:Ethyl Acetate=1:3).

EXAMPLE 7

(15α,13E)-9-Oxo-15-hydroxy-16-(3-methoxymethylphenyl)-17,18,19,20-tetranor-8-azaprost-13-enoic acid N-mesylamide

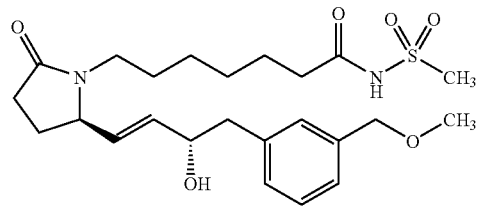

To a solution of the compound prepared in Example 14 (100 mg) in tetrahydrofuran (1 mL), tetrabutylammonium fluoride (0.35 mL; 1.0M tetrahydrofuran solution) was added, and the mixture was stirred for 3 hours at room temperature. The mixture was poured into cold aqueous ammonium chloride solution, and extracted by ethyl acetate. The extract was washed with brine, dried, concentrated under reduced pressure and was purified by column chromatography on silica gel (from hexane:ethyl acetate=1:3 to chloroform:methanol=10:1) to give the title compound (35 mg) having the following physical data.

TLC: Rf 0.38 (Chloroform:Methanol=8:1);
NMR: δ 9.97 (brs, 1H), 7.38-7.08 (m, 4H), 5.75 (dd, J=15.3, 5.4 Hz, 1H), 5.50 (dd, J=15.3, 8.1 Hz, 1H), 4.44 (s, 2H), 4.43 (m, 1H), 4.04 (m, 1H), 3.41 (s, 3H), 3.40 (m, 1H), 3.26 (s, 3H), 3.06-2.72 (m, 3H), 2.52-2.10 (m, 5H), 1.86-1.12 (m, 10H).

EXAMPLE 7(a) To EXAMPLE 7(d)

By the same procedure as describe in Reference Example 14 and Example 7 using the compound prepared in Reference Example 13 or corresponding carboxylic acid derivatives and corresponding sulfonamide derivatives instead of methanesulfonamide, the compound of the present invention having the following physical data were obtained.

Example 7(a)

(15α,13E)-9-Oxo-15-hydroxy-16-(3-methoxymethylphenyl)-17,18,19,20-tetranor-8-azaprost-13-enoic acid N-phenylsulfonylamide

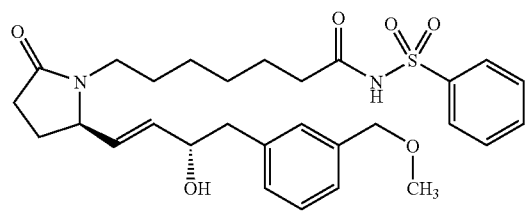

TLC: Rf 0.42 (Chloroform:Methanol=8:1);
NMR: δ 9.84 (brs, 1H), 8.05 (d, J=7.2 Hz, 1H), 7.68-7.46 (m, 3H), 7.38-7.08 (m, 5H), 5.75 (dd, J=15.3, 5.4 Hz, 1H), 5.50 (dd, J=15.3, 8.7 Hz, 1H), 4.45 (s, 2H), 4.45 (m, 1H), 4.03 (m, 1H), 3.41 (s, 3H), 3.40 (m, 1H), 3.06-2.68 (m, 3H), 2.54-2.12 (m, 5H), 1.90-1.06 (m, 10H).

Example 7(b)

(15α,13E)-9-Oxo-15-hydroxy-16-(3-methoxymethylphenyl)-17,18,19,20-tetranor-8-azaprost-13-enoic acid N-benzylsulfonylamide

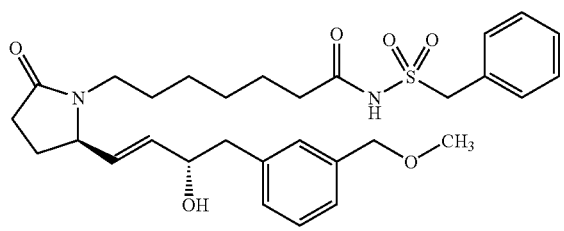

TLC: Rf 0.44 (Chloroform:Methanol=8:1);

NMR: δ 9.46 (brs, 1H), 7.46-7.04 (m, 9H), 5.71 (dd, J=15.3, 5.7 Hz, 1H), 5.46 (dd, J=15.3, 8.7 Hz, 1H), 4.63 (s, 2H), 4.42 (s, 2H), 4.40 (m, 1H), 3.98 (m, 1H), 3.37 (s, 3H), 3.30 (m, 1H), 3.00-2.62 (m, 3H), 2.40-2.06 (m, 5H), 1.82-1.08 (m, 10H).

Example 7(c)

(15α,13E)-9-Oxo-15-hydroxy-16-(4-fluorophenyl)-1,5-(2,5-interthienylene)-2,3,4,17,18,19,20-heptanor-8-azaprost-13-enoic acid N-benzylsulfonylamide

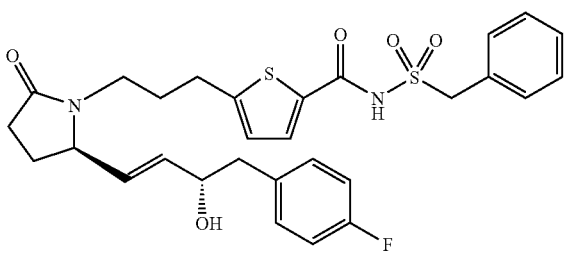

TLC: Rf 0.12 (Chloroform:Methanol=9:1);

NMR: δ 9.15 (br. s, 1H), 7.52 (d, J=3.9 Hz, 1H), 7.39-7.30 (m, 5H), 7.18-7.11 (m, 2H), 7.03-6.96 (m, 2H), 6.79 (d, J=3.9 Hz, 1H), 5.71 (dd, J=15.4, 5.8 Hz, 1H), 5.43 (ddd, J=15.4, 8.8, 1.1 Hz, 1H), 4.76 (s, 2H), 4.38 (m, 1H), 4.00 (m, 1H), 3.41 (m, 1H), 2.86-2.74 (m, 5H), 2.38-2.07 (m, 3H), 1.84-1.60 (m, 3H).

Example 7(d)

(15α,13E)-9-Oxo-15-hydroxy-16-(4-fluorophenyl)-5-(5-benzylsulfonylcarbamoylthiazol-2-yl)-1,2,3,4,17,18,19,20-octanor-5-thia-8-azaprost-13-ene

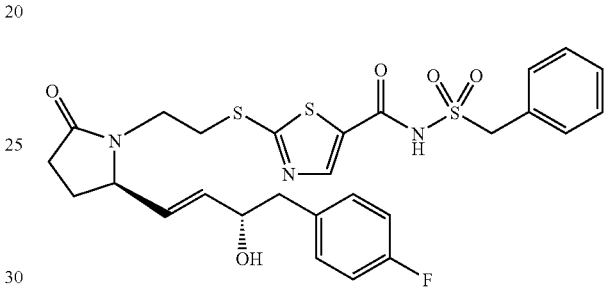

TLC: Rf 0.46 (Chloroform:Methanol:Acetic Acid=9:1:0.2);

NMR: δ 8.20 (s, 1H), 7.34 (s, 5H), 7.18-7.07 (m, 2H), 7.02-6.95 (m, 2H), 5.71 (dd, J=15.3, 5.1 Hz, 1H), 5.47 (dd, J=15.3, 9.0 Hz, 1H), 4.73 (s, 2H), 4.37 (m, 1H), 4.03 (m, 1H), 3.63 (m, 1H), 3.39 (m, 1H), 3.28-3.10 (m, 2H), 2.82-2.71 (m, 2H), 2.25-2.03 (m, 3H); 1.75-1.55 (m, 1H),

REFERENCE EXAMPLE 15

(15α,13E)-9-Thioxo-15-t-butyldimethylsilyloxy-16-(3-methylphenyl)-17,18,19,20-tetranor-5-thia-8-azaprost-13-enoic acid butyl ester

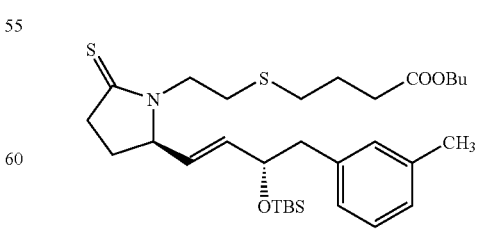

To a solution of (15α,13E)-9-oxo-15-t-butyldimethylsilyloxy-16-(3-methylphenyl)-17,18,19,20-tetranor-5-thia-8-azaprost-13-enoic acid butyl ester (170 mg; this compound were obtained by the same procedure as describe in Reference Example 12 using (15α,13E)-9-oxo-15-hydroxy-16-(3-methylphenyl)-17,18,19,20-tetranor-5-thia-8-azaprost-13-enoic acid butyl ester instead of the compound prepared in Example 1) in toluene (2 mL), 2,4-bis(4-methoxyphenyl), 1,3-dithia-2,4-diphosphetan-2,4-disulfide (Lawesson reagent) (74 mg) was added and the mixture was stirred for 1 hour at 50° C. After cooling, the reaction mixture was purified by column chromatography on silica gel (hexane:ethyl acetate=5:1) to give the title compound (175 mg) having the following physical data.

TLC: Rf 0.53 (Hexane:Ethyl Acetate=4:1).

EXAMPLE 8

(15α,13E)-9-Thioxo-15-hydroxy-16-(3-methylphenyl)-17,18,19,20-tetranor-5-thia-8-azaprost-13-enoic acid butyl ester

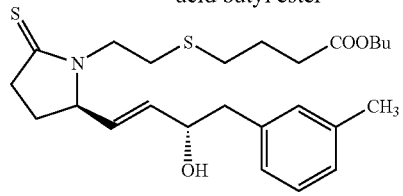

To a solution of the compound prepared in Reference Example 15 (160 mg) in tetrahydrofuran (1.4 mL), tetrabutylammonium fluoride (1.4 mL; 1.0M tetrahydrofuran solution) was added, and the mixture was stirred for 3 hours at room temperature. The mixture was poured into saturated aqueous ammonium chloride solution, and extracted by ethyl acetate. The extract was washed with water and brine successively, dried over anhydrous sodium sulfate, concentrated under reduced pressure and was purified by column chromatography on silica gel (from hexane:ethyl acetate=2:1 to ethyl acetate only) to give the title compound (110 mg) having the following physical data.

TLC: Rf 0.38 (Hexane:Ethyl Acetate=1:1).

EXAMPLE 9

(15α,13E)-9-Thioxo-15-hydroxy-16-(3-methylphenyl)-17,18,19,20-tetranor-5-thia-8-azaprost-13-enoic acid

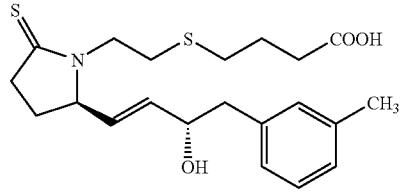

By the same procedure as describe in Example 2 using the compound prepared in Example 8 instead of the compound prepared in Example 1, the compound of the present invention having the following physical data were obtained.

TLC: Rf 0.40 (Chloroform:Methanol=8:1);

NMR: δ 7.22 (dd, J=7.5, 7.5 Hz, 1H), 7.11-6.95 (m, 3H), 5.82 (dd, J=15.3, 5.1 Hz, 1H), 5.55 (ddd, J=15.3, 8.7, 1.2 Hz, 1H), 4.52-4.38 (m, 2H), 4.13 (m, 1H), 3.37 (m, 1H), 3.10-2.39 (m, 12H), 2.35 (s, 3H), 2.27 (m, 1H), 2.00-1.70 (m, 3H).

By the same procedure as describe in Reference Example 15, Examples 8 and 9 using the compound prepared in Reference Example 12 instead of (15α,13E)-9-oxo-15-t-butyldimethylsilyloxy-16-(3-methylphenyl)-17,18,19,20-tetranor-5-thia-8-azaprost-13-enoic acid butyl ester, the compound of the present invention having the following physical data were obtained.

REFERENCE EXAMPLE 16

(15α,13E)-9-Oxo-15-t-butyldimethylsilyloxy-16-(3-methylphenyl)-17,18,19,20-tetranor-5-thia-8-azaprost-13-en-1-yl t-butoxycarbonylglycylglycinate

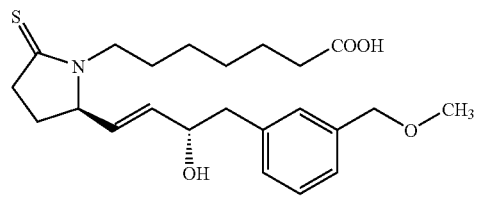

TLC: Rf 0.31 (Methanol:Chloroform=1:10);

NMR: δ 7.40-7.10 (m, 4H), 5.82 (dd, J=15.4, 5.0 Hz, 1H), 5.59 (dd, J=15.4, 8.4 Hz, 1H), 4.50-4.25 (m, 2H), 4.47 (s, 2H), 4.02-3.85 (m, 1H), 3.43 (s, 3H), 3.38-3.10 (m, 1H), 3.10-2.75 (m, 4H), 2.40-2.15 (m, 2H), 2.33 (t, J=7.2 Hz, 2H), 1.90-1.20 (m, 10H).

Example 9(a)

(15α,13E)-9-Thioxo-15-hydroxy-16-(3-methoxymethylphenyl)-17,18,19,20-tetranor-8-azaprost-13-enoic acid

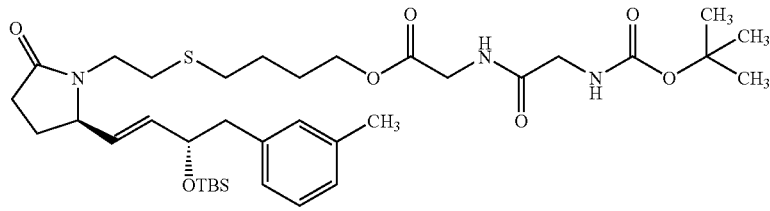

To a solution of (15α,13E)-9-oxo-15-t-butyldimethylsilyloxy-16-(3-methylphenyl)-17,18,19,20-tetranor-5-thia-8-azaprost-13-en-1-ol (170 mg; this compound was prepared by protecting of hydroxy group at C15 position of the methyl ester of the compound prepared in Example 3(j) by t-butyldimethylsilyl group (TBS group) followed by the same-procedure as describe in Example 4) in mixed solvent of methylene chloride (2 mL) and dimethylformammide (1 mL), t-Butoxycarbonylglycylglycin (96 mg), methyl 3-methyl-2-fluoropyridinium tosylate (257 mg) and diisopropylamine (0.18 mL) were added, and the mixture was stirred overnight at room temperature. The reaction mixture was poured into cold water, and was extracted by ethyl acetate. The extract was washed with water and brine successively, dried over anhydrous sodium sulfate, concentrated under reduced pressure and was purified by column chromatography on silica gel (from hexane:ethyl acetate=1:2 to ethyl acetate only) to give the title compound (170 mg) having the following physical data.

TLC: Rf 0.53 (Chloroform:Methanol=8:1).

EXAMPLE 10

(15α,13E)-9-Oxo-15-hydroxy-16-(3-methylphenyl)-17,18,19,20-tetranor-5-thia-8-azaprost-13-en-1-yl t-butoxycarbonylglycylglycinate

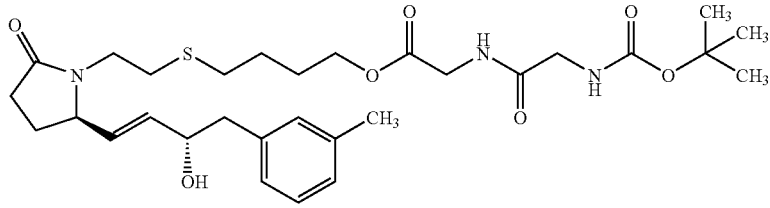

To a solution of the compound prepared in Example 16 (170 mg) in dioxane (0.14 mL), 1N hydrochloric acid (0.14 mL) was added, and the mixture was stirred overnight at room temperature. The mixture was poured into saturated aqueous sodium chloride solution, and extracted by ethyl acetate. The extract was dried over anhydrous sodium sulfate, concentrated under reduced pressure and was purified by column chromatography on silica gel (from hexane:ethyl acetate=1:2 to ethyl acetate, only, then chloroform:methanol=30:1) to give the title compound (100 mg) having the following physical data.

TLC: Rf 0.33 (Chloroform:Methanol=8:1).

EXAMPLE 11

(15α,13E)-9-Oxo-15-hydroxy-16-(3-methylphenyl)-17,18,19,20-tetranor-5-thia-8-azaprost-13-en-1-yl glycylglycinate monohydrochloride

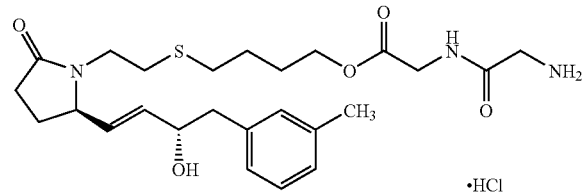

·HCl

To a solution of the compound prepared in Example 10 (65 mg) in benzene (0.55 mL), 4N hydrogenchloride-ethyl acetate (0.14 mL) was added, and the mixture was stirred for 2 hours at room temperature. The mixture was azeotropied with toluene to give the title compound (54 mg) having the following physical data.

TLC: Rf 0.41 (Chloroform:Methanol=4:1);
NMR (CD$_3$OD): δ 7.15 (dd, J=7.5, 7.5 Hz, 1H), 7.08-6.94 (m, 3H), 5.70 (dd, J=15.3, 6.6 Hz, 1H), 5.37 (dd, J=15.3, 8.7 Hz, 1H), 4.33 (m, 1H), 4.24-4.07 (m, 3H), 4.06-3.94 (m, 2H), 3.73 (s, 2H), 3.60-3.40 (m, 2H), 2.95-2.12 (m, 14H), 1.82-1.54 (m, 5H).

EXAMPLE 11(a) TO EXAMPLE 11 (c)

By the same procedure as describe in Reference Example 16, Examples 10 and 11 using corresponding amino acid derivatives instead of t-butoxycarbonylglycylglycine, the compound of the present invention having the following physical data were obtained.

Example 11(a)

(15α,13E)-9-Oxo-15-hydroxy-16-(3-methylphenyl)-17,18,19,20-tetranor-5-thia-8-azaprost-13-en-1-yl glycinate methanesulfonic acid salt

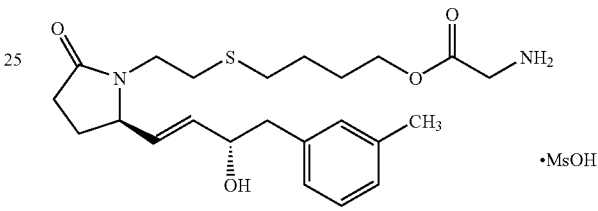

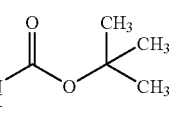

TLC: Rf 0.27 (Chloroform:Methanol=8:1);
NMR (CD$_3$OD): δ 7.15 (dd, J=7.5, 7.5 Hz, 1H), 7.06-6.94 (m, 3H), 5.70 (dd, J=15.3, 6.6 Hz, 1H), 5.37 (ddd, J=15.3, 8.7, 0.9 Hz, 1H), 4.33 (m, 1H), 4.27 (t, J=6.3 Hz, 2H), 4.13 (m, 1H), 3.83 (s, 2H), 3.50 (m, 1H), 2.96-2.10 (m, 15H), 1.88-1.54 (m, 5H).

Example 11(b)

(15α,13E)-9-Oxo-15-hydroxy-16-(3-methylphenyl)-17,18,19,20-tetranor-5-thia-8-azaprost-13-en-1-yl tryptophanate bis-trifluoroacetic acid salt

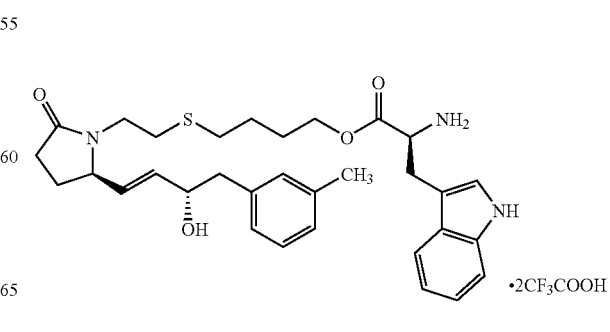

TLC: Rf 0.40 (Chloroform:Methanol=8:1);

NMR (CD₃OD): δ 7.53 (d, J=8.1 Hz, 1H), 7.39 (d, J=8.1 Hz, 1H), 7.24-6.92 (m, 7H), 5.67 (dd, J=15.6, 6.6 Hz, 1H), 5.34 (dd, J=15.6, 9.0 Hz, 1H), 4.30 (t, J=6.9 Hz, 2H), 4.28-4.00 (m, 3H), 3.52-3.30 (m, 3H), 2.94-2.60 (m, 3H), 2.56-2.08 (m, 10H), 1.74-1.32 (m, 5H).

Example 11(c)

(15α,13E)-9-Oxo-15-hydroxy-16-(3-methylphenyl)-17,18,19,20-tetranor-5-thia-8-azaprost-13-en-1-yl tyrosinate trifluoroacetic acid salt

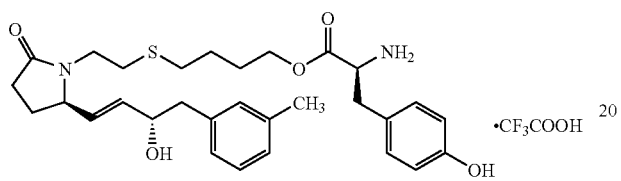

TLC: Rf 0.37 (Chloroform:Methanol=8:1);

NMR (CD₃OD): δ 7.22-6.92 (m, 6H), 6.77 (d, J=8.4 Hz, 2H), 5.69 (dd, J=15.3, 6.6 Hz, 1H), 5.36 (dd, J=15.3, 8.7 Hz, 1H), 4.33 (m, 1H), 4.27-4.15 (m, 3H), 4.12 (m, 1H), 3.47 (m, 1H), 3.16-3.04 (m, 2H), 2.96-2.06 (m, 13H), 1.80-1.48 (m, 5H).

EXAMPLE 12

(15α,13E)-9-Oxo-15-hydroxy-16-(3-chlorophenyl)-17,18,19,20-tetranor-5-thia-8-azaprost-13-enoic acid isopropyloxycarbonylmethyl ester

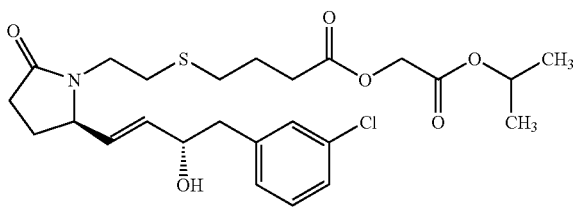

To a solution of the compound prepared in Example 3(b) (31.5 mg) in dimethylformamide (0.7 mL), 2-bromoacetic acid isopropyl ester (16.5 mg) and potassium carbonate (16 mg) was added, and the mixture was stirred for 1.5 hours at 60° C. After cooling, the reaction mixture was added by water and ethyl acetate. The organic layer was washed with water and brine successively, dried over anhydrous sodium sulfate, concentrated under reduced pressure and was purified by column chromatography on silica gel (chloroform:methanol=50:1) to give the title compound (35 mg) having the following physical data.

TLC: Rf 0.45 (Chloroform:Methanol=9:1);

NMR: δ 7.32-7.20 (m, 3H), 7.14-7.06 (m, 1H), 5.74 (dd, J=15.3, 6.0 Hz, 1H), 5.50 (dd, J=15.3, 8.6 Hz, 1H), 5.06 (m, 1H), 4.57 (s, 2H), 4.40 (m, 1H), 4.12 (m, 1H), 3.62 (m, 1H), 2.96 (m, 1H), 2.82 (d, J=6.0 Hz, 2H), 2.71-2.50 (m, 6H), 2.41-2.19 (m, 3H), 2.00-1.90 (m, 2H), 1.73 (m, 1H), 1.25 (d, J=6.3 Hz, 6H).

EXAMPLE 12(a) TO EXAMPLE 12(c)

By the same procedure as describe in Example 12 using the compound prepared in Example 3(b) or corresponding carboxylic acid derivatives and corresponding halide derivatives instead of 2-bromoacetic acid isopropyl ester, the compound of the present invention having the following physical data were obtained.

Example 12(a)

(15α,13E)-9-Oxo-15-hydroxy-16-(3-chlorophenyl)-17,18,19,20-tetranor-5-thia-8-azaprost-13-enoic acid dimethylaminocarbonylmethyl ester

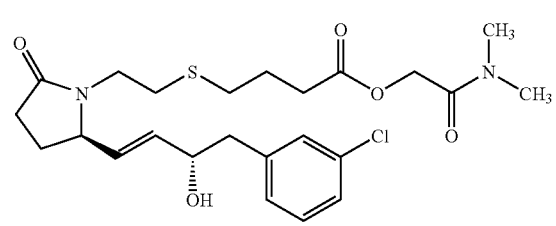

TLC: Rf 0.35 (Chloroform:Methanol=9:1);

NMR: δ 7.28-7.19 (m, 3H), 7.12-7.08 (m, 1H), 5.77 (dd, J=15.3, 5.1 Hz, 1H), 5.54 (ddd, J=15.3, 8.7, 1.2 Hz, 1H), 4.70 (s, 2H), 4.40 (m, 1H), 4.15 (m, 1H), 3.54 (m, 1H), 3.04 (m, 1H), 2.95 (s, 3H), 2.91 (s, 3H), 2.82 (d, J=6.0 Hz, 2H), 2.78-2.53 (m, 6H), 2.40-2.18 (m, 3H), 2.03-1.93 (m, 2H), 1.71 (m, 1H).

Example 12(b)

(15α,13E)-9-Oxo-15-hydroxy-16-(4-fluorophenyl)-17,18,19,20-tetranor-5-thia-8-azaprost-13-enoic acid ethyl ester

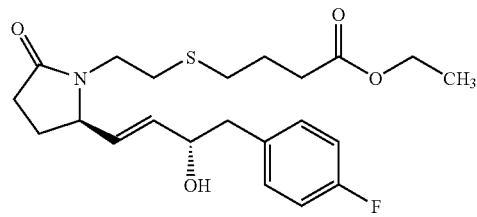

TLC: Rf 0.44 (Chloroform:Methanol=9:1);

NMR: δ 7.21-7.14 (m, 2H), 7.05-6.96 (m, 2H), 5.75 (dd, J=15.6, 6.0 Hz, 1H), 5.50 (dd, J=15.6, 8.4 Hz, 1H), 4.19 (m, 1H), 4.18-4.03 (m, 3H), 3.60 (m, 1H), 2.97 (m, 1H), 2.85-2.79 (m, 2H), 2.70-2.18 (m, 9H), 2.01-1.82 (m, 3H), 1.79-1.60 (m, 1H), 1.25 (t, J=7.2 Hz, 3H).

Example 12(c)

(15α,13E)-9-Oxo-15-hydroxy-16-(4-fluorophenyl)-17,18,19,20-tetranor-5-thia-8-azaprost-13-enoic acid butyl ester

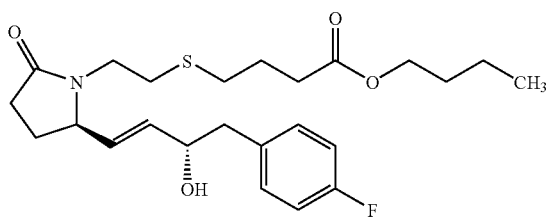

TLC: Rf 0.47 (Ethyl Acetate:Methanol=20:1);

NMR: δ 7.2-7.1 (m, 2H), 7.05-6.95 (m, 2H), 5.75 (dd, J=15, 6 Hz, 1H), 5.51 (dd, J=15, 8 Hz, 1H), 4.45-4.35 (m, 1H), 4.15-4.05 (m, 1H), 4.07 (t, J=7 Hz, 2H), 3.7-3.55 (m, 1H), 3.05-2.9 (m, 1H), 2.82 (d, J=7 Hz, 2H), 2.7-2.45 (m, 4H), 2.4-2.3 (m, 4H), 2.3-2.15 (m, 1H), 2.0 (d, J=4 Hz, 1H), 1.95-1.85 (m, 2H), 1.8-1.65 (m, 1H), 1.65-1.55 (m, 2H), 1.45-1.3 (m, 2H), 0.93 (t, J=7 Hz, 3H).

REFERENCE EXAMPLE 17

(15α,13E)-9-Oxo-15-(tetrahydropyran-2-yloxy)-16-(3-methylphenyl)-1,5-(2,5-interthienylene)-2,3,4,17,18,19,20-heptanor-8-azaprost-13-enoic acid methyl ester

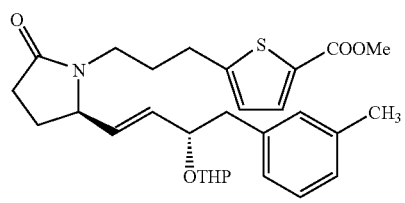

To a solution of (15α,13E)-9-oxo-15-hydroxy-16-(3-methylphenyl)-1,5-(2,5-interthienylene)-2,3,4,17,18,19,20-heptanor-8-azaprost-13-enoic acid methyl ester (111 mg; this is the methyl ester of the compound prepared in Example 2(ww)) in toluene (2 mL), dihydropyran (0.5 mL) and p-toluenesulfonic acid (1 mg) was added, and the mixture was stirred for 6 hours at room temperature. The mixture was added by water and ethyl acetate. The organic layer was washed with water and brine successively, dried over anhydrous sodium sulfate, concentrated under reduced pressure to give the title compound (146 mg) having the following physical data.

REFERENCE EXAMPLE 18

(15α,13E)-9-Oxo-15-(tetrahydropyran-2-yloxy)-16-(3-methylphenyl)-1,5-(2,5-interthienylene)-2,3,4,17,18,19,20-heptanor-8-azaprost-13-en-1-ol

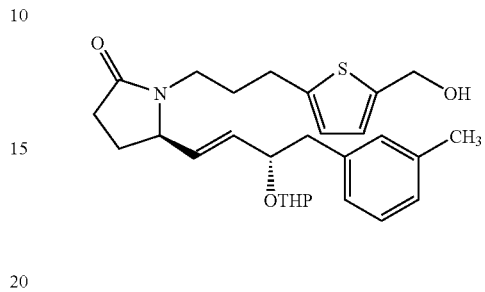

To a solution of the compound prepared in Reference Example 17 (146 mg) in tetrahydrofuran (2.5 mL), lithium borohydride (62 mg) was added, and the mixture was stirred for 7 hours at 50° C. The mixture was added by water and ethyl acetate. The organic layer was washed with water and brine successively, dried over an anhydrous sodium sulfate, concentrated under reduced to give the title compound (101 mg) having the following physical data.

REFERENCE EXAMPLE 19

(15α,13E)-9-Oxo-15-tetrahydropyran-2-yloxy)-16-(3-methylphenyl)-1,5-(2,5-interthienylene)-2,3,4,17,18,19,20-heptanor-8-azaprost-13-en-1-al

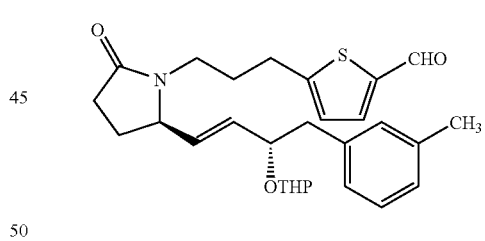

Under atmosphere of argon, a solution of the compound prepared in Reference Example 18 (100 mg) in mixed solvent of ethyl acetate (1 mL) and dimethylsulfoxide (1.5 mL) was added by diisopropylethylamine (0.22 mL). Then sulfur trioxide pyridine complex (100 mg) was added to the mixture on ice bath, and the mixture was stirred for 15 minutes. Water and ethyl acetate were added to the reaction mixture. The organic layer was washed with 1N hydrochloric acid, saturated aqueous sodium hydrogencarbonate and brine successively, dried over an anhydrous sodium sulfate, concentrated under reduced pressure to give the title compound (103 mg) having the following physical data.

TLC: Rf 0.51 (Ethyl Acetate).

EXAMPLE 13

(15α,13E)-9-Oxo-15-hydroxy-16-(3-methylphenyl)-1,5-(2,5-interthienylene)-2,3,4,17,18,19,20-heptanor-8-azaprost-13-en-1-al

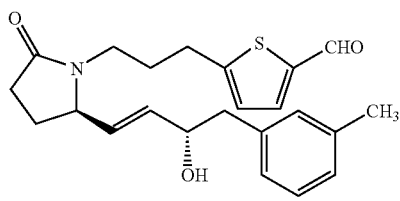

To a solution of the compound prepared in Reference Example 19 (100 mg) in mixed solvent of acetonitrile (1 mL) and methanol (0.5 mL), 0.1N hydrochloric acid was added, and the mixture was stirred for 1 hour at 35° C. Water and ethyl acetate were added to the reaction mixture. The organic layer was washed with saturated aqueous sodium hydrogencarbonate and brine successively, dried over an anhydrous sodium sulfate, concentrated under reduced pressure and was purified by column chromatography on silica gel (from ethyl acetate:hexane=4:1 to ethyl acetate only) to give the title compound (70 mg) having the following physical data.

TLC: Rf 0.34 (Ethyl Acetate);

NMR: δ 9.80 (s, 1H), 7.60 (d, J=3.9 Hz, 1H), 7.20 (t, J=7.4 Hz, 1H), 7.08-6.96 (m, 3H), 6.93 (d, J=3.9 Hz, 1H), 5.73 (dd, J=15.4, 5.8 Hz, 1H), 5.48 (ddd, J=15.4, 8.8, 1.4 Hz, 1H), 4.39 (m, 1H), 4.02 (m, 1H), 3.52 (m, 1H), 2.90-2.77 (m, 5H), 2.47-2.25 (m, 2H), 2.36 (s, 3H), 2.20 (m, 1H), 1.88-1.64 (m, 3H).

Example 13(a)

(15α,13E)-9-Oxo-15-hydroxy-16-(3-chlorophenyl)-17,18,19,20-tetranor-5-thia-8-azaprost-13-en-1-al

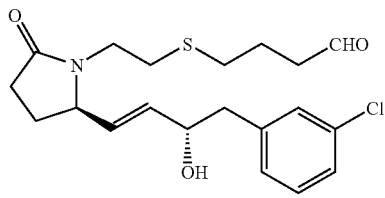

By the same procedure as describe in Reference Examples 17, 18, 19 and Example 13 using the methyl ester of the compound prepared in Example 3(b) instead of the methyl ester of compound prepared in Example 2(ww), the compound of the present invention having the following physical data were obtained.

TLC: Rf 0.13 (Hexane:Ethyl Acetate=1:5);

NMR: δ 9.80 (t, J=1.5 Hz, 1H), 7.27-7.20 (m, 3H), 7.09 (m, 1H), 5.75 (dd, J=15.6, 5.4 Hz, 1H), 5.51 (ddd, J=15.6, 8.7, 1.2 Hz, 1H), 4.43 (m, 1H), 4.09 (m, 1H), 3.60 (m, 1H), 2.95 (m, 1H), 2.84 (d, J=6.6 Hz, 2H), 2.70-2.20 (m, 9H), 2.00-1.60 (m, 3H).

EXAMPLE 14

(15α,13E)-9-Oxo-15-hydroxy-16-(3-aminophenyl)-17,18,19,20-tetranor-5-thia-8-zaprost-13-enoic acid

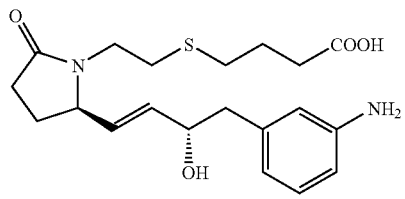

The solution of (15α,13E)-9-oxo-15-hydroxy-16-(3-nitrophenyl)-17,18,19,20-tetranor-5-thia-8-azaprost-13-enoic acid butyl ester (90 mg, this compound was prepared by the same procedure as describe in Reference Example 5 and Example 1 using 9-oxo-12-formyl-13,14,15,16,17,18,19,20-octanor-5-thia-8-azaprostanoic acid butyl ester instead of the compound prepared in Reference Example 4 and 3-(3-nitrophenyl)-2-oxopropylphosphonic acid dimethyl ester instead of 3-(3-methoxymethylphenyl)-2-oxopropylphosphonic acid dimethyl ester) of mixed solvent of methanol (1.4 mL), tetrahydrofuran (0.9 mL), water (0.45 mL) and acetic acid (0.27 mL) was added by Zinc powder (37 mg) under atmosphere of argon, and the mixture was stirred for 30 minutes at room temperature. Water and ethyl acetate were added to the reaction mixture. The organic layer was washed with saturated aqueous sodium hydrogencarbonate and brine successively, dried over an anhydrous sodium sulfate, concentrated under reduced pressure and was purified by column chromatography on silica gel (chloroform:methanol=100:1) and prepared by the same procedure as describe in Example 2 to give the title compound (44 mg) having the following physical data.

TLC: Rf 0.46 (Chloroform:Methanol=9:1);

NMR: δ 7.15-7.04 (m, 1H), 6.64-6.50 (m, 3H), 5.75 (dd, J=15.0, 6.0 Hz, 1H), 5.50 (dd, J=15.0, 8.4 Hz, 1H), 4.40 (m, 1H), 4.10 (m, 1H), 4.00-3.55 (m, 4H), 2.99 (m, 1H), 2.80-2.19 (m, 1H), 1.98-1.80 (m, 2H), 1.78-1.61 (m, 1H).

EXAMPLE 15(a) TO EXAMPLE 15(c)

By the same procedure as describe in Reference Example 16 and Example 10 using (15α,13E)-9-oxo-15-t-butyldimethylsilyloxy-16-phenyl-17,18,19,20-tetranor-5-thia-8-azaprost-13-en-1-ol instead of (15α,13E)-9-oxo-15-t-butyldimethylsilyloxy-16-(3-methylphenyl)-17,18,19,20-tetranor-5-thia-8-azaprost-13-en-1-ol and corresponding carboxylic acid derivatives instead of t-butoxycarbonylglycilglycine, the compound of the present invention having the following physical data were obtained.

The compound prepared in Example 15(c) was done by additional procedure of the same as described in Example 11.

Example 15(a)

(15α,13E)-1-Benzoyloxy-9-oxo-15-hydroxy-16-phenyl-17,18,19,20-tetranor-8-azaprost-13-ene

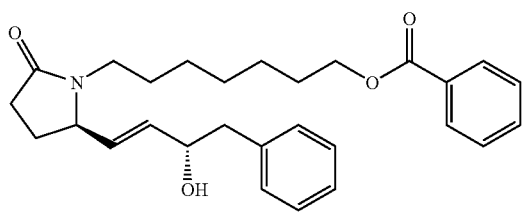

TLC: Rf 0.50 (Chloroform:Methanol=10:1);
NMR: δ 8.05-8.02 (m, 2H), 7.55 (m, 1H), 7.46-7.41 (m, 2H), 7.34-7.18 (m, 5H), 5.73 (dd, J=15.3, 6.0 Hz, 1H), 5.49 (ddd, J=15.3, 8.4, 1.2 Hz, 1H), 4.40 (m, 1H), 4.31 (t, J=6.6 Hz, 2H), 4.02 (m, 1H), 3.48 (m, 1H), 2.85 (d, J=6.6 Hz, 2H), 2.68 (m, 1H), 2.45-2.10 (m, 3H), 1.80-1.20 (m, 11H).

Example 15(b)

(15α,13E)-1-Butanoyloxy-9-oxo-15-hydroxy-16-phenyl-17,18,19,20-tetranor-8-azaprost-13-ene

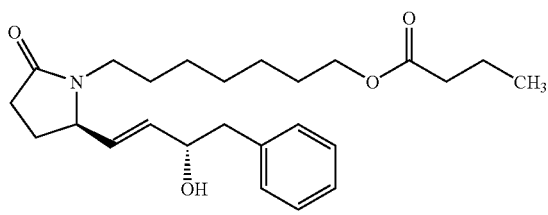

TLC: Rf 0.41 (Chloroform:Methanol=10:1);
NMR: δ 7.34-7.19 (m, 5H), 5.73 (dd, J=15.3, 6.3 Hz, 1H), 5.49 (ddd, J=15.3, 8.4, 1.2 Hz, 1H), 4.41 (m, 1H), 4.05 (t, J=6.6 Hz, 2H), 4.03 (m, 1H), 3.47 (m, 1H), 2.85 (d, J=6.6 Hz, 2H), 2.68 (m, 1H), 2.45-2.10 (m, 5H), 1.80-1.20 (m, 13H), 0.95 (t, J=7.2 Hz, 3H).

Example 15(c)

(15α,13E)-1-(2-Aminoacetyloxy)-9-oxo-15-hydroxy-16-phenyl-17,18,19,20-tetranor-8-azaprost-13-ene trifluoromethanesulfonic acid salt

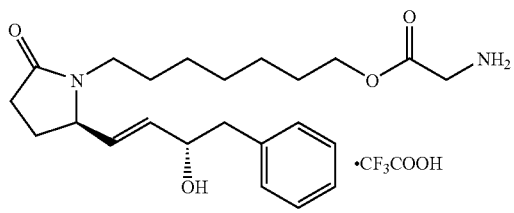

TLC: Rf 0.10 (Chloroform:Methanol=10:1);
NMR: δ 7.32-7.17 (m, 5H), 5.72 (dd, J=15.6, 6.3 Hz, 1H), 5.45 (dd, J=15.6, 8.7 Hz, 1H), 4.39 (m, 1H), 4.19 (t, J=6.3 Hz, 2H), 4.01 (m, 1H), 3.77 (br, 2H), 3.39 (m, 1H), 2.91-2.78 (m, 2H), 2.66 (m, 1H), 2.40-2.10 (m, 3H), 1.75-1.15 (m, 11H).

EXAMPLE 16

(15α,13E)-9-Oxo-15-hydroxy-16-(4-fluorophenyl)-17,18,19,20-tetranor-5-thia-8-azaprost-13-enoic acid 2-pentanoyloxyethyl ester

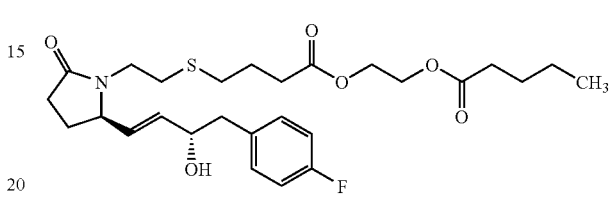

A solution of the compound prepared in Example 3(l) (100 mg), 2-pentanoyloxyethanol (370 mg) and triethylamine (0.071 mL) in ethyl acetate (1.3 mL) was stirred for 5 minutes. The reaction mixture was added by 1-methanesulfonyloxybenzotriazole (65 mg), and the mixture was stirred for 3 hours at room temperature. The reaction mixture was added by water, and was extracted by ethyl acetate. The extract was washed with water, saturated aqueous sodium hydrogencarbonate and brine successively, dried over an anhydrous sodium sulfate, concentrated under reduced pressure and was purified by column chromatography on silica gel (from ethyl acetate:hexane=3:1 to ethyl acetate only) to give the title compound (110 mg) having the following physical data.
TLC: Rf 0.33 (Ethyl Acetate);
NMR: δ 7.23-7.15 (m, 2H), 7.06-6.97 (m, 2H), 5.76 (dd, J=15.0, 5.4 Hz, 1H), 5.50 (dd, J=15.0, 8.7 Hz, 1H), 4.40 (m, 1H), 4.27 (s, 4H), 4.10 (m, 1H), 3.60 (m, 1H), 2.98 (m, 1H), 2.82 (d, J=6.0 Hz, 2H), 2.68-2.20 (m, 11H), 1.96-1.83 (m, 3H), 1.78-1.57 (m, 3H), 1.41-1.29 (m, 2H), 0.92 (t, J=7.2 Hz, 3H).

EXAMPLE 16(a) TO EXAMPLE 16(k)

By the same procedure as describe in Example 16 using the compound prepared in Example 3 or corresponding carboxylic acid derivatives and corresponding alcohol derivatives instead of 2-pentanoyloxyethanol, the compound of the present invention having the following physical data were obtained.

Example 16(a)

(15α,13E)-9-Oxo-15-hydroxy-16-phenyl-17,18,19,20-tetranor-8-azaprost-13-enoic acid 4-phenylbenzyl ester

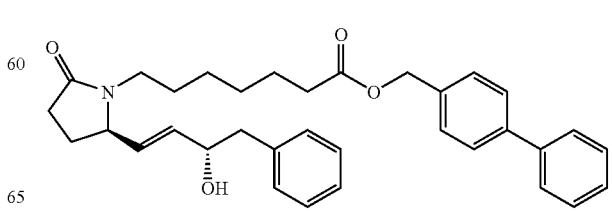

TLC: Rf 0.57 (Chloroform:Methanol:Water=9:1:0.1);
NMR: δ 7.63-7.56 (m, 4H), 7.48-7.18 (m, 10H), 5.71 (dd, J=15.4, 5.8 Hz, 1H), 5.46 (ddd, J=15.4, 8.2, 1.1 Hz, 1H), 5.17 (s, 2H), 4.40 (m, 1H), 3.99 (m, 1H), 3.44 (m, 1H), 2.82 (d, J=6.6 Hz, 2H), 2.66 (m, 1H), 2.40-2.31 (m, 4H), 2.20 (m, 1H), 1.70-1.61 (m, 3H), 1.50-1.20 (m, 6H).

Example 6(b)

(15α,13E)-9-Oxo-15-hydroxy-16-phenyl-17,18,19,20-tetranor-8-azaprost-13-enoic acid 3-phenylphenyl ester

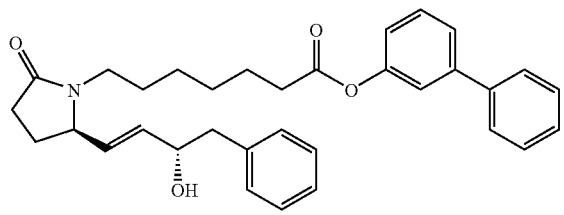

TLC: Rf 0.48 (Hexane:Ethyl Acetate=1:3);
NMR: δ 7.61-7.55 (m, 2H), 7.48-7.17 (m, 11H), 7.05 (m, 1H), 5.72 (dd, J=15.4, 5.8 Hz, 1H), 5.48 (ddd, J=15.4, 8.5, 1.1 Hz, 1H), 4.40 (m, 1H), 4.02 (m, 1H), 3.48 (m, 1H), 2.83 (d, J=6.6 Hz, 2H), 2.72 (m, 10H), 2.59 (t, J=7.4 Hz, 2H), 2.41-2.34 (m, 2H), 2.21 (m, 1H), 1.81-1.62 (m, 3H), 1.54-1.22 (m, 6H).

Example 16(c)

(15α,13E)-9-Oxo-15-hydroxy-16-phenyl-17,18,19,20-tetranor-8-azaprost-13-enoic acid 2-dimethylaminoethyl ester hydrochloride

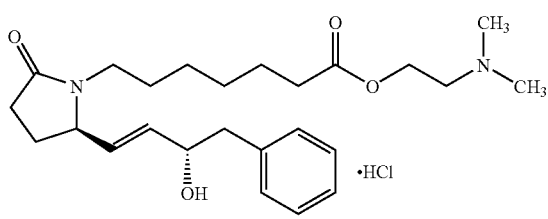

TLC: Rf 0.39 (Chloroform:Methanol=9:1);
NMR (CD₃OD): δ 7.30-7.12 (m, 5H), 5.68 (dd, J=15.3, 6.6 Hz, 1H), 5.36 (dd, J=15.3, 9.0 Hz, 1H), 4.43-4.29 (m, 3H), 4.07 (m, 10H), 3.45 (m, 2H), 3.38-3.20 (m, 1H), 2.94-2.89 (m, 7H), 2.72 (m, 1H), 2.54 (m, 1H), 2.44-2.17 (m, 5H), 1.76-1.56 (m, 3H), 1.55-1.18 (m, 6H).

Example 16(d)

(15α,13E)-9-Oxo-15-hydroxy-16-(4-fluorophenyl)-17,18,19,20-tetranor-5-thia-8-azaprost-13-enoic acid 2-hexanoyloxyethyl ester

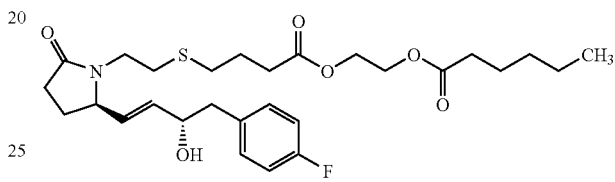

TLC: Rf 0.27 (Ethyl Acetate);
NMR: δ 7.21-7.12 (m, 2H), 7.07-6.97 (m, 2H), 5.75 (dd, J=15.0, 6.0 Hz, 1H), 5.51 (dd, J=15.0, 8.6 Hz, 1H), 4.39 (m, 1H), 4.27 (s, 4H), 4.10 (m, 1H), 3.61 (m, 1H), 2.96 (m, 1H), 2.82 (d, J=6.6 Hz, 2H), 2.70-2.14 (m, 11H), 1.99-1.82 (m, 3H), 1.79-1.55 (m, 2H), 1.40-1.22 (m, 4H), 0.90 (t, J=7.0 Hz, 3H).

Example 16(e)

(15α,13E)-9-Oxo-15-hydroxy-16-(4-fluorophenyl)-17,18,19,20-tetranor-5-thia-8-azaprost-13-enoic acid 2-heptanoyloxyethyl ester TLC: Rf 0.29 (Ethyl Acetate);
NMR: δ 7.21-7.13 (m, 2H), 7.06-6.97 (m, 2H), 5.75 (dd, J=15.0, 6.0 Hz, 1H), 5.50 (dd, J=15.0, 8.4 Hz, 1H), 4.39 (m, 1H), 4.27 (s, 4H), 4.10 (m, 1H), 3.61 (m, 1H), 2.97 (m, 1H), 2.82 (d, J=6.6 Hz, 2H), 2.68-2.16 (m, 11H), 1.97-1.83 (m, 3H), 1.76-1.55 (m, 2H), 1.40-1.20 (m, 6H), 0.89 (t, J=7.0 Hz, 3H).

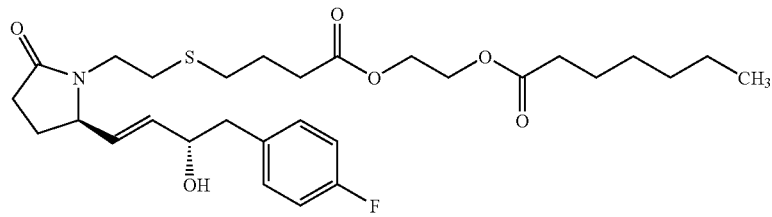

Example 16(f)

(15α,13E)-9-Oxo-15-hydroxy-16-(4-fluorophenyl)-17,18,19,20-tetranor-5-thia-8-azaprost-13-enoic acid 2-octanoyloxyethyl ester

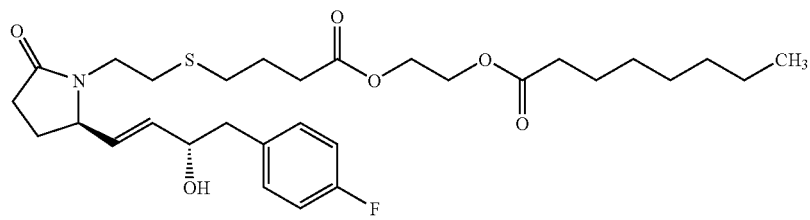

TLC: Rf 0.26 (Ethyl Acetate:Methanol=20:1);

NMR: δ 7.22-7.12 (m, 2H), 7.07-6.97 (m, 2H), 5.75 (dd, J=15.3, 5.4 Hz, 1H), 5.51 (dd, J=15.3, 8.4 Hz, 1H), 4.45-4.36 (m, 1H), 4.26 (s, 4H), 4.18-4.07 (m, 1H), 3.70-3.57 (m, 10H), 3.02-2.90 (m, 1H), 2.82 (d, J=5.4 Hz, 2H), 2.70-2.50 (m, 4H), 2.45 (t, J=7.2 Hz, 2H), 2.40-2.18 (m, 5H), 1.98-1.86 (m, 3H), 1.80-1.50 (m, 3H), 1.40-1.20 (m, 8H), 0.89 (t, J=7.2 Hz, 3H).

Example 16(g)

(15α,13E)-9-Oxo-15-hydroxy-16-(4-fluorophenyl)-17,18,19,20-tetranor-5-thia-8-azaprost-13-enoic acid N-heptanoyl-N-methylcarbamoylmethyl ester

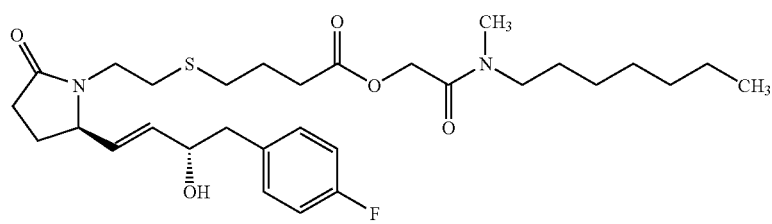

TLC: Rf 0.69 (Chloroform:Methanol=9:1);

NMR: δ 7.21-7.14 (m, 2H), 7.04-6.97 (m, 2H), 5.75 (ddd, J=15.0, 5.4, 1.2 Hz, 1H), 5.53 (dd, J=15, 8.7 Hz, 1H), 4.73-4.65 (m, 2H), 4.39 (m, 1H), 4.13 (m, 1H), 3.58 (m, 1H), 3.39-3.24 (m, 1H), 3.20-3.10 (m, 10H), 3.06 (m, 1H), 2.93-2.77 (m, 5H), 2.71-2.15 (m, 9H), 2.00-1.89 (m, 2H), 1.78-1.42 (m, 3H), 1.40-1.20 (m, 8H), 0.95-0.82 (m, 3H).

Example 16(h)

(15α,13E)-9-Oxo-15-hydroxy-16-(4-fluorophenyl)-17,18,19,20-tetranor-5-thia-8-azaprost-13-enoic acid (4-hexylpiperazin-1-yl)carbonylmethyl ester

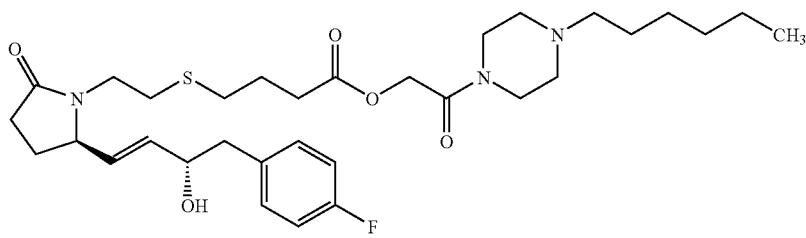

TLC: Rf 0.71 (Chloroform:Methanol=9:1);

NMR: δ 7.22-7.12 (m, 2H), 7.06-6.96 (m, 2H), 5.76 (dd, J=15.3, 5.4 Hz, 1H), 5.52 (dd, J=15.3, 8.7 Hz, 1H), 4.70 (s, 2H), 4.43-4.35 (m, 1H), 4.18-4.07 (m, 1H), 3.70-3.50 (m, 3H), 3.41-3.32 (m, 2H), 3.09-2.97 (m, 1H), 2.81 (d, J=6.6 Hz, 2H), 2.72-2.5 (m, 6H), 2.5-2.2 (m, 9H), 2.01-1.89 (m, 2H), 1.80-1.58 (m, 1H), 1.58-1.41 (m, 2H), 1.41-1.22 (m, 6H), 0.90 (t, J=7.2 Hz, 3H).

Example 16(i)

(15α,13E)-9-Oxo-15-hydroxy-16-(4-fluorophenyl)-17,18,19,20-tetranor-5-thia-8-azaprost-13-enoic acid N-ethyl-N-(2-diethylaminoethyl)carbamoylmethyl ester

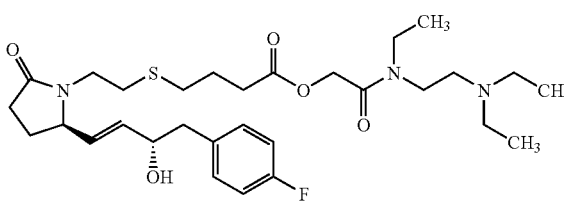

TLC: Rf 0.29 (Chloroform:Methanol=9:1);

NMR: δ 7.25-7.10 (m, 2H), 7.05-6.95 (m, 2H), 5.76 (dd, J=15.0, 5.4 Hz, 1H), 5.60-5.45 (m, 1H), 4.79 and 4.71 (s, 2H), 4.38 (q, J=6.0 Hz, 1H), 4.12 (q, J=7.2 Hz, 1H), 3.65-3.50 (m, 1H), 3.45-3.20 (m, 4H), 3.10-2.95 (m, 1H), 2.82 (d, J=6.0 Hz, 2H), 2.75-2.40 (m, 10H), 2.40-2.15 (m, 4H), 2.05-1.85 (m, 2H), 1.80-1.60 (m, 1H), 1.22 and 1.12 (t, J=7.2 Hz, 3H), 1.05 (t, J=7.2 Hz, 3H), 1.04 (t, J=7.2 Hz, 3H).

Example 16(j)

(15α,13E)-9-Oxo-15-hydroxy-16-(4-fluorophenyl)-17,18,19,20-tetranor-5-thia-8-azaprost-13-enoic acid 2-(2-(dipropylamino)acetyloxy)ethyl ester

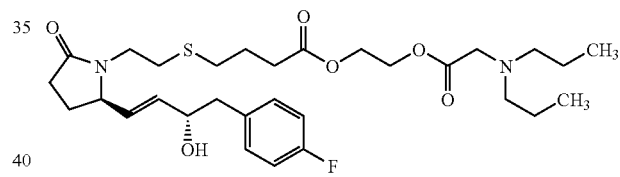

TLC: Rf 0.47 (Chloroform:Methanol=9:1);

NMR: δ 7.21-7.15 (m, 2H), 7.04-6.97 (m, 2H), 5.76 (dd, J=15.3, 5.7 Hz, 1H), 5.50 (ddd, J=15.3, 8.4, 1.0 Hz, 1H), 4.40 (m, 1H), 4.37-4.20 (m, 4H), 4.10 (m, 1H), 3.60 (m, 1H), 3.35 (s, 2H), 2.97 (m, 1H), 2.80 (d, J=6.0 Hz, 2H), 2.65-2.19 (m, 13H), 1.97-1.84 (m, 3H), 1.78-1.40 (m, 5H), 0.88 (t, J=7.5 Hz, 6H).

Example 16(k)

(15α,13E)-9-Oxo-15-hydroxy-16-(4-fluorophenyl)-17,18,19,20-tetranor-5-thia-8-azaprost-13-enoic acid 2-(2-(diethylamino)acetyloxy)ethyl ester

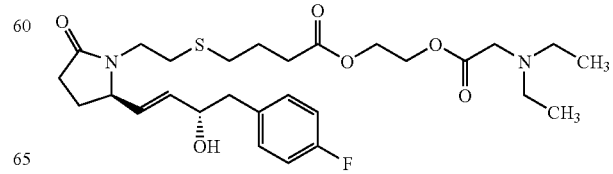

TLC: Rf 0.46 (Chloroform:Methanol=9:1);

NMR: δ 7.20-7.14 (m, 2H), 7.06-6.95 (m, 2H), 5.75 (dd, J=15.3, 5.7 Hz, 1H), 5.50 (dd, J=15.3, 8.4 Hz, 1H), 4.42-4.20 (m, 5H), 4.10 (m, 1H), 3.60 (m, 1H), 3.34 (s, 2H), 2.97 (m, 1H), 2.80 (d, J=7.0 Hz, 2H), 2.70-2.17 (m, 13H), 2.00-1.83 (m, 3H), 1.70 (m, 1H), 1.06 (t, J=7.2 Hz, 6H).

EXAMPLE 17

(15α,13E)-9-Oxo-15-hydroxy-16-(4-fluorophenyl)-17,18,19,20-tetranor-5-thia-8-azaprost-13-enoic acid nonanoyloxymethyl ester

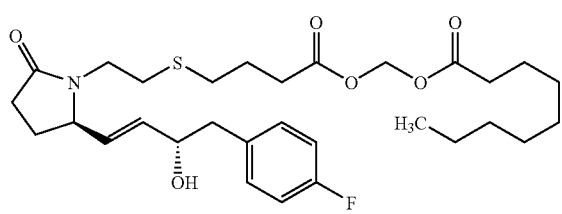

By the same procedure as describe in Example 12 using the compound prepared in Example 3(l) instead of the compound prepared in Example 3(b) and nonanoyloxymethyl chloride instead of 2-bromoacetic acid isopropyl ester, the compound of the present invention having the following physical data were obtained.

TLC: Rf 0.31 (Hexane:Ethyl Acetate=1:4);

NMR: δ 7.21-7.12 (m, 2H), 7.06-6.96 (m, 2H), 5.81-5.69 (m, 3H), 5.50 (dd, J=15.3, 8.4 Hz, 1H), 4.39 (m, 1H), 4.10 (m, 1H), 3.61 (m, 1H), 3.00-2.78 (m, 3H), 2.69-2.17 (m, 11H), 2.00-1.50 (m, 4H), 1.40-1.19 (m, 10H), 0.88 (t, J=7.2 Hz, 3H).

REFERENCE EXAMPLE 20

(9α,11α,15α,13E)-9-Hydroxy-11,15-bis(tetrahydropyran-2-yloxy)-16-(3-methoxymethylphenyl)-17,18,19,20-tetranor-5-thiaprost-13-enoic acid

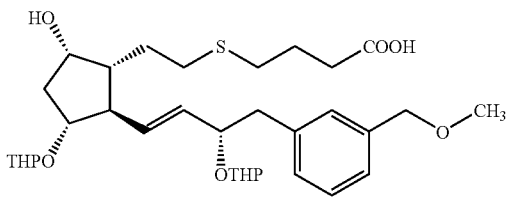

To a solution of (9α,11α,15α,13E)-9-hydroxy-11,15-bis(tetrahydropyran-2-yloxy)-16-(3-methoxymethylphenyl)-17,18,19,20-tetranor-5-thiaprost-13-enoic acid methyl ester (5 g; this is the compound described in Reference Example 28 of WO00/03980) in methanol (8 mL), 2N aqueous sodium hydroxide (8.1 mL) was added, and the mixture was stirred for 1.5 hours at room temperature. After cooling, 2N hydrochloric acid was added to the aqueous layer to acidify, then the mixture was extracted by ethyl acetate. The extract was washed with brine, dried over an anhydrous sodium sulfate, concentrated under reduced pressure to give the title compound having the following physical data, which was used for the next reaction without purification.

TLC: Rf 0.55 (Ethyl Acetate);

NMR: δ 7.3-7.1 (m, 4H), 5.7-5.3 (m, 2H), 4.8-3.1 (m, 9H), 3.5-3.1 (m, 5H), 3.0-2.0 (m, 10H), 2.0-1.3 (m, 18H).

REFERENCE EXAMPLE 21

(9α,11α,15α,13E)-9-Hydroxy-11,15-bis(tetrahydropyran-2-yloxy)-16-(3-methoxymethylphenyl)-17,18,19,20-tetranor-5-thiaprost-13-enoic acid 2-nonanoyloxyethyl ester

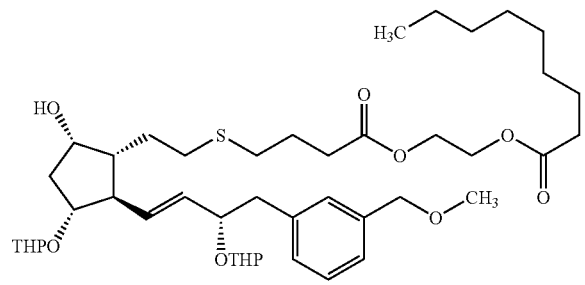

To a solution of the compound prepared in Reference Example 20 in dimethylformamide (16 mL), nonanoic acid 2-bromoethylester (2.35 g), sodium iodide (121 mg) and potassium carbonate (1.67 g) were added, and the mixture was stirred for 2 hours at 50° C. After cooling, the mixture was added by water, and extracted by ethyl acetate. The extract was washed with water and brine, dried over an anhydrous sodium sulfate, concentrated under reduced pressure and was purified by column chromatography on silica gel (ethyl acetate:hexane 1:1) to give the title compound (6.33 g) having the following physical data.

TLC: Rf 0.43 (Hexane:Ethyl Acetate=1:1);

NMR: δ 7.3-7.1 (m, 4H), 5.7-5.3 (m, 2H), 4.75-4.45 (m, 2H), 4.42 (s, 2H), 4.27 (s, 4H), 4.3-3.7 (m, 3H), 3.5-3.2 (m, 5H), 3.0-2.7 (m, 2H), 2.6-2.4 (m, 6H), 2.33 (t, J=7.2 Hz, 2H), 2.3-2.0 (m, 1H), 2.0-1.2 (m, 31H), 0.90 (t, J=7.2 Hz, 3H).

REFERENCE EXAMPLE 22

(11α,15α,13E)-9-Oxo-11,15-bis(tetrahydropyran-2-yloxy)-16-(3-methoxymethylphenyl)-17,18,19,20-tetranor-5-thiaprost-13-enoic acid 2-nonanoyloxyethyl ester

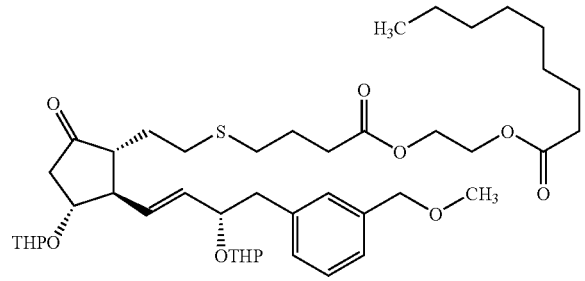

To a solution of the compound prepared in Reference Example 21 (6.33 g) in ethyl acetate (28 mL), diisopropylethylamine (8.35 mL) was added on iced bath. Then sulfur trioxide pyridine complex (3.82 g) and dimethylsulfoxide (14 mL) were added to the mixture, and the mixture was stirred for 20 minutes. The reaction mixture was added by water and was extracted by ethyl acetate. The extract was washed with water and brine successively, dried over an anhydrous sodium sulfate, concentrated under reduced pressure and was purified by column chromatography on silica gel (ethyl acetate:hexane=1:1) to give the title compound (5.12 g) having the following physical data.

TLC: Rf 0.50 (Hexane:Ethyl Acetate=1:1);

NMR: δ 7.3-7.1 (m, 4H), 5.8-5.25 (m, 2H), 4.8-4.5 (m, 2H), 4.42 (s, 2H), 4.4-3.75 (m, 8H), 3.55-3.2 (m, 5H), 3.0-2.65 (m, 3H), 2.65-2.4 (m, 7H), 2.4-2.05 (m, 4H), 1.95-1.2 (m, 28H), 0.88 (t, J=7.2 Hz, 3H).

EXAMPLE 18

(11α,15α,13E)-9-Oxo-11,15-dihydroxy-16-(3-methoxymethylphenyl)-17,18,19,20-tetranor-5-thiaprost-13-enoic acid 2-nonanoyloxyethyl ester

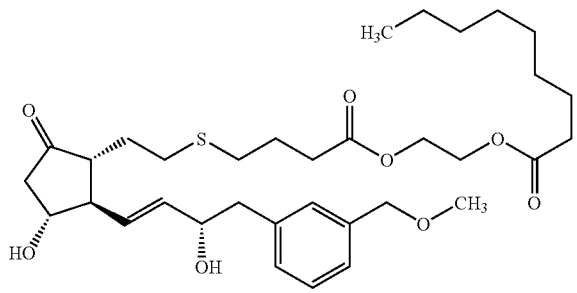

To a solution of the compound prepared in Reference Example 22 (5.12 g) in mixed solvent of methanol (26 mL), 1,2-dimethoxyethane (26 mL) and acetonitrile (26 mL), 0.1N hydrochloric acid (26 mL) was added, and the mixture was stirred for 3 hours at 35° C. The reaction mixture was added by water and was extracted by ethyl acetate. The extract was washed with saturated aqueous sodium hydrogen carbonate solution and brine successively, dried over an anhydrous magnesium sulfate, concentrated under reduced pressure and was purified by column chromatography on silica gel (ethyl acetate:hexane from 3:1 to 4:1, then ethyl acetate only) to give the title compound (2.71 g) having the following physical data.

TLC: Rf 0.33 (Ethyl Acetate);

NMR: δ 7.30 (t, J=8.1 Hz, 1H), 7.23-7.11 (m, 3H), 5.76 (dd, J=15.3, 6.0 Hz, 1H), 5.53 (dd, J=15.3, 8.4 Hz, 1H), 4.48-4.39 (m, 3H), 4.26 (s, 4H), 4.00-3.90 (m, 1H), 3.42 (s, 3H), 3.15-3.08 (br, 1H), 2.91 (dd, J=13.5, 5.4 Hz, 1H), 2.83 (dd, J=13.5, 6.9 Hz, 1H), 2.70 (dd, J=18.6, 7.5 Hz, 1H), 2.65-2.50 (m, 2H), 2.52 (t, J=7.2 Hz, 2H), 2.44 (t, J=7.2 Hz, 2H), 2.36 (t, J=7.2 Hz, 2H), 2.40-2.13 (m, 4H), 1.95-1.82 (m, 3H), 1.74-1.60 (m, 3H), 1.40-1.20 (m, 10H), 0.89 (t, J=7.2 Hz, 3H).

EXAMPLE 18(a) TO EXAMPLE 18(q)

By the same procedure as describe in Reference Examples 21, 22 and Example 18 using corresponding halides instead of nonanoic acid 2-bromoethyl ester, the compound of the present invention having the following physical data were obtained.

Example 18(a)

(11α,15α,13E)-9-Oxo-11,15-dihydroxy-16-(3-methoxymethylphenyl)-17,18,19,20-tetranor-5-thiaprost-13-enoic acid pivaloyloxymethyl ester

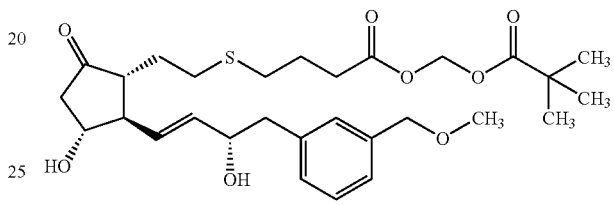

TLC: Rf 0.63 (Chloroform:Methanol=9:1);

NMR: δ 7.33-7.10 (m, 4H), 5.74 (s, 2H), 5.73 (dd, J=15, 6.0 Hz, 1H), 5.53 (ddd, J=15, 8.7, 0.7 Hz, 1H), 4.48-4.37 (m, 3H), 3.94 (m, 1H), 3.42 (s, 3H), 2.90 (dd, J=13, 5.6 Hz, 1H), 2.83 (dd, J=13, 6.9 Hz, 1H), 2.70 (ddd, J=19, 7.5, 1.1 Hz, 1H), 2.62-2.43 (m, 6H), 2.38-2.12 (m, 3H), 1.95-1.81 (m, 3H), 1.74-1.59 (m, 1H), 1.21 (s, 9H).

Example 18(b)

(11α,15α,13E)-9-Oxo-11,15-dihydroxy-16-(3-methoxymethylphenyl)-17,18,19,20-tetranor-5-thiaprost-13-enoic acid 1-cyclohexyloxycarbonyloxyethyl ester

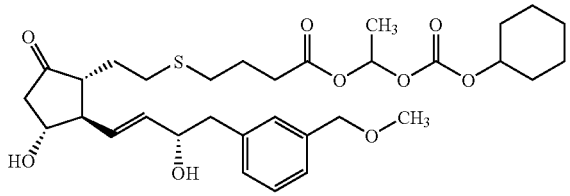

TLC: Rf 0.63 (Chloroform:Methanol=9:1);

NMR: δ 7.33-7.09 (m, 4H), 6.75 (q, J=5.4 Hz, 1H), 5.73 (dd, J=15, 6.3 Hz, 1H), 5.53 (dd, J=15, 8.6 Hz, 1H), 4.63 (m, 1H), 4.48-4.34 (m, 3H), 3.94 (m, 10H), 3.41 (s, 3H), 2.88 (dd, J=14, 5.6 Hz, 1H), 2.82 (dd, J=14, 6.9 Hz, 1H), 2.69 (ddd, J=19, 7.6, 1.0 Hz, 1H), 2.64-2.41 (m, 6H), 2.37-2.12 (m, 3H), 1.98-1.17 (m, 14H), 1.51 (d, J=5.4 Hz, 3H).

Example 18(c)

(11α,15α,13E)-9-Oxo-11,15-dihydroxy-16-(3-methoxymethylphenyl)-17,18,19,20-tetranor-5-thiaprost-13-enoic acid N,N-diethylaminocarbonylmethyl ester

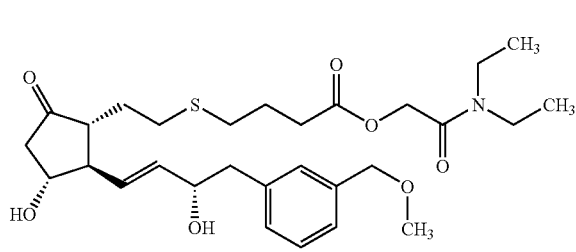

TLC: Rf 0.18 (Ethyl Acetate:Methanol 50:1);

NMR: δ 7.3-7.1 (m, 4H), 5.76 (dd, J=15, 6 Hz, 1H), 5.55 (dd, J=15, 8 Hz, 1H), 4.70 (s, 2H), 4.42 (s, 2H), 4.5-4.4 (m, 1H), 3.90 (q, J=8 Hz, 1H), 3.41 (s, 3H), 3.37 (q, J=7 Hz, 2H), 3.24 (q, J=7 Hz, 2H), 2.95-2.8 (m, 2H), 2.69 (dd, J=18, 7 Hz, 1H), 2.65-2.5 (m, 6H), 2.4-2.1 (m, 4H), 2.4-1.8 (m, br), 2.0-1.8 (m, 2H), 1.75-1.6 (m, 1H), 1.22 (t, J=7 Hz, 3H), 1.15 (t, J=7 Hz, 3H).

Example 18(d)

(11α,15α,13E)-9-Oxo-11,15-dihydroxy-16-(3-methoxymethylphenyl)-17,18,19,20-tetranor-5-thiaprost-13-enoic acid 2-acetyloxyetter

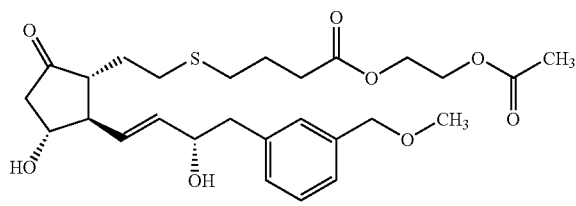

TLC: Rf 0.28 (Ethyl Acetate);

NMR: δ 7.3-7.1 (m, 4H), 5.76 (dd, J=15, 6 Hz, 1H), 5.53 (dd, J=15, 8 Hz, 1H), 4.5-4.4 (m, 3H), 4.27 (s, 4H), 3.94 (brq, 1H), 3.42 (s, 3H), 3.05-3.0 (br, 1H), 2.91 (dd, J=14, 6 Hz, 1H), 2.83 (dd, J=14, 7 Hz, 1H), 2.70 (dd, J=18, 7 Hz, 1H), 2.65-2.5 (m, 2H), 2.51 (t, J=7 Hz, 2H), 2.45 (t, J=7 Hz, 2H), 2.4-2.1 (m, 4H), 2.08 (s, 3H), 1.95-1.8 (m, 3H), 1.8-1.6 (m, 1H).

Example 18(e)

(11α,15α,13E)-9-Oxo-11,15-dihydroxy-16-(3-methoxymethylphenyl)-17,18,19,20-tetranor-5-thiaprost-13-enoic acid benzoylmethyl ester

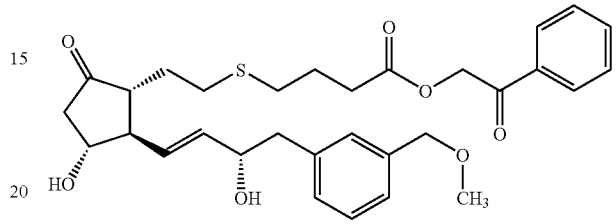

TLC: Rf 0.32 (Ethyl Acetate);

NMR: δ 7.92-7.88 (m, 2H), 7.65-7.59 (m, 1H), 7.52-7.46 (m, 2H), 7.34-7.10 (m, 4H), 5.77 (dd, J=15.6, 5.7 Hz, 1H), 5.54 (dd, J=15.6, 8.4 Hz, 1H), 5.35 (s, 2H), 4.50-4.38 (m, 3H), 4.00-3.89 (m, 1H), 3.41 (s, 3H), 2.87-2.54 (m, 9H), 2.41-2.18 (m, 3H), 2.04-1.84 (m, 3H), 1.78-1.65 (m, 1H).

Example 18(f)

(11α,15α,13E)-9-Oxo-11,15-dihydroxy-16-(3-methoxymethylphenyl)-17,18,19,20-tetranor-5-thiaprost-13-enoic acid isopropyloxycarbonylmethyl ester

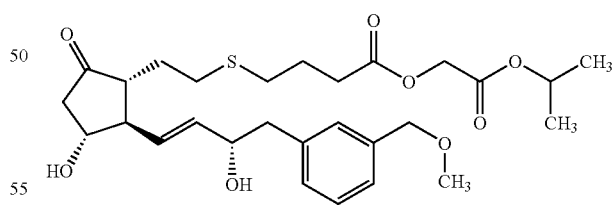

TLC: Rf 0.30 (Ethyl Acetate);

NMR: δ 7.35-7.12 (m, 4H), 5.75 (dd, J=15.0, 5.7 Hz, 1H), 5.53 (dd, J=15.0, 8.4 Hz, 1H), 5.07 (m, 1H), 4.56 (s, 2H), 4.47-4.37 (m, 3H), 3.93 (m, 1H), 3.42 (s, 3H), 3.05-2.50 (m, 10H), 2.39-2.14 (m, 4H), 1.98-1.83 (m, 3H), 1.78-1.60 (m, 1H), 1.25 (d, J=6.3 Hz, 6H).

Example 18(g)

(11α,15α,13E)-9-Oxo-11,15-dihydroxy-16-(3-methoxymethylphenyl)-17,18,19,20-tetranor-5-thiaprost-13-enoic acid N,N-diethylaminocarbonyloxymethyl ester

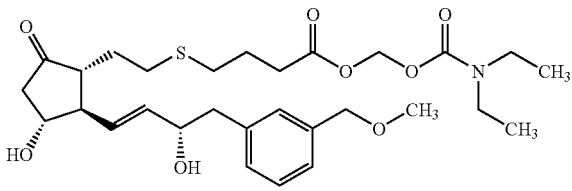

TLC: Rf 0.34 (Ethyl Acetate);
NMR: δ 7.3-7.1 (m, 4H), 5.76 (s, 2H), 5.75 (dd, J=15, 6 Hz, 1H), 5.53 (dd, J=15, 8 Hz, 1H), 4.5-4.35 (m, 3H), 3.93 (brq, 1H), 3.42 (s, 3H), 3.4-3.2 (m, 4H), 2.95-2.8 (m, 2H), 2.70 (dd, J=19, 8 Hz, 1H), 2.65-2.45 (m, 6H), 2.4-2.1 (m, 4H), 1.95-1.8 (m, 4H), 1.75-1.6 (m, 1H), 1.2-1.05 (m, 6H).

Example 18(h)

(11α,15α,13E)-9-Oxo-11,15-dihydroxy-16-(3-methoxymethylphenyl)-17,18,19,20-tetranor-5-thiaprost-13-enoic acid t-butyloxycarbonylmethyl ester

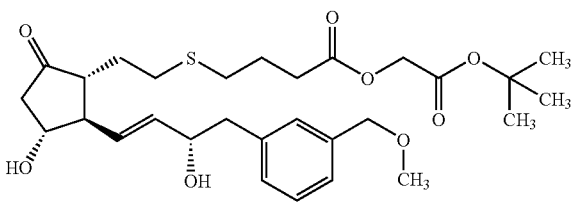

TLC Rf 0.36 (Ethyl Acetate);
NMR: δ 7.35-7.12 (m, 4H), 5.73 (dd, J=15.0, 6.0 Hz, 1H), 5.51 (dd, J=15.0, 8.0 Hz, 1H), 4.50 (s, 2H), 4.43-4.35 (m, 3H), 3.99-3.88 (m, 1H), 3.42-3.20 (m, 4H), 2.89-2.15 (m, 11H), 1.95-1.60 (m, 6H), 1.47 (s, 9H).

Example 18(i)

(11α,15α,13E)-9-Oxo-11,15-dihydroxy-16-(3-methoxymethylphenyl)-17,18,19,20-tetranor-5-thiaprost-13-enoic acid 1-isopropyloxycarbonylethyl ester

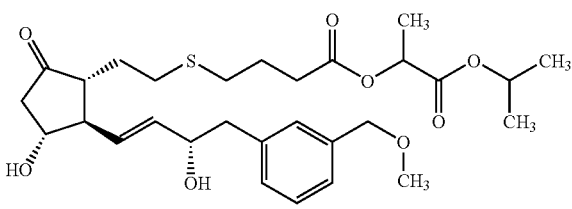

TLC: Rf 0.44 (Ethyl Acetate);
NMR: δ 7.36-7.12 (m, 4H), 5.76 (dd, J=15.0, 5.4 Hz, 1H), 5.53 (dd, J=15.0, 8.4 Hz, 1H), 5.10-4.97 (m, 1H), 4.47-4.38 (m, 3H), 3.99-3.87 (m, 1H), 3.42 (s, 3H), 2.97-2.14 (m, 12H), 1.97-1.61 (m, 7H), 1.46 (d, J=7.2 Hz, 3H), 1.27 and 1.23 (d, J=7.0 Hz, 6H).

Example 18(j)

(11α,15α,13E)-9-Oxo-11,15-dihydroxy-16-(3-methoxymethylphenyl)-17,18,19,20-tetranor-5-thiaprost-13-enoic acid 1-benzoylethyl ester

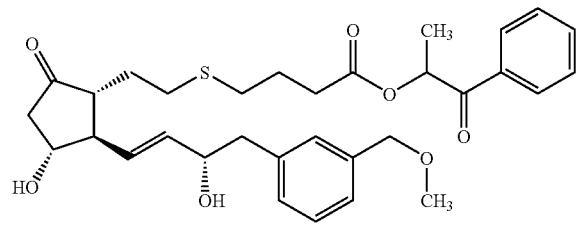

TLC: Rf 0.37 (Ethyl Acetate);
NMR: δ 7.92 (d, J=8.4 Hz, 2H), 7.63-7.57 (m, 1H), 7.51-7.44 (m, 2H), 7.31-7.25 (m, 1H), 7.19-7.10 (m, 3H), 5.95 (q, J=7.20 Hz, 1H), 5.74 (ddd, J=15.3, 5.7, 4.2 Hz, 1H), 5.52 (ddd, J=15.3, 7.5, 1.8 Hz, 1H), 4.47-4.35 (m, 3H), 4.09-3.94 (m, 1H), 3.41 (s, 3H), 3.02-2.13 (m, 14H), 1.97-1.65 (m, 4H), 1.52 (d, J=7.2 Hz, 3H).

Example 18(k)

(11α,15α,13E)-9-Oxo-11,15-dihydroxy-16-(3-methoxymethylphenyl)-17,18,19,20-tetranor-5-thiaprost-13-enoic acid methoxycarbonylmethyl ester

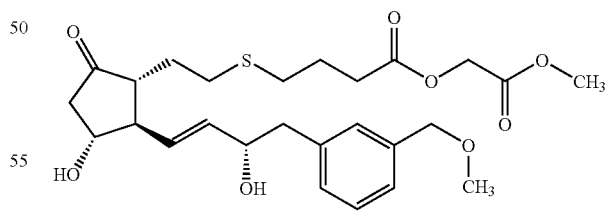

TLC: Rf 0.36 (Chloroform:Methanol 10:1);
NMR: δ 7.32-7.15 (m, 4H), 5.74 (dd, J=15.3, 6.3 Hz, 1H), 5.53 (dd, J=15.3, 8.7 Hz, 1H), 4.62 (s, 2H), 4.42 (m, 2H), 4.39 (m, 1H), 3.94 (m, 1H), 3.76 (s, 3H), 3.41 (s, 3H), 3.24 (brs, 1H), 2.91-2.51 (m, 8H), 2.41-2.14 (m, 4H), 1.95-1.83 (m, 3H), 1.74-1.62 (m, 2H).

Example 18(l)

(11α,15α,13E)-9-Oxo-11,15-dihydroxy-16-(3-methoxymethylphenyl)-17,18,19,20-tetranor-5-thiaprost-13-enoic acid 2-tridecanoyloxyethyl ester

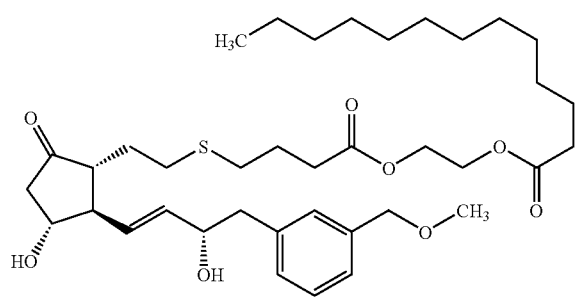

TLC: Rf 0.36 (Ethyl Acetate);
NMR: δ 7.3-7.1 (m, 4H), 5.77 (dd, J=15, 6 Hz, 1H), 5.53 (dd, J=15, 8 Hz, 1H), 4.5-4.4 (m, 3H), 4.25 (s, 4H), 4.0-3.9 (brq, 1H), 3.42 (s, 3H), 2.92 (dd, J=14, 5 Hz, 1H), 2.84 (dd, J=14, 7 Hz, 1H), 2.70 (dd, J=19, 8 Hz, 1H), 2.65-2.5 (m, 2H), 2.50 (t, J=7 Hz, 2H), 2.45 (t, J=7 Hz, 2H), 2.33 (t, J=7 Hz, 2H), 2.4-2.1 (m, 5H), 1.95-1.8 (m, 3H), 1.75-1.5 (m, 3H), 1.4-1.2 (m, 18H), 0.87 (t, J=7 Hz, 3H).

Example 18(m)

(11α,15α,13E)-9-Oxo-11,15-dihydroxy-16-(3-methoxymethylphenyl)-17,18,19,20-tetranor-5-thiaprost-13-enoic acid 2-heptanoyloxyethyl ester

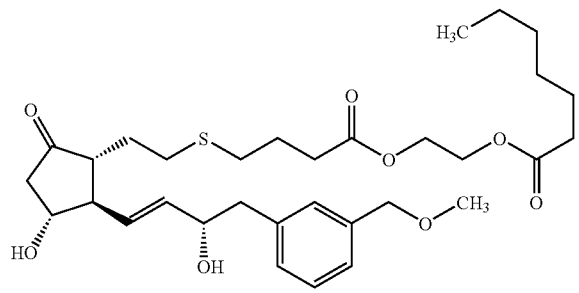

TLC: Rf 0.35 (Ethyl Acetate);
NMR: δ 7.3-7.1 (m, 4H), 5.74 (dd, J=15, 6 Hz, 1H), 5.52 (dd, J=15, 8 Hz, 1H), 4.5-4.3 (m, 3H), 4.26 (s, 4H), 4.0-3.9 (m, 1H), 3.42 (s, 3H), 3.35-3.3 (br, 1H), 2.89 (dd, J=14, 6 Hz, 1H), 2.81 (dd, J=14, 7 Hz, 1H), 2.70 (dd, J=19, 8 Hz, 1H), 2.65-2.5 (m, 2H), 2.52 (t, J=7 Hz, 2H), 2.47 (t, J=7 Hz, 2H), 2.5-2.4 (br, 1H), 2.4-2.15 (m, 5H), 1.95-1.8 (m, 3H), 1.75-1.55 (m, 3H), 1.4-1.2 (m, 6H), 0.90 (t, J=7 Hz, 3H).

Example 18(n)

(11α,15α,13E)-9-Oxo-11,15-dihydroxy-16-(3-methoxymethylphenyl)-17,18,19,20-tetranor-5-thiaprost-13-enoic acid 2-octanoyloxyethyl ester

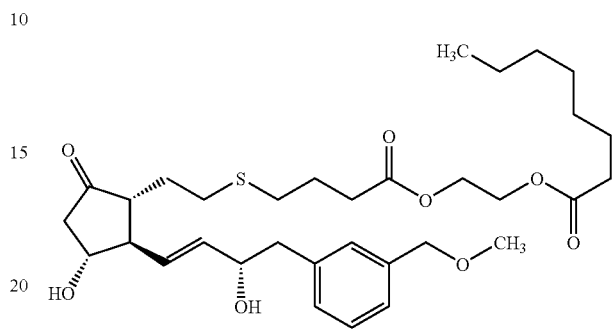

TLC: Rf 0.22 (Hexane:Ethyl Acetate=1:1);
NMR: δ 7.35-7.10 (m, 4H), 5.76 (dd, J=15.3, 5.7 Hz, 1H), 5.53 (dd, J=15.3, 8.7 Hz, 1H), 4.48-4.38 (m, 3H), 4.27 (s, 4H), 3.96 (m, 1H), 3.42 (s, 3H), 3.00-2.80 (m, 3H), 2.78-2.40 (m, 7H), 2.39-2.13 (m, 6H), 1.96-1.80 (m, 3H), 1.78-1.57 (m, 3H), 1.40-1.20 (m, 8H), 0.88 (t, J=7.0 Hz, 3H).

Example 18(o)

(11α,15α,13E)-9-Oxo-11,15-dihydroxy-16-(3-methoxymethylphenyl)-17,18,19,20-tetranor-5-thiaprost-13-enoic acid 2-decanoyloxyethyl ester

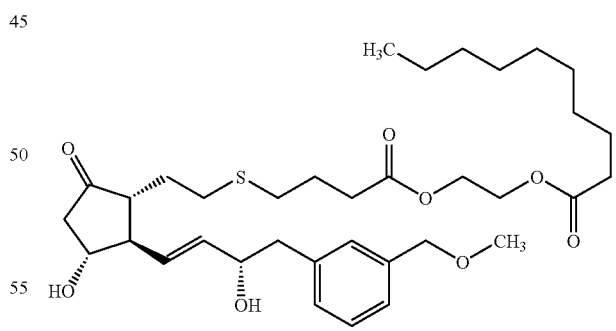

TLC Rf 0.23 (Hexane:Ethyl Acetate=1:1);
NMR: δ 7.36-7.12 (m, 4H), 5.76 (dd, J=15.0, 6.0 Hz, 1H), 5.53 (dd, J=15.0, 8.0 Hz, 1H), 4.44-4.39 (m, 3H), 4.27 (s, 4H), 3.96 (m, 1H), 3.42 (s, 3H), 2.99-2.80 (m, 3H), 2.78-2.40 (m, 7H), 2.39-2.12 (m, 6H), 1.95-1.80 (m, 3H), 1.77-1.60 (m, 3H), 1.39-1.19 (m, 12H), 0.88 (t, J=6.9 Hz, 3H).

Example 18(p)

(11α,15α,13E)-9-Oxo-11,15-dihydroxy-16-(3-methoxymethylphenyl)-17,18,19,20-tetranor-5-thiaprost-13-enoic acid allyloxycarbonylmethyl ester

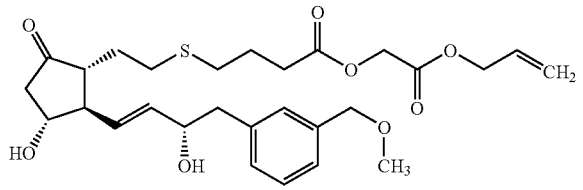

TLC: Rf 0.58 (Ethyl Acetate);
NMR: δ 7.4-7.1 (m, 4H), 6.0-5.8 (m, 1H), 5.78 (dd, J=16, 6 Hz, 1H), 5.53 (dd, J=16, 8 Hz, 1H), 5.4-5.25 (m, 2H), 4.7-4.6 (m, 4H), 4.5-4.4 (m, 3H), 4.0-3.85 (m, 1H), 3.42 (s, 3H), 3.0-2.8 (m, 2H), 2.72 (dd, J=19, 10 Hz, 1H), 2.65-2.5 (m, 6H), 2.4-2.1 (m, 4H), 2.0-1.6 (m, 5H).

Example 18(q)

(11α,15α,13E)-9-Oxo-11,15-dihydroxy-16-(3-methoxymethylphenyl)-17,18,19,20-tetranor-5-thiaprost-13-enoic acid nonanoyloxymethyl ester

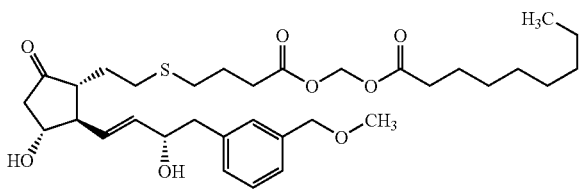

TLC: Rf 0.25 (Hexane:Ethyl Acetate=1:4);
NMR: δ 7.35-7.10 (m, 4H), 5.81-5.69 (m, 3H), 5.52 (dd, J=15.0, 8.7 Hz, 1H), 4.48-4.37 (m, 3H), 3.95 (m, 1H), 3.42 (s, 3H), 3.10 (bs, 1H), 2.92-2.42 (m, 9H), 2.40-2.11 (m, 6H), 1.97-1.80 (m, 3H), 1.78-1.58 (m, 3H), 1.40-1.20 (m, 10H), 0.88 (t, J=7.2 Hz, 3H).

REFERENCE EXAMPLE 23

(11α,15α,13E)-9-Oxo-11,15-bis(tetrahydropyran-2-yloxy)-16-(3-methoxymethylphenyl)-17,18,19,20-tetranor-5-thiaprost-13-enoic acid 2-(tetrahydropyran-2-yloxy)ethyl ester

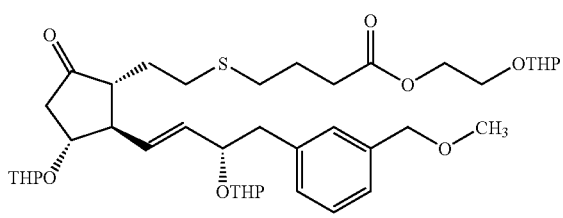

By the same procedure as describe in Reference Examples 21 and 22 using 1-(tetrahydropyran-2-yloxy)-2-bromoethane instead of nonanoic acid 2-bromoethyl ester, the title compound having the following physical data were obtained.
TLC: Rf 0.51 (Hexane:Ethyl Acetate=1:1).

EXAMPLE 19

(11α,15α,13E)-9-Oxo-11,15-dihydroxy-16-(3-methoxymethylphenyl)-17,18,19,20-tetranor-5-thiaprost-13-enoic acid 2-hydroxyethyl ester

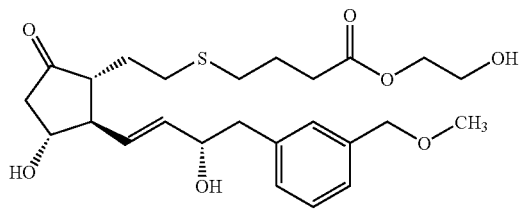

By the same procedure as describe in Example 18 using the compound prepared in Reference Example 23 instead of the compound prepared in Reference Example 22, the compound of the present invention having the following physical data were obtained
TLC: Rf 0.35 (Ethyl Acetate:Methanol=19:1);
NMR: δ 7.32-7.11 (m, 4H), 5.77 (dd, J=15.3, 5.7 Hz, 1H), 5.54 (dd, J=15.3, 8.1 Hz, 1H), 4.48-4.38 (m, 3H), 4.22-4.17 (m, 2H), 4.00-3.90 (m, 1H), 3.82-3.75 (m, 2H), 3.42 (s, 3H), 3.12-2.91 (br, 10H), 2.92 (dd, J=13.5, 5.4 Hz, 1H), 2.84 (dd, J=13.5, 6.9 Hz, 1H), 2.71 (dd, J=18.9, 7.5 Hz, 1H), 2.65-2.50 (m, 2H), 2.52 (t, J=7.2 Hz, 2H), 2.47 (t, J=7.2 Hz, 2H), 2.45-2.15 (m, 5H), 1.95-1.80 (m, 3H), 1.76-1.60 (m, 1H).

REFERENCE EXAMPLE 24

(9α,11α,15α,13E)-9-Trimethylsilyloxy-11,15-bis(tetrahydropyran-2-yloxy)-16-(3-methoxymethylphenyl)-17,18,19,20-tetranor-5-thiaprost-13-enoic acid

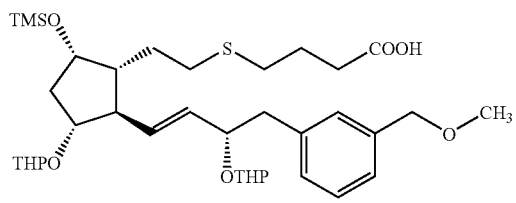

Under atmosphere of argon, a solution of the compound prepared in Reference Example 20 (680 mg) in dry tetrahydrofuran (5 mL), triethylamine (0.94 mL), and trimethylsilyl chloride (0.57 mL) and catalytic amount of dimethylaminopyridine was added successively at room temperature, and the mixture was stirred for 5 hour at room temperature. The reaction mixture was added by water, and was extracted by ethyl acetate. The extract was washed with brine, dried over an anhydrous sodium sulfate, concentrated under reduced pressure to give the title compound having the following physical data, which was used for the next reaction without purification.
TLC Rf 0.45 (Ethyl Acetate).

REFERENCE EXAMPLE 25

(9α,11α,15α,13E)-9-Hydroxy-11,15-bis(tetrahydro-pyran-2-yloxy)-16-(3-methoxymethylphenyl)-17,18,19,20-tetranor-5-thiaprost-13-enoic acid phenyl ester

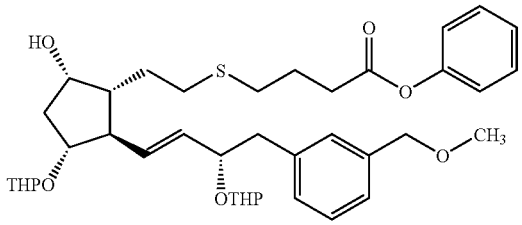

To a solution of the compound prepared in Reference Example 24, triethylamine (0.15 mL) and phenol (53 mg) in acetonitrile (3 mL), 1-hydroxybenzotriazole (50 mg) and 1-ethyl-3-(3-dimethylaminopropyl)carbodiimide monohydrochloride (142 mg) was added under atmosphere of argon at room temperature, and the mixture was stirred for 2 hours at room temperature. The reaction mixture was added by ethyl acetate, was washed with 1N hydrochloric acid (twice), water, saturated aqueous sodium hydrogen carbonate solution and brine successively, dried over an anhydrous sodium sulfate, concentrated under reduced pressure and was purified by column chromatography on silica gel (ethyl acetate:hexane=1:1) to give the title compound (115 mg) having the following physical data.

TLC: Rf 0.35 (Hexane:Ethyl Acetate 1:1).

EXAMPLE 20

(11α,15α,13E)-9-Oxo-11,15-dihydroxy-16-(3-methoxymethylphenyl)-17,18,19,20-tetranor-5-thiaprost-13-enoic acid phenyl ester

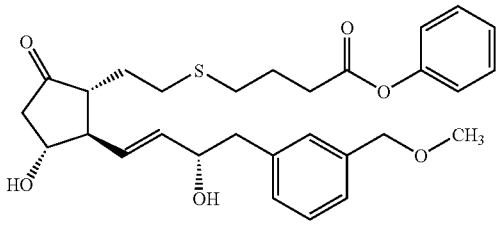

By the same procedure as describe in Reference Example 22 and Example 18 using the compound prepared in Reference Example 25 instead of the compound prepared in Reference Example 21, the compound of the present invention having the following physical data were obtained TLC: Rf 0.34 (Ethyl Acetate);

NMR: δ 7.4-7.0 (m, 9H), 5.74 (dd, J=15, 6 Hz, 1H), 5.51 (dd, J=15, 8 Hz, 1H), 4.5-4.3 (m, 3H), 3.93 (brq, 1H), 3.42 (s, 3H), 3.2-3.1 (br, 1H), 2.88 (dd, J=14, 6 Hz, 1H), 2.80 (dd, J=14, 7 Hz, 1H), 2.75-2.5 (m, 7H), 2.4-2.1 (m, 4H), 2.1-1.95 (m, 2H), 2.0-1.85 (m, 1H), 1.8-1.6 (m, 1H).

EXAMPLE 21

(11α,15α,13E)-9-Oxo-11,15-dihydroxy-16-(3-methoxymethylphenyl)-17,18,19,20-tetranor-5-thiaprost-13-enoic acid carboxymethyl ester

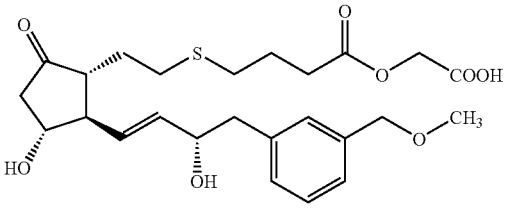

To a solution of the compound prepared in Example 18(p) in dry tetrahydrofuran (1.5 mL), tetrakis(triphenylphosphine)palladium(0) (15 mg) was added under atmosphere of argon. The morpholine (68 μL) was dropped into the mixture, and the mixture was stirred for 30 minutes at room temperature. The reaction mixture was added by ethyl acetate, was washed with 1N hydrochloric acid, water, saturated aqueous sodium hydrogen carbonate solution and brine successively, dried over an anhydrous sodium sulfate, concentrated under reduced pressure and was purified by column chromatography on silica gel (ethyl acetate:acetic acid=100:1) to give the title compound (52 mg) having the following physical data.

TLC: Rf 0.30 (Chloroform:Methanol:Acetic Acid=45:5:1);

NMR: δ 7.3-7.1 (m, 4H), 5.80 (dd, J=15, 6 Hz, 1H), 5.57 (dd, J=15, 8 Hz, 1H), 4.58 (s, 2H), 4.47 (s, 2H), 4.5-4.4 (m, 1H), 4.0-3.9 (m, 1H), 3.23 (s, 3H), 2.93 (dd, J=14, 5 Hz, 1H), 2.81 (dd, J=14, 7 Hz, 1H), 2.8-2.5 (m, 7H), 2.5-2.2 (m, 3H), 2.0-1.8 (m, 3H), 1.8-1.65 (m, 1H).

EXAMPLE 22(a) TO EXAMPLE 22(e)

By the same procedure as describe in Reference Examples 21, 22 and Example 18 using corresponding halides instead of nonanoic acid 2-bromoethyl ester, the compound of the present invention having the following physical data were obtained.

Example 22(a)

(11α,15α,13E)-9-Oxo-11,15-dihydroxy-16-(3-methoxymethylphenyl)-17,18,19,20-tetranor-5-thiaprost-13-enoic acid dipropylcarbamoylmethyl ester

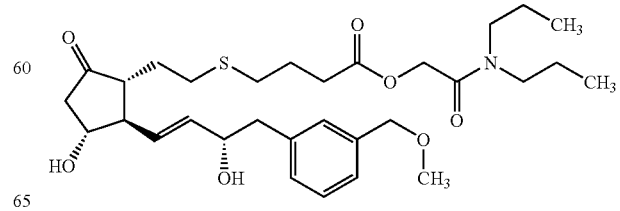

TLC: Rf 0.32 (Ethyl Acetate);

NMR: δ 7.32-7.27 (m, 1H), 7.22-7.13 (m, 3H), 5.74 (dd, J=15.9, 6.3 Hz, 1H), 5.54 (ddd, J=15.9, 8.4, 1.2 Hz, 1H), 4.71 (s, 2H), 4.42 (m, 3H), 3.94 (m, 1H), 3.41 (s, 3H), 3.28 (m, 2H), 3.19-3.08 (m, 3H), 2.95-2.80 (m, 2H), 2.78-2.50 (m, 8H), 2.40-2.18 (m, 3H), 2.00-1.83 (m, 3H), 1.76-1.50 (m, 5H), 0.94 (t, J=7.5 Hz, 3H), 0.88 (t, J=7.5 Hz, 3H).

Example 22(b)

(11α,15α,13E)-9-Oxo-11,15-dihydroxy-16-(3-methoxymethylphenyl)-17,18,19,20-tetranor-5-thiaprost-13-enoic acid dibutylcarbamoylmethyl ester

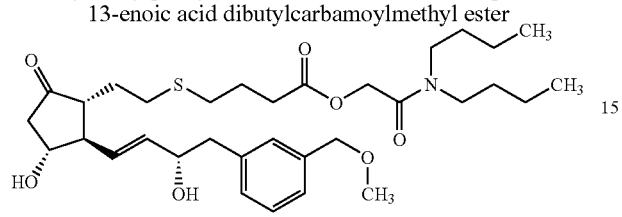

TLC: Rf 0.36 (Ethyl Acetate);

NMR: δ 7.32-7.26 (m, 1H), 7.22-7.13 (m, 3H), 5.74 (dd, J=15.6, 6.0 Hz, 1H), 5.54 (dd, J=15.6, 8.4 Hz, 1H), 4.71 (s, 2H), 4.42 (m, 3H), 3.94 (m, 1H), 3.41 (s, 3H), 3.31 (m, 2H), 3.17 (m, 2H), 3.02 (m, 1H), 2.93-2.82 (m, 2H), 2.77-2.50 (m, 8H), 2.40-2.19 (m, 3H), 2.00-1.83 (m, 3H), 1.77-1.43 (m, 5H), 1.41-1.21 (m, 4H), 0.96 (t, J=7.5 Hz, 3H), 0.91 (t, J=7.5 Hz, 3H).

Example 22(c)

(11α,15α,13E)-9-Oxo-11,15-dihydroxy-16-(3-methoxymethylphenyl)-17,18,19,20-tetranor-5-thiaprost-13-enoic acid 4-pentylbenzoylmethyl ester

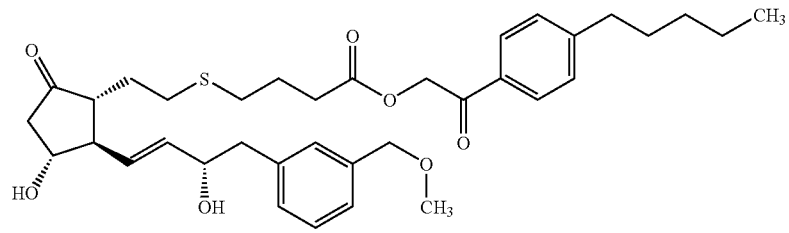

TLC: Rf 0.38 (Hexane:Ethyl Acetate=1:4);

NMR: δ 7.81 (d, J=8.4 Hz, 2H), 7.36-7.23 (m, 3H), 7.21-7.10 (m, 3H), 5.78 (dd, J=15.0, 5.4 Hz, 1H), 5.55 (dd, J=15.0, 8.1 Hz, 1H), 5.33 (s, 2H), 4.47-4.39 (m, 3H), 3.95 (m, 1H), 3.41 (s, 3H), 2.97-2.55 (m, 12H), 2.40-2.18 (m, 4H), 2.03-1.84 (m, 3H), 1.80-1.58 (m, 3H), 1.40-1.22 (m, 4H), 0.89 (t, J=6.6 Hz, 3H).

Example 22(d)

(11α,15α,13E)-9-Oxo-11,15-dihydroxy-16-(3-methoxymethylphenyl)-17,18,19,20-tetranor-5-thiaprost-13-enoic acid 1,1-dimethylheptyloxycarbonylmethyl ester

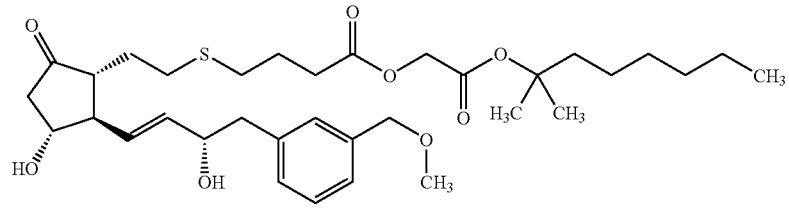

TLC: Rf 0.42 (Hexane:Ethyl Acetate=1:4);

NMR: δ 7.35-7.12 (m, 4H), 5.76 (dd, J=15.3, 5.7 Hz, 1H), 5.53 (dd, J=15.3, 8.1 Hz, 1H), 4.51-4.40 (m, 5H), 3.95 (m, 1H), 3.42 (s, 3H), 3.00 (bs, 1H), 2.96-2.81 (m, 2H), 2.70 (dd, J=18.6, 7.5 Hz, 1H), 2.61-2.48 (m, 6H), 2.40-2.19 (m, 4H), 2.00-1.83 (m, 3H), 1.79-1.60 (m, 3H), 1.44 (s, 6H), 1.38-1.20 (m, 8H), 0.88 (t, J=6.6 Hz, 3H).

Example 22(e)

(11α,15α,13E)-9-Oxo-11,15-dihydroxy-16-(3-methoxymethylphenyl)-17,18,19,20-tetranor-5-thiaprost-13-enoic acid dipentylcarbamoylmethyl ester

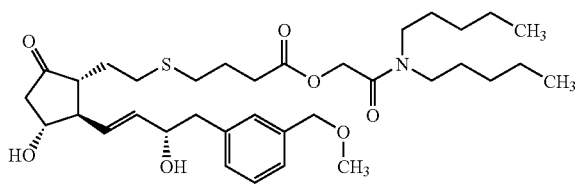

TLC: Rf 0.33 (Hexane:Ethyl Acetate=1:4);
NMR: δ 7.36-7.12 (m, 4H), 5.76 (dd, J=15.0, 5.4 Hz, 1H), 5.55 (dd, J=15.0, 8.7 Hz, 1H), 4.70 (s, 2H), 4.45-4.39 (m, 3H), 3.95 (m, 1H), 3.41 (s, 3H), 3.30 (m, 2H), 3.17 (m, 2H), 3.00 (bs, 1H), 2.98-2.80 (m, 2H), 2.77-2.50 (m, 8H), 2.40-2.19 (m, 3H), 2.00-1.82 (m, 3H), 1.78-1.50 (m, 5H), 1.40-1.20 (m, 8H), 0.98-0.84 (m, 6H).

EXAMPLE 23

(11α,15α,13E)-9-Oxo-11,15-dihydroxy-16-(3-methoxymethylphenyl)-17,18,19,20-tetranor-5-thiaprost-13-enoic acid 2-octyloxyethyl ester

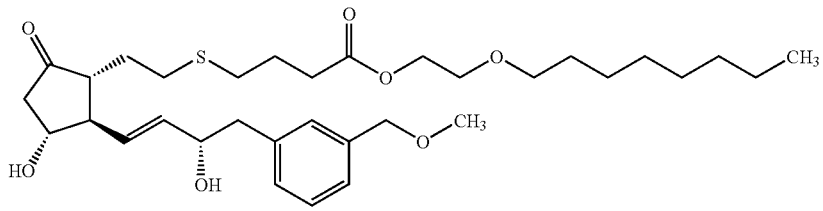

To a solution of (11α,15α,13E)-9-oxo-11,15-dihydroxy-16-(3-methoxymethylphenyl)-17,18,19,20-tetranor-5-thiaprost-13-enoic acid (150 mg; this is the compound described in Example 3 of WO00/03980), 2-octyloxyethanol (296 mg) and triethylamine (0.12 mL) in ethyl acetate (3 mL), 1-mesyloxybenzotriazole (145 mg) was added, and the mixture was stirred for 4 hours at room temperature. The reaction mixture was added by ethyl acetate, The diluted solution was washed with saturated aqueous sodium hydrogen carbonate solution, water and brine successively, dried over an anhydrous sodium sulfate, concentrated under reduced pressure and was purified by column chromatography on silica gel (from ethyl acetate:hexane=2:1 to ethyl acetate only) to give the title compound (137 mg) having the following physical data.
TLC: Rf 0.22 (Ethyl Acetate:Hexane=3:1);
NMR: δ 7.35-7.15 (m, 4H), 5.75 (dd, J=15.3, 6.0 Hz, 1H), 5.53 (dd, J=15.3, 8.7 Hz, 1H), 4.50-4.37 (m, 3H), 4.22 (t, J=5.1 Hz, 2H), 4.00-3.90 (m, 1H), 3.62 (t, J=5.1 Hz, 2H), 3.46 (t, J=6.9 Hz, 2H), 3.42 (s, 3H), 2.90 (dd, J=13.5, 5.4 Hz, 1H), 2.83 (dd, J=13.5, 7.2 Hz, 1H), 2.70 (dd, J=18.6, 7.5 Hz, 1H), 2.65-2.40 (m, 6H), 2.40-2.10 (m, 4H), 1.95-1.80 (m, 4H), 1.80-1.50 (m, 3H), 1.40-1.20 (m, 10H), 0.90 (t, J=6.9 Hz, 3H).

EXAMPLE 23(a) TO EXAMPLE 23(j)

By the same procedure as describe in Example 23 using corresponding alcohol derivatives instead of 2-octyloxyethanol, the compound of the present invention having the following physical data were obtained.

Example 23(a)

(11α,15α,13E)-9-Oxo-11,15-dihydroxy-16-(3-methoxymethylphenyl)-17,18,19,20-tetranor-5-thiaprost-13-enoic acid 2-(2,2-dimethylpentanoyloxy)ethyl ester

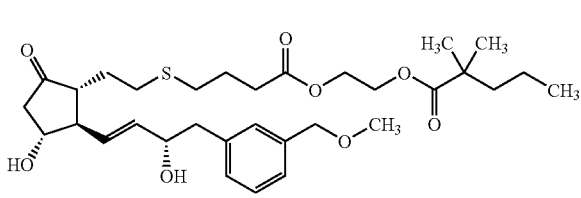

TLC: Rf 0.28 (Ethyl Acetate:Hexane=3:1);
NMR: δ 7.35-7.10 (m, 4H), 5.77 (dd, J=15.3, 5.7 Hz, 1H), 5.53 (dd, J=15.3, 8.4 Hz, 1H), 4.50-4.40 (m, 3H), 4.25 (s, 4H), 4.00-3.90 (m, 1H), 3.41 (s, 3H), 2.96-2.80 (m, 3H), 2.67 (dd, J=18.3, 7.5 Hz, 1H), 2.65-2.50 (m, 2H), 2.50 (t, J=7.2 Hz, 2H), 2.43 (t, J=7.2 Hz, 2H), 2.40-2.10 (m, 4H), 1.95-1.80 (m, 3H), 1.75-1.60 (m, 1H), 1.55-1.45 (m, 2H), 1.30-1.20 (m, 2H), 0.88 (t, J=7.2 Hz, 3H).

Example 23(b)

(11α,15α,13E)-9-Oxo-11,15-dihydroxy-16-(3-methoxymethylphenyl)-17,18,19,20-tetranor-5-thiaprost-13-enoic acid 3-butoxypropyl ester

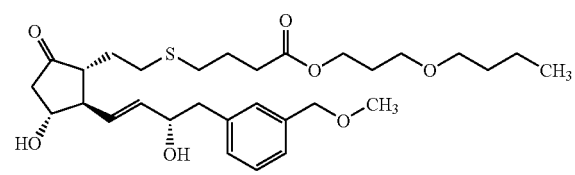

TLC: Rf 0.30 (Ethyl Acetate:Hexane=3:1);
NMR: δ 7.30-7.10 (m, 4H), 5.77 (dd, J=15.3, 5.7 Hz, 1H), 5.53 (dd, J=15.3, 8.4 Hz, 1H), 4.50-4.40 (m, 3H), 4.17 (t, J=7.2 Hz, 2H), 4.00-3.90 (m, 1H), 3.48 (t, J=7.2 Hz, 2H), 3.42 (s, 3H), 3.40 (t, J=6.6 Hz, 2H), 2.97-2.80 (m, 3H), 2.70 (dd, J=19.2, 7.5 Hz, 1H), 2.65-2.50 (m, 2H), 2.50 (t, J=7.2 Hz, 2H), 2.41 (t, J=7.2 Hz, 2H), 2.36-2.14 (m, 4H), 1.95-1.82 (m, 3H), 1.75-1.60 (m, 1H), 1.60-1.50 (m, 2H), 1.42-1.30 (m, 2H), 0.92 (t, J=7.2 Hz, 3H).

Example 23(c)

(11α,15α,13E)-9-Oxo-11,15-dihydroxy-16-(3-methoxymethylphenyl)-17,18,19,20-tetranor-5-thiaprost-13-enoic acid 2-butoxyethyl ester

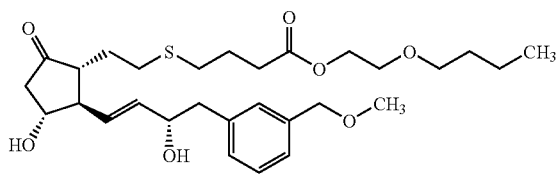

TLC: Rf 0.32 (Ethyl Acetate);
NMR: δ 7.35-7.11 (m, 4H), 5.75 (dd, J=15.3, 5.7 Hz, 1H), 5.53 (dd, J=15.3, 8.7 Hz, 1H), 4.48-4.39 (m, 3H), 4.21 (m, 2H), 3.95 (m, 1H), 3.61 (m, 2H), 3.46 (t, J=6.6 Hz, 2H), 3.42 (s, 3H), 3.00 (m, 1H), 2.98-2.80 (m, 2H), 2.78-2.18 (m, 11H), 1.98-1.81 (m, 3H), 1.78-1.53 (m, 3H), 1.38 (m, 2H), 0.92 (t, J=7.5 Hz, 3H).

Example 23(d)

(11α,15α,13E)-9-Oxo-11,15-dihydroxy-16-(3-methoxymethylphenyl)-17,18,19,20-tetranor-5-thiaprost-13-enoic acid 2-pentyloxyethyl ester

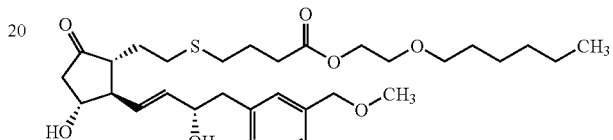

TLC Rf 0.36 (Ethyl Acetate);

NMR: δ 7.35-7.11 (m, 4H), 5.75 (dd, J=15.3, 5.7 Hz, 1H), 5.53 (dd, J=15.3, 8.7 Hz, 1H), 4.48-4.39 (m, 3H), 4.21 (m, 2H), 3.95 (m, 1H), 3.61 (m, 2H), 3.46 (t, J=6.6 Hz, 2H), 3.42 (s, 3H), 2.98-2.80 (m, 3H), 2.78-2.18 (m, 11H), 1.98-1.81 (m, 3H), 1.78-1.53 (m, 3H), 1.38 (m, 4H), 0.92 (t, J=7.5 Hz, 3H).

Example 23(e)

(11α,15α,13E)-9-Oxo-11,15-dihydroxy-16-(3-methoxymethylphenyl)-17,18,19,20-tetranor-5-thiaprost-13-enoic acid 2-hexyloxyethyl ester TLC: Rf 0.39 (Ethyl Acetate);
NMR: δ 7.36-7.12 (m, 4H), 5.76 (dd, J=15.3, 5.7 Hz, 1H), 5.53 (dd, J=15.3, 8.7 Hz, 1H), 4.48-4.40 (m, 3H), 4.21 (m, 2H), 3.95 (m, 1H), 3.61 (m, 2H), 3.47-3.40 (m, 5H), 2.98-2.80 (m, 3H), 2.78-2.40 (m, 7H), 2.38-2.18 (m, 4H), 1.97-1.82 (m, 3H), 1.70 (m, 1H), 1.63-1.52 (m, 2H), 1.40-1.25 (m, 6H), 0.88 (t, J=7.2 Hz, 3H).

Example 23(f)

(11α,15α,13E)-9-Oxo-11,15-dihydroxy-16-(3-methoxymethylphenyl)-17,18,19,20-tetranor-5-thiaprost-13-enoic acid 2-(2,2-dimethyloctanoyloxy)ethyl ester TLC: Rf 0.20 (Ethyl Acetate:Hexane=3:1);
NMR: δ 7.35-7.10 (m, 4H), 5.75 (dd, J=15.3, 6.0 Hz, 1H), 5.53 (dd, J=15.3, 8.4 Hz, 1H), 4.50-4.35 (m, 3H), 4.26 (s, 4H), 4.00-3.90 (m, 1H), 3.42 (s, 3H), 3.20-3.10 (br, 1H), 2.90 (dd, J=13.5, 5.4 Hz, 1H), 2.83 (dd, J=13.5, 7.2 Hz, 1H), 2.70 (dd, J=18.6, 7.2 Hz, 1H), 2.63-2.50 (m, 2H), 2.50 (t, J=7.5 Hz, 2H), 2.43 (t, J=7.2 Hz, 2H), 2.40-2.15 (m, 4H), 1.95-1.80 (m, 3H), 1.80-1.60 (m, 1H), 1.55-1.50 (m, 2H), 1.40-1.15 (m, 8H), 0.90 (t, J=6.9 Hz, 3H).

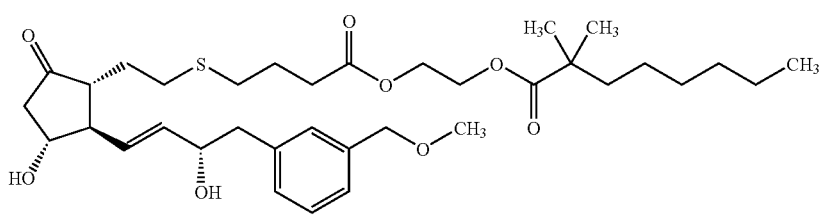

Example 23(g)

(11α,15α,13E)-9-Oxo-11,15-dihydroxy-16-(3-methoxymethylphenyl)-17,18,19,20-tetranor-5-thiaprost-13-enoic acid 2-(2,2-diethylpentaoyloxy)ethyl ester

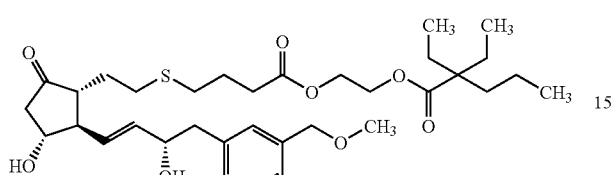

TLC: Rf 0.21 (Ethyl Acetate:Hexane=3:1);

NMR: δ 7.35-7.10 (m, 4H), 5.76 (dd, J=15.3, 6.0 Hz, 1H), 5.53 (dd, J=15.3, 8.4 Hz, 1H), 4.50-4.35 (m, 3H), 4.27 (s, 4H), 4.00-3.90 (m, 1H), 3.42 (s, 3H), 3.05-3.00 (br, 10H), 2.92 (dd, J=13.5, 5.4 Hz, 1H), 2.83 (dd, J=13.5, 7.2 Hz, 1H), 2.70 (dd, J=18.0, 7.2 Hz, 1H), 2.65-2.40 (m, 6H), 2.40-2.10 (m, 4H), 1.95-1.80 (m, 3H), 1.80-1.50 (m, 7H), 1.25-1.10 (m, 2H), 0.90 (t, J=7.2 Hz, 3H), 0.78 (t; J=7.2 Hz, 6H).

Example 23(h)

(11α,15α,13E)-9-Oxo-11,15-dihydroxy-16-(3-methoxymethylphenyl)-17,18,19,20-tetranor-5-thiaprost-13-enoic acid 4-(4-chlorophenyl)phenyl ester

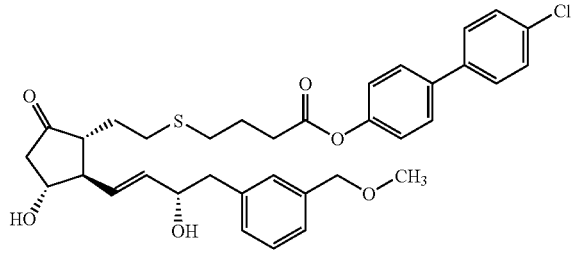

TLC: Rf 0.22 (Hexane:Ethyl Acetate=1:3);

NMR: δ 7.52 (d, J=8.7 Hz, 2H), 7.47 (d, J=8.6 Hz, 2H), 7.40 (d, J=8.6 Hz, 2H), 7.24 (m, 1H), 7.20-7.08 (m, 5H), 5.72 (dd, J=15.3, 6.6 Hz, 1H), 5.51 (dd, J=15.3, 8.4 Hz, 1H), 4.45-4.30 (m, 3H), 3.95 (m, 1H), 3.63 (bs, 1H), 3.40 (s, 3H), 2.90-2.50 (m, 9H), 2.39-2.13 (m, 3H), 2.09-1.82 (m, 3H), 1.70 (m, 1H).

Example 23(i)

(11α,15α,13E)-9-Oxo-11,15-dihydroxy-16-(3-methoxymethylphenyl)-17,18,19,20-tetranor-5-thiaprost-13-enoic acid 2-(adamantan-1-ylcarbonyloxy)ethyl ester

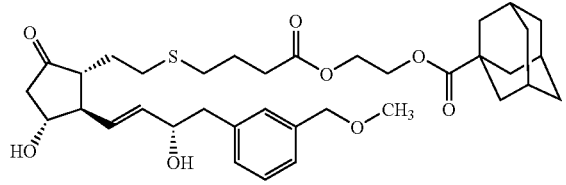

TLC: Rf 0.33 (Ethyl Acetate:Hexane:Methanol=30:10:1);

NMR: δ 7.32-7.11 (m, 4H), 5.75 (dd, J=15.3, 6.0 Hz, 1H), 5.52 (dd, J=15.3, 9.0 Hz, 1H), 4.48-4.36 (m, 3H), 4.31-4.22 (m, 4H), 4.02-3.89 (m, 1H), 3.42 (s, 3H), 3.20-3.12 (br, 1H), 2.90 (dd, J=13.8, 5.4 Hz, 1H), 2.82 (dd, J=13.8, 7.2 Hz, 1H), 2.70 (dd, J=18.3, 7.2 Hz, 1H), 2.65-2.13 (m, 10H), 2.07-1.97 (m, 3H), 1.96-1.80 (m, 9H), 1.80-1.60 (m, 7H).

Example 23(j)

(11α,15α,13E)-9-Oxo-11,15-dihydroxy-16-(3-methoxymethylphenyl)-17,18,19,20-tetranor-5-thiaprost-13-enoic acid 2-(2,2-dipropylpentanoyloxy)ethyl ester

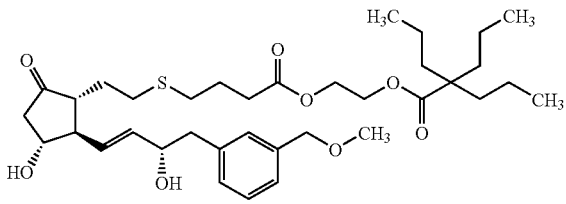

TLC: Rf 0.38 (Ethyl Acetate:Hexane:Methanol 30:10:1);

NMR: δ 7.32-7.12 (m, 4H), 5.75 (dd, J=15.3, 6.0 Hz, 1H), 5.52 (dd, J=15.3, 8.7 Hz, 1H), 4.48-4.32 (m, 3H), 4.25 (s, 4H), 4.02-3.88 (m, 1H), 3.42 (s, 3H), 3.27-3.20 (br, 1H), 2.90 (dd, J=13.5, 5.4 Hz, 1H), 2.82 (dd, J=13.5, 6.9 Hz, 1H), 2.70 (dd, J=18.3, 7.2 Hz, 1H), 2.65-2.12 (m, 10H), 1.94-1.82 (m, 3H), 1.75-1.60 (m, 1H), 1.55-1.45 (m, 6H), 1.22-1.09 (m, 6H), 0.89 (t, J=7.2 Hz, 9H).

EXAMPLE 24

(15α,13E)-9-Oxo-15-hydroxy-16-(4-aminophenyl)-17,18,19,20-tetranor-5-thia-8-azaprost-13-enoic acid

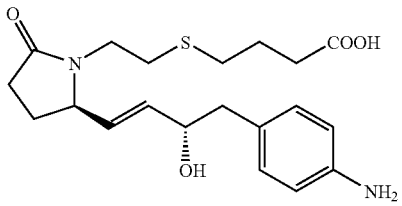

By the same procedure as describe in Reference Example 5, Examples 1, 11 and 2 using the compound prepared in Reference Example 11 instead of the compound prepared in Reference Example 4 and 3-(4-t-butoxycarbonylaminophenyl)-2-oxopropylphosphonic acid dimethyl ester instead of 3-(3-methoxymethylphenyl)-2-oxopropylphosphonic acid dimethyl ester, the compound of the present invention having the following physical data were obtained.

TLC: Rf 0.17 (Chloroform:Methanol=9:1);

NMR: δ 6.98 (d, J=8.4 Hz, 2H), 6.66 (d, J=8.4 Hz, 2H), 5.73 (dd, J=15.9, 6.3 Hz, 1H), 5.47 (dd, J=15.9, 8.4 Hz, 1H), 4.38 (m, 1H), 4.10 (m, 1H), 3.61 (m, 1H), 3.10-2.15 (m, 15H), 2.00-1.81 (m, 2H), 1.73 (m, 1H).

REFERENCE EXAMPLE 26

(2R)-1-(2-Mesyloxyethyl)-2-t-butyldimethylsilyloxymethylpyrrolidin-5-one

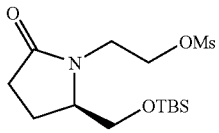

Under atmosphere of argon, to a solution of the compound prepared in Reference Example 7 (11.9 g) in tetrahydrofuran (50 mL), triethylamine (9.07 mL) was added. Then mesyl chloride (3.68 mL) was dropped into the mixture at 0° C., and the mixture was stirred for 30 minutes. The mixture was added by water and was extracted by ethyl acetate. The extract was washed with 1N hydrochloric acid, saturated aqueous sodium hydrogen carbonate solution and brine successively, dried over an anhydrous sodium sulfate, concentrated under reduced pressure to give the title compound having the following physical data, which was used for the next reaction without purification.

TLC: Rf 0.46 (Ethyl Acetate).

REFERENCE EXAMPLE 27

(2R)-1-(2-Iodoethyl)-2-t-butyldimethylsilyloxymethylpyrrolidin-5-one

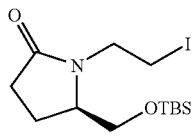

Under atmosphere of argon, to a solution of the compound prepared in Reference Example 26 in acetonitrile (120 mL), sodium iodide (19.5 g) was added, and the mixture was stirred overnight at 80° C. It was cooled to room temperature, the mixture was added by water, and extracted by ethyl acetate. The extract was washed with saturated aqueous sodium hydrogen carbonate solution and brine successively, dried over an anhydrous magnesium sulfate, concentrated under reduced pressure and was purified by column chromatography on silica gel (ethyl acetate:hexane=from 1:3 to 1:1) to give the title compound (11.3 g) having the following physical data.

TLC: Rf 0.63 (Hexane:Ethyl Acetate=1:1);

NMR: δ 3.92 (m, 1H), 3.81-3.69 (m, 2H), 3.62-3.45 (m, 2H), 3.35 (m, 1H), 3.22 (m, 1H), 2.50-2.26 (m, 2H), 2.14 (m, 1H), 1.78 (m, 1H), 0.86 (s, 9H), 0.03 (s, 3H), 0.02 (s, 3H).

REFERENCE EXAMPLE 28

5-(2-((2R)-2-t-Butyldimethylsilyloxymethyl-5-oxopyrrolidin-1-yl)ethylthio)thiophene-2-carboxylic acid ethyl ester

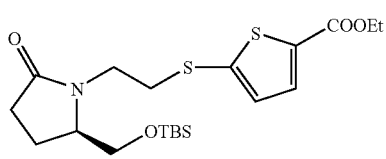

Under atmosphere of argon, to a solution thiophene-2-carboxylic acid ethyl ester (936 mg) in tetrahydrofuran (50 mL), sulfur powder (240 mg) was added, and the mixture was cooled to −78° C. 2.0M lithium diisopropylamide (4.0 mL) was dropped into the mixture, and was stirred for 35 minutes. Then a solution of the compound prepared in Reference Example 27 (1.92 g) in tetrahydrofuran (5 mL) was added, and the mixture was stirred for 1.5 hour at room temperature. The mixture was poured into saturated aqueous ammonium chloride solution, and extracted by t-butyl methyl ether. The extract was washed with saturated aqueous sodium hydrogen carbonate solution, dried over an anhydrous magnesium sulfate, concentrated under reduced pressure and was purified by column chromatography on silica gel (ethyl acetate: hexane=from 1:3 to 1:1) to give the title compound (1.86 g) having the following physical data.

TLC: Rf 0.54 (Hexane:Ethyl Acetate=1:1);

NMR: δ 7.65 (d, J=3.9 Hz, 1H), 7.09 (d, J=3.9 Hz, 1H), 4.32 (q, J=7.5 Hz, 2H), 3.86-3.61 (m, 3H), 3.55 (m, 1H), 3.32

(m, 1H), 3.22-3.00 (m, 2H), 2.50-2.21 (m, 2H), 2.10 (m, 1H), 1.80 (m, 1H), 1.36 (t, J=7.5 Hz, 3H), 0.86 (s, 9H), 0.03 (s, 3H), 0.02 (s, 3H).

REFERENCE EXAMPLE 29

5-(2-((2R)-2-Hydroxymethyl-5-oxopyrrolidin-1-yl)ethylthio)thiophene-2-carboxylic acid ethyl ester

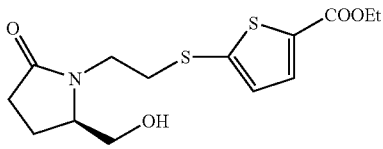

Under atmosphere of argon, to a solution of the compound prepared in Reference Example 28 (1.85 g) in tetrahydrofuran (4 mL), tetrabutylammonium fluoride (6.28 mL) was added, and the mixture was stirred overnight at room temperature. The mixture was added by water, and extracted by ethyl acetate. The extract was washed with brine, dried over an anhydrous sodium sulfate, concentrated under reduced pressure to give the title compound (1.15 g) having the following physical data.

TLC: Rf 0.15 (Ethyl Acetate);
NMR: δ 7.64 (d, J=3.9 Hz, 1H), 7.10 (d, J=3.9 Hz, 1H), 4.33 (q, J=6.9 Hz, 2H), 3.80-3.68 (m, 3H), 3.60 (m, 1H), 3.40 (m, 1H), 3.17 (t, J=7.0 Hz, 2H), 2.58-2.28 (m, 2H), 2.10 (m, 1H), 1.98-1.80 (m, 2H), 1.37 (t, J=7.2 Hz, 3H).

EXAMPLE 25(a) TO EXAMPLE 25(c)

By the same procedure as describe in Reference Examples 11, 5, Examples 1 and 2 using the compound prepared in Reference Example 29 instead of the compound prepared in Reference Example 10 and corresponding phosphonic acid ester derivatives instead of 3-(3-methoxymethylphenyl)-2-oxopropylphosphonic acid dimethyl ester, the compound of the present invention having the following physical data were obtained.

Example 25(a)

(15α,13E)-1,5-(2,5-Interthienylene)-9-oxo-15-hydroxy-16-(4-fluorophenyl)-2,3,4,17,18,19,20-heptanor-5-thia-8-azaprost-13-enoic acid

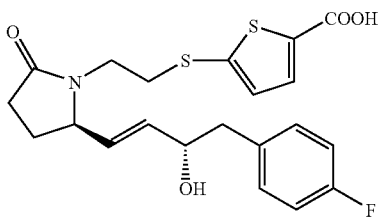

TLC: Rf 0.20 (Chloroform:Methanol:Acetic Acid=9:1:0.1);
NMR: δ 7.68 (d, J=3.9 Hz, 1H), 7.15 (dd, J=8.4, 5.4 Hz, 2H), 7.06 (d, J=3.9 Hz, 1H), 6.98 (t, J=8.4 Hz, 2H), 5.71 (dd, J=15.0, 5.4 Hz, 1H), 5.48 (dd, J=15.0, 9.0 Hz, 1H), 4.37 (m, 1H), 4.11 (m, 1H), 3.82-3.30 (m, 2H), 3.19-2.93 (m, 3H), 2.70 (d, J=6.9 Hz, 2H), 2.50-2.18 (m, 3H), 1.71 (m, 1H).

Example 25(b)

(15α,13E)-1,5-(2,5-Interthienylene)-9-oxo-15-hydroxy-16-(3-chloro-4-fluorophenyl)-2,3,4,17,18,19,20-heptanor-5-thia-8-azaprost-13-enoic acid

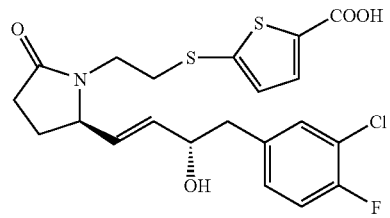

TLC: Rf 0.15 (Chloroform:Methanol=9:1);
NMR: δ 7.66 (d, J=4.2 Hz, 1H), 7.22 (d, J=6.9 Hz, 1H), 7.10-7.00 (m, 3H), 5.69 (dd, J=15.3, 5.4 Hz, 1H), 5.48 (dd, J=15.3, 8.7 Hz, 1H), 4.50 (bs, 2H), 4.37 (m, 1H), 4.10 (m, 1H), 3.75-3.60 (m, 1H), 3.20-2.93 (m, 3H), 2.80-2.68 (m, 2H), 2.50-2.12 (m, 3H), 1.70 (m, 1H).

Example 25(c)

(15α,13E)-1,5-(2,5-Interthienylene)-9-oxo-15-hydroxy-16-(4-fluoro-3-trifluoromethylphenyl)-2,3,4,17,18,19,20-heptanor-5-thia-8-azaprost-13-enoic acid

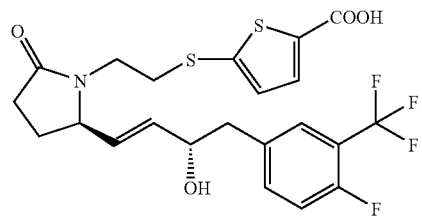

TLC: Rf 0.23 (Chloroform:Methanol:Acetic Acid=9:1:0.1);
NMR: δ 7.65 (d, J=3.9 Hz, 1H), 7.50-7.30 (m, 2H), 7.20-7.00 (m, 2H), 5.72 (dd, J=15.3, 5.1 Hz, 1H), 5.51 (dd, J=15.3, 8.7 Hz, 1H), 4.82 (bs, 2H), 4.40 (m, 1H), 4.12 (m, 1H), 3.65 (m, 1H), 3.23-2.93 (m, 3H), 2.90-2.73 (m, 2H), 2.50-2.10 (m, 3H), 1.70 (m, 1H).

REFERENCE EXAMPLE 30

(4R)-4-t-Butoxycarbonylamino-4-formylbutanoic acid ethyl ester

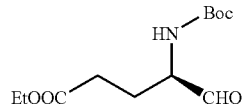

Under atmosphere of argon, to a solution of (4R)-5-hy -2.20 (m, 1H), 2.00-1.85 (m, 1H), 1.43 (s, 9H), 1.27 (t, J=7.2 Hz, 3H).

REFERENCE EXAMPLE 31

(4R,5E)-4-t-Butoxycarbonylamino-7-oxo-8-(4-fluorophenyl)oct-5-enoic acid ethyl ester

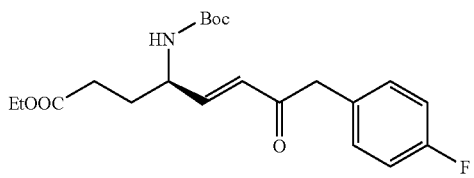

Under atmosphere of argon, to a solution sodium hydride (2.40 g; 62.6% in oil), in tetrahydrofuran (620 mL), a solution of 3-(4-fluorophenyl)-2-oxopropylphosphonic acid dimethyl ester (17.7 g) in tetrahydrofuran (100 mL) was added at 0° C., and the mixture was stirred for 1 hour. The reaction mixture was added by the solution of the compound prepared in Reference Example 30 (14.7 g) in tetrahydrofuran (80 mL) at 0° C., and the mixture was stirred for 20 minutes. The reaction mixture was added by t-butyl methyl ether (800 mL) and water (800 mL). The organic layer was washed with water and brine successively, dried over an anhydrous sodium sulfate, concentrated under reduced pressure to give the crude title compound (25.3 g). 1 g of the crude compound was purified by column chromatography on silica gel (ethyl acetate:hexane=1:3) to give the title compound (636 mg) having the following physical data.

TLC: Rf 0.74 (Ethyl Acetate:Hexane=1:1);
NMR: δ 7.20-7.10 (m, 2H), 7.08-6.96 (m, 2H), 6.76 (dd, J=15.3, 5.1 Hz, 1H), 6.24 (d, J=15.3 Hz, 1H), 4.7-4.6 (m, 1H), 4.4-4.25 (m, 1H), 4.14 (q, J=7.2 Hz, 2H), 3.82 (s, 2H), 2.38 (t, J=7.2 Hz, 2H), 2.00-1.75 (m, 2H), 1.42 (s, 9H), 1.25 (t, J=7.2 Hz, 3H).

REFERENCE EXAMPLE 32

(4R,5E,7S)-4-t-Butoxycarbonylamino-7-hydroxy-8-(4-fluorophenyl)oct-5-enoic acid ethyl ester

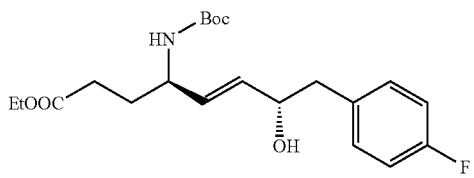

To a solution of the compound prepared in Reference Example 31 (5.56 g) and a solution of (R)-2-methyl-CBS-oxazaborolidine (4.3 mL; 1.0M toluene solution) in dry tetrahydrofuran (30 mL), borane tetrahydrofuran complex (8.6 mL; 1.0M) was added, and the mixture was stirred for 15 minutes. To the mixture, methanol was added, and was diluted by ethyl acetate. The diluted solution was washed with 1N hydrochloric acid, water and brine successively, dried over an anhydrous magnesium sulfate, concentrated under reduced pressure to give the title compound having the following physical data.

TLC: Rf 0.80 (Ethyl Acetate);
NMR: δ 7.20-7.09 (m, 2H), 7.02-6.93 (m, 2H), 5.67 (dd, J=15.6, 5.7 Hz, 1H), 5.52 (dd, J=15.6, 6.0 Hz, 1H), 4.56-4.43 (br, 1H), 4.35-4.27 (m, 1H), 4.20-4.05 (m, 3H), 2.85-2.68 (m, 2H), 2.30 (t, J=6.9 Hz, 2H), 1.90-1.70 (m, 2H), 1.43 (s, 9H), 1.26 (t, J=7.2 Hz, 3H).

REFERENCE EXAMPLE 33

(4R,5E,7S)-4-Amino-7-hydroxy-8-(4-fluorophenyl)oct-5-enoic acid hydrochloride

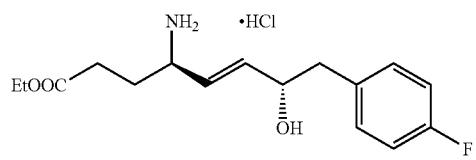

To a solution of the compound prepared in Reference Example 32 in ethanol (12 mL), 4N hydrogen chloride-dioxane solution (14 mL) was added at 0° C., and the mixture was stirred for 4 hours. The mixture was concentrated under reduced pressure. The obtained crude was dissolved in ethyl acetate (25 mL) with heat, then cooled to room temperature overnight. The precipitate was filtrated, washed with cold ethyl acetate, dried to give the title compound (2.37 g) having the following physical data.

TLC: Rf 0.05 (Ethyl Acetate);
NMR (CD$_3$OD): δ 7.28-7.19 (m, 2H), 7.04-6.93 (m, 2H), 5.92 (dd, J=15.6, 4.8 Hz, 1H), 5.53 (dd, J=15.6, 8.7 Hz, 1H), 4.41-4.32 (m, 1H), 4.15 (q, J=7.2 Hz, 2H), 3.80-3.70 (m, 1H), 2.81 (d, J=5.7 Hz, 2H), 2.28 (t, J=6.9 Hz, 2H), 2.09-1.97 (m, 1H), 1.84-1.75 (m, 1H), 1.24 (t, J=7.2 Hz, 3H).

EXAMPLE 26

(15α,13E)-9-Oxo-15-hydroxy-16-(4-fluorophenyl)-17,18,19,20-tetranor-5-thia-8-azaprost-13-enoic acid ethyl ester

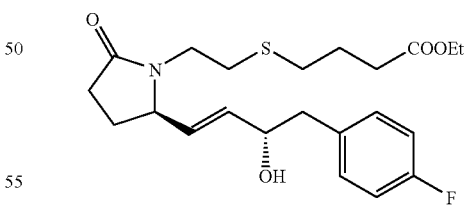

Under atmosphere of argon, to a solution of 4-(formylmethylthio)butanoic acid ethyl ester (1.82 g) in dry tetrahydrofuran (15 mL), a compound prepared in Reference Example 33 (2.27 g) was added at room temperature, and the mixture was stirred for 1.5 hours. Then sodium triacetoxyborohydride (2.91 g) was added to the mixture, and the mixture was stirred overnight at room temperature. The reaction mixture was diluted by ethyl acetate The diluted solution was washed with water 1N hydrochloric acid and brine successively, dried over an anhydrous sodium sulfate, concentrated under reduced pressure and purified by column chromatography on silica gel (ethyl acetate:methanol=30:1) to give the title compound (1.80 g) having the following physical data.

TLC: Rf 0.33 (Ethyl Acetate).

TLC: Rf 0.44 (Chloroform:Methanol=9:1);

NMR: δ 7.21-7.14 (m, 2H), 7.05-6.96 (m, 2H), 5.75 (dd, J=15.6, 6.0 Hz, 1H), 5.50 (dd, J=15.6, 8.4 Hz, 1H), 4.19 (m, 1H), 4.18-4.03 (m, 3H), 3.60 (m, 1H), 2.97 (m, 1H), 2.85-2.79 (m, 2H), 2.70-2.18 (m, 9H), 2.01-1.82 (m, 3H), 1.79-1.60 (m, 1H), 1.25 (t, J=7.2 Hz, 3H).

EXAMPLE 27

(15α,13E)-9-Oxo-15-hydroxy-16-(4-fluorophenyl)-17,18,19,20-tetranor-5-thia-8-azaprost-13-enoic aid

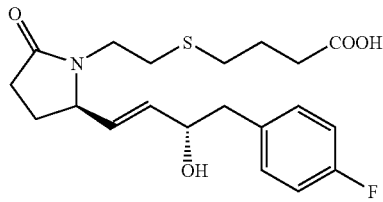

By the same procedure as describe in Example 2 using the compound prepared in Example 26 instead of the compound prepared in Example 1, the compound of the present invention having the following physical data were obtained.

TLC: Rf 0.38 (Chloroform:Methanol:Water=9:1:0.1);

NMR: δ 7.20-7.16 (m, 2H), 7.04-6.96 (m, 2H), 5.75 (dd, J=15.4, 6.0 Hz, 1H), 5.50 (ddd, J=15.4, 8.5, 1.1 Hz, 1H), 4.39 (m, 1H), 4.11 (m, 1H), 3.62 (m, 1H), 2.95 (m, 1H), 2.82 (d, J=6.6 Hz, 2H), 2.67-2.53 (m, 4H), 2.52-2.43 (m, 2H), 2.39 (t, J=7.1 Hz, 2H), 2.22 (m, 1H), 1.94-1.83 (m, 2H), 1.68 (m, 1H).

EXAMPLE 27(a) TO EXAMPLE 27(i)

By the same procedure as describe in Reference Examples 31, 32, 33, Examples 26 and 2 using corresponding phosphonic acid ester derivatives instead of 3-(4-fluorophenyl)-2-oxopropylphosphonic acid dimethyl ester and corresponding carboxylic acid ester derivatives instead of 4-(formylmethylthio)butanoic acid ethyl ester, the compound of the present invention having the following physical data were obtained.

The compound prepared in Example 27(b) was done by additional procedure of the same as described in Example 5 after the procedure of the same as described in Reference Example 32.

Example 27(a)

(15α,13E)-9-Oxo-15-hydroxy-16-(3-(benzofuran-2-yl)phenyl)-17,18,19,20-tetranor-5-thia-8-azaprost-13-enoic acid

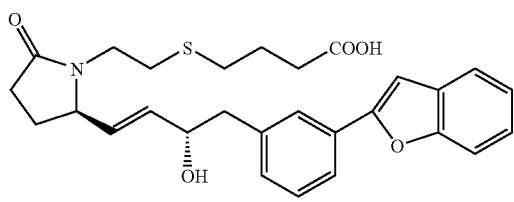

TLC: Rf 0.53 (Chloroform:Methanol 9:1);

NMR: δ 7.76-7.70 (m, 2H), 7.59 (d, J=8.4 Hz, 1H), 7.52 (d, J=8.4 Hz, 1H), 7.40 (dd, J=8.4, 8.4 Hz, 1H), 7.33-7.17 (m, 3H), 7.04 (s, 1H), 5.79 (dd, J=15.3, 5.7 Hz, 1H), 5.51 (dd, J=15.3, 8.4 Hz, 1H), 4.55-4.44 (m, 1H), 4.16-4.07 (m, 1H), 3.68-3.54 (m, 1H), 3.02-2.90 (m, 3H), 2.70-2.10 (m, 9H), 1.92-1.78 (m, 2H), 1.78-1.62 (m, 1H).

Example 27(b)

(15α)-9-Oxo-15-hydroxy-16-(3-methylphenyl)-5-(4-carboxythiazol-2-yl)-1,2,3,4,17,18,19,20-octanor-5-thia-8-azaprostane

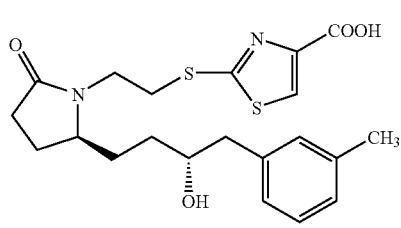

TLC: Rf 0.19 (Chloroform:Methanol:Acetic Acid=9:1:0.1);

NMR: δ 8.07 (s, 1H), 7.21 (t, J=7.2 Hz, 1H), 7.10-6.95 (m, 3H), 3.97-3.80 (m, 2H), 3.72 (m, 1H), 3.60-3.25 (m, 3H), 2.84-2.63 (m, 2H), 2.55-2.22 (m, 5H), 2.14 (m, 1H), 1.93 (m, 1H), 1.78-1.41 (m, 4H).

Example 27(c)

(15α,13E)-1,6-(1,4-Interphenylene)-9-oxo-15-hydroxy-16-(3-methylphenyl)-2,3,4,5,17,18,19,20-octanor-8-azaprost-13-enoic acid

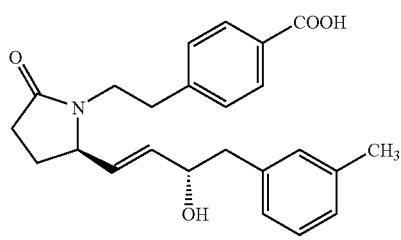

TLC: Rf 0.27 (Chloroform:Methanol=9:1);

NMR: δ 8.02 (d, J=8.1 Hz, 2H), 7.30-7.15 (m, 3H), 7.10-6.97 (m, 3H), 5.64 (dd, J=15.6, 6.3 Hz, 1H), 5.37 (dd, J=15.6, 8.7 Hz, 1H), 4.41-4.32 (m, 1H), 3.83-3.70 (m, 2H), 3.09-2.95 (m, 1H), 2.95-2.75 (m, 4H), 2.48-2.25 (m, 5H), 2.20-2.13 (m, 1H), 1.72-1.58 (m, 1H).

Example 27(d)

(15α,13E)-7-(6-Carboxyindol-3-yl)-9-oxo-15-hydroxy-16-(3-methylphenyl)-1,2,3,4,5,6,17,18,19,20-decanor-8-azaprost-13-ene

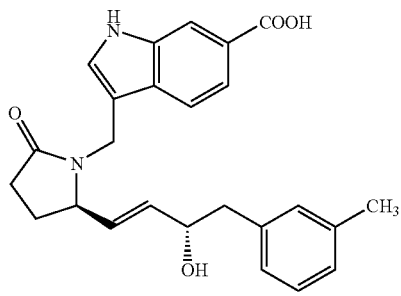

TLC: Rf 0.21 (Dichloromethane:Methanol=9:1);
NMR (DMSO-d$_6$): δ 8.08 (d, J=1.2 Hz, 1H), 7.68 (d, J=8.1 Hz, 1H), 7.56 (d, J=8.1 Hz, 1H), 7.20-7.10 (m, 2H), 7.10-6.95 (m, 3H), 5.60 (dd, J=15.3, 6.6 Hz, 1H), 5.43 (dd, J=15.3, 5.4 Hz, 1H), 4.95-4.80 (m, 2H), 4.37 (q, J=6.6 Hz, 1H), 3.90-3.75 (m, 2H), 2.91 (dd, J=13.5, 6.6 Hz, 1H), 2.70 (dd, J=13.5, 7.5 Hz, 1H), 2.50-2.20 (m, 5H), 2.15-2.00 (m, 1H), 1.75-1.60 (m, 1H).

Example 27(e)

(15α,13E)-9-Oxo-15-hydroxy-16-(3-methylphenyl)-5-(4-carboxythiazol-2-yl)-1,2,3,4,17,18,19,20-octanor-8-azaprost-13-ene

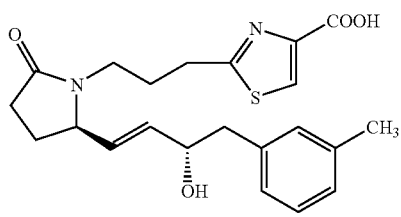

TLC: Rf 0.25 (Chloroform:Methanol:Acetic Acid=9:1:0.1);
NMR: δ 8.12 (s, 1H), 7.18 (m, 1H), 7.05-6.97 (m, 3H), 5.75 (dd, J=15.3, 5.7 Hz, 1H), 5.60-5.20 (m, 3H), 4.40 (m, 1H), 4.07 (m, 1H), 3.51 (m, 1H), 3.07-2.85 (m, 3H), 2.79 (d, J=6.6 Hz, 2H), 2.50-2.12 (m, 6H), 2.04-1.90 (m, 2H), 1.70 (m, 1H).

Example 27(f)

(15α,13E)-9-Oxo-15-hydroxy-16-(3-methylphenyl)-5-(4-carboxyoxazol-2-yl)-1,2,3,4,17,18,19,20-octanor-8-azaprost-13-ene

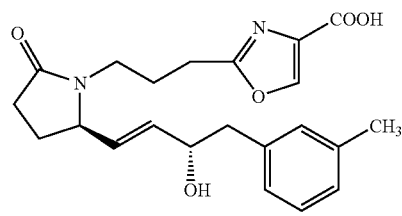

TLC: Rf 0.21 (Chloroform:Methanol:Acetic Acid=9:1:0.1);
NMR: δ 8.19 (s, 10H), 7.20 (m, 1H), 7.06-6.97 (m, 3H), 5.78 (dd, J=15.3, 6.0 Hz, 1H), 5.50 (ddd, J=15.3, 9.0, 1.2 Hz, 1H), 4.40 (m, 2H), 4.07 (m, 1H), 3.47 (m, 1H), 2.94 (m, 1H), 2.83-2.75 (m, 4H), 2.50-2.10 (m, 6H), 2.05-1.83 (m, 2H), 1.64 (m, 1H).

Example 27(g)

(15α,13E)-1,7-(2,5-Interthienylene)-9-oxo-15-hydroxy-16-(3-methylphenyl)-2,3,4,5,6,17,18,19,20-nonanor-8-azaprost-13-enoic acid

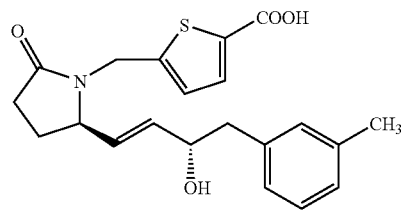

TLC: Rf 0.18 (Dichloromethane:Methanol=9:1);
NMR: δ 7.70 (d, J=3.9 Hz, 1H), 7.21 (t, J=7.8 Hz, 1H), 7.10-6.98 (m, 3H), 6.88 (d, J=3.9 Hz, 1H), 5.75 (dd, J=15.0, 6.0 Hz, 1H), 5.46 (dd, J=15.0, 8.7 Hz, 1H), 4.88 (d, J=16.2 Hz, 1H), 4.50-4.40 (m, 1H), 4.10-4.00 (m, 1H), 3.88 (d, J=16.2 Hz, 1H), 2.82 (d, J=6.6 Hz, 2H), 2.50-2.15 (m, 6H), 1.80-1.70 (m, 1H).

Example 27(h)

(15α,13E)-1,6-(1,4-Interphenylene)-9-oxo-15-hydroxy-16-(3-(benzofuran-2-yl)phenyl)-2,3,4,5,17,18,19,20-octanor-8-azaprost-13-enoic acid

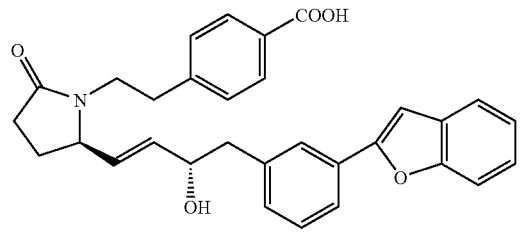

TLC: Rf 0.31 (Dichloromethane:Methanol=9:1);

NMR: δ 7.98 (d, J=8.1 Hz, 2H), 7.78-7.70 (m, 2H), 7.58 (d, J=8.1 Hz, 1H), 7.51 (d, J=8.1 Hz, 1H), 7.38 (t, J=7.8 Hz, 1H), 7.34-7.16 (m, 5H), 7.03 (s, 1H), 5.65 (dd, J=15.0, 6.0 Hz, 1H), 5.37 (dd, J=15.0, 7.8 Hz, 1H), 4.50-4.40 (m, 1H), 3.80-3.65 (m, 2H), 3.05-2.60 (m, 5H), 2.40-2.20 (m, 2H), 2.20-2.00 (m, 1H), 1.70-1.55 (m, 1H).

Example 27(i)

(15α,13E)-1,5-(2,5-Interthienylene)-9-oxo-15-hydroxy-16-(3-(benzofuran-2-yl)phenyl)-2,3,4,17,18,19,20-heptanor-8-azaprost-13-enoic acid

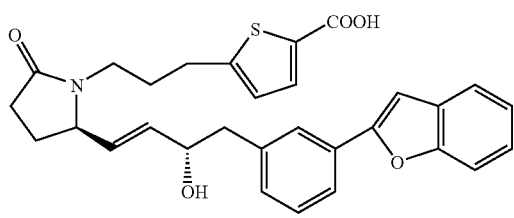

TLC: Rf 0.59 (Dichloromethane:Methanol:Acetic Acid=90:10:1);

NMR: δ 7.74-7.68 (m, 2H), 7.61 (d, J=3.9 Hz, 1H), 7.57 (d, J=8.4 Hz, 1H), 7.50 (d, J=8.4 Hz, 1H), 7.38 (t, J=7.8 Hz, 1H), 7.32-7.14 (m, 3H), 7.02 (s, 1H), 6.73 (d, J=3.9 Hz, 1H), 5.75 (dd, J=15.3, 6.3 Hz, 1H), 5.47 (dd, J=15.3, 8.4 Hz, 1H), 4.50-4.40 (m, 1H), 4.05-3.95 (m, 1H), 3.65-3.40 (m, 1H), 2.90 (d, J=6.9 Hz, 2H), 2.85-2.70 (m, 3H), 2.50-2.10 (m, 3H), 1.85-1.65 (m, 3H).

REFERENCE EXAMPLE 34

(2R)-1-(2-(3-Cyclopentylpropanoyloxy)ethyl)-2-t-butyldimethylsilyloxymethylpyrrolidin-5-one

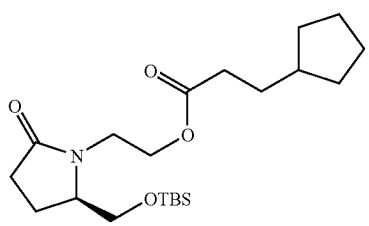

Under atmosphere of argon, to a solution of the compound prepared in Reference Example 7 (3.78 g) and triethylamine (2.9 mL) in methylene chloride (30 mL), 3-cyclopentylpropanoyl chloride (2.67 g) was added at 0° C., and the mixture was stirred for 2 hours. The mixture was poured into water and was extracted by diethyl ether. The extract was washed with brine, dried over an anhydrous sodium sulfate, concentrated under reduced pressure to give the title compound having the following physical data, which was used for the next reaction without purification.

TLC: Rf 0.40 (Ethyl Acetate:Hexane=1:1).

REFERENCE EXAMPLE 35

(2R)-1-(2-(3-Cyclopentylpropanoyloxy)ethyl)-2-hydroxymethylpyrrolidin-5-one

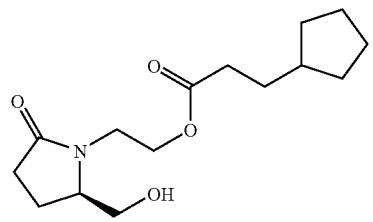

Under atmosphere of argon, to a solution of the compound prepared in Reference Example 34 in tetrahydrofuran (20 mL), tetrabutylammonium fluoride (16.6 mL; 1.0 M tetrahydrofuran solution) was added at room temperature, and the mixture was stirred for 2 hours. The mixture was poured into saturated aqueous ammounium chloride solution, and extracted by ethyl acetate. The extract was washed with saturated aqueous ammounium chloride solution and brine successively, dried over an anhydrous sodium sulfate, concentrated under reduced pressure and purified by column chromatography on silica gel (from ethyl acetate:hexane=2:1 to ethyl acetate:methanol=40:1) to give the title compound (2.40 g) having the following physical data.

TLC: Rf 0.35 (Ethyl Acetate:Methanol=20:1).

REFERENCE EXAMPLE 36

(2R)-1-(2-(3-Cyclopentylpropanoyloxy)ethyl)-2-formylpyrrolidin-5-one

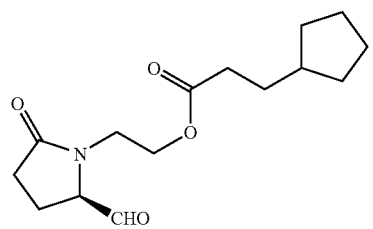

Under atmosphere of argon, to a solution of the compound prepared in Reference Example 35 (2.40 g) and diisopropylethylamine (8.7 mL) in mixed solvent of ethyl acetate (15 mL) and dimethylsulfoxide (15 mL), sulfur trioxide pyridine complex (3.98 g) was added, and the mixture was stirred for 30 minutes. The reaction mixture was added by small amount of water, and was poured into 1N hydrochloric acid, and was extracted by ethyl acetate. The extract was washed with water and brine successively, dried over an anhydrous magnesium sulfate, concentrated under reduced pressure to give the title compound having the following physical data, which was used for the next reaction without purification.

TLC: Rf 0.57 (Ethyl Acetate:Methanol=20:1).

REFERENCE EXAMPLE 37

(13E)-9,15-Dioxo-16-(4-fluorophenyl)-6-(3-cyclopentylpropanoyloxy)-1,2,3,4,5,17,18,19,20-nonanor-8-azaprost-13-ene

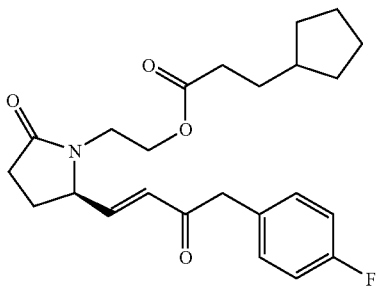

Under atmosphere of argon, to a solution of 3-(4-fluorophenyl)-2-oxopropylphosphonic acid dimethyl ester (2.31 g) in dry tetrahydrofuran (90 mL), sodium hydride (341 mg; 62.6% in oil) was added at room temperature, and the mixture was stirred for 30 minutes. Then the compound prepared in Reference Example 36 was added to the mixture and the mixture was stirred for 1 hour. The reaction mixture was diluted by t-butyl methyl ether. The diluted solution was washed with water and brine successively, dried over an anhydrous magnesium sulfate, concentrated under reduced pressure to give the title compound having the following physical data, which was used for the next reaction without purification.

TLC: Rf 0.75 (Ethyl Acetate:Methanol=20:1).

REFERENCE EXAMPLE 38

(15α,13E)-9-Oxo-15-hydroxy-16-(4-fluorophenyl)-6-(3-cyclopentylpropanoyloxy)-1,2,3,4,5,17,18,19,20-nonanor-8-azaprost-13-ene

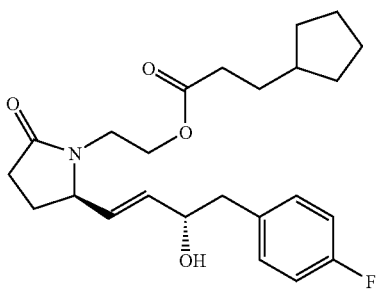

Under atmosphere of argon, a solution of the compound prepared in Reference Example 37 and (R)-2-methyl-CBS-oxazaborolidine (2.7 mL; 1.0 M toluene solution) in dry tetrahydrofuran (10 mL) was added by borane tetrahydrofuran complex (5.4 mL; 1.0M tetrahydrofuran solution) at 0° C., and the mixture was stirred for 20 minutes. The mixture was added by methanol, and diluted by ethyl acetate. The organic layer was washed with 1N hydrochloric acid, water and brine successively, dried over an anhydrous sodium sulfate, concentrated under reduced pressure and was purified by column chromatography on silica gel (from ethyl acetate:hexane: methanol=30:10:1 to ethyl acetate:methanol=30:1) to give the title compound (2.58 g) having the following physical data.

TLC: Rf 0.50 (Ethyl Acetate:Methanol=20:1).

REFERENCE EXAMPLE 39

(15α,13E)-9-Oxo-15-t-butyldimethylsilyloxy-16-(4-fluorophenyl)-6-(3-cyclopentylpropanoyloxy)-1,2,3,4,5,17,18,19,20-nonanor-8-azaprost-13-ene

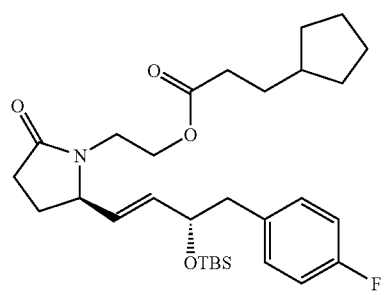

Under atmosphere of argon, a solution of the compound prepared in Reference Example 38 (2.08 g) and imidazole (0.61 g) in dimethylformamide (15 mL) was added by t-butyldimethylsilyl chloride (1.13 g) at room temperature. After the mixture was stirred overnight, the reaction mixture was diluted by t-butyl methyl ether. The extract was washed with water and brine successively, dried over an anhydrous sodium sulfate, concentrated under reduced pressure was purified by column chromatography on silica gel (ethyl acetate: hexane=from 1:2 to 1:1) to give the title compound (1.56 g) having the following physical data.

TLC: Rf 0.81 (Ethyl Acetate).

REFERENCE EXAMPLE 40

(15α,13E)-9-Oxo-15-t-butyldimethylsilyloxy-16-(4-fluorophenyl)-6-hydroxy-1,2,3,4,5,17,18,19,20-nonanor-8-azaprost-13-ene

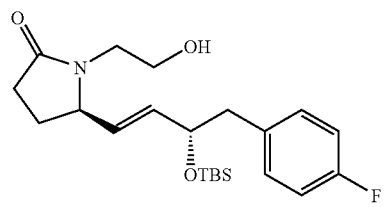

To a solution of the compound prepared in Reference Example 39 (1.56 g) in mixed solvent of methanol (5 mL) and 1,2-dimethoxyethane (5 mL), 2N aqueous sodium hydroxide solution (3 mL) was added at room temperature, and the mixture was stirred for 1 hour. The reaction mixture was diluted by t-butyl methyl ether and tetrahydrofuran. The diluted solution was washed with water and brine successively, dried over an anhydrous sodium sulfate, concentrated under reduced pressure to give the title compound having the following physical data, which was used for the next reaction without purification.

TLC: Rf 0.15 (Ethyl Acetate).

REFERENCE EXAMPLE 41

(15α,13E)-9-Oxo-15-t-butyldimethylsilyloxy-16-(4-fluorophenyl)-6-mesyloxy-1,2,3,4,5,17,18,19,20-nonanor-8-azaprost-13-ene

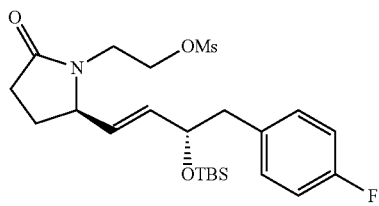

Under atmosphere of argon, to a solution of the compound prepared in Reference Example 40 (600 mg) and triethylamine (0.31 mL) in tetrahydrofuran (6 mL), mesyl chloride (0.14 mL) was added at 0° C., and the mixture was stirred for 1 hour. The reaction mixture was diluted by t-butyl methyl ether. The diluted solution was washed with 1N hydrochloric acid, water and brine successively, dried over an anhydrous sodium sulfate, concentrated under reduced pressure to give the title compound having the following physical data, which was used for the next reaction without purification TLC: Rf 0.60 (Ethyl Acetate).

REFERENCE EXAMPLE 42

(15α,13E)-9-Oxo-15-t-butyldimethylsilyloxy-16-(4-fluorophenyl)-6-iodo-1,2,3,4,5,17,18,19,20-nonanor-8-azaprost-13-ene

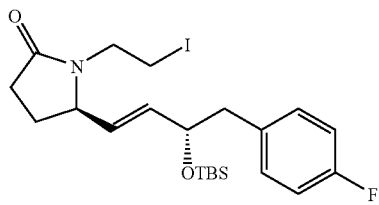

A suspension of the compound prepared in Reference Example 41 and sodium iodide (450 mg) in acetonitrile (15 mL) was refluxed for 12 hours. It was cooled to room temperature, the mixture was poured into water, and extracted by t-butyl methyl ether. The extract was washed with saturated aqueous sodium thiosulfate solution and brine successively, dried over an anhydrous sodium sulfate, concentrated under reduced pressure and was purified by column chromatography on silica gel (ethyl acetate:hexane=1:2) to give the title compound (630 mg) having the following physical data.

TLC: Rf 0.92 (Ethyl Acetate).

REFERENCE EXAMPLE 43

(15α,13E)-3,3-Ethano-9-oxo-15-t-butyldimethylsilyloxy-16-(4-fluorophenyl)-17,18,19,20-tetranor-5-thia-8-azaprost-13-enoic acid methyl ester

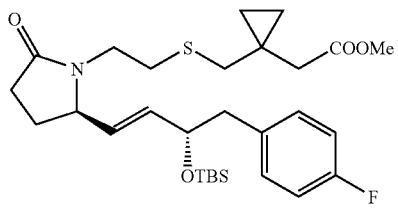

Under atmosphere of argon, to a solution of the compound prepared in Reference Example 42 (90 mg) and 2-(1-(acetylthiomethyl)cyclopropyl)acetic acid methyl ester (42 mg) in dry methanol (2 mL), potassium carbonate (58 mg) was added at room temperature, and the mixture was stirred for 6 hours. The reaction mixture was diluted by t-butyl methyl ether. The diluted solution was washed with saturated aqueous ammounium chloride solution and brine successively, dried over an anhydrous sodium sulfate, concentrated under reduced pressure and was purified by column chromatography on silica gel (ethyl acetate:hexane from 1:3 to 1:1) to give the title compound (90 mg) having the following physical data.

TLC: Rf 0.42 (Ethyl Acetate:Hexane=1:1).

EXAMPLE 28

(15α,13E)-3,3-Ethano-9-oxo-15-hydroxy-16-(4-fluorophenyl)-17,18,19,20-tetranor-5-thia-8-azaprost-13-enoic acid

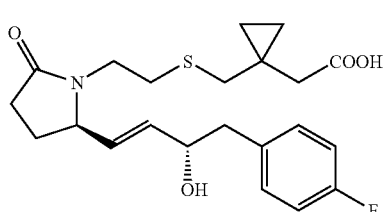

By the same procedure as describe in Examples 7 and 2 using the compound prepared in Reference Example 43 instead of the compound prepared in Reference Example 14, the compound of the present invention having the following physical data were obtained.

TLC: Rf 0.50 (Chloroform:Methanol=9:1);
NMR: δ 7.22-7.13 (m, 2H), 7.08-6.96 (m, 2H), 5.76 (dd, J=15.3, 5.7 Hz, 1H), 5.51 (dd, J=15.3, 8.7 Hz, 1H), 4.48-4.38 (m, 1H), 4.16-4.05 (m, 1H), 3.67-3.53 (m, 1H), 3.10-2.95 (m, 1H), 2.88-2.79 (m, 2H), 2.76 (d, J=13.5 Hz, 1H), 2.68-2.50 (m, 4H), 2.43-2.16 (m, 5H), 1.75-1.63 (m, 1H), 0.65-0.50 (m, 4H).

EXAMPLE 28(a) TO EXAMPLE 28(b)

By the same procedure as describe in Reference Example 43, Examples 7 and 2 using corresponding derivatives instead of 2-(1-(acetylthiomethyl)cyclopropyl)acetic acid methyl ester, the compound of the present invention having the following physical data were obtained.

Example 28(a)

(15α,13E)-1,5-(1,4-Interphenylene)-9-oxo-15-hydroxy-16-(4-fluorophenyl)-2,3,4,17,18,19,20-heptanor-5-tha-8-azaprost-13-enoic acid

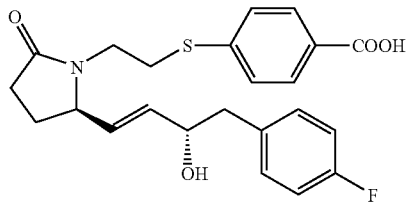

TLC: Rf 0.45 (Chloroform:Methanol=9:1);
NMR: δ 8.00 (d, J=8.4 Hz, 2H), 7.38 (d, J=8.4 Hz, 2H), 7.20-7.10 (m, 2H), 7.07-6.96 (m, 2H), 5.65 (dd, J=15.3, 5.4 Hz, 1H), 5.47 (dd, J=15.3, 9.3 Hz, 1H), 4.35 (m, 1H), 4.10 (m, 1H), 3.67 (m, 1H), 3.30-3.00 (m, 3H), 2.75 (d, J=6.9 Hz, 2H), 2.48-2.08 (m, 3H), 1.70 (m, 1H).

Example 28(b)

(15α,13E)-1,5-(1,3-Interphenylene)-9-oxo-15-hydroxy-16-(4-fluorophenyl)-2,3,4,17,18,19,20-heptanor-5-thia-8-azaprost-13-enoic acid

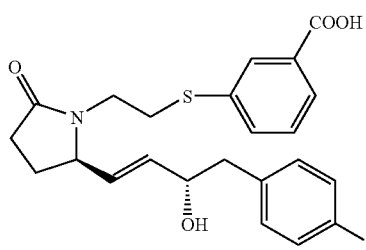

TLC: Rf 0.45 (Chloroform:Methanol=9:1);
NMR: δ 8.05 (m, 1H), 7.88 (d, J=7.8 Hz, 1H), 7.58 (d, J=8.4 Hz, 1H), 7.38 (t, J=7.8 Hz, 1H), 7.18-7.02 (m, 2H), 7.01-6.93 (m, 2H), 5.68 (dd, J=15.6, 5.7 Hz, 1H), 5.45 (dd, J=15.6, 8.7 Hz, 1H), 4.60 (bs, 2H), 4.33 (m, 1H), 4.10 (m, 1H), 3.64 (m, 1H), 3.22-2.98 (m, 3H), 2.75 (d, J=6.6 Hz, 2H), 2.50-2.08 (m, 3H), 1.68 (m, 1H).

EXAMPLE 29(a) To EXAMPLE 29(m)

By the same procedure as describe in Reference Example 5, Examples 1 and 2 using the compound prepared in Reference Example 11 or corresponding carboxylic acid ester derivatives instead of the compound prepared in Reference Example 4 and corresponding phosphonic acid ester derivatives instead of 3-(3-methoxymethylphenyl)-2-oxopropylphosphonic acid dimethyl ester, the compound of the present invention having the following physical data were obtained.

Example 29(a)

(15α,13E)-9-Oxo-15-hydroxy-16-(3-(4-fluoromethylbenzyloxy)phenyl)-17,18,19,20-tetranor-5-thia-8-azaprost-13-enoic acid

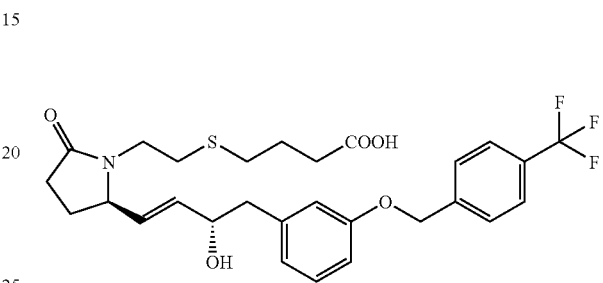

TLC: Rf 0.44 (Chloroform:Methanol 9:1);
NMR: δ 7.65 (d, J=8.1 Hz, 2H), 7.55 (d, J=8.1 Hz, 2H), 7.28-7.20 (m, 1H), 6.88-6.78 (m, 3H), 5.75 (dd, J=15.3, 5.7 Hz, 1H), 5.48 (dd, J=15.3, 8.1 Hz, 1H), 5.12 (s, 2H), 4.41 (q, J=6.3 Hz, 1H), 4.3-3.4 (br), 4.17-4.07 (m, 1H), 3.68-3.57 (m, 1H), 3.01-2.88 (m, 1H), 2.82 (d, J=6.3 Hz, 2H), 2.70-2.10 (m, 9H), 1.96-1.82 (m, 2H), 1.78-1.62 (m, 1H).

Example 29(b)

(15α,13E)-9-Oxo-15-hydroxy-16-(3-(pyridin-3-ylmethoxy)phenyl)-17,18,19,20-tetranor-5-thia-8-azaprost-13-enoic acid

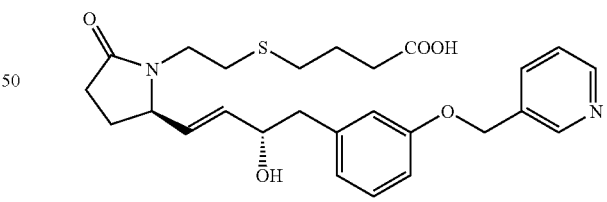

TLC: Rf 0.47 (Chloroform:Methanol=9:1);
NMR: δ 8.72 (s, 10H), 8.45 (d, J=3.3 Hz, 1H), 7.85 (d, J=7.8 Hz, 1H), 7.39 (dd, J=7.8, 3.3 Hz, 1H), 7.16 (dd, J=8.1, 8.1 Hz, 1H), 7.04 (s, 1H), 6.80-6.75 (m, 2H), 5.85 (dd, J=15.3, 4.8 Hz, 1H), 5.62 (dd, J=15.3, 8.7 Hz, 1H), 5.24 (d, J=13.2 Hz, 1H), 5.17 (d, J=13.2 Hz, 1H), 4.35-4.30 (m, 1H), 4.20-4.10 (m, 1H), 3.53-3.40 (m, 1H), 3.30-3.16 (m, 1H), 2.8-2.3 (m, 10H), 2.3-2.1 (m, 1H), 1.95-1.8 (m, 2H), 1.8-1.6 (m, 1H).

Example 29(c)

(15α,13E)-9-Oxo-15-hydroxy-16-cyclopropyl-17,18,19,20-tetranor-5-thia-8-azaprost-13-enoic acid

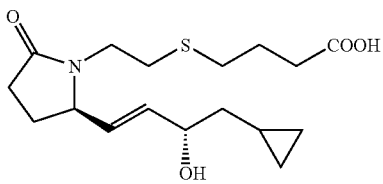

TLC: Rf 0.39 (Chloroform:Methanol=9:1);

NMR: δ 5.80 (dd, J=15.6, 6.0 Hz, 1H), 5.58 (ddd, J=15.6, 8.4, 1.0 Hz, 1H), 4.30 (m, 1H), 4.15 (m, 1H), 3.77-3.05 (m, 4H), 2.77-2.08 (m, 9H), 2.00-1.70 (m, 3H), 1.53-1.41 (m, 2H), 0.72 (m, 1H), 0.60-0.42 (m, 2H), 0.20-0.02 (m, 2H).

Example 29(d)

(15α,13E)-9-Oxo-15-hydroxy-16-phenyl-5-(4-carboxythiazol-2-yl)-1,2,3,4,17,18,19,20-octanor-5-thia-8-azaprost-13-ene

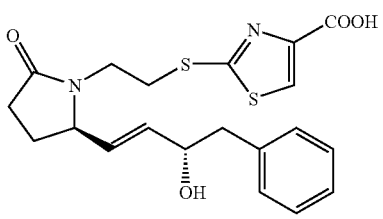

TLC: Rf 0.24 (Chloroform:Methanol=9:1);

NMR: δ 8.09 (s, 1H), 7.38-7.14 (m, 5H), 5.80 (dd, J=15.3, 6.0 Hz, 1H), 5.47 (dd, J=15.3, 8.7 Hz, 1H), 4.40 (m, 1H), 4.21-3.61 (m, 4H), 3.38-3.16 (m, 3H), 2.97-2.79 (m, 2H), 2.52-2.18 (m, 3H), 1.76 (m, 1H).

Example 29(e)

(15α,13E)-9-Oxo-15-hydroxy-16-(3-methylphenyl)-5-(4-carboxythiazol-2-yl)-1,2,3,4,17,18,19,20-octanor-5-thia-8-azaprost-13-ene

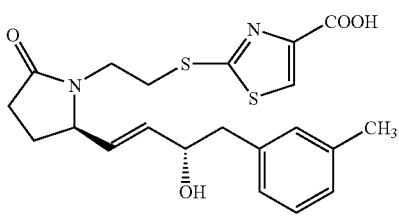

TLC: Rf 0.27 (Chloroform:Methanol=9:1);

NMR: δ 8.08 (s, 1H), 7.20 (m, 1H), 7.08-6.95 (m, 3H), 5.80 (dd, J=15.3, 5.7 Hz, 1H), 5.50 (dd, J=15.3, 8.7 Hz, 1H), 4.40 (m, 1H), 4.12 (m, 1H), 3.70 (m, 1H), 3.50-2.95 (m, 5H), 2.85-2.78 (m, 2H), 2.50-2.19 (m, 6H), 1.77 (m, 1H).

Example 29(f)

(15α,13E)-9-Oxo-15-hydroxy-16-(3-(pyridin-2-ylmethoxy)phenyl)-17,18,19,20-tetranor-5-thia-8-azaprost-13-enoic acid

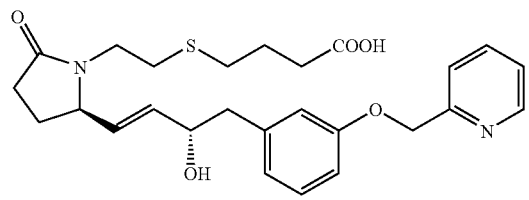

TLC: Rf 0.30 (Chloroform:Methanol=9:1);

NMR: δ 8.57 (d, J=5.4 Hz, 1H), 7.80 (dt, J=1.5, 7.5 Hz, 1H), 7.60 (d, J=7.5 Hz, 1H), 7.32 (m, 1H), 7.22 (t, J=7.8 Hz, 1H), 6.99-6.85 (m, 2H), 6.80 (d, J=7.8 Hz, 1H), 5.85 (dd, J=15.0, 4.8 Hz, 1H), 5.59 (ddd, J=15.0, 8.7, 1.2 Hz, 1H), 5.32 (s, 2H), 4.43 (m, 1H), 4.11 (m, 1H), 3.43 (m, 1H), 3.18 (m, 1H), 2.88-2.18 (m, 13H), 1.97-1.83 (m, 2H), 1.72 (m, 10H).

Example 29(g)

(15α,13E)-9-Oxo-15-hydroxy-16-(3-(pyridin-4-ylmethoxy)phenyl)-17,18,19,20-tetranor-5-thia-8-azaprost-13-enoic acid

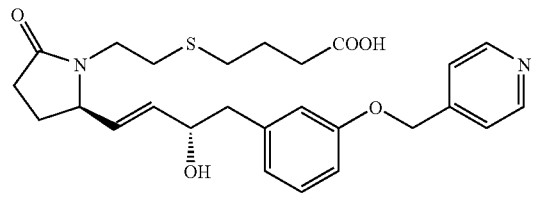

TLC: Rf 0.30 (Chloroform:Methanol=9:1);

NMR: δ 8.58 (d, J=6.0 Hz, 2H), 7.39 (d, J=6.0 Hz, 2H), 7.22 (t, J=7.8 Hz, 1H), 6.88-6.70 (m, 3H), 5.72 (dd, J=15.3, 5.7 Hz, 1H), 5.45 (dd, J=15.3, 8.1 Hz, 1H), 5.12 (s, 2H), 4.32 (m, 1H), 4.11 (m, 1H), 3.59 (m, 1H), 3.30 (m, 1H), 2.99 (m, 1H), 2.78 (m, 2H), 2.69-2.12 (m, 10H), 1.98-1.80 (m, 2H), 1.63 (m, 1H).

Example 29(h)

(15α,13E)-9-Oxo-15-hydroxy-16-(3-(pyridin-2-yl)phenyl)-17,18,19,20-tetranor-5-thia-8-azaprost-13-enoic acid

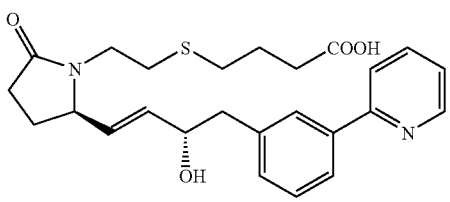

TLC: Rf 0.37 (Chloroform:Methanol=9:1);
NMR: δ 8.74 (m, 1H), 7.93 (s, 1H), 7.84 (dt, J=1.8, 7.8 Hz, 1H), 7.72 (d, J=7.8 Hz, 1H), 7.65 (d, J=8.1 Hz, 1H), 7.42 (t, J=7.5 Hz, 1H), 7.37-7.23 (m, 2H), 5.88 (dd, J=15.0, 4.5 Hz, 1H), 5.64 (ddd, J=15.0, 9.0, 1.5 Hz, 1H), 5.45 (bs, 2H), 4.58 (m, 1H), 4.10 (m, 1H), 3.40 (m, 1H), 3.21 (m, 1H), 3.02-2.80 (m, 2H), 2.78-2.10 (m, 9H), 1.99-1.82 (m, 2H), 1.73 (m, 1H).

Example 29(i)

(15α,13E)-9-Oxo-15-hydroxy-16-cyclopentyl-5-(4-carboxythiazol-2-yl)-1,2,3,4,17,18,19,20-octanor-5-thia-8-azaprost-13-ene

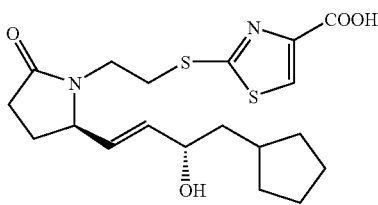

TLC: Rf 0.22 (Chloroform:Methanol 9:2);
NMR: δ 8.10 (s, 1H), 5.79 (dd, J=15.6, 6.0 Hz, 1H), 5.55 (d, J=15.6, 8.7 Hz, 1H), 4.40-3.63 (m, 5H), 3.58-3.24 (m, 3H), 2.57-2.08 (m, 3H), 1.98-1.40 (m, 10H), 1.10 (m, 2H).

Example 29(j)

(15α,13E)-9-Oxo-15-hydroxy-16-(3-(2,2,2-trifluoroethoxymethyl)phenyl)-5-(4-carboxythiazol-2-yl)-1,2,3,4,17,18,19,20-octanor-5-thia-8-azaprost-13-ene

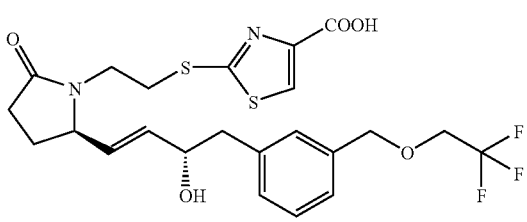

TLC: Rf 0.19 (Chloroform:Methanol=9:2);
NMR: δ 8.08 (s, 1H), 7.37-7.10 (m, 4H), 5.80 (dd, J=15.3, 5.7 Hz, 1H), 5.52 (dd, J=15.3, 8.4 Hz, 1H), 4.80-4.50 (m, 3H), 4.41 (m, 1H), 4.11 (m, 1H), 3.94-3.62 (m, 4H), 3.39-3.19 (m, 3H), 2.88-2.79 (m, 2H), 2.50-2.17 (m, 3H), 1.72 (m, 1H).

Example 29(k)

(15α,13E)-9-Oxo-15-hydroxy-16-(3-(benzofuran-2-yl)phenyl)-5-(4-carboxythiazol-2-yl)-1,2,3,4,17,18,19,20-octanor-5-thia-8-azaprost-13-ene

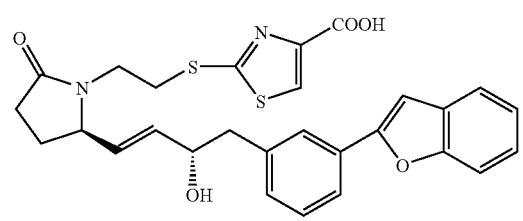

TLC: Rf 0.24 (Chloroform:Methanol:Acetic Acid 9:1:0.1);
NMR: δ 8.05 (s, 1H), 7.80-7.65 (m, 2H), 7.58 (d, J=7.5 Hz, 1H), 7.51 (d, J=7.5 Hz, 1H), 7.39 (t, J=7.8 Hz, 1H), 7.35-7.15 (m, 3H), 7.03 (s, 1H), 5.82 (dd, J=15.0, 5.7 Hz, 1H), 5.52 (d, J=15.0, 8.7 Hz, 1H), 4.50 (m, 1H), 4.19-4.02 (m, 1H), 3.70 (m, 1H), 3.36-3.08 (m, 3H), 3.00-2.82 (m, 2H), 2.50-2.10 (m, 3H), 1.72 (m, 1H).

Example 29(l)

(15α,13E)-9-Oxo-15-hydroxy-16-(5-methylfuran-2-yl)-5-(4-carboxythiazol-2-yl)-1,2,3,4,17,18,19,20-octanor-5-thia-8-azaprost-13-ene

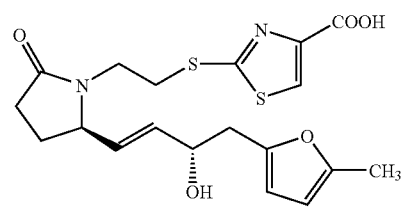

TLC: Rf 0.26 (Dichloromethane:Methanol:Acetic Acid=9:1:0.1);
NMR: δ 8.09 (s, 1H), 5.96 (d, J=3.0 Hz, 1H), 5.90-5.84 (m, 1H), 5.79 (dd, J=15.3, 6.0 Hz, 1H), 5.55 (ddd, J=15.3, 6.0, 1.2 Hz, 1H), 4.45 (q, J=6.3 Hz, 1H), 4.12 (q, J=7.5 Hz, 1H), 3.84-3.72 (m, 1H), 3.46-3.18 (m, 3H), 2.82 (d, J=6.3 Hz, 2H), 2.50-2.20 (m, 3H), 2.24 (s, 3H), 1.80-1.70 (m, 1H).

Example 29(m)

(15α,13E)-9-Oxo-15-hydroxy-16-(4-fluorophenyl)-5-(6-carboxypyridin-2-yl)-1,2,3,4,17,18,19,20-octanor-5-thia-8-azaprost-13-ene

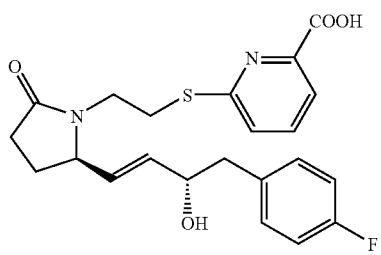

TLC: Rf 0.21 (Chloroform:Methanol=4:1);

NMR: δ 7.97 (m, 1H), 7.69 (m, 1H), 7.38 (m, 1H), 7.21-7.15 (m, 2H), 7.06-6.97 (m, 2H), 5.75 (dd, J=15.0, 5.7 Hz, 1H), 5.51 (ddd, J=15.0, 8.4, 1.0 Hz, 1H), 4.40 (m, 1H), 4.10 (m, 1H), 3.58 (m, 1H), 3.38-3.15 (m, 3H), 2.83 (d, J=6.6 Hz, 2H), 2.57-2.20 (m, 3H), 1.77 (m, 1H).

EXAMPLE 30(a) To EXAMPLE 30(e)

By the same procedure as describe in Example 16 using the compound prepared in Example 3(l) or Example 29(e) and corresponding alcohol derivatives instead of 2-pentanoyloxyethanol, the compound of the present invention having the following physical data were obtained.

Example 30(a)

(15α,13E)-9-Oxo-15-hydroxy-16-(4-fluorophenyl)-17,18,19,20-tetranor-5-thia-8-azaprost-13-enoic acid dibutylcarbamoylmethyl ester

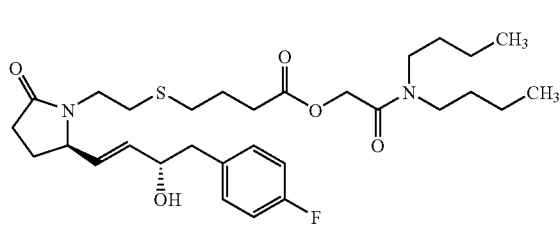

TLC: Rf 0.73 (Chloroform:Methanol=9:1);

NMR: δ 7.17 (m, 2H), 6.99 (m, 2H), 5.75 (dd, J=15.6, 5.1 Hz, 1H), 5.52 (dd, J=15.6, 8.4 Hz, 1H), 4.69 (s, 2H), 4.40 (m, 1H), 4.11 (m, 1H), 3.58 (m, 1H), 3.28 (m, 2H), 3.20-3.00 (m, 3H), 2.81 (d, J=6.6 Hz, 2H), 2.70-2.47 (m, 7H), 2.40-2.18 (m, 3H), 1.95 (m, 2H), 1.88-1.42 (m, 5H), 1.41-1.22 (m, 4H), 1.00-0.83 (m, 6H).

Example 30(b)

(15α,13E)-9-Oxo-15-hydroxy-16-(4-fluorophenyl)-17,18,19,20-tetranor-5-thia-8-azaprost-13-enoic acid 2-(2,2-diethylpentanoyloxy)ethyl ester

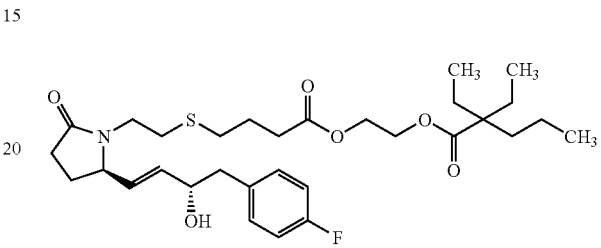

TLC: Rf 0.29 (Ethyl Acetate);

NMR: δ 7.22-7.13 (m, 2H), 7.07-6.97 (m, 2H), 5.75 (dd, J=15.3, 6.0 Hz, 1H), 5.50 (dd, J=15.3, 8.7 Hz, 1H), 4.43-4.32 (m, 1H), 4.25 (s, 4H), 4.18-4.06 (m, 1H), 3.79-3.56 (m, 1H), 3.02-2.88 (m, 1H), 2.86-2.79 (m, 2H), 2.70-2.48 (m, 4H), 2.48-2.31 (m, 4H), 2.31-2.17 (m, 1H), 1.97-1.82 (m, 3H), 1.78-1.60 (m, 1H), 1.60-1.48 (m, 6H), 1.22-1.10 (m, 2H), 0.89 (t, J=7.2 Hz, 3H), 0.77 (t, J=7.5 Hz, 6H).

Example 30(c)

(15α,13E)-9-Oxo-15-hydroxy-16-(4-fluorophenyl)-17,18,19,20-tetranor-5-thia-8-azaprost-13-enoic acid 2-(adamantan-1-ylcarbonyloxy)ethyl ester

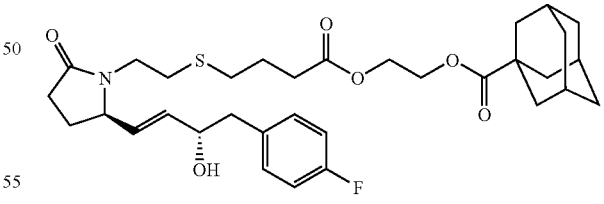

TLC: Rf 0.64 (Dichloromethane:Methanol=9:1);

NMR: δ 7.20-7.10 (m, 2H), 7.05-6.95 (m, 2H), 5.74 (dd, J=14.7, 6.0 Hz, 1H), 5.50 (ddd, J=14.7, 8.4, 1.5 Hz, 1H), 4.45-4.35 (m, 1H), 4.30-4.20 (m, 4H), 4.15-4.05 (m, 1H), 3.70-3.55 (m, 1H), 3.00-2.90 (m, 1H), 2.81 (d, J=6.0 Hz, 2H), 2.70-2.35 (m, 8H), 2.30-2.15 (m, 1H), 2.05-1.95 (m, 3H), 1.95-1.80 (m, 9H), 1.80-1.60 (m, 6H).

Example 30(d)

(15α,13E)-9-Oxo-15-hydroxy-16-(4-fluorophenyl)-17,18,19,20-tetranor-5-thia-8-azaprost-13-enoic acid 2-(1-ethyl-1-methylbutanoyloxy)ethyl ester

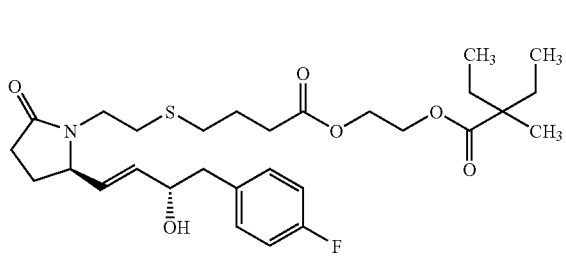

TLC: Rf 0.34 (Ethyl Acetate);
NMR: δ 7.20-7.10 (m, 2H), 7.05-6.95 (m, 2H), 5.23 (dd, J=15.6, 6.0 Hz, 1H), 5.50 (ddd, J=15.6, 8.4, 1.5 Hz, 1H), 4.40-4.30 (m, 1H), 4.27 (s, 4H), 4.15-4.05 (m, 1H), 3.70-3.50 (m, 1H), 3.00-2.90 (m, 1H), 2.81 (d, J=6.6 Hz, 2H), 2.70-2.15 (m, 8H), 1.95-1.85 (m, 3H), 1.75-1.60 (m, 3H), 1.50-1.40 (m, 2H), 1.09 (s, 3H), 0.82 (t, J=7.5 Hz, 6H).

Example 30(e)

(15α,13E)-9-Oxo-15-hydroxy-16-(3-methylphenyl)-5-(4-(2-(1-ethyl-1-methylbutanoyloxy)ethoxycarbonyl)thiazol-2-yl)-1,2,3,4,17,18,19,20-octanor-5-thia-8-azaprost-13-ene

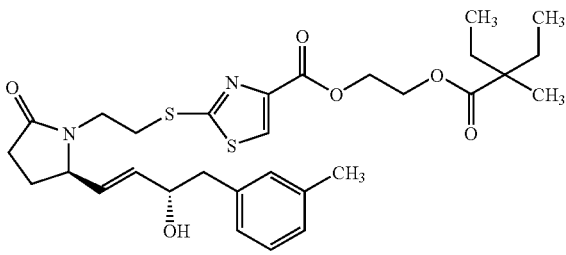

TLC: Rf 0.30 (Ethyl Acetate);
NMR: δ 7.99 (s, 1H), 7.17 (t, J=7.5 Hz, 1H), 7.05-7.00 (m, 1H), 7.00-6.90 (m, 2H), 5.80 (dd, J=15.3, 6.0 Hz, 1H), 5.50 (ddd, J=16.2, 8.7, 1.5 Hz, 1H), 4.56-4.45 (m, 2H), 4.40-4.30 (m, 3H), 4.25-4.15 (m, 1H), 3.75-3.65 (m, 1H), 3.40 (t, J=6.6 Hz, 2H), 3.30-3.15 (m, 1H), 2.80-2.75 (m, 2H), 2.40-2.15 (m, 6H), 2.08 (d, J=4.5 Hz, 1H), 1.80-1.60 (m, 3H), 1.50-1.40 (m, 2H), 1.09 (s, 3H), 0.80 (t, J=7.5 Hz, 6H).

EXAMPLE 31

(15α,13E)-9-Oxo-15-hydroxy-16-(3,4-dihydroxyphenyl)-17,18,19,20-tetranor-5-thia-8-azaprost-13-enoic acid

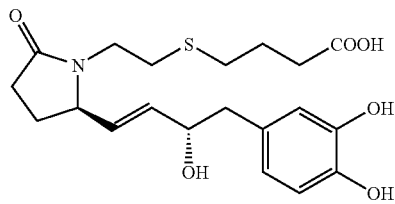

By the same procedure as describe in Reference Example 5, Examples 1, 7 and 2 using 9-oxo-12-formyl-13,14,15,16,17,18,19,20-octanoyl-5-thia-8-azaprostanoic acid butyl ester instead of the compound prepared in Reference Example 4 and 3-(3,4-bis(t-butyldimethylsilyloxy)phenyl)-2-oxopropylphosphonic acid dimethyl ester instead of 3-(3-methoxymethylphenyl)-2-oxopropylphosphonic acid dimethyl ester, the compound of the present invention having the following physical data were obtained.

TLC: Rf 0.14 (Dichloromethane:Methanol:Acetic Acid=90:10:1);
NMR (CD₃OD): δ 6.67 (d, J=7.8 Hz, 1H), 6.61 (d, J=1.8 Hz, 1H), 6.49 (dd, J=7.8, 1.8 Hz, 1H), 5.68 (dd, J=15.3, 7.2 Hz, 1H), 5.33 (dd, J=15.3, 9.0 Hz, 1H), 4.30-4.20 (m, 1H), 4.20-4.10 (m, 1H), 3.55-3.45 (m, 1H), 2.90-2.70 (m, 2H), 2.70-2.15 (m, 10H), 1.95-1.80 (m, 2H), 1.80-1.60 (m, 1H).

EXAMPLE 32

(15α,13E)-1,6-(1,4-Interphenylene)-9-oxo-15-hydroxy-16-(3-(2-methylphenyl)phenyl)-2,3,4,5,17,18,19,20-octanor-8-azaprost-13-enoic acid

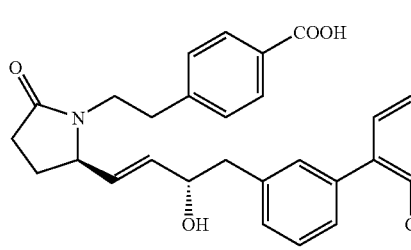

By the same procedure as describe in Reference Examples 31, 32, 33, Examples 26 and 2 using 3-(3-(2-methylphenyl)phenyl)-2-oxopropylphosphonic acid dimethyl ester instead of 3-(4-fluorophenyl)-2-oxopropylphosphonic acid dimethyl ester and 4-(formylmethyl)benzoic acid ethyl ester instead of 4-(formylmethylthio)butanoic acid ethyl ester, the compound of the present invention having the following physical data were obtained.

TLC: Rf 0.41 (Dichloromethane:Methanol=9:1);
NMR: δ 7.99 (d, J=8.4 Hz, 2H), 7.40-7.14 (m, 10H), 5.65 (dd, J=15.3, 6.0 Hz, 1H), 5.39 (dd, J=15.3, 8.7 Hz, 1H), 4.45-4.35 (m, 1H), 3.85-3.70 (m, 2H), 3.05-2.70 (m, 5H), 2.40-2.20 (m, 5H), 2.20-2.00 (m, 1H), 1.70-1.55 (m, 1H).

EXAMPLE 32(a) To EXAMPLE 32(s)

By the same procedure as describe in Reference Examples 31, 32, 33, Examples 26 and 2 using corresponding phosphonic acid ester instead of 3-(3-(2-methylphenyl)phenyl)-2-oxopropylphosphonic acid dimethyl ester and corresponding carboxylic acid ester derivatives instead of 4-(formylmethyl)benzoic acid ethyl ester, the compound of the present invention having the following physical data were obtained:

Example 32(a)

(15α,13E)-1,6-(1,4-Interphenylene)-9-oxo-15-hydroxy-16-(3-(3-methylphenyl)phenyl)-2,3,4,5,17,18,19,20-octanor-8-azaprost-13-enoic acid

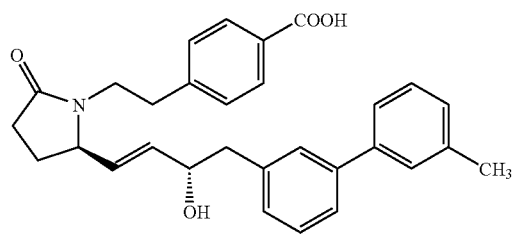

TLC: Rf 0.32 (Dichloromethane:Methanol=9:1);

N1M: δ 7.98 (d, J=8.4 Hz, 2H), 7.50-7.30 (m, 6H), 7.24-7.14 (m, 4H), 5.64 (dd, J=15.3, 6.0 Hz, 1H), 5.36 (dd, J=15.3, 8.4 Hz, 1H), 4.50-4.40 (m, 1H), 3.80-3.65 (m, 2H), 3.00-2.70 (m, 5H), 2.45-2.20 (m, 5H), 2.20-2.00 (m, 1H), 1.70-1.55 (m, 1H).

Example 32(b)

(15α,13E)-1,6-(1,4-Interphenylene)-9-oxo-15-hydroxy-16-(3-(4-methylphenyl)phenyl)-2,3,4,5,17,18,19,20-octanor-8-azaprost-13-enoic acid

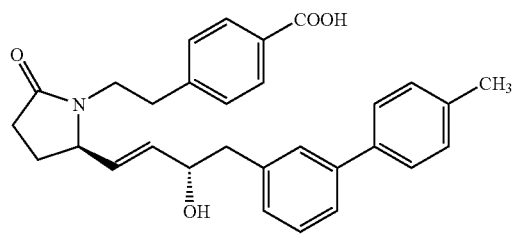

TLC: Rf 0.32 (Dichloromethane:Methanol:Water=9:1);

NMR: δ 7.98 (d, J=8.4 Hz, 2H), 7.50-7.44 (m, 3H), 7.44-7.32 (m, 2H), 7.28-7.14 (m, 5H), 5.64 (dd, J=15.6, 6.0 Hz, 1H), 5.36 (dd, J=15.6, 8.7 Hz, 1H), 4.45-4.35 (m, 1H), 3.80-3.65 (m, 2H), 3.00-2.70 (m, 5H), 2.40-2.20 (m, 5H), 2.20-2.00 (m, 1H), 1.70-1.55 (m, 1H).

Example 32(c)

(15α,13E)-1,6-(1,4-Interphenylene)-9-oxo-15-hydroxy-16-(3-(4-trifluoromethylphenyl)phenyl)-2,3,4,5,17,18,19,20-octanor-8-azaprost-13-enoic acid

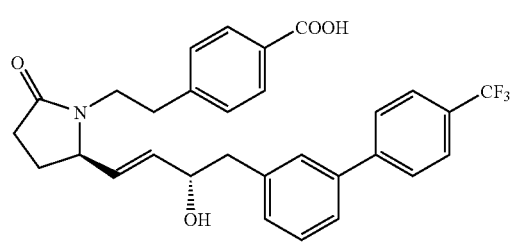

TLC: Rf 0.51 (Chloroform:Methanol:Acetic Acid=9:1:0.1);

NMR: δ 8.00 (d, J=8.1 Hz, 2H), 7.69 (m, 4H), 7.55-7.13 (m, 6H), 5.65 (dd, J=15.0, 6.0 Hz, 1H), 5.39 (dd, J=15.0, 8.4 Hz, 1H), 4.41 (m, 1H), 3.81-3.69 (m, 2H), 3.10-2.70 (m, 5H), 2.43-1.30 (m, 5H).

Example 32(d)

(15α,13E)-1,6-(1,4-Interphenylene)-9-oxo-15-hydroxy-16-(3-(3,5-ditrifluoromethylphenyl)phenyl)-2,3,4,5,17,18,19,20-octanor-8-azaprost-13-enoic acid

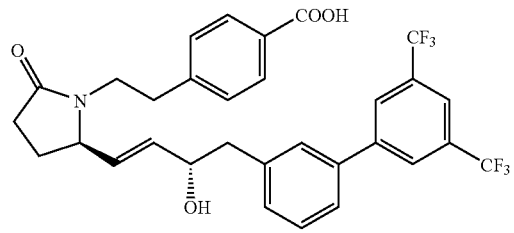

TLC: Rf 0.53 (Chloroform:Methanol:Acetic Acid=9:1:0.1);

NMR: δ 8.01-7.98 (m, 4H), 7.86 (s, 1H), 7.58-7.40 (m, 3H), 7.37-7.20 (m, 3H), 5.68 (dd, J=15.6, 6.0 Hz, 1H), 5.44 (dd, J=15.6, 8.4 Hz, 1H), 4.43 (m, 1H), 3.83-3.78 (m, 2H), 3.18-2.80 (m, 6H), 2.42-2.22 (m, 2H), 2.14 (m, 1H), 1.65 (m, 1H).

Example 32(e)

(15α,13E)-1,6-(1,4-Interphenylene)-9-oxo-15-hydroxy-16-(3-(4-t-butylphenyl)phenyl)-2,3,4,5,17,18,19,20-octanor-8-azaprost-13-enoic acid

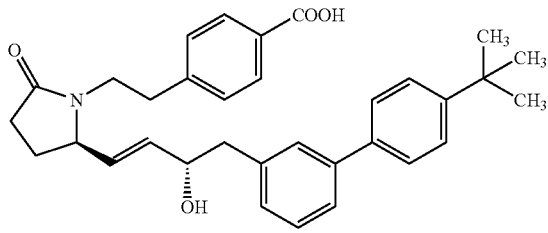

TLC: Rf 0.51 (Chloroform:Methanol:Acetic Acid=9:1:0.1);
NMR: δ 7.98 (d, J=8.4 Hz, 2H), 7.59-7.33 (m, 7H), 7.25-7.16 (m, 3H), 5.63 (dd, J=15.3, 5.7 Hz, 1H), 5.39 (dd, J=15.3, 9.0 Hz, 1H), 4.21 (m, 1H), 3.80-3.65 (m, 2H), 3.00-2.68 (m, 6H), 2.40-1.40 (m, 4H), 1.35 (s, 9H).

Example 32(f)

(15α)-9-Oxo-15-hydroxy-16-(3-phenylphenyl)-5-(4-carboxythiazol-2-yl)-1,2,3,4,17,18,19,20-octanor-5-thia-8-azaprostane

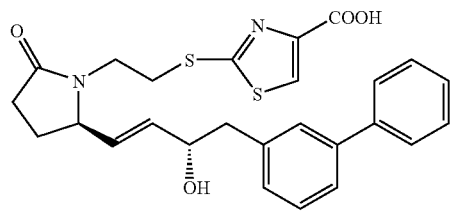

TLC: Rf 0.32 (Chloroform:Methanol:Acetic Acid=9:1:0.1);
NMR: δ 1.72 (m, 1H) 2.30 (m, 3H) 3.06 (m, 7H) 3.68 (m, 1H) 4.11 (m, 1H) 4.47 (m, 1H) 5.51 (dd, J=15.38, 8.79 Hz, 1H) 5.82 (dd, J=15.38, 5.77 Hz, 1H) 7.35 (m, 9H) 8.07 (s, 1H).

Example 32(g)

(15α)-9-Oxo-15-hydroxy-16-(3-(4-methylphenyl)phenyl)-5-(4-carboxythiazol-2-yl)-1,2,3,4,17,18,19,20-octanor-5-thia-8-azaprostane

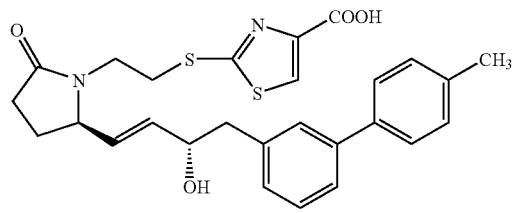

TLC: Rf 0.33 (Chloroform:Methanol:Acetic Acid=9:1:0.1);
NMR: δ 1.71 (m, 1H) 2.38 (m, 8H) 2.92 (m, 2H) 3.23 (m, 3H) 3.69 (m, 1H) 4.10 (m, 1H) 4.47 (m, 1H) 5.51 (dd, J=15.38, 8.52 Hz, 1H) 5.82 (dd, J=15.38, 5.77 Hz, 1H) 7.31 (m, 8H) 8.01 (s, 1H).

Example 32(h)

(15α)-9-Oxo-15-hydroxy-16-(3-(4-chlorophenyl)phenyl)-5-(4-carboxythiazol-2-yl)-1,2,3,4,17,18,19,20-octanor-5-thia-8-azaprostane

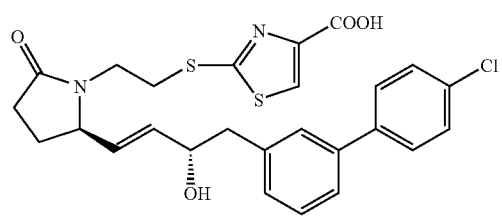

TLC: Rf 0.28 (Chloroform:Methanol:Acetic Acid=9:1:0.1);
NMR: δ 1.69 (m, 1H) 2.30 (m, 3H) 2.90 (m, 2H) 3.44 (m, 6H) 4.11 (m, 1H) 4.46 (m, 1H) 5.52 (dd, J=15.38, 8.79 Hz, 1H) 5.83 (dd, J=15.38, 5.77 Hz, 1H) 7.35 (m, 8H) 8.07 (s, 1H).

Example 32(i)

(15α)-9-Oxo-15-hydroxy-16-(3-(4-methoxyphenyl)phenyl)-5-(4-carboxythiazol-2-yl)-1,2,3,4,17,18,19,20-octanor-5-thia-8-azaprostane

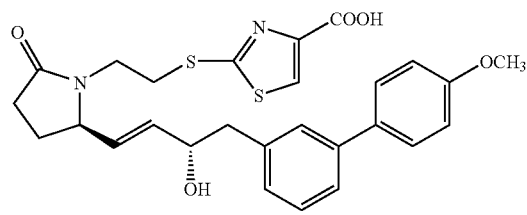

TLC: Rf 0.32 (Chloroform:Methanol:Acetic Acid=9:1:0.1);
NMR: δ 1.70 (m, 1H) 2.53 (m, 7H) 3.21 (m, 3H) 3.69 (m, 1H) 3.85 (s, 3H) 4.09 (m, 1H) 4.46 (m, 1H) 5.51 (dd, J=15.38, 8.79 Hz, 1H) 5.82 (dd, J=15.38, 6.04 Hz, 1H) 7.22 (m, 8H) 8.07 (s, 1H).

Example 32(i)

(15α,13E)-9-Oxo-15-hydroxy-16-(3-(naphthalen-2-yl)phenyl)-17,18,19,20-tetranor-5-thia-8-azaprost-13-enoic acid

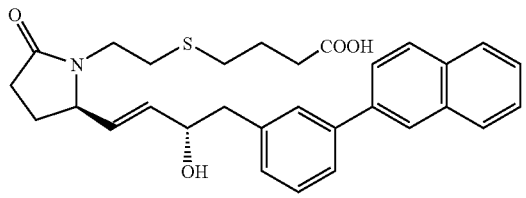

TLC: Rf 0.46 (Chloroform:Methanol=9:1);

NMR: δ 8.03 (s, 1H), 7.94-7.82 (m, 3H), 7.73 (dd, J=8.7, 2.1 Hz, 1H), 7.64-7.57 (m, 1H), 7.57-7.40 (m, 4H), 7.21 (d, J=1.5 Hz, 1H), 5.79 (dd, J=15.3, 6.0 Hz, 1H), 5.49 (ddd, J=15.3, 8.7, 1.2 Hz, 1H), 4.54-4.44 (m, 1H), 4.14-4.04 (m, 1H), 3.66-3.52 (m, 1H), 3.00-2.85 (m, 3H), 2.60-2.10 (m, 9H), 1.90-1.60 (m, 3H).

Example 32(k)

(15α,13E)-9-Oxo-15-hydroxy-16-(3-(benzoxazol-2-yl)phenyl)-17,18,19,20-tetranor-5-thia-8-azaprost-13-enoic acid

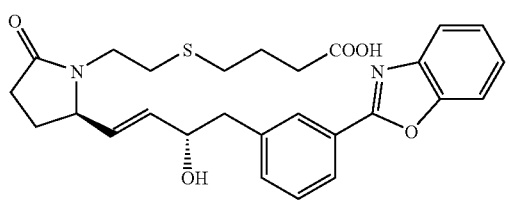

TLC: Rf 0.43 (Chloroform:Methanol=9:1);

NMR: δ 8.31 and 8.24 (s, 1H), 8.08 (d, J=7.8 Hz, 1H), 7.82-7.74 (m, 1H), 7.64-7.56 (m, 1H), 7.48 (t, J=7.8 Hz, 1H), 7.44-7.34 (m, 3H), 5.89 (dd, J=15.6, 4.5 Hz, 1H), 5.63 (dd, J=15.6, 7.5 Hz, 1H), 4.65-4.55 and 4.55-4.45 (m, 1H), 4.20-4.05 (m, 1H), 3.55-3.40 (m, 1H), 3.30-3.10 (m, 1H), 3.30 (dd, J=13.8, 5.1 Hz, 1H), 2.89 (dd, J=13.8, 8.7 Hz, 1H), 2.75-2.15 (m, 9H), 1.95-1.85 (m, 2H), 1.80-1.60 (m, 1H).

Example 32(l)

(15α,13E)-9-Oxo-15-hydroxy-16-(3-(benzothiazol-2-yl)phenyl)-17,18,19,20-tetranor-5-thia-8-azaprost-13-enoic acid

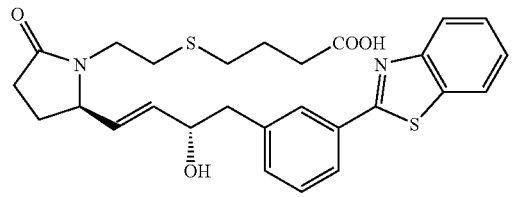

TLC: Rf 0.38 (Chloroform:Methanol=9:1);

NMR: δ 8.14 (s, 1H), 8.09 (d, J=8.1 Hz, 1H), 7.91 (d, J=7.8 Hz, 1H), 7.84 (d, J=7.8 Hz, 1H), 7.56-7.32 (m, 4H), 5.88 (dd, J=15.0, 5.1 Hz, 1H), 5.61 (ddd, J=15.0, 8.7, 1.5 Hz, 1H), 4.60-4.45 (m, 1H), 4.20-4.05 (m, 1H), 3.55-3.40 (m, 1H), 3.25-3.05 (m, 1H), 3.01 (dd, J=13.8, 4.8 Hz, 1H), 2.88 (dd, J=13.8, 8.7 Hz, 1H), 2.70-2.10 (m, 9H), 1.96-1.82 (m, 2H), 1.80-1.60 (m, 1H).

Example 32(m)

(15α-9-Oxo-15-hydroxy-16-(3-(naphthalen-2-yl)phenyl)-5-(4-carboxythiazol-2-yl)-1,2,3,4,17,18,19,20-octanor-5-thia-8-azaprostane

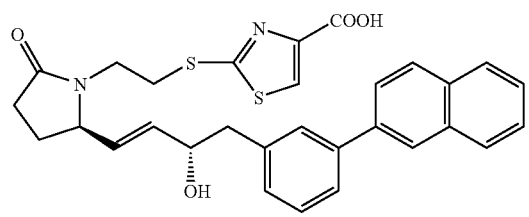

TLC: Rf 0.40 (Dichloromethane:Methanol:Acetic Acid=9:1:0.1);

NMR: δ 8.05-8.00 (m, 2H), 7.93-7.82 (m, 3H), 7.71 (dd, J=8.4, 1.8 Hz, 1H), 7.61 (d, J=7.8 Hz, 1H), 7.56-7.47 (m, 4H), 7.42 (t, J=7.8 Hz, 1H), 7.19 (d, J=7.8 Hz, 1H), 5.84 (dd, J=15.3, 5.7 Hz, 1H), 5.52 (dd, J=15.3, 8.7 Hz, 1H), 4.49 (q, J=6.0 Hz, 1H), 4.15-4.05 (m, 1H), 3.75-3.65 (m, 1H), 3.35-3.05 (m, 3H), 2.95 (dd, J=7.2, 3.3 Hz, 2H), 2.50-2.10 (m, 3H), 1.80-1.60 (m, 1H).

Example 32(n)

(15α)-9-Oxo-15-hydroxy-16-(3-(benzoxazol-2-yl)phenyl)-5-(4-carboxythiazol-2-yl)-1,2,3,4,17,18,19,20-octanor-5-thia-8-azaprostane

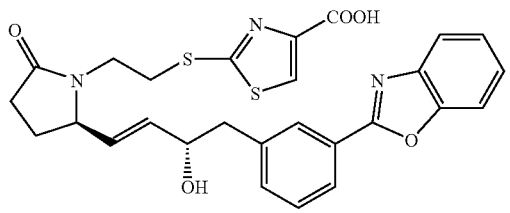

TLC: Rf 0.36 (Dichloromethane:Methanol:Acetic Acid=9:1:0.1);

NMR: δ 8.45 and 8.32 (s, 1H), 8.12 (s, 1H), 8.06 (d, J=7.5 Hz, 1H), 7.90-7.82 (m, 1H), 7.64-7.58 (m, 1H), 7.50-7.36 (m, 4H), 5.94 (dd, J=15.6, 4.5 Hz, 1H), 5.78 (dd, J=15.6, 6.3 Hz, 1H), 4.70-4.50 (m, 1H), 4.15 (q, J=7.2 Hz, 1H), 3.60-3.20 (m, 4H), 3.00 (dd, J=14.4, 4.2 Hz, 1H), 2.85 (dd, J=14.4, 9.0 Hz, 1H), 2.50-2.15 (m, 3H), 1.85-1.70 (m, 1H).

Example 32(o)

(15α)-9-Oxo-15-hydroxy-16-(3-(benzothiazol-2-yl)phenyl)-5-(4-carboxythiazol-2-yl)-1,2,3,4,17,18,19,20-octanor-5-thia-8-azaprostane

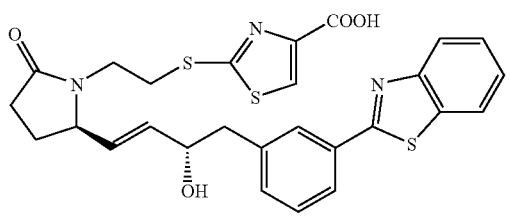

TLC: Rf 0.37 (Dichloromethane:Methanol:Acetic Acid=9:1:0.1);

NMR: δ 8.29 (s, 1H), 8.20-8.14 (m, 1H), 8.11 (s, 1H), 7.92 (d, J=7.2 Hz, 1H), 7.79 (d, J=7.8 Hz, 1H), 7.60-7.30 (m, 4H), 5.90 (dd, J=15.3, 3.9 Hz, 1H), 5.71 (dd, J=15.3, 9.0 Hz, 1H), 4.60-4.45 (m, 1H), 4.20-4.05 (m, 1H), 3.60-3.15 (m, 4H), 2.98 (dd, J=14.1, 4.5 Hz, 1H), 2.83 (dd, J=14.1, 9.0 Hz, 1H), 2.50-2.10 (m, 3H), 1.85-1.70 (m, 1H).

Example 32(p)

(15α,13E)-9-Oxo-15-hydroxy-16-(3-(isoindolin-2-yl)phenyl)-17,18,19,20-tetranor-5-thia-8-azaprost-13-enoic acid

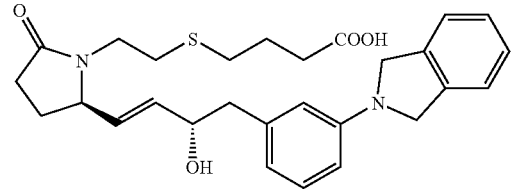

TLC: Rf 0.36 (Chloroform:Methanol=9:1);

NMR: δ 1.79 (m, 3H) 2.72 (m, 13H) 3.59 (m, 1H) 4.12 (m, 1H) 4.49 (m, 1H) 4.78 (m, 4H) 5.55 (dd, J=15.66, 8.79 Hz, 1H) 5.81 (dd, J=15.66, 5.49 Hz, 1H) 6.57 (m, 2H) 7.33 (m, 6H).

Example 32(q)

(15α,13E)-9-Oxo-15-hydroxy-16-(3-(indol-5-yl)phenyl)-17,18,19,20-tetranor-5-thia-8-azaprost-13-enoic acid

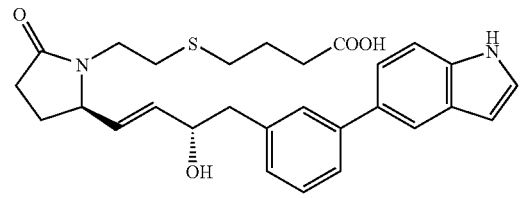

TLC: Rf 0.40 (Chloroform:Methanol=9:1);

NMR: δ 2.09 (m, 13H) 2.90 (m, 3H) 3.54 (m, 1H) 4.07 (m, 1H) 4.48 (m, 1H) 5.46 (ddd, J=15.38, 8.79, 1.10 Hz, 1H) 5.78 (dd, J=15.38, 5.77 Hz, 1H) 6.60 (m, 1H) 7.14 (m, 1H) 7.25 (m, 2H) 7.46 (m, 4H) 7.84 (m, 1H) 8.35 (brs, 1H).

Example 32(r)

(15α)-9-Oxo-15-hydroxy-16-(3-(isoindolin-2-yl)phenyl)-5-(4-carboxythiazol-2-yl)-1,2,3,4,17,18,19,20-octanor-5-thia-8-azaprostane

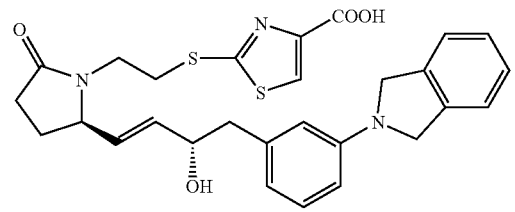

TLC: Rf 0.38 (Dichloromethane:Methanol:Acetic Acid 9:1:0.1);

NMR: δ 8.04 (s, 1H), 7.70-7.00 (m, 5H), 6.60-6.40 (m, 3H), 6.00-5.75 (m, 1H), 5.65-5.50 (m, 1H), 4.64 (s, 4H), 4.50-4.40 (m, 1H), 4.20-4.10 (m, 1H), 3.80-3.60 (m, 1H), 3.50-3.00 (m, 3H), 3.00-2.75 (m, 2H), 2.50-2.10 (m, 3H), 1.85-1.65 (m, 1H).

Example 32(s)

(15α)-9-Oxo-15-hydroxy-16-(3-(indol-5-yl)phenyl)-5-(4-carboxythiazol-2-yl)-1,2,3,4,17,18,19,20-octanor-5-thia-8-azaprostane

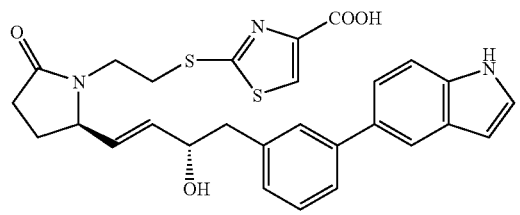

TLC: Rf 0.36 (Dichloromethane:Methanol:Acetic Acid=9:1:0.1);

NMR (CD$_3$OD): δ 10.47 (s, 1H), 8.17 and 8.14 (s, 1H), 7.80-7.74 (m, 1H), 7.50-7.22 (m, 6H), 7.14-7.05 (m, 1H), 6.50-6.46 (m, 1H), 5.74 (dd, J=15.0, 6.9 Hz, 1H), 5.28 (dd, J=15.0, 9.0 Hz, 1H), 4.45-4.30 (m, 1H), 4.30-4.15 (m, 1H), 3.55-3.45 (m, 1H), 3.30-3.20 (m, 1H), 3.20-2.70 (m, 4H), 2.35-2.00 (m, 3H), 1.70-1.50 (m, 1H).

Formulation Example 1

The following compounds were admixed in conventional method and punched out to obtain 100 tablets each containing 0.5 mg of active ingredient.

| | |
|---|---|
| (15α,13E)-9-Oxo-15-hydroxy-16-(3-methoxymethylphenyl)-17,18,19,20-tetranor-8-azaprost-13-enoic acid•α-cyclodextrin | 250 mg (active ingredient 50 mg) |
| Carboxymethylcellulose calcium | 200 mg |
| Magnesium stearate | 100 mg |
| Micro crystalline cellulose | 9.2 g |

Formulation Example 2

The following components were admixed in a conventional method, and the solution was sterilized in a conventional method, placed 1 ml portions into ampoules and freeze-dried in a conventional method to obtain 100 ampoules each containing 0.2 mg of active ingredient.

| | |
|---|---|
| (15α,13E)-9-Oxo-15-hydroxy-16-(3-methoxymethylphenyl)-17,18,19,20-tetranor-8-azaprost-13-enoic acid•α-cyclodextrin | 100 mg (active ingredient 20 mg) |
| Mannit | 5 g |
| Distilled water | 100 ml |

Formulation Example 3

Polylactate-glycolate copolymer (abbreviated as PLGA) (polylactate:glycolate=1:1 (mol %), weight-average molecular weight 80,000, 90 mg, Mitsui chemical Co., Ltd.) and solution of the compound of the present invention (10 mg) in methylene chloride (3 mL) were prepared. To 0.1% polyvinylalcohol (Nacalai Tesque) solution (300 ml) stirred with 6000 rpm by using TK robomix (Tokusyukika, MARK II 2.5 type), the solution prepared above was added, and the mixture was stirred for 2 minutes at room temperature to make O/W emulsion. This O/W emulsion was stirred for 3 hours at room temperature, volatilise methylene chloride. After oil layer was solidified, the residue was centrifugated for 10 minutes with 1000 rpm by using centrifugal machine (Hitachi, 05PR-22). After removing supernatant, the residue was dispersed with distilled water for injection (35 mL), it was centrifugated for 10 minutes with 1000 rpm by using centrifugal machine again (twice), rinsed the sample to remove free drug etc. Finally, after removing a supernatant and drying a precipitate under reduced pressure microsphere was prepared.

The compounds of the present invention which were used for this microsphere pharmaceutical were showed in the following.

Formulation Example 3(1): Example 18
Formulation Example 3(2): Example 16(f)
Formulation Example 3(3): Example 16(e)

Test of Formulation 1:

The microsphere prepared in Formulation Examples 3(1) and 3(2) was added by acetonitrile solution containing proper internal standard compound and ultrasonicated to dissolve. Content of the compound in the solution was determined by using HPLC, then the rate of inclusion of the compound in microsphere was calculated by the equation as shown below.

The rate of inclusion of the compound=Measured content/Theoretical content multiplied by 100

The rates of the Formulation Examples 3(1), 3(2) and 3(3) are 93%, 100% and 96% each.

Test of Formulation 2:

The microsphere prepared in Formulation Examples 3(1) was suspended in saline (prepared 10 mg/kg as content of the compound). The suspension was administered into regio cervicalis posterior of SD-strain male rat by subcutaneous injection. Blood samples are collected at regular time intervals after administration under anesthesia with ether. And plasma separated from the blood was solid-phase extracted, and the concentration was determined by using liquid chromatograph mass spectrometer (LC/MS/MS).

It was confirmed that the blood concentration of the compound was sustained at the day of 21.

Pharmacological Activity of the Compounds of the Invention:

For example, the pharmacological activities of the compounds of the invention were confirmed in experiments performed in a laboratory using the cells which express prostanoid receptor sub-types.

(i) Experiment for receptor-binding using cells which express prostanoid receptor sub-types According to the method of Sugimoto et al. (J. Biol. Chem., 267, 6463-6466 (1992)), CHO cells which expressed prostanoid receptor sub-types (murine EP$_1$, EP$_2$, EP$_{3α}$, and EP$_4$, respectively) were prepared and used as membrane authentic samples.

A reaction solution (200 μl) containing the prepared membrane fraction (0.5 mg/ml) and $^3$H-PGE$_2$ was incubated at room temperature for 1 hour. The reaction was terminated with ice cold buffer (3 ml), and the reaction mixture was filtered under suction through a glass filter (GF/B), on which the binding $^3$H-PGE$_2$ was trapped, and the binding radioactivity was measured by means of a liquid scintillator.

The Kd value was obtained from the Acatchard plots [*Ann. N.Y. Acad. Sci.*, 51, 660 (1949)]. Non-specific binding was obtained as the binding in the presence of an excess amount (2.5 μM) of unlabelled PGE$_2$. Measurement of the binding inhibition for $^3$H-PGE$_2$ with the compounds of the invention was performed by adding $^3$H-PGE$_2$ (2.5 nM) and a series of concentrations of the compound of the invention. In this reaction, the following buffer was used in all cases.

Buffer: 10 mM potassium phosphate (pH 6.9), 1 mM EDTA, 10 mM MgCl$_2$, and 0.1M NaCl.

Dissociation constant Ki (μM) of each compound was calculated from the following equation.

$$Ki=IC_{50}/(1+([C]/Kd))$$

The binding activities of the compounds of the invention to the EP$_4$ receptor are shown in Table 121.

TABLE 121

| Example | Dissociation Constant Ki (nM) |
|---|---|
| 2 (pp) | 0.24 |
| 3 (e) | 0.71 |

(ii) Activity of EP$_4$ Receptor Agonist

Experiment for measurement of the activity of an EP$_4$ receptor agonist with the cells expressing prostanoid receptor sub-types According to the method of Nishigaki et al. (*FEBS lett.*, 364, 339-341 (1995)), CHO cells which expressed mouse EP$_4$ receptor sub-types were prepared, inoculated on a 24-well microplate at 10$^5$ cells/well, and incubated for 2 days for use in the experiment. Each well was washed with 500 μl of MEM (minimum essential medium), added 450 μl of an assay medium (MEM containing 1 mmol/L of IBMX and 1% BSA), and incubated at 37° C. for 10 minutes. Then, 50 μl of a solution containing PGE$_2$ alone or PGE$_2$ and a test compound was added to start the reaction, which was conducted at 37° C. for 10 minutes and terminated with addition of 500 μl of ice-cold trichloroacetic acid (10% w/v). The reaction mixture was once treated by freezing (−80° C.) and thawing, and the cells were removed with a scraper and centrifuged at 13,000 rpm for 3 minutes to give a supernatant, of which the AMP concentration was determined with a cAMP assay kit. That is, a buffer solution provided for the [$^{125}$I]cAMP assay kit (Amersham) was added to 125 μl of the above supernatant to be 500 μl, which was mixed with 1 ml of 0.5 mol/L tri-n-octylamine/chloroform solution to eliminate trichloroacetic acid contained in the chloroform layer. The aqueous layer as a sample was measured to determined the cAMP amount contained in the sample according to the method as described in an instruction provided in the [$^{125}$I]cAMP assay kit.

The agonistic effect (EC$_{50}$ value) of the compounds of the invention was determined by calculating 50% productivity of cAMP when the maximum effect of PGE$_2$ alone was regarded as 100%.

As a result, the compounds of the invention were found to have a significant and potent activity as EP$_4$ receptor agonist.

(iii) Inhibitive Effect for TNF-α Production

In male SD rats, LPS (10 μg/2 ml/kg) was injected through the tail vein, and after a lapse of 90 minutes the blood was collected in a heparinized condition from the abdominal vena cava to prepare the plasma. The amount of TNF-α in the plasma was determined by an ELISA kit (Rat TNF-α Immunoassay kit; Biosource). The compound of the invention was dissolved in an equimolar amount of 0.02 mole/L sodium hydroxide solution, diluted with distilled water, and orally given 30 minutes before administration of LPS. The concentration at which the production of TNF-α was inhibited by 50% was regarded as the effective concentration (IC$_{50}$) when the plasma TNF-α concentration in a control group (LPS-treated but no compound given) was 100%. As a result, the compound of the invention showed a significant effect for inhibition of TNF-α production.

(iv) Inhibitive Effect for Chronic Articular Rheumatism (1) Arthritis Induced by Collagen in Rats Experiment was performed according to the method of Osterman et al. (*Inflamm. Res.*, 44, 258-263). An inducing agent (an emulsion prepared by adding an equal volume of physiological saline and 2 equivalent volume of incomplete Freund adjuvant to 0.3% solution of type II collagen of bovine origin) 0.1 ml each was applied intracutaneously to the 4 sites of the back of a female DA/Slc rat. After a lapse of 1 week, the same inducing agent was further applied intracutaneously to the tail root to induce arthritis. At 27 days the limbs were scored responding to the degree of redness and edema and assessed as 30 was regarded as full scores. The compound of the invention was dissolved in an equimolar amount of 0.02 mole/L sodium hydroxide solution, diluted with distilled water, and orally given 3 times a day from the next day of the first administration of inducer.

Result:

The effect of the compound of the invention for collagen-induced arthritis in rats is shown in Table 122.

TABLE 122

| Compound | Dose | Arthritic Score (Means ± SE) |
|---|---|---|
| Example 2 | vehicle | 24.6 ± 1.0 |
|  | 1000 μg/kg | 17.3 ± 1.5* |
| Example 3 (b) | vehicle | 24.6 ± 1.0 |
|  | 300 μg/kg | 19.3 ± 1.4* |
| Example 3 (l) | vehicle | 27.0 ± 1.2 |
|  | 100 μg/kg | 16.3 ± 3.0* |
| Example 3 (kk) | vehicle | 23.4 ± 3.0 |
|  | 100 μg/kg | 11.9 ± 3.6* |
| Example 4 (h) | vehicle | 27.0 ± 1.2 |
|  | 300 μg/kg | 9.8 ± 1.9* |

*p < 0.05

As a result, significant improvement of the condition of arthritis and inhibition of the increase of limb volume (edema) were recognized by administration of the compounds of the invention in comparison with those of a control group (distilled water was orally given 3 times a day).

(2) Arthritis Induced by Cocktail Antibodies in Mice

A cocktail of antibodies to type II collagen was intravenously applied to male DBA/1JNCrj mice at a dose of 2 mg/0.5 ml/mouse. After a lapse of 3 days, lipopolysaccharide was intraperitoneally applied at a dose of 25 μg/0.1 ml/mouse to induce arthritis. At 10 days the limbs were respectively scored responding to the degree of redness and edema and assessed as 4 was regarded as full scores. The compound of the invention was dissolved in an equimolar amount of 0.02 mole/L sodium hydroxide solution, diluted with distilled water, and orally given 3 times a day from 30 minutes before the administration of lipopolysaccharide.

As a result, significant improvement of the condition of arthritis and inhibition of the increase of limb volume (edema) were recognized by administration of the compounds of the invention in comparison with those of a control group (distilled water was orally given 3 times a day).

(v) Effect on the Promotion of Osteogenesis 1

Female SD rats (11 weeks of age; average weight 271 g) were employed in 5 rats for each group. Rat was cut open at the lateral abdomen under anesthetization with pentobarbital to remove the ovary and then sutured. In a sham group, incision and suture were made but no removal of the ovary was made.

From 6 days after the surgical operation, the compound of the invention (dissolved in an equimolar amount of 0.02 mole/L sodium hydroxide solution, and diluted with distilled water) were orally give 3 times a day for 2 months. To the control group and the sham group was given physiological saline. After termination of the test, the animals of each group were killed and subjected to autopsy. The bone density of the cancellous region of left thigh bone was measured by means of an apparatus for measuring the bone density of peripheral bone (XCT-960A, Norland/Stratech).

As a result, the compound of the invention significantly increased the bone density when compared with a control group (no administration).

(vi) Effect on the Promotion of Osteogenesis 2

Using beagle/CSK dogs of approximately 6 months of age, the effect on the promotion of osteogenesis can be examined.

The compound of the invention was dissolved in physiological saline and orally administered over 4 weeks. To a control group was give an equal volume of physiological saline. After completion of the administration, the dogs were killed, subjected to autopsy, and the area and density of bone were measured.

(1) Measurement of Bone Area

The removed thigh bone was fixed with 10% buffered formalin solution and cut in round slices perpendicularly to the bone axis in 10 mm width at the center position of 25 mm from the trochlear fossa; the surface near the epiphysis was photographed with a camera at a certain distance, and the picture was sent into a computer to measure the bone surface by image analysis.

(2) Measurement of Bone Density

The sample of 1 cm in width used in (1) was taken radiographs in side view, and the picture was sent into a computer to measure the radiation dose per unit area in the area of a certain width to obtain the bone density (Micro Focus X-Ray Enlargement Camera System μFX-1000 (FUJIFILM)).

(vii) Effect of Accelerating Cure of Bone Fracture 1

This can be achieved according to the method of Markel et al. (*J. Bone and Joint Surgery*, 73A, 914-923, 1991). Using beagle/CSK dogs of approximately 6 months of age, the femoral tibia is fractured under anesthesia and taken radiographs periodically for 3 months to assess the progress of cure. Thus, the effect of accelerating cure of bone fracture can easily be judged. The compound of the invention is orally administered everyday. To a control group is given distilled water. When the effect of acceleration of cure is recognized, the tibia is removed and the bone density and strength can be measured to further assess quantitatively.

(viii) Inhibitive Effect for Gastric Ulcer

To SD rats was orally administered 20 mg/kg of indomethacin to induce gastric ulcer. After a lapse of 6 hours, the stomach was removed to measure the ulcerous area of mucosa. The compound of the invention was orally administered 30 minutes before administration of indomethacin. As a result, the compound of the invention significantly reduced the ulcerous area when compared to the control group (no administration).

(ix) Effect of Accelerating Cure of Bone Fracture

According to the methods of R. Sakai (*Bone*, 25, 191-196 (1999)), H. Kawaguchi (*Endocrinology*, 135, 774-781 (1994)) and T. Hoshino (*J. Biomed Mater Res.*, 51, 229-306 (2000)), a bone fracture model was prepared with male IGS rats of 8 weeks of age. Hair of the left hind-limb of a rat was cut under anesthetization with pentobarbital Na, and Viccillin S 500 (500 mg potency) (Meiji Seika) was intramuscularly injected at a dose of 10 mg potency/100 μl distilled water/body. Then, the skin on the fibula (from the back of knee joint to tendo Achillis) was incised to ablate the muscular tissue and expose the fibula. The fibula was cut off approximately at the central position to make a fracture portion, which was then restored to its former condition, and the incised portion was closed by suture with disinfection by iodine tincture/disinfectant ethanol. After making the fracture portion and before closing the wound of operation, a physiological saline solution containing 0.2% Tween 80 microsphere (containing 0.3 mg/kg as an active drug; about 60 μl) prepared in Formulation Example 3(1) was added only once. In addition, Compound (1) as a control for comparison was infused continuously for 2 hours twice a day through a catheter attached to the carotid artery. This was made until the last day of the experiment. At the 21st day of the experiment, the rats were subjected to euthanasia with $CO_2$, and the connective tissue of the hind-limbs, including muscle, was eliminated to obtain both of the fibulae. The recovered fibulae were taken radiographs to assess development of the cure of fracture based on the presence of a fracture line and callus formation, and the density and strength of the bone around the fracture portion were measured.

(1) Measurement of the Bone Density of the Callus Region Using a Micro Focus X-Ray Enlargement Camera System The bone density of the callus region at the fracture position of the recovered fibula was measured referring to the reports of C. Matsumoto (*Calcif Tissue Int*, 55, 324-329 (1994)), Kaoru Yamazaki (*Nihon Rinsyo*, 56, 1464-1468 (1998)), and Keiichi Nakagawa (*Sentan Iryo*, 4(6), (1996)). Radiophotographs were taken at 4 magnifications using a micro focus X-ray enlargement camera system (FUJIFILM)/imaging plate (BAS-IP MS 2025; FUJIFILM) in a radiation condition of 40 kV tube voltage, 100 μA tube current, and radiation time 5 seconds. During photographing, a phantom for quantitative analysis of bone salt for mice (Kyoto Kagaku Co.) was set together in order to make an analytical curve for measurement of bone density. The image was read by a Bio-imaging Analyzer BAS-1800 (FUJIFILM)/Image Reader (FUJIFILM) and processed with an Image Gauge, ver.3.1.12 (FUJIFILM). Based on the fracture line (surface) as a callus region, the region of interest (hereinafter sometimes referred to as ROI) was set at the position of 3 mm in the remote direction (ankle) and in the proximal direction (knee) respectively to calculate the bone density of each ROI from the analytical curve obtained from the phantom for quantitative analysis of bone salt. The bone density of the callus region at the fracture side was calculated from the following equation and represented by means±standard error ($mg/cm^2$).

Bone density in callus region={([bone density in proximal callus region]×A)+([bone density in remote callus region]×B)}/(A+B)

A represents the ROI area in the proximal callus region;
B represents the ROI area in the remote callus region.

(2) Measurement of the Bone Strength by a Bending Test at Three Points

According to the report of T. Hoshino (*J Biomed Mater Res.*, 51, 229-306 (2000)), a bending test at three points was performed. Using an Instron Universal Material Testing Machine Type 5544 (Instron Japan)/Merlin (Instron Japan; version 22043), fracture strength and energy absorption were measured in a condition of 2.5 mm/sec of bending rate and 10 mm of sample holder width. The bone strength data was calculated as relative strength of the non-fractured side versus the fractured side for the respective individuals and represented by means±standard error (% of intact).

Result:

The effect of accelerating cure of bone fracture when the fractured portion was treated only once with microsphere (containing 0.3 mg/kg as an active drug) prepared in Formulation Example 3(1) or a reference (physiological saline containing 0.2% Tween 80) is shown in Table 123.

The effect of accelerating cure of bone fracture when the fractured portion was treated only once with microsphere (containing 1 mg/kg as an active drug) prepared in Formulation Example 3(3) or a reference (physiological saline containing 0.2% Tween 80) is shown in Table 123.

TABLE 123

|  | Bone Density (mg/cm$^2$) | Fracture Strength (% of intact) |
|---|---|---|
| Formulation Example 3(1) | 60.9 ± 4.0 | 149.8 ± 12.4% |
| Reference (Control) | 39.8 ± 2.7 | 62.8 ± 8.5% |

TABLE 124

|  | Bone Density (mg/cm$^2$) | Fracture Strength (% of intact) |
|---|---|---|
| Formulation Example 3(3) | 51.6 ± 3.8 | 114.6 ± 10.4% |
| Reference (Control) | 36.5 ± 2.5 | 55.3 ± 5.7% |

The effect of accelerating cure of bone fracture when Compound (1) (50 ng/kg/min) and a reference (physiological saline) were administered intravenously for 2 hours twice a day for 21 days is shown in Table 125.

TABLE 125

|  | Bone Density (mg/cm$^2$) | Fracture Strength (% of intact) |
|---|---|---|
| Compound | 42.8 ± 2.58 | 30.4 ± 12.4% |
| Reference (Control) | 35.2 ± 1.91 | 55.2 ± 9.77% |

As clearly seen from Tables 123 and 124 in comparison with Table 125, the effect of accelerating cure of bone fracture when treated only once with microspheres which were prepared in Formulation Examples 3(1) and 3(3) were much higher than that of Compound (1) which was administered intravenously for 21 days.

(x) Inhibitive Effect on Ulcerous Colitis

7% Sodium dextran sulfate aqueous solution (hereinafter abbreviated to as SDS) was given freely to male C57BL/6 mice. From the beginning of drinking, the body weight and clinical score were recorded every other day. The clinical score was calculated as the sum of diarrhea score (normal: 0; soft: 2; diarrhea: 4) and hematochezia (normal: 0; bleeding: 2; heavy bleeding: 4). At 10 days after taking of the SDS aqueous solution, the blood was collected from the vena cava under ethereal anesthesia in the presence of heparin, and the hematocrit value was measured by a hemocytometer. During a period of from 0 day to 10th day after taking of the SDS aqueous solution, the compound of the invention was orally administered twice a day at a dose of 10, 30, 100 or 300 µg/10 ml/kg. As a result, the compound of the invention showed a significant inhibitive effect on ulcerous colitis.

The invention claimed is:

1. A pharmaceutical composition comprising a compound selected from the group of formula (I-2)

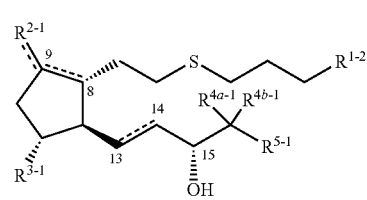

(I-2)

wherein $R^{1-2}$ is (2) —COO—$Y^2$—$R^{9-2}$, (3) —COO—$Z^{1-2}$—$Z^{2-2}$—$Z^{3-2}$, wherein $Y^2$ is bond or C1-10 alkylene, $R^{9-2}$ is (1) phenyl or (2) biphenyl optionally substituted by 1-3 C1-10 alkyl, C 1-10 alkoxy or halogen atom, $Z^{1-2}$ is (1) C1-15 alkylene, $Z^{2-2}$ is (1) —CO—, (2) —OCO—, (3) —COO—, (4) —CONR$^{11-2}$—, (6) —O—,

(13) —OCONR$^{17-2}$— or

(14) —OCOO—, $Z^{3-2}$ is (1) hydrogen atom, (2) C1-15 alkyl, (3) C2-15 alkenyl, (5) ring1$^2$ or ring1$^2$ is (1) C3-15 mono-, bi- or tri-carbocyclic aryl which may be partially or fully saturated $R^{11-2}$ and $R^{17-2}$ are each independently, hydrogen atom or C1-15 alkyl, m-2 is 1 or 2, $R^{2-1}$ is oxo, $R^{3-1}$ is hydrogen atom or hydroxy, $R^{4a-1}$ and $R^{4b-1}$ are each independently, hydrogen atom or C1-4 alkyl, $R^{5-1}$ is phenyl substituted by C1-4 alkyloxy-C1-4 alkyl, === is single bond or double bond, wherein when $R^{2-1}$ is O—COR$^{8-1}$, C8-9 position is double bond, or a non-toxic salt thereof, or cyclodextrin clathrate thereof, as an active ingredient.

2. A sustained release formulation comprising a compound selected from the group of formula (I-2)

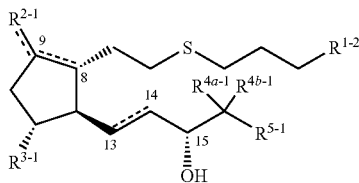

wherein
R$^{1\text{-}2}$ is
(2) —COO—Y$^2$—R$^{9\text{-}2}$,
(3) —COO—Z$^{1\text{-}2}$—Z$^{2\text{-}2}$—Z$^{3\text{-}2}$,
wherein Y$^2$ is bond or C1-10 alkylene,
R$^{9\text{-}2}$ is (1) phenyl or (2) biphenyl optionally substituted by 1-3 C1-10 alkyl, C1-10 alkoxy or halogen atom,
Z$^{1\text{-}2}$ is
(1) C1-15 alkylene,
Z$^{2\text{-}2}$ is
(1) —CO—,
(2) —OCO—,
(3) —COO—,
(4) —CONR$^{11\text{-}2}$—,
(6) —O—,
(13) —OCONR$^{17\text{-}2}$— or
(14) —OCOO—,
Z$^{3\text{-}2}$ is
(1) hydrogen atom,
(2) C1-15 alkyl,
(3) C2-15 alkenyl or
(5) ring1$^2$,
ring1$^2$ is
(1) C3-15 mono-, bi- or tri-carbocyclic aryl which may be partially or fully saturated or
R$^{11\text{-}2}$ and R$^{17\text{-}2}$ are each independently, hydrogen atom or C1-15 alkyl,
m-2 is 1 or 2,
R$^{2\text{-}1}$ is oxo,
R$^{3\text{-}1}$ is hydrogen atom or hydroxy,
R$^{4a\text{-}1}$ and R$^{4b\text{-}1}$ are each independently, hydrogen atom or C1-4 alkyl,
R$^{5\text{-}1}$ is phenyl substituted by C1-4 alkyloxy-C1-4 alkyl;
═══ is single bond or double bond,
wherein when R$^{2\text{-}1}$ is O—COR$^{8\text{-}1}$, C8-9 position is double bond,
or a non-toxic salt thereof, or cyclodextrin clathrate thereof, as an active ingredient.

3. The formulation according to claim 2, wherein the sustained release formulation is a microsphere, a microcapsule, a nanosphere or a film.

4. A compound of formula (I-2)

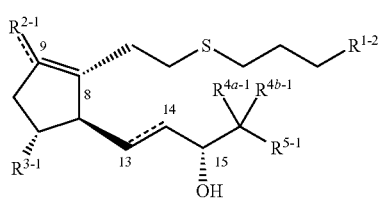

wherein
R$^{1\text{-}2}$ is
(2) —COO—Y$^2$—R$^{9\text{-}2}$,
(3) —COO—Z$^{1\text{-}2}$—Z$^{2\text{-}2}$—Z$^{3\text{-}2}$,
wherein Y$^2$ is bond or C1-10 alkylene,
R$^{9\text{-}2}$ is (1) phenyl or (2) biphenyl optionally substituted by 1-3 C1-10 alkyl, C1-10 alkoxy or halogen atom,
Z$^{1\text{-}2}$ is
(1) C1-15 alkylene,
Z$^{2\text{-}2}$ is
(1) —CO—,
(2) —OCO—,
(3) —COO—,
(4) —CONR$^{11\text{-}2}$—,
(6) —O—,
(13) —OCONR$^{17\text{-}2}$— or
(14) —OCOO—,
Z$^{3\text{-}2}$ is
(1) hydrogen atom,
(2) C1-15 alkyl,
(3) C2-15 alkenyl or
(5) ring1$^2$,
ring1$^2$ is
(1) C3-15 mono-, bi- or tri-carbocyclic aryl which may be partially or fully saturated or
R$^{11\text{-}2}$ and R$^{17\text{-}2}$ are each independently, hydrogen atom or C1-15 alkyl,
m-2 is 1 or 2,
R$^{2\text{-}1}$ is oxo,
R$^{3\text{-}1}$ is hydrogen atom or hydroxy,
R$^{4a\text{-}1}$ and R$^{4b\text{-}1}$ are each independently, hydrogen atom or C1-4 alkyl,
R$^{5\text{-}1}$ is phenyl substituted by C1-4 alkyloxy-C1-4 alkyl;
═══ is single bond or double bond,
wherein when R$^{2\text{-}1}$ is O—COR$^{8\text{-}1}$, C8-9 position is double bond,
or a non-toxic salt thereof, or cyclodextrin clathrate thereof.

5. The compound according to claim 4, which is a compound selected from the group consisting of
(1) (11α,15α,13E)-9-oxo-11,15-dihydroxy-16-(3-methoxymethylphenyl)-17,18,19,20-tetranor-5-thiaprost-13-enoic acid 2-nonanoyloxyethyl ester,
(2) (11α,15α,13E)-9-oxo-11,15-dihydroxy-16-(3-ethoxymethylphenyl)-17,18,19,20-tetranor-5-thiaprost-13-enoic acid pivaloyloxymethyl ester,
(3) (11α,15α,13E)-9-oxo-11,15-dihydroxy-16-(3-methoxymethylphenyl)-17,18,19,20-tetranor-5-thiaprost-13-enoic acid 1-cyclohexyloxycarbonyloxyethyl ester,
(4) (11α,15α,13E)-9-oxo-11,15-dihydroxy-16-(3-methoxymethylphenyl)-17,18,19,20-tetranor-5-thiaprost-13-enoic acid N,N-diethylaminocarbonylmethyl ester,
(5) (11α,15α,13E)-9-oxo-11,15-dihydroxy-16-(3-methoxymethylphenyl)-17,18,19,20-tetranor-5-thiaprost-13-enoic acid 2-acetyloxyethyl ester,
(6) (11α,15α,13E)-9-oxo-11,15-dihydroxy-16-(3-methoxymethylphenyl)-17,18,19,20-tetranor-5-thiaprost-13-enoic acid benzoylmethyl ester,
(7) (11α,15α,13E)-9-oxo-11,15-dihydroxy-16-(3-methoxymethylphenyl)-17,18,19,20-tetranor-5-thiaprost-13-enoic acid isopropyloxycarbonylmethyl ester,
(8) (11α,15α,13E)-9-oxo-11,15-dihydroxy-16-(3-methoxymethylphenyl)-17,18,19,20-tetranor-5-thiaprost-13-enoic acid N,N-diethylaminocarbonyloxymethyl ester, (9) (11α,15α,13E)-9-oxo-11,15-dihydroxy-16-(3-methoxymethylphenyl)-17,18,19,20-tetranor-5-thiaprost-13-enoic acid t-butyloxycarbonylmethyl ester,
(10) (11α,15α,13E)-9-oxo-11,15-dihydroxy-16-(3-methoxymethylphenyl)-17,18,19,20-tetranor-5-thiaprost-13-enoic acid 1-isopropyloxycarbonylethyl ester,
(11) (11α,15α,13E)-9-oxo-11,15-dihydroxy-16-(3-methoxymethylphenyl)-17,18,19,20-tetranor-5-thiaprost-13-enoic acid 1-benzoylethyl ester,
(12) (11α,15α,13E)-9-oxo-11,15-dihydroxy-16-(3-methoxymethylphenyl)-17,18,19,20-tetranor-5-thiaprost-13-enoic acid methoxycarbonylmethyl ester,
(13) (11α,15α,13E)-9-oxo-11,15-dihydroxy-16-(3-methoxymethylphenyl)-17,18,19,20-tetranor-5-thiaprost-13-enoic acid 2-tridecanoyloxyethyl ester,
(14) (11α,15α,13E)-9-oxo-11,15-dihydroxy-16-(3-methoxymethylphenyl)-17,18,19,20-tetranor-5-thiaprost-13-enoic acid 2-heptanoyloxyethyl ester,
(15) (11α,15α,13E)-9-oxo-11,15-dihydroxy-16-(3-methoxymethylphenyl)-17,18,19,20-tetranor-5-thiaprost-13-enoic acid 2-octanoyloxyethyl ester,
(16) (11α,15α,13E)-9-oxo-11,15-dihydroxy-16-(3-methoxymethylphenyl)-17,18,19,20-tetranor-5-thiaprost-13-enoic acid 2-decanoyloxyethyl ester,
(17) (11α,15α,13E)-9-oxo-11,15-dihydroxy-16-(3-methoxymethylphenyl)-17,18,19,20-tetranor-5-thiaprost-13-enoic acid allyloxycarbonylmethyl ester,
(18) (11α,15α,13E)-9-oxo-11,15-dihydroxy-16-(3-methoxymethylphenyl)-17,18,19,20-tetranor-5-thiaprost-13-enoic acid nonanoyloxymethyl ester,
(19) (11α,15α,13E)-9-oxo-11,15-dihydroxy-16-(3-methoxymethylphenyl)-17,18,19,20-tetranor-5-thiaprost-13-enoic acid 2-hydroxyethyl ester,
(20) (11α,15α,13E)-9-oxo-11,15-dihydroxy-16-(3-methoxymethylphenyl)-17,18,19,20-tetranor-5-thiaprost-13-enoic acid phenyl ester,
(21) (11α,15α,13E)-9-oxo-11,15-dihydroxy-16-(3-methoxymethylphenyl)-17,18,19,20-tetranor-5-thiaprost-13-enoic acid carboxymethyl ester,
(22) (11α,15α,13E)-9-oxo-11,15-dihydroxy-16-(3-methoxymethylphenyl)-17,18,19,20-tetranor-5-thiaprost-13-enoic acid dipropylcarbamoylmethyl ester,
(23) (11α,15α,13E)-9-oxo-11,15-dihydroxy-16-(3-methoxymethylphenyl)-17,18,19,20-tetranor-5-thiaprost-13-enoic acid dibutylcarbamoylmethyl ester,
(24) (11α,15α,13E)-9-oxo-11,15-dihydroxy-16-(3-methoxymethylphenyl)-17,18,19,20-tetranor-5-thiaprost-13-enoic acid 4-pentylbenzoylmethyl ester,
(25) (11α,15α,13E)-9-oxo-11,15-dihydroxy-16-(3-methoxymethylphenyl)-17,18,19,20-tetranor-5-thiaprost-13-enoic acid 1,1-dimethylheptyloxycarbonylmethyl ester,
(26) (11α,15α,13E)-9-oxo-11,15-dihydroxy-16-(3-methoxymethylphenyl)-17,18,19,20-tetranor-5-thiaprost-13-enoic acid dipentylcarbamoylmethyl ester,
(27) (11α,15α,13E)-9-oxo-11,15-dihydroxy-16-(3-methoxymethylphenyl)-17,18,19,20-tetranor-5-thiaprost-13-enoic acid 2-octyloxyethyl ester,
(28) (11α,15α,13E)-9-oxo-11,15-dihydroxy-16-(3-methoxymethylphenyl)-17,18,19,20-tetranor-5-thiaprost-13-enoic acid 2-(2,2-dimethylpentanoyloxy)ethyl ester,
(29) (11α,15α,13E)-9-oxo-11,15-dihydroxy-16-(3-methoxymethylphenyl)-17,18,19,20-tetranor-5-thiaprost-13-enoic acid 3-butoxypropyl ester,
(30) (11α,15α,13E)-9-oxo-11,15-dihydroxy-16-(3-methoxymethylphenyl)-17,18,19,20-tetranor-5-thiaprost-13-enoic acid 2-butoxyethyl ester,
(31) (11α,15α,13E)-9-oxo-11,15-dihydroxy-16-(3-methoxymethylphenyl)-17,18,19,20-tetranor-5-thiaprost-13-enoic acid 2-pentyloxyethyl ester,
(32) (11α,15α,13E)-9-oxo-11,15-dihydroxy-16-(3-methoxymethylphenyl)-17,18,19,20-tetranor-5-thiaprost-13-enoic acid 2-hexyloxyethyl ester,
(33) (11α,15α,13E)-9-oxo-11,15-dihydroxy-16-(3-methoxymethylphenyl)-17,18,19,20-tetranor-5-thiaprost-13-enoic acid 2-(2,2-dimethyloctanoyloxy)ethyl ester,
(34) (11α,15α,13E)-9-oxo-11,15-dihydroxy-16-(3-methoxymethylphenyl)-17,18,19,20-tetranor-5-thiaprost-13-enoic acid 2-(2,2-diethylpentanoyloxy)ethyl ester,
(35) (11α,15α,13E)-9-oxo-11,15-dihydroxy-16-(3-methoxymethylphenyl)-17,18,19,20-tetranor-5-thiaprost-13-enoic acid 4-(4-chlorophenyl)phenyl ester,
(36) (11α,15α,13E)-9-oxo-11,15-dihydroxy-16-(3-methoxymethylphenyl)-17,18,19,20-tetranor-5-thiaprost-13-enoic acid 2-(adamantan-1-ylcarbonyloxy)ethyl ester, and
(37) (11α,15α,13E)-9-oxo-11,15-dihydroxy-16-(3-methoxymethylphenyl)-17,18,19,20-tetranor-5-thiaprost-13-enoic acid 2-(2,2-dipropylpentanoyloxy)ethyl ester,
or a non-toxic salt thereof, or a cyclodextrin clathrate thereof.

6. A compound of (11α,15α,13E)-9-oxo-11,15-dihydroxy-16-(3-methoxymethylphenyl)-17,18,19,20-tetranor-5-thiaprost-3-enoic acid 2-nonanoyloxyethyl ester, a non-toxic salt thereof, or a cyclodextrin clathrate thereof.

7. A method for treatment of decreased bone mass in a subject in need of such treatment comprising administering to said subject an effective amount of a compound selected from the group of formula (I-2)

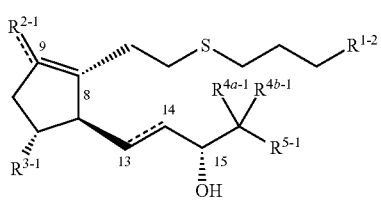

(I-2)

wherein
$R^{1-2}$ is
(2) —COO—$Y^2$—$R^{9-2}$,
(3) —COO—$Z^{1-2}$—$Z^{2-2}$—$Z^{3-2}$,
wherein $Y^2$ is bond or C1-10 alkylene,
$R^{9-2}$ is (1) phenyl or (2) biphenyl optionally substituted by 1-3 C1-10 alkyl, C1-10 alkoxy or halogen atom,
$Z^{1-2}$ is
(1) C1-15 alkylene,
$Z^{2-2}$ is
(1) —CO—,
(2) —OCO—,
(3) —COO—,
(4) —CONR$^{11-2}$—,
(6) —O—,
(13) —OCONR$^{17-2}$— or
(14) —OCOO—,
$Z^{3-2}$ is
(1) hydrogen atom,
(2) C1-15 alkyl,
(3) C2-15 alkenyl or
(5) ring1$^2$ or ring1$^2$ is (1) C3-15 mono-, bi- or tri-carbocyclic aryl which may be partially or fully saturated
$R^{11-2}$ and $R^{17-2}$ are each independently, hydrogen atom or C1-15 alkyl,
m-2 is 1 or 2,
$R^{2-1}$ is oxo,
$R^{3-1}$ is hydrogen atom or hydroxy,
$R^{4a-1}$ and $R^{4b-1}$ are each independently, hydrogen atom or C1-4 alkyl,
$R^{5-1}$ is phenyl substituted by C1-4 alkyloxy-C1-4 alkyl,
⸗ is single bond or double bond,
wherein when $R^{2-1}$ is O—$COR^{8-1}$, C8-9 position is double bond,
or a non-toxic salt thereof, or a cyclodextrin clathrate thereof.

8. The method according to claim 7, wherein the decreased bone mass is fracture.

\* \* \* \* \*